United States Patent
Mjalli et al.

(10) Patent No.: US 8,598,353 B2
(45) Date of Patent: *Dec. 3, 2013

(54) BENZAZOLE DERIVATIVES, COMPOSITIONS, AND METHODS OF USE AS β-SECRETASE INHIBITORS

(75) Inventors: Adnan M. M. Mjalli, Oak Ridge, NC (US); David R. Jones, Milford, OH (US); Devi Reddy Gohimukkula, Jamestown, NC (US); Guoxiang Huang, Kernersville, NC (US); Jeff J. Zhu, High Point, NC (US); Mohan Rao, Greensboro, NC (US); Robert C. Andrews, Jamestown, NC (US); Tan Ren, Colfax, NC (US)

(73) Assignee: High Point Pharmaceuticals, LLC, High Point, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/950,718

(22) Filed: Nov. 19, 2010

(65) Prior Publication Data

US 2011/0065713 A1    Mar. 17, 2011

Related U.S. Application Data

(63) Continuation of application No. 11/885,096, filed as application No. PCT/US2006/009049 on Mar. 14, 2006.

(60) Provisional application No. 60/661,349, filed on Mar. 14, 2005.

(51) Int. Cl.
*C07D 401/12* (2006.01)
*A61K 31/4725* (2006.01)

(52) U.S. Cl.
USPC .......................................... 546/148; 514/307

(58) Field of Classification Search
USPC .......................................... 546/148; 514/307
See application file for complete search history.

(56) References Cited

U.S. PATENT DOCUMENTS

| | | |
|---|---|---|
| 3,336,191 A | 8/1967 | Craig et al. |
| 3,401,173 A | 9/1968 | Chow et al. |
| 5,744,346 A | 4/1998 | Chrysler et al. |
| 5,942,400 A | 8/1999 | Anderson et al. |
| 5,998,398 A | 12/1999 | Daluge et al. |
| 6,207,693 B1 | 3/2001 | Setoi et al. |
| 6,303,600 B1 | 10/2001 | Cox et al. |
| 6,329,163 B1 | 12/2001 | Anderson et al. |
| 6,353,010 B1 | 3/2002 | Dyke et al. |
| 6,420,534 B1 | 7/2002 | Gurney et al. |
| 6,440,698 B1 | 8/2002 | Gurney et al. |
| 6,448,271 B1 | 9/2002 | Lubisch et al. |
| 6,489,328 B2 | 12/2002 | Snow et al. |
| 6,506,769 B2 | 1/2003 | Snow et al. |
| 6,545,127 B1 | 4/2003 | Tang et al. |
| 6,562,783 B2 | 5/2003 | Qiao et al. |
| 6,610,734 B2 | 8/2003 | Kreft et al. |
| 6,627,409 B2 | 9/2003 | Hook |
| 6,627,739 B1 | 9/2003 | Anderson et al. |
| 6,660,741 B2 | 12/2003 | Bornmann et al. |
| 6,696,437 B1 | 2/2004 | Lubisch et al. |
| 6,699,671 B1 | 3/2004 | Gurney et al. |
| 6,706,485 B1 | 3/2004 | Gurney et al. |
| 6,706,742 B2 | 3/2004 | De Nanteuil et al. |
| 6,713,276 B2 | 3/2004 | Cordell et al. |
| 6,727,074 B2 | 4/2004 | Gurney et al. |
| 6,737,510 B1 | 5/2004 | Gurney et al. |
| 6,753,163 B2 | 6/2004 | Gurney et al. |
| 6,790,610 B2 | 9/2004 | Gurney et al. |
| 6,825,023 B1 | 11/2004 | Gurney et al. |
| 6,825,219 B2 | 11/2004 | Cywin et al. |
| 6,828,117 B2 | 12/2004 | Gurney et al. |
| 6,835,565 B1 | 12/2004 | Gurney et al. |
| 7,338,956 B2 * | 3/2008 | Strobel et al. ............ 514/255.05 |
| 7,820,821 B2 | 10/2010 | Mjalli et al. |
| 8,377,983 B2 | 2/2013 | Mjalli et al. |
| 2002/0055459 A1 | 5/2002 | Chopra et al. |
| 2002/0081634 A1 | 6/2002 | Gurney et al. |
| 2002/0115616 A1 | 8/2002 | Boyd et al. |
| 2002/0123484 A1 | 9/2002 | Das et al. |
| 2002/0128255 A1 | 9/2002 | Beck et al. |
| 2002/0143177 A1 | 10/2002 | Beck et al. |
| 2002/0157122 A1 | 10/2002 | Wong et al. |
| 2002/0159991 A1 | 10/2002 | Cordell et al. |
| 2002/0187928 A1 | 12/2002 | Qiao et al. |
| 2002/0194632 A1 | 12/2002 | McConlogue et al. |
| 2003/0083356 A1 | 5/2003 | Schostarez et al. |
| 2003/0092003 A1 | 5/2003 | Blatt et al. |
| 2003/0095958 A1 | 5/2003 | Bhisetti et al. |
| 2003/0097004 A1 | 5/2003 | Taveras et al. |
| 2003/0109559 A1 | 6/2003 | Gailunas et al. |
| 2003/0125257 A1 | 7/2003 | Brockhaus et al. |
| 2003/0134854 A1 | 7/2003 | Flohr et al. |
| 2003/0143708 A1 | 7/2003 | Blatt et al. |
| 2003/0144286 A1 | 7/2003 | Frenkel et al. |

(Continued)

FOREIGN PATENT DOCUMENTS

EP    1502916    2/2005
GB    1122957    8/1968

(Continued)

OTHER PUBLICATIONS

Wermuth (The Practice of Medicinal Chemistry (2nd Ed., 2003), Ch. 13).*
Marcin et al. (Bioorganic & Medicinal Chemistry Letters, vol. 21, Issue 1, Jan. 1, 2011, pp. 537-541).*
Kubinyi (3D QSAR in Drug Design: Ligand-Protein Interactions and Molecular Similarity, vol. 2-3, Springer, 1998, 800 pages). Pages 243-244 provided.*
Wermuth, The Practice of Medicinal Chemsitry, 2d ed. (2003), 768 pages. Chs. 9-10 provided.*
Office Action for U.S. Appl. No. 11/374,723, dated Mar. 21, 2008.

(Continued)

*Primary Examiner* — Robert Havlin
(74) *Attorney, Agent, or Firm* — Samuel B. Rollins

(57) ABSTRACT

The present invention is directed to benzazole compounds that inhibit β-site amyloid precursor protein-cleaving enzyme (BACE) and that may be useful in the treatment or prevention of diseases in which BACE is involved, such as Alzheimer's disease. The invention is also directed to pharmaceutical compositions comprising these compounds and the use of these compounds and compositions in the prevention or treatment of such diseases in which BACE is involved.

14 Claims, No Drawings

(56) References Cited

U.S. PATENT DOCUMENTS

| | | | |
|---|---|---|---|
| 2003/0167486 | A1 | 9/2003 | Jacobsen et al. |
| 2003/0236267 | A1 | 12/2003 | Kobayashi et al. |
| 2004/0005691 | A1 | 1/2004 | Chou et al. |
| 2004/0006119 | A1 | 1/2004 | Lang et al. |
| 2004/0014194 | A1 | 1/2004 | Beyer et al. |
| 2004/0034078 | A1 | 2/2004 | Skalitzky et al. |
| 2004/0063645 | A1 | 4/2004 | Botyanszki et al. |
| 2004/0097547 | A1 | 5/2004 | Taveras et al. |
| 2004/0110743 | A1 | 6/2004 | Miyamato et al. |
| 2004/0110808 | A1 | 6/2004 | Strobe et al. |
| 2004/0146953 | A1 | 7/2004 | Blackstock et al. |
| 2004/0147454 | A1 | 7/2004 | Yang |
| 2004/0171881 | A1 | 9/2004 | John et al. |
| 2004/0180939 | A1 | 9/2004 | John et al. |
| 2004/0209925 | A1 | 10/2004 | Pulley et al. |
| 2004/0214846 | A1 | 10/2004 | Hom et al. |
| 2004/0214890 | A1 | 10/2004 | Fobian et al. |
| 2004/0234976 | A1 | 11/2004 | Gurney et al. |
| 2004/0241792 | A1 | 12/2004 | Yan et al. |
| 2004/0248232 | A1 | 12/2004 | Hook |
| 2004/0253245 | A1 | 12/2004 | Briend et al. |
| 2004/0253706 | A1 | 12/2004 | Yan et al. |
| 2004/0254213 | A1 | 12/2004 | Beck |
| 2004/0254341 | A1 | 12/2004 | Yan et al. |
| 2004/0254342 | A1 | 12/2004 | Yan et al. |
| 2004/0266871 | A1 | 12/2004 | Schostarez et al. |
| 2005/0049263 | A1 | 3/2005 | Kasibhatla et al. |
| 2005/0176792 | A1 | 8/2005 | Moriarty et al. |
| 2005/0203146 | A1 | 9/2005 | Herpin et al. |
| 2006/0223849 | A1 | 10/2006 | Mjalli et al. |
| 2007/0219235 | A1 | 9/2007 | Mjalli et al. |

FOREIGN PATENT DOCUMENTS

| | | |
|---|---|---|
| WO | 98/24771 | 6/1998 |
| WO | 01/00611 | 1/2001 |
| WO | 01/21615 | 3/2001 |
| WO | 01/25238 | 4/2001 |
| WO | 02/14319 | 2/2002 |
| WO | 02/069965 | 9/2002 |
| WO | 03/032984 | 4/2003 |
| WO | 03/041708 | 5/2003 |
| WO | 03/053939 | 7/2003 |
| WO | 03/075921 | 9/2003 |
| WO | 03/087089 | 10/2003 |
| WO | 03/105846 | 12/2003 |
| WO | 2004/014369 | 2/2004 |
| WO | 2004/043916 | 5/2004 |
| WO | 2004/050619 | 6/2004 |
| WO | 2004/054974 | 7/2004 |
| WO | 2004/062625 | 7/2004 |
| WO | 2005/044793 | 5/2005 |
| WO | 2005/108399 | 11/2005 |
| WO | 2005/112932 | 12/2005 |
| WO | WO 2007/095124 | 8/2007 |

OTHER PUBLICATIONS

Office Action for U.S. Appl. No. 11/374,723, dated Sep. 2, 2008.
Office Action for U.S. Appl. No. 11/374,723, dated Dec. 19, 2008.
Office Action for U.S. Appl. No. 11/374,723, dated Mar. 11, 2009.
Office Action for U.S. Appl. No. 11/374,723, dated Sep. 14, 2009.
Advisory Action for U.S. Appl. No. 11/374,723, dated Dec. 31, 2009.
PCT International Search Report for App. No. PCT/US06/009049, dated Apr. 4, 2007.
Agarwal et al., J. Biosciences, vol. 48, pp. 823-838 (1993).
Andrau et al., J. Biol. Chem., vol. 278, pp. 25859-25866 (2003).
Asai et al., Biochem. Biophys. Res. Comm., vol. 301, pp. 231-235 (2003).
Citron et al., Trends in Pharm. Sci., vol. 25, pp. 92-97 (2004).
Colciaghi et al., Neurology, vol. 62, pp. 498-501 (2004).
De Strooper et al., Nature, vol. 402, pp. 471-472 (1999).
Dingwall et al., J. Clin. Invest., vol. 108, pp. 1243-1246 (2001).
Elliott et al., Bioorg. Med. Chem. Lett., vol. 13, pp. 3593-3596 (2003).
Eriksen et al., J. Clin. Invest., vol. 112, pp. 440-449 (2003).
Fukumoto et al., Am J. Pathology, vol. 164, pp. 719-725 (2004).
Greeve et al., J. Neurosci., vol. 20, pp. 7345-7352 (2000).
Gruninger-Leitch et al., J. Biol. Chem., vol. 277, pp. 4687-4693 (2002).
Haas et al., Eu. Mol. Biol. Org. J., vol. 23, pp. 483-488 (2004).
Hanui et al., J. Biol. Chem., vol. 275, pp. 21099-21106 (2000).
Kajkowski et al., J. Biol. Chem., vol. 276, pp. 18748-18756 (2001).
Kamenetz et al., Neuron, vol. 37, pp. 925-937 (2003).
Kametaka et al., J. Biol. Chem., vol. 278, pp. 15239-15245 (2003).
Kennedy et al., Anal. Biochem., vol. 319, pp. 49-55 (2003).
King et al., Exper. Neurology, vol. 185, pp. 208-219 (2004).
Kumar et al., In. J. Chem., vol. 20B, pp. 1068-1071 (1981).
Lammich et al., Proc. Nat'l Acad. Sci., vol. 96, pp. 3922-3927 (1999).
Leissing et al., Proc. Nat'l Acad. Sci., vol. 99, pp. 4697-4702 (2002).
Li et al., Proc. Nat'l Acad. Sci., vol. 100, pp. 259-264 (2003).
Lin et al., Proc. Nat'l Acad. Sci., vol. 97, pp. 1456-1460 (2000).
Liu et al., Brain Res., vol. 961, pp. 88-91 (2003).
Maiorini et al., J. Clin. Pharm. Therapeutics, vol. 27, pp. 169-183 (2002).
Malherbe et al., Mol. Brain Res., vol. 71, pp. 159-170 (1999).
Marcinkeviciene et al., J. Biol. Chem., vol. 276, pp. 23790-23794 (2001).
McClendon et al., "Cell-Free Assays for v-Secretase Activity" FASEB J., published online Oct. 6, 2000.
Michaelis et al., J. Pharm. Exper. Ther., vol. 304, pp. 897-904 (2003).
Ohno et al., Neuron, vol. 41, pp. 27-33 (2004).
Scholefield et al., J. Cell Biol. vol. 163, pp. 97-107 (2003).
Selkoe et al., J. Clin. Invest., vol. 110, pp. 1375-1381 (2002).
Shahani et al., Cell. Mol. Life Sci., vol. 59, pp. 1668-1680 (2002).
Carlson et al., Nature Neurosci., vol. 6, pp. 328-330 (2003).
Cheng et al., Bioorg. Med. Chem. Lett., vol. 15, pp. 267-269 (2005).
Citron et al., Nature Neurosci. Supp., vol. 5, pp. 1055-1057 (2002).
De Jonghe et al., Human Mol. Genetics, vol. 10, pp. 1665-1671 (2001).
Denny et al., J. Med. Chem., vol. 33, pp. 814-819 (1990).
Goldberg et al., J. Med. Chem., vol. 46, pp. 1337-1349 (2003).
Hom et al., J. Med. Chem., vol. 47, pp. 158-164 (2004).
Hom et al., J. Med. Chem., vol. 46, pp. 1799-1802 (2003).
Iversen et al., Nature, vol. 417, pp. 231-233 (2002).
Puglielli et al., Nature Neurosci., vol. 6, pp. 345-351 (2003).
Roberds et al., Human Mol. Genetics, vol. 10, pp. 1317-1324 (2001).
Sinha et al., Nature, vol. 402, pp. 537-540 (1999).
Snow et al., J. Med. Chem., vol. 45, pp. 3394-3405 (2002).
Snow et al., Tetrahedron Lett., vol. 43, pp. 7553-7556 (2002).
Stachel et al., J. Med. Chem., vol. 47, pp. 6447-6450 (2004).
Toulokhonova et al., J. Biol. Chem., vol. 278, pp. 4582-4589 (2003).
Van Dorpe et al., Am. J. Pathology, vol. 157, pp. 1283-1298 (2000).
Varghese et al., J. Med. Chem., vol. 46, pp. 4625-4630 (2003).
Vattemi et al., The Lancet, vol. 358, pp. 1962-1964 (2001).
Wolfe et al., Nature Rev., vol. 1, pp. 859-866 (2002).
Wolozin et al., Proc. Nat'l Acad. Sci., vol. 98, pp. 5371-5373 (2001).
International Preliminary Report on Patentability for PCT App. No. PCT/US06/009049, dated Sep. 18, 2007.
Yan et al., J. Biol. Chem., vol. 276, pp. 34019-34027 (2001).
Yan et al., Nature, vol. 402, pp. 533-537 (1999).
Zhang et al., J. Biol. Chem., vol. 277, pp. 15069-15075 (2002).
Wolozin et al., Neuron, vol. 41, pp. 7-10 (2004).
European Search Report for related European Patent Application No. 12150487.2, mailed May 3, 2012.
International Preliminary Report on Patentability for International Application PCT/US2007/003579 issued Aug. 12, 2008.
International Search Report and Written Opinion for PCT Application No. PCT/US2006/009049, mailed Apr. 4, 2007.
Office Action from EP Application No. 07 750 418.1 issued on Dec. 1, 2008.
Written Opinion of the ISA for PCT/US2007/003579 mailed Sep. 4, 2007.

\* cited by examiner

BENZAZOLE DERIVATIVES, COMPOSITIONS, AND METHODS OF USE AS β-SECRETASE INHIBITORS

STATEMENT OF RELATED APPLICATION

This application is a continuation of U.S. patent application Ser. No. 11/885,096, which is a §371 national stage application of PCT Application No. PCT/US2006/009049, filed Mar. 14, 2006, which claims the benefit of priority of U.S. Provisional Patent Application No. 60/661,349, filed Mar. 14, 2005. The disclosures of each of the aforementioned applications are expressly incorporated herein in their entirety as though fully set forth in the present application.

FIELD OF INVENTION

The present invention relates to benzazole derivatives useful as inhibitors of β-secretase, the β-site amyloid precursor protein-cleaving enzyme (BACE).

BACKGROUND

Alzheimer's disease is characterized by the abnormal deposition of β-amyloid (Aβ) in the brain in the form of extra-cellular plaques and intra-cellular neurofibrillary tangles. The rate of amyloid accumulation is a combination of the rates of Aβ formation, aggregation and egress from the brain. It is generally accepted that the main constituent of amyloid plaques is the 4 kD amyloid protein (βA4, also referred to as Aβ, β-protein and βAP) which is a proteolytic product of a precursor protein of much larger size.

Amyloid precursor protein (APP) is a 695-770 amino acid glycoprotein, expressed in the neurons and glial cells in peripheral tissues. APP has a receptor-like structure with a large ectodomain, a membrane spanning region, and a short cytoplasmic tail. Aβ is a 39-42 amino acid peptide, constitutes part of the ectodomain of APP, and extends partly to the transmembrane domain of APP.

At least two secretory mechanisms exist which release APP from the membrane and generate soluble, truncated forms of APP (sAPP). Proteases that release APP and its fragments from the membrane are termed "secretases." Most sAPP is released by a putative α-secretase that cleaves within the Aβ protein to release sAPPα and precludes the release of intact Aβ. A smaller portion of sAPP is released by a β-secretase that cleaves near the $NH_2$-terminus of APP and produces COOH-terminal fragments (CTFs) which contain the complete Aβ domain.

Thus, the activity of β-secretase or β-site amyloid precursor protein-cleaving enzyme ("BACE") leads to the abnormal cleavage of APP, production of Aβ, and accumulation of β-amyloid plaques in the brain, which is characteristic of Alzheimer's disease. In addition, the processing of APP by β-secretase is thought to be the rate determining step in Aβ production. Therefore, therapeutic agents that can inhibit BACE may be useful for the treatment of Alzheimer's disease.

The compounds of the present invention may be useful for treating Alzheimer's disease by inhibiting the activity of the BACE, thus preventing or reducing the rate of formation of insoluble Aβ.

SUMMARY OF THE INVENTION

The present invention is directed to benzazole compounds that inhibit β-site amyloid precursor protein-cleaving enzyme (BACE) and that may be useful in the treatment or prevention of diseases in which BACE is involved, such as Alzheimer's disease. The invention is also directed to pharmaceutical compositions comprising these compounds and the use of these compounds and compositions in the prevention or treatment of such diseases in which BACE is involved.

In one aspect, the present invention provides compounds of Formula (I) as shown below. In another aspect, the present invention provides methods for the preparation of compounds of Formula (I).

In another aspect, the present invention provides pharmaceutical compositions comprising a compound of Formula (I). In an embodiment, the pharmaceutical composition comprises a compound of Formula (I) and a pharmaceutically acceptable carrier, excipient, diluent, or mixture thereof. In another aspect, the present invention provides a method for the preparation of a pharmaceutical composition comprising a compound of Formula (I).

In another aspect, the present invention provides methods of treatment or prevention comprising administering a compound of Formula (I) or a pharmaceutical composition comprising a compound of Formula (I) to a subject having a disorder or disease in which BACE is involved.

In another aspect, the present invention provides methods of treatment or prevention comprising administering a compound of Formula (I) or a pharmaceutical composition comprising a compound of Formula (I) to a subject having a disorder or disease or at risk for having a disorder or disease, wherein the disorder or disease is selected from the group consisting of: Alzheimer's disease, mild cognitive impairment, Down's syndrome, Hereditary Cerebral Hemorrhage with Amyloidosis of the Dutch-Type, cerebral amyloid angiopathy, degenerative dementia, diffuse Lewy body type of Alzheimer's disease or central or peripheral amyloid diseases.

Additional features of the present invention are described hereinafter.

DETAILED DESCRIPTION

In a first aspect, the present invention provides certain substituted benzazole compounds. Such compounds are useful in the reduction of the proteolytic activity of BACE, as will be discussed in more detail below.

In another aspect, the present invention provides a compound of Formula (I)

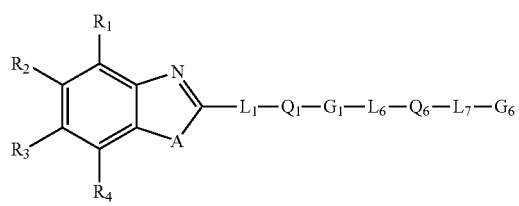

(I)

wherein
A is —O—, —S—, or —N($R_5$)—,
    wherein $R_5$ is selected from the group consisting of:
      a) -hydrogen;
      b) -alkyl;
      c) -aryl;
      d) -heteroaryl;
      e) -cycloalkyl;

f) -heterocyclyl;
g) -alkylene-aryl;
h) -alkylene-heteroaryl;
i) -alkylene-cycloalkyl; and
j) -alkylene-heterocyclyl;

$L_1$, $L_6$, and $L_7$ are independently selected from the group consisting of:
a direct bond, —$CH_2$—, —O—, —N($R_6$)—, —C(O)—, —CON($R_6$)—, —N($R_6$)C(O)—, —N($R_6$)CON($R_7$)—, —N($R_6$)C(O)O—, —OC(O)N($R_6$)—, —N($R_6$)$SO_2$—, —$SO_2$N($R_6$)—, —C(O)—O—, —O—C(O)—, —S—, —S(O)—, —S(O)$_2$—, and —N($R_6$)$SO_2$N($R_7$)—,
wherein $R_6$ and $R_7$ are independently selected from the group consisting of: -hydrogen, -alkyl, -aryl, and -alkylene-aryl;

$Q_1$ and $Q_6$ are independently selected from the group consisting of direct bond, alkylene, alkenylene, and alkynylene;

$G_1$ is selected from the group consisting of: heterocyclylene, cycloalkylene, heterocyclylene, arylene, heteroarylene, fused arylcycloalkylene, fused cycloalkylarylene, fused cycloalkylheteroarylene, fused heterocyclylarylene, and fused heterocyclylheteroarylene group wherein $G_1$ may be optionally substituted 1 to 7 times, wherein the substituents are independently selected from the group consisting of:
a) -halo;
b) -cyano;
c) -nitro;
d) -perhaloalkyl;
e) —$R_8$;
f) -$L_2$-$R_8$;
g) -$L_2$-$Q_2$-$R_8$; and
h) -$Q_2$-$L_2$-$R_8$;
wherein
$R_8$ is selected from the group consisting of hydrogen, -alkyl, -aryl, and alkylene-aryl;
$Q_2$ is selected from the group consisting of a direct bond, alkylene, alkenylene, and alkynylene;
$L_2$ is selected from the group consisting of a direct bond, —$CH_2$—, —O—, —N($R_9$)—, —C(O)—, —CON($R_9$)—, —N($R_9$)C(O)—, —N($R_9$)CON($R_{10}$)—, —N($R_9$)C(O)O—, —OC(O)N($R_9$)—, —N($R_9$)$SO_2$—, —$SO_2$N($R_9$)—, —C(O)—O—, —O—C(O)—, —S—, —S(O)—, —S(O)$_2$—, and —N($R_9$)$SO_2$N($R_{10}$)—,
wherein $R_9$ and $R_{10}$ are independently selected from the group consisting of: -hydrogen, -alkyl, -aryl, and -alkylene-aryl; or $R_9$ and $R_{10}$ are taken together with the atoms to which they are attached to form a heterocyclic ring of 5 to 7 members containing 0-2 additional heteroatoms independently selected from oxygen, nitrogen, and sulfur;

$G_6$ is selected from the group consisting of: hydrogen, heterocyclyl, cycloalkyl, heterocyclyl, aryl, heteroaryl, fused arylcycloalkyl, fused cycloalkylaryl, fused cycloalkylheteroaryl, fused heterocyclylaryl, and fused heterocyclylheteroaryl group, wherein $G_6$ is optionally substituted 1 to 7 times, wherein the substituents are independently selected from the group consisting of:
a) -halo;
b) -cyano;
c) -nitro;
d) -perhaloalkyl;
e) —$R_{108}$;
f) -$L_{102}$-$R_{108}$;
g) -$L_{102}$-$Q_{102}$-$R_{108}$; and
h) -$Q_{102}$-$L_{102}$-$R_{108}$;
wherein
$R_{108}$ is selected from the group consisting of hydrogen, -alkyl, -aryl, and alkylene-aryl;
$Q_{102}$ is selected from the group consisting of a direct bond, alkylene, alkenylene, and alkynylene;
$L_{102}$ is selected from the group consisting of a direct bond, —$CH_2$—, —O—, —N($R_{109}$)—, —C(O)—, —CON($R_{109}$)—, —N($R_{109}$)C(O)—, —N($R_{109}$)CON($R_{110}$)—, —N($R_{109}$)C(O)O—, —OC(O)N($R_{109}$)—, —N($R_{109}$)$SO_2$—, —$SO_2$N($R_{109}$)—, —C(O)—O—, —O—C(O)—, —S—, —S(O)—, —S(O)$_2$—, and —N($R_{109}$)$SO_2$N($R_{110}$)—,
wherein $R_{109}$ and $R_{110}$ are independently selected from the group consisting of: -hydrogen, -alkyl, -aryl, and -alkylene-aryl; or $R_{109}$ and $R_{110}$ are taken together with the atoms to which they are attached to form a heterocyclic ring of 5 to 7 members containing 0-2 additional heteroatoms independently selected from oxygen, nitrogen, and sulfur;

$R_1$, $R_2$, $R_3$, and $R_4$ are independently selected from the group consisting of
a) —H;
b) —$NH_2$;
c) -carboxy;
d) -cyano;
e) -halogen;
f) -nitro;
g) —OH
h) -alkyl;
i) -aryl;
j) -alkylene-aryl;
k) —K-alkyl;
l) —K-aryl;
m) —K-alkylene-aryl;
n) -$L_3$-$G_2$-$G_3$; and
o) -$L_8$-$Q_8$-$L_9$-$G_8$-$L_{18}$-$Q_{18}$-$L_{19}$-$G_{18}$;
wherein at least one of $R_1$, $R_2$, $R_3$, and $R_4$ is not hydrogen; and
wherein
K is selected from the group consisting of: —C(O)—O—, —O—C(O)—, —C(O)—NH—, —NH—C(O)—, —$SO_2$—, —$SO_2$—NH—, —NH—$SO_2$—, and —C(O)—;
$Q_8$ and $Q_{18}$ are independently selected from the group consisting of a direct bond, alkylene, alkenylene, and alkynylene;
$L_3$, $L_8$, $L_9$, $L_{18}$, and $L_{19}$ are independently selected from the group consisting of:
a direct bond, —$CH_2$—, —O—, —N($R_{26}$)—, —C(O)—, —CON($R_{26}$)—, —N($R_{26}$)C(O)—, —N($R_{26}$)CON($R_{27}$)—, —N($R_{26}$)C(O)O—, —OC(O)N($R_{26}$)—, —N($R_{26}$)$SO_2$—, —$SO_2$N($R_{26}$)—, —C(O)—O—, —O—C(O)—, —S—, —S(O)—, —S(O)$_2$—, —N($R_{26}$)$SO_2$N($R_{27}$)—, —C(O)—N($R_{26}$)—C(=NH)—N($R_{27}$)—, and —C(O)—N($R_{26}$)—N($R_{27}$)—
wherein $R_{26}$ and $R_{27}$ are independently selected from the group consisting of: hydrogen, -alkyl, -aryl, -alkylene-aryl, or $R_{26}$ and $R_{27}$ are taken together with the atoms to which they are attached to form a heterocyclic ring of 5 to 7 members containing 0-2 additional heteroatoms independently selected from oxygen, nitrogen, and sulfur;
$G_2$ is selected from the group consisting of:
direct bond, alkylene, alkenylene, alkynylene, and

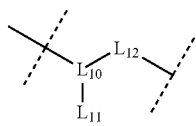

wherein
$L_{10}$ is selected from the group consisting of alkyline, cycloalkyline, heteroaryline, aryline, and heterocyclyline;
$L_{12}$ is selected from the group consisting of —O—, —C(O)—N($R_{11}$)—, —C(O)—O—, —C(O)—, and —N($R_{11}$)—CO—N($R_{12}$)—, wherein $R_{11}$ and $R_{12}$ independently comprise hydrogen, -aryl, -alkyl, and -alkylene-aryl;
$L_{11}$ is selected from the group consisting of hydrogen, -alkyl, -alkenyl, alkynyl, -aryl, -alkylene-aryl, -alkylene -heteroaryl, alkylene-O-alkylene-aryl, -alkylene-S-alkylene-aryl, -alkylene-O-alkyl, -alkylene-S-alkyl, -alkylene-NH$_2$, -alkylene-OH, -alkylene-SH, -alkylene-C(O)—O$R_{13}$, -alkylene-C(O)—N$R_{13}R_{14}$, -alkylene-N$R_{13}R_{14}$, -alkylene-N($R_{13}$)—C(O)—$R_{14}$, -alkylene-N($R_{13}$)—S(O)$_2$—$R_{14}$, and the side chain of a natural or non-natural amino acid, wherein
  $R_{13}$ and $R_{14}$ independently comprise hydrogen, -aryl, -alkyl, and -alkylene-aryl; or
  $R_{13}$ and $R_{14}$ may be taken together to form a ring having the formula —(CH$_2$)$_q$—Y—(CH$_2$)$_r$— bonded to the nitrogen atom to which $R_{13}$ and $R_{14}$ are attached, wherein q and r are, independently, 1, 2, 3, or 4; Y is —CH$_2$—, —C(O)—, —O—, —N(H)—, —S—, —S(O)—, —SO$_2$—, —CON(H)—, —NHC(O)—, —NHCON(H)—, —NHSO$_2$—, —SO$_2$N(H)—, —(O)CO—, —NHSO$_2$NH—, —OC(O)—, —N($R_{15}$)—, —N(C(O)$R_{15}$)—, —N(C(O)NH$R_{15}$)—, —N(SO$_2$NH$R_{15}$)—, —N(SO$_2R_{15}$)—, and —N(C(O)O$R_{15}$)—, wherein $R_{15}$ is selected from the group consisting of hydrogen, -alkyl, -aryl, and -alkylene-aryl; or
  $R_{13}$ and $R_{14}$ may be taken together, with the nitrogen atom to which they are attached, to form a heterocyclyl or heteroaryl ring; and
$G_3$ and $G_{18}$ are independently selected from the group consisting of hydrogen, alkyl, cycloalkyl, heterocyclyl, aryl, heteroaryl, fused arylcycloalkyl, fused cycloalkylaryl, fused cycloalkylheteroaryl, fused heterocyclylaryl, and fused heterocyclylheteroaryl group, wherein $G_3$ and $G_{18}$ may be optionally substituted 1 to 7 times, wherein the substituents are independently selected from group consisting of:
  a) -halo;
  b) —NH$_2$;
  c) -carboxy;
  d) -cyano;
  e) -nitro;
  f) —OH;
  g) -haloalkyl;
  h) -perhaloalkyl;
  i) —$R_{16}$;
  j) -$L_4$-$R_{16}$;
  k) -$L_4$-$Q_4$-$R_{16}$; and
  l) -$Q_4$-$L_4$-$R_{16}$;

wherein
  $R_{16}$ is selected from the group consisting of hydrogen, -alkyl, -cycloalkyl, -aryl, -heterocyclyl, -heteroaryl, and -alkylene-aryl;
  $Q_4$ is selected from the group consisting of direct bond, alkylene, alkenylene, and alkynylene;
  $L_4$ is selected from the group consisting of direct bond, —CH$_2$—, —O—, —N($R_{18}$)—, —C(O)—, —CON($R_{18}$)—, —N($R_{18}$)C(O)—, —N($R_{18}$)CON($R_{19}$)—, —N($R_{18}$)C(O)O—, —OC(O)N($R_{18}$)—, —N($R_{18}$)SO$_2$—, —SO$_2$N($R_{18}$)—, —C(O)—O—, —O—C(O)—, —S—, —S(O)—, —S(O)$_2$—, and —N($R_{18}$)SO$_2$N($R_{19}$)—;
  wherein
    $R_{18}$ and $R_{19}$ are independently selected from the group consisting of: -hydrogen, -alkyl, -aryl, and -alkylene-aryl;
  $G_8$ is selected from the group consisting of alkylene, cycloalkylene, heterocyclylene, arylene, heteroarylene, fused arylcycloalkylene, fused cycloalkylarylene, fused cycloalkylheteroarylene, fused heterocyclylarylene, and fused heterocyclylheteroarylene group, wherein $G_8$ may be optionally substituted 1 to 7 times, wherein the substituents are independently selected from group consisting of:
    a) -halo;
    b) —NH$_2$;
    c) -carboxy;
    d) -cyano;
    e) -nitro;
    f) —OH;
    g) -haloalkyl;
    h) -perhaloalkyl;
    i) —$R_{116}$;
    j) -$L_{114}$-$R_{116}$;
    k) -$L_{114}$-$Q_{114}$-$R_{116}$; and
    l) -$Q_{114}$-$L_{114}$-$R_{116}$;
  wherein
    $R_{116}$ is selected from the group consisting of hydrogen, -alkyl, -cycloalkyl, -aryl, -heterocyclyl, -heteroaryl, and -alkylene-aryl;
    $Q_{114}$ is selected from the group consisting of direct bond, alkylene, alkenylene, and alkynylene;
    $L_{114}$ is selected from the group consisting of direct bond, —CH$_2$—, —O—, —N($R_{118}$)—, —C(O)—, —CON($R_{118}$)—, —N($R_{118}$)C(O)—, —N($R_{118}$)CON($R_{119}$)—, —N($R_{118}$)C(O)O—, —OC(O)N($R_{118}$)—, —N($R_{118}$)SO$_2$—, —SO$_2$N($R_{118}$)—, —C(O)—O—, —O—C(O)—, —S—, —S(O)—, —S(O)$_2$—, and —N($R_{118}$)SO$_2$N($R_{119}$)—;
    wherein
      $R_{118}$ and $R_{119}$ are independently selected from the group consisting of: hydrogen, -alkyl, -aryl, and -alkylene-aryl;
wherein the alkyl, cycloalkyl, heterocyclyl, aryl, heteroaryl, fused arylcycloalkyl, fused cycloalkylaryl, fused cycloalkylheteroaryl, fused heterocyclylaryl, and fused heterocyclylheteroaryl groups in $R_1$ to $R_{119}$, $L_1$ to $L_{114}$, $G_1$ to $G_{118}$, and $Q_1$ to $Q_{114}$ may be optionally substituted 1-4 times with a substituent selected from the group consisting of:
  a) —H;
  b) -halo;
  c) -hydroxyl;
  d) -amino;
  e) -cyano;
  f) -carbamoyl;
  g) -carboxyl;

h) —Z-alkyl;
i) —Z-haloalkyl;
j) —Z-perhaloalkyl;
k) —Z-aryl;
l) —Z-alkylene-aryl;
m) —Z-cycloalkyl;
n) —Z-alkylene-cycloalkyl;
o) —Z-heterocyclyl;
p) —Z-alkylene-heterocyclyl;
q) —Z-heteroaryl; and
r) —Z-alkylene-heteroaryl;
wherein Z is selected from the group consisting of a direct bond, —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, and —O—CO—,
or a pharmaceutically acceptable salt, ester, or prodrug thereof.

In an embodiment of the compound of Formula (I), A is —N(R$_5$)—.

In another embodiment of the compound of Formula (I), A is —N(R$_5$)—, and Q$_1$, G$_1$, L$_6$, Q$_6$, L$_7$, and G$_6$ are taken together to form a group selected from the group consisting of: isoquinoline-3-yl, and (phenylethynyl)-pyridine-2-yl.

In another embodiment of the compound of Formula (I), A is —N(R$_5$)—, and R$_1$ or R$_4$ is the group imidazole-2-ylcarbamoyl. In another embodiment of the compound of Formula (I), A is —N(R$_5$)—, and R$_1$ or R$_4$ is the group imidazole-2-ylcarbamoyl and R$_2$ and R$_3$ are hydrogen.

In another embodiment of the compound of Formula (I),
L$_1$ is —NH—C(O)—, —NH—, —C(O)—NH—, —NH—C(O)—NH—, or a direct bond;
Q$_1$ is a direct bond;
G$_1$ is phenyl, indole, isoquinoline, pyridine, pyrimidine, benzofuran, benzothiophene, benzimidazole, furan, imidazole, 1-oxo-1,2-dihydroisoquinoline, 1,2,3,4-tetrahydroisoquinoline, cinnoline, quinoxaline, [1,8]-naphthyridine, 2,3-dihydro-[1,4]-dioxino-[2,3-g]-isoquinoline, 1,3-dioxolo-[4,5-g]-isoquinoline, 1,3,4,9-tetrahydro-beta-carboline, thieno-[2,3-c]-pyridine, imidazole-[1,2-a]-pyridine, imidazole-[2,1-b]-thiazole, wherein G$_1$ is substituted or unsubstituted.

In another embodiment of the compound of Formula (I),
L$_1$ is —NH—C(O)—, —NH—, —C(O)—NH—, —NH—C(O)—NH—, or a direct bond;
Q$_1$ is a direct bond;
G$_1$ is phenyl, indole, isoquinoline, pyridine, pyrimidine, benzofuran, benzothiophene, benzimidazole, furan, imidazole, 1-oxo-1,2-dihydroisoquinoline, 1,2,3,4-tetrahydroisoquinoline, cinnoline, quinoxaline, [1,8]-naphthyridine, 2,3-dihydro-[1,4]-dioxino-[2,3-g]-isoquinoline, 1,3-dioxolo-[4,5-g]-isoquinoline, 1,3,4,9-tetrahydro-beta-carboline, thieno-[2,3-c]-pyridine, imidazole-[1,2-a]-pyridine, imidazole-[2,1-b]-thiazole, wherein substituted or unsubstituted;
L$_6$, Q$_6$, L$_7$ are direct bonds, and
G$_6$ is hydrogen.

In another embodiment of the compound of Formula (I),
L$_1$ is —NH—C(O)—, —NH—, —C(O)—NH—, —NH—C(O)—NH—, or a direct bond;
Q$_1$ is a direct bond;
G$_1$ is phenyl, indole-2-yl, indole-3-yl, isoquinoline-1-yl, isoquinoline-3-yl, isoquinoline-5-yl, isoquinoline-6-yl, pyridine-2-yl, pyridine-3-yl, pyridine-4-yl, pyrimidine-2-yl, pyrimidine-4-yl, benzimidazole-2-yl, 1-oxo-1,2-dihydroisoquinoline-3-yl, 1,2,3,4-tetrahydroisoquinoline-1-yl, 1,2,3,4-tetrahydroisoquinoline-3-yl, 1,2,3,4-tetrahydroisoquinoline-5-yl, 1,2,3,4-tetrahydroisoquinoline-6-yl, cinnoline-3-yl, quinoxaline-2-yl, [1,8]-naphthyridine-8-yl, 2,3-dihydro[1,4]dioxino[2,3-g]-isoquinoline-8-yl, 1,3-dioxolo[4,5-g]-isoquinoline-7-yl, 1,3,4,9-tetrahydro-beta-carboline-3-yl, thieno-[2,3-c]-pyridine-5-yl, thieno-[2,3-c]-pyridine-6-yl, imidazole-[1,2-a]-pyridine-2-yl, imidazole-[1,2-a]-pyridine-3-yl, or imidazole-[2,1-b]-thiazole-6-yl, wherein G$_1$ is substituted or unsubstituted;
L$_6$, Q$_6$, L$_7$ are direct bonds; and
G$_6$ is hydrogen.

In another embodiment of the compound of Formula (I),
L$_1$ is —NH—C(O)—, —NH—, —C(O)—NH—, —NH—C(O)—NH—, or a direct bond;
Q$_1$ is a direct bond;
G$_1$ is phenyl, isoquinoline-1-yl, isoquinoline-3-yl, isoquinoline-5-yl, isoquinoline-6-yl, pyridine-2-yl, pyridine-3-yl, pyridine-4-yl, pyrimidine-2-yl, or pyrimidine-4-yl, wherein G$_1$ is substituted or unsubstituted;
L$_6$, Q$_6$, L$_7$ are direct bonds; and
G$_6$ is hydrogen.

In another embodiment of the compound of Formula (I),
L$_1$ is —NH—C(O)—, —NH—, —C(O)—NH—, —NH—C(O)—NH—, or a direct bond;
Q$_1$ is a direct bond;
G$_1$ is phenyl, pyridine-2-yl, pyridine-3-yl, or pyridine-4-yl, wherein G$_1$ is substituted or unsubstituted;
L$_6$ is a direct bond, —CH$_2$—, or —O—;
Q$_6$ is a direct bond, lower alkylene, or —C≡C—;
L$_7$ is a direct bond, —CH$_2$—, or —O—; and
G$_6$ is phenyl, furan, pyridine, thiophene, cyclopropyl, cyclopentyl, cyclohexyl, imidazole, pyrazole, or isoxazole, wherein G$_6$ is substituted or unsubstituted.

In another embodiment of the compound of Formula (I), L$_1$ is —N(H)—C(O)—, and Q$_1$, G$_1$, L$_6$, Q$_6$, L$_7$, and G$_6$ are taken together to form a group selected from the group consisting of: [1,3]Dioxolo[4,5-g]isoquinoline-7-yl, 1,2,3,4-tetrahydro-isoquinoline-6-yl, 1,2,3,4-tetrahydro-isoquinoline-3-yl, 1-(2-alkylsulfanyl-ethyl)-isoquinoline-3-yl, 1-(2-alkylsulfonyl-ethyl)-isoquinoline-3-yl, 1-(tetrahydro-pyran-4-yl)-isoquinoline-3-yl, 1-alkyl-6-haloalkoxy-isoquinoline-3-yl, 1-alkyl-7-haloalkoxy-isoquinoline-3-yl, 1-alkyl-isoquinoline-3-yl, 1-cycloalkylmethyl-7-alkoxy-isoquinoline-3-yl, 2,3-dihydro-[1,4]dioxino[2,3-g]isoquinoline-8-yl, 4-alkoxy-quinoline-2-yl, 5,8-dialkoxy-isoquinoline-3-yl, 6,7-Bis-(alkoxy-ethoxy)-isoquinoline-3-yl, 6,7-alkoxy-isoquinoline-1-yl, 7-alkoxy-1-alkyl-isoquinoline-3-yl, 7-alkoxy-isoquinoline-1-yl, 7-alkylsulfonyl-1-alkyl-isoquinoline-3-yl, 7-halo-8-alkoxy-isoquinoline-3-yl, 7-hydroxy-1-alkyl-isoquinoline-3-yl, 7-methanesulfonylamino-isoquinoline-3-yl, alkoxy-isoquinoline-3-yl, alkyl-isoquinoline-3-yl, benzyloxy-isoquinoline-3-yl, cycloalkoxy-isoquinoline-3-yl, isoquinoline-3-yl, 1-oxo-1,2-dihydro-isoquinoline-3-yl, isoquinoline-5-yl, and nitro-isoquinoline-3-yl.

In another embodiment of the compound of Formula (I), L$_1$ is —N(H)—C(O)—, and Q$_1$, G$_1$, L$_6$, Q$_6$, L$_7$, and G$_6$ are taken together to form a group selected from the group consisting of: 2-(alkoxycarbonyl)-1,2,3,4-tetrahydro-isoquinoline-6-yl, 2-(alkoxycarbonyl)-1,2,3,4-tetrahydro-isoquinoline-3-yl, 2-(alkoxycarbonyl)-6,7-dialkoxy-1,2,3,4-tetrahydroisoquinoline-1-yl, 2-alkyl-1,2,3,4-tetrahydro-isoquinoline-3-yl, 2-alkylsulfonyl-1,2,3,4-tetrahydro-isoquinoline-6-yl, 2-alkylsulfonyl-1,2,3,4-tetrahydro-isoquinoline-3-yl, 2-benzenesulfonyl-1,2,3,4-tetrahydro-isoquinoline-6-yl, and 2-benzyl-1,2,3,4-tetrahydro-isoquinoline-6-yl.

In another embodiment of the compound of Formula (I), L$_1$ is —N(H)—C(O)—, and Q$_1$, G$_1$, L$_6$, Q$_6$, L$_7$, and G$_6$ are taken together to form a group selected from the group consisting of: ((alkyloxyphenyl)-ethynyl)-pyridine-2-yl, ((alkylphenyl)-ethynyl)-pyridine-2-yl, ((halophenyl)-ethynyl)-pyridine-2-yl, ((thiophen-3-yl)-ethynyl)-pyridine-2-yl, (1-phenyl-ethoxy)-pyridine-3-yl, (3-cycloalkyl-prop-1-ynyl)-pyridine-2-yl, (3-hydroxy-3-methyl-but-1-ynyl)-pyridine-2-yl, (alkoxy)-pyridine-3-yl, (alkoxy-phenyl)-pyridine-3-yl, (alkoxy-phenylethynyl)-pyridine-2-yl, (alkyl-phenylethynyl)-pyridine-2-yl, (alkylsulfonyl-phenyl)-pyridine-2-yl, (alkylsulfonyl-phenylethynyl)-pyridine-2-yl, (alkynyl)-pyridine-2-yl, (alkynyl)-pyridine-3-yl, (aminomethyl-phenyl)-pyridine-2-yl, (benzyloxy)-pyridine-2-yl, (benzyloxy)-pyridine-3-yl, (carbamoyl-phenyl)-pyridine-2-yl, (cyanomethyl-phenyl)-pyridine-2-yl, (cyano-phenyl)-pyridine-2-yl, (cyano-phenyl)-pyridine-3-yl, (cyano-phenyl)-pyridine-4-yl, (cycloalkoxy)-pyridine-3-yl, (cycloalkyl-alkoxy)-pyridine-2-yl, (cycloalkyl-alkoxy)-pyridine-3-yl, (cycloalkyl-ethynyl)-pyridine-2-yl, (cycloalkylethynyl)-pyridine-3-yl, (dialkylamino-phenylethynyl)-pyridine-2-yl, (dihalo-phenyl)-pyridine-3-yl, (haloalkoxy-phenyl)-pyridine-2-yl, (haloalkoxy-phenyl)-pyridine-3-yl, (haloalkyl-phenyl)-pyridine-2-yl, (halo-phenyl)-pyridine-2-yl, (halo-phenyl)-pyridine-3-yl, (halo-phenylethynyl)-pyridine-2-yl, (phenylalkoxy)-pyridine-2-yl, (phenyl-alkyl)-pyridine-3-yl, (phenylethynyl)-pyridine-2-yl, (phenylethynyl)-pyridine-3-yl, (phenylethynyl)-pyridine-4-yl, (pyridin-3-ylethenyl)-pyridine-2-yl, (thiophen-2-yl)-pyridine-2-yl, [2,3']bipyridinyl-6-yl, [2,4']bipyridinyl-6-yl, 2-(cyano-phenyl)-pyridine-4-yl, 2-(halo-phenoxy)-pyridine-3-yl, 2-(phenoxy)-pyridine-3-yl, phenethyl-pyridine-2-yl, 3-halo-6-(alk-1-ynyl)-pyridine-2-yl, 5-(phenoxy)-pyridine-3-yl, 6-(3-cyano-phenyl)-pyridine-2-yl, cyano-pyridine-2-yl, cyano-pyridine-3-yl, cyano-pyridine-4-yl, ethynyl-pyridine-2-yl, ethynyl-pyridine-3-yl, ethynyl-pyridine-4-yl, halo-pyridine-2-yl, halo-pyridine-3-yl, phenyl-pyridine-2-yl, phenyl-pyridine-3-yl, and phenyl-pyridine-4-yl.

In another embodiment of the compound of Formula (I), $L_1$ is —N(H)—C(O)—, and $Q_1$, $G_1$, $L_6$, $Q_6$, $L_7$, and $G_6$ are taken together to form a group selected from the group consisting of: cinnoline-3-yl, quinoxaline-2-yl, [1,8]Naphthyridine-2-yl, cyano-phenyl, (cyano-phenyl)-phenyl, (pyridin-3-yl)-phenyl, (pyridin-4-yl)-phenyl, (haloalkyl-pyridin-2-yl)-phenyl, (haloalkyl-phenoxy)-phenyl, 2-(alkoxycarbonyl)-2,3,4,9-tetrahydro-1H-beta-carboline-3-yl, 1-phenyl-2-(alkoxycarbonyl)-2,3,4,9-tetrahydro-1H-beta-carboline-3-yl, 2,3,4,9-tetrahydro-1H-beta-carboline-3-yl, 6-(phenyl)-pyrimidine-4-yl, 6-(halophenyl)-pyrimidine-4-yl, 2,6-dialkoxy-pyrimidine-4-yl, thieno[2,3-c]pyridine-5-yl, thieno[3,2-c]pyridine-6-yl, 2-alkyl-imidazo[1,2-a]pyridine-3-yl, imidazo[1,2-a]pyridine-2-yl, 5-alkyl-imidazo[1,2-a]pyridine-2-yl, imidazo[2,1-b]thiazole-6-yl, and 8-alkyl-imidazo[1,2-a]pyridine-2-yl.

In another embodiment of the compound of Formula (I), A is —N($R_5$)—, and $R_1$ or $R_4$ is -$L_8$-$Q_8$-$L_9$-$G_8$-$L_{18}$-$Q_{18}$-$L_{19}$-$G_{18}$,
wherein
$L_8$ is a direct bond, —$CH_2$—, —C(O)—O—, —C(O)—N($R_{26}$)—, or —N($R_{26}$)—C(O)—,
$Q_8$ is a direct bond or alkylene,
$L_9$ is a direct bond,
$G_8$ is imidazole, 4,5,6,7-tetrahydro-thiazolo[5,4-c]pyridine, imidazolepyridine, piperidine, 1,2,3,4-tetrahydroisoquinoline, phenyl, cycloalkyl, purine, isoquinoline, benzimidazole, oxazole, pyrrazole, pyrimidine, 4,5,6,7-tetrahydro-1H-benzimidazole, or furan, wherein $G_8$ is substituted or unsubstituted,
$L_{18}$ is a direct bond, —$SO_2$—, —O—, or —C(O)—,
$Q_{18}$ is a direct bond or alkylene,
$L_{19}$ is a direct bond, and
$G_{18}$ is hydrogen, phenyl, quinoline, isoquinoline, cycloalkyl, pyridine, furan, alkyl, pyrrole, thiazole, imidazole, thiophene, or pyrrolidine, wherein $G_{18}$ is substituted or unsubstituted.

In another embodiment of the compound of Formula (I), A is —N($R_5$)—, and $R_1$ or $R_4$ is -$L_8$-$Q_8$-$L_9$-$G_8$-$L_{18}$-$Q_{18}$-$L_{19}$-$G_{18}$, wherein $L_9$, $G_8$, $L_{18}$, $Q_{18}$, $L_{19}$, and $G_{18}$ are taken together to form a group selected from the group consisting of: piperidin-4-yl, and 1-(alkoxycarbonyl)-piperidin-4-yl.

In another embodiment of the compound of Formula (I), A is —N($R_5$)—, and $R_1$ or $R_4$ is -$L_8$-$Q_8$-$L_9$-$G_8$-$L_{18}$-$Q_{18}$-$L_{19}$-$G_{18}$, wherein $L_9$, $G_8$, $L_{18}$, $Q_{18}$, $L_{19}$, and $G_{18}$ are taken together to form a group selected from the group consisting of: 1H-pyrazol-3-yl, imidazol-2-yl, imidazol-1-yl, 4,5-dialkyl-imidazol-2-yl, 4-phenyl-1H-imidazol-2-yl, 4-(halo-phenyl)-1H-imidazol-2-yl, 5-adamantan-1-yl-1H-imidazol-2-yl, 5-alkyl-1H-imidazol-2-yl, 5-benzyl-1H-imidazol-2-yl, 4-alkyl-oxazol-2-yl, and furan-2-ylmethyl.

In another embodiment of the compound of Formula (I), A is —N($R_5$)—, and $R_1$ or $R_4$ is -$L_8$-$Q_8$-$L_9$-$G_8$-$L_{18}$-$Q_{18}$-$L_{19}$-$G_{18}$, wherein $L_9$, $G_8$, $L_{18}$, $Q_{18}$, $L_{19}$, and $G_{18}$ are taken together to form a group selected from the group consisting of: cycloalkyl, alkyl, 2-alkylsulfanyl-ethyl, (alkoxy-phenyl)-ethyl, (alkoxy-phenyl)-methyl, 2-(alkoxyphenyl)-ethyl, 2-(phenoxy-phenyl)-ethyl, 1-(alkylsulfonyl-phenyl)-ethyl, benzyl, cyano-benzyl, alkoxy-benzyl, alkyl-benzyl, alkylsulfonyl-benzyl, dihalo-benzyl, haloalkyl-benzyl, haloalkyl-halo-benzyl, haloalkoxy-benzyl, halo-benzyl, sulfamoyl-benzyl, alkoxyphenyl, halo-phenyl, and alkylsulfonyl-phenyl.

In another embodiment of the compound of Formula (I), A is —N($R_5$)—, and $R_1$ or $R_4$ is -$L_8$-$Q_8$-$L_9$-$G_9$-$L_{18}$-$Q_{18}$-$L_{19}$-$G_{18}$, wherein $L_9$, $G_9$, $L_{18}$, $Q_{18}$, $L_{19}$, and $G_{18}$ are taken together to form a group selected from the group consisting of: benzimidazole-2-yl, benzimidazole-5-yl, benzimidazole-6-yl, isoquinoline-3-yl, isoquinoline-6-yl, 4,5,6,7-tetrahydro-benzimidazole-2-yl, 4,5,6,7-tetrahydro-benzothiazole-2-yl, 5,5-dialkyl-7-oxo-4,5,6,7-tetrahydro-benzothiazol-2-yl, 6-(alkyl)-4,5,6,7-tetrahydro-benzothiazol-2-yl, 1,2,3,4-tetrahydro-isoquinolin-6-yl, 2-(alkoxycarbonyl)-1,2,3,4-tetrahydro-isoquinolin-6-yl, 7H-purin-8-yl, and 2-amino-pyrimidin-4-yl.

In another embodiment of the compound of Formula (I), A is —N($R_5$)—, and $R_1$ or $R_4$ is -$L_9$-$Q_8$-$L_9$-$G_8$-$L_{19}$-$Q_{18}$-$L_{19}$-$G_{18}$, wherein $Q_8$, $L_9$, $G_9$, $L_{18}$, $Q_{18}$, $L_{19}$, and $G_{18}$ are taken together to form a group selected from the group consisting of: (piperidin-3R-yl)methyl, (piperidin-3S-yl)methyl, (piperidin-4-yl)-methyl, (1-(alkoxycarbonyl)-piperidin-3-yl)-methyl, (1-(cycloalkylmethyl)-piperidin-3-yl)methyl, (1-(cycloalkylmethyl)-piperidin-4-yl)methyl, (piperidin-4-yl)-methyl, (1-(alkoxycarbonyl)-piperidin-4-yl)-methyl, [1-(carboxylic acid methyl ester)-piperidin-3R-yl]methyl, [1-(carboxylic acid methyl ester)-piperidin-3S-yl]methyl, [1-(cycloalkylmethyl)-piperidin-3S-yl]methyl, [1-(cycloalkylmethyl)-piperidin-3R-yl]methyl, 1-(1-alkyl-1H-imidazol-2-ylmethyl)-piperidin-3-ylmethyl, 1-(1-alkyl-1H-imidazol-4-ylmethyl)-piperidin-3-ylmethyl, 1-(1H-imidazol-2-ylmethyl)-piperidin-3-ylmethyl, 1-(cycloalkylmethyl)-piperidin-3R-yl]methyl, 1-[1-(alkoxycarbonyl)-pyrrolidine-2R-ylmethyl]-piperidin-3-ylmethyl, 1-[1-(alkoxycarbonyl)-pyrrolidine-2S-ylmethyl]-piperidin-3-ylmethyl, 2-(piperidin-3-yl)-ethyl, 2-(piperidin-4-yl)-ethyl, 2-[1-(alkoxycarbonyl)-piperidin-3-yl]-ethyl, and 2-[1-(alkoxycarbonyl)-piperidin-4-yl]-ethyl.

In another embodiment of the compound of Formula (I), A is —N(R$_5$)—, and R$_1$ or R$_4$ is -L$_8$-Q$_8$-L$_9$-G$_8$-L$_{18}$-Q$_{18}$-L$_{19}$-G$_{18}$, wherein Q$_8$, L$_9$, G$_8$, L$_{18}$, Q$_{18}$, L$_{19}$, and G$_{18}$ are taken together to form a group selected from the group consisting of: 4,5,6,7-tetrahydro-thiazolo[5,4-c]pyridin-2-yl, 3H-imidazo[4,5-c]pyridin-2-yl, 3H-imidazo[4,5-c]pyridin-2-yl, [5-(2,4-dialkoxy-benzyl)-4,5,6,7-tetrahydro-thiazolo[5,4-c]pyridin-2-yl, (5-alkyl-3H-imidazol-4-ylmethyl)-4,5,6,7-tetrahydro-thiazolo[5,4-c]pyridin-2-yl, 5-[1-(alkoxycarbonyl)-pyrrolidin-2S-ylmethyl]-4,5,6,7-tetrahydro-thiazolo[5,4-c]pyridin-2-yl, 5-[1-(alkoxycarbonyl)-pyrrolidin-2R-ylmethyl]-4,5,6,7-tetrahydro-thiazolo[5,4-c]pyridin-2-yl, 5-(1-alkyl-1H-imidazol-2-ylmethyl)-4,5,6,7-tetrahydro-thiazolo[5,4-c]pyridin-2-yl, 5-(1-alkyl-1H-pyrrol-2-ylmethyl)-4,5,6,7-tetrahydro-thiazolo[5,4-c]pyridin-2-yl, 5-(3-alkylsulfanyl-propyl)-4,5,6,7-tetrahydro-thiazolo[5,4-c]pyridin-2-yl, 5-(3-alkylsulfinyl-propyl)-4,5,6,7-tetrahydro-thiazolo[5,4-c]pyridin-2-yl, 5-(3-alkylsulfonyl-propyl)-4,5,6,7-tetrahydro-thiazolo[5,4-c]pyridin-2-yl, 5-(3H-imidazol-4-ylmethyl)-4,5,6,7-tetrahydro-thiazolo[5,4-c]pyridin-2-yl, 5-(alkoxy-benzyl)-4,5,6,7-tetrahydro-thiazolo[5,4-c]pyridin-2-yl, 5-(alkylsulfonyl)-4,5,6,7-tetrahydro-thiazolo[5,4-c]pyridin-2-yl, 5-(alkoxycarbonyl)-4,5,6,7-tetrahydro-thiazolo[5,4-c]pyridin-2-yl, 5-(cycloalkylmethyl)-4,5,6,7-tetrahydro-thiazolo[5,4-c]pyridin-2-yl, 5-(halo-benzyl)-4,5,6,7-tetrahydro-thiazolo[5,4-c]pyridin-2-yl, 5-(imidazol-2-ylmethyl)-4,5,6,7-tetrahydro-thiazolo[5,4-c]pyridin-2-yl, 5-(quinolin-3-ylmethyl)-4,5,6,7-tetrahydro-thiazolo[5,4-c]pyridin-2-yl, 5-alkyl-4,5,6,7-tetrahydro-thiazolo[5,4-c]pyridin-2-yl, 5-alkylcarbamoyl-4,5,6,7-tetrahydro-thiazolo[5,4-c]pyridin-2-yl, 5-alkylsulfonyl-4,5,6,7-tetrahydro-thiazolo[5,4-c]pyridin-2-yl, 5-benzoyl-4,5,6,7-tetrahydro-thiazolo[5,4-c]pyridin-2-yl, 5-benzyl-4,5,6,7-tetrahydro-thiazolo[5,4-c]pyridin-2-yl, 5-cycloalkylmethyl-4,5,6,7-tetrahydro-thiazolo[5,4-c]pyridin-2-yl, 5-furan-3-ylmethyl-4,5,6,7-tetrahydro-thiazolo[5,4-c]pyridin-2-yl, 5-phenethyl-4,5,6,7-tetrahydro-thiazolo[5,4-c]pyridin-2-yl, 5-pyridin-3-ylmethyl-4,5,6,7-tetrahydro-thiazolo[5,4-c]pyridin-2-yl, 5-pyrrolidin-2S-ylmethyl-4,5,6,7-tetrahydro-thiazolo[5,4-c]pyridin-2-yl, 5-thiazol-2-ylmethyl-4,5,6,7-tetrahydro-thiazolo[5,4-c]pyridin-2-yl, 5-thiophen-2-ylmethyl-4,5,6,7-tetrahydro-thiazolo[5,4-c]pyridin-2-yl, and 5-thiophen-3-ylmethyl-4,5,6,7-tetrahydro-thiazolo[5,4-c]pyridin-2-yl.

In another embodiment, the present invention provides a compound of Formula (Ia)

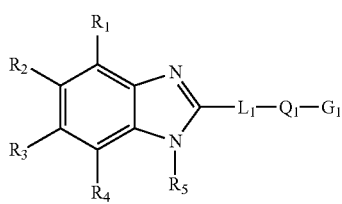

(Ia)

wherein

L$_1$ is selected from the group consisting of:
a direct bond, —CH$_2$—, —O—, —N(R$_6$)—, —C(O)—, —CON(R$_6$)—, —N(R$_6$)C(O)—, —N(R$_6$)CON(R$_7$)—, —N(R$_6$)C(O)O—, —OC(O)N(R$_6$)—, —N(R$_6$)SO$_2$—, —SO$_2$N(R$_6$)—, —C(O)—O—, —O—C(O)—, —S—, —S(O)—, —S(O)$_2$—, and —N(R$_6$)SO$_2$N(R$_7$)—,
wherein R$_6$ and R$_7$ are independently selected from the group consisting of: hydrogen, -alkyl, -aryl, and -alkylene-aryl;

Q$_1$ is selected from the group consisting of direct bond and alkylene;

G$_1$ is selected from the group consisting of:
aryl, heteroaryl, fused arylcycloalkyl, fused cycloalkylaryl, fused cycloalkylheteroaryl, fused heterocyclylaryl, and fused heterocyclylheteroaryl group, and G$_1$ is optionally substituted 1 to 7 times, wherein the substituents are independently selected from the group consisting of:
a) -halo;
b) -cyano;
c) -nitro;
d) -perhaloalkyl;
e) —R$_8$;
f) -L$_2$-R$_8$;
g) -L$_2$-Q$_2$-R$_8$; and
h) -Q$_2$-L$_2$-R$_8$;
wherein
R$_8$ is selected from the group consisting of hydrogen, -alkyl, -aryl, and alkylene-aryl;
Q$_2$ is selected from the group consisting of alkylene, alkenylene, and alkynylene;
L$_2$ is selected from the group consisting of —CH$_2$—, —O—, —N(R$_9$)—, —C(O)—, —CON(R$_9$)—, —N(R$_9$)C(O)—, —N(R$_9$)CON(R$_{19}$)—, —N(R$_9$)C(O)O—, —OC(O)N(R$_9$)—, —N(R$_9$)SO$_2$—, —SO$_2$N(R$_9$)—, —C(O)—O—, —O—C(O)—, —S—, —S(O)—, —S(O)$_2$—, and —N(R$_9$)SO$_2$N(R$_{10}$)—,
wherein R$_9$ and R$_{10}$ are independently selected from the group consisting of: hydrogen, -alkyl, -aryl, and -alkylene-aryl;

R$_1$, R$_2$, R$_3$, and R$_4$ are independently selected from the group consisting of
a) —H;
b) -alkyl;
c) -aryl;
d) -alkylene-aryl;
e) —K-alkyl;
f) —K-aryl;
g) —K-alkylene-aryl; and
h) -L$_3$-G$_2$-G$_3$;
wherein
K is selected from the group consisting of: —C(O)—O—, —O—C(O)—, —C(O)—NH—, —NH—C(O)—, —SO$_2$—, —SO$_2$—NH—, —NH—SO$_2$—, and —C(O)—;

L$_3$ is selected from the group consisting of: a direct bond, —CH$_2$—, —O—, —N(R$_{26}$)—, —C(O)—, —CON(R$_{26}$)—, —N(R$_{26}$)C(O)—, —N(R$_{26}$)CON(R$_{27}$)—, —N(R$_{26}$)C(O)O—, —OC(O)N(R$_{26}$)—, —N(R$_{26}$)SO$_2$—, —SO$_2$N(R$_{26}$)—, —C(O)—O—, —O—C(O)—, —S—, —S(O)—, —S(O)$_2$—, and —N(R$_{26}$)SO$_2$N(R$_{27}$)—
wherein R$_{26}$ and R$_{27}$ are independently selected from the group consisting of: -hydrogen, -alkyl, -aryl, and -alkylene-aryl;

G$_2$ is selected from the group consisting of:
a direct bond, and

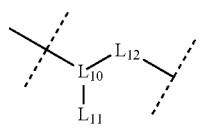

wherein
- $L_{10}$ is selected from the group consisting of alkyline, cycloalkyline, heteroaryline, aryline, and heterocyclyline;
- $L_{12}$ is selected from the group consisting of —O—, —C(O)—N($R_{11}$)—, —C(O)—O—, —C(O)—, and —N($R_{11}$)—CO—N($R_{12}$)—, wherein $R_{11}$ and $R_{12}$ independently comprise hydrogen, -aryl, -alkyl, and -alkylene-aryl;
- $L_{11}$ is selected from the group consisting of hydrogen, -alkyl, -alkenyl, -alkynyl, -aryl, -alkylene-aryl, -alkylene-heteroaryl, alkylene-O-alkylene-aryl, -alkylene-S-alkylene-aryl, -alkylene-O-alkyl, -alkylene-S-alkyl, -alkylene-NH$_2$, -alkylene-OH, -alkylene-SH, -alkylene-C(O)—, $OR_{13}$, -alkylene-C(O)—$NR_{13}R_{14}$, -alkylene-$NR_{13}R_{14}$, -alkylene-N($R_{13}$)—C(O)—$R_{14}$, -alkylene-N($R_{13}$)—S(O)$_2$—$R_{14}$, and the side chain of a natural or non-natural amino acid, wherein
  - $R_{13}$ and $R_{14}$ independently comprise hydrogen, -aryl, -alkyl, and -alkylene-aryl; or
  - $R_{13}$ and $R_{14}$ may be taken together to form a ring having the formula —(CH$_2$)$_q$—Y—(CH$_2$)$_r$— bonded to the nitrogen atom to which $R_{13}$ and $R_{14}$ are attached, wherein q and r are, independently, 1, 2, 3, or 4; Y is —CH$_2$—, —C(O)—, —O—, —N(H)—, —S—, —S(O)—, —SO$_2$—, —CON(H)—, —NHC(O)—, —NHCON(H)—, —NHSO$_2$—, —SO$_2$N(H)—, —(O)CO—, —NHSO$_2$NH—, —OC(O)—, —N($R_{15}$)—, —N(C(O)$R_{15}$)—, —N(C(O)NH$R_{15}$)—, —N(SO$_2$NH$R_{15}$)—, —N(SO$_2$$R_{15}$)—, and —N(C(O)O$R_{15}$)—, wherein $R_{15}$ is selected from the group consisting of hydrogen, -alkyl, -aryl, and -alkylene-aryl; or
  - $R_{13}$ and $R_{14}$ may be taken together, with the nitrogen atom to which they are attached, to form a heterocyclyl or heteroaryl ring; and
- $G_3$ is selected from the group consisting of hydrogen, alkyl, aryl, heteroaryl, fused arylcycloalkyl, fused cycloalkylaryl, fused cycloalkylheteroaryl, fused heterocyclylaryl, and fused heterocyclylheteroaryl group, wherein $G_3$ is optionally substituted 1 to 7 times, wherein the substituents are independently selected from group consisting of:
  a) -halo;
  b) -cyano;
  c) -nitro;
  d) -perhaloalkyl;
  e) —$R_{16}$;
  f) -$L_4$-$R_{16}$;
  g) -$L_4$-$Q_4$-$R_{16}$; and
  h) -$Q_4$-$L_4$-$R_{16}$;
  wherein
  - $R_{16}$ is selected from the group consisting of hydrogen, -alkyl, -aryl, and -alkylene-aryl;
  - $Q_4$ is selected from the group consisting of alkylene, alkenylene, and alkynylene;
  - $L_4$ is selected from the group consisting of —CH$_2$—, —O—, —N($R_{18}$)—, —C(O)—, —CON($R_{18}$)—, —N($R_{18}$)C(O)—, —N($R_{18}$)CON($R_{19}$)—, —N($R_{18}$)C(O)O—, —OC(O)N($R_{19}$)—, —N($R_{18}$)SO$_2$—, —SO$_2$N($R_{19}$)—, —C(O)—O—, —O—C(O)—, —S—, —S(O)—, —S(O)$_2$—, and —N($R_{18}$)SO$_2$N($R_{19}$)—;
  wherein
  - $R_{18}$ and $R_{19}$ are independently selected from the group consisting of: -hydrogen, -alkyl, -aryl, and -alkylene-aryl; and wherein at least one of $R_1$-$R_4$ is the group -$L_3$-$G_2$-$G_3$; and
$R_5$ is selected from the group consisting of:
  a) -hydrogen; and
  b) -alkyl; and
wherein the aryl and/or alkyl group(s) in $R_1$ to $R_{27}$, $L_1$ to $L_{12}$, $G_1$ to $G_3$ may be optionally substituted 1-4 times with a substituent selected from the group consisting of:
  a) —H;
  b) -halo;
  c) -hydroxyl;
  d) -cyano;
  e) -carbamoyl;
  f) -carboxyl;
  g) —Z-alkyl;
  h) —Z-aryl;
  i) —Z-alkylene-aryl;
  wherein Z is selected from the group consisting of —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, and —O—CO—, or a pharmaceutically acceptable salt, ester, or prodrug thereof.

In an embodiment of the compound of Formula (Ia),
- $L_1$ is —NH—C(O)—, —NH—, or a direct bond;
- $Q_1$ is a direct bond;
- $G_1$ is phenyl, biphenyl, naphthyl, indole, isoquinolyl, pyridine, or pyrimidine; and wherein
at least one of $R_1$-$R_4$ is the group -$L_3$-$G_2$-$G_3$, wherein
- $L_3$ is selected from the group consisting of
  a) —CO$_2$—;
  b) —C(O)NH—; and
  c) —NH—
- $G_2$ is a direct bond, or alkylene; and
- $G_3$ is selected from the group consisting alkyl, phenyl, naphthyl, biphenyl, alkylene-phenyl, pyrole, thiophene, indole, imidazole, tetrazole, thiazole, 1,3,4-thiadiazole, pyrimidine, pyridine, benzimidazole, and benzthiazole, wherein $G_3$ is optionally substituted 1 to 7 times with a group selected from the group consisting of:
  a) -halo;
  b) -cyano;
  c) -nitro;
  d) -perhaloalkyl;
  e) —$R_{16}$;
  f) -$L_4$-$R_{16}$;
  g) -$L_4$-$Q_4$-$R_{16}$; and
  h) -$Q_2$-$L_4$-$R_{16}$;
  wherein
  - $R_{16}$ is selected from the group consisting of hydrogen, -alkyl, -aryl, and -alkylene-aryl;
  - $Q_4$ is selected from the group consisting of alkylene, -alkenylene, and -alkynylene;

L₄ is selected from the group consisting of
—CH₂—, —O—, —N(R₁₈)—, —C(O)—,
—CON(R₁₈)—, —N(R₁₈)C(O)—, —N(R₁₈)
CON(R₁₉)—, —N(R₁₈)C(O)O—, —OC(O)N
(R₁₈)—, —N(R₁₈)SO₂—, —SO₂N(R₁₈)—,
—C(O)—O—, —O—C(O)—, —S—,
—S(O)—, —S(O)₂—,
and —N(R₁₈)SO₂N(R₁₉)—;
wherein
R₁₈ and R₁₉ are independently selected from the group consisting of: hydrogen, -alkyl, -aryl, and -alkylene-aryl.

In another embodiment of the compound of Formula (Ia),
L₁ is a direct bond, —NH—C(O)—, or —NH—;
Q₁ is a direct bond;
G₁ is phenyl, biphenyl, isoquinolyl, pyridine, or pyrimidine; and
at least one of R₁-R₄ is the group -L₃-G₂-G₃, wherein
L₃ is —C(O)—NH—;
G₂ is

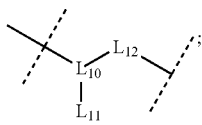

wherein
L₁₀ is defined as above,
L₁₁ is defined as above, and
L₁₂ is —C(O)—NH—; and
G₃ is selected from the group consisting alkyl, phenyl, naphthyl, biphenyl, alkylene-phenyl, pyrole, imidazole, tetrazole, thiazole, 1,3,4-thiadiazole, pyrimidine, pyridine, benzimidazole, and benzthiazole, wherein G₃ is optionally substituted 1 to 7 times with a group selected from the group consisting of
a) -halo;
b) -cyano;
c) -nitro;
d) -perhaloalkyl;
e) —R₁₆;
f) -L₄-R₁₆;
g) -L₄-Q₄-R₁₆; and
h) -Q₂-L₄-R₁₆;
wherein
R₁₆ is selected from the group consisting of hydrogen, -alkyl, -aryl, and -alkylene-aryl;
Q₄ is selected from the group consisting of alkylene, alkenylene, and alkynylene;
L₄ is selected from the group consisting of
—CH₂—, —O—, —N(R₁₈)—, —C(O)—,
—CON(R₁₈)—, —N(R₁₈)C(O)—, —N(R₁₈)
CON(R₁₉)—, —N(R₁₈)C(O)O—, —OC(O)N
(R₁₈)—, —N(R₁₈)SO₂—, —SO₂N(R₁₈)—,
—C(O)—O—, —O—C(O)—, —S—,
—S(O)—, —S(O)₂—,
and —N(R₁₈)SO₂N(R₁₉)—;
wherein
R₁₈ and R₁₉ are independently selected from the group consisting of: hydrogen, -alkyl, -aryl, and -alkylene-aryl.
In another embodiment of the compound of Formula (Ia),
G₃ is imidazole or benzimidazole.

In another embodiment of the compound of Formula (Ia),
G₁ is isoquinoline.
In another embodiment of the compound of Formula (Ia), the compound of Formula (Ia) has the formula

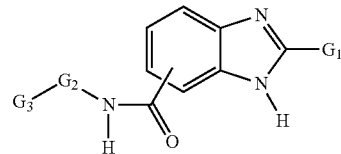

wherein
G₁ is unsubstituted 2-isoquinoline-3yl or pyridin-2yl; and
G₂ and G₃ together form a group selected from phenyl, isobutyl, n-butyl, 1H-imidazol-2-yl, [1,3,4]-thiadiazol-2-yl, thiazol-2-yl, 1H-imidazol-2-yl, benzothiazol-2-yl, pyridin-2-yl, pyridin-3-yl, and 4-phenyl-1H-imidazol-2-yl.

In another embodiment of the compound of Formula (Ia), the compound of Formula (Ia) has the formula

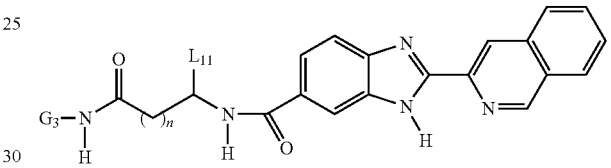

wherein
L₁₁ is 2,2 dimethyl propyl, 2-chloro-benzyl, 2-fluorobenzyl, 2-phenyl-ethyl, 3,4,5-trifluoro benzyl, 3,5-difluoro-benzyl, 3-chloro benzyl, 3-fluoro benzyl, 3-fluoro-phenyl, 3-methoxy phenyl, 3-trifluoromethyl benzyl, 4-chloro benzyl, 4-fluoro benzyl, 4-methoxy phenyl, 4-methyl benzyl, 4-phenyl-benzyl, Benzyl, Butyl-2yl, Isobutyl, Isopropyl, cyclopropyl, or phenyl,
n is 0 or 1 and
G₃ is 1H-benzimidazol-2-yl, 1H-imidazol-2-yl, pyridin-2yl, or thiazol-2-yl.
In another embodiment of the compound of Formula (Ia), the compound of Formula (Ia) has the formula

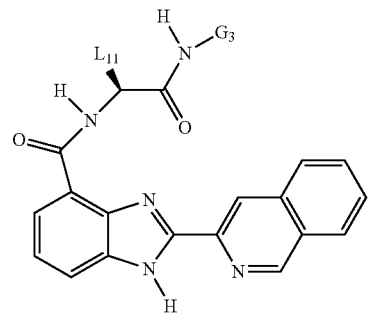

wherein
L₁₁ is benzyl or 3,5-difluorobenzyl, and
G₃ is methyl, isobutyl, 1H-imidazol-2yl, thiazol-2yl, benzthiazole-2yl, 1H-Benzimidazol-2-yl, 2-methyl-piperidine-1-carboxylic acid tert-butyl ester, or 3-methyl-piperidine-1-carboxylic acid tert-butyl ester.

In another embodiment of the compound of Formula (Ia), the compound of Formula (Ia) has the formula

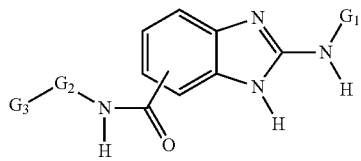

wherein

G$_1$ is unsubstituted 2-isoquinolin-3-yl, 5-bromopyridin-2-yl, phenyl, or pyridin-2-yl;

G$_2$ and G$_3$ are taken together to form a group selected from the group consisting of (benzothiazol-2yl)methyl, 1H-imidazol-2-yl, 2,4-dichlorobenzyl, 2,5-dichlorophenyl, 3-hydroxypropyl, 3-tert-butylphenyl, 4'-biphenyl, 4-chlorophenyl, 4-fluorophenyl, 4-methoxyphenyl, 4-methylbenzyl, 4-phenoxyphenyl, 4-phenylthiazol-2-yl, 4-phenylthiazol-2-yl, 4-tert-butyl-benzyl, benz1H-imidazol-2-yl, benzothiazol-6-yl, benzothiazol-2-yl, benzyl, methyl, phenyl, pyridin-2-yl, and thiazol-2-yl.

In another embodiment of the compound of Formula (Ia), the compound of Formula (Ia) has the formula

G$_1$ is 1,5-dimethyl-indole-2yl, 1-benzyl-indole-2-yl, 1H-imidazol-2-yl, 1H-Indazoline-3yl, 1H-indole-2-yl, 1-methyl-Indazoline-3yl, 1-methyl-indole-2-yl, 1-n-propyl-indole-2yl, 2,4-difluorophenyl, 2-Chloro-phenyl, 2-fluorophenyl, 2-isoquinolin-3-yl, 3,4-dimethoxyphenyl, 3-Chloro-phenyl, 3-fluoro-phenyl, 3-methoxy-4-fluorophenyl, 4'-biphenyl, 4-fluorobenzyl, 4-fluorophenyl, 4-isopropyl-phenyl, 4-methoxy-phenyl, 4-nitro-phenyl, 4-phenoxyphenyl, 4-tert-butyl-phenyl, 4-trifluoromethylphenyl, 5-Chloro-benzofuran-2-yl, 5-methyl-indole-2-yl, 5-phenoxy-pyridin-2-yl, 6,7-dimethoxy-2-isoquinolin-3-yl, benzofuran-2-yl, benzothiophene-2-yl, furan-3yl, naphthalin-2-yl, phenyl, quinolin-2-yl, or quinolin-3yl; and G$_2$ and G$_3$ are taken together to form a group selected from the group consisting of (1-methylbenzimidazole-2-yl)methyl, (1R)-phenyl ethyl, (1S)-phenyl ethyl, (5-methylfuran-2-yl)-methyl, (benzothiophene-2-yl)methyl, (benzthiazol-2-yl)methyl, (thiophene-2-yl)ethyl, (thiophene-2-yl)methyl, {1,3,4}-thiadiazol-2-yl, 1H-benzimidazol-2-yl, 1H-benzimidazol-2-yl, 1H-benzimidazol-2-yl, 1H-benzimidazole-2-yl methyl, 1H-imidazol-2-yl, 1H-indazole-5-yl, 2-(1H-benzimidazole-2-yl)-ethyl, 2,3,4,9-tetrahydro-1H-beta-carboline-2-yl, 2-phenyoxy-phenyl, 3-phenoxy-phenyl, 4-phenoxy-phenyl, 4-phenyl-1H-imidazol-2-yl, benzthiazol-2-yl, benzyl, ethyl, furan-2-yl methyl, phenethyl, phenyl, pyridin-2-yl, pyridin-3-yl, quinolin-3-yl, tert-butyl, thiazol-2-yl, and thiazole-2-yl-methyl.

In another embodiment of the compound of Formula (Ia), the compound of Formula (Ia) has the formula

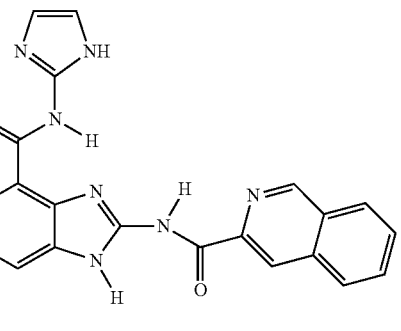

wherein,

G$_2$ and G$_3$ are taken together to form a group selected from the group consisting of isopropyl, isobutyl, and phenyl.

In another embodiment of the compound of Formula (Ia), the compound of Formula (Ia) has the formula

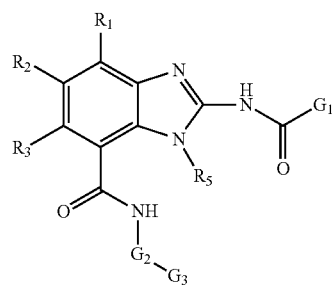

wherein R$_1$, R$_2$, R$_3$, R$_5$, G$_1$, G$_2$, and G$_3$ are defined as above for the compound of Formula (Ia).

In another embodiment of the compound of Formula (Ia), the compound of Formula (Ia) has the formula

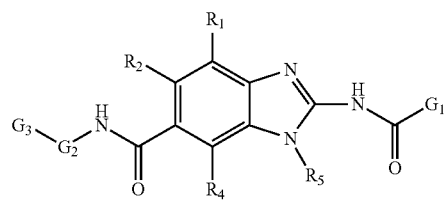

wherein R$_1$, R$_2$, R$_3$, R$_5$, G$_1$, G$_2$, and G$_3$ are defined as above for the compound of Formula (Ia).

In another embodiment of the compound of Formula (Ia), the compound of Formula (Ia) has the formula

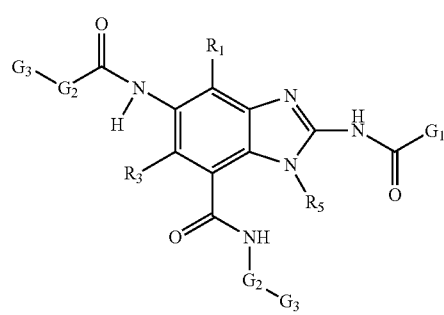

wherein R$_1$, R$_3$, R$_5$, G$_1$, G$_2$, and G$_3$ are defined as above for the compound of Formula (Ia).

In another embodiment, the present invention provides a compound of Formula (Ib)

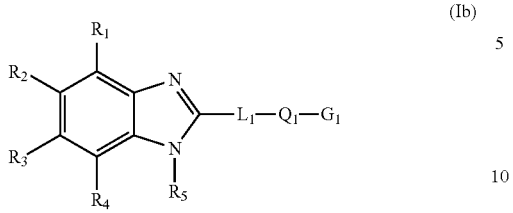

(Ib)

wherein
L₁ is —N(R₆)—, wherein R₆ is selected from the group consisting of: hydrogen, -alkyl, -aryl, and -alkylene-aryl;
Q₁ is a direct bond;
G₁ is hydrogen:
R₁, R₂, R₃, and R₄ are independently selected from the group consisting of
a) —H;
b) -alkyl;
c) -aryl;
d) -alkylene-aryl;
e) —K-alkyl;
f) —K-aryl;
g) —K-alkylene-aryl; and
h) -L₃-G₂-G₃;
wherein at least one of R₁-R₄ is not hydrogen; and
wherein
K is selected from the group consisting of: —C(O)—O—, —O—C(O)—, —C(O)—NH—, —NH—C(O)—, —SO₂—, —SO₂—NH—, —NH—SO₂—, and —C(O)—;
L₃ is selected from the group consisting of: a direct bond, —CH₂—, —O—, —N(R₂₆)—, —C(O)—, —CON(R₂₆)—, —N(R₂₆)C(O)—, —N(R₂₆)CON(R₂₇)—, —N(R₂₆)C(O)O—, —OC(O)N(R₂₆)—, —N(R₂₆)SO₂—, —SO₂N(R₂₆)—, —C(O)—O—, —O—C(O)—, —S—, —S(O)—, —S(O)₂—, and —N(R₂₆)SO₂N(R₂₇)—
wherein R₂₆ and R₂₇ are independently selected from the group consisting of: -hydrogen, -alkyl, -aryl, and -alkylene-aryl;
G₂ is selected from the group consisting of:
a direct bond, and

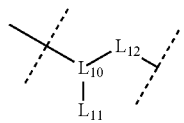

wherein
L₁₀ is selected from the group consisting of alkyline, cycloalkyline, heteroaryline, aryline, and heterocyclyline;
L₁₂ is selected from the group consisting of —O—, —C(O)—N(R₁₁)—, —C(O)—O—, —C(O)—, and —N(R₁₁)—CO—N(R₁₂)—, wherein R₁₁ and R₁₂ independently comprise hydrogen, -aryl, -alkyl, and -alkylene-aryl;
L₁₁ is selected from the group consisting of hydrogen, -alkyl, -alkenyl, -alkynyl, -aryl, -alkylene-aryl, -alkylene -heteroaryl, alkylene-O-alkylene-aryl, -alkylene-5-alkylene-aryl, -alkylene-O-alkyl, -alkylene-5-alkyl, -alkylene-NH₂, -alkylene-OH, -alkylene-SH, -alkylene-C(O)—OR₁₃, -alkylene-C(O)—NR₁₃R₁₄, -alkylene-NR₁₃R₁₄, -alkylene-N(R₁₃)—C(O)—R₁₄, -alkylene-N(R₁₃)—S(O)₂—R₁₄, and the side chain of a natural or non-natural amino acid, wherein
R₁₃ and R₁₄ independently comprise hydrogen, -aryl, -alkyl, and -alkylene-aryl; or
R₁₃ and R₁₄ may be taken together to form a ring having the formula —(CH₂)_q—Y—(CH₂)_r— bonded to the nitrogen atom to which R₁₃ and R₁₄ are attached, wherein q and r are, independently, 1, 2, 3, or 4; Y is —CH₂—, —C(O)—, —O—, —N(H)—, —S—, —S(O)—, —SO₂—, —CON(H)—, —NHC(O)—, —NHCON(H)—, —NHSO₂—, —SO₂N(H)—, —(O)CO—, —NHSO₂NH—, —OC(O)—, —N(R₁₅)—, —N(C(O)R₁₅)—, —N(C(O)NHR₁₅)—, —N(SO₂NHR₁₅)—, —N(SO₂R₁₅)—, and —N(C(O)OR₁₅)—, wherein R₁₅ is selected from the group consisting of hydrogen, -alkyl, -aryl, and -alkylene-aryl; or
R₁₃ and R₁₄ may be taken together, with the nitrogen atom to which they are attached, to form a heterocyclyl or heteroaryl ring; and
G₃ is selected from the group consisting of hydrogen, alkyl, aryl, heteroaryl, fused arylcycloalkyl, fused cycloalkylaryl, fused cycloalkylheteroaryl, fused heterocyclylaryl, and fused heterocyclylheteroaryl group, wherein G₃ is optionally substituted 1 to 7 times, wherein the substituents are independently selected from group consisting of:
a) -halo;
b) -cyano;
c) -nitro;
d) -perhaloalkyl;
e) —R₁₆;
f) -L₄-R₁₆;
g) -L₄-Q₄-R₁₆; and
h) -Q₄-L₄-R₁₆;
wherein
R₁₆ is selected from the group consisting of hydrogen, -alkyl, -aryl, and -alkylene-aryl;
Q₄ is selected from the group consisting of alkylene, alkenylene, and alkynylene;
L₄ is selected from the group consisting of —CH₂—, —O—, —N(R₁₈)—, —C(O)—, —CON(R₁₈)—, —N(R₁₈)C(O)—, —N(R₁₈)CON(R₁₉)—, —N(R₁₈)C(O)O—, —OC(O)N(R₁₈)—, —N(R₁₈)SO₂—, —SO₂N(R₁₈)—, —C(O)—O—, —O—C(O)—, —S—, —S(O)—, —S(O)₂—, and —N(R₅₈)SO₂N(R₁₉)—;
wherein
R₁₈ and R₁₉ are independently selected from the group consisting of: -hydrogen, -alkyl, -aryl, and -alkylene-aryl; and
R₅ is selected from the group consisting of:
a) -hydrogen; and
b) -alkyl; and
wherein the aryl and/or alkyl group(s) in R₁ to R₁₉, L₁ to L₁₂, G₂ and G₃ may be optionally substituted 1-4 times with a substituent selected from the group consisting of:
a) —H;
b) -halo;
c) -hydroxyl;
d) -cyano;
e) -carbamoyl;
f) -carboxyl;
g) —Z-alkyl;
h) —Z-aryl;
i) —Z-alkylene-aryl;

wherein Z is selected from the group consisting of —CH$_2$—, —O—, —N(H), —S—, SO$_2$—, —CON(H)—, —NHC(O)—, —NHCON(H)—, —NHSO$_2$—, —SO$_2$N(H)—, —C(O)—O—, —NHSO$_2$NH—, and —O—CO—, or a pharmaceutically acceptable salt, ester, or prodrug thereof.

In an embodiment of the compound of Formula (Ib),
L$_1$ is —NH—C(O)—, —NH—, or a direct bond; and
at least one of R$_1$-R$_4$ is the group -L$_3$-G$_2$-G$_3$, wherein
  L$_3$ is selected from the group consisting of
    a) a direct bond;
    b) —CO$_2$—;
    c) —C(O)NH—; and
    d) —NH—
  G$_2$ is a direct bond, or alkylene; and
  G$_3$ is selected from the group consisting alkyl, phenyl, naphthyl, biphenyl, alkylene-phenyl, pyrole, thiophene, indole, imidazole, tetrazole, thiazole, 1,3,4-thiadiazole, pyrimidine, pyridine, benzimidazole, and benzthiazole, wherein G$_3$ is optionally substituted 1 to 7 times with a group selected from the group consisting of:
    a) -halo;
    b) -cyano;
    c) -nitro;
    d) -perhaloalkyl;
    e) —R$_{16}$;
    f) -L$_4$-R$_{16}$;
    g) -L$_4$-Q$_4$-R$_{16}$; and
    h) -Q$_2$-L$_4$-R$_{16}$;
    wherein
      R$_{16}$ is selected from the group consisting of hydrogen, -alkyl, -aryl, and -alkylene-aryl;
      Q$_4$ is selected from the group consisting of -alkylene, -alkenylene, and -alkynylene;
      L$_4$ is selected from the group consisting of —CH$_2$—, —O—, —N(R$_{18}$)—, —C(O)—, —CON(R$_{18}$)—, —N(R$_{19}$)C(O)—, —N(R$_{18}$)CON(R$_{19}$)—, —N(R$_{18}$)C(O)O—, —OC(O)N(R$_{18}$)—, —N(R$_{18}$)SO$_2$—, —SO$_2$N(R$_{18}$)—, —C(O)—O—, —O—C(O)—, —S—, —S(O)—, —S(O)$_2$—, and —N(R$_{18}$)SO$_2$N(R$_{19}$)—;
    wherein
R$_{18}$ and R$_{19}$ are independently selected from the group consisting of: hydrogen, -alkyl, -aryl, and -alkylene-aryl.

In the compounds of Formula (I), the various functional groups represented should be understood to have a point of attachment at the functional group having the hyphen. In other words, in the case of —C$_{1-10}$ alkylene-aryl, it should be understood that the point of attachment is the alkylene group; an example would be benzyl. In the case of a group such as —C(O)—NH—C$_{1-10}$ alkylene-aryl, the point of attachment is the carbonyl carbon.

The term "BACE inhibitor" or "inhibitor of BACE" is used to signify a compound having a structure as defined herein, which is capable of interacting with BACE and inhibiting its enzymatic activity. Inhibiting BACE enzymatic activity means reducing the ability of BACE to cleave a peptide or protein. The peptide or protein may be APP, and a BACE inhibitor may reduce the ability of BACE to cleave APP near the NH$_2$ terminus of APP and produce COOH-terminal fragments (CTFs) that contain the complete Aβ domain. In various embodiments, such reduction of BACE activity is at least about 50%, at least about 75%, at least about 90%, at least about 95%, or at least about 99%. In various embodiments, the concentration of BACE inhibitor required to reduce a BACE's enzymatic activity is less than about 30 μM, less than about 10 μM, or less than about 1 μM.

Also included within the scope of the invention are the individual enantiomers of the compounds represented by Formula (I) above as well as any wholly or partially racemic mixtures thereof. The present invention also covers the individual enantiomers of the compounds represented by Formula (I) above as mixtures with diastereoisomers thereof in which one or more stereocenters are inverted. Unless otherwise stated, structures depicted herein are also meant to include compounds which differ only in the presence of one or more isotopically enriched atoms. For example, compounds having the present structure except for the replacement of a hydrogen atom by a deuterium or tritium, or the replacement of a carbon atom by a $^{13}$C- or $^{14}$C-enriched carbon are within the scope of the invention.

In another aspect, the present invention provides a pharmaceutically acceptable salt, solvate, or prodrug of compounds of Formula (I). In an embodiment, the prodrug comprises a biohydrolyzable ester or biohydrolyzable amide of a compound of Formula (I).

Examples of compounds of Formula (I) of the present invention having potentially useful biological activity are listed by name below in Table 1. The ability of compounds Formula (I) to inhibit the proteolytic activity of BACE was established with representative compounds of Formula (I) listed in Table 1 using the enzyme assay described in the Examples section. The compounds of Formula (I) in Table 1 inhibit BACE in the enzyme assay with an IC$_{50}$ of less than or equal to 30 μM.

Examples of compounds of Formula (I) of the present invention are shown in Table 1 and in the Examples section.

TABLE 1

| Ex. | Structure | Name |
|---|---|---|
| 1 | 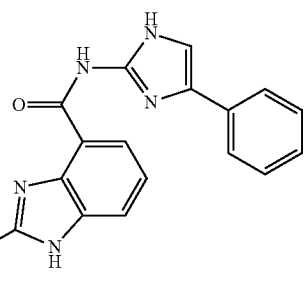 | 2-Isoquinolin-3-yl-1H-benzoimidazole-4-carboxylic acid (4-phenyl-1H-imidazol-2-yl)-amide |

TABLE 1-continued

| Ex. | Structure | Name |
|---|---|---|
| 2 | 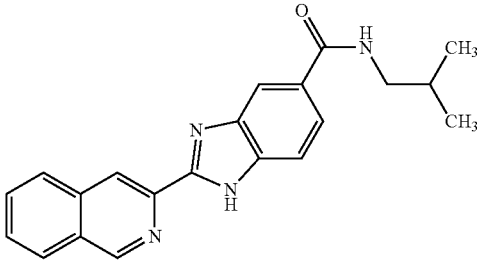 [SMILES: CC(C)CNC(=O)c1ccc2[nH]c(-c3cc4ccccc4cn3)nc2c1] | 2-Isoquinolin-3-yl-1H-benzoimidazole-5-carboxylic acid isobutyl-amide |
| 3 | 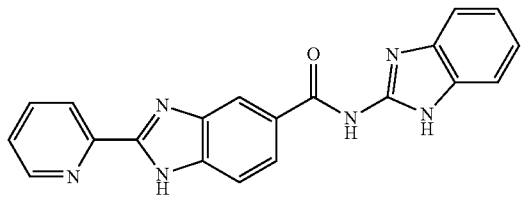 [SMILES: O=C(Nc1nc2ccccc2[nH]1)c1ccc2[nH]c(-c3ccccn3)nc2c1] | 2-Pyridin-2-yl-1H-benzoimidazole-5-carboxylic acid (1H-benzoimidazol-2-yl)-amide |
| 4 | 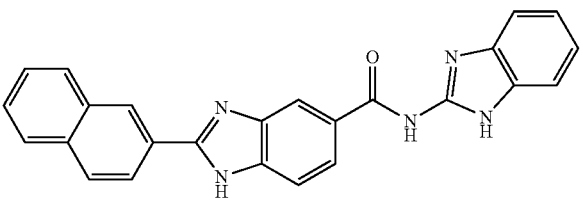 [SMILES: O=C(Nc1nc2ccccc2[nH]1)c1ccc2[nH]c(-c3ccc4ccccc4c3)nc2c1] | 2-Naphthalen-2-yl-1H-benzoimidazole-5-carboxylic acid (1H-benzoimidazol-2-yl)-amide |
| 5 | 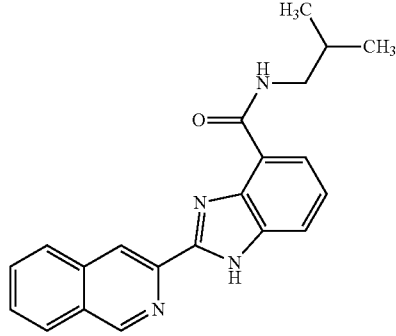 [SMILES: CC(C)CNC(=O)c1cccc2[nH]c(-c3cc4ccccc4cn3)nc12] | 2-Isoquinolin-3-yl-1H-benzoimidazole-4-carboxylic acid isobutyl-amide |
| 6 | 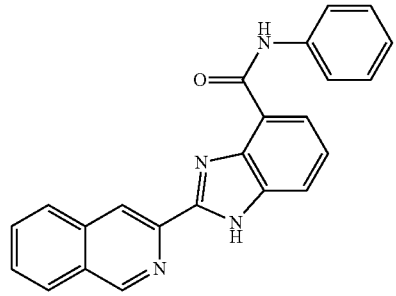 [SMILES: O=C(Nc1ccccc1)c1cccc2[nH]c(-c3cc4ccccc4cn3)nc12] | 2-Isoquinolin-3-yl-1H-benzoimidazole-4-carboxylic acid phenylamide |

TABLE 1-continued

| Ex. | Structure | Name |
|---|---|---|
| 7 | 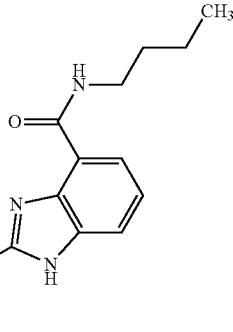 | 2-Isoquinolin-3-yl-1H-benzoimidazole-4-carboxylic acid butylamide |
| 8 | 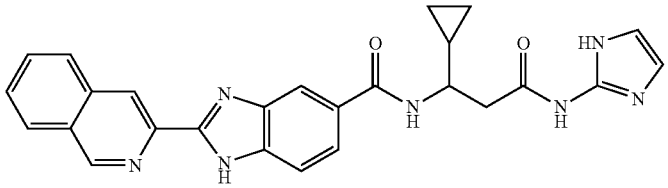 [SMILES: O=C(CC(NC(=O)c1ccc2[nH]c(-c3cc4ccccc4cn3)nc2c1)C1CC1)Nc1ncc[nH]1] | 2-Isoquinolin-3-yl-1H-benzoimidazole-5-carboxylic acid [1-cyclopropyl-2-(1H-imidazol-2-ylcarbamoyl)-ethyl]-amide |
| 9 | 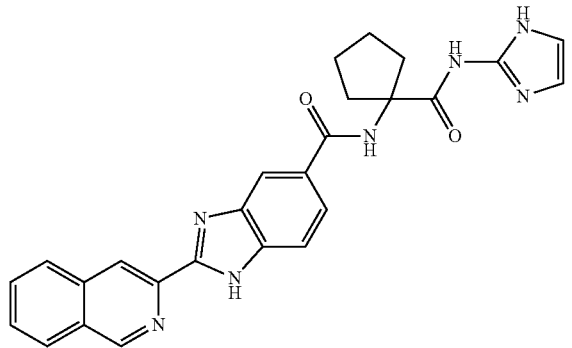 [SMILES: O=C(NC1(C(=O)Nc2ncc[nH]2)CCCC1)c1ccc2[nH]c(-c3cc4ccccc4cn3)nc2c1] | 2-Isoquinolin-3-yl-1H-benzoimidazole-5-carboxylic acid [1-(1H-imidazol-2-ylcarbamoyl)-cyclopentyl]-amide |
| 10 | 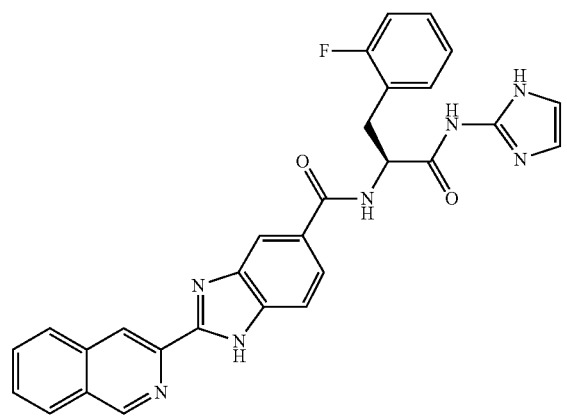 [SMILES: O=C(N[C@@H](Cc1ccccc1F)C(=O)Nc1ncc[nH]1)c1ccc2[nH]c(-c3cc4ccccc4cn3)nc2c1] | 2-Isoquinolin-3-yl-1H-benzoimidazole-5-carboxylic acid [2-(2-fluoro-phenyl)-1S-(1H-imidazol-2-ylcarbamoyl)-ethyl]-amide |

TABLE 1-continued

| Ex. | Structure | Name |
|---|---|---|
| 11 | 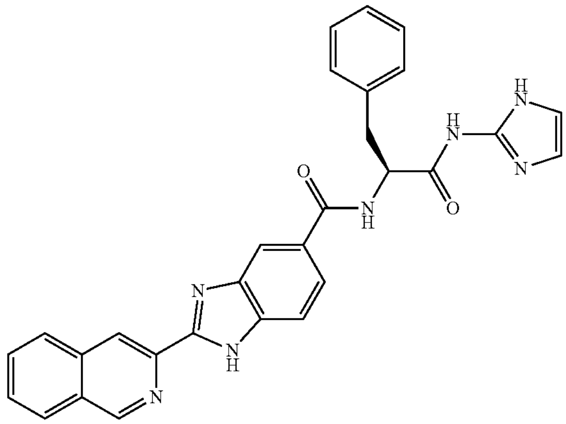 [SMILES: O=C(N[C@@H](Cc1ccccc1)C(=O)Nc1ncc[nH]1)c1ccc2[nH]c(-c3cc4ccccc4cn3)nc2c1] | 2-Isoquinolin-3-yl-1H-benzoimidazole-5-carboxylic acid [1S-(1H-imidazol-2-ylcarbamoyl)-2-phenyl-ethyl]-amide |
| 12 | 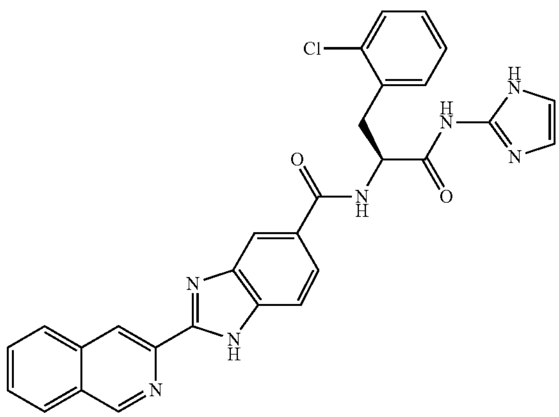 [SMILES: O=C(N[C@@H](Cc1ccccc1Cl)C(=O)Nc1ncc[nH]1)c1ccc2[nH]c(-c3cc4ccccc4cn3)nc2c1] | 2-Isoquinolin-3-yl-1H-benzoimidazole-5-carboxylic acid [2-(2-chloro-phenyl)-1S-(1H-imidazol-2-ylcarbamoyl)-ethyl]-amide |
| 13 | 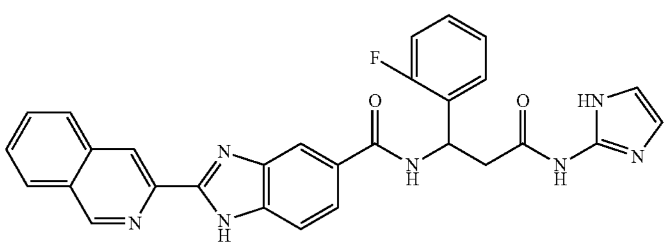 | 2-Isoquinolin-3-yl-1H-benzoimidazole-5-carboxylic acid [1-(2-fluoro-phenyl)-2-(1H-imidazol-2-ylcarbamoyl)-ethyl]-amide |
| 14 | 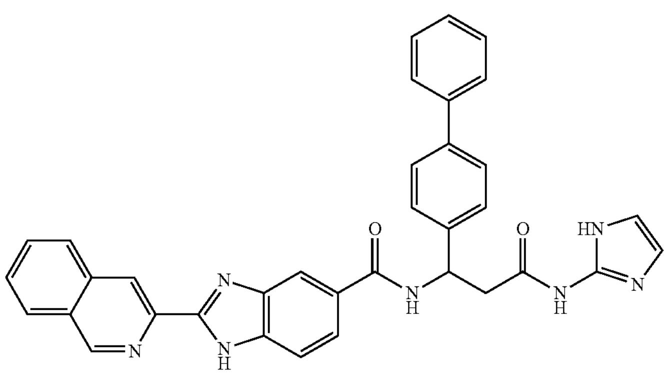 [SMILES: O=C(CC(NC(=O)c1ccc2[nH]c(-c3cc4ccccc4cn3)nc2c1)c1ccc(-c2ccccc2)cc1)Nc1ncc[nH]1] | 2-Isoquinolin-3-yl-1H-benzoimidazole-5-carboxylic acid [1-biphenyl-4-yl-2-(1H-imidazol-2-ylcarbamoyl)-ethyl]-amide |

TABLE 1-continued

| Ex. | Structure | Name |
|---|---|---|
| 15 | 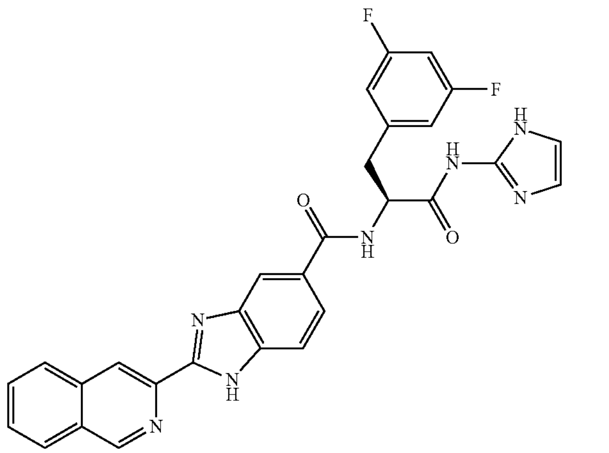 [SMILES: O=C(N[C@@H](Cc1cc(F)cc(F)c1)C(=O)Nc1ncc[nH]1)c1ccc2[nH]c(-c3cc4ccccc4cn3)nc2c1] | 2-Isoquinolin-3-yl-1H-benzoimidazole-5-carboxylic acid [2-(3,5-difluoro-phenyl)-1S-(1H-imidazol-2-ylcarbamoyl)-ethyl]-amide |
| 16 | 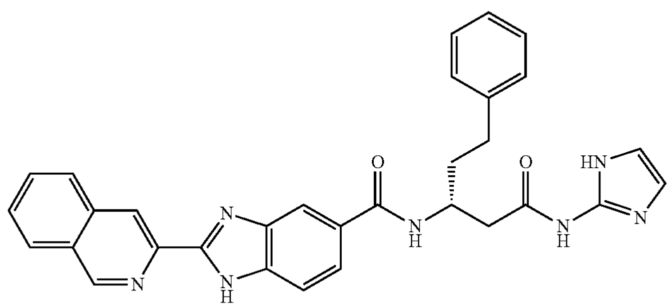 [SMILES: O=C(C[C@@H](CCc1ccccc1)NC(=O)c1ccc2[nH]c(-c3cc4ccccc4cn3)nc2c1)Nc1ncc[nH]1] | 2-Isoquinolin-3-yl-1H-benzoimidazole-5-carboxylic acid {1R-[(1H-imidazol-2-ylcarbamoyl)-methyl]-3-phenyl-propyl}-amide |
| 17 | 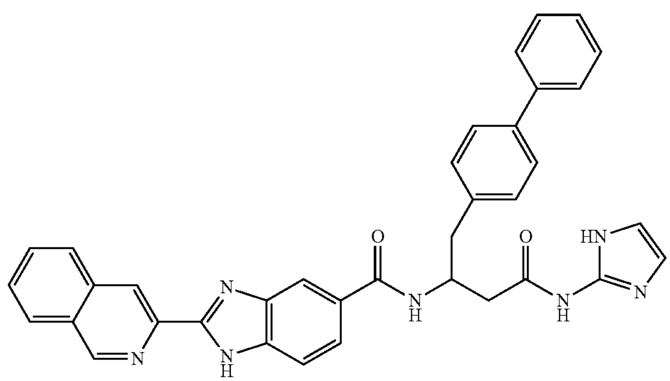 [SMILES: O=C(CC(Cc1ccc(-c2ccccc2)cc1)NC(=O)c1ccc2[nH]c(-c3cc4ccccc4cn3)nc2c1)Nc1ncc[nH]1] | 2-Isoquinolin-3-yl-1H-benzoimidazole-5-carboxylic acid {2-biphenyl-4-yl-1-[(1H-imidazol-2-ylcarbamoyl)-methyl]-ethyl}-amide |
| 18 | 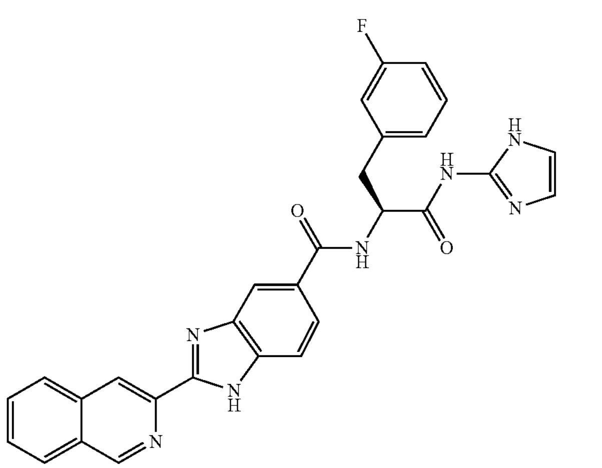 [SMILES: O=C(N[C@@H](Cc1cccc(F)c1)C(=O)Nc1ncc[nH]1)c1ccc2[nH]c(-c3cc4ccccc4cn3)nc2c1] | 2-Isoquinolin-3-yl-1H-benzoimidazole-5-carboxylic acid [2-(3-fluoro-phenyl)-1S-(1H-imidazol-2-ylcarbamoyl)-ethyl]-amide |

TABLE 1-continued

| Ex. | Structure | Name |
|---|---|---|
| 19 | 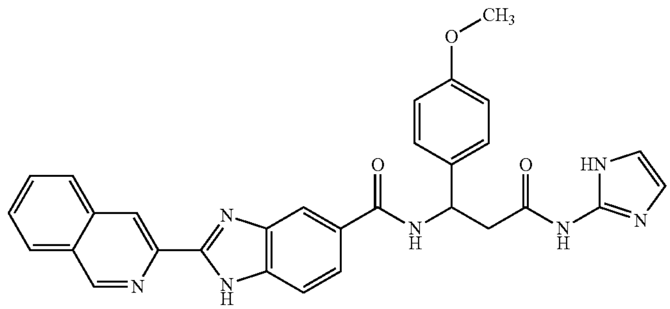 [SMILES: COc1ccc(C(CC(=O)Nc2ncc[nH]2)NC(=O)c2ccc3[nH]c(-c4cc5ccccc5cn4)nc3c2)cc1] | 2-Isoquinolin-3-yl-1H-benzoimidazole-5-carboxylic acid [2-(1H-imidazol-2-ylcarbamoyl)-1S-(4-methoxy-phenyl)-ethyl]-amide |
| 20 | 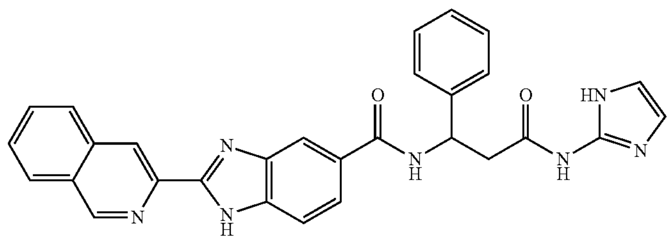 [SMILES: O=C(CC(NC(=O)c1ccc2[nH]c(-c3cc4ccccc4cn3)nc2c1)c1ccccc1)Nc1ncc[nH]1] | 2-Isoquinolin-3-yl-1H-benzoimidazole-5-carboxylic acid [2-(1H-imidazol-2-ylcarbamoyl)-1-phenyl-ethyl]-amide |
| 21 | 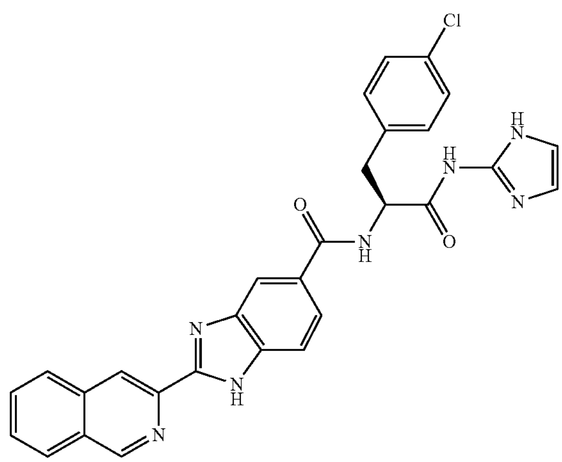 [SMILES: O=C(N[C@@H](Cc1ccc(Cl)cc1)C(=O)Nc1ncc[nH]1)c1ccc2[nH]c(-c3cc4ccccc4cn3)nc2c1] | 2-Isoquinolin-3-yl-1H-benzoimidazole-5-carboxylic acid [2-(4-chloro-phenyl)-1S-(1H-imidazol-2-ylcarbamoyl)-ethyl]-amide |
| 22 | 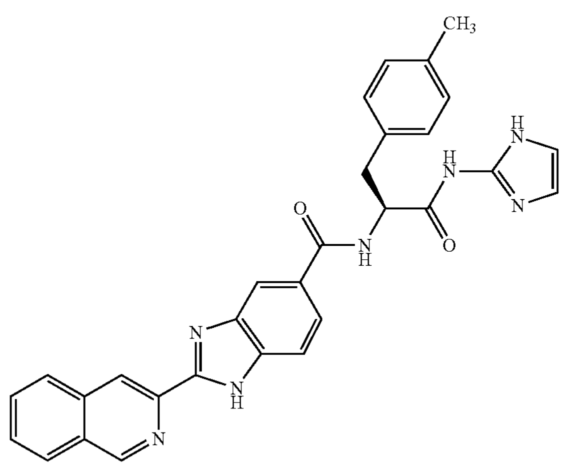 [SMILES: Cc1ccc(C[C@H](NC(=O)c2ccc3[nH]c(-c4cc5ccccc5cn4)nc3c2)C(=O)Nc2ncc[nH]2)cc1] | 2-Isoquinolin-3-yl-1H-benzoimidazole-5-carboxylic acid [1S-(1H-imidazol-2-ylcarbamoyl)-2-p-tolyl-ethyl]-amide |

TABLE 1-continued

| Ex. | Structure | Name |
|---|---|---|
| 23 | 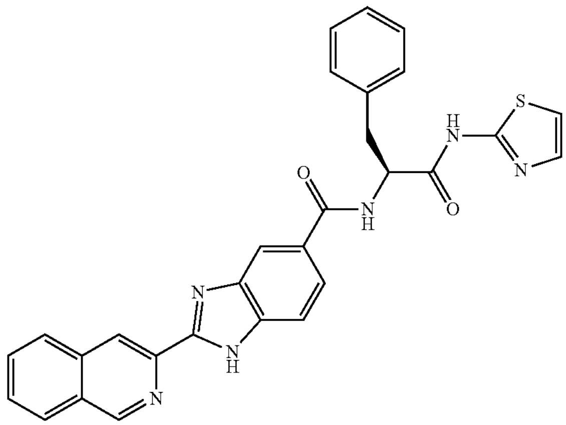 [SMILES: O=C(N[C@@H](Cc1ccccc1)C(=O)Nc1nccs1)c1ccc2[nH]c(-c3cc4ccccc4cn3)nc2c1] | 2-Isoquinolin-3-yl-1H-benzoimidazole-5-carboxylic acid [2-phenyl-1S-(thiazol-2-ylcarbamoyl)-ethyl]-amide |
| 24 | 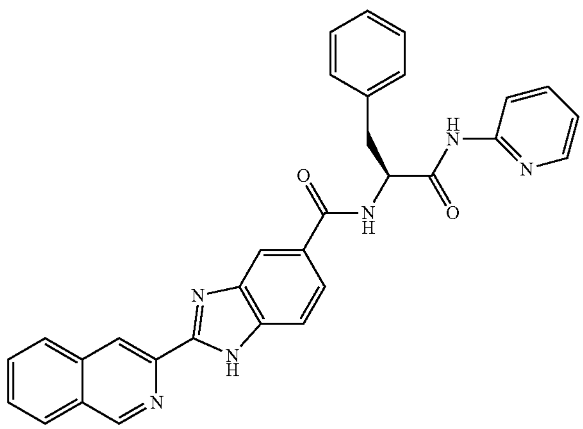 [SMILES: O=C(N[C@@H](Cc1ccccc1)C(=O)Nc1ccccn1)c1ccc2[nH]c(-c3cc4ccccc4cn3)nc2c1] | 2-Isoquinolin-3-yl-1H-benzoimidazole-5-carboxylic acid [2-phenyl-1S-(pyridin-2-ylcarbamoyl)-ethyl]-amide |
| 25 | 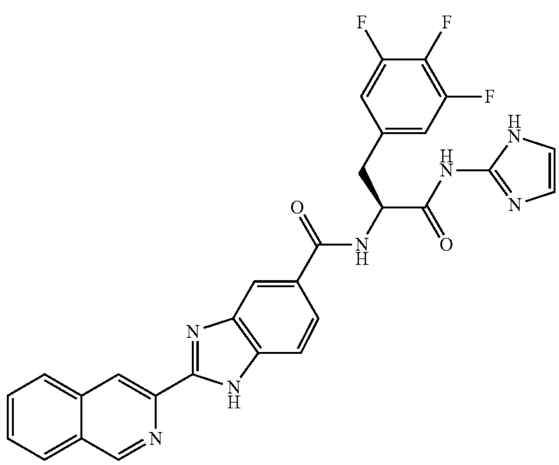 [SMILES: O=C(N[C@@H](Cc1cc(F)c(F)c(F)c1)C(=O)Nc1ncc[nH]1)c1ccc2[nH]c(-c3cc4ccccc4cn3)nc2c1] | 2-Isoquinolin-3-yl-1H-benzoimidazole-5-carboxylic acid [1S-(1H-imidazol-2-ylcarbamoyl)-2-(3,4,5-trifluoro-phenyl)-ethyl]-amide |
| 26 | 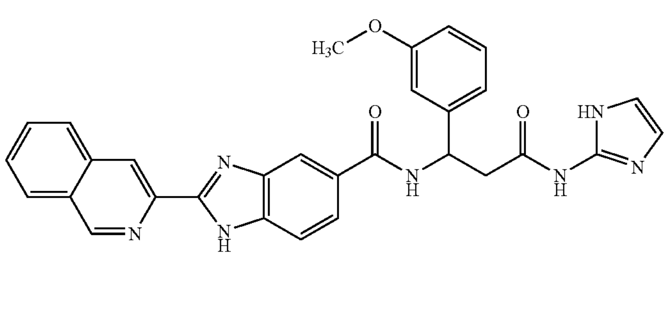 [SMILES: COc1cccc(C(CC(=O)Nc2ncc[nH]2)NC(=O)c2ccc3[nH]c(-c4cc5ccccc5cn4)nc3c2)c1] | 2-Isoquinolin-3-yl-1H-benzoimidazole-5-carboxylic acid [2-(1H-imidazol-2-ylcarbamoyl)-1-(3-methoxy-phenyl)-ethyl]-amide |

TABLE 1-continued

| Ex. | Structure | Name |
|---|---|---|
| 27 | 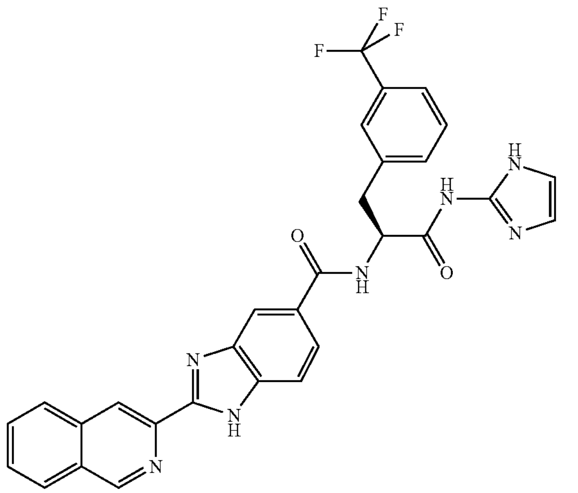 [SMILES: O=C(N[C@@H](Cc1cccc(C(F)(F)F)c1)C(=O)Nc1ncc[nH]1)c1ccc2[nH]c(-c3cc4ccccc4cn3)nc2c1] | 2-Isoquinolin-3-yl-1H-benzoimidazole-5-carboxylic acid [1S-(1H-imidazol-2-ylcarbamoyl)-2-(3-trifluoromethyl-phenyl)-ethyl]-amide |
| 28 | 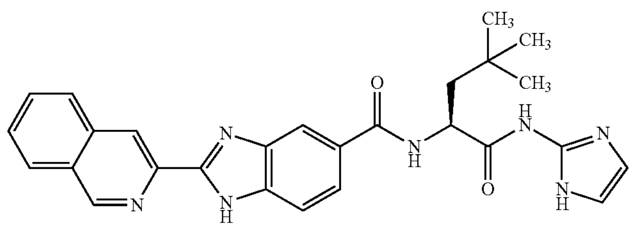 [SMILES: CC(C)(C)C[C@H](NC(=O)c1ccc2[nH]c(-c3cc4ccccc4cn3)nc2c1)C(=O)Nc1ncc[nH]1] | 2-Isoquinolin-3-yl-1H-benzoimidazole-5-carboxylic acid [1S-(1H-imidazol-2-ylcarbamoyl)-3,3-dimethyl-butyl]-amide |
| 29 | 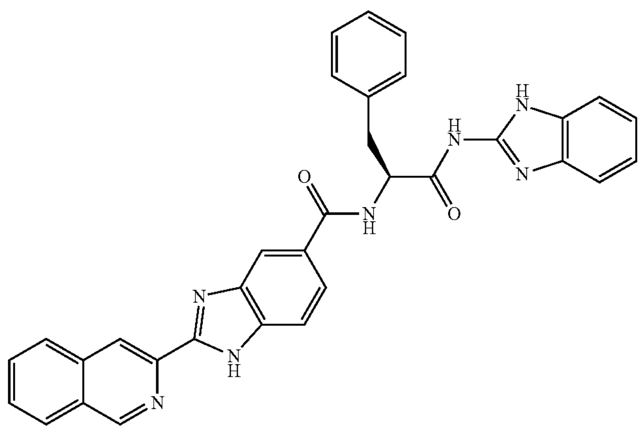 [SMILES: O=C(N[C@@H](Cc1ccccc1)C(=O)Nc1nc2ccccc2[nH]1)c1ccc2[nH]c(-c3cc4ccccc4cn3)nc2c1] | 2-Isoquinolin-3-yl-1H-benzoimidazole-5-carboxylic acid [1S-(1H-benzoimidazol-2-ylcarbamoyl)-2-phenyl-ethyl]-amide |
| 30 | 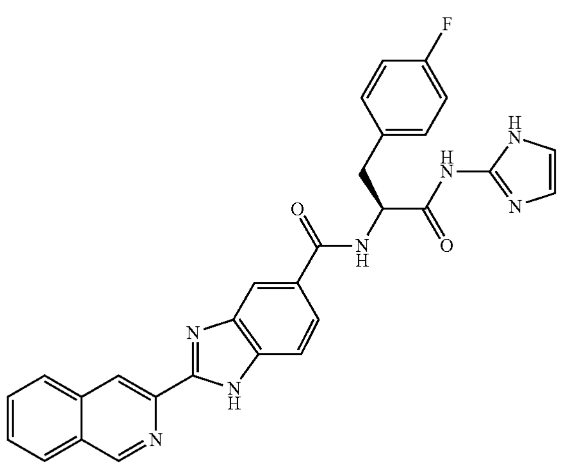 [SMILES: O=C(N[C@@H](Cc1ccc(F)cc1)C(=O)Nc1ncc[nH]1)c1ccc2[nH]c(-c3cc4ccccc4cn3)nc2c1] | 2-Isoquinolin-3-yl-1H-benzoimidazole-5-carboxylic acid [2-(4-fluoro-phenyl)-1S-(1H-imidazol-2-ylcarbamoyl)-ethyl]-amide |

TABLE 1-continued

| Ex. | Structure | Name |
|---|---|---|
| 31 | 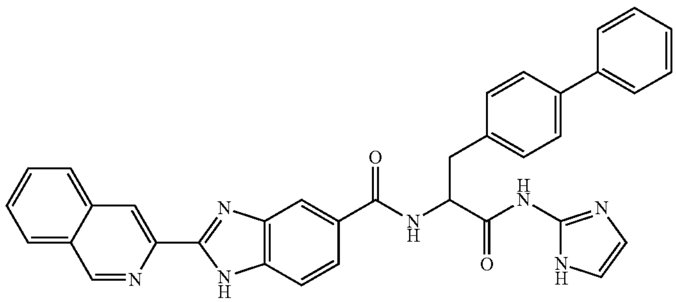 [SMILES: O=C(NC(Cc1ccc(-c2ccccc2)cc1)C(=O)Nc1ncc[nH]1)c1ccc2[nH]c(-c3cc4ccccc4cn3)nc2c1] | 2-Isoquinolin-3-yl-1H-benzoimidazole-5-carboxylic acid [2-biphenyl-4-yl-1-(1H-imidazol-2-ylcarbamoyl)-ethyl]-amide |
| 32 | 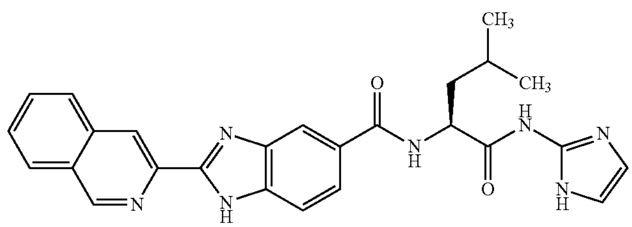 [SMILES: CC(C)C[C@H](NC(=O)c1ccc2[nH]c(-c3cc4ccccc4cn3)nc2c1)C(=O)Nc1ncc[nH]1] | 2-Isoquinolin-3-yl-1H-benzoimidazole-5-carboxylic acid [1S-(1H-imidazol-2-ylcarbamoyl)-3-methyl-butyl]-amide |
| 33 | 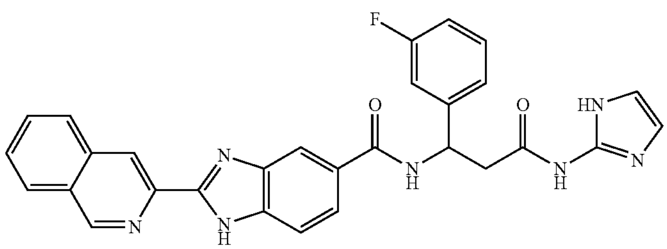 [SMILES: O=C(CC(NC(=O)c1ccc2[nH]c(-c3cc4ccccc4cn3)nc2c1)c1cccc(F)c1)Nc1ncc[nH]1] | 2-Isoquinolin-3-yl-1H-benzoimidazole-5-carboxylic acid [1S-(3-fluoro-phenyl)-2-(1H-imidazol-2-ylcarbamoyl)-ethyl]-amide |
| 34 | 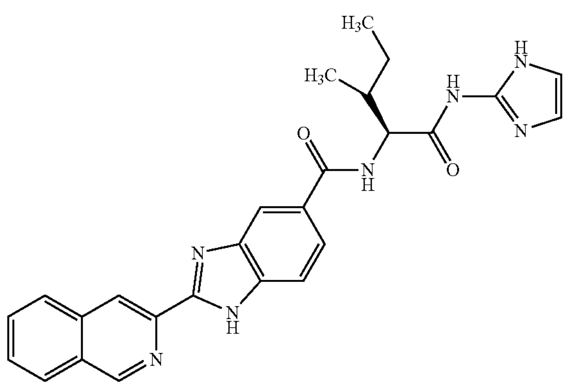 [SMILES: CCC(C)[C@H](NC(=O)c1ccc2[nH]c(-c3cc4ccccc4cn3)nc2c1)C(=O)Nc1ncc[nH]1] | 2-Isoquinolin-3-yl-1H-benzoimidazole-5-carboxylic acid [1S-(1H-imidazol-2-ylcarbamoyl)-2-methyl-butyl]-amide |
| 35 | 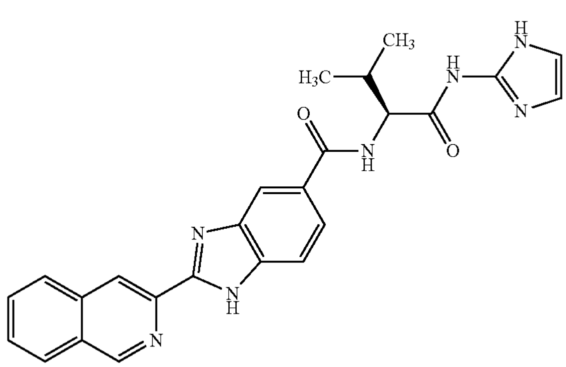 [SMILES: CC(C)[C@H](NC(=O)c1ccc2[nH]c(-c3cc4ccccc4cn3)nc2c1)C(=O)Nc1ncc[nH]1] | 2-Isoquinolin-3-yl-1H-benzoimidazole-5-carboxylic acid [1S-(1H-imidazol-2-ylcarbamoyl)-2-methyl-propyl]-amide |

TABLE 1-continued

| Ex. | Structure | Name |
|---|---|---|
| 36 | 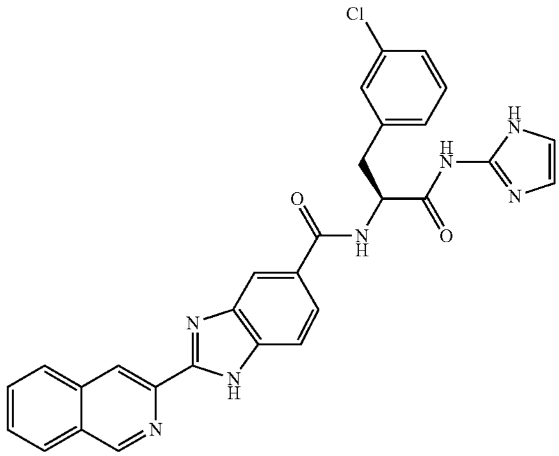 [SMILES: O=C(N[C@@H](Cc1cccc(Cl)c1)C(=O)Nc1ncc[nH]1)c1ccc2[nH]c(-c3cc4ccccc4cn3)nc2c1] | 2-Isoquinolin-3-yl-1H-benzoimidazole-5-carboxylic acid [2-(3-chloro-phenyl)-1S-(1H-imidazol-2-ylcarbamoyl)-ethyl]-amide |
| 37 | 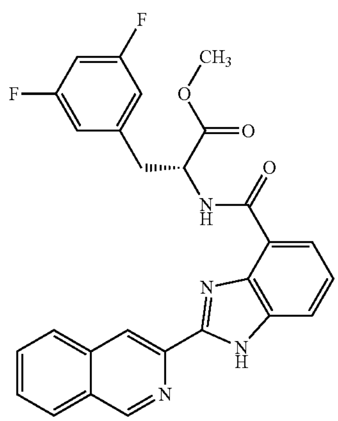 [SMILES: COC(=O)[C@@H](Cc1cc(F)cc(F)c1)NC(=O)c1cccc2[nH]c(-c3cc4ccccc4cn3)nc12] | 3-(3,5-Difluoro-phenyl)-2S-[(2-isoquinolin-3-yl-1H-benzoimidazole-4-carbonyl)-amino]-propionic acid methyl ester |
| 38 | 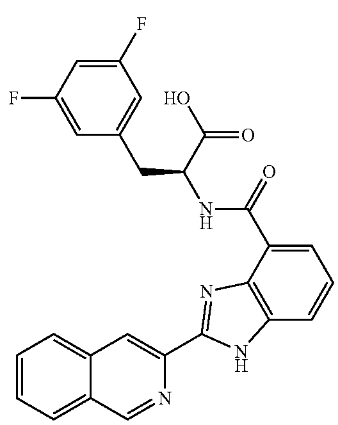 [SMILES: O=C(N[C@@H](Cc1cc(F)cc(F)c1)C(=O)O)c1cccc2[nH]c(-c3cc4ccccc4cn3)nc12] | 3-(3,5-Difluoro-phenyl)-2S-[(2-isoquinolin-3-yl-1H-benzoimidazole-4-carbonyl)-amino]-propionic acid |

TABLE 1-continued

| Ex. | Structure | Name |
|---|---|---|
| 39 | 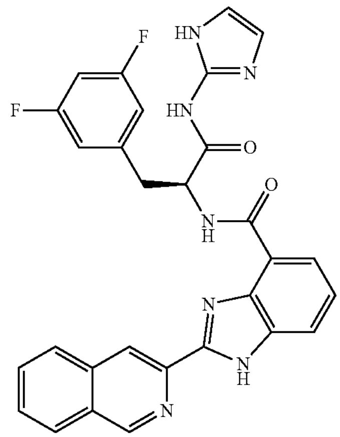 [SMILES: O=C(N[C@@H](Cc1cc(F)cc(F)c1)C(=O)Nc1ncc[nH]1)c1cccc2[nH]c(-c3cc4ccccc4cn3)nc12] | 2-Isoquinolin-3-yl-1H-benzoimidazole-4-carboxylic acid [2-(3,5-difluoro-phenyl)-1S-(1H-imidazol-2-ylcarbamoyl)-ethyl]-amide |
| 40 | 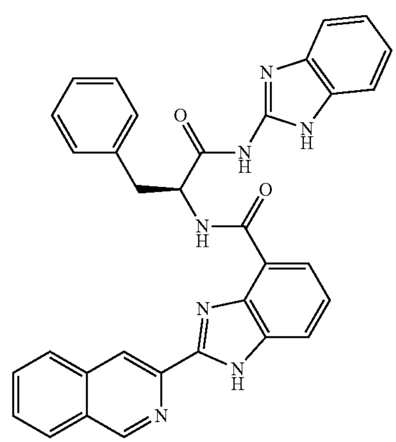 [SMILES: O=C(N[C@@H](Cc1ccccc1)C(=O)Nc1nc2ccccc2[nH]1)c1cccc2[nH]c(-c3cc4ccccc4cn3)nc12] | 2-Isoquinolin-3-yl-1H-benzoimidazole-4-carboxylic acid [1S-(1H-benzoimidazol-2-ylcarbamoyl)-2-phenyl-ethyl-amide |
| 41 | 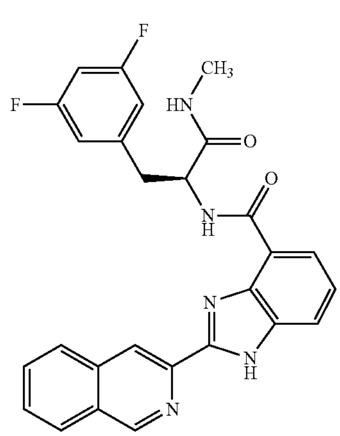 [SMILES: CNC(=O)[C@H](Cc1cc(F)cc(F)c1)NC(=O)c1cccc2[nH]c(-c3cc4ccccc4cn3)nc12] | 2-Isoquinolin-3-yl-1H-benzoimidazole-4-carboxylic acid [2-(3,5-difluoro-phenyl)-1S-methylcarbamoyl-ethyl]-amide |

TABLE 1-continued
| Ex. | Structure | Name |
|---|---|---|
| 42 | 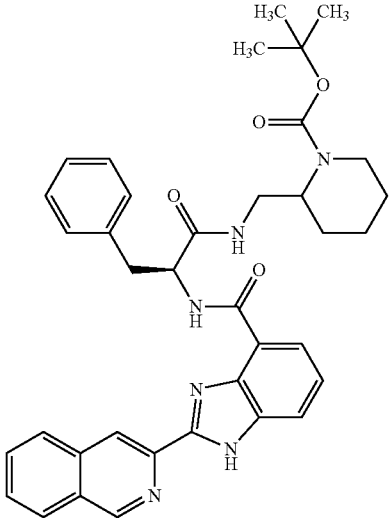 [SMILES: CC(C)(C)OC(=O)N1CCCCC1CNC(=O)[C@H](Cc1ccccc1)NC(=O)c1cccc2[nH]c(-c3cc4ccccc4cn3)nc12] | 2S-({2-[(2-Isoquinolin-3-yl-1H-benzoimidazole-4-carbonyl)-amino]-3-phenyl-propionylamino}-methyl)-piperidine-1-carboxylic acid tert-butyl ester |
| 43 | 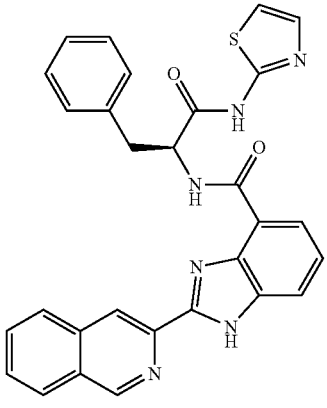 [SMILES: O=C(N[C@@H](Cc1ccccc1)C(=O)Nc1nccs1)c1cccc2[nH]c(-c3cc4ccccc4cn3)nc12] | 2-Isoquinolin-3-yl-1H-benzoimidazole-4-carboxylic acid [2-phenyl-1S-(thiazol-2-ylcarbamoyl)-ethyl]-amide |
| 44 | 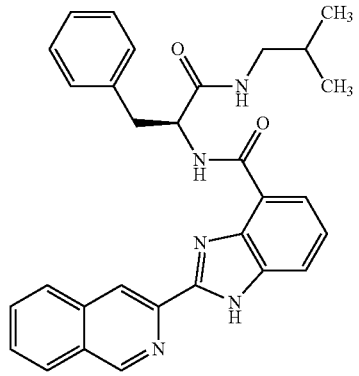 [SMILES: CC(C)CNC(=O)[C@H](Cc1ccccc1)NC(=O)c1cccc2[nH]c(-c3cc4ccccc4cn3)nc12] | 2-Isoquinolin-3-yl-1H-benzoimidazole-4-carboxylic acid (1S-isobutylcarbamoyl-2-phenyl-ethyl)-amide |

TABLE 1-continued

| Ex. | Structure | Name |
|---|---|---|
| 45 | 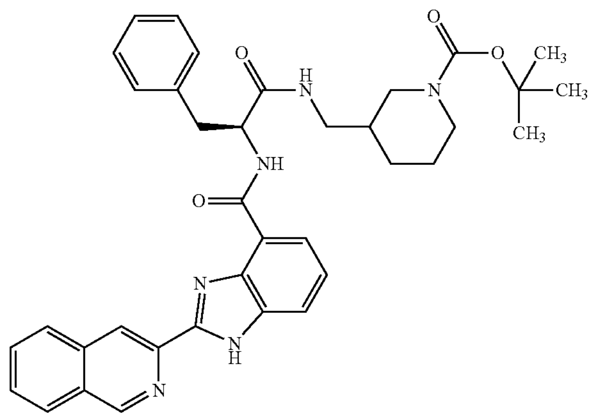 [SMILES: CC(C)(C)OC(=O)N1CCCC(CNC(=O)[C@H](Cc2ccccc2)NC(=O)c2cccc3[nH]c(-c4cc5ccccc5cn4)nc23)C1] | 3-({2S-[(2-Isoquinolin-3-yl-1H-benzoimidazole-4-carbonyl)-amino]-3-phenyl-propionylamino}-methyl)-piperidine-1-carboxylic acid tert-butyl ester |
| 46 | 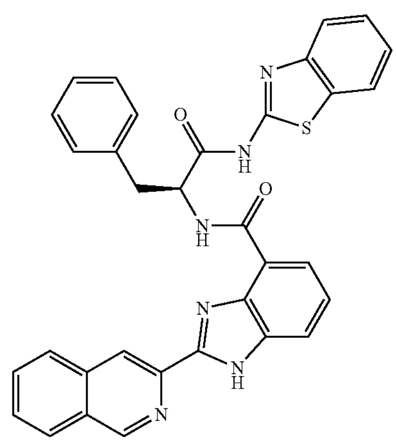 [SMILES: O=C(N[C@@H](Cc1ccccc1)C(=O)Nc1nc2ccccc2s1)c1cccc2[nH]c(-c3cc4ccccc4cn3)nc12] | 2-Isoquinolin-3-yl-1H-benzoimidazole-4-carboxylic acid [1S-(benzothiazol-2-ylcarbamoyl)-2-phenyl-ethyl]-amide |
| 47 | 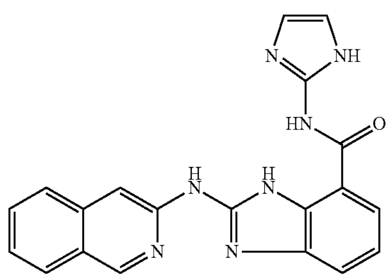 [SMILES: O=C(Nc1ncc[nH]1)c1cccc2nc(Nc3cc4ccccc4cn3)[nH]c12] | 2-(Isoquinolin-3-ylamino)-3H-benzoimidazole-4-carboxylic acid (1H-imidazol-2-yl)-amide |
| 48 | 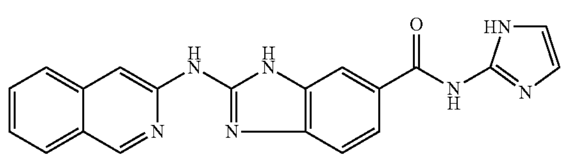 [SMILES: O=C(Nc1ncc[nH]1)c1ccc2nc(Nc3cc4ccccc4cn3)[nH]c2c1] | 2-(Isoquinolin-3-ylamino)-3H-benzoimidazole-5-carboxylic acid (1H-imidazol-2-yl)-amide |
| 49 | 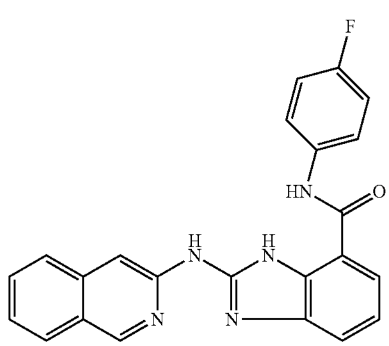 [SMILES: O=C(Nc1ccc(F)cc1)c1cccc2nc(Nc3cc4ccccc4cn3)[nH]c12] | 2-(Isoquinolin-3-ylamino)-3H-benzoimidazole-4-carboxylic acid (4-fluoro-phenyl)-amide |

TABLE 1-continued

| Ex. | Structure | Name |
|---|---|---|
| 50 | 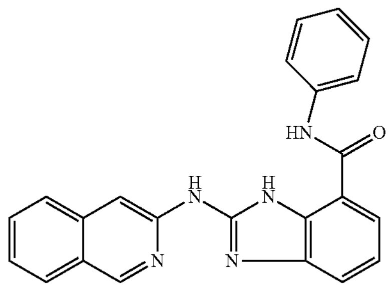 [SMILES: O=C(Nc1ccccc1)c1cccc2nc(Nc3cc4ccccc4cn3)[nH]c12] | 2-(Isoquinolin-3-ylamino)-3H-benzoimidazole-4-carboxylic acid phenylamide |
| 51 | 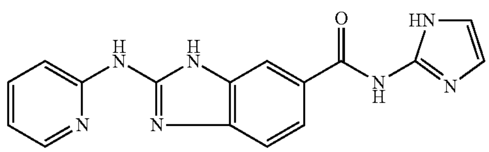 [SMILES: O=C(Nc1ncc[nH]1)c1ccc2nc(Nc3ccccn3)[nH]c2c1] | 2-(Pyridin-2-ylamino)-3H-benzoimidazole-5-carboxylic acid (1H-imidazol-2-yl)-amide |
| 52 | 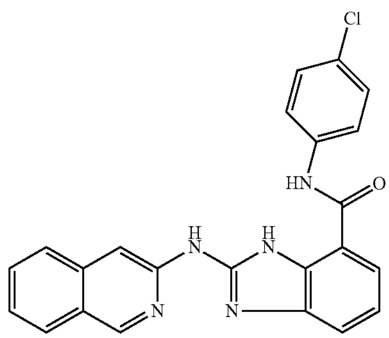 [SMILES: O=C(Nc1ccc(Cl)cc1)c1cccc2nc(Nc3cc4ccccc4cn3)[nH]c12] | 2-(Isoquinolin-3-ylamino)-3H-benzoimidazole-4-carboxylic acid (4-chloro-phenyl)-amide |
| 53 | 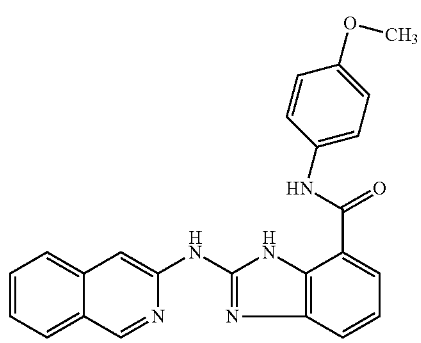 [SMILES: COc1ccc(NC(=O)c2cccc3nc(Nc4cc5ccccc5cn4)[nH]c23)cc1] | 2-(Isoquinolin-3-ylamino)-3H-benzoimidazole-4-carboxylic acid (4-methoxy-phenyl)-amide |
| 54 | 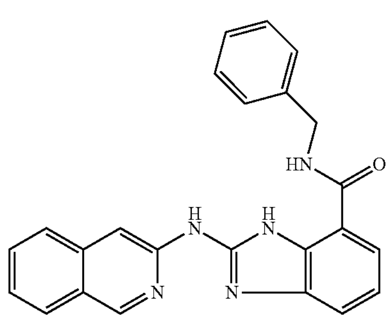 [SMILES: O=C(NCc1ccccc1)c1cccc2nc(Nc3cc4ccccc4cn3)[nH]c12] | 2-(Isoquinolin-3-ylamino)-3H-benzoimidazole-4-carboxylic acid benzylamide |

TABLE 1-continued

| Ex. | Structure | Name |
|---|---|---|
| 55 | 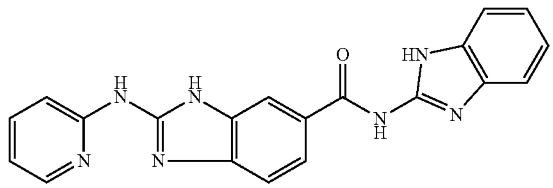 [SMILES: O=C(Nc1nc2ccccc2[nH]1)c1ccc2nc(Nc3ccccn3)[nH]c2c1] | 2-(Pyridin-2-ylamino)-3H-benzoimidazole-5-carboxylic acid (1H-benzoimidazol-2-yl)-amide |
| 56 | 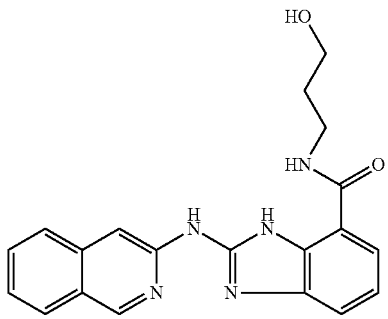 [SMILES: O=C(NCCCO)c1cccc2nc(Nc3cc4ccccc4cn3)[nH]c12] | 2-(Isoquinolin-3-ylamino)-3H-benzoimidazole-4-carboxylic acid (3-hydroxy-propyl)-amide |
| 57 | 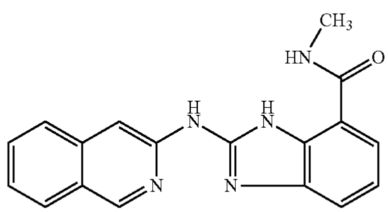 [SMILES: CNC(=O)c1cccc2nc(Nc3cc4ccccc4cn3)[nH]c12] | 2-(Isoquinolin-3-ylamino)-3H-benzoimidazole-4-carboxylic acid methylamide |
| 58 | 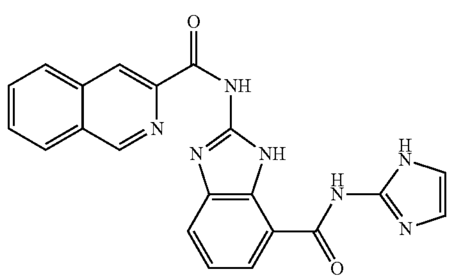 [SMILES: O=C(Nc1nc2cccc(C(=O)Nc3ncc[nH]3)c2[nH]1)c1cc2ccccc2cn1] | Isoquinoline-3-carboxylic acid [7-(1H-imidazol-2-ylcarbamoyl)-1H-benzoimidazol-2-yl]-amide |
| 59 | 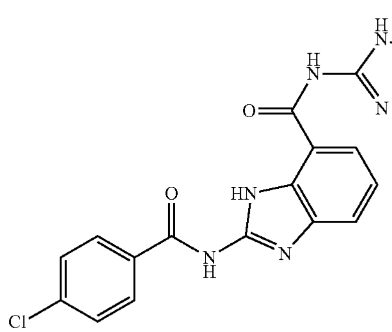 | 2-(4-Chloro-benzoylamino)-3H-benzoimidazole-4-carboxylic acid (1H-imidazol-2-yl)-amide |
| 60 | 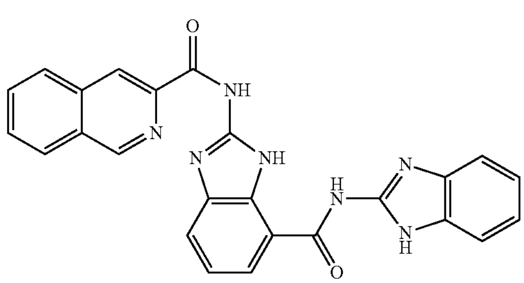 [SMILES: O=C(Nc1nc2cccc(C(=O)Nc3nc4ccccc4[nH]3)c2[nH]1)c1cc2ccccc2cn1] | Isoquinoline-3-carboxylic acid [7-(1H-benzoimidazol-2-ylcarbamoyl)-1H-benzoimidazol-2-yl]-amide |

TABLE 1-continued

| Ex. | Structure | Name |
|---|---|---|
| 61 | 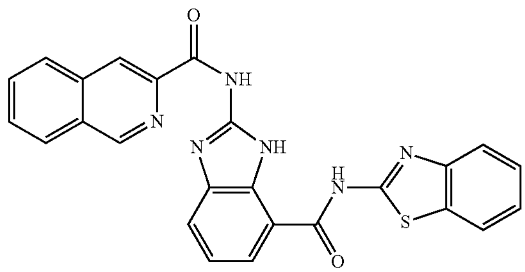 [SMILES: O=C(Nc1nc2cccc(C(=O)Nc3nc4ccccc4s3)c2[nH]1)c1cc2ccccc2cn1] | Isoquinoline-3-carboxylic acid [7-(benzothiazol-2-ylcarbamoyl)-1H-benzoimidazol-2-yl]-amide |
| 62 | 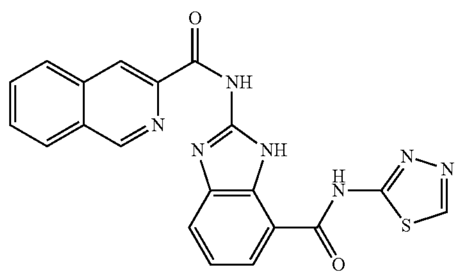 [SMILES: O=C(Nc1nc2cccc(C(=O)Nc3nncs3)c2[nH]1)c1cc2ccccc2cn1] | Isoquinoline-3-carboxylic acid [7-([1,3,4]thiadiazol-2-ylcarbamoyl)-1H-benzoimidazol-2-yl]-amide |
| 63 | 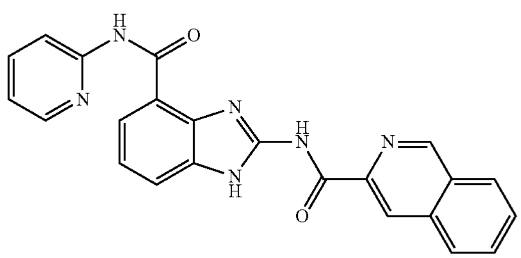 [SMILES: O=C(Nc1nc2c(C(=O)Nc3ccccn3)cccc2[nH]1)c1cc2ccccc2cn1] | Isoquinoline-3-carboxylic acid [4-(pyridin-2-ylcarbamoyl)-1H-benzoimidazol-2-yl]-amide |
| 64 | 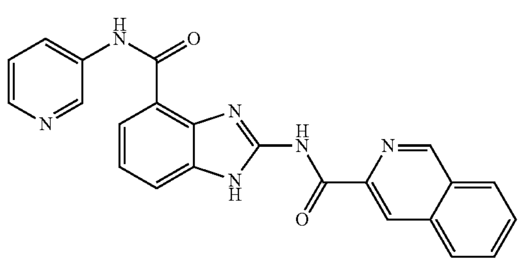 [SMILES: O=C(Nc1nc2c(C(=O)Nc3cccnc3)cccc2[nH]1)c1cc2ccccc2cn1] | Isoquinoline-3-carboxylic acid [4-(pyridin-3-ylcarbamoyl)-1H-benzoimidazol-2-yl]-amide |
| 65 | 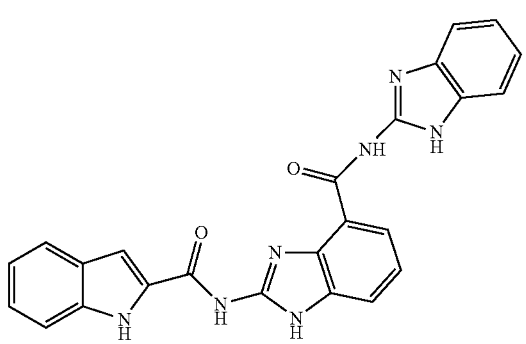 [SMILES: O=C(Nc1nc2c(C(=O)Nc3nc4ccccc4[nH]3)cccc2[nH]1)c1cc2ccccc2[nH]1] | 2-[(1H-Indole-2-carbonyl)-amino]-1H-benzoimidazole-4-carboxylic acid (1H-benzoimidazol-2-yl)-amide |

TABLE 1-continued

| Ex. | Structure | Name |
|---|---|---|
| 66 | 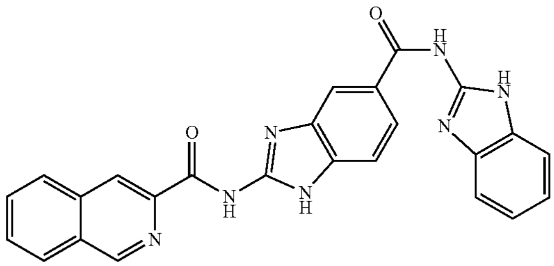 [SMILES: O=C(Nc1nc2ccccc2[nH]1)c1ccc2[nH]c(NC(=O)c3cc4ccccc4cn3)nc2c1] | Isoquinoline-3-carboxylic acid [5-(1H-benzoimidazol-2-ylcarbamoyl)-1H-benzoimidazol-2-yl]-amide |
| 67 | 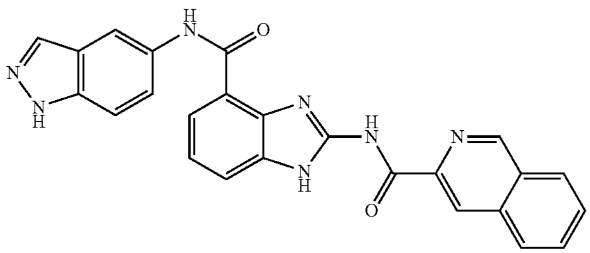 [SMILES: O=C(Nc1nc2c(C(=O)Nc3ccc4[nH]ncc4c3)cccc2[nH]1)c1cc2ccccc2cn1] | Isoquinoline-3-carboxylic acid [4-(1H-indazol-5-ylcarbamoyl)-1H-benzoimidazol-2-yl]-amide |
| 68 | 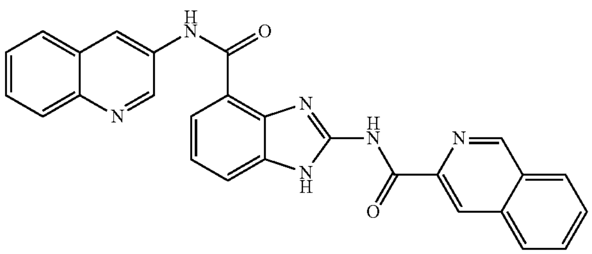 [SMILES: O=C(Nc1nc2c(C(=O)Nc3cnc4ccccc4c3)cccc2[nH]1)c1cc2ccccc2cn1] | Isoquinoline-3-carboxylic acid [4-(quinolin-3-ylcarbamoyl)-1H-benzoimidazol-2-yl]-amide |
| 69 | 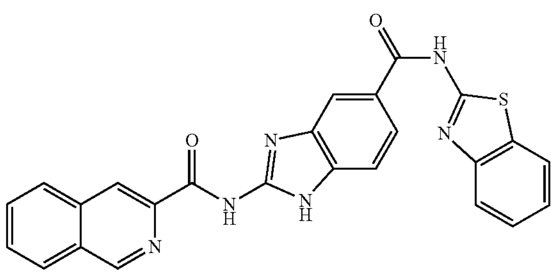 [SMILES: O=C(Nc1nc2ccccc2s1)c1ccc2[nH]c(NC(=O)c3cc4ccccc4cn3)nc2c1] | Isoquinoline-3-carboxylic acid [5-(benzothiazol-2-ylcarbamoyl)-1H-benzoimidazol-2-yl]-amide |
| 70 | 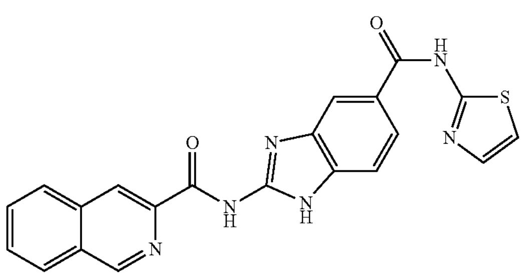 [SMILES: O=C(Nc1nccs1)c1ccc2[nH]c(NC(=O)c3cc4ccccc4cn3)nc2c1] | Isoquinoline-3-carboxylic acid [5-(thiazol-2-ylcarbamoyl)-1H-benzoimidazol-2-yl]-amide |
| 71 | 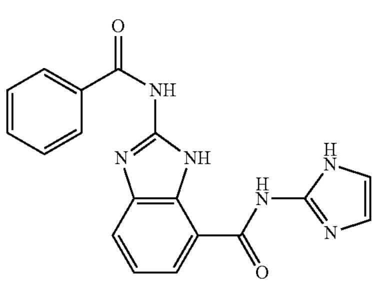 [SMILES: O=C(Nc1nc2cccc(C(=O)Nc3ncc[nH]3)c2[nH]1)c1ccccc1] | 2-Benzoylamino-3H-benzoimidazole-4-carboxylic acid (1H-imidazol-2-yl)-amide |

TABLE 1-continued

| Ex. | Structure | Name |
|---|---|---|
| 72 | 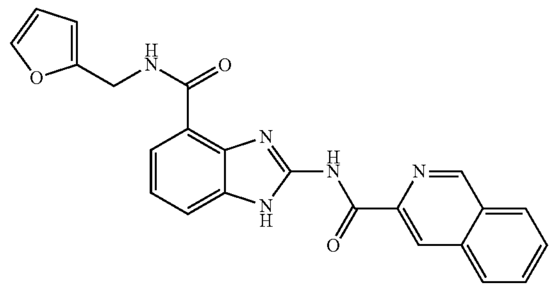 | Isoquinoline-3-carboxylic acid {4-[(furan-2-ylmethyl)-carbamoyl]-1H-benzoimidazol-2-yl}-amide |
| 73 | 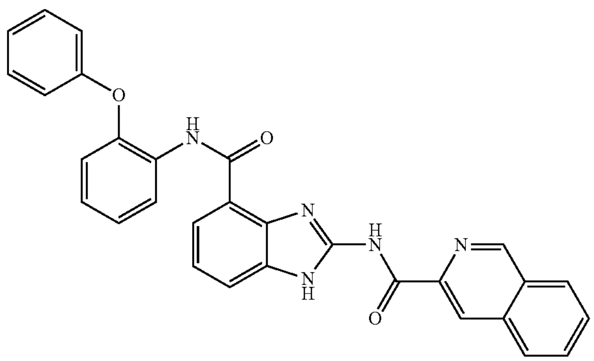 [SMILES: O=C(Nc1nc2c(C(=O)Nc3ccccc3Oc3ccccc3)cccc2[nH]1)c1cc2ccccc2cn1] | Isoquinoline-3-carboxylic acid [4-(2-phenoxy-phenylcarbamoyl)-1H-benzoimidazol-2-yl]-amide |
| 74 | 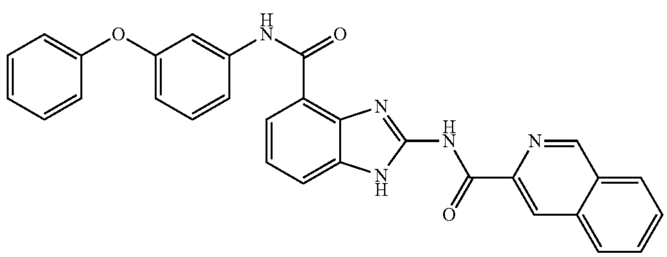 [SMILES: O=C(Nc1nc2c(C(=O)Nc3cccc(Oc4ccccc4)c3)cccc2[nH]1)c1cc2ccccc2cn1] | Isoquinoline-3-carboxylic acid [4-(3-phenoxy-phenylcarbamoyl)-1H-benzoimidazol-2-yl]-amide |
| 75 | 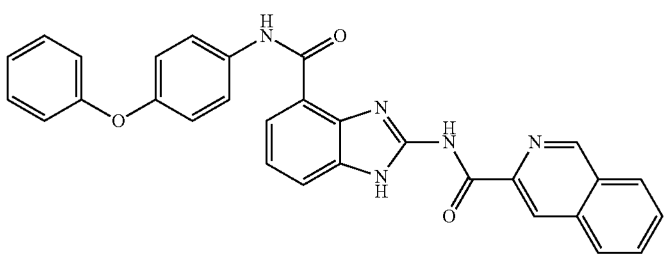 [SMILES: O=C(Nc1nc2c(C(=O)Nc3ccc(Oc4ccccc4)cc3)cccc2[nH]1)c1cc2ccccc2cn1] | Isoquinoline-3-carboxylic acid [4-(4-phenoxy-phenylcarbamoyl)-1H-benzoimidazol-2-yl]-amide |
| 76 | 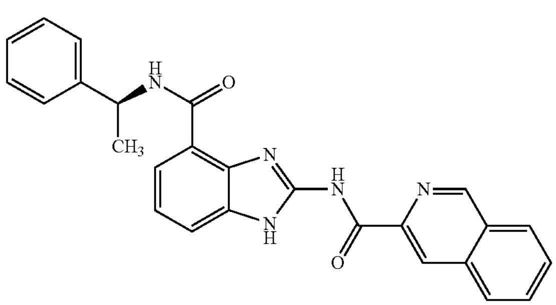 [SMILES: C[C@H](NC(=O)c1cccc2[nH]c(NC(=O)c3cc4ccccc4cn3)nc12)c1ccccc1] | Isoquinoline-3-carboxylic acid [4-(1S-phenyl-ethylcarbamoyl)-1H-benzoimidazol-2-yl]-amide |

TABLE 1-continued

| Ex. | Structure | Name |
|---|---|---|
| 77 | 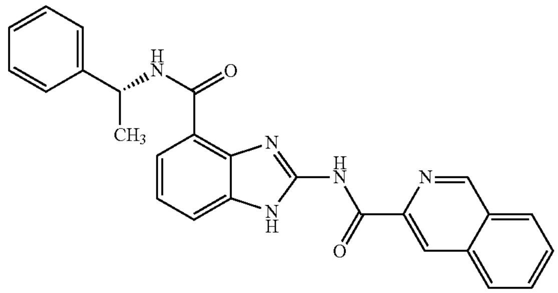 [SMILES: C[C@@H](NC(=O)c1cccc2[nH]c(NC(=O)c3cc4ccccc4cn3)nc12)c1ccccc1] | Isoquinoline-3-carboxylic acid [4-(1S-phenyl-ethylcarbamoyl)-1H-benzoimidazol-2-yl]-amide |
| 78 | 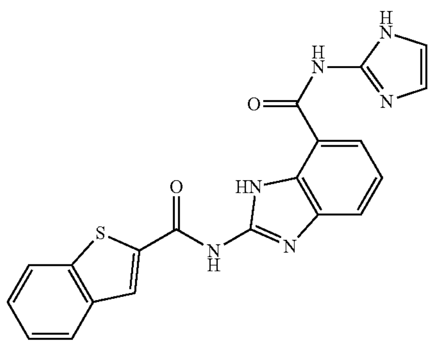 [SMILES: O=C(Nc1nc2cccc(C(=O)Nc3ncc[nH]3)c2[nH]1)c1cc2ccccc2s1] | 2-[(Benzo[b]thiophene-2-carbonyl)-amino]-3H-benzoimidazole-4-carboxylic acid (1H-imidazol-2-yl)-amide |
| 79 | 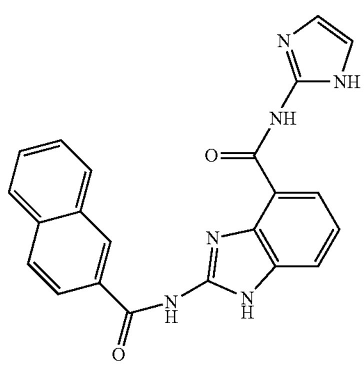 [SMILES: O=C(Nc1nc2c(C(=O)Nc3ncc[nH]3)cccc2[nH]1)c1ccc2ccccc2c1] | 2-[(Naphthalene-2-carbonyl)-amino]-1H-benzoimidazole-4-carboxylic acid (1H-imidazol-2-yl)-amide |
| 80 | 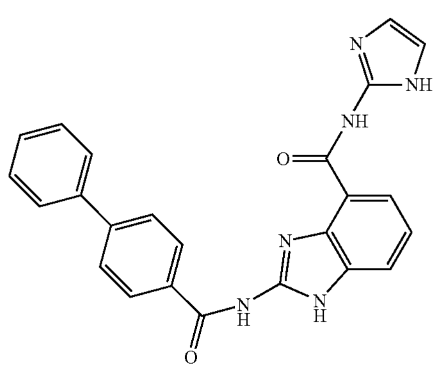 [SMILES: O=C(Nc1nc2c(C(=O)Nc3ncc[nH]3)cccc2[nH]1)c1ccc(-c2ccccc2)cc1] | 2-[(Biphenyl-4-carbonyl)-amino]-1H-benzoimidazole-4-carboxylic acid (1H-imidazol-2-yl)-amide |

TABLE 1-continued

| Ex. | Structure | Name |
|---|---|---|
| 81 | 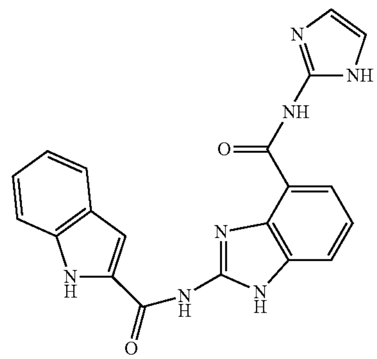 [SMILES: O=C(Nc1nc2c(C(=O)Nc3ncc[nH]3)cccc2[nH]1)c1cc2ccccc2[nH]1] | 2-[(1H-Indole-2-carbonyl)-amino]-1H-benzoimidazole-4-carboxylic acid (1H-imidazol-2-yl)-amide |
| 82 | 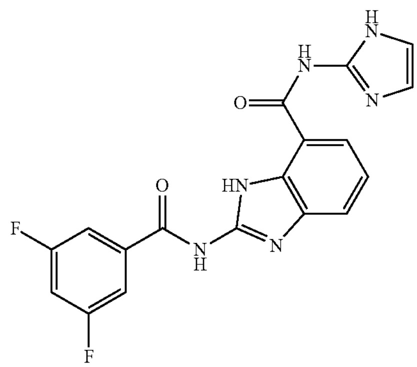 [SMILES: O=C(Nc1nc2cccc(C(=O)Nc3ncc[nH]3)c2[nH]1)c1cc(F)cc(F)c1] | 2-(3,5-Difluoro-benzoylamino)-3H-benzoimidazole-4-carboxylic acid (1H-imidazol-2-yl)-amide |
| 83 | 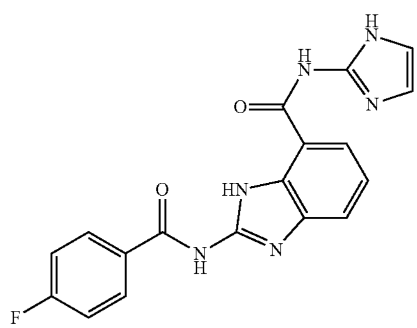 [SMILES: O=C(Nc1nc2cccc(C(=O)Nc3ncc[nH]3)c2[nH]1)c1ccc(F)cc1] | 2-(4-Fluoro-benzoylamino)-3H-benzoimidazole-4-carboxylic acid (1H-imidazol-2-yl)-amide |
| 84 | 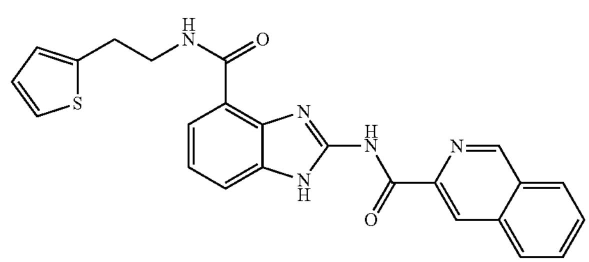 [SMILES: O=C(Nc1nc2c(C(=O)NCCc3cccs3)cccc2[nH]1)c1cc2ccccc2cn1] | Isoquinoline-3-carboxylic acid [4-(2-thiophen-2-yl-ethylcarbamoyl)-1H-benzoimidazol-2-yl]-amide |
| 85 | 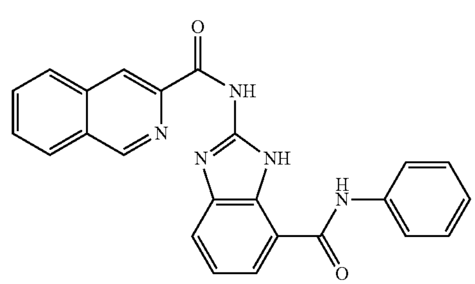 [SMILES: O=C(Nc1nc2cccc(C(=O)Nc3ccccc3)c2[nH]1)c1cc2ccccc2cn1] | soquinoline-3-carboxylic acid (7-phenylcarbamoyl-1H-benzoimidazol-2-yl)-amide |

TABLE 1-continued

| Ex. | Structure | Name |
|---|---|---|
| 86 | 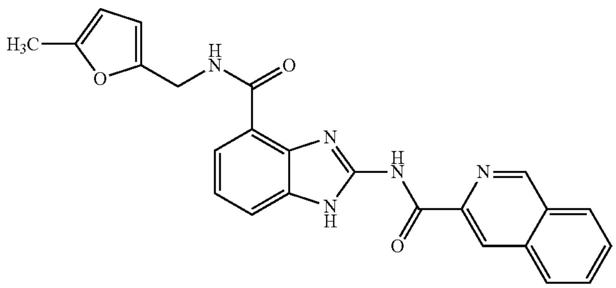 [SMILES: Cc1ccc(CNC(=O)c2cccc3[nH]c(NC(=O)c4cc5ccccc5cn4)nc23)o1] | Isoquinoline-3-carboxylic acid {4-[(5-methyl-furan-2-ylmethyl)-carbamoyl]-1H-benzoimidazol-2-yl}-amide |
| 87 | 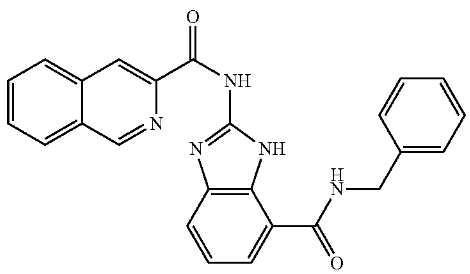 [SMILES: O=C(Nc1nc2cccc(C(=O)NCc3ccccc3)c2[nH]1)c1cc2ccccc2cn1] | Isoquinoline-3-carboxylic acid (7-benzylcarbamoyl-1H-benzoimidazol-2-yl)-amide |
| 88 | 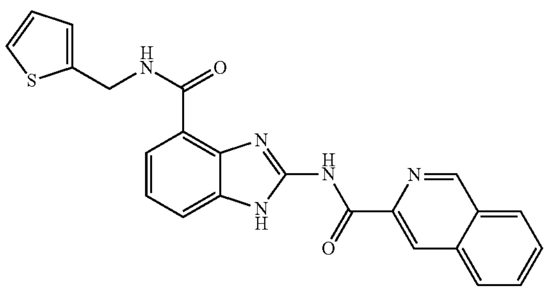 | Isoquinoline-3-carboxylic acid {4-[(thiophen-2-ylmethyl)-carbamoyl]-1H-benzoimidazol-2-yl}-amide |
| 89 | 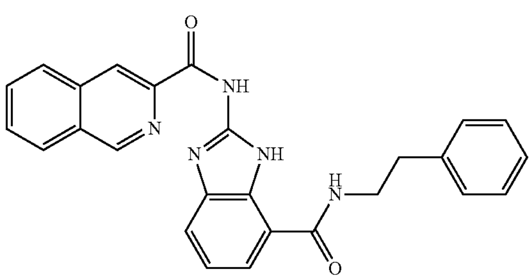 [SMILES: O=C(Nc1nc2cccc(C(=O)NCCc3ccccc3)c2[nH]1)c1cc2ccccc2cn1] | Isoquinoline-3-carboxylic acid (7-phenethylcarbamoyl-1H-benzoimidazol-2-yl)-amide |
| 90 | 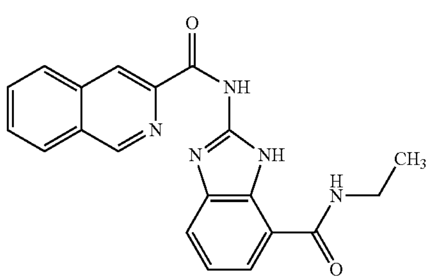 [SMILES: CCNC(=O)c1cccc2nc(NC(=O)c3cc4ccccc4cn3)[nH]c12] | Isoquinoline-3-carboxylic acid (7-ethylcarbamoyl-1H-benzoimidazol-2-yl)-amide |

TABLE 1-continued

| Ex. | Structure | Name |
|---|---|---|
| 91 | 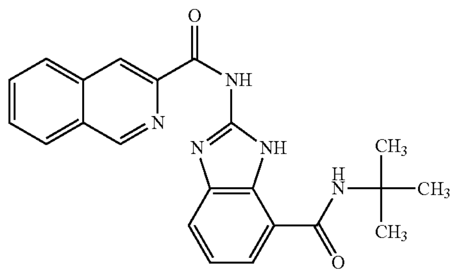 [SMILES: CC(C)(C)NC(=O)c1cccc2nc(NC(=O)c3cc4ccccc4cn3)[nH]c12] | Isoquinoline-3-carboxylic acid (7-tert-butylcarbamoyl-1H-benzoimidazol-2-yl)-amide |
| 92 | 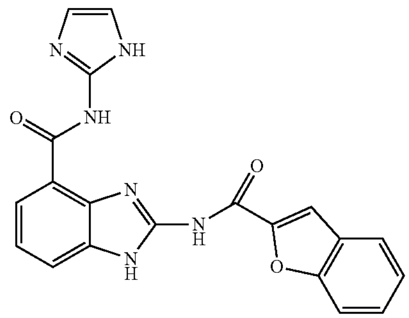 [SMILES: O=C(Nc1nc2c(C(=O)Nc3ncc[nH]3)cccc2[nH]1)c1cc2ccccc2o1] | 2-[(Benzofuran-2-carbonyl)-amino]-1H-benzoimidazole-4-carboxylic acid (1H-imidazol-2-yl)-amide |
| 93 | 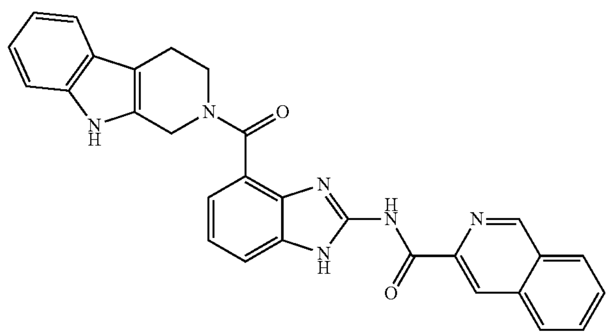 [SMILES: O=C(Nc1nc2c(C(=O)N3CCc4c([nH]c5ccccc45)C3)cccc2[nH]1)c1cc2ccccc2cn1] | Isoquinoline-3-carboxylic acid [4-(1,3,4,9-tetrahydro-beta-carboline-2-carbonyl)-1H-benzoimidazol-2-yl]-amide |
| 94 | 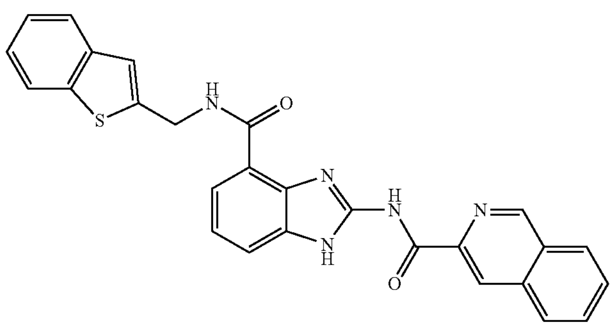 [SMILES: O=C(Nc1nc2c(C(=O)NCc3cc4ccccc4s3)cccc2[nH]1)c1cc2ccccc2cn1] | Isoquinoline-3-carboxylic acid {4-[(benzo[b]thiophen-2-ylmethyl)-carbamoyl]-1H-benzoimidazol-2-yl}-amide |
| 95 | 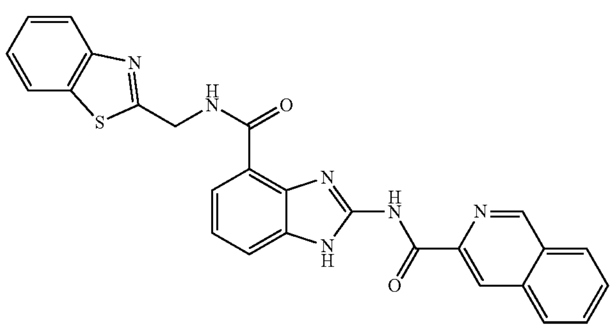 [SMILES: O=C(Nc1nc2c(C(=O)NCc3nc4ccccc4s3)cccc2[nH]1)c1cc2ccccc2cn1] | Isoquinoline-3-carboxylic acid {4-[(benzothiazol-2-ylmethyl)-carbamoyl]-1H-benzoimidazol-2-yl}-amide |

TABLE 1-continued

| Ex. | Structure | Name |
|---|---|---|
| 96 | 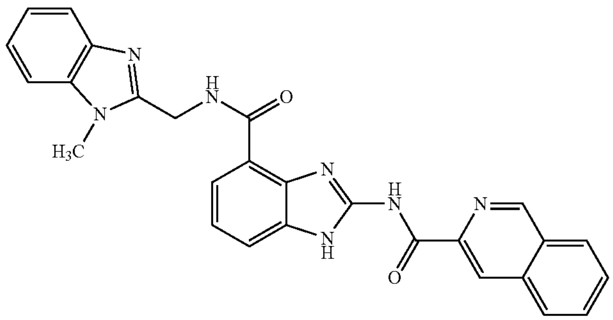 [SMILES: Cn1c(CNC(=O)c2cccc3[nH]c(NC(=O)c4cc5ccccc5cn4)nc23)nc2ccccc21] | Isoquinoline-3-carboxylic acid {4-[(1-methyl-1H-benzoimidazol-2-ylmethyl)-carbamoyl]-1H-enzoimidazol-2-yl}-amide |
| 97 | 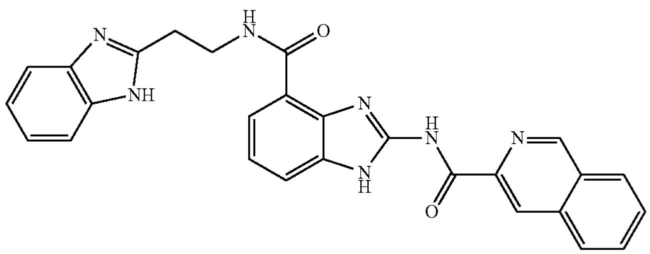 [SMILES: O=C(Nc1nc2c(C(=O)NCCc3nc4ccccc4[nH]3)cccc2[nH]1)c1cc2ccccc2cn1] | Isoquinoline-3-carboxylic acid {4-[2-(1H-benzoimidazol-2-yl)-ethylcarbamoyl]-1H-benzoimidazol-2-yl}-amide |
| 98 | 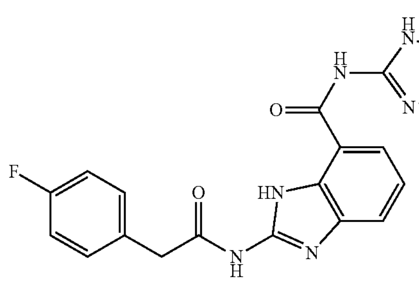 | 2-[2-(4-Fluoro-phenyl)-acetylamino]-3H-benzoimidazole-4-carboxylic acid (1H-imidazol-2-yl)-amide |
| 99 | 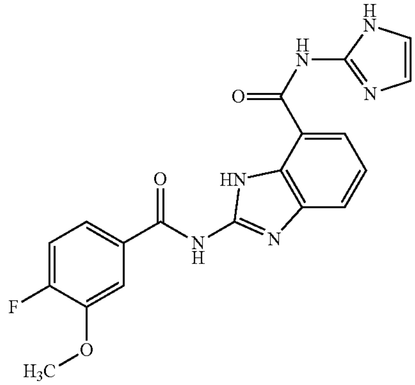 [SMILES: COc1cc(C(=O)Nc2nc3cccc(C(=O)Nc4ncc[nH]4)c3[nH]2)ccc1F] | 2-(4-Fluoro-3-methoxy-benzoylamino)-3H-benzoimidazole-4-carboxylic acid (1H-imidazol-2-yl)-amide |

TABLE 1-continued

| Ex. | Structure | Name |
|---|---|---|
| 100 | 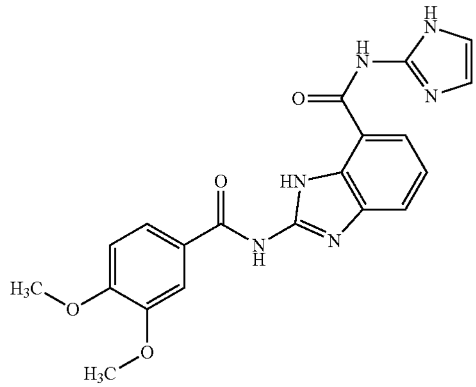 [SMILES: COc1ccc(C(=O)Nc2nc3cccc(C(=O)Nc4ncc[nH]4)c3[nH]2)cc1OC] | 2-(3,4-Dimethoxy-benzoylamino)-3H-benzoimidazole-4-carboxylic acid (1H-imidazol-2-yl)-amide |
| 101 | 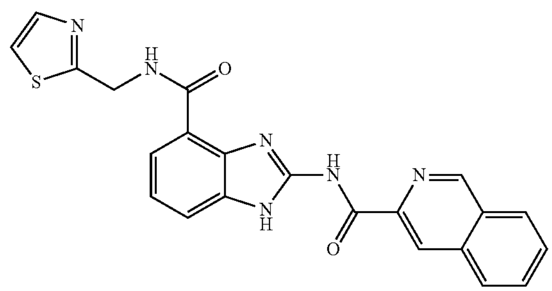 [SMILES: O=C(Nc1nc2c(C(=O)NCc3nccs3)cccc2[nH]1)c1cc2ccccc2cn1] | Isoquinoline-3-carboxylic acid {4-[(thiazol-2-ylmethyl)-carbamoyl]-1H-benzoimidazol-2-yl}-amide |
| 102 | 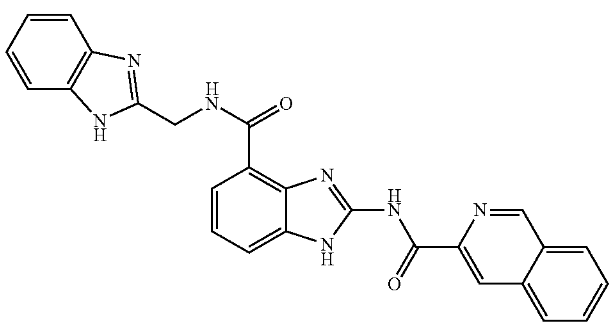 [SMILES: O=C(Nc1nc2c(C(=O)NCc3nc4ccccc4[nH]3)cccc2[nH]1)c1cc2ccccc2cn1] | Isoquinoline-3-carboxylic acid {4-[(1H-benzoimidazol-2-ylmethyl)-carbamoyl]-1H-benzoimidazol-2-yl}-amide |
| 103 | 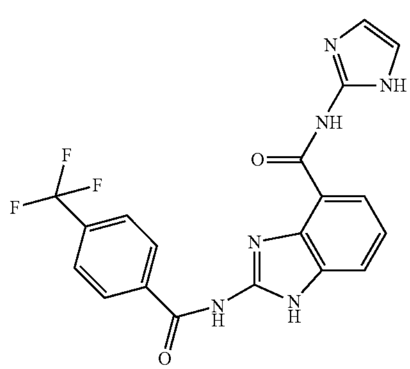 [SMILES: O=C(Nc1nc2c(C(=O)Nc3ncc[nH]3)cccc2[nH]1)c1ccc(C(F)(F)F)cc1] | 2-(4-Trifluoromethyl-benzoylamino)-1H-benzoimidazole-4-carboxylic acid (1H-imidazol-2-yl)-amide |

TABLE 1-continued
| Ex. | Structure | Name |
|---|---|---|
| 104 | 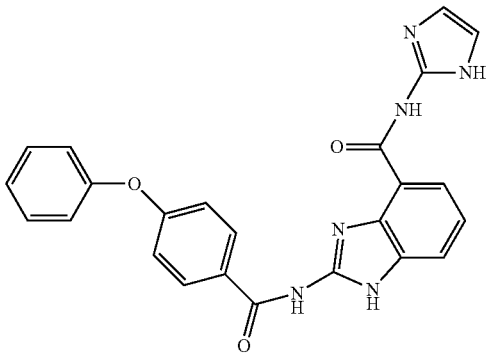 [SMILES: O=C(Nc1nc2c(C(=O)Nc3ncc[nH]3)cccc2[nH]1)c1ccc(Oc2ccccc2)cc1] | 2-(4-Phenoxy-benzoylamino)-1H-benzoimidazole-4-carboxylic acid (1H-imidazol-2-yl)-amide |
| 105 | 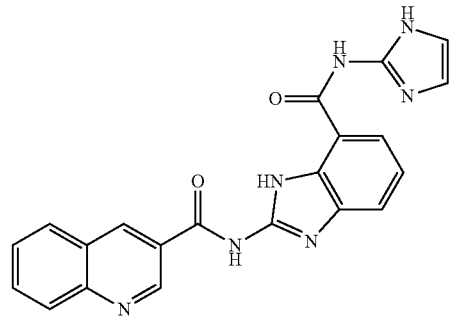 [SMILES: O=C(Nc1nc2cccc(C(=O)Nc3ncc[nH]3)c2[nH]1)c1cnc2ccccc2c1] | Quinoline-3-carboxylic acid [7-(1H-imidazol-2-ylcarbamoyl)-1H-benzoimidazol-2-yl]-amide |
| 106 | 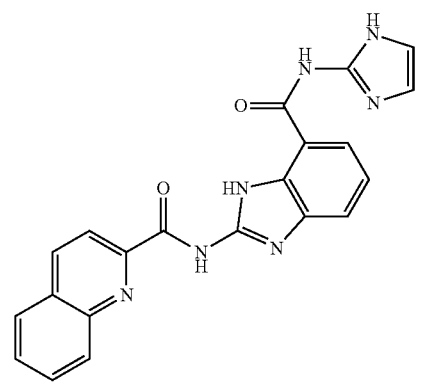 [SMILES: O=C(Nc1nc2cccc(C(=O)Nc3ncc[nH]3)c2[nH]1)c1ccc2ccccc2n1] | Quinoline-2-carboxylic acid [7-(1H-imidazol-2-ylcarbamoyl)-1H-benzoimidazol-2-yl]-amide |
| 107 | 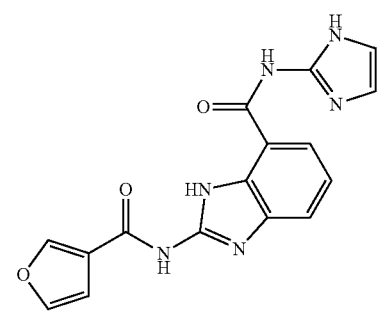 [SMILES: O=C(Nc1nc2cccc(C(=O)Nc3ncc[nH]3)c2[nH]1)c1ccoc1] | 2-[(Furan-3-carbonyl)-amino]-3H-benzoimidazole-4-carboxylic acid (1H-imidazol-2-yl)-amide |

TABLE 1-continued

| Ex. | Structure | Name |
|---|---|---|
| 108 | 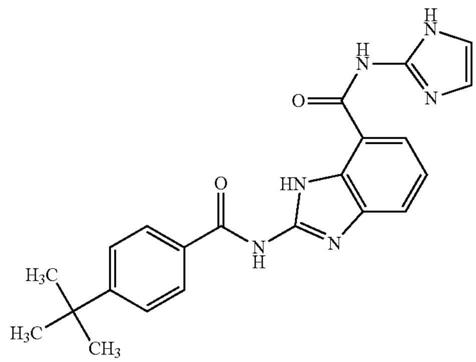 [SMILES: CC(C)(C)c1ccc(C(=O)Nc2nc3cccc(C(=O)Nc4ncc[nH]4)c3[nH]2)cc1] | 2-(4-tert-Butyl-benzoylamino)-3H-benzoimidazole-4-carboxylic acid (1H-imidazol-2-yl)-amide |
| 109 | 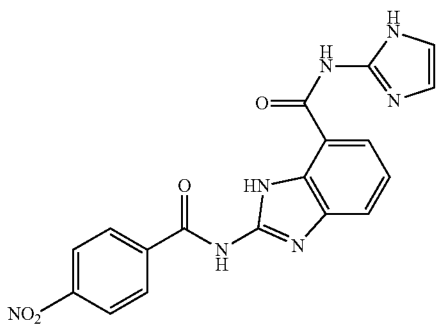 [SMILES: O=C(Nc1nc2cccc(C(=O)Nc3ncc[nH]3)c2[nH]1)c1ccc([N+](=O)[O-])cc1] | 2-(4-Nitro-benzoylamino)-3H-benzoimidazole-4-carboxylic acid (1H-imidazol-2-yl)-amide |
| 110 | 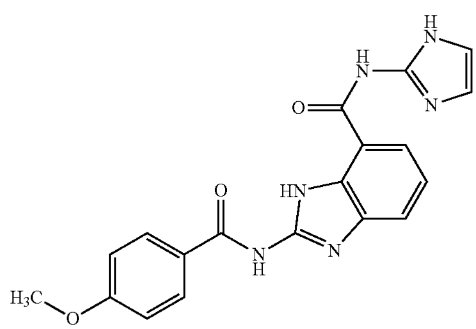 [SMILES: COc1ccc(C(=O)Nc2nc3cccc(C(=O)Nc4ncc[nH]4)c3[nH]2)cc1] | 2-(4-Methoxy-benzoylamino)-3H-benzoimidazole-4-carboxylic acid (1H-imidazol-2-yl)-amide |
| 111 | 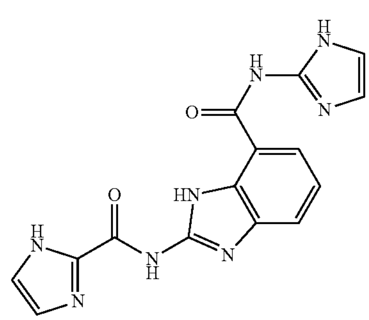 [SMILES: O=C(Nc1nc2cccc(C(=O)Nc3ncc[nH]3)c2[nH]1)c1ncc[nH]1] | 2-[(1H-Imidazole-2-carbonyl)-amino]-3H-benzoimidazole-4-carboxylic acid (1H-imidazol-2-yl)-amide |

TABLE 1-continued
| Ex. | Structure | Name |
|---|---|---|
| 112 | 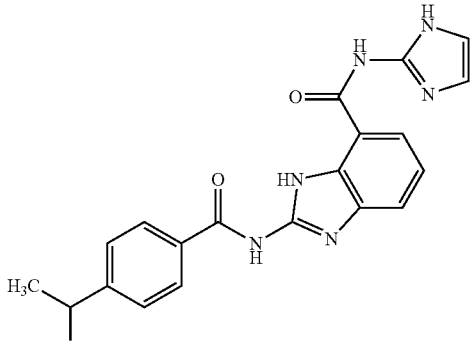 | 2-(4-Isopropyl-benzoylamino)-3H-benzoimidazole-4-carboxylic acid (1H-imidazol-2-yl)-amide |
| 113 | 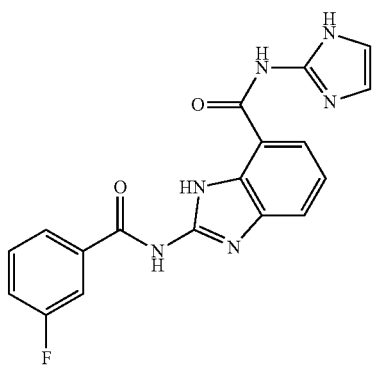 [SMILES: O=C(Nc1nc2cccc(C(=O)Nc3ncc[nH]3)c2[nH]1)c1cccc(F)c1] | 2-(3-Fluoro-benzoylamino)-3H-benzoimidazole-4-carboxylic acid (1H-imidazol-2-yl)-amide |
| 114 | 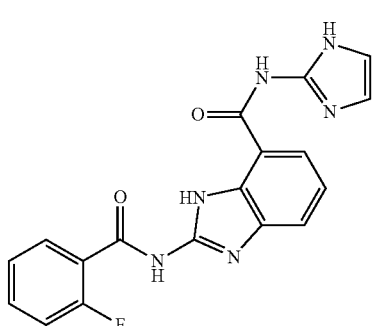 | 2-(2-Fluoro-benzoylamino)-3H-benzoimidazole-4-carboxylic acid (1H-imidazol-2-yl)-amide |
| 115 | 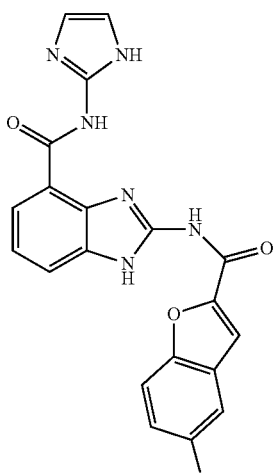 | 2-[(5-Chloro-benzofuran-2-carbonyl)-amino]-1H-benzoimidazole-4-carboxylic acid (1H-imidazol-2-yl)-amide |

TABLE 1-continued

| Ex. | Structure | Name |
|---|---|---|
| 116 | 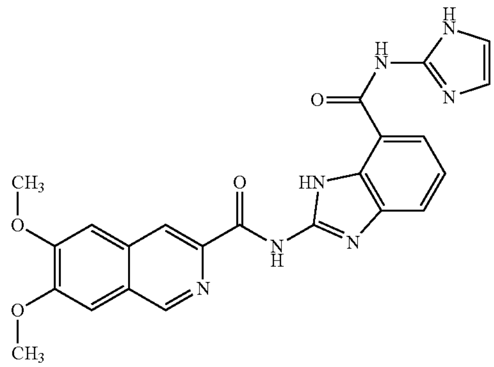 [SMILES: COc1cc2cnc(C(=O)Nc3nc4cccc(C(=O)Nc5ncc[nH]5)c4[nH]3)cc2cc1OC] | 6,7-Dimethoxy-isoquinoline-3-carboxylic acid [7-(1H-imidazol-2-ylcarbamoyl)-1H-benzoimidazol-2-yl]-amide |
| 117 | 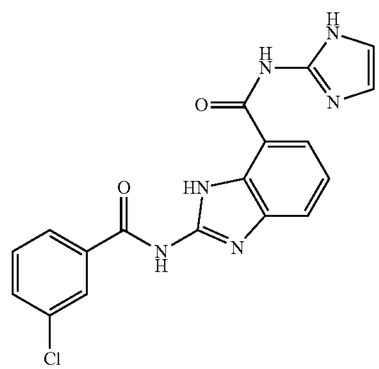 [SMILES: O=C(Nc1nc2cccc(C(=O)Nc3ncc[nH]3)c2[nH]1)c1cccc(Cl)c1] | 6,7-Dimethoxy-isoquinoline-3-carboxylic acid [7-(1H-imidazol-2-ylcarbamoyl)-1H-benzoimidazol-2-yl]-amide |
| 118 | 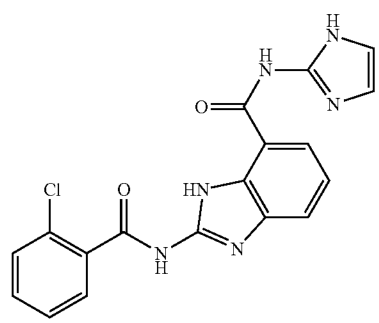 [SMILES: O=C(Nc1nc2cccc(C(=O)Nc3ncc[nH]3)c2[nH]1)c1ccccc1Cl] | 2-(2-Chloro-benzoylamino)-3H-benzoimidazole-4-carboxylic acid (1H-imidazol-2-yl)-amide |
| 119 | 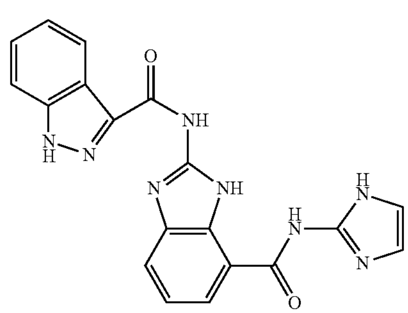 [SMILES: O=C(Nc1nc2cccc(C(=O)Nc3ncc[nH]3)c2[nH]1)c1n[nH]c2ccccc12] | 1H-Indazole-3-carboxylic acid [7-(1H-imidazol-2-ylcarbamoyl)-1H-benzoimidazol-2-yl]-amide |

TABLE 1-continued

| Ex. | Structure | Name |
| --- | --- | --- |
| 120 | 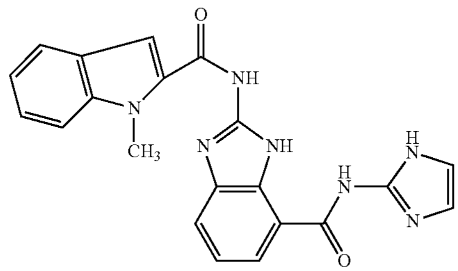 [SMILES: Cn1c(C(=O)Nc2nc3cccc(C(=O)Nc4ncc[nH]4)c3[nH]2)cc2ccccc21] | 2-[(1-Methyl-1H-indole-2-carbonyl)-amino]-3H-benzoimidazole-4-carboxylic acid (1H-imidazol-2-yl)-amide |
| 121 | 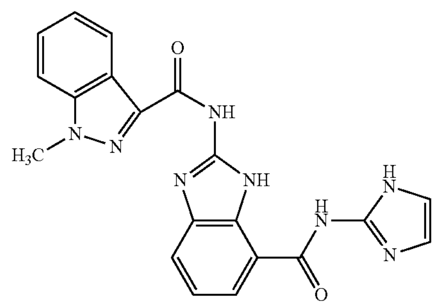 [SMILES: Cn1nc(C(=O)Nc2nc3cccc(C(=O)Nc4ncc[nH]4)c3[nH]2)c2ccccc21] | 1-Methyl-1H-indazole-3-carboxylic acid [7-(1H-imidazol-2-ylcarbamoyl)-1H-benzoimidazol-2-yl]-amide |
| 122 | 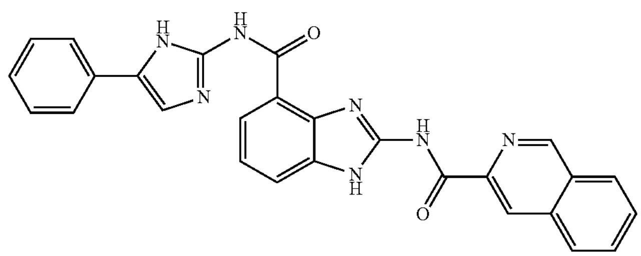 [SMILES: O=C(Nc1nc2c(C(=O)Nc3ncc(-c4ccccc4)[nH]3)cccc2[nH]1)c1cc2ccccc2cn1] | Isoquinoline-3-carboxylic acid [4-(5-phenyl-1H-imidazol-2-ylcarbamoyl)-1H-benzoimidazol-2-yl]-amide |
| 123 | 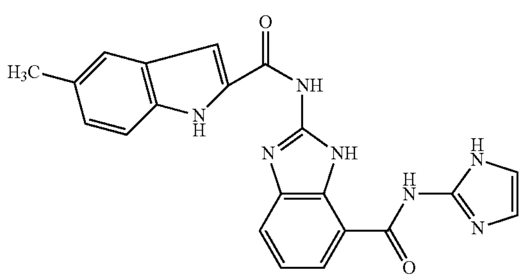 [SMILES: Cc1ccc2[nH]c(C(=O)Nc3nc4cccc(C(=O)Nc5ncc[nH]5)c4[nH]3)cc2c1] | 2-[(5-Methyl-1H-indole-2-carbonyl)-amino]-3H-benzoimidazole-4-carboxylic acid (1H-imidazol-2-yl)-amide |
| 124 | 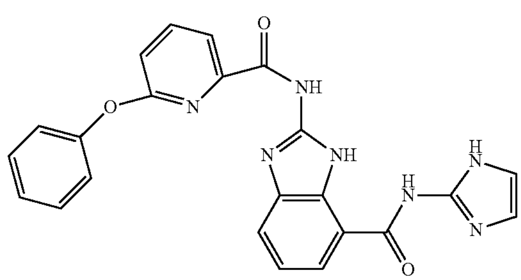 [SMILES: O=C(Nc1nc2cccc(C(=O)Nc3ncc[nH]3)c2[nH]1)c1cccc(Oc2ccccc2)n1] | 2-[(6-Phenoxy-pyridine-2-carbonyl)-amino]-3H-benzoimidazole-4-carboxylic acid (1H-imidazol-2-yl)-amide |

TABLE 1-continued

| Ex. | Structure | Name |
|---|---|---|
| 125 | 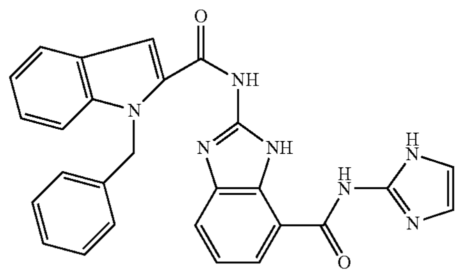 [SMILES: O=C(Nc1ncc[nH]1)c1cccc2nc(NC(=O)c3cc4ccccc4n3Cc3ccccc3)[nH]c12] | 2-[(1-Benzyl-1H-indole-2-carbonyl)-amino]-3H-benzoimidazole-4-carboxylic acid (1H-imidazol-2-yl)-amide |
| 126 | 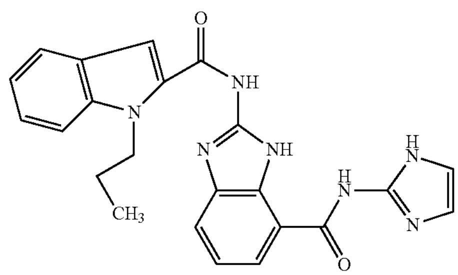 [SMILES: CCCn1c(C(=O)Nc2nc3cccc(C(=O)Nc4ncc[nH]4)c3[nH]2)cc2ccccc21] | 2-[(1-Propyl-1H-indole-2-carbonyl)-amino]-3H-benzoimidazole-4-carboxylic acid (1H-imidazol-2-yl)-amide |
| 127 | 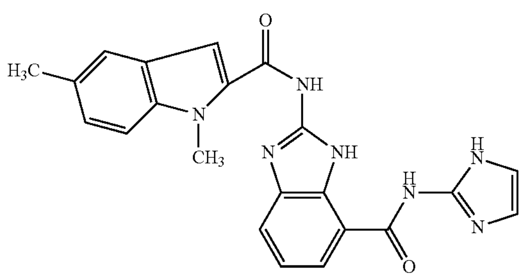 [SMILES: Cc1ccc2c(c1)cc(C(=O)Nc1nc3cccc(C(=O)Nc4ncc[nH]4)c3[nH]1)n2C] | 2-[(1,5-Dimethyl-1H-indole-2-carbonyl)-amino]-3H-benzoimidazole-4-carboxylic acid (1H-imidazol-2-yl)-amide |
| 128 | 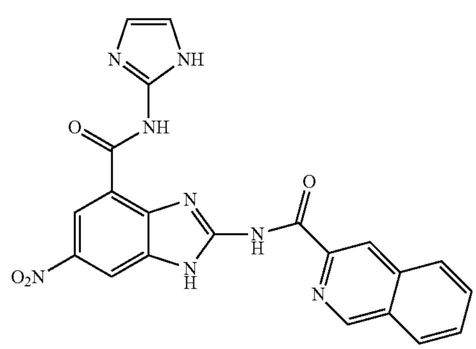 [SMILES: O=C(Nc1nc2c(C(=O)Nc3ncc[nH]3)cc([N+](=O)[O-])cc2[nH]1)c1cc2ccccc2cn1] | Isoquinoline-3-carboxylic acid [4-(1H-imidazol-2-ylcarbamoyl)-6-nitro-1H-benzoimidazol-2-yl]-amide |
| 129 | 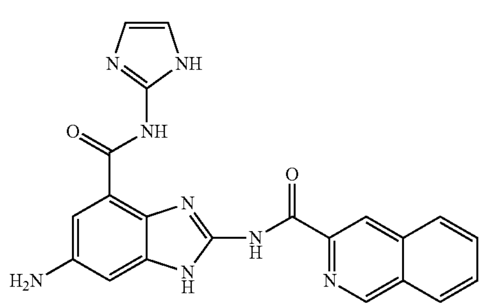 [SMILES: Nc1cc(C(=O)Nc2ncc[nH]2)c2nc(NC(=O)c3cc4ccccc4cn3)[nH]c2c1] | Isoquinoline-3-carboxylic acid [6-amino-4-(1H-imidazol-2-ylcarbamoyl)-1H-benzoimidazol-2-yl]-amide |

| Ex. | Structure | Name |
|---|---|---|
| 130 | 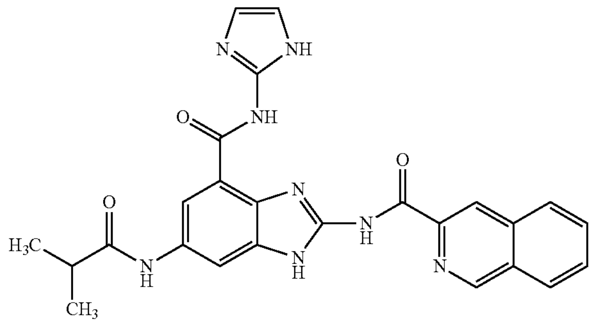 [SMILES: CC(C)C(=O)Nc1cc(C(=O)Nc2ncc[nH]2)c2nc(NC(=O)c3cc4ccccc4cn3)[nH]c2c1] | Isoquinoline-3-carboxylic acid [4-(1H-imidazol-2-ylcarbamoyl)-6-isobutyrylamino-1H-benzoimidazol-2-yl]-amide |
| 131 | 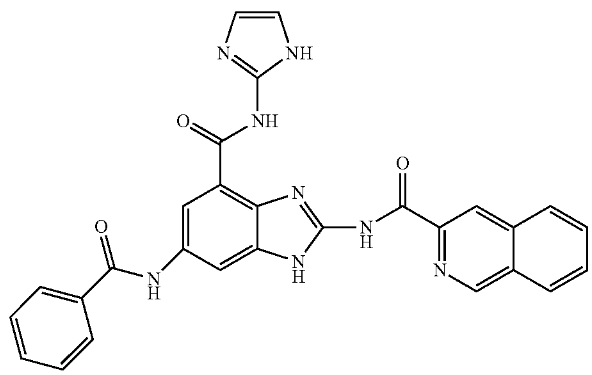 [SMILES: O=C(Nc1cc(C(=O)Nc2ncc[nH]2)c2nc(NC(=O)c3cc4ccccc4cn3)[nH]c2c1)c1ccccc1] | Isoquinoline-3-carboxylic acid [6-benzoylamino-4-(1H-imidazol-2-ylcarbamoyl)-1H-benzoimidazol-2-yl]-amide |
| 132 | 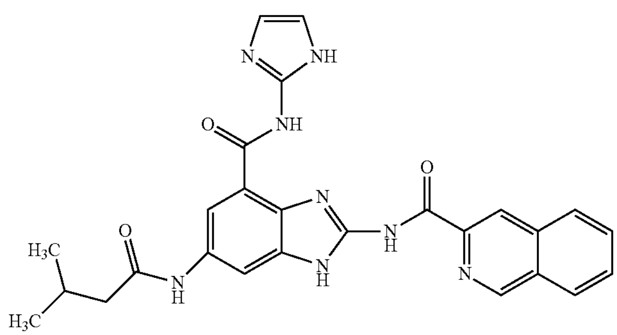 [SMILES: CC(C)CC(=O)Nc1cc(C(=O)Nc2ncc[nH]2)c2nc(NC(=O)c3cc4ccccc4cn3)[nH]c2c1] | Isoquinoline-3-carboxylic acid [4-(1H-imidazol-2-ylcarbamoyl)-6-(3-methyl-butyrylamino)-1H-benzoimidazol-2-yl]-amide |
| 133 | 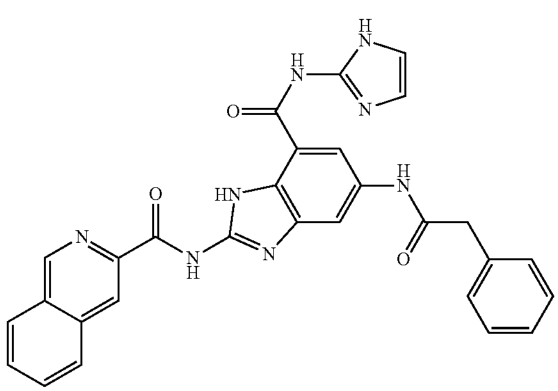 [SMILES: O=C(Cc1ccccc1)Nc1cc(C(=O)Nc2ncc[nH]2)c2[nH]c(NC(=O)c3cc4ccccc4cn3)nc2c1] | Isoquinoline-3-carboxylic acid [7-(1H-imidazol-2-ylcarbamoyl)-5-phenylacetylamino-1H-benzoimidazol-2-yl]-amide |

TABLE 1-continued

| Ex. | Structure | Name |
|---|---|---|
| 134 | 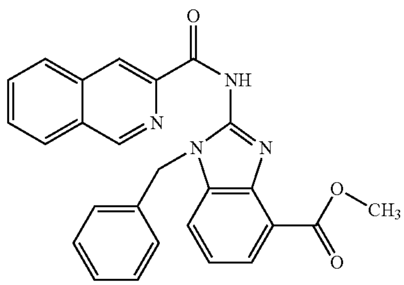 [SMILES: COC(=O)c1cccc2c1nc(NC(=O)c1cc3ccccc3cn1)n2Cc1ccccc1] | 1-Benzyl-2-[(isoquinoline-3-carbonyl)-amino]-1H-benzoimidazole-4-carboxylic acid methyl ester |
| 135 | 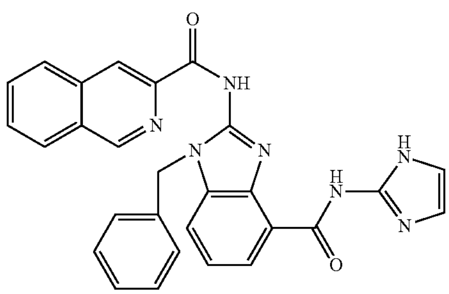 [SMILES: O=C(Nc1nc2c(C(=O)Nc3ncc[nH]3)cccc2n1Cc1ccccc1)c1cc2ccccc2cn1] | Isoquinoline-3-carboxylic acid [1-benzyl-4-(1H-imidazol-2-ylcarbamoyl)-1H-benzoimidazol-2-yl]-amide |
| 136 | 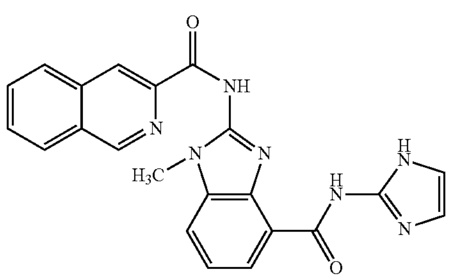 [SMILES: Cn1c(NC(=O)c2cc3ccccc3cn2)nc2c(C(=O)Nc3ncc[nH]3)cccc21] | Isoquinoline-3-carboxylic acid [4-(1H-imidazol-2-ylcarbamoyl)-1-methyl-1H-benzoimidazol-2-yl]-amide |
| 137 | 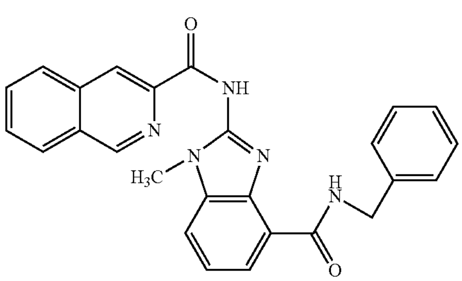 [SMILES: Cn1c(NC(=O)c2cc3ccccc3cn2)nc2c(C(=O)NCc3ccccc3)cccc21] | Isoquinoline-3-carboxylic acid (4-benzylcarbamoyl-1-methyl-1H-benzoimidazol-2-yl)-amide |
| 138 | 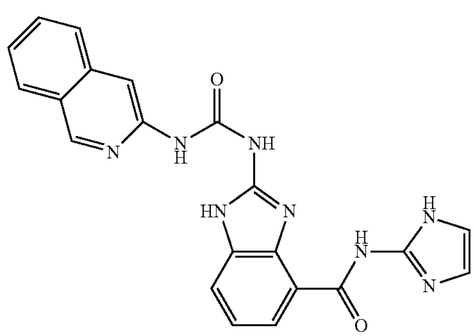 [SMILES: O=C(Nc1cc2ccccc2cn1)Nc1nc2c(C(=O)Nc3ncc[nH]3)cccc2[nH]1] | 2-(3-Isoquinolin-3-yl-ureido)-1H-benzoimidazole-4-carboxylic acid (1H-imidazol-2-yl)-amide |

TABLE 1-continued

| Ex. | Structure | Name |
| --- | --- | --- |
| 139 | 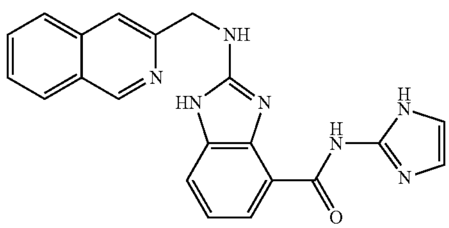 [SMILES: O=C(Nc1ncc[nH]1)c1cccc2[nH]c(NCc3cc4ccccc4cn3)nc12] | 2-[(Isoquinolin-3-ylmethyl)-amino]-1H-benzoimidazole-4-carboxylic acid (1H-imidazol-2-yl)-amide |
| 140 | 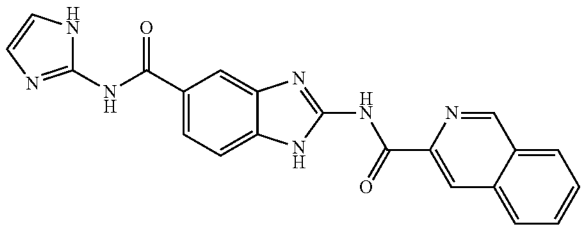 [SMILES: O=C(Nc1ncc[nH]1)c1ccc2[nH]c(NC(=O)c3cc4ccccc4cn3)nc2c1] | Isoquinoline-3-carboxylic acid [5-(1H-imidazol-2-ylcarbamoyl)-1H-benzoimidazol-2-yl]-amide |
| 141 | 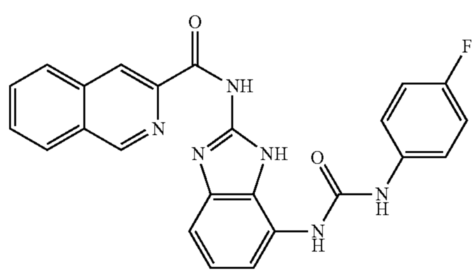 [SMILES: O=C(Nc1ccc(F)cc1)Nc1cccc2nc(NC(=O)c3cc4ccccc4cn3)[nH]c12] | Isoquinoline-3-carboxylic acid {7-[3-(4-fluoro-phenyl)-ureido]-1H-benzoimidazol-2-yl}-amide |
| 142 | 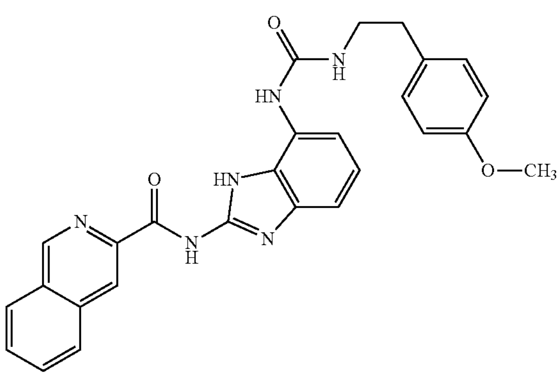 [SMILES: COc1ccc(CCNC(=O)Nc2cccc3nc(NC(=O)c4cc5ccccc5cn4)[nH]c23)cc1] | Isoquinoline-3-carboxylic acid (7-{3-[2-(4-methoxy-phenyl)-ethyl]-ureido}-1H-benzoimidazol-2-yl)-amide |
| 143 | 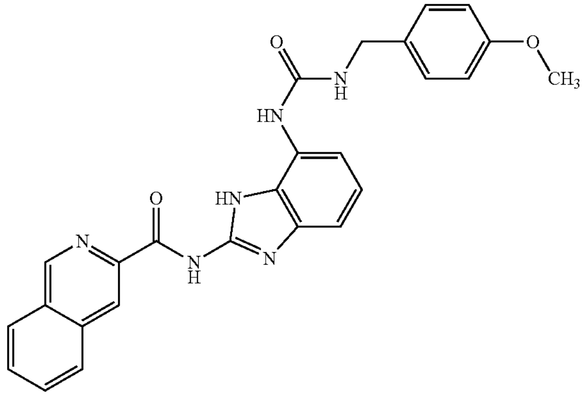 [SMILES: COc1ccc(CNC(=O)Nc2cccc3nc(NC(=O)c4cc5ccccc5cn4)[nH]c23)cc1] | Isoquinoline-3-carboxylic acid {7-[3-(4-methoxy-benzyl)-ureido]-1H-benzoimidazol-2-yl}-amide |

TABLE 1-continued

| Ex. | Structure | Name |
|---|---|---|
| 144 | 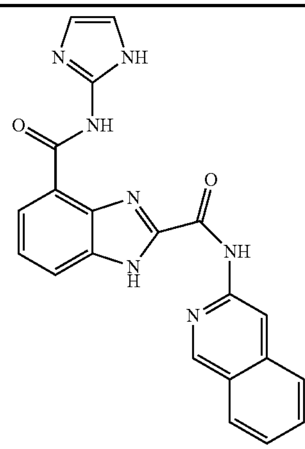 | 1H-Benzoimidazole-2,4-dicarboxylic acid 4-[(1H-imidazol-2-yl)-amide] 2-isoquinolin-3-ylamide |
| 145 | 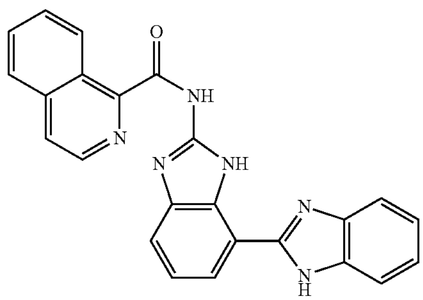 [SMILES: O=C(Nc1nc2cccc(-c3nc4ccccc4[nH]3)c2[nH]1)c1nccc2ccccc12] | Isoquinoline-1-carboxylic acid (1H,3'H-[2,4']bibenzoimidazolyl-2'-yl)-amide |
| 146 | 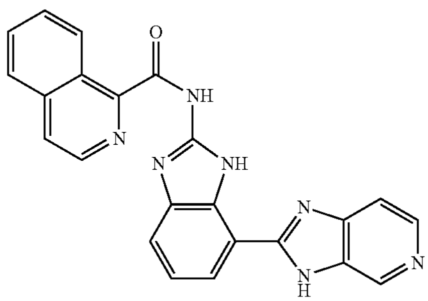 [SMILES: O=C(Nc1nc2cccc(-c3nc4ccncc4[nH]3)c2[nH]1)c1nccc2ccccc12] | Isoquinoline-1-carboxylic acid [7-(3H-imidazo[4,5-c]pyridin-2-yl)-1H-benzoimidazol-2-yl]-amide |
| 147 | 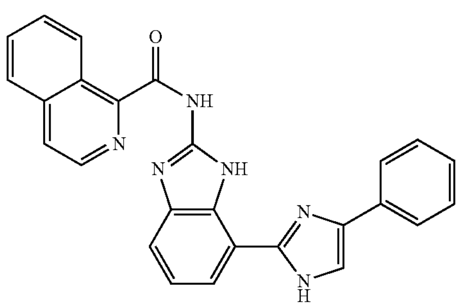 [SMILES: O=C(Nc1nc2cccc(-c3nc(-c4ccccc4)c[nH]3)c2[nH]1)c1nccc2ccccc12] | Isoquinoline-1-carboxylic acid [7-(4-phenyl-1H-imidazol-2-yl)-1H-benzoimidazol-2-yl]-amide |
| 148 | 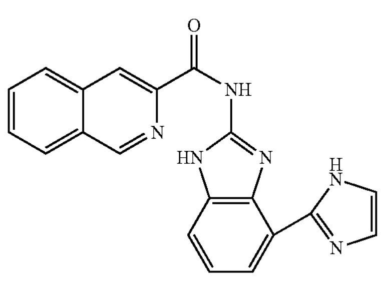 [SMILES: O=C(Nc1nc2c(-c3ncc[nH]3)cccc2[nH]1)c1cc2ccccc2cn1] | Isoquinoline-3-carboxylic acid [4-(1H-imidazol-2-yl)-1H-benzoimidazol-2-yl]-amide |

TABLE 1-continued

| Ex. | Structure | Name |
|---|---|---|
| 149 | 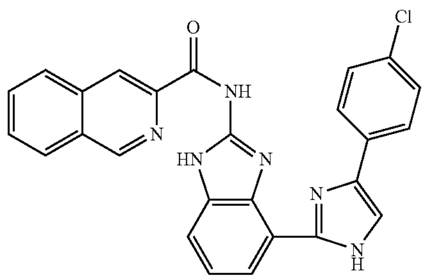 [SMILES: O=C(Nc1nc2c(-c3nc(-c4ccc(Cl)cc4)c[nH]3)cccc2[nH]1)c1cc2ccccc2cn1] | Isoquinoline-3-carboxylic acid {4-[4-(4-chloro-phenyl)-1H-imidazol-2-yl]-1H-benzoimidazol-2-yl}-amide |
| 150 | 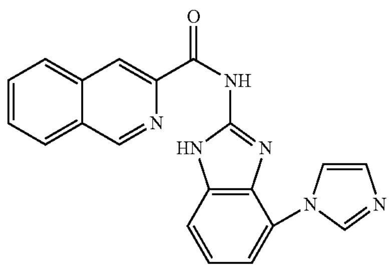 [SMILES: O=C(Nc1nc2c(-n3ccnc3)cccc2[nH]1)c1cc2ccccc2cn1] | Isoquinoline-3-carboxylic acid (4-imidazol-1-yl-1H-benzoimidazol-2-yl)-amide |
| 151 | 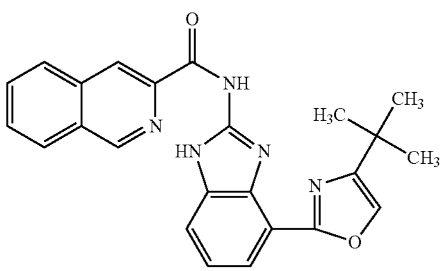 [SMILES: CC(C)(C)c1coc(-c2cccc3[nH]c(NC(=O)c4cc5ccccc5cn4)nc23)n1] | Isoquinoline-3-carboxylic acid [4-(4-tert-butyl-oxazol-2-yl)-1H-benzoimidazol-2-yl]-amide |
| 152 | 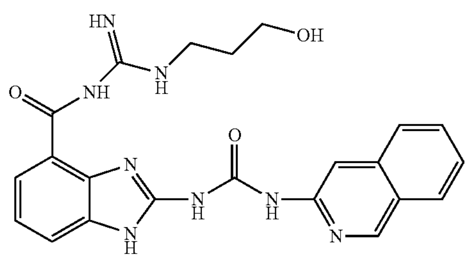 [SMILES: N=C(NCCCO)NC(=O)c1cccc2[nH]c(NC(=O)Nc3cc4ccccc4cn3)nc12] | 1-{4-[N'-(3-Hydroxy-propyl)-guanidinocarbonyl]-1H-benzoimidazol-2-yl}-3-isoquinolin-3-yl-urea |
| 153 | 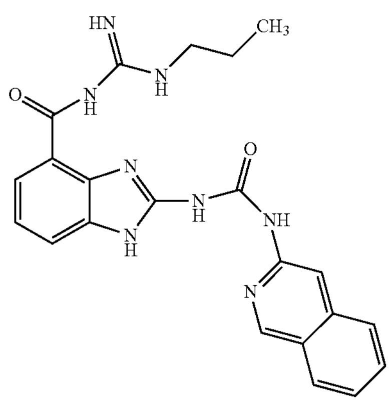 [SMILES: CCCNC(=N)NC(=O)c1cccc2[nH]c(NC(=O)Nc3cc4ccccc4cn3)nc12] | 1-Isoquinolin-3-yl-3-[4-(N'-propyl-guanidinocarbonyl)-1H-benzoimidazol-2-yl]-urea |

TABLE 1-continued

| Ex. | Structure | Name |
| --- | --- | --- |
| 154 | 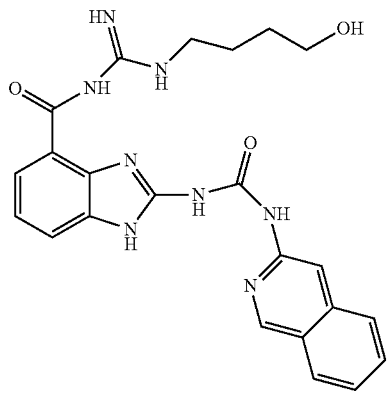 [SMILES: N=C(NCCCCO)NC(=O)c1cccc2[nH]c(NC(=O)Nc3cc4ccccc4cn3)nc12] | 1-{4-[N'-(4-Hydroxy-butyl)-guanidinocarbonyl]-1H-benzoimidazol-2-yl}-3-isoquinolin-3-yl-urea |
| 155 | 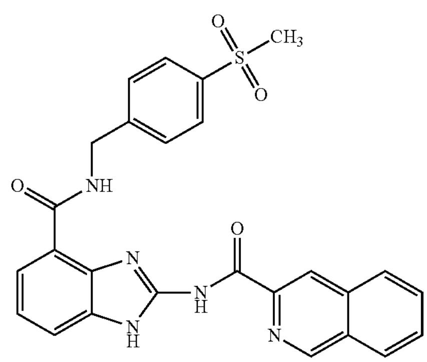 [SMILES: CS(=O)(=O)c1ccc(CNC(=O)c2cccc3[nH]c(NC(=O)c4cc5ccccc5cn4)nc23)cc1] | Isoquinoline-3-carboxylic acid [4-(4-methanesulfonyl-benzylcarbamoyl)-1H-benzoimidazol-2-yl]-amide |
| 156 | 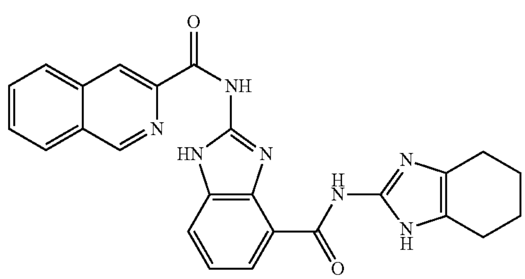 [SMILES: O=C(Nc1nc2c(C(=O)Nc3nc4c([nH]3)CCCC4)cccc2[nH]1)c1cc2ccccc2cn1] | Isoquinoline-3-carboxylic acid [4-(4,5,6,7-tetrahydro-1H-benzoimidazol-2-ylcarbamoyl)-1H-benzoimidazol-2-yl]-amide |
| 157 | 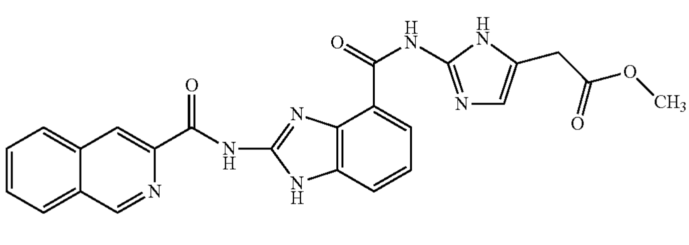 [SMILES: COC(=O)Cc1cnc(NC(=O)c2cccc3[nH]c(NC(=O)c4cc5ccccc5cn4)nc23)[nH]1] | 2-({2-[(Isoquinoline-3-carbonyl)-amino]-1H-benzoimidazole-4-carbonyl}-amino)-3H-imidazol-4-yl]-acetic acid methyl ester |
| 158 | 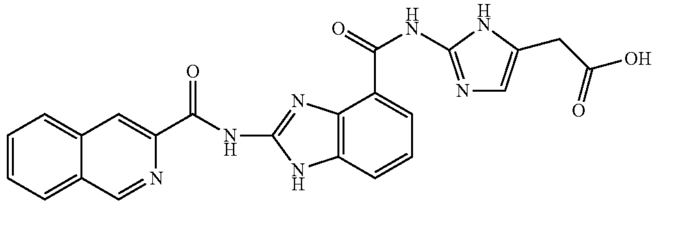 [SMILES: O=C(O)Cc1cnc(NC(=O)c2cccc3[nH]c(NC(=O)c4cc5ccccc5cn4)nc23)[nH]1] | [2-({2-[(Isoquinoline-3-carbonyl)-amino]-1H-benzoimidazole-4-carbonyl}-amino)-3H-imidazol-4-yl]-acetic acid |

TABLE 1-continued

| Ex. | Structure | Name |
|---|---|---|
| 159 | 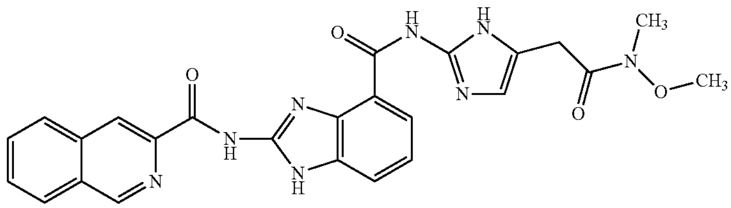 [SMILES: CON(C)C(=O)Cc1cnc(NC(=O)c2cccc3[nH]c(NC(=O)c4cc5ccccc5cn4)nc23)[nH]1] | Isoquinoline-3-carboxylic acid (4-{5-[(methoxy-methyl-carbamoyl)-methyl]-1H-imidazol-2-ylcarbamoyl}-1H-benzoimidazol-2-yl)-amide |
| 160 | 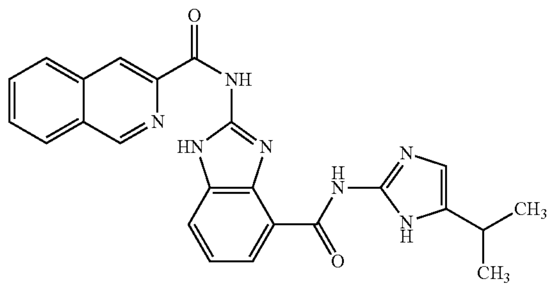 [SMILES: CC(C)c1cnc(NC(=O)c2cccc3[nH]c(NC(=O)c4cc5ccccc5cn4)nc23)[nH]1] | Isoquinoline-3-carboxylic acid [4-(5-isopropyl-1H-imidazol-2-ylcarbamoyl)-1H-benzoimidazol-2-yl]-amide |
| 161 | 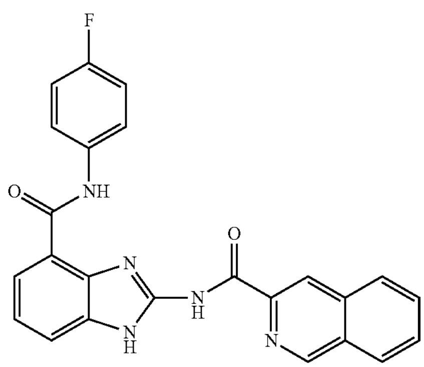 [SMILES: O=C(Nc1nc2c(C(=O)Nc3ccc(F)cc3)cccc2[nH]1)c1cc2ccccc2cn1] | Isoquinoline-3-carboxylic acid [4-(4-fluoro-phenylcarbamoyl)-1H-benzoimidazol-2-yl]-amide |
| 162 | 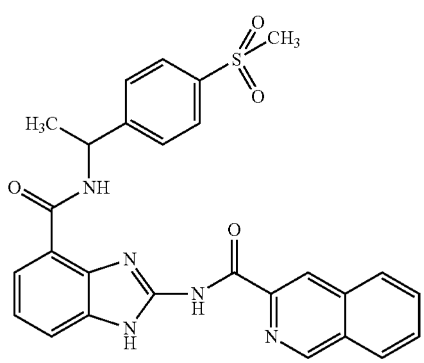 [SMILES: CC(NC(=O)c1cccc2[nH]c(NC(=O)c3cc4ccccc4cn3)nc12)c1ccc(S(C)(=O)=O)cc1] | Isoquinoline-3-carboxylic acid {4-[1-(4-methanesulfonyl-phenyl)-ethylcarbamoyl]-1H-benzoimidazol-2-yl}-amide |
| 163 | 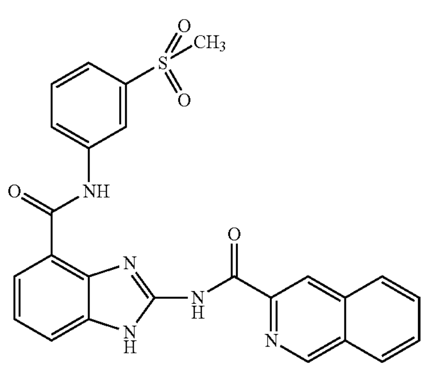 [SMILES: CS(=O)(=O)c1cccc(NC(=O)c2cccc3[nH]c(NC(=O)c4cc5ccccc5cn4)nc23)c1] | Isoquinoline-3-carboxylic acid [4-(3-methanesulfonyl-phenylcarbamoyl)-1H-benzoimidazol-2-yl]-amide |

| Ex. | Structure | Name |
|---|---|---|
| 164 | 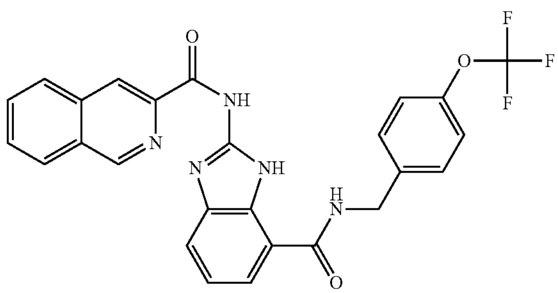 [SMILES: O=C(Nc1nc2cccc(C(=O)NCc3ccc(OC(F)(F)F)cc3)c2[nH]1)c1cc2ccccc2cn1] | Isoquinoline-3-carboxylic acid [7-(4-trifluoromethoxy-benzylcarbamoyl)-1H-benzoimidazol-2-yl]-amide |
| 165 | 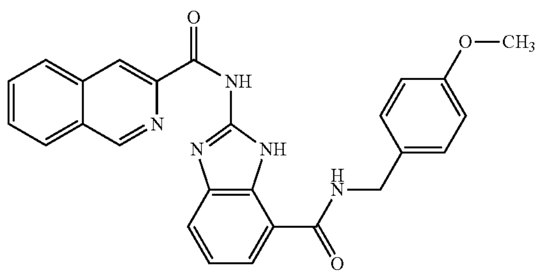 [SMILES: COc1ccc(CNC(=O)c2cccc3nc(NC(=O)c4cc5ccccc5cn4)[nH]c23)cc1] | Isoquinoline-3-carboxylic acid [7-(4-methoxy-benzylcarbamoyl)-1H-benzoimidazol-2-yl]-amide |
| 166 | 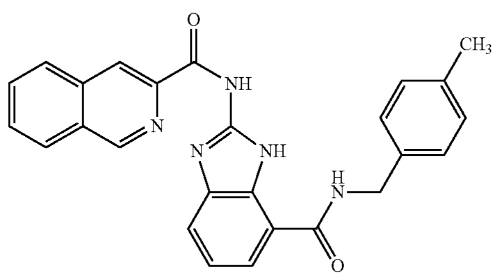 [SMILES: Cc1ccc(CNC(=O)c2cccc3nc(NC(=O)c4cc5ccccc5cn4)[nH]c23)cc1] | Isoquinoline-3-carboxylic acid [7-(4-methyl-benzylcarbamoyl)-1H-benzoimidazol-2-yl]-amide |
| 167 | 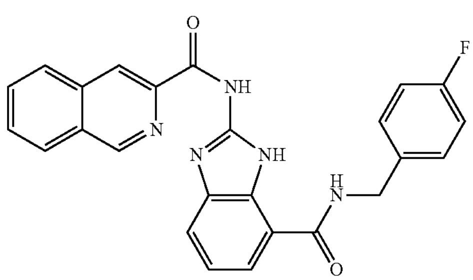 [SMILES: O=C(Nc1nc2cccc(C(=O)NCc3ccc(F)cc3)c2[nH]1)c1cc2ccccc2cn1] | Isoquinoline-3-carboxylic acid [7-(4-fluoro-benzylcarbamoyl)-1H-benzoimidazol-2-yl]-amide |
| 168 | 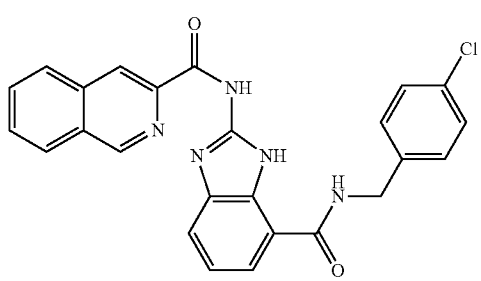 [SMILES: O=C(Nc1nc2cccc(C(=O)NCc3ccc(Cl)cc3)c2[nH]1)c1cc2ccccc2cn1] | Isoquinoline-3-carboxylic acid [7-(4-chloro-benzylcarbamoyl)-1H-benzoimidazol-2-yl]-amide |

TABLE 1-continued

| Ex. | Structure | Name |
|---|---|---|
| 169 | 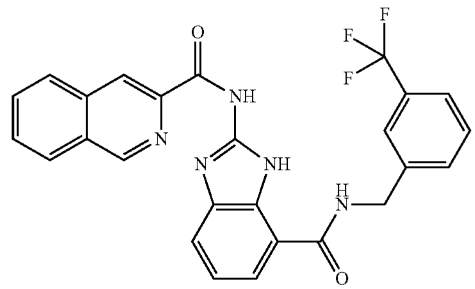 [SMILES: O=C(Nc1nc2cccc(C(=O)NCc3cccc(C(F)(F)F)c3)c2[nH]1)c1cc2ccccc2cn1] | Isoquinoline-3-carboxylic acid [7-(3-trifluoromethyl-enzylcarbamoyl)-1H-benzoimidazol-2-yl]-amide |
| 170 | 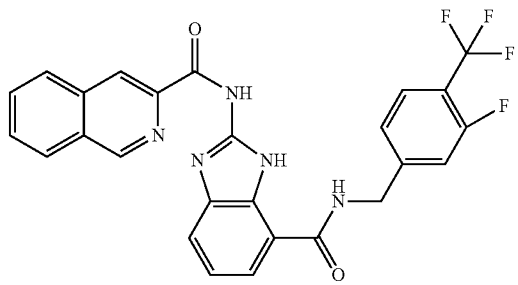 [SMILES: O=C(Nc1nc2cccc(C(=O)NCc3ccc(C(F)(F)F)c(F)c3)c2[nH]1)c1cc2ccccc2cn1] | Isoquinoline-3-carboxylic acid [7-(3-fluoro-4-trifluoromethyl-benzylcarbamoyl)-1H-benzoimidazol-2-yl]-amide |
| 171 | 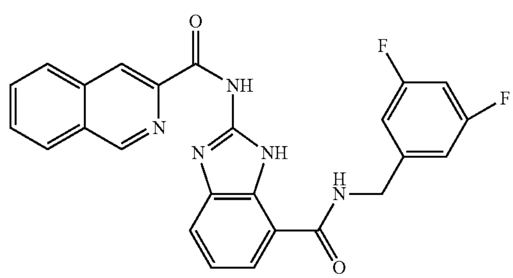 [SMILES: O=C(Nc1nc2cccc(C(=O)NCc3cc(F)cc(F)c3)c2[nH]1)c1cc2ccccc2cn1] | Isoquinoline-3-carboxylic acid [7-(3,5-difluoro-benzylcarbamoyl)-1H-benzoimidazol-2-yl]-amide |
| 172 | 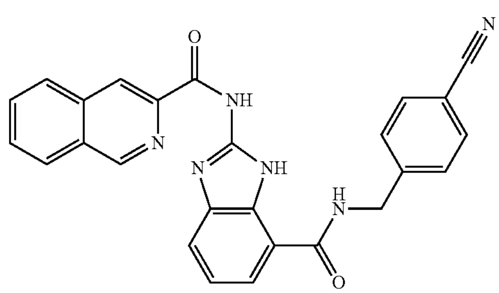 [SMILES: N#Cc1ccc(CNC(=O)c2cccc3nc(NC(=O)c4cc5ccccc5cn4)[nH]c23)cc1] | Isoquinoline-3-carboxylic acid [7-(4-cyano-benzylcarbamoyl)-1H-benzoimidazol-2-yl]-amide |
| 173 | 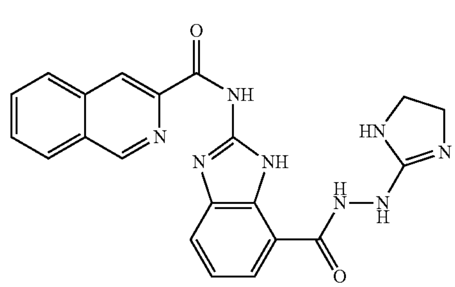 [SMILES: O=C(Nc1nc2cccc(C(=O)NNC3=NCCN3)c2[nH]1)c1cc2ccccc2cn1] | Isoquinoline-3-carboxylic acid {7-[N'-(4,5-dihydro-1H-imidazol-2-yl)-hydrazinocarbonyl]-1H-benzoimidazol-2-yl}-amide |

TABLE 1-continued

| Ex. | Structure | Name |
| --- | --- | --- |
| 174 | 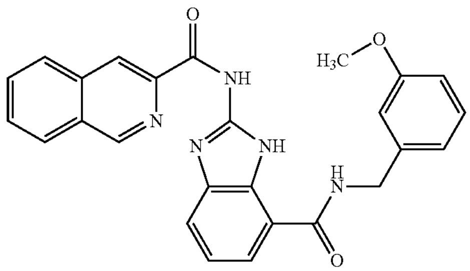 [SMILES: COc1cccc(CNC(=O)c2cccc3nc(NC(=O)c4cc5ccccc5cn4)[nH]c23)c1] | Isoquinoline-3-carboxylic acid [7-(3-methoxy-benzylcarbamoyl)-1H-benzoimidazol-2-yl]-amide |
| 175 | 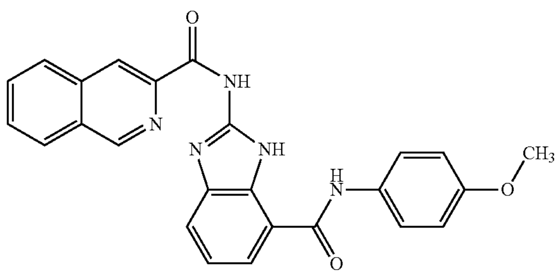 [SMILES: COc1ccc(NC(=O)c2cccc3nc(NC(=O)c4cc5ccccc5cn4)[nH]c23)cc1] | Isoquinoline-3-carboxylic acid [7-(4-methoxy-phenylcarbamoyl)-1H-benzoimidazol-2-yl]-amide |
| 176 | 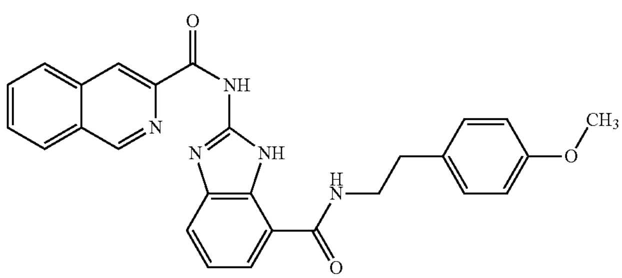 [SMILES: COc1ccc(CCNC(=O)c2cccc3nc(NC(=O)c4cc5ccccc5cn4)[nH]c23)cc1] | Isoquinoline-3-carboxylic acid {7-[2-(4-methoxy-phenyl)-ethylcarbamoyl]-1H-benzoimidazol-2-yl}-amide |
| 177 | 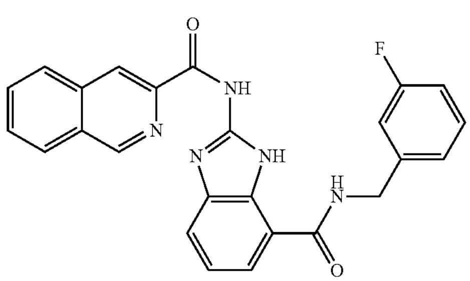 [SMILES: O=C(Nc1nc2cccc(C(=O)NCc3cccc(F)c3)c2[nH]1)c1cc2ccccc2cn1] | Isoquinoline-3-carboxylic acid [7-(3-fluoro-benzylcarbamoyl)-1H-benzoimidazol-2-yl]-amide |
| 178 | 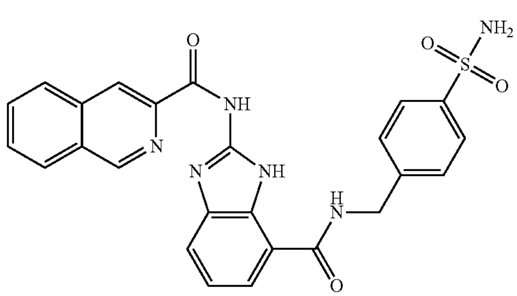 [SMILES: NS(=O)(=O)c1ccc(CNC(=O)c2cccc3nc(NC(=O)c4cc5ccccc5cn4)[nH]c23)cc1] | Isoquinoline-3-carboxylic acid [7-(4-sulfamoyl-benzylcarbamoyl)-1H-benzoimidazol-2-yl]-amide |

TABLE 1-continued

| Ex. | Structure | Name |
|---|---|---|
| 179 | 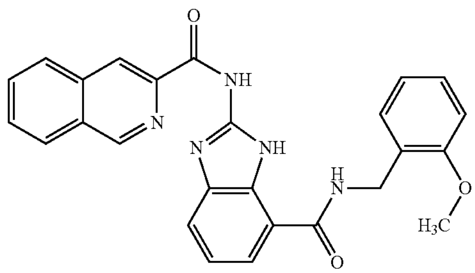 [SMILES: COc1ccccc1CNC(=O)c1cccc2nc(NC(=O)c3cc4ccccc4cn3)[nH]c12] | Isoquinoline-3-carboxylic acid [7-(2-methoxy-benzylcarbamoyl)-1H-benzoimidazol-2-yl]-amide |
| 180 | 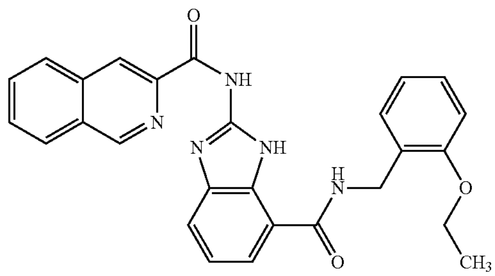 [SMILES: CCOc1ccccc1CNC(=O)c1cccc2nc(NC(=O)c3cc4ccccc4cn3)[nH]c12] | Isoquinoline-3-carboxylic acid [7-(2-ethoxy-benzylcarbamoyl)-1H-benzoimidazol-2-yl]-amide |
| 181 | 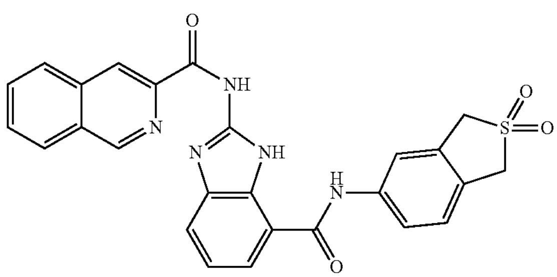 [SMILES: O=C(Nc1nc2cccc(C(=O)Nc3ccc4c(c3)CS(=O)(=O)C4)c2[nH]1)c1cc2ccccc2cn1] | Isoquinoline-3-carboxylic acid [7-(2,2-dioxo-1,3-dihydrobenzo[c]thiophen-5-ylcarbamoyl)-1H-benzoimidazol-2-yl]-amide |
| 182 | 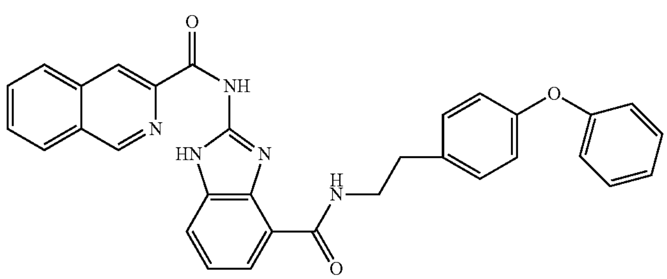 [SMILES: O=C(Nc1nc2c(C(=O)NCCc3ccc(Oc4ccccc4)cc3)cccc2[nH]1)c1cc2ccccc2cn1] | Isoquinoline-3-carboxylic acid {4-[2-(4-phenoxy-phenyl)-ethylcarbamoyl]-1H-benzoimidazol-2-yl}-amide |
| 183 | 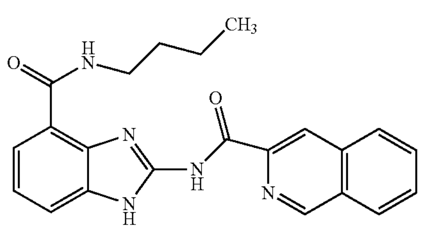 [SMILES: CCCCNC(=O)c1cccc2[nH]c(NC(=O)c3cc4ccccc4cn3)nc12] | Isoquinoline-3-carboxylic acid (4-butylcarbamoyl-1H-benzoimidazol-2-yl)-amide |
| 184 | 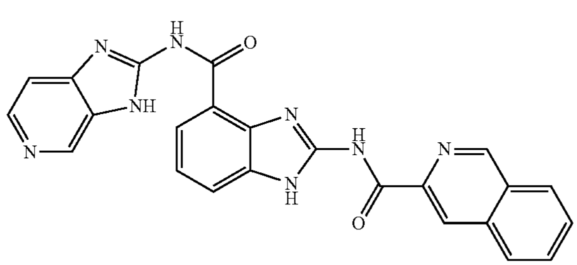 [SMILES: O=C(Nc1nc2c(C(=O)Nc3nc4ccncc4[nH]3)cccc2[nH]1)c1cc2ccccc2cn1] | Isoquinoline-3-carboxylic acid [4-(3H-imidazo[4,5-c]pyridin-2-ylcarbamoyl)-1H-benzoimidazol-2-yl]-amide |

TABLE 1-continued

| Ex. | Structure | Name |
|---|---|---|
| 185 | 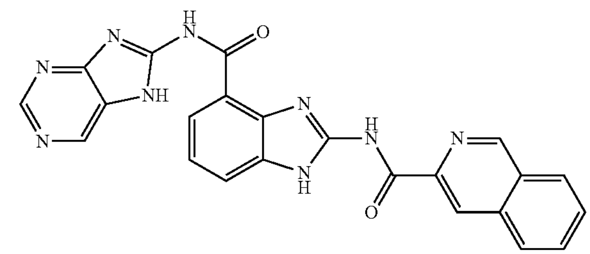 [SMILES: O=C(Nc1nc2c(C(=O)Nc3nc4ncncc4[nH]3)cccc2[nH]1)c1cc2ccccc2cn1] | Isoquinoline-3-carboxylic acid [4-(7H-purin-8-ylcarbamoyl)-1H-benzoimidazol-2-yl]-amide |
| 186 | 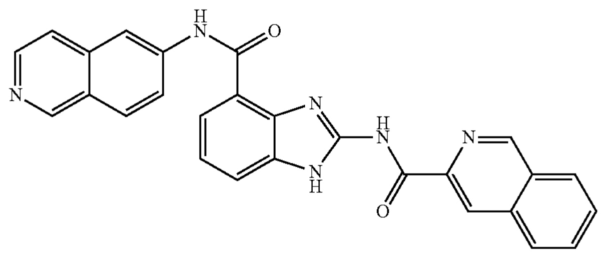 [SMILES: O=C(Nc1nc2c(C(=O)Nc3ccc4cnccc4c3)cccc2[nH]1)c1cc2ccccc2cn1] | Isoquinoline-3-carboxylic acid [4-(isoquinolin-6-ylcarbamoyl)-1H-benzoimidazol-2-yl]-amide |
| 187 | 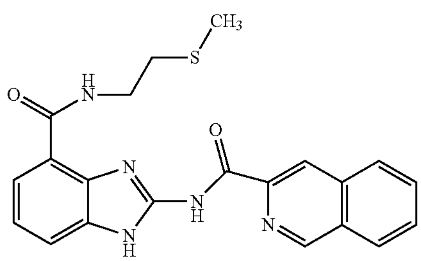 [SMILES: CSCCNC(=O)c1cccc2[nH]c(NC(=O)c3cc4ccccc4cn3)nc12] | Isoquinoline-3-carboxylic acid [4-(2-methylsulfanyl-ethylcarbamoyl)-1H-benzoimidazol-2-yl]-amide |
| 188 | 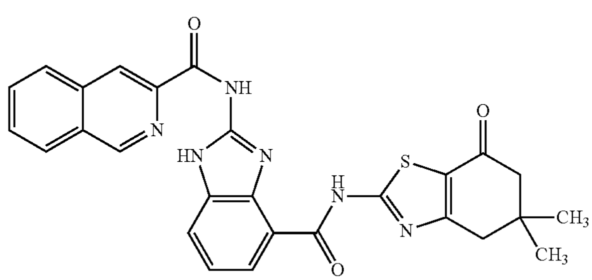 [SMILES: CC1(C)CC(=O)c2sc(NC(=O)c3cccc4[nH]c(NC(=O)c5cc6ccccc6cn5)nc34)nc2C1] | Isoquinoline-3-carboxylic acid [4-(5,5-dimethyl-7-oxo-4,5,6,7-tetrahydro-benzothiazol-2-ylcarbamoyl)-1H-benzoimidazol-2-yl]-amide |
| 189 | 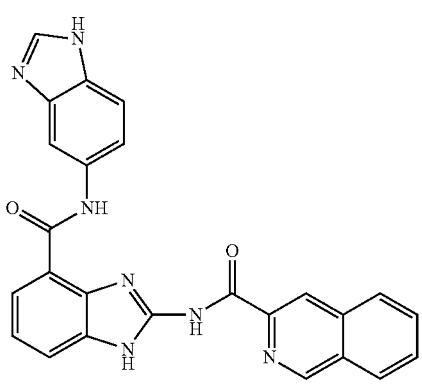 [SMILES: O=C(Nc1nc2c(C(=O)Nc3ccc4[nH]cnc4c3)cccc2[nH]1)c1cc2ccccc2cn1] | Isoquinoline-3-carboxylic acid [4-(1H-benzoimidazol-5-ylcarbamoyl)-1H-benzoimidazol-2-yl]-amide |

| Ex. | Structure | Name |
| --- | --- | --- |
| 190 | 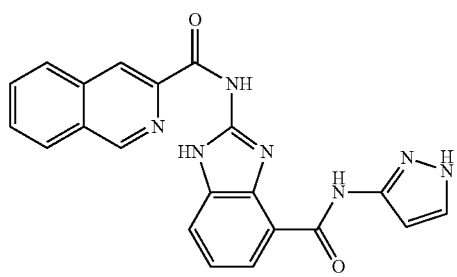 [SMILES: O=C(Nc1nc2c(C(=O)Nc3cc[nH]n3)cccc2[nH]1)c1cc2ccccc2cn1] | Isoquinoline-3-carboxylic acid [4-(1H-pyrazol-3-ylcarbamoyl)-1H-benzoimidazol-2-yl]-amide |
| 191 | 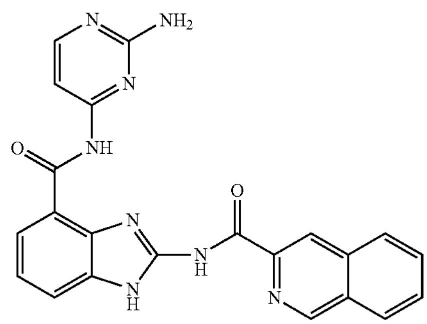 [SMILES: Nc1nccc(NC(=O)c2cccc3[nH]c(NC(=O)c4cc5ccccc5cn4)nc23)n1] | Isoquinoline-3-carboxylic acid [4-(2-amino-pyrimidin-4-ylcarbamoyl)-1H-benzoimidazol-2-yl]-amide |
| 192 | 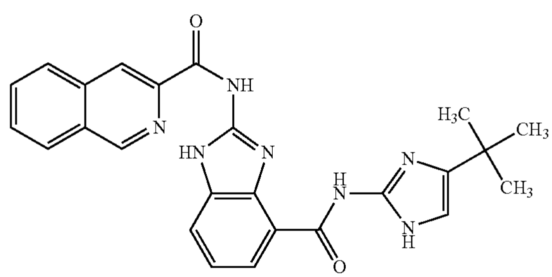 [SMILES: CC(C)(C)c1c[nH]c(NC(=O)c2cccc3[nH]c(NC(=O)c4cc5ccccc5cn4)nc23)n1] | Isoquinoline-3-carboxylic acid [4-(4-tert-butyl-1H-imidazol-2-ylcarbamoyl)-1H-benzoimidazol-2-yl]-amide |
| 193 | 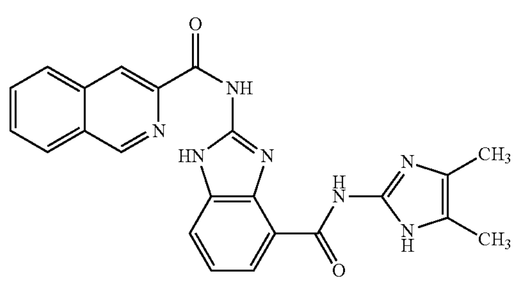 [SMILES: Cc1nc(NC(=O)c2cccc3[nH]c(NC(=O)c4cc5ccccc5cn4)nc23)[nH]c1C] | Isoquinoline-3-carboxylic acid [4-(4,5-dimethyl-1H-imidazol-2-ylcarbamoyl)-1H-benzoimidazol-2-yl]-amide |
| 194 | 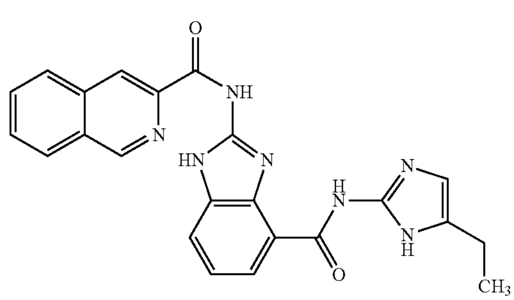 [SMILES: CCc1cnc(NC(=O)c2cccc3[nH]c(NC(=O)c4cc5ccccc5cn4)nc23)[nH]1] | Isoquinoline-3-carboxylic acid [4-(5-ethyl-1H-imidazol-2-ylcarbamoyl)-1H-benzoimidazol-2-yl]-amide |

TABLE 1-continued

| Ex. | Structure | Name |
|---|---|---|
| 195 | 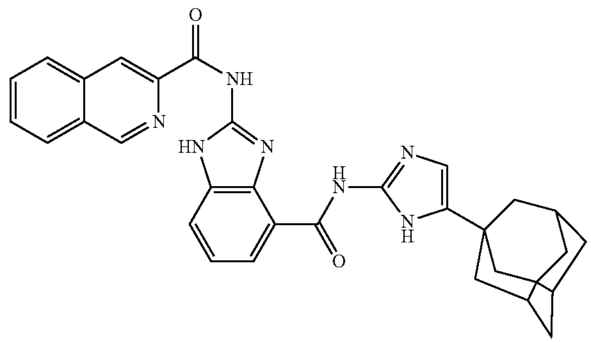 [SMILES: O=C(Nc1nc2c(C(=O)Nc3ncc(C45CC6CC7CC(C4)C7(C6)C5)[nH]3)cccc2[nH]1)c1cc2ccccc2cn1] | Isoquinoline-3-carboxylic acid [4-(5-adamantan-1-yl-1H-imidazol-2-ylcarbamoyl)-1H-benzoimidazol-2-yl]-amide |
| 196 | 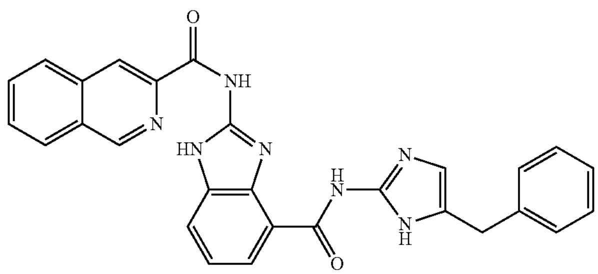 [SMILES: O=C(Nc1nc2c(C(=O)Nc3ncc(Cc4ccccc4)[nH]3)cccc2[nH]1)c1cc2ccccc2cn1] | Isoquinoline-3-carboxylic acid [4-(5-benzyl-1H-imidazol-2-ylcarbamoyl)-1H-benzoimidazol-2-yl]-amide |
| 197 | 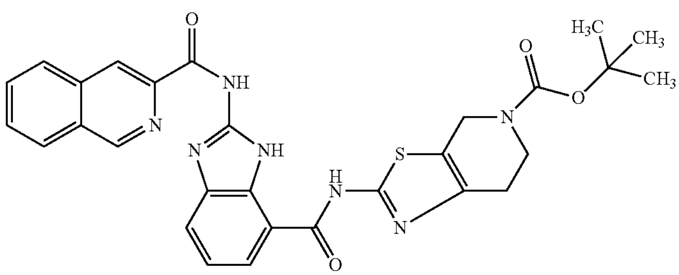 [SMILES: CC(C)(C)OC(=O)N1CCc2nc(NC(=O)c3cccc4nc(NC(=O)c5cc6ccccc6cn5)[nH]c34)sc2C1] | 2-({2-[(Isoquinoline-3-carbonyl)-amino]-3H-benzoimidazole-4-carbonyl}-amino)-6,7-dihydro-4H-thiazolo[5,4-c]pyridine-5-carboxylic acid tert-butyl ester |
| 198 | 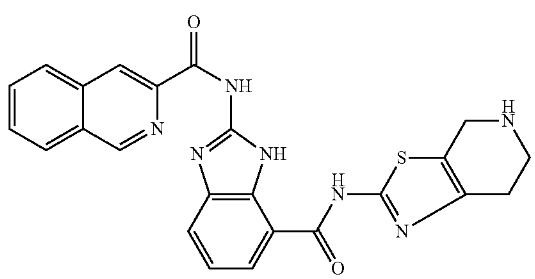 [SMILES: O=C(Nc1nc2cccc(C(=O)Nc3nc4c(s3)CNCC4)c2[nH]1)c1cc2ccccc2cn1] | Isoquinoline-3-carboxylic acid [7-(4,5,6,7-tetrahydro-thiazolo[5,4-c]pyridin-2-ylcarbamoyl)-1H-benzoimidazol-2-yl]-amide |
| 199 | 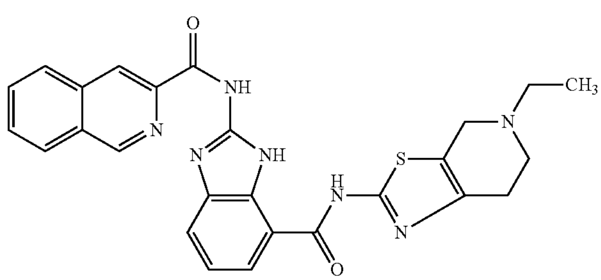 [SMILES: CCN1CCc2nc(NC(=O)c3cccc4nc(NC(=O)c5cc6ccccc6cn5)[nH]c34)sc2C1] | Isoquinoline-3-carboxylic acid [7-(5-ethyl-4,5,6,7-tetrahydro-thiazolo[5,4-c]pyridin-2-ylcarbamoyl)-1H-benzoimidazol-2-yl]-amide |

TABLE 1-continued

| Ex. | Structure | Name |
|---|---|---|
| 200 | 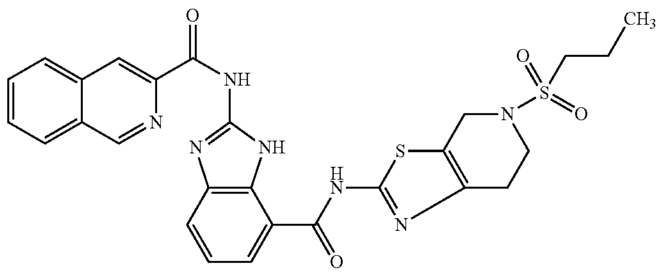 [SMILES: CCCS(=O)(=O)N1CCc2nc(NC(=O)c3cccc4nc(NC(=O)c5cc6ccccc6cn5)[nH]c34)sc2C1] | Isoquinoline-3-carboxylic acid {7-[5-(propane-1-sulfonyl)-4,5,6,7-tetrahydro-thiazolo[5,4-c]pyridin-2-ylcarbamoyl]-1H-benzoimidazol-2-yl}-amide |
| 201 | 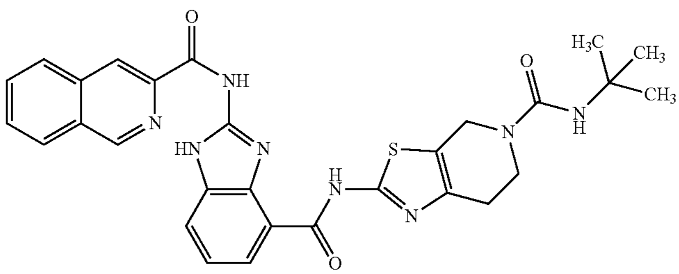 [SMILES: CC(C)(C)NC(=O)N1CCc2nc(NC(=O)c3cccc4[nH]c(NC(=O)c5cc6ccccc6cn5)nc34)sc2C1] | Isoquinoline-3-carboxylic acid [4-(5-tert-butylcarbamoyl-4,5,6,7-tetrahydro-thiazolo[5,4-c]pyridin-2-ylcarbamoyl)-1H-benzoimidazol-2-yl]-amide |
| 202 | 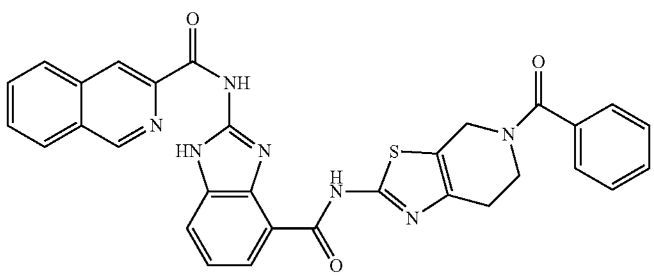 [SMILES: O=C(Nc1nc2c(C(=O)Nc3nc4c(s3)CN(C(=O)c3ccccc3)CC4)cccc2[nH]1)c1cc2ccccc2cn1] | Isoquinoline-3-carboxylic acid [4-(5-benzoyl-4,5,6,7-tetrahydro-thiazolo[5,4-c]pyridin-2-ylcarbamoyl)-1H-benzoimidazol-2-yl]-amide |
| 203 | 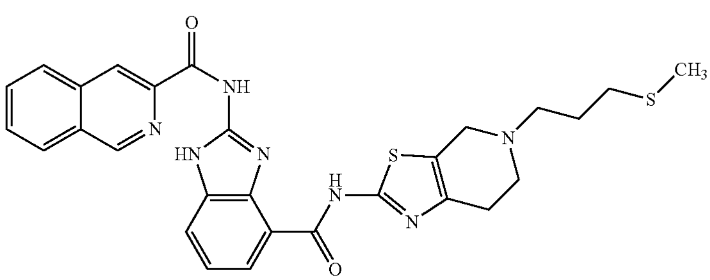 [SMILES: CSCCCN1CCc2nc(NC(=O)c3cccc4[nH]c(NC(=O)c5cc6ccccc6cn5)nc34)sc2C1] | Isoquinoline-3-carboxylic acid {4-[5-(3-methylsulfanyl-propyl)-4,5,6,7-tetrahydro-thiazolo[5,4-c]pyridin-2-ylcarbamoyl]-1H-benzoimidazol-2-yl}-amide |
| 204 | 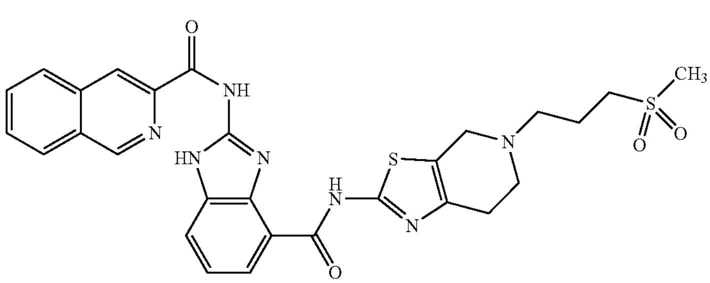 [SMILES: CS(=O)(=O)CCCN1CCc2nc(NC(=O)c3cccc4[nH]c(NC(=O)c5cc6ccccc6cn5)nc34)sc2C1] | Isoquinoline-3-carboxylic acid {4-[5-(3-methanesulfonyl-propyl)-4,5,6,7-tetrahydro-thiazolo[5,4-c]pyridin-2-ylcarbamoyl]-1H-benzoimidazol-2-yl}-amide |

TABLE 1-continued

| Ex. | Structure | Name |
|---|---|---|
| 205 | 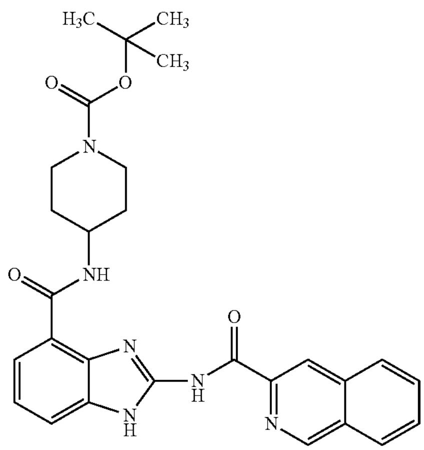 [SMILES: CC(C)(C)OC(=O)N1CCC(NC(=O)c2cccc3[nH]c(NC(=O)c4cc5ccccc5cn4)nc23)CC1] | 4-({2-[(Isoquinoline-3-carbonyl)-amino]-1H-benzoimidazole-4-carbonyl}-amino)-piperidine-1-carboxylic acid tert-butyl ester |
| 206 | 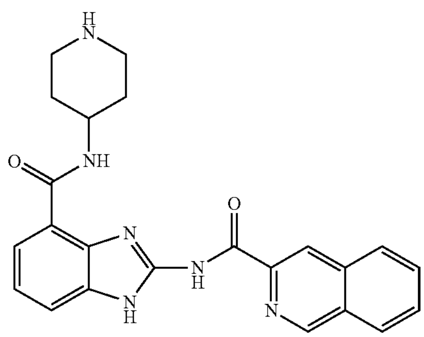 [SMILES: O=C(Nc1nc2c(C(=O)NC3CCNCC3)cccc2[nH]1)c1cc2ccccc2cn1] | Isoquinoline-3-carboxylic acid [4-(piperidin-4-ylcarbamoyl)-1H-benzoimidazol-2-yl]-amide |
| 207 | 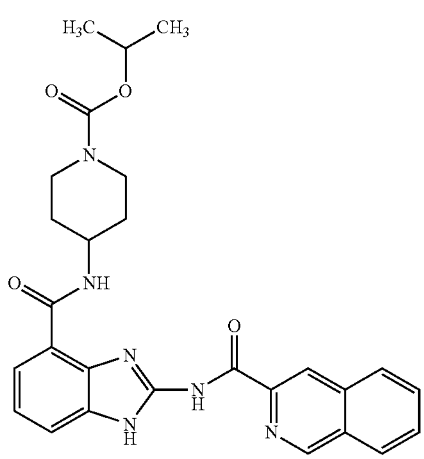 [SMILES: CC(C)OC(=O)N1CCC(NC(=O)c2cccc3[nH]c(NC(=O)c4cc5ccccc5cn4)nc23)CC1] | 4-({2-[(Isoquinoline-3-carbonyl)-amino]-1H-benzoimidazole-4-carbonyl}-amino)-piperidine-1-carboxylic acid isopropyl ester |
| 208 | 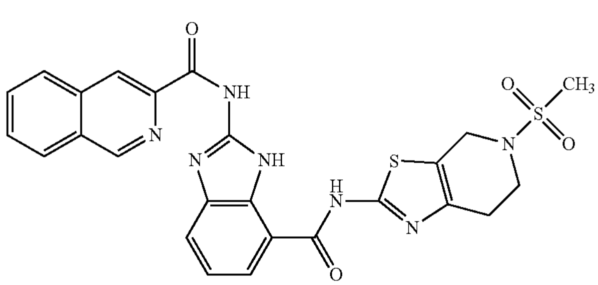 [SMILES: CS(=O)(=O)N1CCc2nc(NC(=O)c3cccc4nc(NC(=O)c5cc6ccccc6cn5)[nH]c34)sc2C1] | Isoquinoline-3-carboxylic acid [7-(5-methanesulfonyl-4,5,6,7-tetrahydro-thiazolo[5,4-c]pyridin-2-ylcarbamoyl)-1H-benzoimidazol-2-yl]-amide |

TABLE 1-continued

| Ex. | Structure | Name |
|---|---|---|
| 209 | 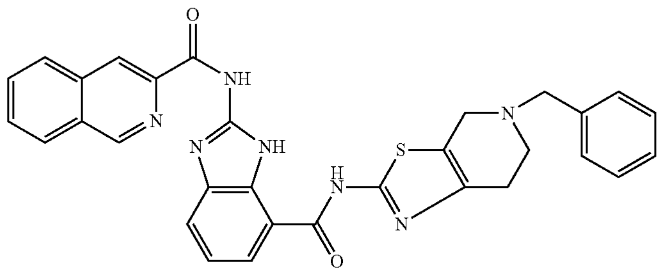 [SMILES: O=C(Nc1nc2cccc(C(=O)Nc3nc4c(s3)CN(Cc3ccccc3)CC4)c2[nH]1)c1cc2ccccc2cn1] | Isoquinoline-3-carboxylic acid [7-(5-benzyl-4,5,6,7-tetrahydro-thiazolo[5,4-c]pyridin-2-ylcarbamoyl)-1H-benzoimidazol-2-yl]-amide |
| 210 | 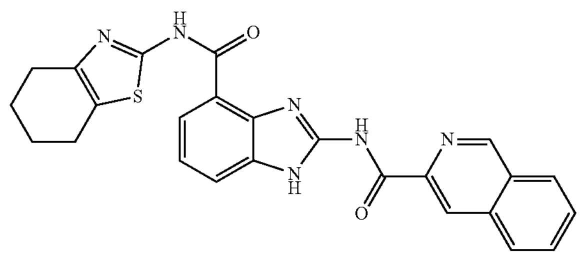 [SMILES: O=C(Nc1nc2c(C(=O)Nc3nc4c(s3)CCCC4)cccc2[nH]1)c1cc2ccccc2cn1] | Isoquinoline-3-carboxylic acid [4-(4,5,6,7-tetrahydro-benzothiazol-2-ylcarbamoyl)-1H-benzoimidazol-2-yl]-amide |
| 211 | 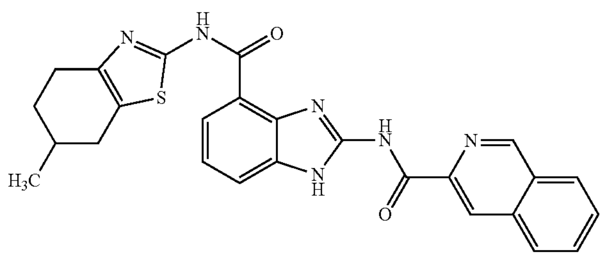 [SMILES: CC1CCc2nc(NC(=O)c3cccc4[nH]c(NC(=O)c5cc6ccccc6cn5)nc34)sc2C1] | Isoquinoline-3-carboxylic acid [4-(6-methyl-4,5,6,7-tetrahydro-benzothiazol-2-ylcarbamoyl)-1H-benzoimidazol-2-yl]-amide |
| 212 | 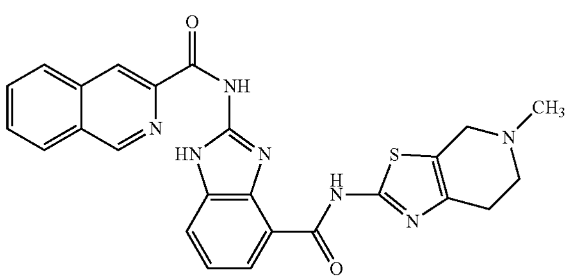 [SMILES: CN1CCc2nc(NC(=O)c3cccc4[nH]c(NC(=O)c5cc6ccccc6cn5)nc34)sc2C1] | Isoquinoline-3-carboxylic acid [4-(5-methyl-4,5,6,7-tetrahydro-thiazolo[5,4-c]pyridin-2-ylcarbamoyl)-1H-benzoimidazol-2-yl]-amide |
| 213 | 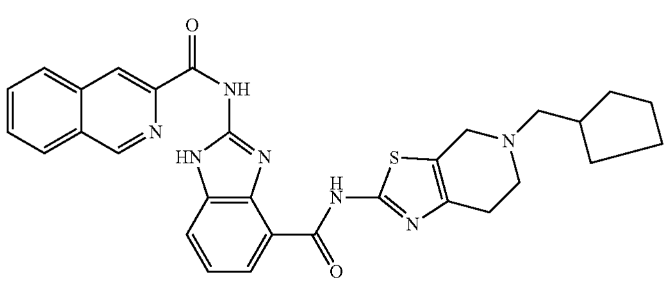 [SMILES: O=C(Nc1nc2c(C(=O)Nc3nc4c(s3)CN(CC3CCCC3)CC4)cccc2[nH]1)c1cc2ccccc2cn1] | Isoquinoline-3-carboxylic acid [4-(5-cyclopentylmethyl-4,5,6,7-tetrahydro-thiazolo[5,4-c]pyridin-2-ylcarbamoyl)-1H-enzoimidazol-2-yl]-amide |

TABLE 1-continued

| Ex. | Structure | Name |
|---|---|---|
| 214 | 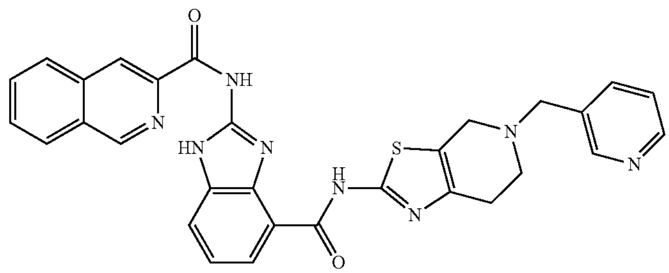 [SMILES: O=C(Nc1nc2c(C(=O)Nc3nc4c(s3)CN(Cc3cccnc3)CC4)cccc2[nH]1)c1cc2ccccc2cn1] | Isoquinoline-3-carboxylic acid [4-(5-pyridin-3-ylmethyl-4,5,6,7-tetrahydro-thiazolo[5,4-c]pyridin-2-ylcarbamoyl)-1H-benzoimidazol-2-yl]-amide |
| 215 | 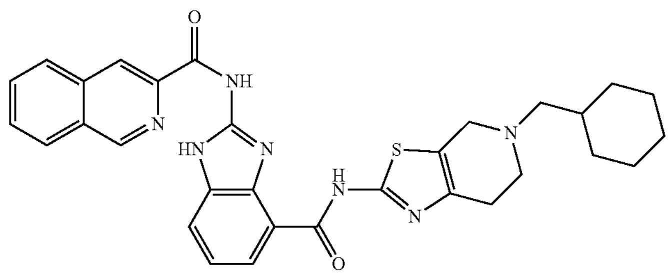 [SMILES: O=C(Nc1nc2c(C(=O)Nc3nc4c(s3)CN(CC3CCCCC3)CC4)cccc2[nH]1)c1cc2ccccc2cn1] | Isoquinoline-3-carboxylic acid [4-(5-cyclohexylmethyl-4,5,6,7-tetrahydro-thiazolo[5,4-c]pyridin-2-ylcarbamoyl)-1H-benzoimidazol-2-yl]-amide |
| 216 | 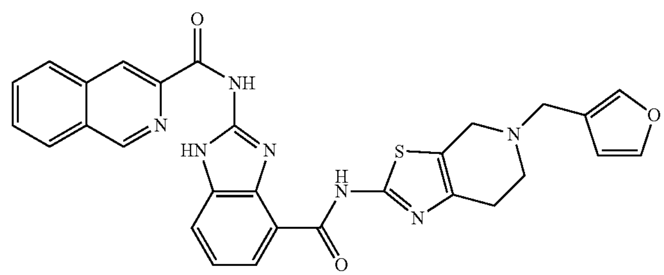 [SMILES: O=C(Nc1nc2c(C(=O)Nc3nc4c(s3)CN(Cc3ccoc3)CC4)cccc2[nH]1)c1cc2ccccc2cn1] | Isoquinoline-3-carboxylic acid [4-(5-furan-3-ylmethyl-4,5,6,7-tetrahydro-thiazolo[5,4-c]pyridin-2-ylcarbamoyl)-1H-benzoimidazol-2-yl]-amide |
| 217 | 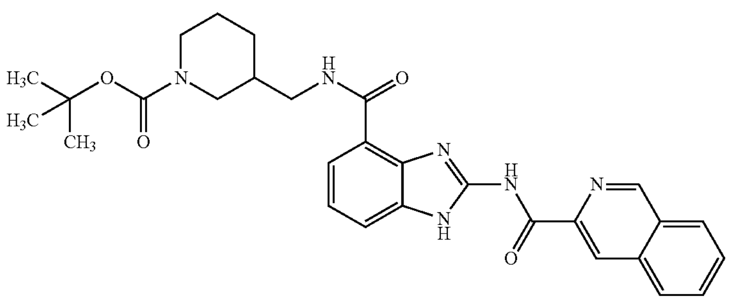 | 3-[({2-[(Isoquinoline-3-carbonyl)-amino]-1H-benzoimidazole-4-carbonyl}-amino)-methyl]-piperidine-1-carboxylic acid tert-butyl ester |
| 218 | 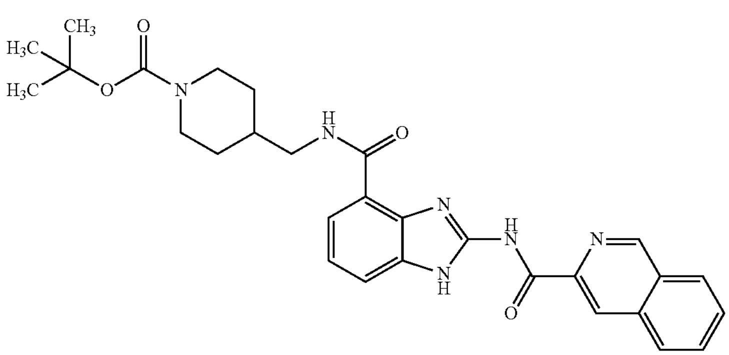 [SMILES: CC(C)(C)OC(=O)N1CCC(CNC(=O)c2cccc3[nH]c(NC(=O)c4cc5ccccc5cn4)nc23)CC1] | 4-[({2-[(Isoquinoline-3-carbonyl)-amino]-1H-benzoimidazole-4-carbonyl}-amino)-methyl]-piperidine-1-carboxylic acid tert-butyl ester |

| Ex. | Structure | Name |
|---|---|---|
| 219 | 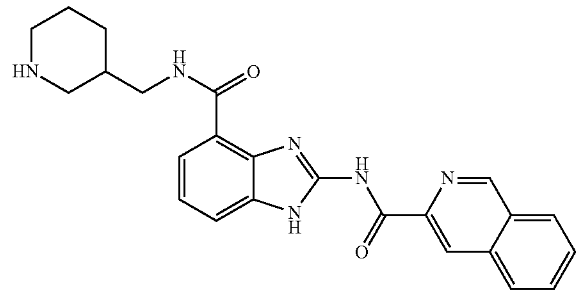 [SMILES: O=C(Nc1nc2c(C(=O)NCC3CCCNC3)cccc2[nH]1)c1cc2ccccc2cn1] | Isoquinoline-3-carboxylic acid {4-[(piperidin-3-ylmethyl)-carbamoyl]-1H-benzoimidazol-2-yl}-amide |
| 220 | 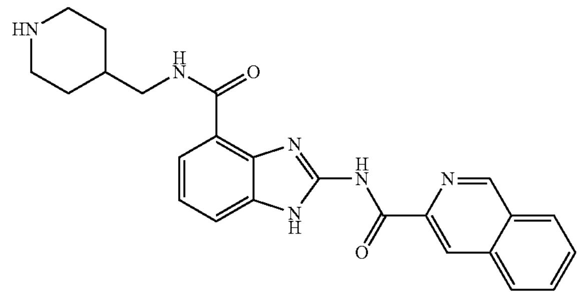 [SMILES: O=C(Nc1nc2c(C(=O)NCC3CCNCC3)cccc2[nH]1)c1cc2ccccc2cn1] | Isoquinoline-3-carboxylic acid {4-[(piperidin-4-ylmethyl)-carbamoyl]-1H-benzoimidazol-2-yl}-amide |
| 221 | 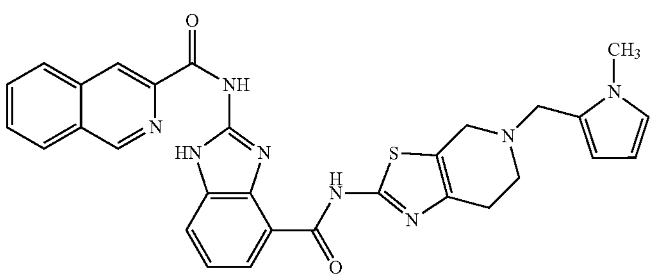 [SMILES: Cn1cccc1CN1CCc2nc(NC(=O)c3cccc4[nH]c(NC(=O)c5cc6ccccc6cn5)nc34)sc2C1] | Isoquinoline-3-carboxylic acid {4-[5-(1-methyl-1H-pyrrol-2-ylmethyl)-4,5,6,7-tetrahydro-thiazolo[5,4-c]pyridin-2-ylcarbamoyl]-1H-benzoimidazol-2-yl}-amide |
| 222 | 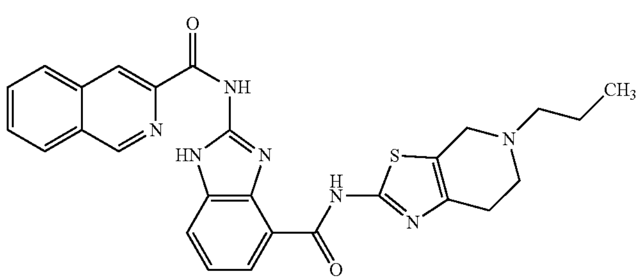 [SMILES: CCCN1CCc2nc(NC(=O)c3cccc4[nH]c(NC(=O)c5cc6ccccc6cn5)nc34)sc2C1] | Isoquinoline-3-carboxylic acid [4-(5-propyl-4,5,6,7-tetrahydro-thiazolo[5,4-c]pyridin-2-ylcarbamoyl)-1H-benzoimidazol-2-yl]-amide |
| 223 | 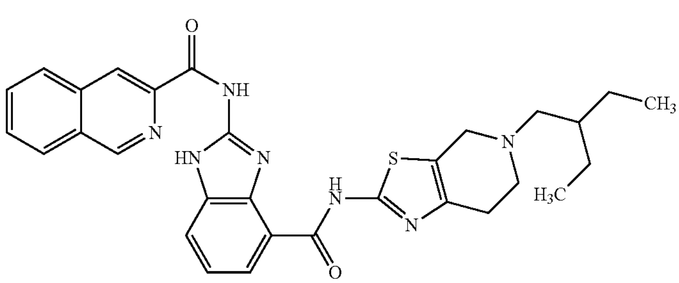 [SMILES: CCC(CC)CN1CCc2nc(NC(=O)c3cccc4[nH]c(NC(=O)c5cc6ccccc6cn5)nc34)sc2C1] | Isoquinoline-3-carboxylic acid {4-[5-(2-ethyl-butyl)-4,5,6,7-tetrahydro-thiazolo[5,4-c]pyridin-2-ylcarbamoyl]-1H-benzoimidazol-2-yl}-amide |

TABLE 1-continued

| Ex. | Structure | Name |
|---|---|---|
| 224 | 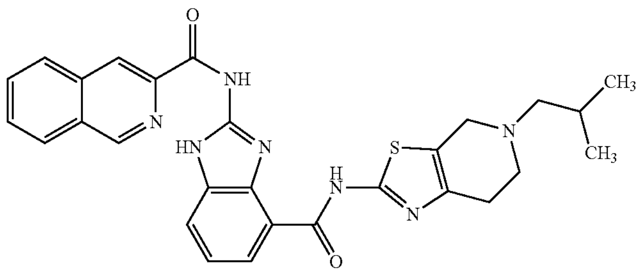 [SMILES: CC(C)CN1CCc2nc(NC(=O)c3cccc4[nH]c(NC(=O)c5cc6ccccc6cn5)nc34)sc2C1] | Isoquinoline-3-carboxylic acid [4-(5-isobutyl-4,5,6,7-tetrahydro-thiazolo[5,4-c]pyridin-2-ylcarbamoyl)-1H-benzoimidazol-2-yl]-amide |
| 225 | 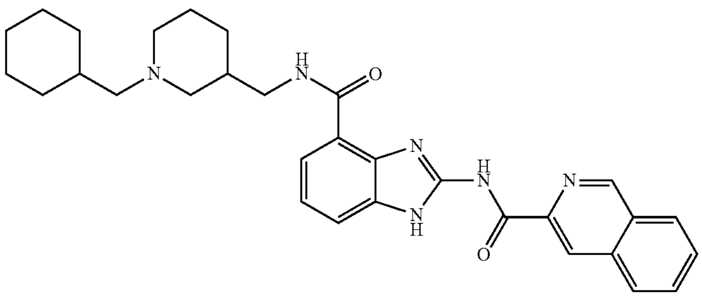 [SMILES: O=C(Nc1nc2c(C(=O)NCC3CCCN(CC4CCCCC4)C3)cccc2[nH]1)c1cc2ccccc2cn1] | Isoquinoline-3-carboxylic acid {4-[(1-cyclohexylmethyl-piperidin-3-ylmethyl)-carbamoyl]-1H-benzoimidazol-2-yl}-amide |
| 226 | 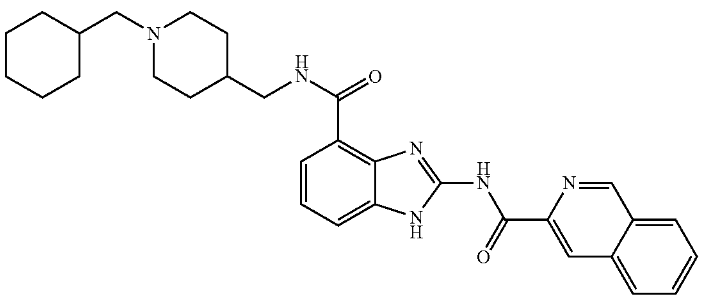 [SMILES: O=C(Nc1nc2c(C(=O)NCC3CCN(CC4CCCCC4)CC3)cccc2[nH]1)c1cc2ccccc2cn1] | Isoquinoline-3-carboxylic acid {4-[(1-cyclohexylmethyl-piperidin-4-ylmethyl)-carbamoyl]-1H-benzoimidazol-2-yl}-amide |
| 227 | 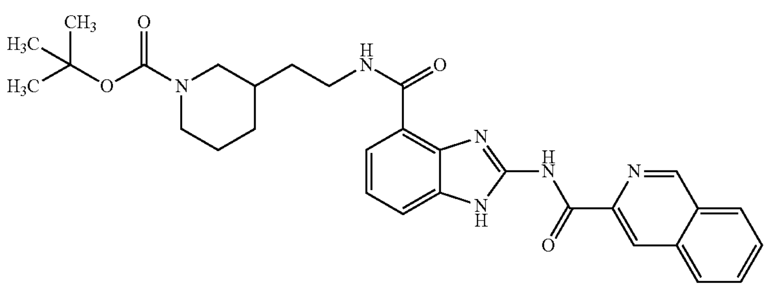 [SMILES: CC(C)(C)OC(=O)N1CCCC(CCNC(=O)c2cccc3[nH]c(NC(=O)c4cc5ccccc5cn4)nc23)C1] | 3-[2-({2-[(Isoquinoline-3-carbonyl)-amino]-1H-benzoimidazole-4-carbonyl}-amino)-ethyl]-piperidine-1-carboxylic acid tert-butyl ester |
| 228 | 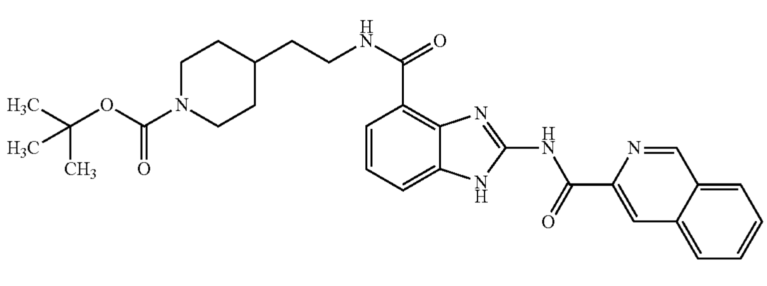 [SMILES: CC(C)(C)OC(=O)N1CCC(CCNC(=O)c2cccc3[nH]c(NC(=O)c4cc5ccccc5cn4)nc23)CC1] | 4-[2-({2-[(Isoquinoline-3-carbonyl)-amino]-1H-benzoimidazole-4-carbonyl}-amino)-ethyl]-piperidine-1-carboxylic acid tert-butyl ester |

TABLE 1-continued

| Ex. | Structure | Name |
|---|---|---|
| 229 | 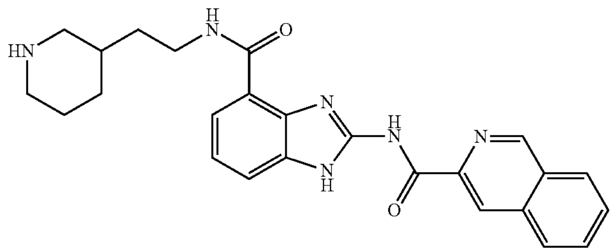 [SMILES: O=C(Nc1nc2c(C(=O)NCCC3CCCNC3)cccc2[nH]1)c1cc2ccccc2cn1] | isoquinoline-3-carboxylic acid [4-(2-piperidin-3-yl-ethylcarbamoyl)-1H-benzoimidazol-2-yl]-amide |
| 230 | 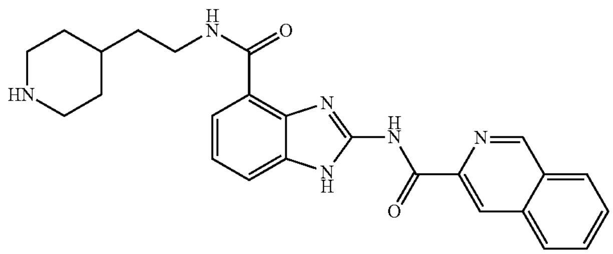 [SMILES: O=C(Nc1nc2c(C(=O)NCCC3CCNCC3)cccc2[nH]1)c1cc2ccccc2cn1] | Isoquinoline-3-carboxylic acid [4-(2-piperidin-4-yl-ethylcarbamoyl)-1H-benzoimidazol-2-yl]-amide |
| 231 | 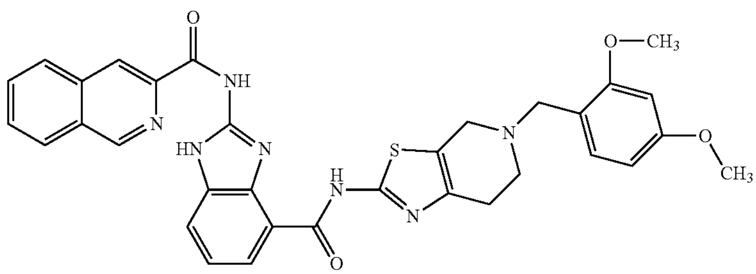 [SMILES: COc1ccc(CN2CCc3nc(NC(=O)c4cccc5[nH]c(NC(=O)c6cc7ccccc7cn6)nc45)sc3C2)c(OC)c1] | Isoquinoline-3-carboxylic acid {4-[5-(2,4-dimethoxy-benzyl)-4,5,6,7-tetrahydro-thiazolo[5,4-c]pyridin-2-ylcarbamoyl]-1H-benzoimidazol-2-yl}-amide |
| 232 | 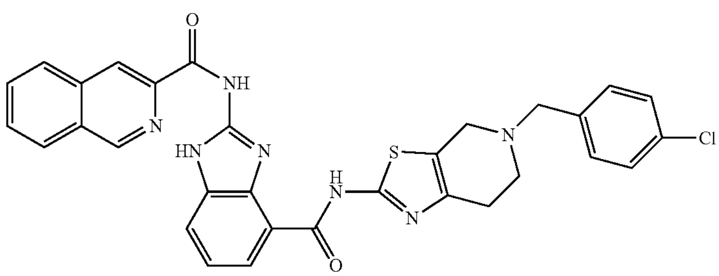 [SMILES: O=C(Nc1nc2c(C(=O)Nc3nc4c(s3)CN(Cc3ccc(Cl)cc3)CC4)cccc2[nH]1)c1cc2ccccc2cn1] | Isoquinoline-3-carboxylic acid {4-[5-(4-chloro-benzyl)-4,5,6,7-tetrahydro-thiazolo[5,4-c]pyridin-2-ylcarbamoyl]-1H-benzoimidazol-2-yl}-amide |
| 233 | 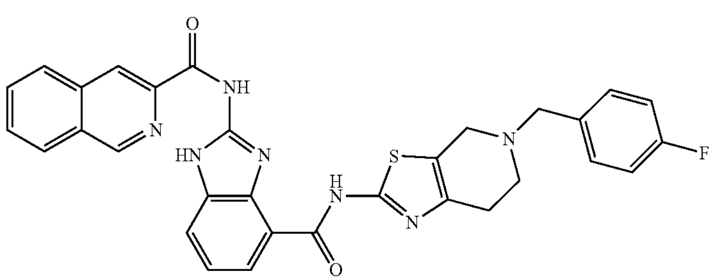 [SMILES: O=C(Nc1nc2c(C(=O)Nc3nc4c(s3)CN(Cc3ccc(F)cc3)CC4)cccc2[nH]1)c1cc2ccccc2cn1] | Isoquinoline-3-carboxylic acid {4-[5-(4-fluoro-benzyl)-4,5,6,7-tetrahydro-thiazolo[5,4-c]pyridin-2-ylcarbamoyl]-1H-benzoimidazol-2-yl}-amide |
| 234 | 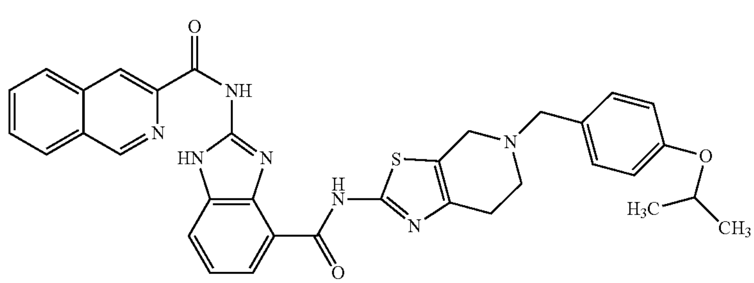 [SMILES: CC(C)Oc1ccc(CN2CCc3nc(NC(=O)c4cccc5[nH]c(NC(=O)c6cc7ccccc7cn6)nc45)sc3C2)cc1] | Isoquinoline-3-carboxylic acid {4-[5-(4-isopropoxy-benzyl)-4,5,6,7-tetrahydro-thiazolo[5,4-c]pyridin-2-ylcarbamoyl]-1H-benzoimidazol-2-yl}-amide |

TABLE 1-continued

| Ex. | Structure | Name |
|---|---|---|
| 235 | 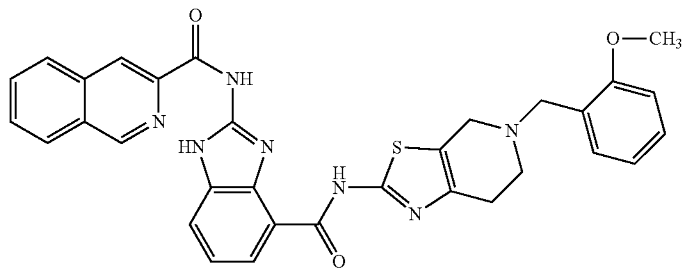 [SMILES: COc1ccccc1CN1CCc2nc(NC(=O)c3cccc4[nH]c(NC(=O)c5cc6ccccc6cn5)nc34)sc2C1] | Isoquinoline-3-carboxylic acid {4-[5-(2-methoxy-benzyl)-4,5,6,7-tetrahydro-thiazolo[5,4-c]pyridin-2-ylcarbamoyl]-1H-benzoimidazol-2-yl}-amide |
| 236 | 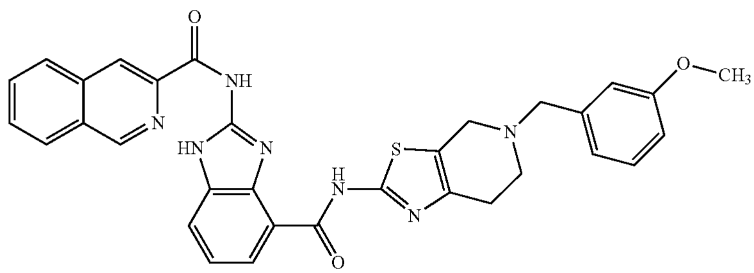 [SMILES: COc1cccc(CN2CCc3nc(NC(=O)c4cccc5[nH]c(NC(=O)c6cc7ccccc7cn6)nc45)sc3C2)c1] | Isoquinoline-3-carboxylic acid {4-[5-(3-methoxy-benzyl)-4,5,6,7-tetrahydro-thiazolo[5,4-c]pyridin-2-ylcarbamoyl]-1H-benzoimidazol-2-yl}-amide |
| 237 | 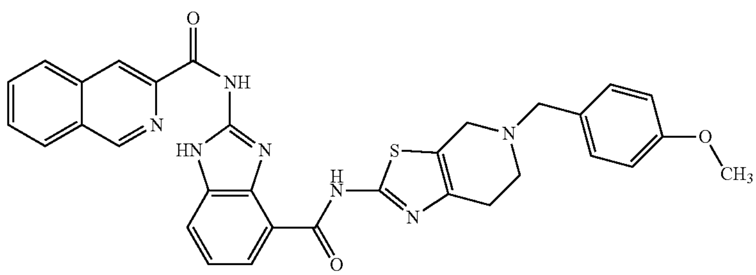 [SMILES: COc1ccc(CN2CCc3nc(NC(=O)c4cccc5[nH]c(NC(=O)c6cc7ccccc7cn6)nc45)sc3C2)cc1] | Isoquinoline-3-carboxylic acid {4-[5-(4-methoxy-benzyl)-4,5,6,7-tetrahydro-thiazolo[5,4-c]pyridin-2-ylcarbamoyl]-1H-benzoimidazol-2-yl}-amide |
| 238 | 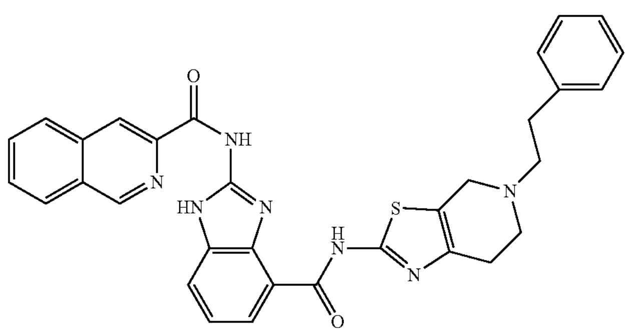 [SMILES: O=C(Nc1nc2c(C(=O)Nc3nc4c(s3)CN(CCc3ccccc3)CC4)cccc2[nH]1)c1cc2ccccc2cn1] | Isoquinoline-3-carboxylic acid [4-(5-phenethyl-4,5,6,7-tetrahydro-thiazolo[5,4-c]pyridin-2-ylcarbamoyl)-1H-benzoimidazol-2-yl]-amide |
| 239 | 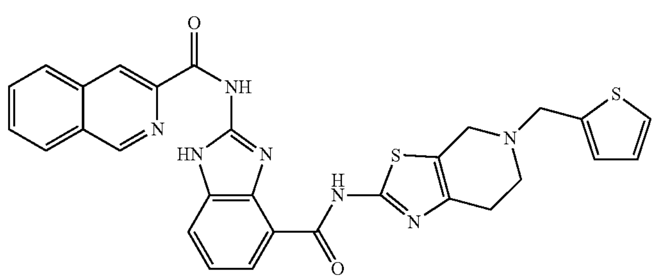 [SMILES: O=C(Nc1nc2c(C(=O)Nc3nc4c(s3)CN(Cc3cccs3)CC4)cccc2[nH]1)c1cc2ccccc2cn1] | Isoquinoline-3-carboxylic acid [4-(5-thiophen-2-ylmethyl-4,5,6,7-tetrahydro-thiazolo[5,4-c]pyridin-2-ylcarbamoyl)-1H-benzoimidazol-2-yl]-amide |

TABLE 1-continued

| Ex. | Structure | Name |
|---|---|---|
| 240 | 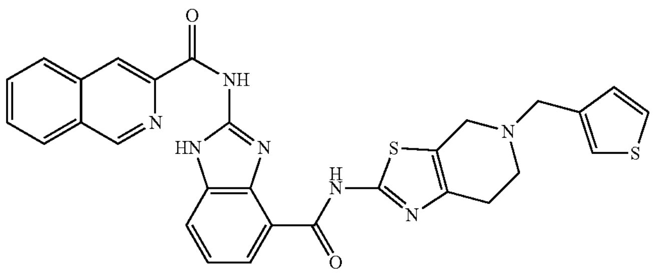 [SMILES: O=C(Nc1nc2c(C(=O)Nc3nc4c(s3)CN(Cc3ccsc3)CC4)cccc2[nH]1)c1cc2ccccc2cn1] | Isoquinoline-3-carboxylic acid [4-(5-thiophen-3-ylmethyl-4,5,6,7-tetrahydro-thiazolo[5,4-c]pyridin-2-ylcarbamoyl)-1H-benzoimidazol-2-yl]-amide |
| 241 | 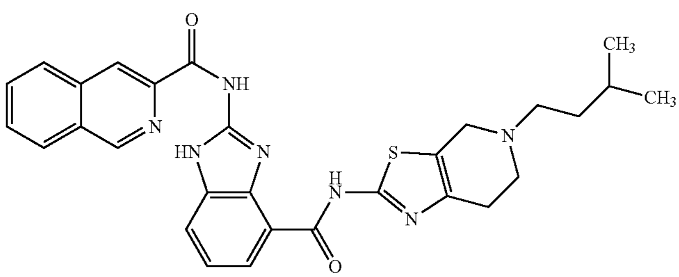 [SMILES: CC(C)CCN1CCc2nc(NC(=O)c3cccc4[nH]c(NC(=O)c5cc6ccccc6cn5)nc34)sc2C1] | Isoquinoline-3-carboxylic acid {4-[5-(3-methyl-butyl)-4,5,6,7-tetrahydro-thiazolo[5,4-c]pyridin-2-ylcarbamoyl]-1H-benzoimidazol-2-yl}-amide |
| 242 | 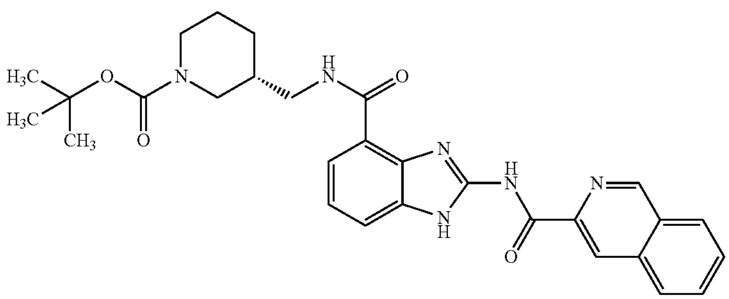 | 3R-[({2-[(Isoquinoline-3-carbonyl)-amino]-1H-benzoimidazole-4-carbonyl}-amino)-methyl]-piperidine-1-carboxylic acid tert-butyl ester |
| 243 | 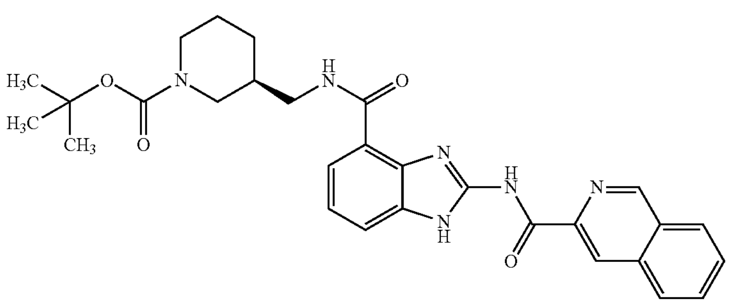 [SMILES: CC(C)(C)OC(=O)N1CCC[C@@H](CNC(=O)c2cccc3[nH]c(NC(=O)c4cc5ccccc5cn4)nc23)C1] | 3S-[({2-[(Isoquinoline-3-carbonyl)-amino]-1H-benzoimidazole-4-carbonyl}-amino)-methyl]-piperidine-1-carboxylic acid tert-butyl ester |
| 244 | 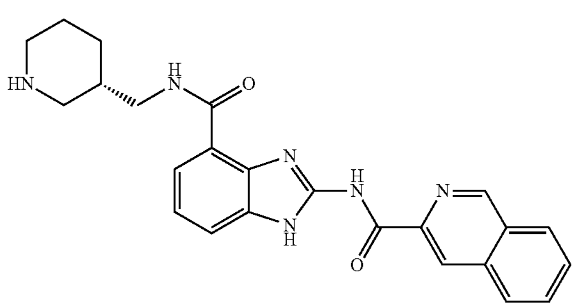 | Isoquinoline-3-carboxylic acid {4-[(piperidin-3S-ylmethyl)-carbamoyl]-1H-benzoimidazol-2-yl}-amide |

TABLE 1-continued

| Ex. | Structure | Name |
|---|---|---|
| 245 | 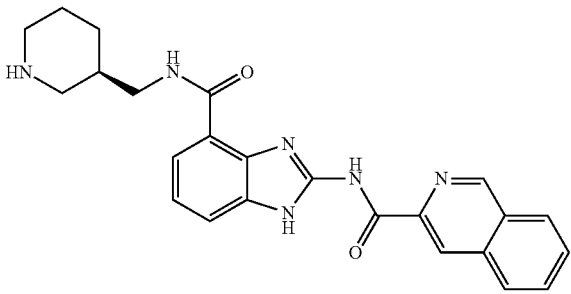 [SMILES: O=C(Nc1nc2c(C(=O)NC[C@@H]3CCCNC3)cccc2[nH]1)c1cc2ccccc2cn1] | Isoquinoline-3-carboxylic acid {4-[(piperidin-3R-ylmethyl)-carbamoyl]-1H-benzoimidazol-2-yl}-amide |
| 246 | 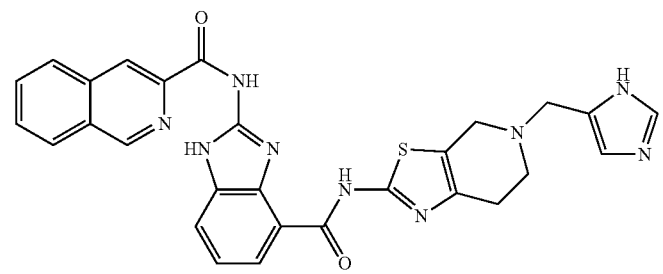 [SMILES: O=C(Nc1nc2c(C(=O)Nc3nc4c(s3)CN(Cc3cnc[nH]3)CC4)cccc2[nH]1)c1cc2ccccc2cn1] | Isoquinoline-3-carboxylic acid {4-[5-(3H-imidazol-4-ylmethyl)-4,5,6,7-tetrahydro-thiazolo[5,4-c]pyridin-2-ylcarbamoyl]-1H-benzoimidazol-2-yl}-amide |
| 247 | 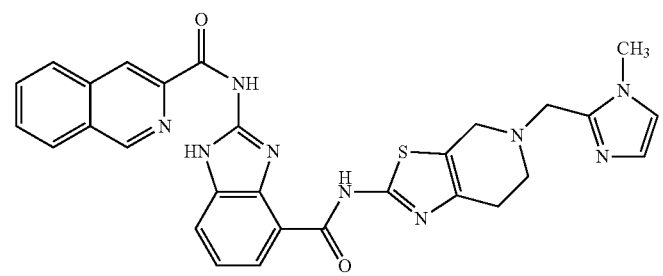 [SMILES: Cn1ccnc1CN1CCc2nc(NC(=O)c3cccc4[nH]c(NC(=O)c5cc6ccccc6cn5)nc34)sc2C1] | Isoquinoline-3-carboxylic acid {4-[5-(1-methyl-1H-imidazol-2-ylmethyl)-4,5,6,7-tetrahydro-thiazolo[5,4-c]pyridin-2-ylcarbamoyl]-1H-benzoimidazol-2-yl}-amide |
| 248 | 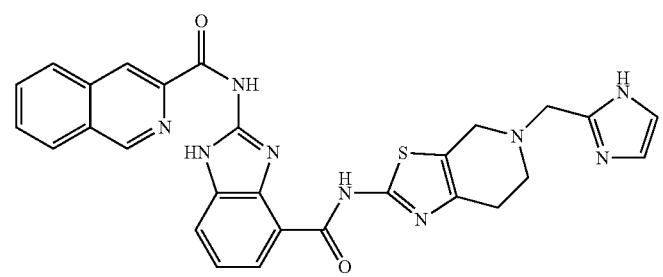 [SMILES: O=C(Nc1nc2c(C(=O)Nc3nc4c(s3)CN(Cc3ncc[nH]3)CC4)cccc2[nH]1)c1cc2ccccc2cn1] | Isoquinoline-3-carboxylic acid {4-[5-(1H-imidazol-2-ylmethyl)-4,5,6,7-tetrahydro-thiazolo[5,4-c]pyridin-2-ylcarbamoyl]-1H-benzoimidazol-2-yl}-amide |
| 249 | 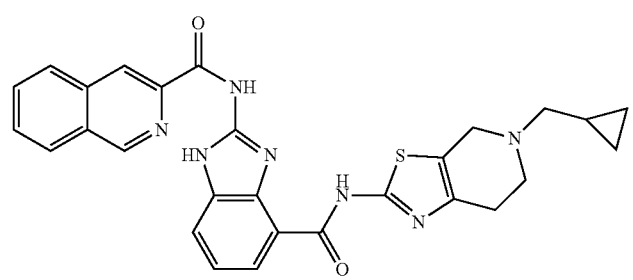 [SMILES: O=C(Nc1nc2c(C(=O)Nc3nc4c(s3)CN(CC3CC3)CC4)cccc2[nH]1)c1cc2ccccc2cn1] | Isoquinoline-3-carboxylic acid [4-(5-cyclopropylmethyl-4,5,6,7-tetrahydro-thiazolo[5,4-c]pyridin-2-ylcarbamoyl)-1H-benzoimidazol-2-yl]-amide |

| Ex. | Structure | Name |
| --- | --- | --- |
| 250 | 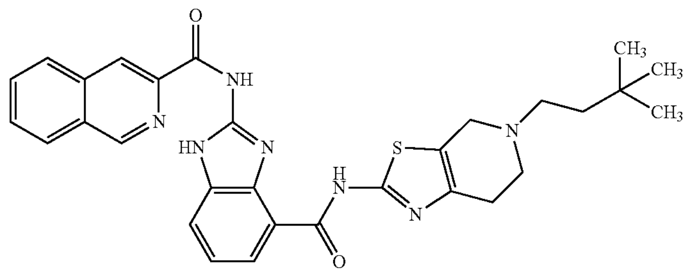 [SMILES: CC(C)(C)CCN1CCc2nc(NC(=O)c3cccc4[nH]c(NC(=O)c5cc6ccccc6cn5)nc34)sc2C1] | Isoquinoline-3-carboxylic acid {4-[5-(3,3-dimethyl-butyl)-4,5,6,7-tetrahydro-thiazolo[5,4-c]pyridin-2-ylcarbamoyl]-1H-benzoimidazol-2-yl}-amide |
| 251 | 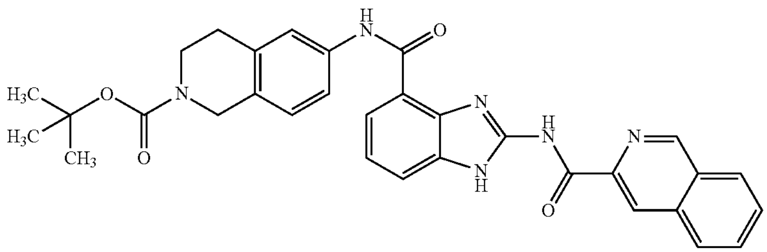 [SMILES: CC(C)(C)OC(=O)N1CCc2cc(NC(=O)c3cccc4[nH]c(NC(=O)c5cc6ccccc6cn5)nc34)ccc2C1] | 6-({2-[(Isoquinoline-3-carbonyl)-amino]-1H-benzoimidazole-4-carbonyl}-amino)-3,4-diydro-1H-isoquinoline-2-carboxylic acid tert-butyl ester |
| 252 | 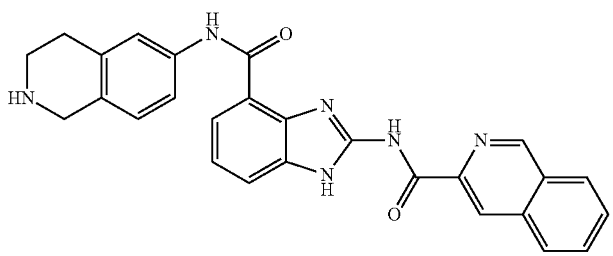 [SMILES: O=C(Nc1nc2c(C(=O)Nc3ccc4c(c3)CCNC4)cccc2[nH]1)c1cc2ccccc2cn1] | Isoquinoline-3-carboxylic acid [4-(1,2,3,4-tetrahydro-isoquinolin-6-ylcarbamoyl)-1H-benzoimidazol-2-yl]-amide |
| 253 | 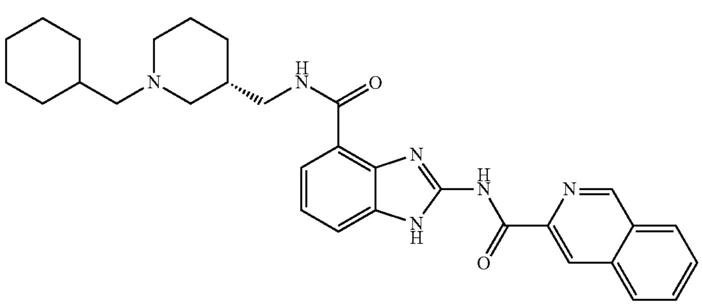 | Isoquinoline-3-carboxylic acid {4-[(1-cyclohexylmethyl-piperidin-3S-ylmethyl)-carbamoyl]-1H-benzoimidazol-2-yl}-amide |
| 254 | 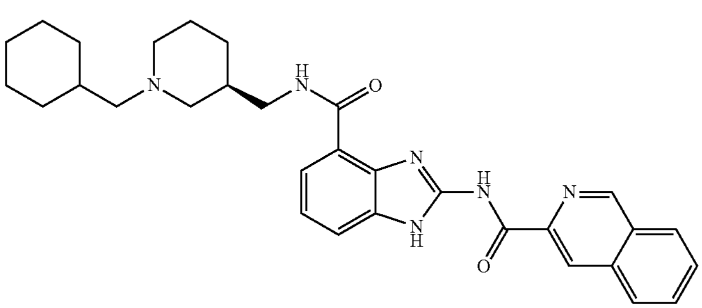 [SMILES: O=C(Nc1nc2c(C(=O)NC[C@@H]3CCCN(CC4CCCCC4)C3)cccc2[nH]1)c1cc2ccccc2cn1] | Isoquinoline-3-carboxylic acid {4-[(1-cyclohexylmethyl-piperidin-3R-ylmethyl)-carbamoyl]-1H-benzoimidazol-2-yl}-amide |

TABLE 1-continued

| Ex. | Structure | Name |
|---|---|---|
| 255 | 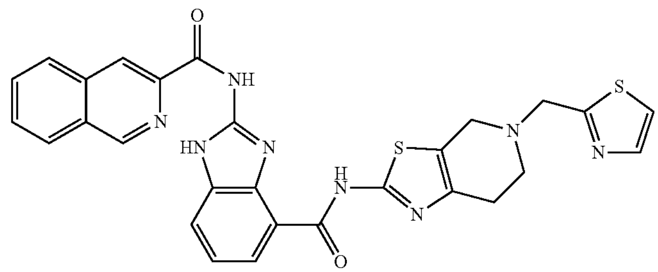 [SMILES: O=C(Nc1nc2c(C(=O)Nc3nc4c(s3)CN(Cc3nccs3)CC4)cccc2[nH]1)c1cc2ccccc2cn1] | Isoquinoline-3-carboxylic acid [4-(5-thiazol-2-ylmethyl-4,5,6,7-tetrahydro-thiazolo[5,4-c]pyridin-2-ylcarbamoyl)-1H-benzoimidazol-2-yl]-amide |
| 256 | 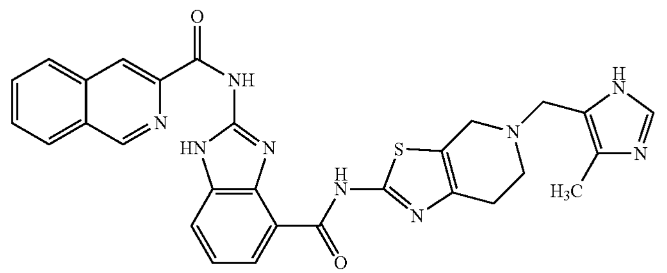 [SMILES: Cc1nc[nH]c1CN1CCc2nc(NC(=O)c3cccc4[nH]c(NC(=O)c5cc6ccccc6cn5)nc34)sc2C1] | Isoquinoline-3-carboxylic acid {4-[5-(5-methyl-3H-imidazol-4-ylmethyl)-4,5,6,7-tetrahydro-thiazolo[5,4-c]pyridin-2-ylcarbamoyl]-1H-benzoimidazol-2-yl}-amide |
| 257 | 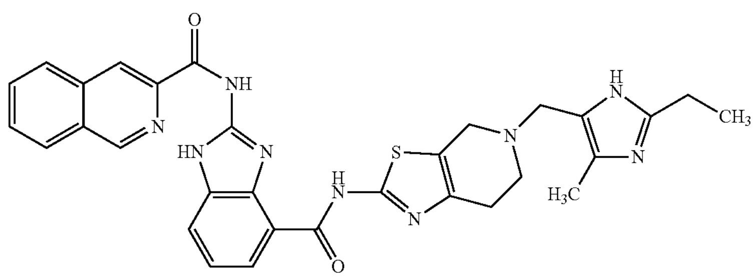 [SMILES: CCc1nc(C)c(CN2CCc3nc(NC(=O)c4cccc5[nH]c(NC(=O)c6cc7ccccc7cn6)nc45)sc3C2)[nH]1] | Isoquinoline-3-carboxylic acid {4-[5-(2-ethyl-5-methyl-3H-imidazol-4-ylmethyl)-4,5,6,7-tetrahydro-thiazolo[5,4-c]pyridin-2-ylcarbamoyl]-1H-benzoimidazol-2-yl}-amide |
| 258 | 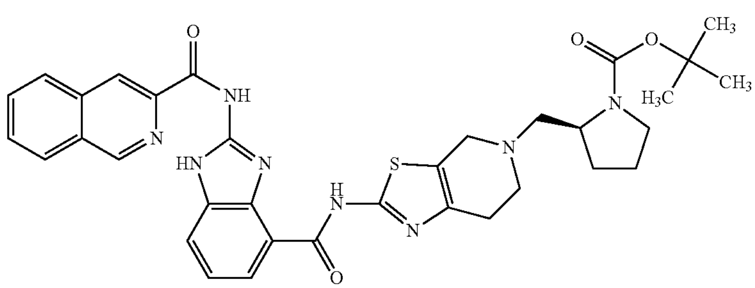 [SMILES: CC(C)(C)OC(=O)N1CCC[C@H]1CN1CCc2nc(NC(=O)c3cccc4[nH]c(NC(=O)c5cc6ccccc6cn5)nc34)sc2C1] | 2S-[2-({2-[(Isoquinoline-3-carbonyl)-amino]-1H-benzoimidazole-4-carbonyl}-amino)-6,7-dihydro-4H-thiazolo[5,4-c]pyridin-5-ylmethyl]-pyrrolidine-1-carboxylic acid tert-butyl ester |
| 259 | 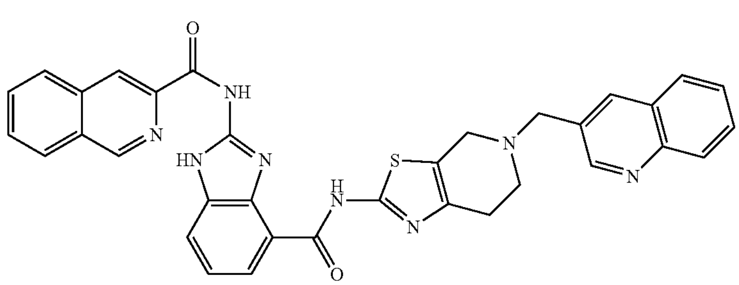 [SMILES: O=C(Nc1nc2c(C(=O)Nc3nc4c(s3)CN(Cc3cnc5ccccc5c3)CC4)cccc2[nH]1)c1cc2ccccc2cn1] | Isoquinoline-3-carboxylic acid [4-(5-quinolin-3-ylmethyl-4,5,6,7-tetrahydro-thiazolo[5,4-c]pyridin-2-ylcarbamoyl)-1H-benzoimidazol-2-yl]-amide |

TABLE 1-continued

| Ex. | Structure | Name |
|---|---|---|
| 260 | 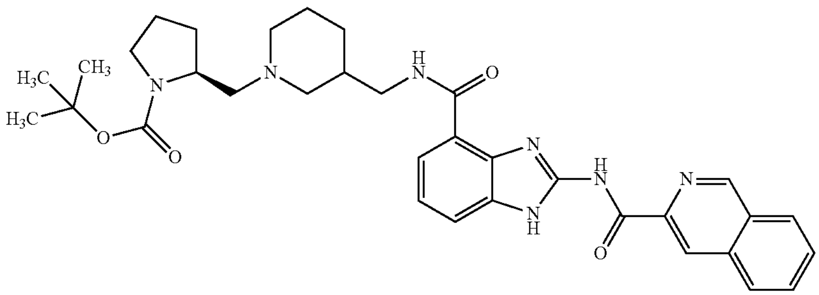 [SMILES: CC(C)(C)OC(=O)N1CCC[C@H]1CN1CCCC(CNC(=O)c2cccc3[nH]c(NC(=O)c4cc5ccccc5cn4)nc23)C1] | 2S-{3-[({2-[(Isoquinoline-3-carbonyl)-amino]-1H-benzoimidazole-4-carbonyl}-amino)-methyl]-piperidin-1-ylmethyl}-pyrrolidine-1-carboxylic acid tert-butyl ester |
| 261 | 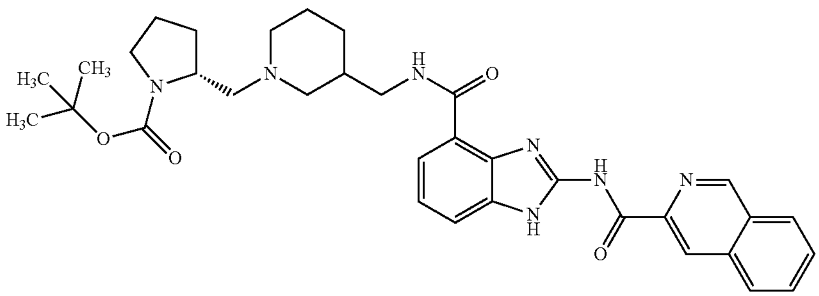 [SMILES: CC(C)(C)OC(=O)N1CCC[C@@H]1CN1CCCC(CNC(=O)c2cccc3[nH]c(NC(=O)c4cc5ccccc5cn4)nc23)C1] | 2R-{3-[({2-[(Isoquinoline-3-carbonyl)-amino]-1H-benzoimidazole-4-carbonyl}-amino)-methyl]-piperidin-1-ylmethyl}-pyrrolidine-1-carboxylic acid tert-butyl ester |
| 262 | 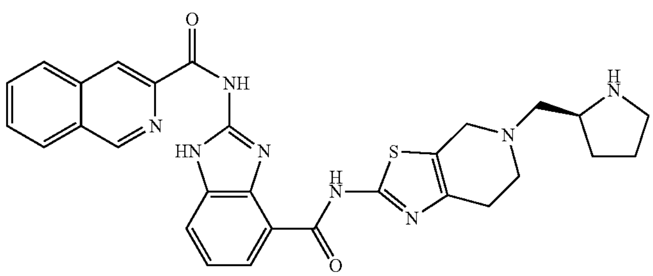 [SMILES: O=C(Nc1nc2c(C(=O)Nc3nc4c(s3)CN(C[C@@H]3CCCN3)CC4)cccc2[nH]1)c1cc2ccccc2cn1] | Isoquinoline-3-carboxylic acid [4-(5-pyrrolidin-2S-ylmethyl-4,5,6,7-tetrahydro-thiazolo[5,4-c]pyridin-2-ylcarbamoyl)-1H-benzoimidazol-2-yl]-amide |
| 263 | 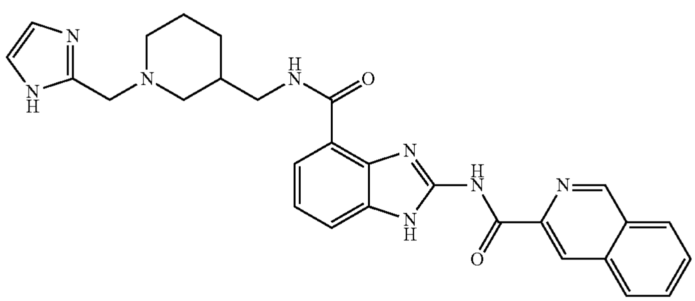 [SMILES: O=C(Nc1nc2c(C(=O)NCC3CCCN(Cc4ncc[nH]4)C3)cccc2[nH]1)c1cc2ccccc2cn1] | Isoquinoline-3-carboxylic acid (4-{[1-(1H-imidazol-2-ylmethyl)-piperidin-3-ylmethyl]-carbamoyl}-1H-benzoimidazol-2-yl)-amide |
| 264 | 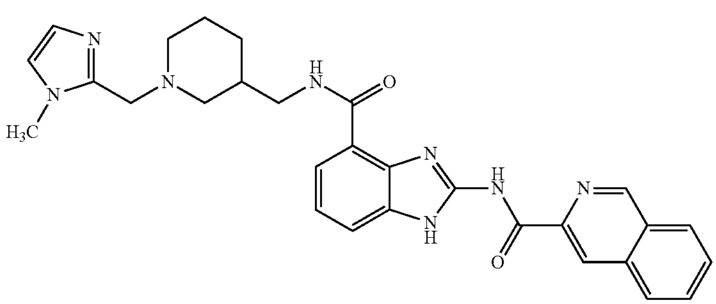 [SMILES: Cn1ccnc1CN1CCCC(CNC(=O)c2cccc3[nH]c(NC(=O)c4cc5ccccc5cn4)nc23)C1] | Isoquinoline-3-carboxylic acid (4-{[1-(1-methyl-1H-imidazol-2-ylmethyl)-piperidin-3-ylmethyl]-carbamoyl}-1H-benzoimidazol-2-yl)-amide |

TABLE 1-continued

| Ex. | Structure | Name |
|---|---|---|
| 265 | 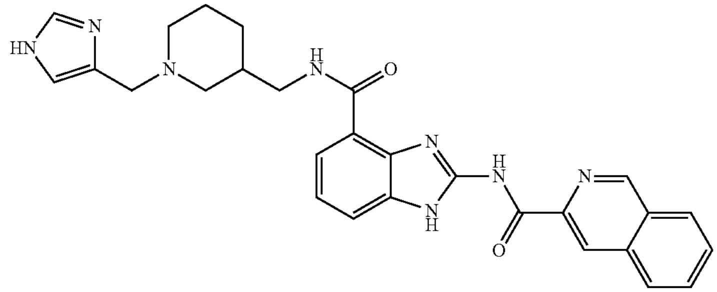 [SMILES: O=C(Nc1nc2c(C(=O)NCC3CCCN(Cc4c[nH]cn4)C3)cccc2[nH]1)c1cc2ccccc2cn1] | Isoquinoline-3-carboxylic acid (4-{[1-(1H-imidazol-4-ylmethyl)-piperidin-3-ylmethyl]-carbamoyl}-1H-benzoimidazol-2-yl)-amide |
| 266 | 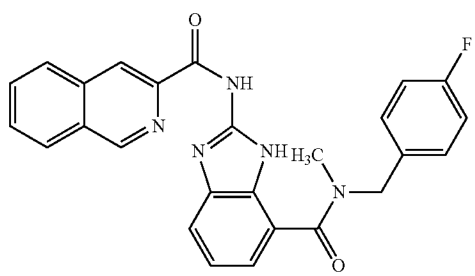 [SMILES: CN(Cc1ccc(F)cc1)C(=O)c1cccc2nc(NC(=O)c3cc4ccccc4cn3)[nH]c12] | Isoquinoline-3-carboxylic acid {7-[(4-fluoro-benzyl)-methyl-arbamoyl]-1H-benzoimidazol-2-yl}-amide |
| 267 | 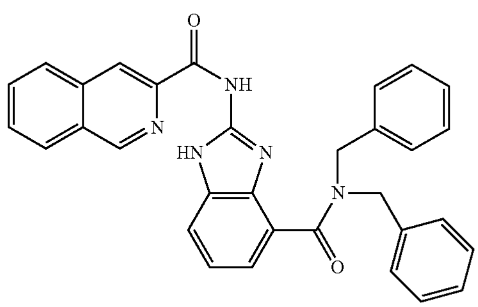 [SMILES: O=C(Nc1nc2c(C(=O)N(Cc3ccccc3)Cc3ccccc3)cccc2[nH]1)c1cc2ccccc2cn1] | Isoquinoline-3-carboxylic acid (4-dibenzylcarbamoyl-1H-benzoimidazol-2-yl)-amide |
| 268 | 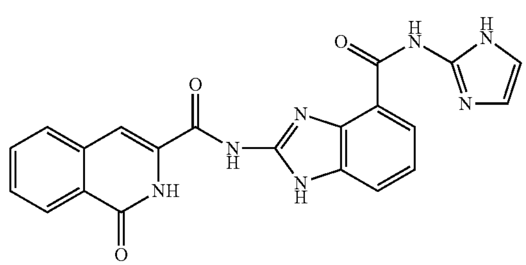 [SMILES: O=C(Nc1nc2c(C(=O)Nc3ncc[nH]3)cccc2[nH]1)c1cc2ccccc2c(=O)[nH]1] | 1-Oxo-1,2-dihydro-isoquinoline-3-carboxylic acid [4-(1H-imidazol-2-ylcarbamoyl)-1H-benzoimidazol-2-yl]-amide |
| 269 | 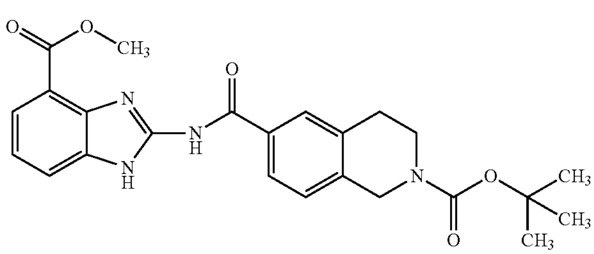 [SMILES: COC(=O)c1cccc2[nH]c(NC(=O)c3ccc4c(c3)CCN(C(=O)OC(C)(C)C)C4)nc12] | 6-(4-Methoxycarbonyl-1H-benzoimidazol-2-ylcarbamoyl)-3,4-dihydro-1H-isoquinoline-2-carboxylic acid tert-butyl ester |

TABLE 1-continued

| Ex. | Structure | Name |
|---|---|---|
| 270 | 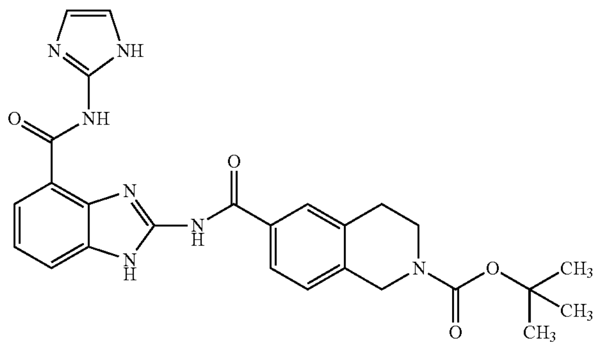 [SMILES: CC(C)(C)OC(=O)N1CCc2cc(C(=O)Nc3nc4c(C(=O)Nc5ncc[nH]5)cccc4[nH]3)ccc2C1] | 6-[4-(1H-Imidazol-2-ylcarbamoyl)-1H-benzoimidazol-2-ylcarbamoyl]-3,4-dihydro-1H-isoquinoline-2-carboxylic acid tert-butyl ester |
| 271 | 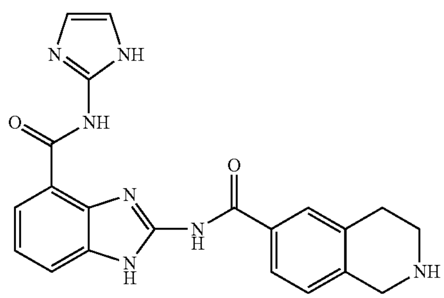 [SMILES: O=C(Nc1nc2c(C(=O)Nc3ncc[nH]3)cccc2[nH]1)c1ccc2c(c1)CCNC2] | 1,2,3,4-Tetrahydro-isoquinoline-6-carboxylic acid [4-(1H-imidazol-2-ylcarbamoyl)-1H-benzoimidazol-2-yl]-amide |
| 272 | 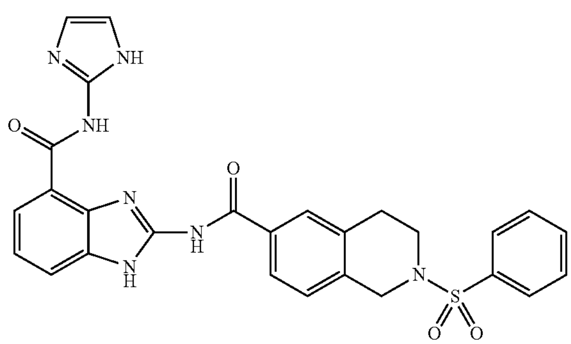 [SMILES: O=C(Nc1nc2c(C(=O)Nc3ncc[nH]3)cccc2[nH]1)c1ccc2c(c1)CCN(S(=O)(=O)c1ccccc1)C2] | 2-Benzenesulfonyl-1,2,3,4-tetrahydro-isoquinoline-6-carboxylic acid [4-(1H-imidazol-2-ylcarbamoyl)-1H-benzoimidazol-2-yl]-amide |
| 273 | 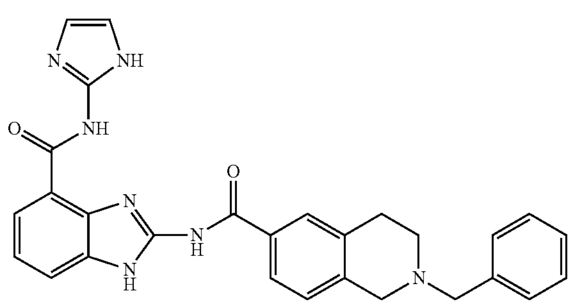 [SMILES: O=C(Nc1nc2c(C(=O)Nc3ncc[nH]3)cccc2[nH]1)c1ccc2c(c1)CCN(Cc1ccccc1)C2] | 2-Benzyl-1,2,3,4-tetrahydro-isoquinoline-6-carboxylic acid [4-(1H-imidazol-2-ylcarbamoyl)-1H-benzoimidazol-2-yl]-amide |

TABLE 1-continued

| Ex. | Structure | Name |
|---|---|---|
| 274 | 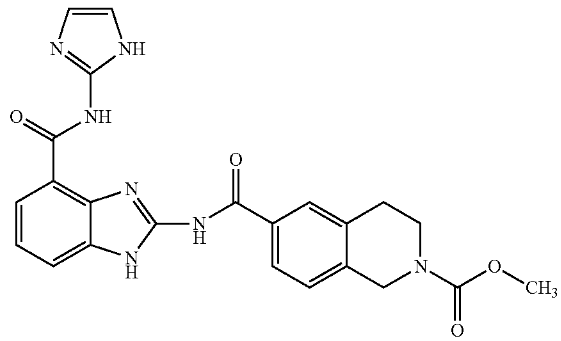 [SMILES: COC(=O)N1CCc2cc(C(=O)Nc3nc4c(C(=O)Nc5ncc[nH]5)cccc4[nH]3)ccc2C1] | 6-[4-(1H-Imidazol-2-ylcarbamoyl)-1H-benzoimidazol-2-ylcarbamoyl]-3,4-dihydro-1H-isoquinoline-2-carboxylic acid methyl ester |
| 275 | 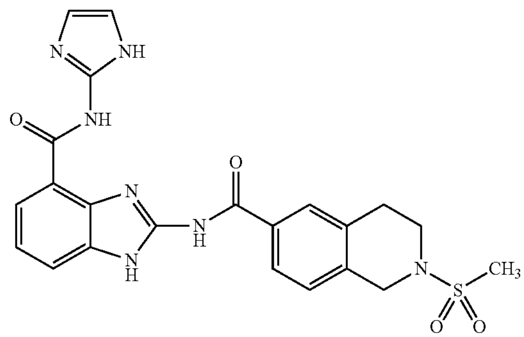 [SMILES: CS(=O)(=O)N1CCc2cc(C(=O)Nc3nc4c(C(=O)Nc5ncc[nH]5)cccc4[nH]3)ccc2C1] | 2-Methanesulfonyl-1,2,3,4-tetrahydro-isoquinoline-6-carboxylic acid [4-(1H-imidazol-2-ylcarbamoyl)-1H-benzoimidazol-2-yl]-amide |
| 276 | 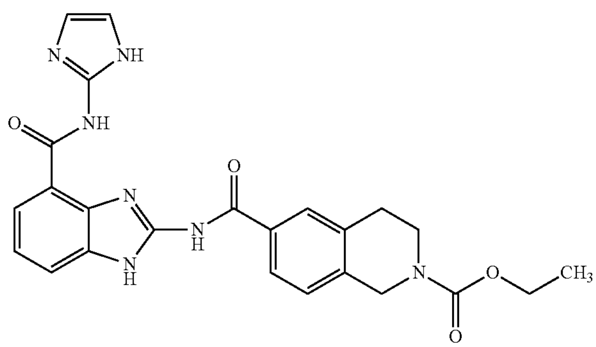 [SMILES: CCOC(=O)N1CCc2cc(C(=O)Nc3nc4c(C(=O)Nc5ncc[nH]5)cccc4[nH]3)ccc2C1] | 6-[4-(1H-Imidazol-2-ylcarbamoyl)-1H-benzoimidazol-2-ylcarbamoyl]-3,4-dihydro-1H-isoquinoline-2-carboxylic acid ethyl ester |
| 277 | 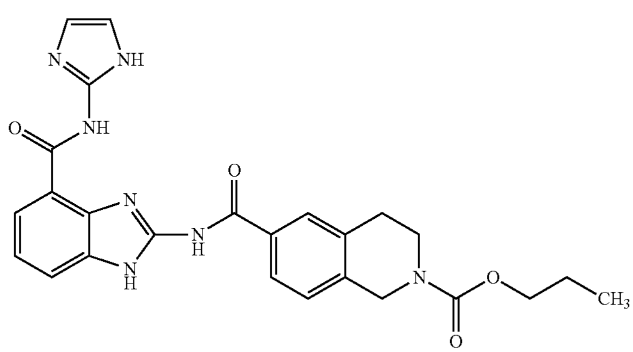 [SMILES: CCCOC(=O)N1CCc2cc(C(=O)Nc3nc4c(C(=O)Nc5ncc[nH]5)cccc4[nH]3)ccc2C1] | 6-[4-(1H-Imidazol-2-ylcarbamoyl)-1H-benzoimidazol-2-ylcarbamoyl]-3,4-dihydro-1H-isoquinoline-2-carboxylic acid propyl ester |

TABLE 1-continued

| Ex. | Structure | Name |
|---|---|---|
| 278 | 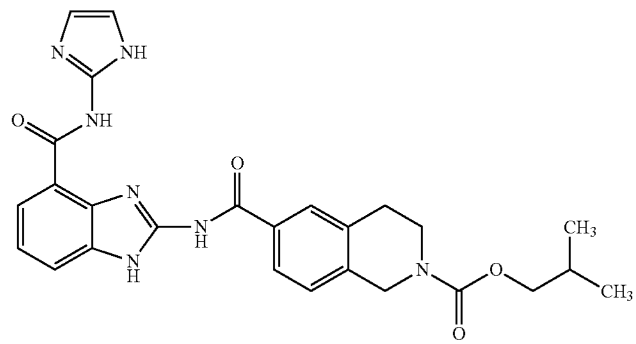 [SMILES: CC(C)COC(=O)N1CCc2cc(C(=O)Nc3nc4c(C(=O)Nc5ncc[nH]5)cccc4[nH]3)ccc2C1] | 6-[4-(1H-Imidazol-2-ylcarbamoyl)-1H-benzoimidazol-2-ylcarbamoyl]-3,4-dihydro-1H-isoquinoline-2-carboxylic acid isobutyl ester |
| 279 | 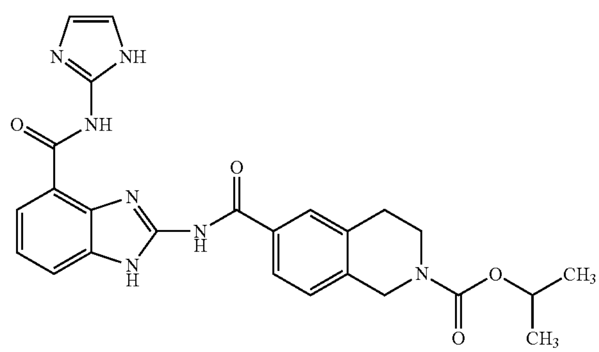 [SMILES: CC(C)OC(=O)N1CCc2cc(C(=O)Nc3nc4c(C(=O)Nc5ncc[nH]5)cccc4[nH]3)ccc2C1] | 6-[4-(1H-Imidazol-2-ylcarbamoyl)-1H-benzoimidazol-2-ylcarbamoyl]-3,4-dihydro-1H-isoquinoline-2-carboxylic acid isopropyl ester |
| 280 | 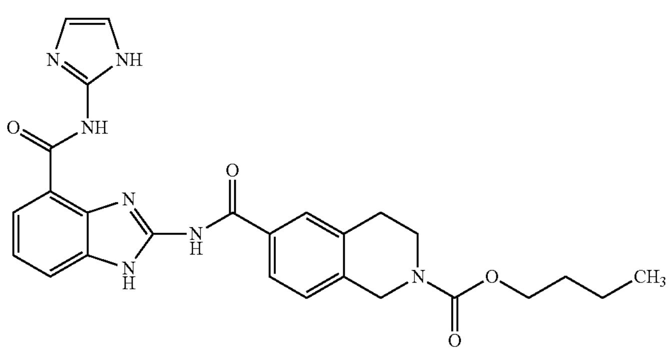 [SMILES: CCCCOC(=O)N1CCc2cc(C(=O)Nc3nc4c(C(=O)Nc5ncc[nH]5)cccc4[nH]3)ccc2C1] | 6-[4-(1H-Imidazol-2-ylcarbamoyl)-1H-benzoimidazol-2-ylcarbamoyl]-3,4-dihydro-1H-isoquinoline-2-carboxylic acid butyl ester |
| 281 | 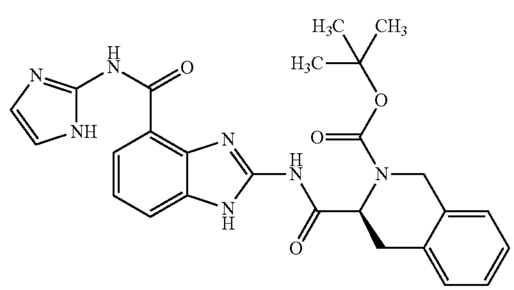 [SMILES: CC(C)(C)OC(=O)N1Cc2ccccc2C[C@H]1C(=O)Nc1nc2c(C(=O)Nc3ncc[nH]3)cccc2[nH]1] | 3S-[4-(1H-Imidazol-2-ylcarbamoyl)-1H-benzoimidazol-2-ylcarbamoyl]-3,4-dihydro-1H-isoquinoline-2-carboxylic acid tert-butyl ester |
| 282 | 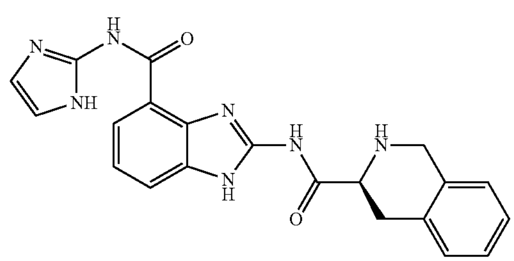 [SMILES: O=C(Nc1ncc[nH]1)c1cccc2[nH]c(NC(=O)[C@@H]3Cc4ccccc4CN3)nc12] | 1,2,3,4-Tetrahydro-isoquinoline-3S-carboxylic acid [4-(1H-imidazol-2-ylcarbamoyl)-1H-benzoimidazol-2-yl]-amide |

TABLE 1-continued

| Ex. | Structure | Name |
|---|---|---|
| 283 | 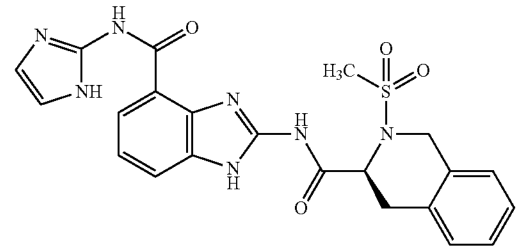 [SMILES: CS(=O)(=O)N1Cc2ccccc2C[C@H]1C(=O)Nc1nc2c(C(=O)Nc3ncc[nH]3)cccc2[nH]1] | 2-Methanesulfonyl-1,2,3,4-tetrahydro-isoquinoline-3S-carboxylic acid [4-(1H-imidazol-2-ylcarbamoyl)-1H-benzoimidazol-2-yl]-amide |
| 284 | 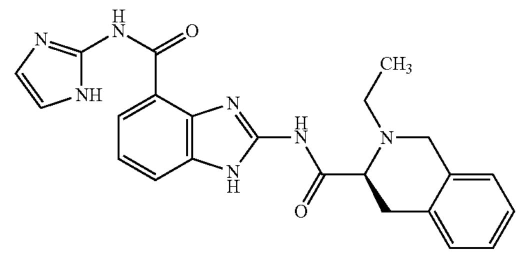 [SMILES: CCN1Cc2ccccc2C[C@H]1C(=O)Nc1nc2c(C(=O)Nc3ncc[nH]3)cccc2[nH]1] | 2-Ethyl-1,2,3,4-tetrahydro-isoquinoline-3S-carboxylic acid [4-(1H-imidazol-2-ylcarbamoyl)-1H-benzomidazol-2-yl]-amide |
| 285 | 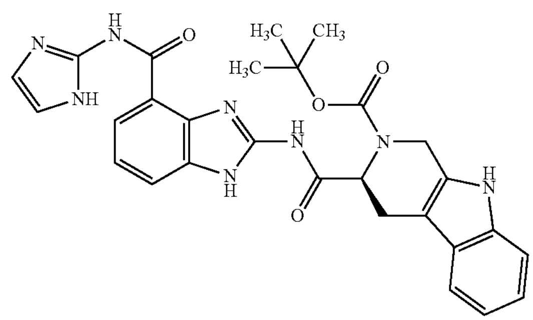 [SMILES: CC(C)(C)OC(=O)N1Cc2[nH]c3ccccc3c2C[C@H]1C(=O)Nc1nc2c(C(=O)Nc3ncc[nH]3)cccc2[nH]1] | 3S-[4-(1H-Imidazol-2-ylcarbamoyl)-1H-benzoimidazol-2-ylcarbamoyl]-1,3,4,9-tetrahydro-beta-carboline-2-carboxylic acid tert-butyl ester |
| 286 | 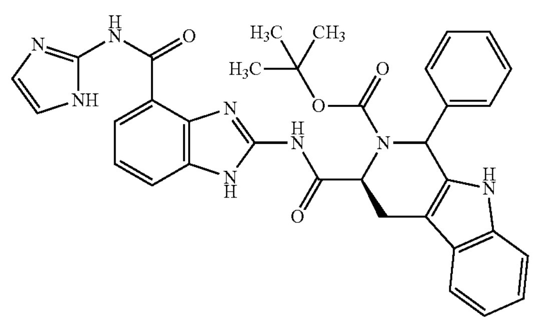 | 3S-[4-(1H-Imidazol-2-ylcarbamoyl)-1H-benzoimidazol-2-ylcarbamoyl]-1-phenyl-1,3,4,9-tetrahydro-beta-carboline-2-carboxylic acid tert-butyl ester |
| 287 | 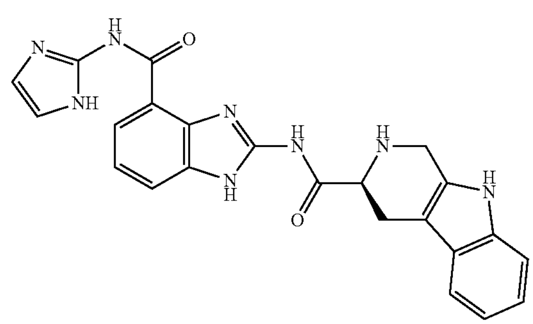 [SMILES: O=C(Nc1ncc[nH]1)c1cccc2[nH]c(NC(=O)[C@@H]3Cc4c([nH]c5ccccc45)CN3)nc12] | 2,3,4,9-Tetrahydro-1H-beta-carboline-3-carboxylic acid [4-(1H-imidazol-2-ylcarbamoyl)-1H-benzoimidazol-2-yl]-amide |

TABLE 1-continued

| Ex. | Structure | Name |
|---|---|---|
| 288 | 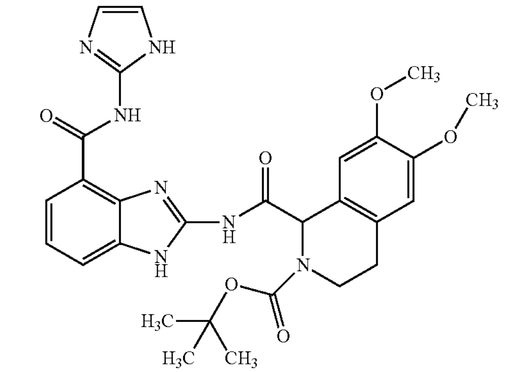 [SMILES: COc1cc2c(cc1OC)C(C(=O)Nc1nc3c(C(=O)Nc4ncc[nH]4)cccc3[nH]1)N(C(=O)OC(C)(C)C)CC2] | 1-[4-(1H-Imidazol-2-ylcarbamoyl)-1H-benzoimidazol-2-ylcarbamoyl]-6,7-dimethoxy-3,4-dihydro-1H-isoquinoline-2-carboxylic acid tert-butyl ester |
| 289 | 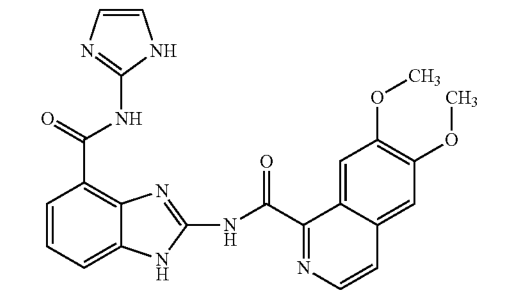 [SMILES: COc1cc2ccnc(C(=O)Nc3nc4c(C(=O)Nc5ncc[nH]5)cccc4[nH]3)c2cc1OC] | 6,7-Dimethoxy-isoquinoline-1-carboxylic acid [4-(1H-imidazol-2-ylcarbamoyl)-1H-benzoimidazol-2-yl]-amide |
| 290 | 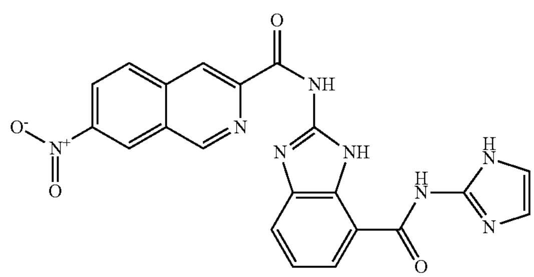 [SMILES: O=C(Nc1nc2cccc(C(=O)Nc3ncc[nH]3)c2[nH]1)c1cc2ccc([N+](=O)[O-])cc2cn1] | 7-Nitro-isoquinoline-3-carboxylic acid [7-(1H-imidazol-2-ylcarbamoyl)-1H-benzoimidazol-2-yl]-amide |
| 291 | 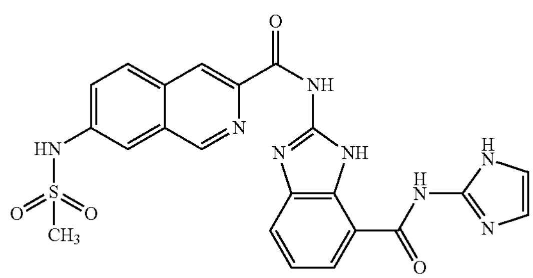 [SMILES: CS(=O)(=O)Nc1ccc2cc(C(=O)Nc3nc4cccc(C(=O)Nc5ncc[nH]5)c4[nH]3)ncc2c1] | 7-Methanesulfonylamino-isoquinoline-3-carboxylic acid [7-(1H-imidazol-2-ylcarbamoyl)-1H-benzoimidazol-2-yl]-amide |
| 292 | 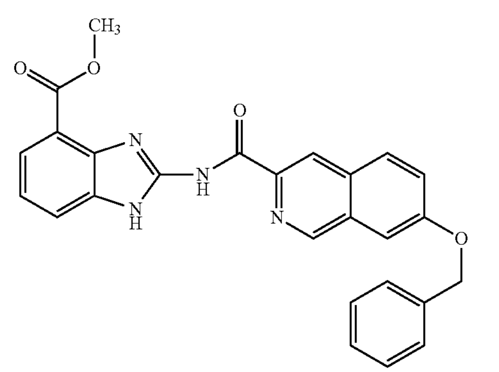 [SMILES: COC(=O)c1cccc2[nH]c(NC(=O)c3cc4ccc(OCc5ccccc5)cc4cn3)nc12] | 2-[(7-Benzyloxy-isoquinoline-3-carbonyl)-amino]-1H-benzoimidazole-4-carboxylic acid methyl ester |

TABLE 1-continued

| Ex. | Structure | Name |
|---|---|---|
| 293 | 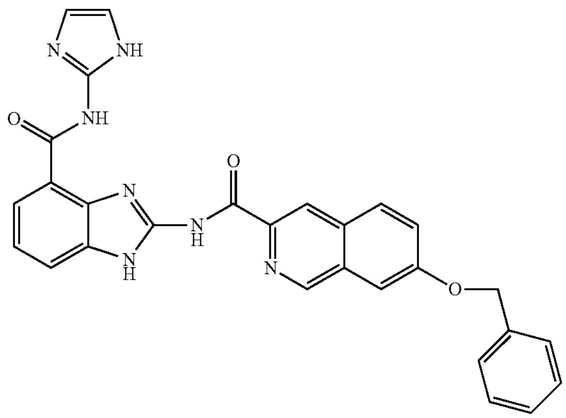 [SMILES: O=C(Nc1nc2c(C(=O)Nc3ncc[nH]3)cccc2[nH]1)c1cc2ccc(OCc3ccccc3)cc2cn1] | 7-Benzyloxy-isoquinoline-3-carboxylic acid [4-(1H-imidazol-2-ylcarbamoyl)-1H-benzoimidazol-2-yl]-amide |
| 294 | 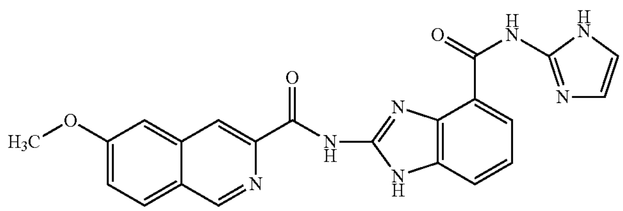 [SMILES: COc1ccc2cnc(C(=O)Nc3nc4c(C(=O)Nc5ncc[nH]5)cccc4[nH]3)cc2c1] | 6-Methoxy-isoquinoline-3-carboxylic acid [4-(1H-imidazol-2-ylcarbamoyl)-1H-benzoimidazol-2-yl]-amide |
| 295 | 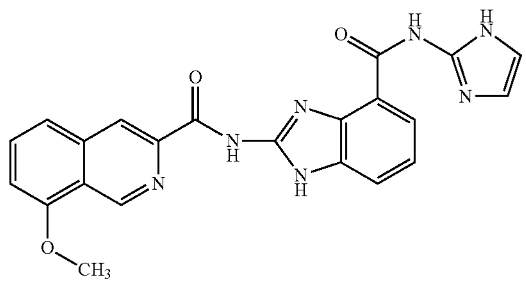 [SMILES: COc1cccc2cc(C(=O)Nc3nc4c(C(=O)Nc5ncc[nH]5)cccc4[nH]3)ncc12] | 8-Methoxy-isoquinoline-3-carboxylic acid [4-(1H-imidazol-2-ylcarbamoyl)-1H-benzoimidazol-2-yl]-amide |
| 296 | 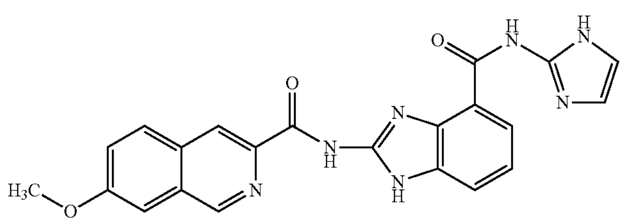 [SMILES: COc1ccc2cc(C(=O)Nc3nc4c(C(=O)Nc5ncc[nH]5)cccc4[nH]3)ncc2c1] | 7-Methoxy-isoquinoline-3-carboxylic acid [4-(1H-imidazol-2-ylcarbamoyl)-1H-benzoimidazol-2-yl]-amide |
| 297 | 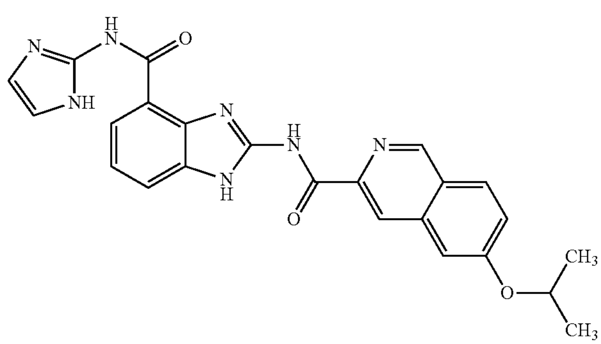 [SMILES: CC(C)Oc1ccc2cnc(C(=O)Nc3nc4c(C(=O)Nc5ncc[nH]5)cccc4[nH]3)cc2c1] | 6-Isopropoxy-isoquinoline-3-carboxylic acid [4-(1H-imidazol-2-ylcarbamoyl)-1H-benzoimidazol-2-yl]-amide |

TABLE 1-continued

| Ex. | Structure | Name |
|---|---|---|
| 298 | 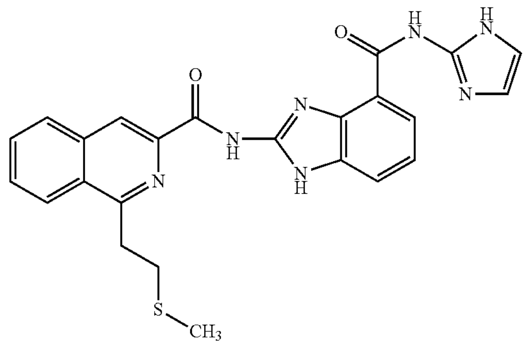 [SMILES: CSCCc1nc(C(=O)Nc2nc3c(C(=O)Nc4ncc[nH]4)cccc3[nH]2)cc2ccccc12] | 1-(2-Methylsulfanyl-ethyl)-isoquinoline-3-carboxylic acid [4-(1H-imidazol-2-ylcarbamoyl)-1H-benzoimidazol-2-yl]-amide |
| 299 | 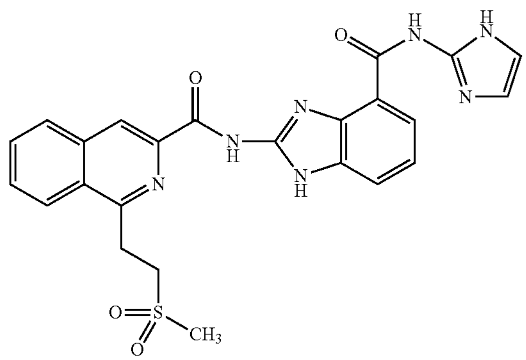 [SMILES: CS(=O)(=O)CCc1nc(C(=O)Nc2nc3c(C(=O)Nc4ncc[nH]4)cccc3[nH]2)cc2ccccc12] | 1-(2-Methanesulfonyl-ethyl)-isoquinoline-3-carboxylic acid [4-(1H-imidazol-2-ylcarbamoyl)-1H-benzoimidazol-2-yl]-amide |
| 300 | 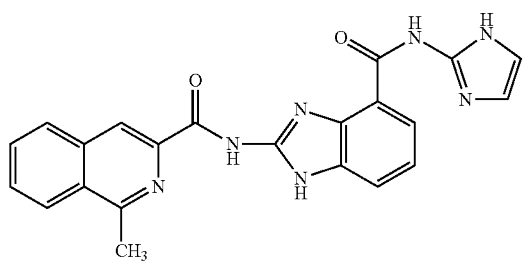 [SMILES: Cc1nc(C(=O)Nc2nc3c(C(=O)Nc4ncc[nH]4)cccc3[nH]2)cc2ccccc12] | 1-Methyl-isoquinoline-3-carboxylic acid [4-(1H-imidazol-2-ylcarbamoyl)-1H-benzoimidazol-2-yl]-amide |
| 301 | 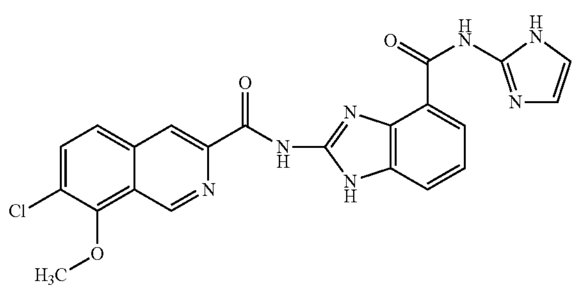 [SMILES: COc1c(Cl)ccc2cc(C(=O)Nc3nc4c(C(=O)Nc5ncc[nH]5)cccc4[nH]3)ncc12] | 7-Chloro-8-methoxy-isoquinoline-3-carboxylic acid [4-(1H-imidazol-2-ylcarbamoyl)-1H-benzoimidazol-2-yl]-amide |
| 302 | 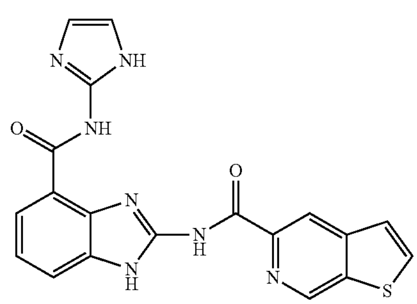 [SMILES: O=C(Nc1nc2c(C(=O)Nc3ncc[nH]3)cccc2[nH]1)c1cc2ccsc2cn1] | Thieno[2,3-c]pyridine-5-carboxylic acid [4-(1H-imidazol-2-ylcarbamoyl)-1H-benzoimidazol-2-yl]-amide |

TABLE 1-continued

| Ex. | Structure | Name |
|---|---|---|
| 303 | 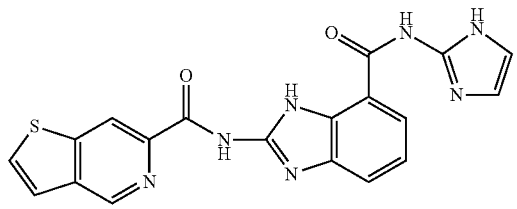 [SMILES: O=C(Nc1nc2cccc(C(=O)Nc3ncc[nH]3)c2[nH]1)c1cc2sccc2cn1] | Thieno[3,2-c]pyridine-6-carboxylicacid [7-(1H-imidazol-2-ylcarbamoyl)-1H-benzoimidazol-2-yl]-amide |
| 304 | 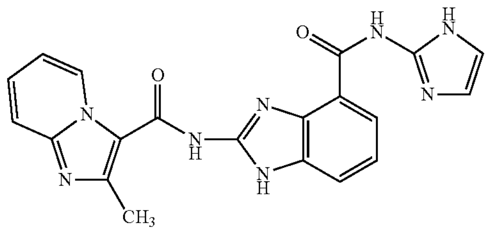 [SMILES: Cc1nc2ccccn2c1C(=O)Nc1nc2c(C(=O)Nc3ncc[nH]3)cccc2[nH]1] | 2-[(2-Methyl-imidazo[1,2-a]pyridine-3-carbonyl)-amino]-1H-benzoimidazole-4-carboxylic acid (1H-imidazol-2-yl)-amide |
| 305 | 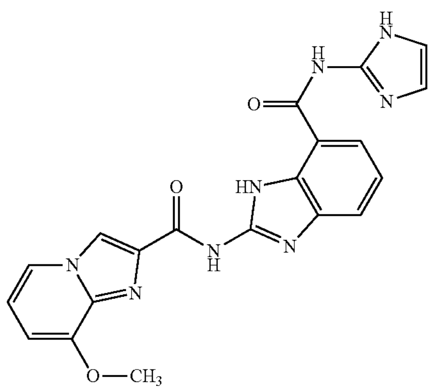 [SMILES: COc1cccn2cc(C(=O)Nc3nc4cccc(C(=O)Nc5ncc[nH]5)c4[nH]3)nc12] | 2-[(8-Methoxy-imidazo[1,2-a]pyridine-2-carbonyl)-amino]-3H-benzoimidazole-4-carboxylic acid (1H-imidazol-2-yl)-amide |
| 306 | 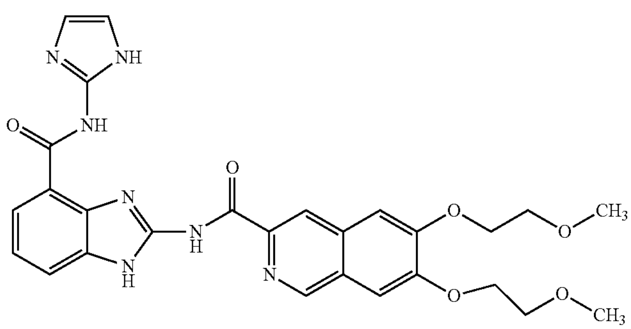 [SMILES: COCCOc1cc2cnc(C(=O)Nc3nc4c(C(=O)Nc5ncc[nH]5)cccc4[nH]3)cc2cc1OCCOC] | 6,7-Bis-(2-methoxy-ethoxy)-isoquinoline-3-carboxylic acid [4-(1H-imidazol-2-ylcarbamoyl)-1H-benzoimidazol-2-yl]-amide |
| 307 | 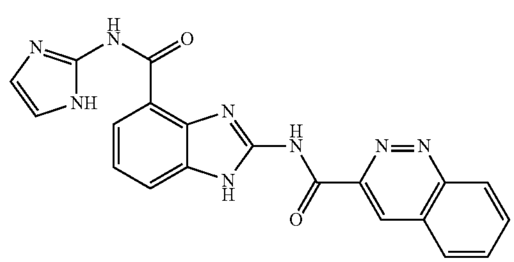 [SMILES: O=C(Nc1nc2c(C(=O)Nc3ncc[nH]3)cccc2[nH]1)c1cc2ccccc2nn1] | Cinnoline-3-carboxylic acid [4-(1H-imidazol-2-ylcarbamoyl)-1H-benzoimidazol-2-yl]-amide |

TABLE 1-continued

| Ex. | Structure | Name |
| --- | --- | --- |
| 308 | 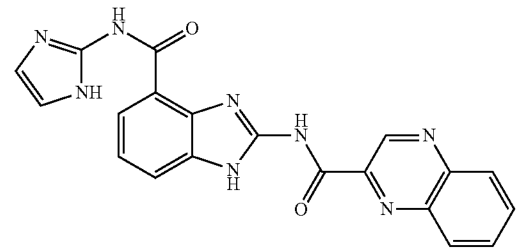 [SMILES: O=C(Nc1nc2c(C(=O)Nc3ncc[nH]3)cccc2[nH]1)c1cnc2ccccc2n1] | Quinoxaline-2-carboxylic acid [4-(1H-imidazol-2-ylcarbamoyl)-1H-benzoimidazol-2-yl]-amide |
| 309 | 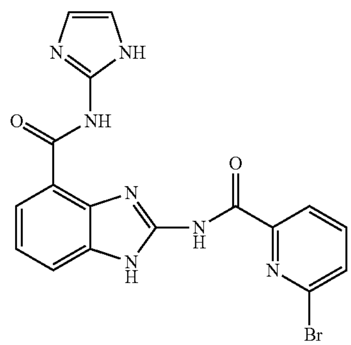 [SMILES: O=C(Nc1nc2c(C(=O)Nc3ncc[nH]3)cccc2[nH]1)c1cccc(Br)n1] | 2-[(6-Bromo-pyridine-2-carbonyl)-amino]-1H-benzoimidazole-4-carboxylic acid (1H-imidazol-2-yl)-amide |
| 310 | 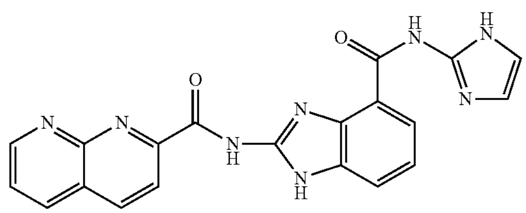 [SMILES: O=C(Nc1nc2c(C(=O)Nc3ncc[nH]3)cccc2[nH]1)c1ccc2cccnc2n1] | [1,8]Naphthyridine-2-carboxylic acid [4-(1H-imidazol-2-ylcarbamoyl)-1H-benzoimidazol-2-yl]-amide |
| 311 | 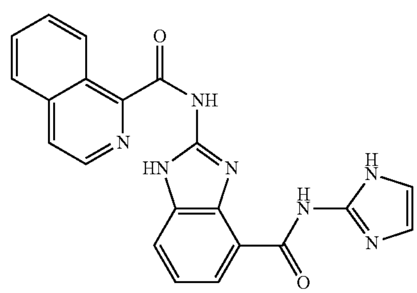 [SMILES: O=C(Nc1nc2c(C(=O)Nc3ncc[nH]3)cccc2[nH]1)c1nccc2ccccc12] | Isoquinoline-1-carboxylic acid [4-(1H-imidazol-2-ylcarbamoyl)-1H-benzoimidazol-2-yl]-amide |
| 312 | 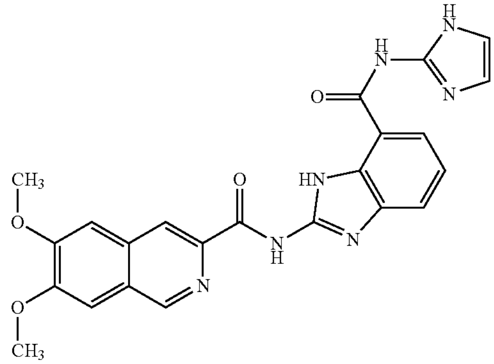 [SMILES: COc1cc2cnc(C(=O)Nc3nc4cccc(C(=O)Nc5ncc[nH]5)c4[nH]3)cc2cc1OC] | 6,7-Dimethoxy-isoquinoline-3-carboxylic acid [4-(1H-imidazol-2-ylcarbamoyl)-1H-benzoimidazol-2-yl]-amide |

TABLE 1-continued

| Ex. | Structure | Name |
| --- | --- | --- |
| 313 | 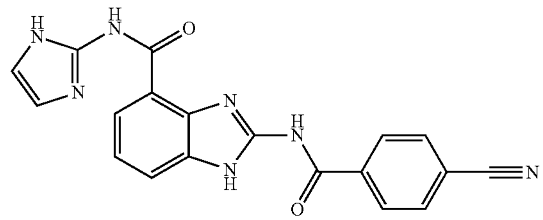 [SMILES: N#Cc1ccc(C(=O)Nc2nc3c(C(=O)Nc4ncc[nH]4)cccc3[nH]2)cc1] | 2-(4-Cyano-benzoylamino)-1H-benzoimidazole-4-carboxylic acid (1H-imidazol-2-yl)-amide |
| 314 | 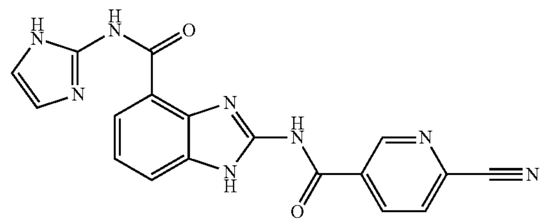 [SMILES: N#Cc1ccc(C(=O)Nc2nc3c(C(=O)Nc4ncc[nH]4)cccc3[nH]2)cn1] | 2-[(6-Cyano-pyridine-3-carbonyl)-amino]-1H-benzoimidazole-4-carboxylic acid (1H-imidazol-2-yl)-amide |
| 315 | 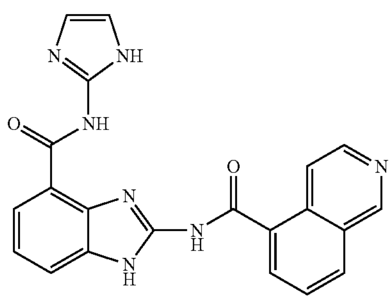 [SMILES: O=C(Nc1nc2c(C(=O)Nc3ncc[nH]3)cccc2[nH]1)c1cccc2cnccc12] | Isoquinoline-5-carboxylic acid [4-(1H-imidazol-2-ylcarbamoyl)-1H-benzoimidazol-2-yl]-amide |
| 316 | 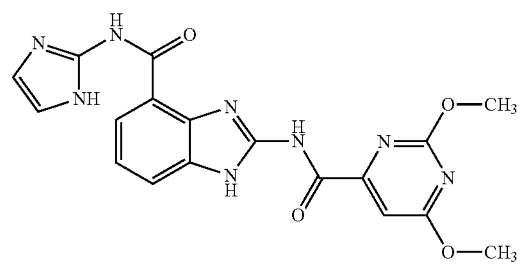 [SMILES: COc1cc(C(=O)Nc2nc3c(C(=O)Nc4ncc[nH]4)cccc3[nH]2)nc(OC)n1] | 2-[(2,6-Dimethoxy-pyrimidine-4-carbonyl)-amino]-1H-benzoimidazole-4-carboxylic acid (1H-imidazol-2-yl)-amide |
| 317 | 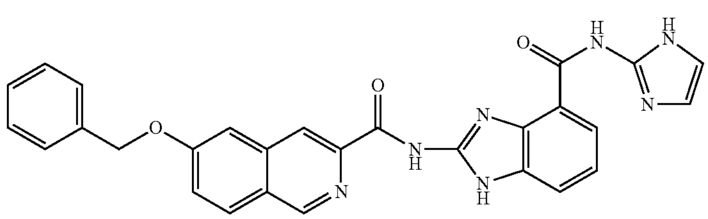 [SMILES: O=C(Nc1nc2c(C(=O)Nc3ncc[nH]3)cccc2[nH]1)c1cc2cc(OCc3ccccc3)ccc2cn1] | 6-Benzyloxy-isoquinoline-3-carboxylic acid [4-(1H-imidazol-2-ylcarbamoyl)-1H-benzoimidazol-2-yl]-amide |
| 318 | 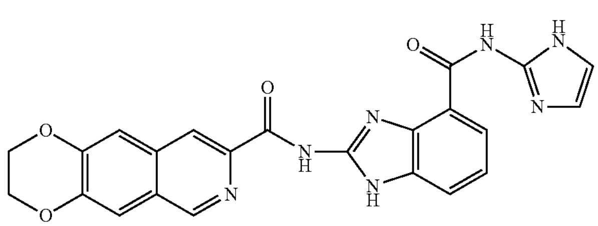 [SMILES: O=C(Nc1nc2c(C(=O)Nc3ncc[nH]3)cccc2[nH]1)c1cc2cc3c(cc2cn1)OCCO3] | 2,3-Dihydro-[1,4]dioxino[2,3-g]isoquinoline-8-carboxylic acid [4-(1H-imidazol-2-ylcarbamoyl)-1H-benzoimidazol-2-yl]-amide |

TABLE 1-continued

| Ex. | Structure | Name |
|---|---|---|
| 319 | 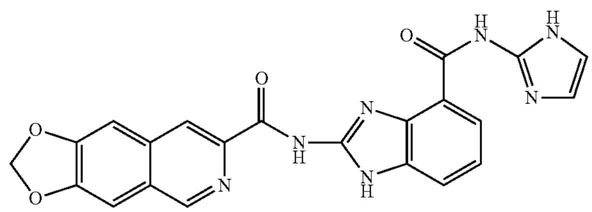 [SMILES: O=C(Nc1nc2c(C(=O)Nc3ncc[nH]3)cccc2[nH]1)c1cc2cc3c(cc2cn1)OCO3] | [1,3]Dioxolo[4,5-g]isoquinoline-7-carboxylic acid [4-(1H-imidazol-2-ylcarbamoyl)-1H-benzoimidazol-2-yl]-amide |
| 320 | 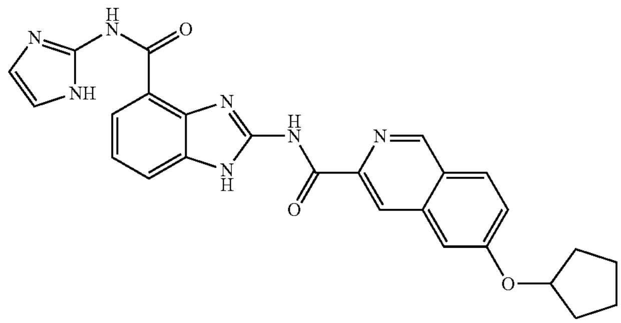 [SMILES: O=C(Nc1nc2c(C(=O)Nc3ncc[nH]3)cccc2[nH]1)c1cc2cc(OC3CCCC3)ccc2cn1] | 6-Cyclopentyloxy-isoquinoline-3-carboxylic acid [4-(1H-imidazol-2-ylcarbamoyl)-1H-benzoimidazol-2-yl]-amide |
| 321 | 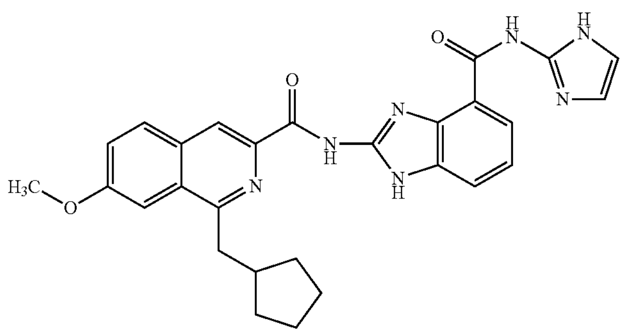 [SMILES: COc1ccc2cc(C(=O)Nc3nc4c(C(=O)Nc5ncc[nH]5)cccc4[nH]3)nc(CC3CCCC3)c2c1] | 1-Cyclopentylmethyl-7-methoxy-isoquinoline-3-carboxylic acid [4-(1H-imidazol-2-ylcarbamoyl)-1H-benzoimidazol-2-yl]-amide |
| 322 | 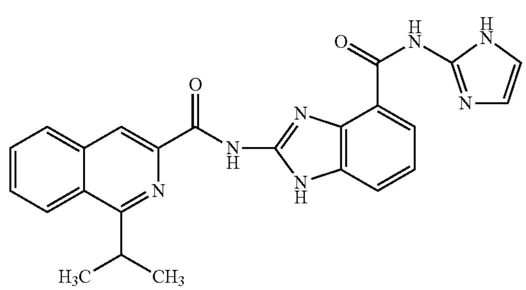 [SMILES: CC(C)c1nc(C(=O)Nc2nc3c(C(=O)Nc4ncc[nH]4)cccc3[nH]2)cc2ccccc12] | 1-Isopropyl-isoquinoline-3-carboxylic acid [4-(1H-imidazol-2-ylcarbamoyl)-1H-benzoimidazol-2-yl]-amide |
| 323 | 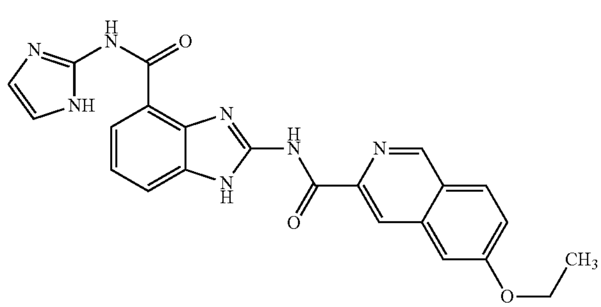 [SMILES: CCOc1ccc2cnc(C(=O)Nc3nc4c(C(=O)Nc5ncc[nH]5)cccc4[nH]3)cc2c1] | 6-Ethoxy-isoquinoline-3-carboxylicacid [4-(1H-imidazol-2-ylcarbamoyl)-1H-benzoimidazol-2-yl]-amide |

TABLE 1-continued

| Ex. | Structure | Name |
|---|---|---|
| 324 | 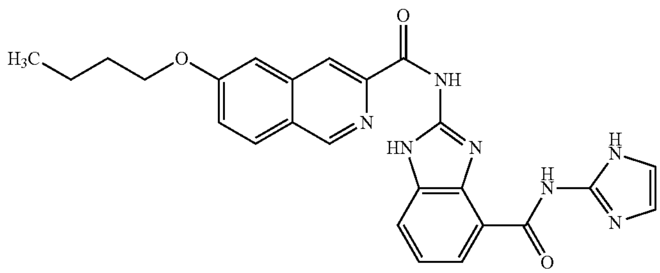 [SMILES: CCCCOc1ccc2cnc(C(=O)Nc3nc4c(C(=O)Nc5ncc[nH]5)cccc4[nH]3)cc2c1] | 6-Butoxy-isoquinoline-3-carboxylic acid [4-(1H-imidazol-2-lcarbamoyl)-1H-benzoimidazol-2-yl]-amide |
| 325 | 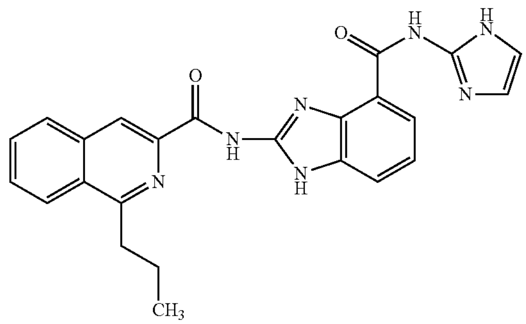 [SMILES: CCCc1nc(C(=O)Nc2nc3c(C(=O)Nc4ncc[nH]4)cccc3[nH]2)cc2ccccc12] | 1-Propyl-isoquinoline-3-carboxylic acid [4-(1H-imidazol-2-lcarbamoyl)-1H-benzoimidazol-2-yl]-amide |
| 326 | 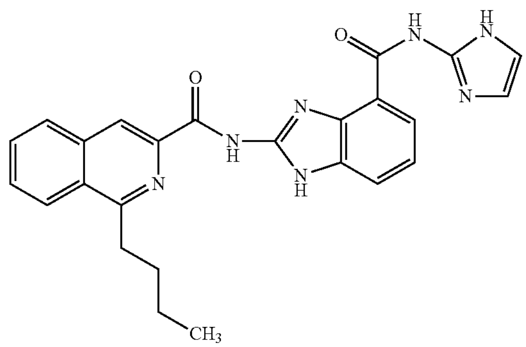 | 1-Butyl-isoquinoline-3-carboxylic acid [4-(1H-imidazol-2-lcarbamoyl)-1H-benzoimidazol-2-yl]-amide |
| 327 | 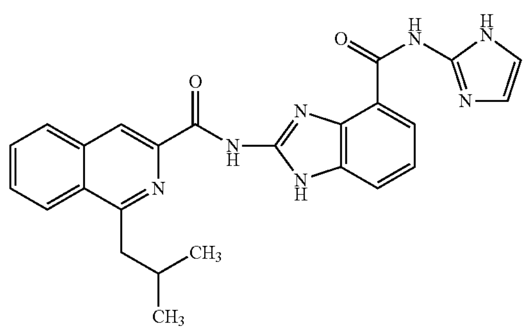 [SMILES: CC(C)Cc1nc(C(=O)Nc2nc3c(C(=O)Nc4ncc[nH]4)cccc3[nH]2)cc2ccccc12] | 1-Isobutyl-isoquinoline-3-carboxylic acid [4-(1H-imidazol-2-ylcarbamoyl)-1H-benzoimidazol-2-yl]-amide |
| 328 | 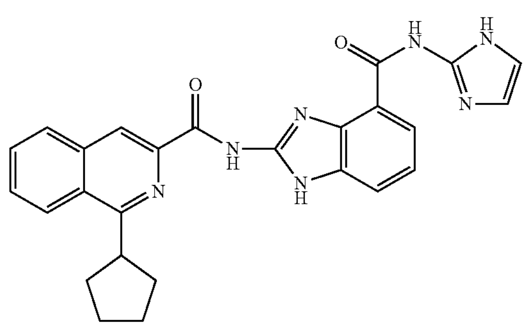 [SMILES: O=C(Nc1nc2c(C(=O)Nc3ncc[nH]3)cccc2[nH]1)c1cc2ccccc2c(C2CCCC2)n1] | 1-Cyclopentyl-isoquinoline-3-carboxylic acid [4-(1H-imidazol-2-ylcarbamoyl)-1H-benzoimidazol-2-yl]-amide |

TABLE 1-continued

| Ex. | Structure | Name |
| --- | --- | --- |
| 329 | 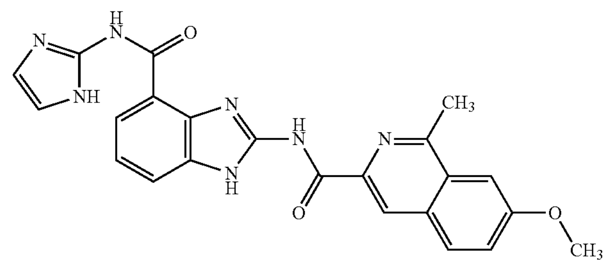 [SMILES: COc1ccc2cc(C(=O)Nc3nc4c(C(=O)Nc5ncc[nH]5)cccc4[nH]3)nc(C)c2c1] | 7-Methoxy-1-methyl-isoquinoline-3-carboxylic acid [4-(1H-imidazol-2-ylcarbamoyl)-1H-benzoimidazol-2-yl]-amide |
| 330 | 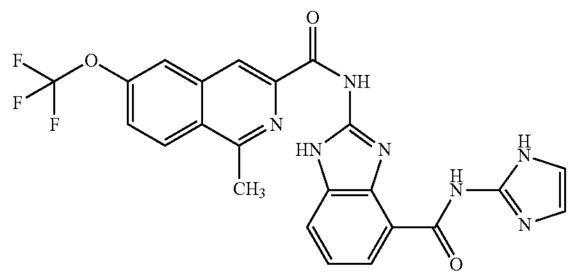 [SMILES: Cc1nc(C(=O)Nc2nc3c(C(=O)Nc4ncc[nH]4)cccc3[nH]2)cc2cc(OC(F)(F)F)ccc12] | 1-Methyl-6-trifluoromethoxy-isoquinoline-3-carboxylic acid [4-(1H-imidazol-2-ylcarbamoyl)-1H-benzoimidazol-2-yl]-amide |
| 331 | 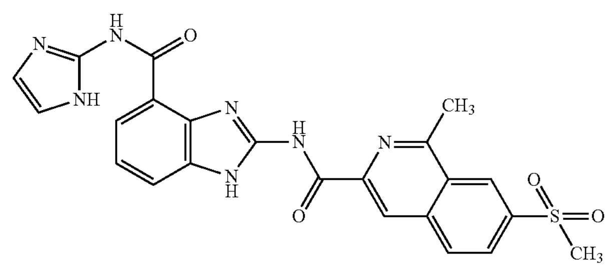 [SMILES: Cc1nc(C(=O)Nc2nc3c(C(=O)Nc4ncc[nH]4)cccc3[nH]2)cc2ccc(S(C)(=O)=O)cc12] | 7-Methanesulfonyl-1-methyl-isoquinoline-3-carboxylic acid [4-(1H-imidazol-2-ylcarbamoyl)-1H-benzoimidazol-2-yl]-amide |
| 332 | 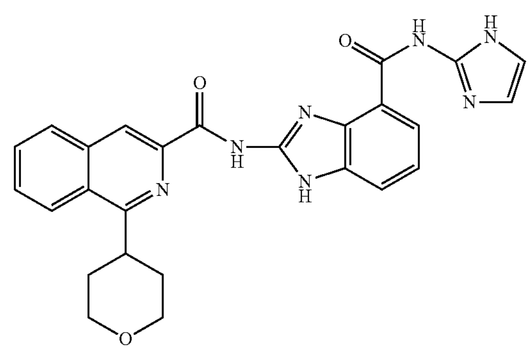 [SMILES: O=C(Nc1nc2c(C(=O)Nc3ncc[nH]3)cccc2[nH]1)c1cc2ccccc2c(C2CCOCC2)n1] | 1-(Tetrahydro-pyran-4-yl)-isoquinoline-3-carboxylic acid [4-(1H-imidazol-2-ylcarbamoyl)-1H-benzoimidazol-2-yl]-amide |
| 333 | 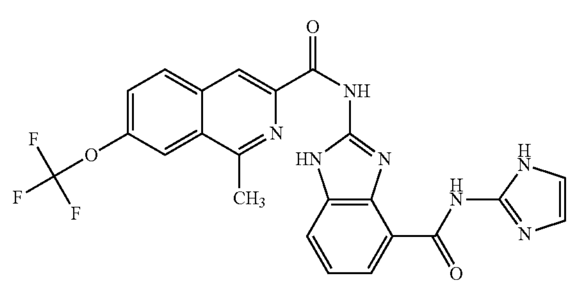 [SMILES: Cc1nc(C(=O)Nc2nc3c(C(=O)Nc4ncc[nH]4)cccc3[nH]2)cc2ccc(OC(F)(F)F)cc12] | 1-Methyl-7-trifluoromethoxy-isoquinoline-3-carboxylic acid [4-(1H-imidazol-2-ylcarbamoyl)-1H-benzoimidazol-2-yl]-amide |

TABLE 1-continued

| Ex. | Structure | Name |
|---|---|---|
| 334 | 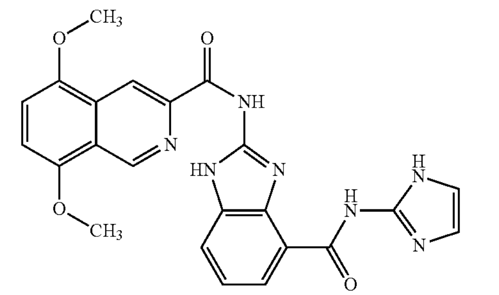 [SMILES: COc1ccc(OC)c2cc(C(=O)Nc3nc4c(C(=O)Nc5ncc[nH]5)cccc4[nH]3)ncc12] | 5,8-Dimethoxy-isoquinoline-3-carboxylic acid [4-(1H-imidazol-2-ylcarbamoyl)-1H-benzoimidazol-2-yl]-amide |
| 335 | 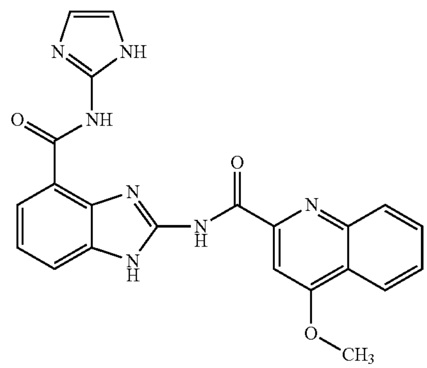 [SMILES: COc1cc(C(=O)Nc2nc3c(C(=O)Nc4ncc[nH]4)cccc3[nH]2)nc2ccccc12] | 4-Methoxy-quinoline-2-carboxylic acid [4-(1H-imidazol-2-ylcarbamoyl)-1H-benzoimidazol-2-yl]-amide |
| 336 | 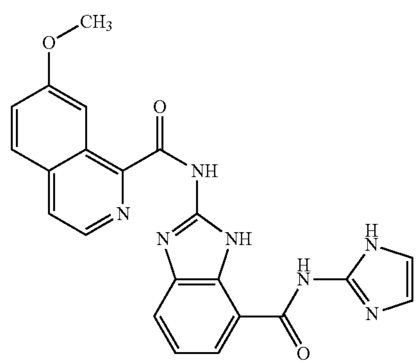 [SMILES: COc1ccc2ccnc(C(=O)Nc3nc4cccc(C(=O)Nc5ncc[nH]5)c4[nH]3)c2c1] | 7-Methoxy-isoquinoline-1-carboxylic acid [7-(1H-imidazol-2-ylcarbamoyl)-1H-benzoimidazol-2-yl]-amide |
| 337 | 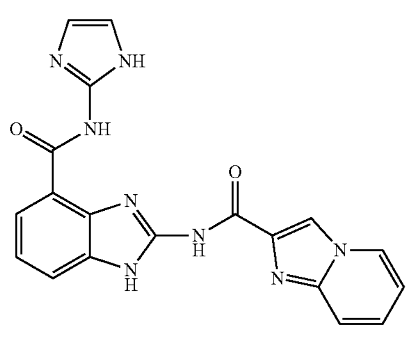 [SMILES: O=C(Nc1nc2c(C(=O)Nc3ncc[nH]3)cccc2[nH]1)c1cn2ccccc2n1] | 2-[(Imidazo[1,2-a]pyridine-2-carbonyl)-amino]-1H-benzoimidazole-4-carboxylic acid (1H-imidazol-2-yl)-amide |
| 338 | 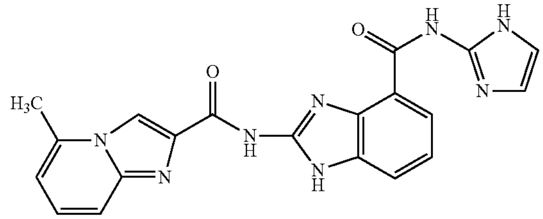 [SMILES: Cc1cccc2nc(C(=O)Nc3nc4c(C(=O)Nc5ncc[nH]5)cccc4[nH]3)cn12] | 2-[(5-Methyl-imidazo[1,2-a]pyridine-2-carbonyl)-amino]-1H-benzoimidazole-4-carboxylic acid (1H-imidazol-2-yl)-amide |

TABLE 1-continued

| Ex. | Structure | Name |
|---|---|---|
| 339 | 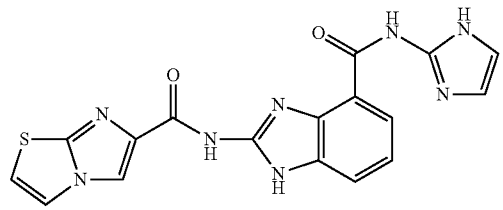 [SMILES: O=C(Nc1nc2c(C(=O)Nc3ncc[nH]3)cccc2[nH]1)c1cn2ccsc2n1] | 2-[(Imidazo[2,1-b]thiazole-6-carbonyl)-amino]-1H-benzoimidazole-4-carboxylic acid (1H-imidazol-2-yl)-amide |
| 340 | 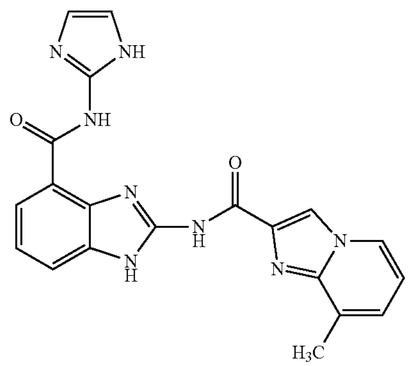 [SMILES: Cc1cccn2cc(C(=O)Nc3nc4c(C(=O)Nc5ncc[nH]5)cccc4[nH]3)nc12] | 2-[(8-Methyl-imidazo[1,2-a]pyridine-2-carbonyl)-amino]-1H-benzoimidazole-4-carboxylic acid (1H-imidazol-2-yl)-amide |
| 341 | 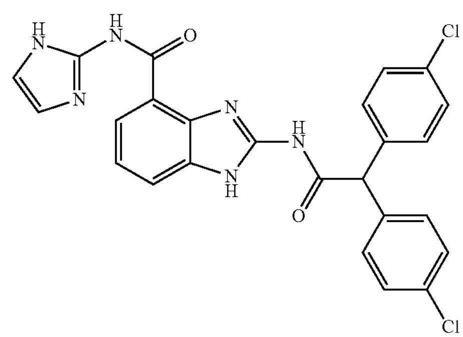 [SMILES: O=C(Nc1ncc[nH]1)c1cccc2[nH]c(NC(=O)C(c3ccc(Cl)cc3)c3ccc(Cl)cc3)nc12] | 2-[2,2-Bis-(4-chloro-phenyl)-acetylamino]-1H-benzoimidazole-4-carboxylic acid (1H-imidazol-2-yl)-amide |
| 342 | 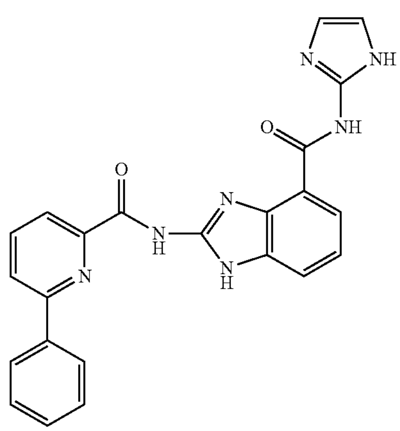 [SMILES: O=C(Nc1nc2c(C(=O)Nc3ncc[nH]3)cccc2[nH]1)c1cccc(-c2ccccc2)n1] | 2-[(6-Phenyl-pyridine-2-carbonyl)-amino]-1H-benzoimidazole-4-carboxylic acid (1H-imidazol-2-yl)-amide |

TABLE 1-continued

| Ex. | Structure | Name |
|---|---|---|
| 343 | 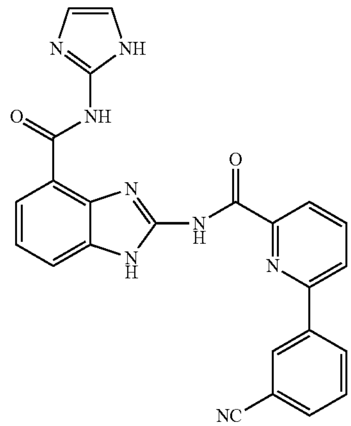 [SMILES: N#Cc1cccc(-c2cccc(C(=O)Nc3nc4c(C(=O)Nc5ncc[nH]5)cccc4[nH]3)n2)c1] | 2-{[6-(3-Cyano-phenyl)-pyridine-2-carbonyl]-amino}-1H-benzoimidazole-4-carboxylic acid (1H-imidazol-2-yl)-amide |
| 344 | 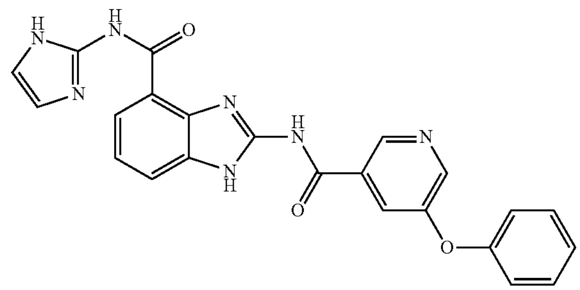 [SMILES: O=C(Nc1nc2c(C(=O)Nc3ncc[nH]3)cccc2[nH]1)c1cncc(Oc2ccccc2)c1] | 2-[(5-Phenoxy-pyridine-3-carbonyl)-amino]-1H-benzoimidazole-4-carboxylic acid (1H-imidazol-2-yl)-amide |
| 345 | 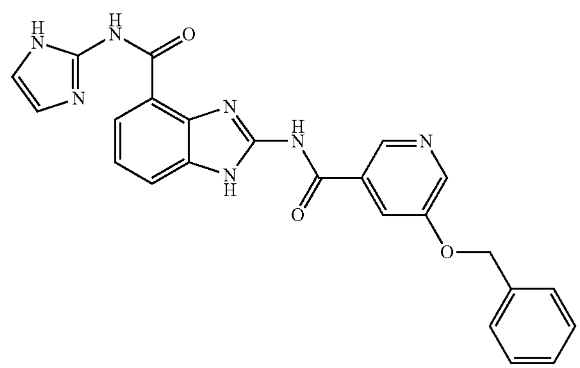 [SMILES: O=C(Nc1nc2c(C(=O)Nc3ncc[nH]3)cccc2[nH]1)c1cncc(OCc2ccccc2)c1] | 2-[(5-Benzyloxy-pyridine-3-carbonyl)-amino]-1H-benzoimidazole-4-carboxylic acid (1H-imidazol-2-yl)-amide |
| 346 | 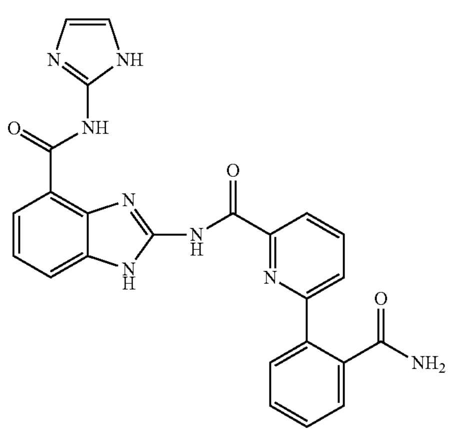 [SMILES: NC(=O)c1ccccc1-c1cccc(C(=O)Nc2nc3c(C(=O)Nc4ncc[nH]4)cccc3[nH]2)n1] | 2-{[6-(2-Carbamoyl-phenyl)-pyridine-2-carbonyl]-amino}-1H-benzoimidazole-4-carboxylic acid (1H-imidazol-2-yl)-amide |

TABLE 1-continued

| Ex. | Structure | Name |
|---|---|---|
| 347 | 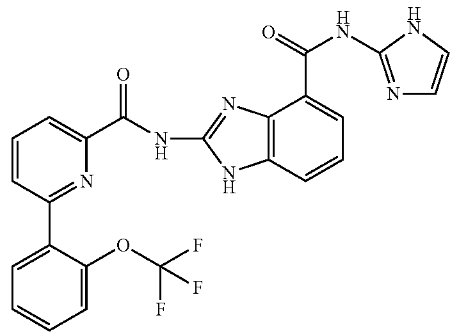 [SMILES: O=C(Nc1nc2c(C(=O)Nc3ncc[nH]3)cccc2[nH]1)c1cccc(-c2ccccc2OC(F)(F)F)n1] | 2-{[6-(2-Trifluoromethoxy-phenyl)-pyridine-2-carbonyl]-amino}-1H-benzoimidazole-4-carboxylic acid (1H-imidazol-2-yl)-amide |
| 348 | 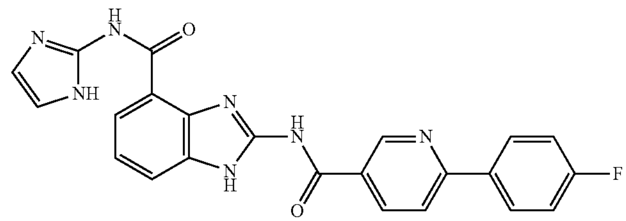 [SMILES: O=C(Nc1nc2c(C(=O)Nc3ncc[nH]3)cccc2[nH]1)c1ccc(-c2ccc(F)cc2)nc1] | 2-{[6-(4-Fluoro-phenyl)-pyridine-3-carbonyl]-amino}-1H-benzoimidazole-4-carboxylic acid (1H-imidazol-2-yl)-amide |
| 349 | 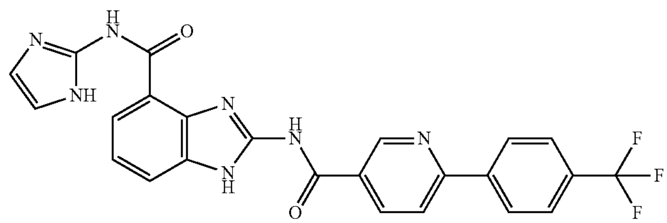 [SMILES: O=C(Nc1nc2c(C(=O)Nc3ncc[nH]3)cccc2[nH]1)c1ccc(-c2ccc(C(F)(F)F)cc2)nc1] | 2-{[6-(4-Trifluoromethyl-phenyl)-pyridine-3-carbonyl]-amino}-1H-benzoimidazole-4-carboxylic acid (1H-imidazol-2-yl)-amide |
| 350 | 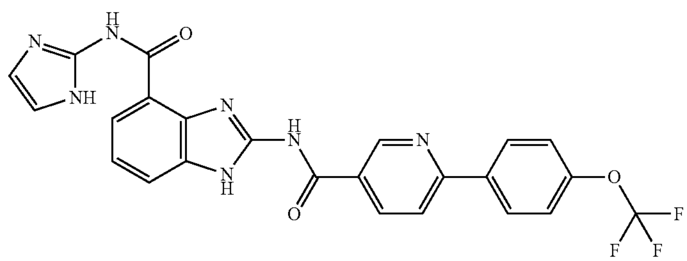 [SMILES: O=C(Nc1nc2c(C(=O)Nc3ncc[nH]3)cccc2[nH]1)c1ccc(-c2ccc(OC(F)(F)F)cc2)nc1] | 2-{[6-(4-Trifluoromethoxy-phenyl)-pyridine-3-carbonyl]-amino}-1H-benzoimidazole-4-carboxylic acid (1H-imidazol-2-yl)-amide |
| 351 | 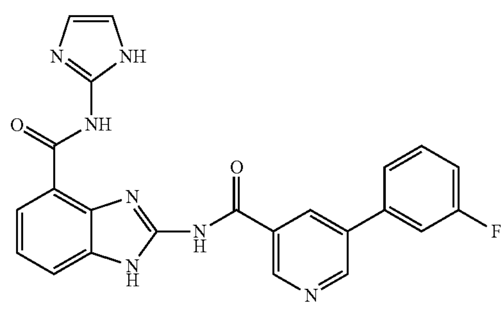 [SMILES: O=C(Nc1nc2c(C(=O)Nc3ncc[nH]3)cccc2[nH]1)c1cncc(-c2cccc(F)c2)c1] | 2-{[5-(3-Fluoro-phenyl)-pyridine-3-carbonyl]-amino}-1H-benzoimidazole-4-carboxylic acid (1H-imidazol-2-yl)-amide |
| 352 | 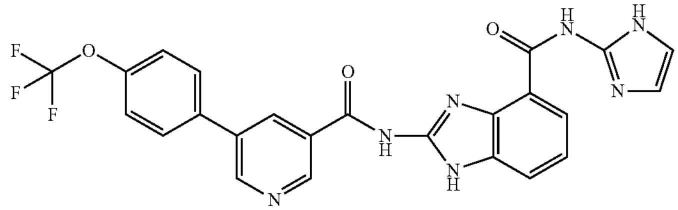 [SMILES: O=C(Nc1nc2c(C(=O)Nc3ncc[nH]3)cccc2[nH]1)c1cncc(-c2ccc(OC(F)(F)F)cc2)c1] | 2-{[5-(4-Trifluoromethoxy-phenyl)-pyridine-3-carbonyl]-amino}-1H-benzoimidazole-4-carboxylic acid (1H-imidazol-2-yl)-amide |

TABLE 1-continued

| Ex. | Structure | Name |
|---|---|---|
| 353 | 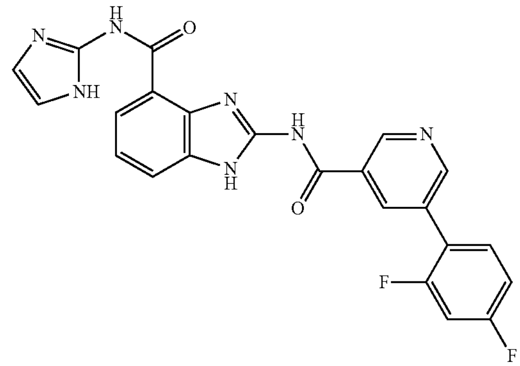 [SMILES: O=C(Nc1nc2c(C(=O)Nc3ncc[nH]3)cccc2[nH]1)c1cncc(-c2ccc(F)cc2F)c1] | 2-{[5-(2,4-Difluoro-phenyl)-pyridine-3-carbonyl]-amino}-1H-benzoimidazole-4-carboxylic acid (1H-imidazol-2-yl)-amide |
| 354 | 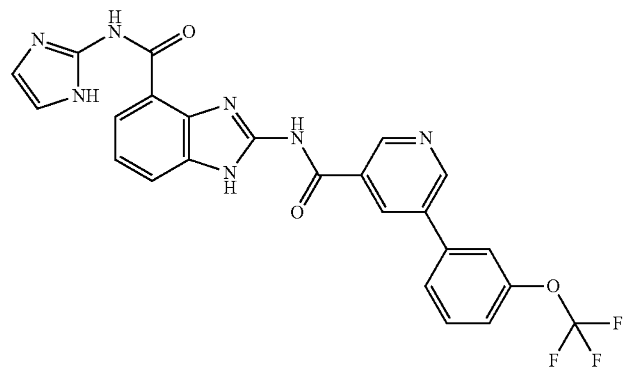 [SMILES: O=C(Nc1nc2c(C(=O)Nc3ncc[nH]3)cccc2[nH]1)c1cncc(-c2cccc(OC(F)(F)F)c2)c1] | 2-{[5-(3-Trifluoromethoxy-phenyl)-pyridine-3-carbonyl]-amino}-1H-benzoimidazole-4-carboxylic acid (1H-imidazol-2-yl)-amide |
| 355 | 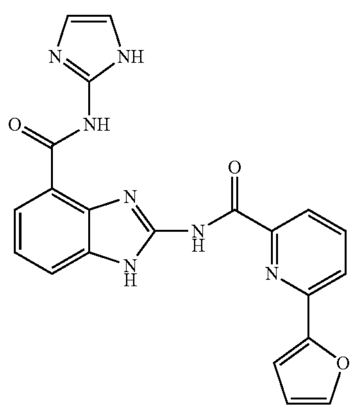 [SMILES: O=C(Nc1nc2c(C(=O)Nc3ncc[nH]3)cccc2[nH]1)c1cccc(-c2ccco2)n1] | 2-[(6-Furan-2-yl-pyridine-2-carbonyl)-amino]-1H-benzoimidazole-4-carboxylic acid (1H-imidazol-2-yl)-amide |
| 356 | 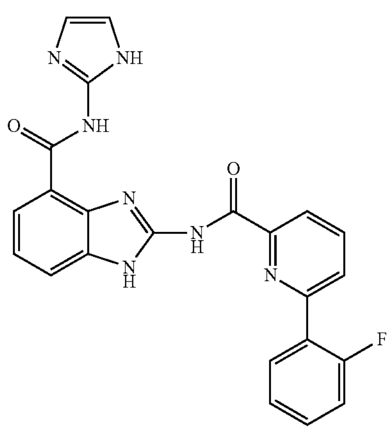 [SMILES: O=C(Nc1nc2c(C(=O)Nc3ncc[nH]3)cccc2[nH]1)c1cccc(-c2ccccc2F)n1] | 2-{[6-(2-Fluoro-phenyl)-pyridine-2-carbonyl]-amino}-1H-benzoimidazole-4-carboxylic acid (1H-imidazol-2-yl)-amide |

TABLE 1-continued

| Ex. | Structure | Name |
|---|---|---|
| 357 | 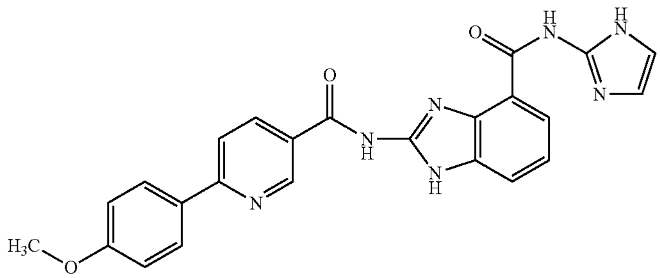 [SMILES: COc1ccc(-c2ccc(C(=O)Nc3nc4c(C(=O)Nc5ncc[nH]5)cccc4[nH]3)cn2)cc1] | 2-{[6-(4-Methoxy-phenyl)-pyridine-3-carbonyl]-amino}-1H-benzoimidazole-4-carboxylic acid (1H-imidazol-2-yl)-amide |
| 358 | 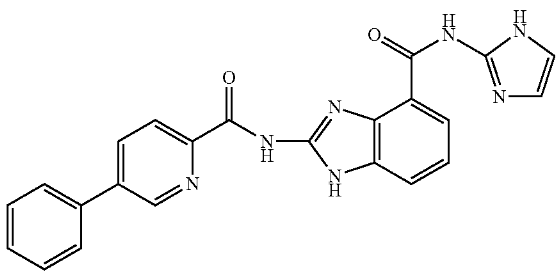 [SMILES: O=C(Nc1nc2c(C(=O)Nc3ncc[nH]3)cccc2[nH]1)c1ccc(-c2ccccc2)cn1] | 2-[(5-Phenyl-pyridine-2-carbonyl)-amino]-1H-benzoimidazole-4-carboxylic acid (1H-imidazol-2-yl)-amide |
| 359 | 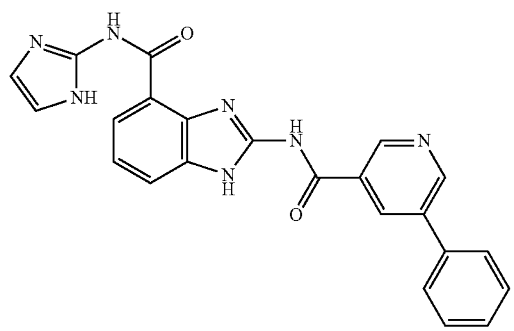 [SMILES: O=C(Nc1nc2c(C(=O)Nc3ncc[nH]3)cccc2[nH]1)c1cncc(-c2ccccc2)c1] | 2-[(5-Phenyl-pyridine-2-carbonyl)-amino]-1H-benzoimidazole-4-carboxylic acid (1H-imidazol-2-yl)-amide |
| 360 | 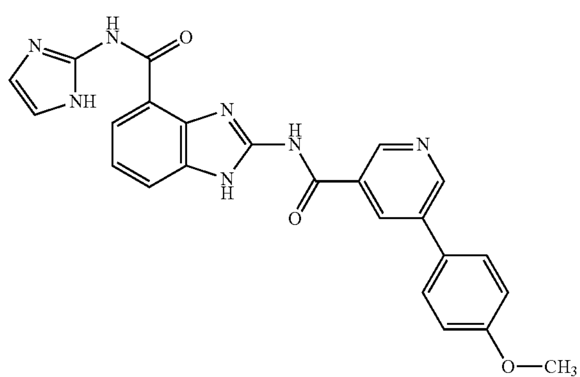 [SMILES: COc1ccc(-c2cncc(C(=O)Nc3nc4c(C(=O)Nc5ncc[nH]5)cccc4[nH]3)c2)cc1] | 2-{[5-(4-Methoxy-phenyl)-pyridine-3-carbonyl]-amino}-1H-benzoimidazole-4-carboxylic acid (1H-imidazol-2-yl)-amide |
| 361 | 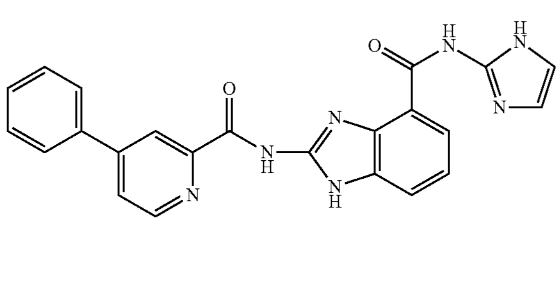 [SMILES: O=C(Nc1nc2c(C(=O)Nc3ncc[nH]3)cccc2[nH]1)c1cc(-c2ccccc2)ccn1] | 2-[(4-Phenyl-pyridine-2-carbonyl)-amino]-1H-benzoimidazole-4-carboxylic acid (1H-imidazol-2-yl)-amide |

TABLE 1-continued

| Ex. | Structure | Name |
|---|---|---|
| 362 | 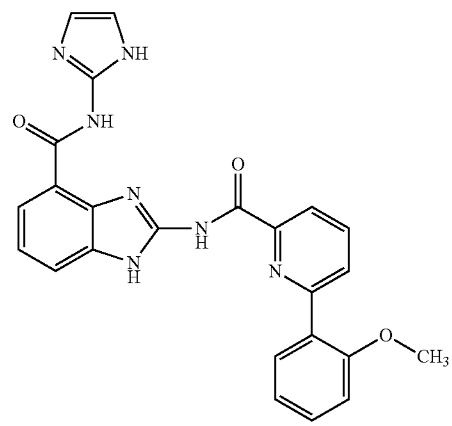 [SMILES: COc1ccccc1-c1cccc(C(=O)Nc2nc3c(C(=O)Nc4ncc[nH]4)cccc3[nH]2)n1] | 2-{[6-(2-Methoxy-phenyl)-pyridine-3-carbonyl]-amino}-1H-benzoimidazole-4-carboxylic acid (1H-imidazol-2-yl)-amide |
| 363 | 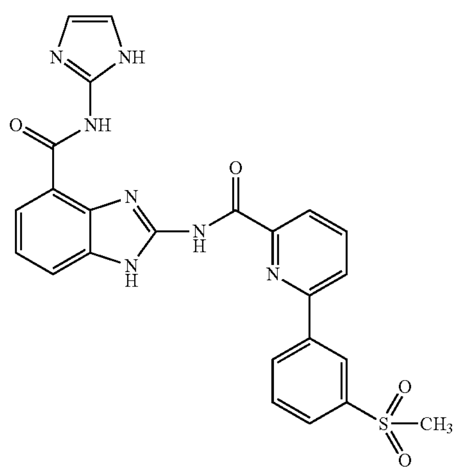 [SMILES: CS(=O)(=O)c1cccc(-c2cccc(C(=O)Nc3nc4c(C(=O)Nc5ncc[nH]5)cccc4[nH]3)n2)c1] | 2-{[6-(3-Methanesulfonyl-phenyl)-pyridine-2-carbonyl]-amino}-1H-benzoimidazole-4-carboxylic acid (1H-imidazol-2-yl)-amide |
| 364 | 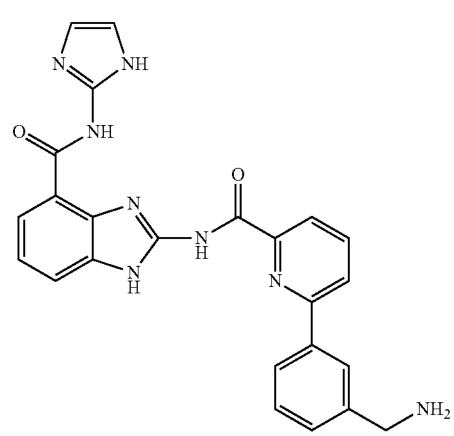 [SMILES: NCc1cccc(-c2cccc(C(=O)Nc3nc4c(C(=O)Nc5ncc[nH]5)cccc4[nH]3)n2)c1] | 2-{[6-(3-Aminomethyl-phenyl)-pyridine-2-carbonyl]-amino}-1H-benzoimidazole-4-carboxylic acid (1H-imidazol-2-yl)-amide |

TABLE 1-continued

| Ex. | Structure | Name |
|---|---|---|
| 365 | 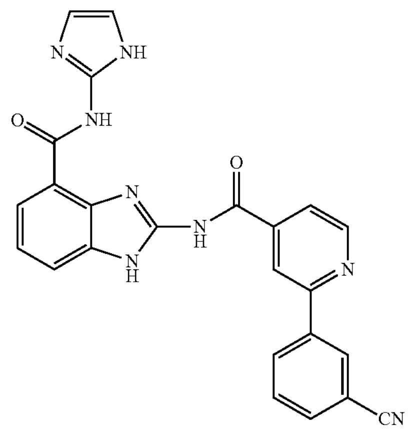 [SMILES: N#Cc1cccc(-c2cc(C(=O)Nc3nc4c(C(=O)Nc5ncc[nH]5)cccc4[nH]3)ccn2)c1] | 2-{[2-(3-Cyano-phenyl)-pyridine-4-carbonyl]-amino}-1H-benzoimidazole-4-carboxylic acid (1H-imidazol-2-yl)-amide |
| 366 | 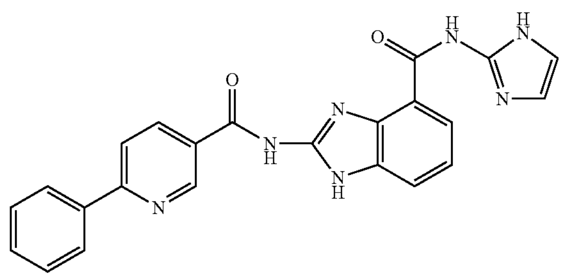 [SMILES: O=C(Nc1nc2c(C(=O)Nc3ncc[nH]3)cccc2[nH]1)c1ccc(-c2ccccc2)nc1] | 2-[(6-Phenyl-pyridine-3-carbonyl)-amino]-1H-benzoimidazole-4-carboxylic acid (1H-imidazol-2-yl)-amide |
| 367 | 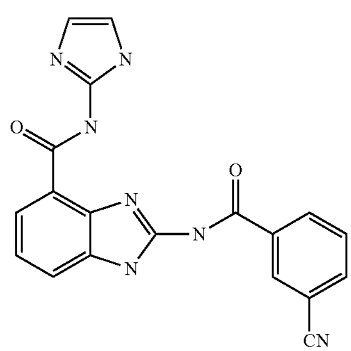 [SMILES: N#Cc1cccc(C(=O)Nc2nc3c(C(=O)Nc4ncc[nH]4)cccc3[nH]2)c1] | 2-(3-Cyano-benzoylamino)-1H-benzoimidazole-4-carboxylic acid (1H-imidazol-2-yl)-amide |
| 368 | 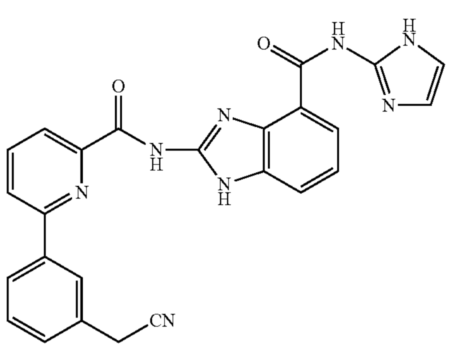 [SMILES: N#CCc1cccc(-c2cccc(C(=O)Nc3nc4c(C(=O)Nc5ncc[nH]5)cccc4[nH]3)n2)c1] | 2-{[6-(3-Cyanomethyl-phenyl)-pyridine-2-carbonyl]-amino}-1H-benzoimidazole-4-carboxylic acid (1H-imidazol-2-yl)-amide |

TABLE 1-continued

| Ex. | Structure | Name |
|---|---|---|
| 369 | 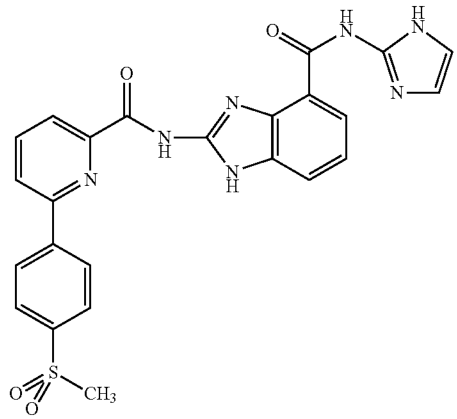 [SMILES: CS(=O)(=O)c1ccc(-c2cccc(C(=O)Nc3nc4c(C(=O)Nc5ncc[nH]5)cccc4[nH]3)n2)cc1] | 2-{[6-(4-Methanesulfonyl-phenyl)-pyridine-2-carbonyl]-amino}-1H-benzoimidazole-4-carboxylic acid (1H-imidazol-2-yl)-amide |
| 370 | 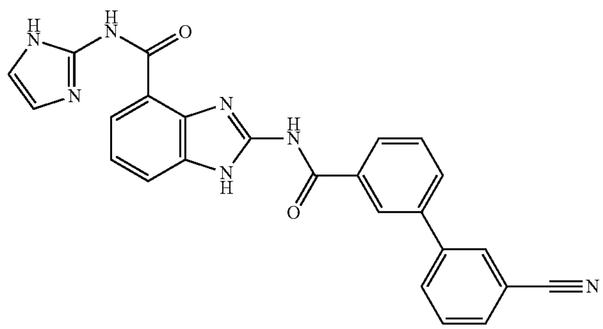 [SMILES: N#Cc1cccc(-c2cccc(C(=O)Nc3nc4c(C(=O)Nc5ncc[nH]5)cccc4[nH]3)c2)c1] | 2-[(3'-Cyano-biphenyl-3-carbonyl)-amino]-1H-benzoimidazole-4-carboxylic acid (1H-imidazol-2-yl)-amide |
| 371 | 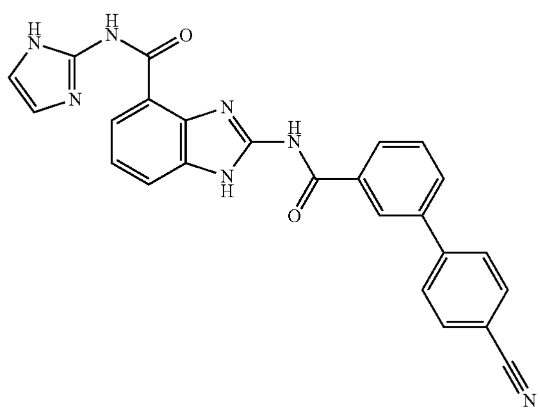 [SMILES: N#Cc1ccc(-c2cccc(C(=O)Nc3nc4c(C(=O)Nc5ncc[nH]5)cccc4[nH]3)c2)cc1] | 2-[(4'-Cyano-biphenyl-3-carbonyl)-amino]-1H-benzoimidazole-4-carboxylic acid (1H-imidazol-2-yl)-amide |
| 372 | 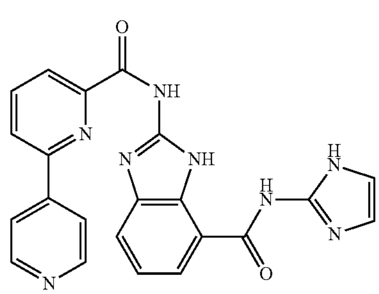 [SMILES: O=C(Nc1nc2cccc(C(=O)Nc3ncc[nH]3)c2[nH]1)c1cccc(-c2ccncc2)n1] | [2,4']Bipyridinyl-6-carboxylic acid[7-(1H-imidazol-2-ylcarbamoyl)-1H-benzoimidazol-2-yl]-amide |

TABLE 1-continued

| Ex. | Structure | Name |
|---|---|---|
| 373 | 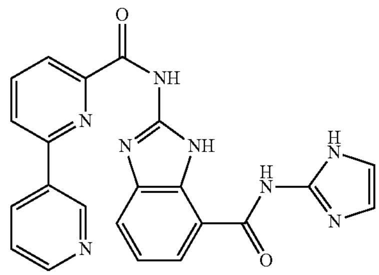 [SMILES: O=C(Nc1nc2cccc(C(=O)Nc3ncc[nH]3)c2[nH]1)c1cccc(-c2cccnc2)n1] | [2,3']Bipyridinyl-6-carboxylic acid[7-(1H-imidazol-2-ylcarbamoyl)-1H-benzoimidazol-2-yl]-amide |
| 374 | 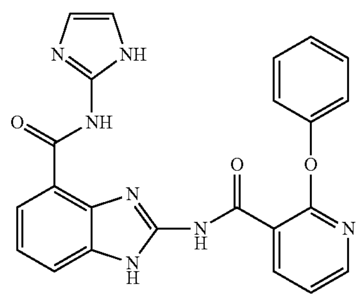 [SMILES: O=C(Nc1nc2c(C(=O)Nc3ncc[nH]3)cccc2[nH]1)c1cccnc1Oc1ccccc1] | 2-[(2-Phenoxy-pyridine-3-carbonyl)-amino]-1H-benzoimidazole-4-carboxylic acid (1H-imidazol-2-yl)-amide |
| 375 | 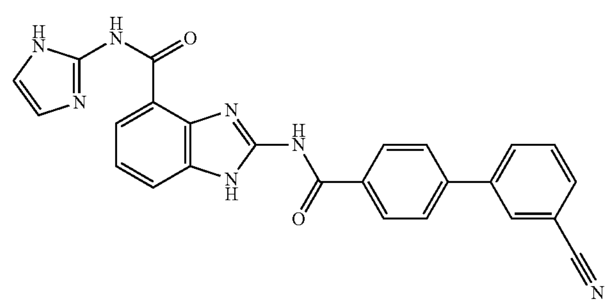 [SMILES: N#Cc1cccc(-c2ccc(C(=O)Nc3nc4c(C(=O)Nc5ncc[nH]5)cccc4[nH]3)cc2)c1] | 2-[(3'-Cyano-biphenyl-4-carbonyl)-amino]-1H-benzoimidazole-4-carboxylic acid (1H-imidazol-2-yl)-amide |
| 376 | 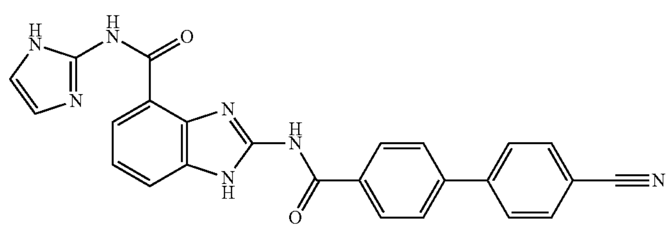 [SMILES: N#Cc1ccc(-c2ccc(C(=O)Nc3nc4c(C(=O)Nc5ncc[nH]5)cccc4[nH]3)cc2)cc1] | 2-[(4'-Cyano-biphenyl-4-carbonyl)-amino]-1H-benzoimidazole-4-carboxylic acid (1H-imidazol-2-yl)-amide |
| 377 | 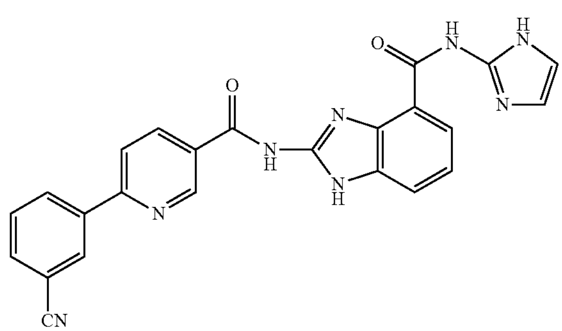 [SMILES: N#Cc1cccc(-c2ccc(C(=O)Nc3nc4c(C(=O)Nc5ncc[nH]5)cccc4[nH]3)cn2)c1] | 2-{[6-(3-Cyano-phenyl)-pyridine-3-carbonyl]-amino}-1H-benzoimidazole-4-carboxylic acid (1H-imidazol-2-yl)-amide |

TABLE 1-continued

| Ex. | Structure | Name |
|---|---|---|
| 378 | 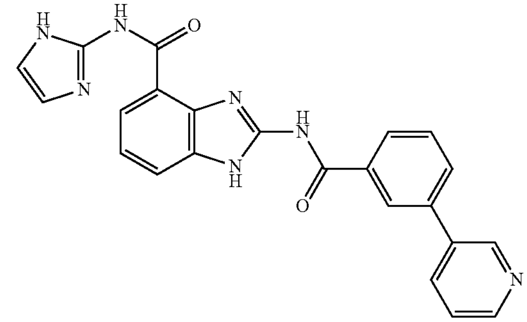 [SMILES: O=C(Nc1nc2c(C(=O)Nc3ncc[nH]3)cccc2[nH]1)c1cccc(-c2cccnc2)c1] | 2-(3-Pyridin-3-yl-benzoylamino)-1H-benzoimidazole-4-carboxylic acid (1H-imidazol-2-yl)-amide |
| 379 | 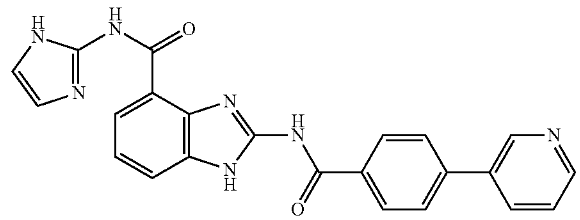 [SMILES: O=C(Nc1nc2c(C(=O)Nc3ncc[nH]3)cccc2[nH]1)c1ccc(-c2cccnc2)cc1] | 2-(4-Pyridin-3-yl-benzoylamino)-1H-benzoimidazole-4-carboxylic acid (1H-imidazol-2-yl)-amide |
| 380 | 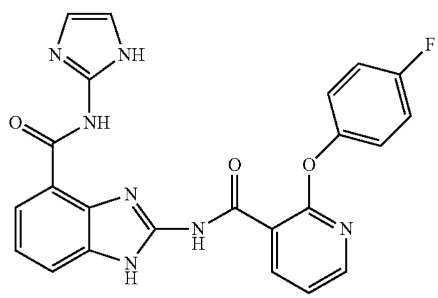 [SMILES: O=C(Nc1nc2c(C(=O)Nc3ncc[nH]3)cccc2[nH]1)c1cccnc1Oc1ccc(F)cc1] | 2-{[2-(4-Fluoro-phenoxy)-pyridine-3-carbonyl]-amino}-1H-benzoimidazole-4-carboxylic acid (1H-imidazol-2-yl)-amide |
| 381 | 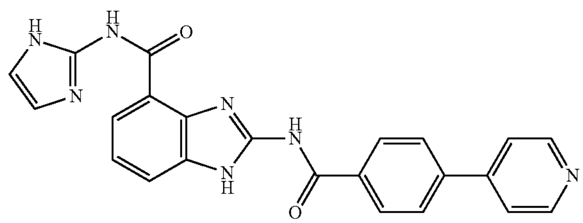 [SMILES: O=C(Nc1nc2c(C(=O)Nc3ncc[nH]3)cccc2[nH]1)c1ccc(-c2ccncc2)cc1] | 2-(4-Pyridin-4-yl-benzoylamino)-1H-benzoimidazole-4-carboxylic acid (1H-imidazol-2-yl)-amide |
| 382 | 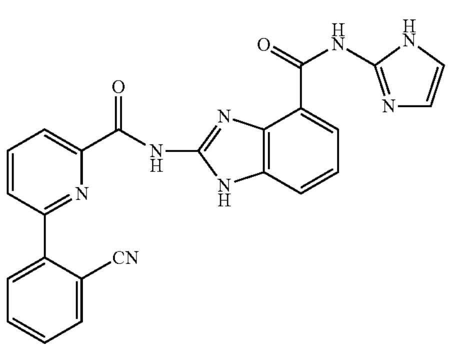 [SMILES: N#Cc1ccccc1-c1cccc(C(=O)Nc2nc3c(C(=O)Nc4ncc[nH]4)cccc3[nH]2)n1] | 2-{[6-(2-Cyano-phenyl)-pyridine-2-carbonyl]-amino}-1H-benzoimidazole-4-carboxylic acid (1H-imidazol-2-yl)-amide |

TABLE 1-continued

| Ex. | Structure | Name |
|---|---|---|
| 383 | 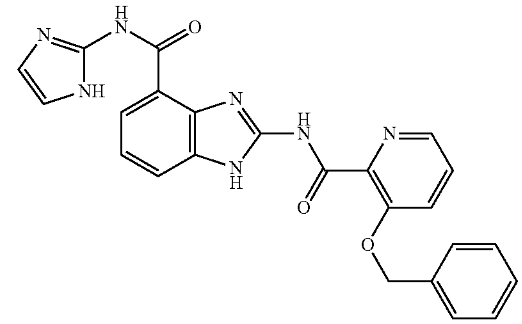 [SMILES: O=C(Nc1nc2c(C(=O)Nc3ncc[nH]3)cccc2[nH]1)c1ncccc1OCc1ccccc1] | 2-[(3-Benzyloxy-pyridine-2-carbonyl)-amino]-1H-benzoimidazole-4-carboxylic acid (1H-imidazol-2-yl)-amide |
| 384 | 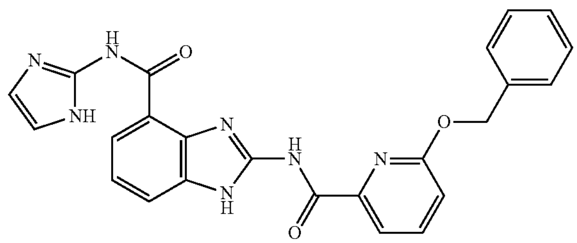 [SMILES: O=C(Nc1nc2c(C(=O)Nc3ncc[nH]3)cccc2[nH]1)c1cccc(OCc2ccccc2)n1] | 2-[(6-Benzyloxy-pyridine-2-carbonyl)-amino]-1H-benzoimidazole-4-carboxylic acid (1H-imidazol-2-yl)-amide |
| 385 | 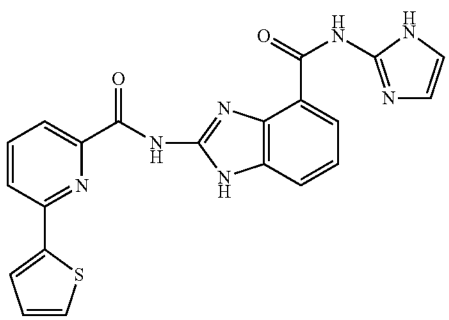 [SMILES: O=C(Nc1nc2c(C(=O)Nc3ncc[nH]3)cccc2[nH]1)c1cccc(-c2cccs2)n1] | 2-[(6-Thiophen-2-yl-pyridine-2-carbonyl)-amino]-1H-benzoimidazole-4-carboxylic acid (1H-imidazol-2-yl)-amide |
| 386 | 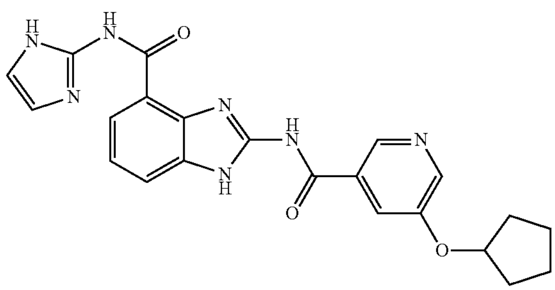 [SMILES: O=C(Nc1nc2c(C(=O)Nc3ncc[nH]3)cccc2[nH]1)c1cncc(OC2CCCC2)c1] | 2-[(5-Cyclopentyloxy-pyridine-2-3-carbonyl)-amino]-1H-benzoimidazole-4-carboxylic acid (1H-imidazol-2-yl)-amide |
| 387 | 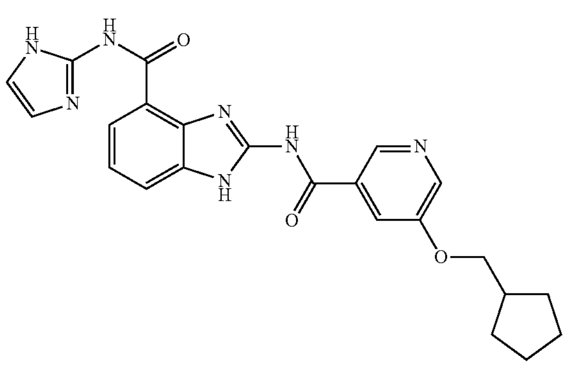 [SMILES: O=C(Nc1nc2c(C(=O)Nc3ncc[nH]3)cccc2[nH]1)c1cncc(OCC2CCCC2)c1] | 2-[(5-Cyclopentylmethoxy-pyridine-3-carbonyl)-amino]-1H-benzoimidazole-4-carboxylic acid (1H-imidazol-2-yl)-amide |

TABLE 1-continued

| Ex. | Structure | Name |
|---|---|---|
| 388 | 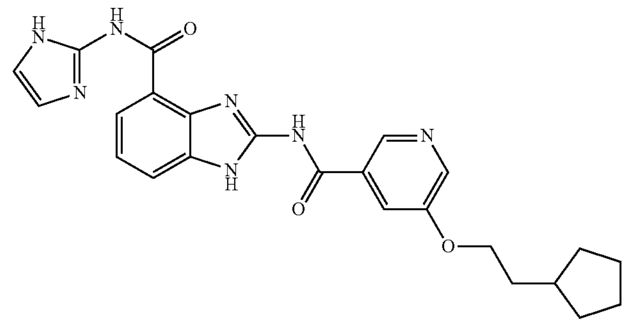 [SMILES: O=C(Nc1nc2c(C(=O)Nc3ncc[nH]3)cccc2[nH]1)c1cncc(OCCC2CCCC2)c1] | 2-{[5-(2-Cyclopentyl-ethoxy)-pyridine-3-carbonyl]-amino}-1H-benzoimidazole-4-carboxylic acid (1H-imidazol-2-yl)-amide |
| 389 | 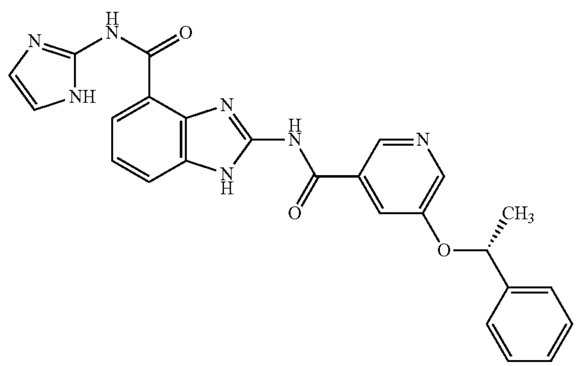 [SMILES: C[C@@H](Oc1cncc(C(=O)Nc2nc3c(C(=O)Nc4ncc[nH]4)cccc3[nH]2)c1)c1ccccc1] | 2-{[5-(1-(1R)-Phenyl-ethoxy)-pyridine-3-carbonyl]-amino}-1H-benzoimidazole-4-carboxylic acid (1H-imidazol-2-yl)-amide |
| 390 | 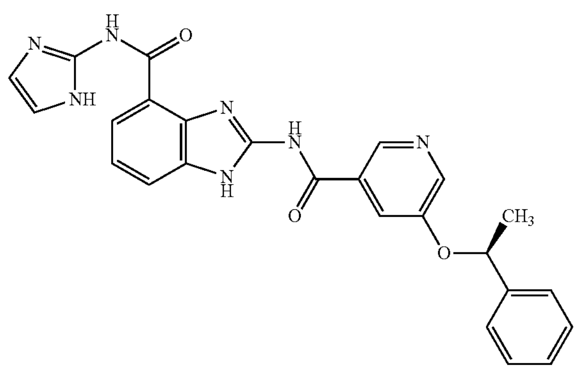 [SMILES: C[C@H](Oc1cncc(C(=O)Nc2nc3c(C(=O)Nc4ncc[nH]4)cccc3[nH]2)c1)c1ccccc1] | 2-{[5-(1-(1S)-Phenyl-ethoxy)-pyridine-3-carbonyl]-amino}-1H-benzoimidazole-4-carboxylic acid (1H-imidazol-2-yl)-amide |
| 391 | 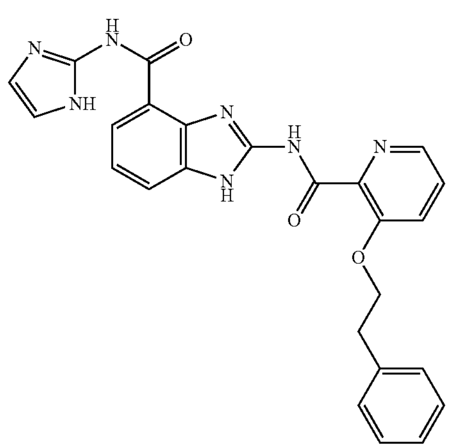 [SMILES: O=C(Nc1nc2c(C(=O)Nc3ncc[nH]3)cccc2[nH]1)c1ncccc1OCCc1ccccc1] | 2-[(3-Phenethyloxy-pyridine-2-carbonyl)-amino]-1H-benzoimidazole-4-carboxylic acid (1H-imidazol-2-yl)-amide |

TABLE 1-continued

| Ex. | Structure | Name |
|---|---|---|
| 392 | 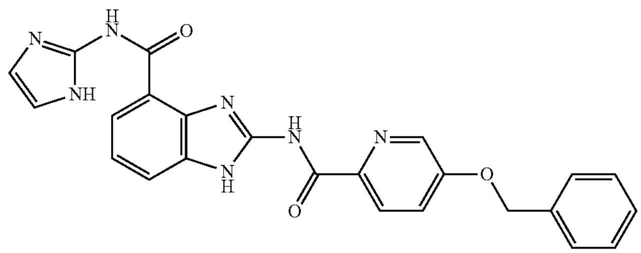 [SMILES: O=C(Nc1nc2c(C(=O)Nc3ncc[nH]3)cccc2[nH]1)c1ccc(OCc2ccccc2)cn1] | 2-[(5-Benzyloxy-pyridine-2-carbonyl)-amino]-1H-benzoimidazole-4-carboxylic acid (1H-imidazol-2-yl)-amide |
| 393 | 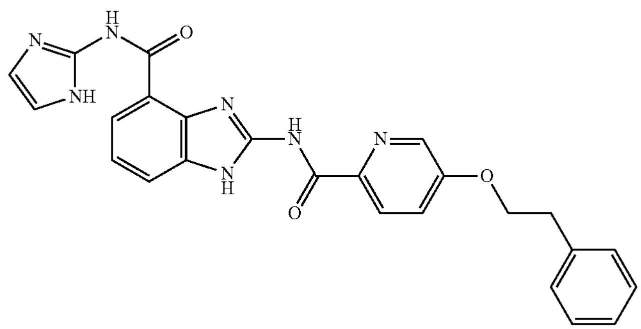 [SMILES: O=C(Nc1nc2c(C(=O)Nc3ncc[nH]3)cccc2[nH]1)c1ccc(OCCc2ccccc2)cn1] | 2-[(5-Phenethyloxy-pyridine-2-carbonyl)-amino]-1H-benzoimidazole-4-carboxylic acid (1H-imidazol-2-yl)-amide |
| 394 | 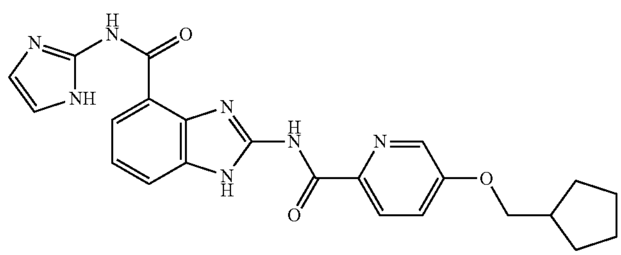 [SMILES: O=C(Nc1nc2c(C(=O)Nc3ncc[nH]3)cccc2[nH]1)c1ccc(OCC2CCCC2)cn1] | 2-[(5-Cyclopentylmethoxy-pyridine-2-carbonyl)-amino]-1H-benzoimidazole-4-carboxylic acid (1H-imidazol-2-yl)-amide |
| 395 | 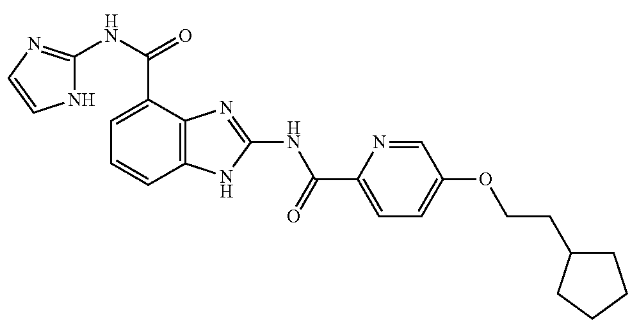 [SMILES: O=C(Nc1nc2c(C(=O)Nc3ncc[nH]3)cccc2[nH]1)c1ccc(OCCC2CCCC2)cn1] | 2-{[5-(2-Cyclopentyl-ethoxy)-pyridine-2-carbonyl]-amino}-1H-benzoimidazole-4-carboxylic acid (1H-imidazol-2-yl)-amide |
| 396 | 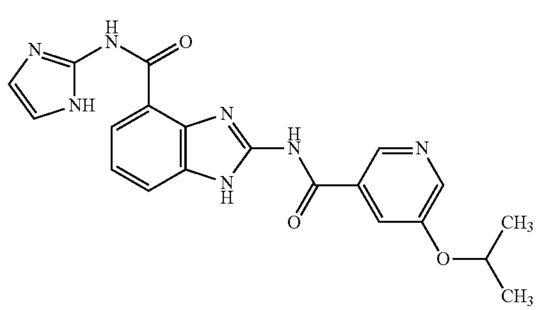 [SMILES: CC(C)Oc1cncc(C(=O)Nc2nc3c(C(=O)Nc4ncc[nH]4)cccc3[nH]2)c1] | 2-[(5-Isopropoxy-pyridine-3-carbonyl)-amino]-1H-benzoimidazole-4-carboxylic acid (1H-imidazol-2-yl)-amide |

TABLE 1-continued

| Ex. | Structure | Name |
|---|---|---|
| 397 | 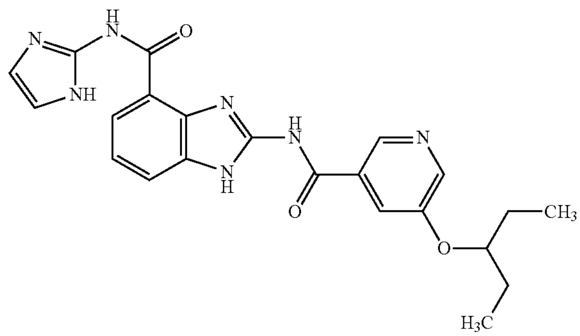 [SMILES: CCC(CC)Oc1cncc(C(=O)Nc2nc3c(C(=O)Nc4ncc[nH]4)cccc3[nH]2)c1] | 2-{[5-(1-Ethyl-propoxy)-pyridine-3-carbonyl]-amino}-1H-benzoimidazole-4-carboxylic acid (1H-imidazol-2-yl)-amide |
| 398 | 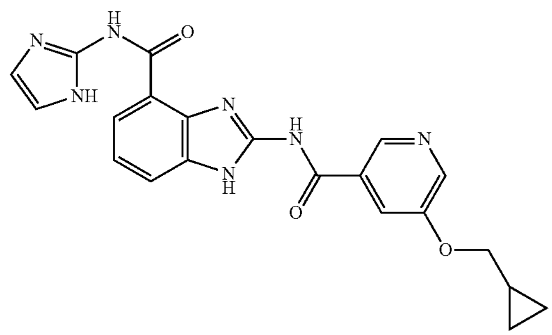 [SMILES: O=C(Nc1nc2c(C(=O)Nc3ncc[nH]3)cccc2[nH]1)c1cncc(OCC2CC2)c1] | 2-[(5-Cyclopropylmethoxy-pyridine-3-carbonyl)-amino]-1H-benzoimidazole-4-carboxylic acid (1H-imidazol-2-yl)-amide |
| 399 | 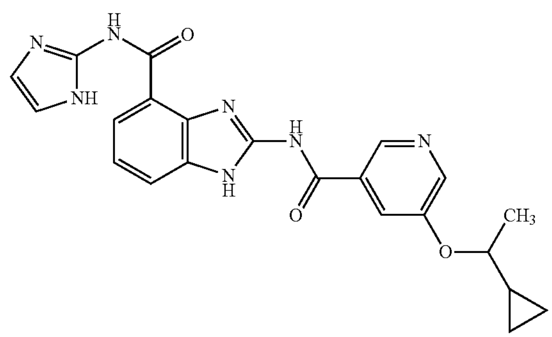 [SMILES: CC(Oc1cncc(C(=O)Nc2nc3c(C(=O)Nc4ncc[nH]4)cccc3[nH]2)c1)C1CC1] | 2-{[5-(1-Cyclopropyl-ethoxy)-pyridine-3-carbonyl]-amino}-1H-benzoimidazole-4-carboxylic acid (1H-imidazol-2-yl)-amide |
| 400 | 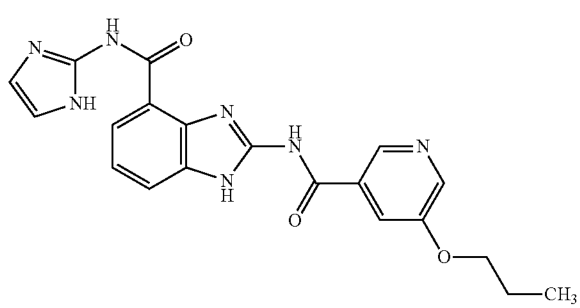 [SMILES: CCCOc1cncc(C(=O)Nc2nc3c(C(=O)Nc4ncc[nH]4)cccc3[nH]2)c1] | 2-[(5-Propoxy-pyridine-3-carbonyl)-amino]-1H-benzoimidazole-4-carboxylic acid (1H-imidazol-2-yl)-amide |

TABLE 1-continued

| Ex. | Structure | Name |
|---|---|---|
| 401 | 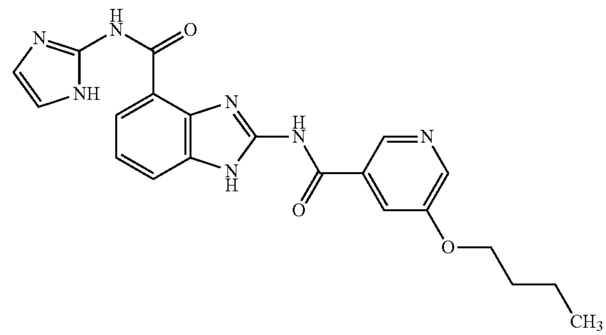 [SMILES: CCCCOc1cncc(C(=O)Nc2nc3c(C(=O)Nc4ncc[nH]4)cccc3[nH]2)c1] | 2-[(5-Butoxy-pyridine-3-carbonyl)-amino]-1H-benzoimidazole-4-carboxylic acid (1H-imidazol-2-yl)-amide |
| 402 | 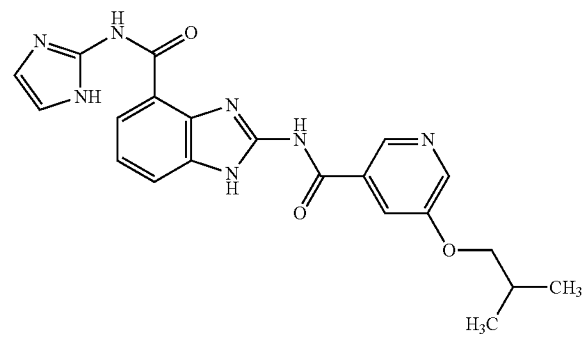 [SMILES: CC(C)COc1cncc(C(=O)Nc2nc3c(C(=O)Nc4ncc[nH]4)cccc3[nH]2)c1] | 2-[(5-Isobutoxy-pyridine-3-carbonyl)-amino]-1H-benzoimidazole-4-carboxylic acid (1H-imidazol-2-yl)-amide |
| 403 | 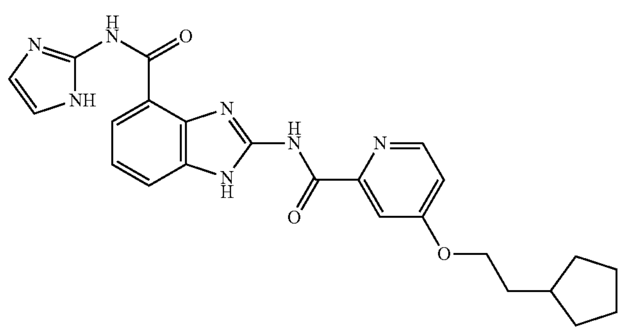 [SMILES: O=C(Nc1nc2c(C(=O)Nc3ncc[nH]3)cccc2[nH]1)c1cc(OCCC2CCCC2)ccn1] | 2-{[4-(2-Cyclopentyl-ethoxy)-pyridine-2-carbonyl]-amino}-1H-benzoimidazole-4-carboxylic acid (1H-imidazol-2-yl)-amide |
| 404 | 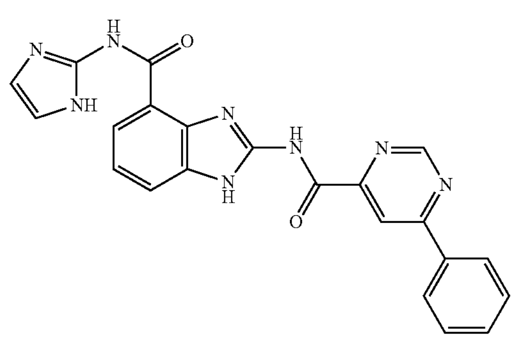 [SMILES: O=C(Nc1nc2c(C(=O)Nc3ncc[nH]3)cccc2[nH]1)c1cc(-c2ccccc2)ncn1] | 2-[(6-Phenyl-pyrimidine-4-carbonyl)-amino]-1H-benzoimidazole-4-carboxylic acid (1H-imidazol-2-yl)-amide |

| Ex. | Structure | Name |
|---|---|---|
| 405 | 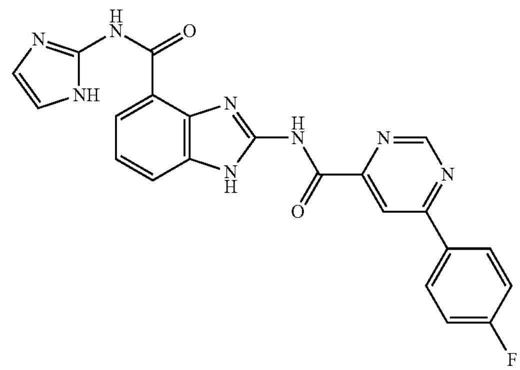 [SMILES: O=C(Nc1nc2c(C(=O)Nc3ncc[nH]3)cccc2[nH]1)c1cc(-c2ccc(F)cc2)ncn1] | 2-{[6-(4-Fluoro-phenyl)-pyrimidine-4-carbonyl]-amino}-1H-benzoimidazole-4-carboxylic acid (1H-imidazol-2-yl)-amide |
| 406 | 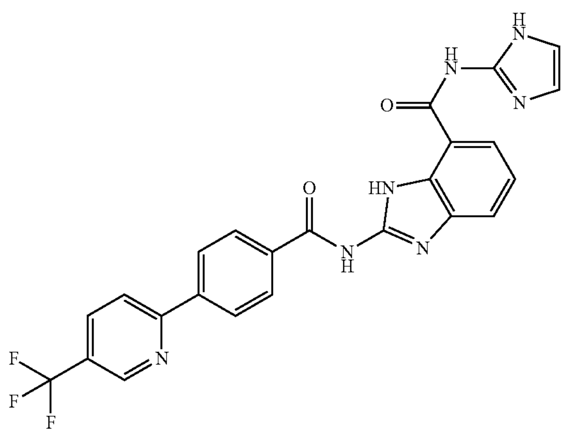 [SMILES: O=C(Nc1nc2cccc(C(=O)Nc3ncc[nH]3)c2[nH]1)c1ccc(-c2ccc(C(F)(F)F)cn2)cc1] | 2-[4-(5-Trifluoromethyl-pyridin-2-yl)-benzoylamino]-3H-benzoimidazole-4-carboxylic acid (1H-imidazol-2-yl)-amide |
| 407 | 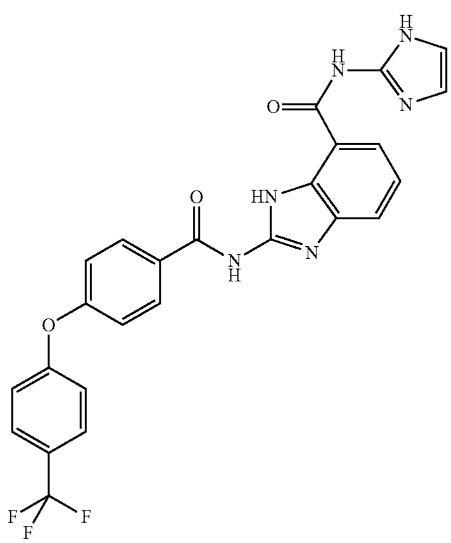 [SMILES: O=C(Nc1nc2cccc(C(=O)Nc3ncc[nH]3)c2[nH]1)c1ccc(Oc2ccc(C(F)(F)F)cc2)cc1] | 2-[4-(4-Trifluoromethyl-phenoxy)-benzoylamino]-3H-benzoimidazole-4-carboxylic acid (1H-imidazol-2-yl)-amide |

TABLE 1-continued

| Ex. | Structure | Name |
|---|---|---|
| 408 | 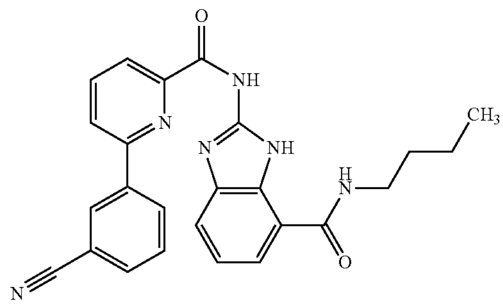 [SMILES: CCCCNC(=O)c1cccc2nc(NC(=O)c3cccc(-c4cccc(C#N)c4)n3)[nH]c12] | 2-{[6-(3-Cyano-phenyl)-pyridine-2-carbonyl]-amino}-3H-benzoimidazole-4-carboxylic acid butylamide |
| 409 | 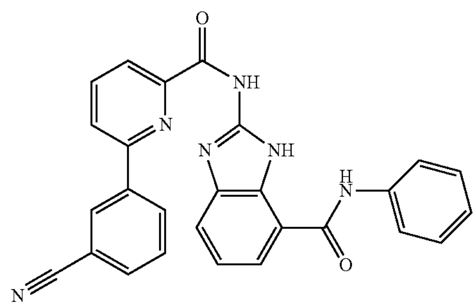 [SMILES: N#Cc1cccc(-c2cccc(C(=O)Nc3nc4cccc(C(=O)Nc5ccccc5)c4[nH]3)n2)c1] | 2-{[6-(3-Cyano-phenyl)-pyridine-2-carbonyl]-amino}-3H-benzoimidazole-4-carboxylic acid phenylamide |
| 410 | 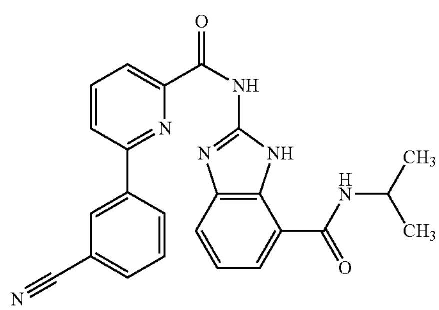 [SMILES: CC(C)NC(=O)c1cccc2nc(NC(=O)c3cccc(-c4cccc(C#N)c4)n3)[nH]c12] | 2-{[6-(3-Cyano-phenyl)-pyridine-2-carbonyl]-amino}-3H-benzoimidazole-4-carboxylic acid isopropylamide |
| 411 | 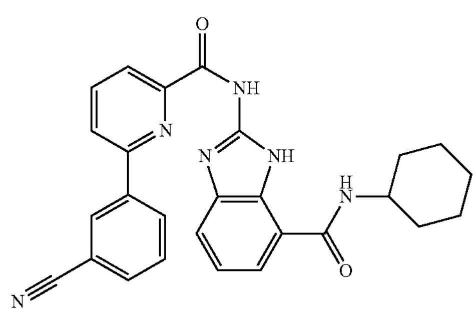 [SMILES: N#Cc1cccc(-c2cccc(C(=O)Nc3nc4cccc(C(=O)NC5CCCCC5)c4[nH]3)n2)c1] | 2-{[6-(3-Cyano-phenyl)-pyridine-2-carbonyl]-amino}-3H-benzoimidazole-4-carboxylic acid cyclohexylamide |
| 412 | 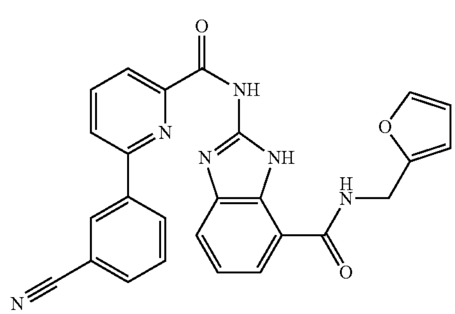 [SMILES: N#Cc1cccc(-c2cccc(C(=O)Nc3nc4cccc(C(=O)NCc5ccco5)c4[nH]3)n2)c1] | 2-{[6-(3-Cyano-phenyl)-pyridine-2-carbonyl]-amino}-3H-benzoimidazole-4-carboxylic acid (furan-2-ylmethyl)-amide |

TABLE 1-continued

| Ex. | Structure | Name |
|---|---|---|
| 413 | 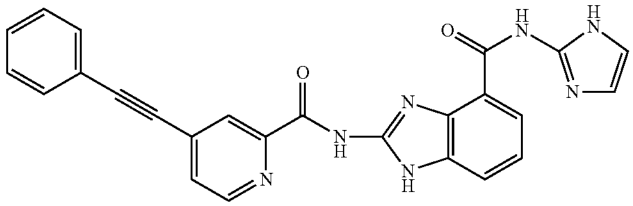 [SMILES: O=C(Nc1nc2c(C(=O)Nc3ncc[nH]3)cccc2[nH]1)c1cc(C#Cc2ccccc2)ccn1] | 2-[(4-Phenylethynyl-pyridine-2-carbonyl)-amino]-1H-benzoimidazole-4-carboxylic acid (1H-imidazol-2-yl)-amide |
| 414 | 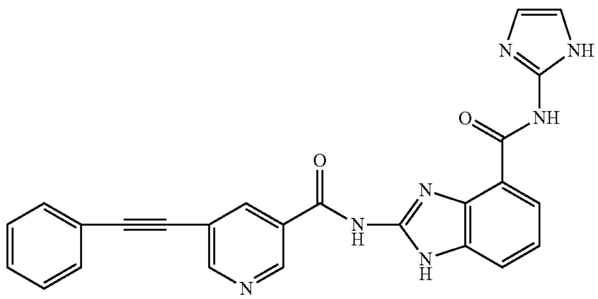 [SMILES: O=C(Nc1nc2c(C(=O)Nc3ncc[nH]3)cccc2[nH]1)c1cncc(C#Cc2ccccc2)c1] | 2-[(5-Phenylethynyl-pyridine-3-carbonyl)-amino]-1H-benzoimidazole-4-carboxylic acid (1H-imidazol-2-yl)-amide |
| 415 | 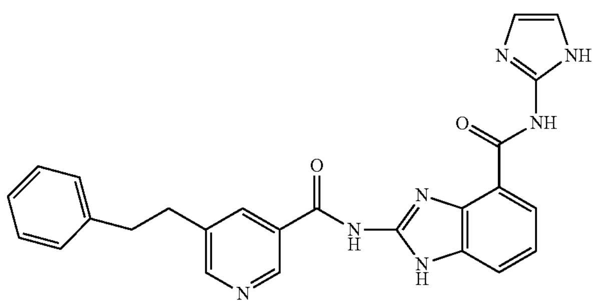 [SMILES: O=C(Nc1nc2c(C(=O)Nc3ncc[nH]3)cccc2[nH]1)c1cncc(CCc2ccccc2)c1] | 2-[(5-Phenethyl-pyridine-3-carbonyl)-amino]-1H-benzoimidazole-4-carboxylic acid (1H-imidazol-2-yl)-amide |
| 416 | 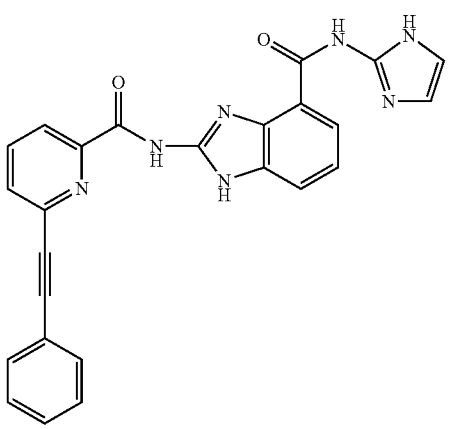 [SMILES: O=C(Nc1nc2c(C(=O)Nc3ncc[nH]3)cccc2[nH]1)c1cccc(C#Cc2ccccc2)n1] | 2-[(6-Phenylethynyl-pyridine-2-carbonyl)-amino]-1H-benzoimidazole-4-carboxylic acid (1H-imidazol-2-yl)-amide |

TABLE 1-continued

| Ex. | Structure | Name |
| --- | --- | --- |
| 417 | 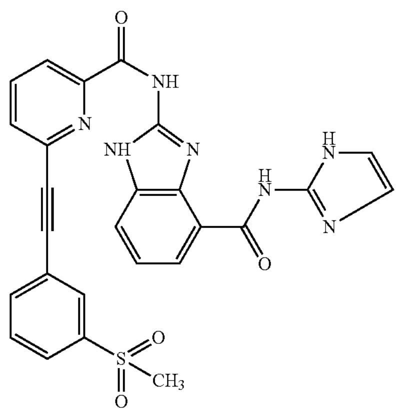 [SMILES: CS(=O)(=O)c1cccc(C#Cc2cccc(C(=O)Nc3nc4c(C(=O)Nc5ncc[nH]5)cccc4[nH]3)n2)c1] | 2-{[6-(3-Methanesulfonyl-phenylethynyl)-pyridine-2-carbonyl]-amino}-1H-benzoimidazole-4-carboxylic acid (1H-imidazol-2-yl)-amide |
| 418 | 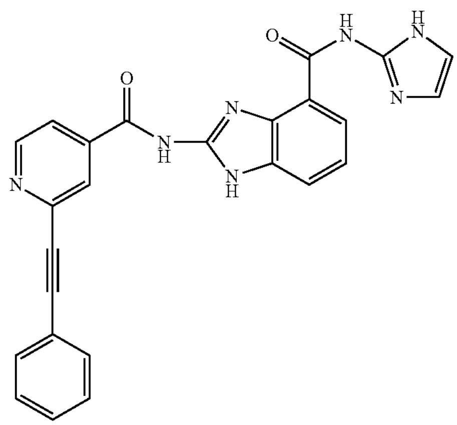 [SMILES: O=C(Nc1nc2c(C(=O)Nc3ncc[nH]3)cccc2[nH]1)c1ccnc(C#Cc2ccccc2)c1] | 2-[(2-Phenylethynyl-pyridine-4-carbonyl)-amino]-1H-benzoimidazole-4-carboxylic acid (1H-imidazol-2-yl)-amide |
| 419 | 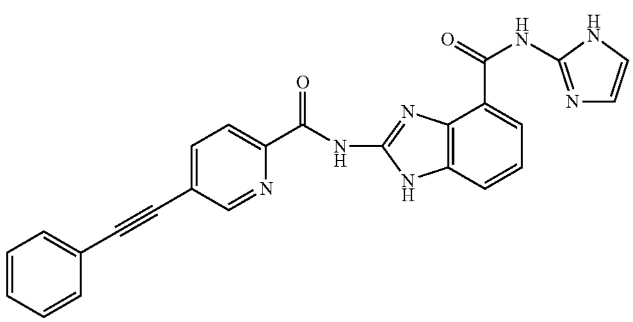 [SMILES: O=C(Nc1nc2c(C(=O)Nc3ncc[nH]3)cccc2[nH]1)c1ccc(C#Cc2ccccc2)cn1] | 2-[(5-Phenylethynyl-pyridine-2-carbonyl)-amino]-1H-benzoimidazole-4-carboxylic acid (1H-imidazol-2-yl)-amide |
| 420 | 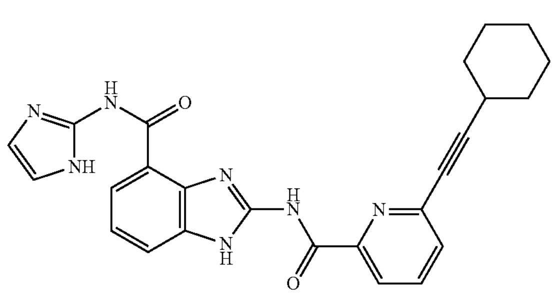 [SMILES: O=C(Nc1nc2c(C(=O)Nc3ncc[nH]3)cccc2[nH]1)c1cccc(C#CC2CCCCC2)n1] | 2-[(6-Cyclohexylethynyl-pyridine-2-carbonyl)-amino]-1H-benzoimidazole-4-carboxylic acid (1H-imidazol-2-yl)-amide |

TABLE 1-continued

| Ex. | Structure | Name |
|---|---|---|
| 421 | 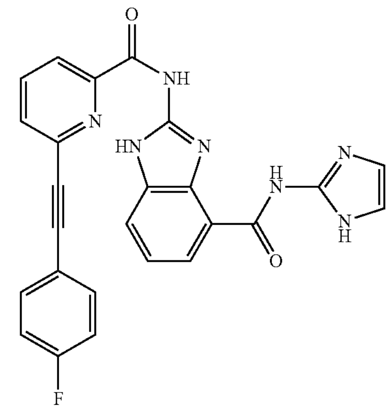 [SMILES: O=C(Nc1nc2c(C(=O)Nc3ncc[nH]3)cccc2[nH]1)c1cccc(C#Cc2ccc(F)cc2)n1] | 2-{[6-(4-Fluoro-phenylethynyl)-pyridine-2-carbonyl]-amino}-1H-benzoimidazole-4-carboxylic acid (1H-imidazol-2-yl)-amide |
| 422 | 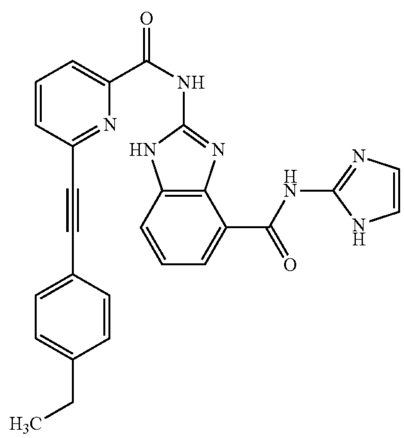 [SMILES: CCc1ccc(C#Cc2cccc(C(=O)Nc3nc4c(C(=O)Nc5ncc[nH]5)cccc4[nH]3)n2)cc1] | 2-{[6-(4-Ethyl-phenylethynyl)-pyridine-2-carbonyl]-amino}-1H-benzoimidazole-4-carboxylic acid (1H-imidazol-2-yl)-amide |
| 423 | 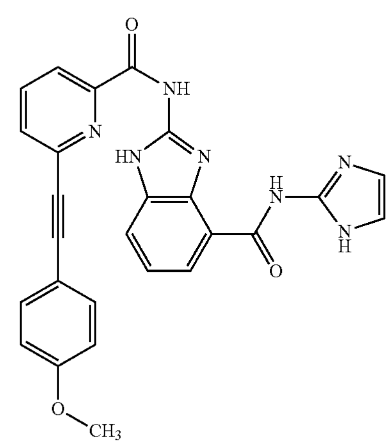 [SMILES: COc1ccc(C#Cc2cccc(C(=O)Nc3nc4c(C(=O)Nc5ncc[nH]5)cccc4[nH]3)n2)cc1] | 2-{[6-(4-Methoxy-phenylethynyl)-pyridine-2-carbonyl]-amino}-1H-benzoimidazole-4-carboxylic acid (1H-imidazol-2-yl)-amide |

TABLE 1-continued

| Ex. | Structure | Name |
|---|---|---|
| 424 | 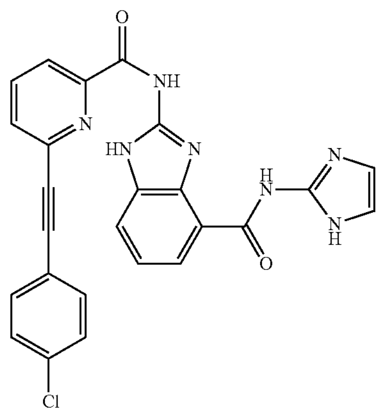 [SMILES: O=C(Nc1nc2c(C(=O)Nc3ncc[nH]3)cccc2[nH]1)c1cccc(C#Cc2ccc(Cl)cc2)n1] | 2-{[6-(4-Chloro-phenylethynyl)-pyridine-2-carbonyl]-amino}-1H-benzoimidazole-4-carboxylic acid (1H-imidazol-2-yl)-amide |
| 425 | 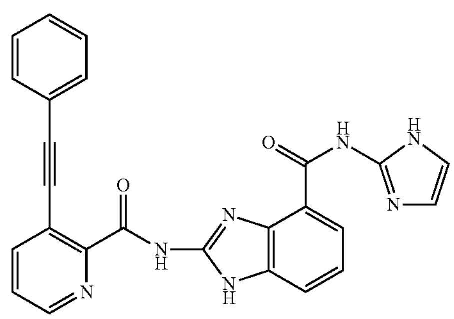 [SMILES: O=C(Nc1nc2c(C(=O)Nc3ncc[nH]3)cccc2[nH]1)c1ncccc1C#Cc1ccccc1] | 2-[(3-Phenylethynyl-pyridine-2-carbonyl)-amino]-1H-benzoimidazole-4-carboxylic acid (1H-imidazol-2-yl)-amide |
| 426 | 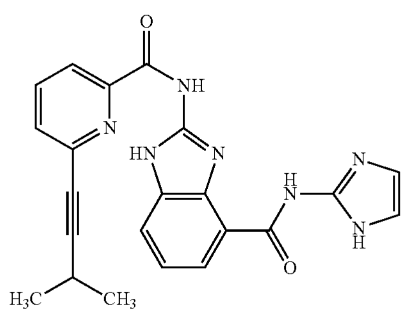 [SMILES: CC(C)C#Cc1cccc(C(=O)Nc2nc3c(C(=O)Nc4ncc[nH]4)cccc3[nH]2)n1] | 2-{[6-(3-Methyl-but-1-ynyl)-pyridine-2-carbonyl]-amino}-1H-benzoimidazole-4-carboxylic acid (1H-imidazol-2-yl)-amide |
| 427 | 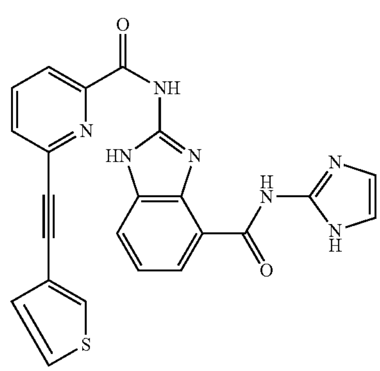 [SMILES: O=C(Nc1nc2c(C(=O)Nc3ncc[nH]3)cccc2[nH]1)c1cccc(C#Cc2ccsc2)n1] | 2-[(6-Thiophen-3-ylethynyl-pyridine-2-carbonyl]-amino}-1H-benzoimidazole-4-carboxylic acid (1H-imidazol-2-yl)-amide |

TABLE 1-continued

| Ex. | Structure | Name |
|---|---|---|
| 428 | 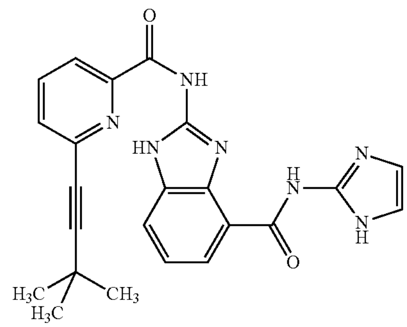 [SMILES: CC(C)(C)C#Cc1cccc(C(=O)Nc2nc3c(C(=O)Nc4ncc[nH]4)cccc3[nH]2)n1] | 2-{[6-(3,3-Dimethyl-but-1-ynyl)-pyridine-2-carbonyl]-amino}-1H-benzoimidazole-4-carboxylic acid (1H-imidazol-2-yl)-amide |
| 429 | 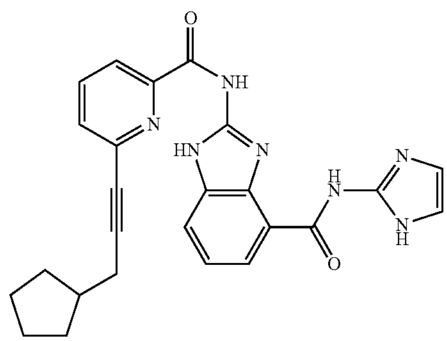 [SMILES: O=C(Nc1nc2c(C(=O)Nc3ncc[nH]3)cccc2[nH]1)c1cccc(C#CCC2CCCC2)n1] | 2-{[6-(3-Cyclopentyl-prop-1-ynyl)-pyridine-2-carbonyl]-amino}-1H-benzoimidazole-4-carboxylic acid (1H-imidazol-2-yl)-amide |
| 430 | 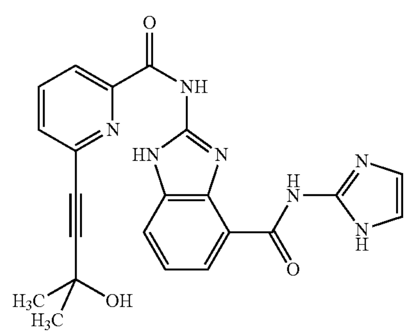 [SMILES: CC(C)(O)C#Cc1cccc(C(=O)Nc2nc3c(C(=O)Nc4ncc[nH]4)cccc3[nH]2)n1] | 2-{[6-(3-Hydroxy-3-methyl-but-1-ynyl)-pyridine-2-carbonyl]-amino}-1H-benzoimidazole-4-carboxylic acid (1H-imidazol-2-yl)-amide |
| 431 | 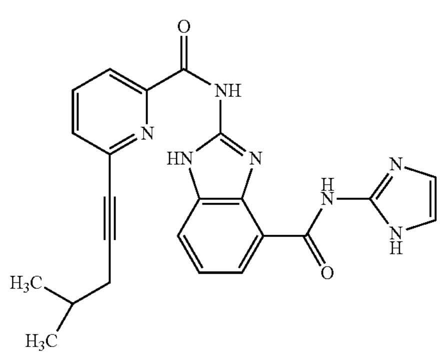 [SMILES: CC(C)CC#Cc1cccc(C(=O)Nc2nc3c(C(=O)Nc4ncc[nH]4)cccc3[nH]2)n1] | 2-{[6-(4-Methyl-pent-1-ynyl)-pyridine-2-carbonyl]-amino}-1H-benzoimidazole-4-carboxylic acid (1H-imidazol-2-yl)-amide |

TABLE 1-continued

| Ex. | Structure | Name |
|---|---|---|
| 432 | 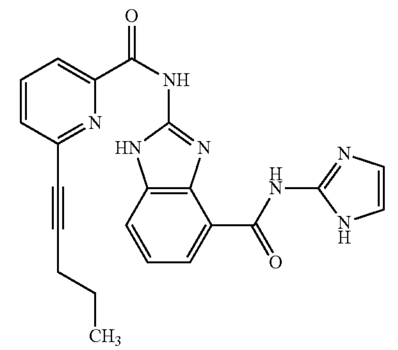 [SMILES: CCCC#Cc1cccc(C(=O)Nc2nc3c(C(=O)Nc4ncc[nH]4)cccc3[nH]2)n1] | 2-[(6-Pent-1-ynyl-pyridine-2-carbonyl)-amino]-1H-benzoimidazole-4-carboxylic acid (1H-imidazol-2-yl)-amide |
| 433 | 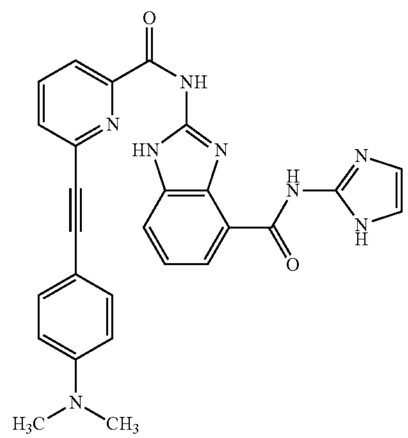 [SMILES: CN(C)c1ccc(C#Cc2cccc(C(=O)Nc3nc4c(C(=O)Nc5ncc[nH]5)cccc4[nH]3)n2)cc1] | 2-{[6-(4-Dimethylamino-phenylethynyl)-pyridine-2-carbonyl]-amino}-1H-benzoimidazole-4-carboxylic acid (1H-imidazol-2-yl)-amide |
| 434 | 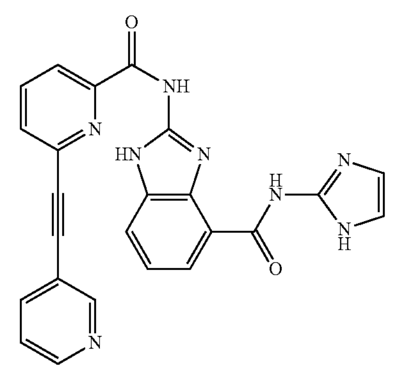 [SMILES: O=C(Nc1nc2c(C(=O)Nc3ncc[nH]3)cccc2[nH]1)c1cccc(C#Cc2cccnc2)n1] | 2-[(6-Pyridin-3-ylethynyl-pyridine-2-carbonyl)-amino]-1H-benzoimidazole-4-carboxylic acid (1H-imidazol-2-yl)-amide |
| 435 | 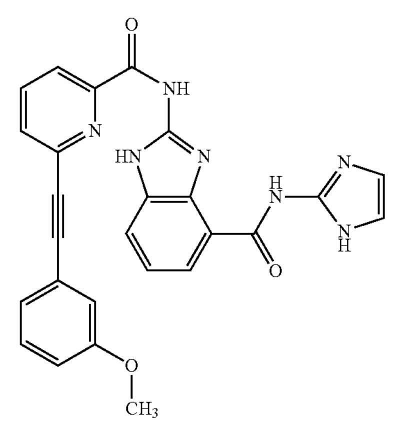 [SMILES: COc1cccc(C#Cc2cccc(C(=O)Nc3nc4c(C(=O)Nc5ncc[nH]5)cccc4[nH]3)n2)c1] | 2-{[6-(3-Methoxy-phenylethynyl)-pyridine-2-carbonyl]-amino-1H-benzoimidazole-4-carboxylic acid (1H-imidazol-2-yl)-amide |

TABLE 1-continued

| Ex. | Structure | Name |
|---|---|---|
| 436 | 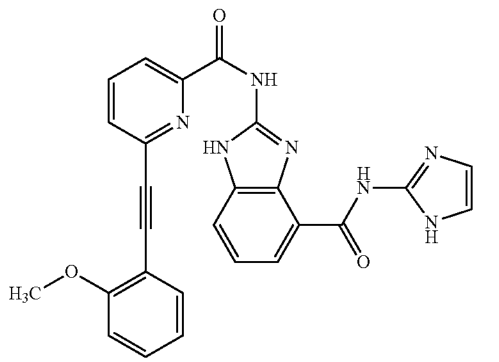 [SMILES: COc1ccccc1C#Cc1cccc(C(=O)Nc2nc3c(C(=O)Nc4ncc[nH]4)cccc3[nH]2)n1] | 2-{[6-(3-Methoxy-phenylethynyl)-pyridine-2-carbonyl]-amino-1H-benzoimidazole-4-carboxylic acid (1H-imidazol-2-yl)-amide |
| 437 | 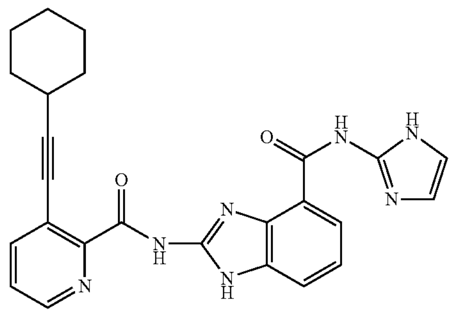 [SMILES: O=C(Nc1nc2c(C(=O)Nc3ncc[nH]3)cccc2[nH]1)c1ncccc1C#CC1CCCCC1] | 2-[(3-Cyclohexylethynyl-pyridine-2-carbonyl)-amino]-1H-benzoimidazole-4-carboxylic acid (1H-imidazol-2-yl)-amide |
| 438 | 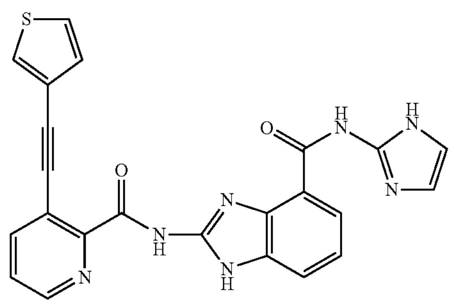 [SMILES: O=C(Nc1nc2c(C(=O)Nc3ncc[nH]3)cccc2[nH]1)c1ncccc1C#Cc1ccsc1] | 2-[(3-Thiophen-3-ylethynyl-pyridine-2-carbonyl)-amino]-1H-benzoimidazole-4-carboxylic acid (1H-imidazol-2-yl)-amide |
| 439 | 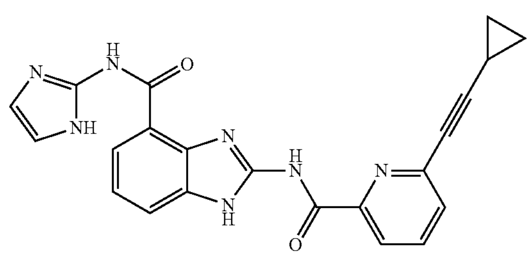 [SMILES: O=C(Nc1nc2c(C(=O)Nc3ncc[nH]3)cccc2[nH]1)c1cccc(C#CC2CC2)n1] | 2-[(6-Cyclopropylethynyl-pyridine-2-carbonyl)-amino]-1H-benzoimidazole-4-carboxylic acid (1H-imidazol-2-yl)-amide |
| 440 | 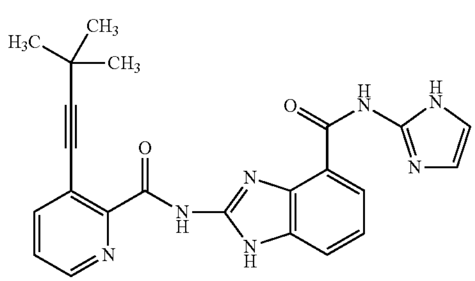 [SMILES: CC(C)(C)C#Cc1cccnc1C(=O)Nc1nc2c(C(=O)Nc3ncc[nH]3)cccc2[nH]1] | 2-{[3-(3,3-Dimethyl-but-1-ynyl)-pyridine-2-carbonyl]-amino}-1H-benzoimidazole-4-carboxylic acid (1H-imidazol-2-yl)-amide |

TABLE 1-continued

| Ex. | Structure | Name |
|---|---|---|
| 441 | 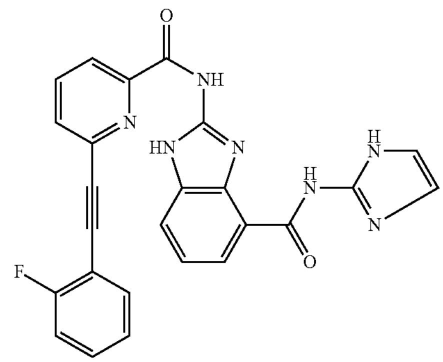 [SMILES: O=C(Nc1nc2c(C(=O)Nc3ncc[nH]3)cccc2[nH]1)c1cccc(C#Cc2ccccc2F)n1] | 2-{[6-(2-Fluoro-phenylethynyl)-pyridine-2-carbonyl]-amino}-1H-benzoimidazole-4-carboxylic acid (1H-imidazol-2-yl)-amide |
| 442 | 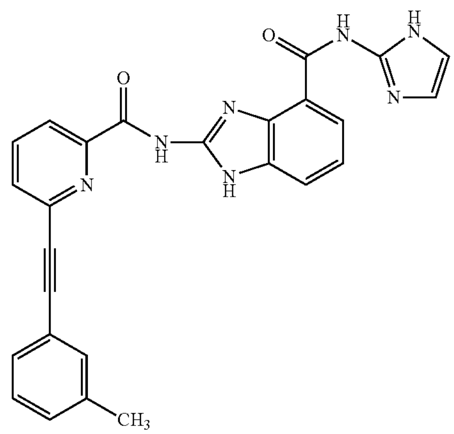 [SMILES: Cc1cccc(C#Cc2cccc(C(=O)Nc3nc4c(C(=O)Nc5ncc[nH]5)cccc4[nH]3)n2)c1] | 2-[(6-m-Tolylethynyl-pyridine-2-carbonyl)-amino]-1H-benzoimidazole-4-carboxylic acid (1H-imidazol-2-yl)-amide |
| 443 | 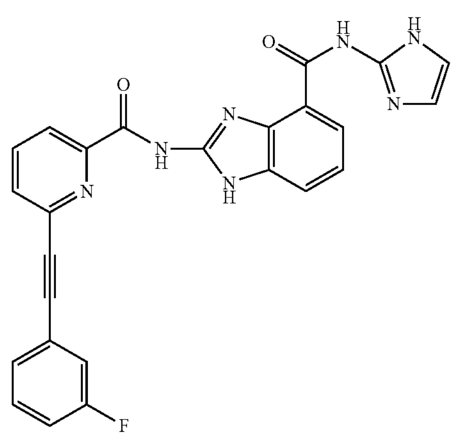 [SMILES: O=C(Nc1nc2c(C(=O)Nc3ncc[nH]3)cccc2[nH]1)c1cccc(C#Cc2cccc(F)c2)n1] | 2-{[6-(3-Fluoro-phenylethynyl)-pyridine-2-carbonyl]-amino}-1H-benzoimidazole-4-carboxylic acid (1H-imidazol-2-yl)-amide |

TABLE 1-continued

| Ex. | Structure | Name |
|---|---|---|
| 444 | 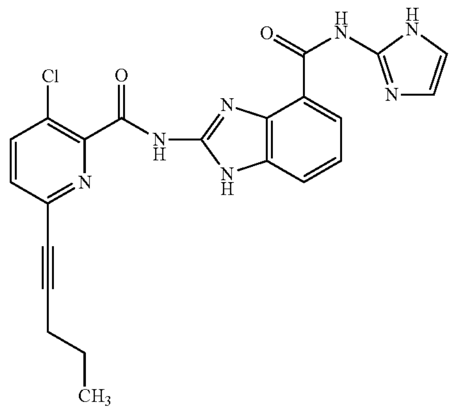 [SMILES: CCCC#Cc1ccc(Cl)c(C(=O)Nc2nc3c(C(=O)Nc4ncc[nH]4)cccc3[nH]2)n1] | 2-[(3-Chloro-6-pent-1-ynyl-pyridine-2-carbonyl)-amino]-1H-benzoimidazole-4-carboxylic acid (1H-imidazol-2-yl)-amide |
| 445 | 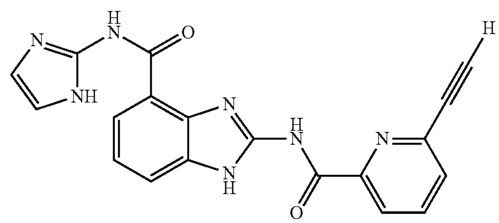 [SMILES: C#Cc1cccc(C(=O)Nc2nc3c(C(=O)Nc4ncc[nH]4)cccc3[nH]2)n1] | 2-[(6-Ethynyl-pyridine-2-carbonyl)-amino]-1H-benzoimidazole-4-carboxylic acid (1H-imidazol-2-yl)-amide |
| 446 | 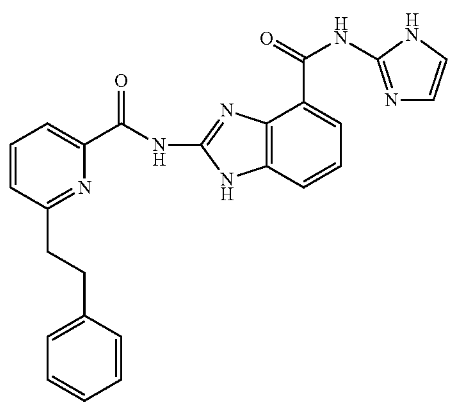 [SMILES: O=C(Nc1nc2c(C(=O)Nc3ncc[nH]3)cccc2[nH]1)c1cccc(CCc2ccccc2)n1] | 2-[(6-Phenethyl-pyridine-2-carbonyl)-amino]-1H-benzoimidazole-4-carboxylic acid (1H-imidazol-2-yl)-amide |
| 447 | 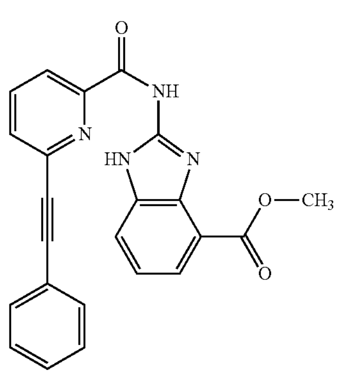 [SMILES: COC(=O)c1cccc2[nH]c(NC(=O)c3cccc(C#Cc4ccccc4)n3)nc12] | 2-[(6-Phenylethynyl-pyridine-2-carbonyl)-amino]-1H-benzoimidazole-4-carboxylic acid methyl ester |

TABLE 1-continued

| Ex. | Structure | Name |
|---|---|---|
| 448 | 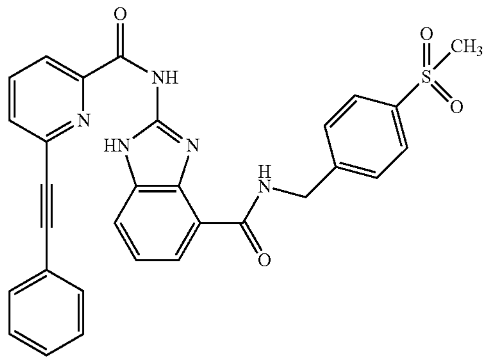 [SMILES: CS(=O)(=O)c1ccc(CNC(=O)c2cccc3[nH]c(NC(=O)c4cccc(C#Cc5ccccc5)n4)nc23)cc1] | 2-[(6-Phenylethynyl-pyridine-2-carbonyl)-amino]-1H-benzoimidazole-4-carboxylic acid 4-methanesulfonyl-benzylamide |
| 449 | 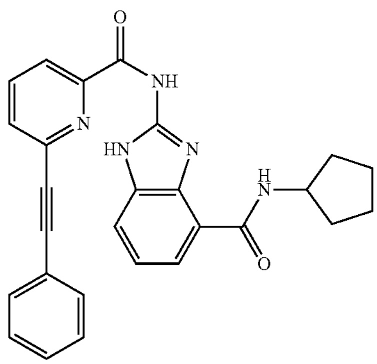 [SMILES: O=C(Nc1nc2c(C(=O)NC3CCCC3)cccc2[nH]1)c1cccc(C#Cc2ccccc2)n1] | 2-[(6-Phenylethynyl-pyridine-2-carbonyl)-amino]-1H-benzoimidazole-4-carboxylic acid cyclopentylamide |
| 450 | 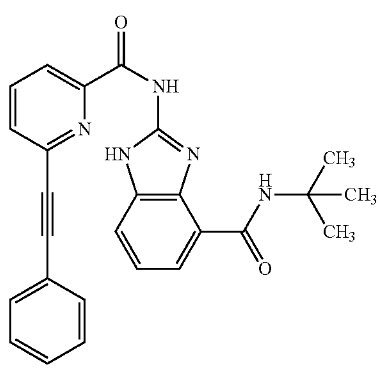 [SMILES: CC(C)(C)NC(=O)c1cccc2[nH]c(NC(=O)c3cccc(C#Cc4ccccc4)n3)nc12] | 2-[(6-Phenylethynyl-pyridine-2-carbonyl)-amino]-1H-benzoimidazole-4-carboxylic acid tert-butylamide |
| 451 | 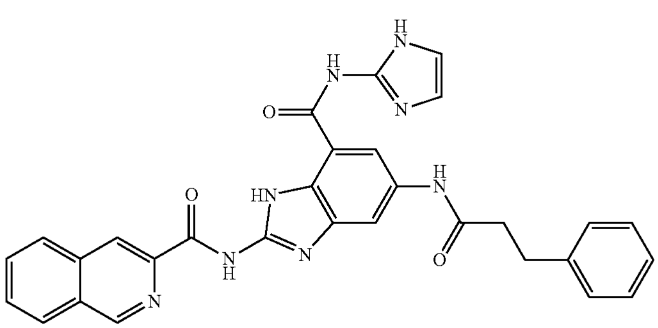 [SMILES: O=C(CCc1ccccc1)Nc1cc(C(=O)Nc2ncc[nH]2)c2[nH]c(NC(=O)c3cc4ccccc4cn3)nc2c1] | Isoquinoline-3-carboxylic acid [7-(1H-imidazol-2-ylcarbamoyl)-5-(3-phenyl-propionylamino)-1H-benzoimidazol-2-yl]-amide |

TABLE 1-continued

| Ex. | Structure | Name |
|---|---|---|
| 452 | 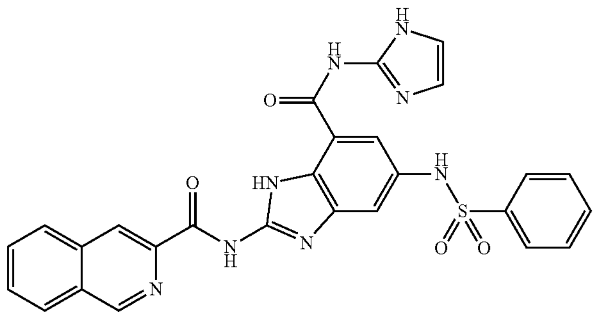 [SMILES: O=C(Nc1nc2cc(NS(=O)(=O)c3ccccc3)cc(C(=O)Nc3ncc[nH]3)c2[nH]1)c1cc2ccccc2cn1] | Isoquinoline-3-carboxylic acid [5-benzenesulfonylamino-7-(1H-imidazol-2-ylcarbamoyl)-1H-benzoimidazol-2-yl]-amide |
| 453 | 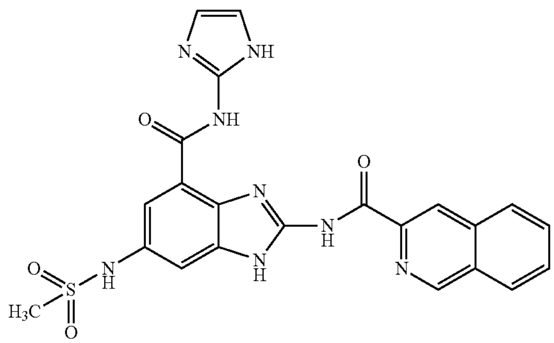 [SMILES: CS(=O)(=O)Nc1cc(C(=O)Nc2ncc[nH]2)c2nc(NC(=O)c3cc4ccccc4cn3)[nH]c2c1] | Isoquinoline-3-carboxylic acid [4-(1H-imidazol-2-ylcarbamoyl)-6-methanesulfonylamino-1H-benzoimidazol-2-yl]-amide |
| 454 | 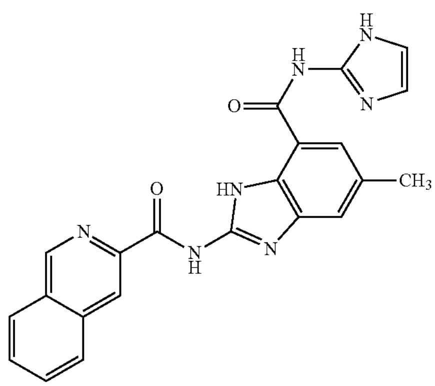 [SMILES: Cc1cc(C(=O)Nc2ncc[nH]2)c2[nH]c(NC(=O)c3cc4ccccc4cn3)nc2c1] | Isoquinoline-3-carboxylic acid [7-(1H-imidazol-2-ylcarbamoyl)-5-methyl-1H-benzoimidazol-2-yl]-amide |
| 455 | 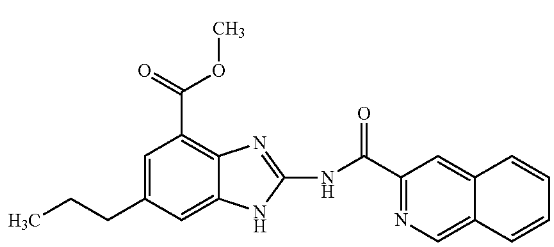 [SMILES: CCCc1cc(C(=O)OC)c2nc(NC(=O)c3cc4ccccc4cn3)[nH]c2c1] | 2-[(Isoquinoline-3-carbonyl)-amino]-6-propyl-1H-benzoimidazole-4-carboxylic acid methyl ester |

TABLE 1-continued

| Ex. | Structure | Name |
| --- | --- | --- |
| 456 | 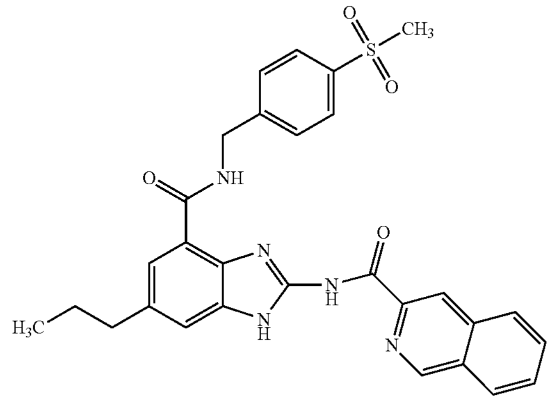 [SMILES: CCCc1cc(C(=O)NCc2ccc(S(C)(=O)=O)cc2)c2nc(NC(=O)c3cc4ccccc4cn3)[nH]c2c1] | Isoquinoline-3-carboxylic acid [4-(4-methanesulfonyl-benzylcarbamoyl)-6-propyl-1H-benzoimidazol-2-yl]-amide |
| 457 | 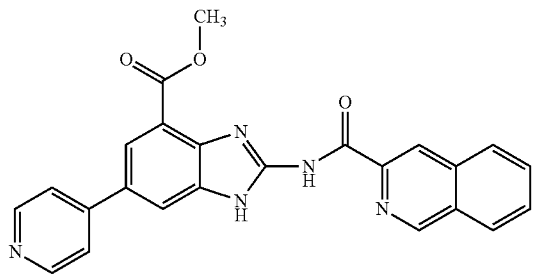 [SMILES: COC(=O)c1cc(-c2ccncc2)cc2[nH]c(NC(=O)c3cc4ccccc4cn3)nc12] | 2-[(Isoquinoline-3-carbonyl)-amino]-6-pyridin-4-yl-1H-benzoimidazole-4-carboxylic acid methyl ester |
| 458 | 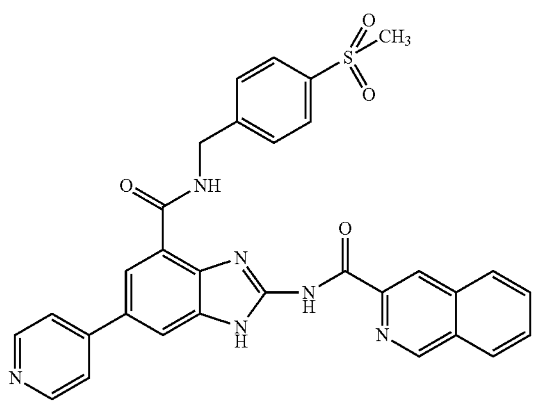 [SMILES: CS(=O)(=O)c1ccc(CNC(=O)c2cc(-c3ccncc3)cc3[nH]c(NC(=O)c4cc5ccccc5cn4)nc23)cc1] | Isoquinoline-3-carboxylic acid [4-(4-methanesulfonyl-benzylcarbamoyl)-6-pyridin-4-yl-1H-benzoimidazol-2-yl]-amide |
| 459 | 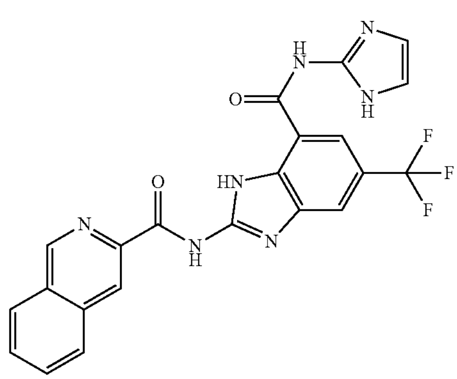 [SMILES: O=C(Nc1nc2cc(C(F)(F)F)cc(C(=O)Nc3ncc[nH]3)c2[nH]1)c1cc2ccccc2cn1] | Isoquinoline-3-carboxylic acid [7-(1H-imidazol-2-ylcarbamoyl)-5-trifluoromethyl-1H-benzoimidazol-2-yl]-amide |

TABLE 1-continued

| Ex. | Structure | Name |
|---|---|---|
| 460 | 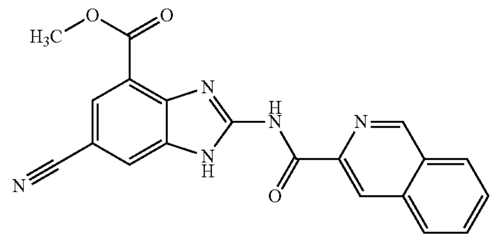 [SMILES: COC(=O)c1cc(C#N)cc2[nH]c(NC(=O)c3cc4ccccc4cn3)nc12] | 6-Cyano-2-[(isoquinoline-3-carbonyl)-amino]-1H-benzoimidazole-4-carboxylic acid methyl ester |
| 461 | 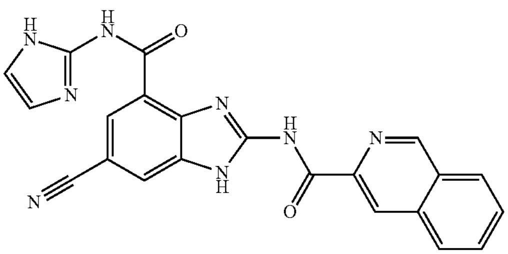 [SMILES: N#Cc1cc(C(=O)Nc2ncc[nH]2)c2nc(NC(=O)c3cc4ccccc4cn3)[nH]c2c1] | Isoquinoline-3-carboxylic acid [6-cyano-4-(1H-imidazol-2-ylcarbamoyl)-1H-benzoimidazol-2-yl]-amide |
| 462 | 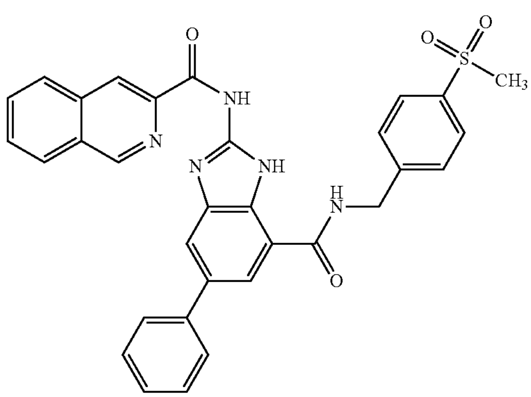 [SMILES: CS(=O)(=O)c1ccc(CNC(=O)c2cc(-c3ccccc3)cc3nc(NC(=O)c4cc5ccccc5cn4)[nH]c23)cc1] | Isoquinoline-3-carboxylic acid [7-(4-methanesulfonyl-benzylcarbamoyl)-5-phenyl-1H-benzoimidazol-2-yl]-amide |
| 463 | 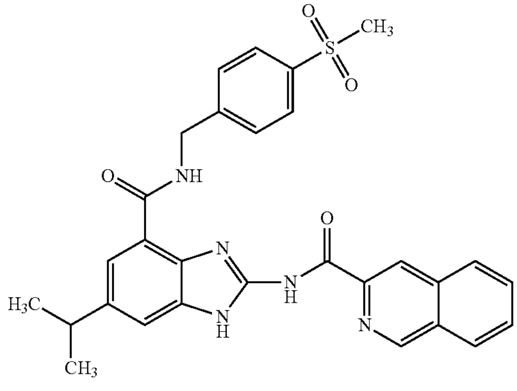 [SMILES: CC(C)c1cc(C(=O)NCc2ccc(S(C)(=O)=O)cc2)c2nc(NC(=O)c3cc4ccccc4cn3)[nH]c2c1] | Isoquinoline-3-carboxylic acid [6-isopropyl-4-(4-methanesulfonyl-benzylcarbamoyl)-1H-benzoimidazol-2-yl]-amide |

TABLE 1-continued

| Ex. | Structure | Name |
|---|---|---|
| 464 | 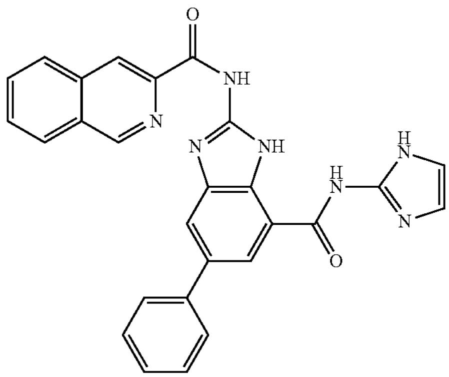 [SMILES: O=C(Nc1nc2cc(-c3ccccc3)cc(C(=O)Nc3ncc[nH]3)c2[nH]1)c1cc2ccccc2cn1] | Isoquinoline-3-carboxylic acid [7-(1H-imidazol-2-ylcarbamoyl)-5-phenyl-1H-benzoimidazol-2-yl]-amide |
| 465 | 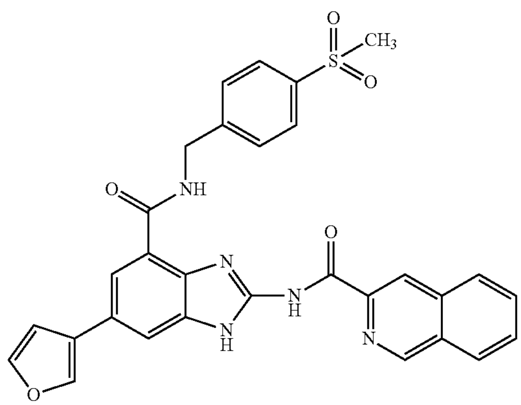 | Isoquinoline-3-carboxylic acid [6-furan-3-yl-4-(4-methanesulfonyl-benzylcarbamoyl)-1H-benzoimidazol-2-yl]-amide |
| 466 | 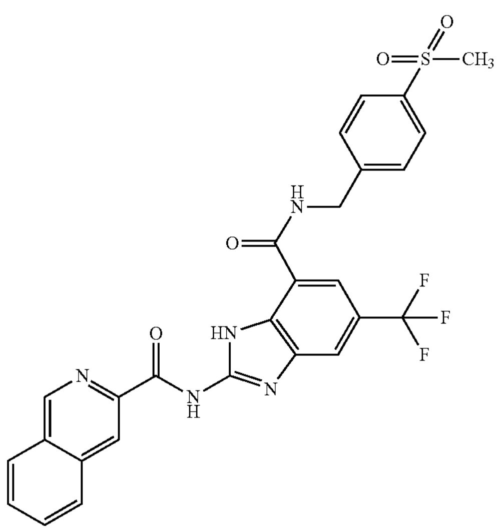 [SMILES: CS(=O)(=O)c1ccc(CNC(=O)c2cc(C(F)(F)F)cc3nc(NC(=O)c4cc5ccccc5cn4)[nH]c23)cc1] | Isoquinoline-3-carboxylic acid [7-(4-methanesulfonyl-benzylcarbamoyl)-5-trifluoromethyl-1H-benzoimidazol-2-yl]-amide |

TABLE 1-continued

| Ex. | Structure | Name |
|---|---|---|
| 467 | 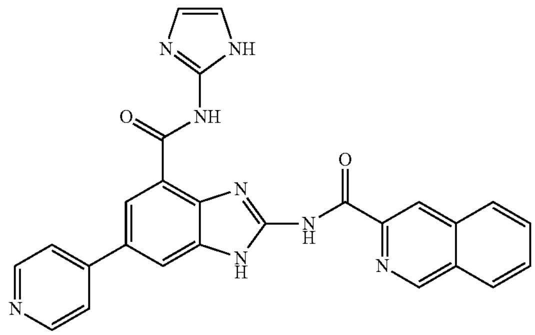 [SMILES: O=C(Nc1nc2c(C(=O)Nc3ncc[nH]3)cc(-c3ccncc3)cc2[nH]1)c1cc2ccccc2cn1] | Isoquinoline-3-carboxylic acid [4-(1H-imidazol-2-ylcarbamoyl)-6-pyridin-4-yl-1H-benzoimidazol-2-yl]-amide |
| 468 | 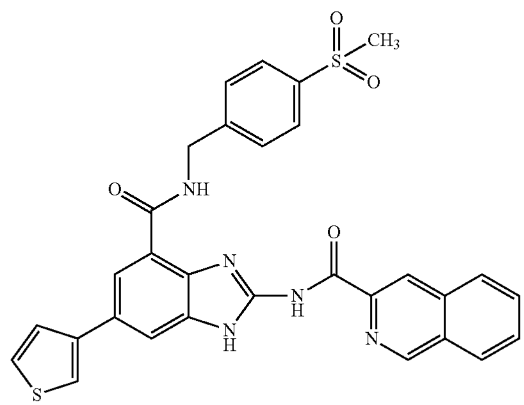 [SMILES: CS(=O)(=O)c1ccc(CNC(=O)c2cc(-c3ccsc3)cc3[nH]c(NC(=O)c4cc5ccccc5cn4)nc23)cc1] | Isoquinoline-3-carboxylic acid [4-(4-methanesulfonyl-benzylcarbamoyl)-6-thiophen-3-yl-1H-benzoimidazol-2-yl]-amide |
| 469 | 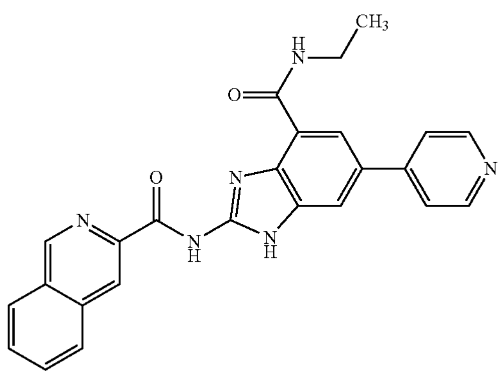 [SMILES: CCNC(=O)c1cc(-c2ccncc2)cc2[nH]c(NC(=O)c3cc4ccccc4cn3)nc12] | Isoquinoline-3-carboxylic acid (4-ethylcarbamoyl-6-pyridin-4-yl-1H-benzoimidazol-2-yl)-amide |
| 470 | 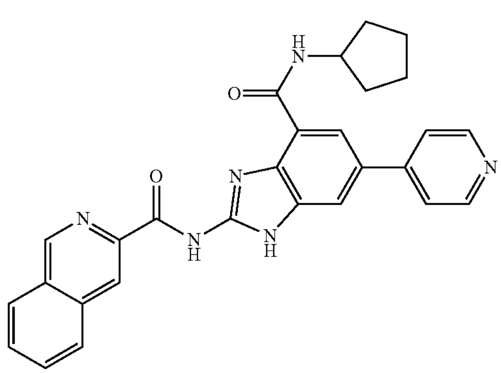 [SMILES: O=C(Nc1nc2c(C(=O)NC3CCCC3)cc(-c3ccncc3)cc2[nH]1)c1cc2ccccc2cn1] | Isoquinoline-3-carboxylic acid (4-cyclopentylcarbamoyl-6-pyridin-4-yl-1H-benzoimidazol-2-yl)-amide |

| Ex. | Structure | Name |
|---|---|---|
| 471 | 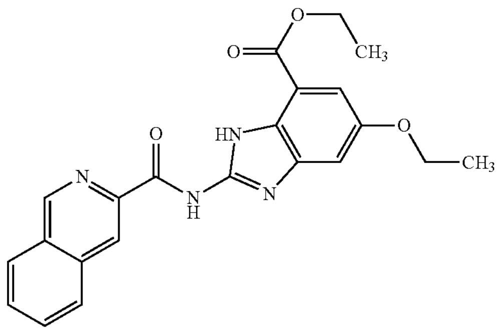 [SMILES: CCOC(=O)c1cc(OCC)cc2nc(NC(=O)c3cc4ccccc4cn3)[nH]c12] | 6-Ethoxy-2-[(isoquinoline-3-carbonyl)-amino]-3H-benzoimidazole-4-carboxylic acid ethyl ester |
| 472 | 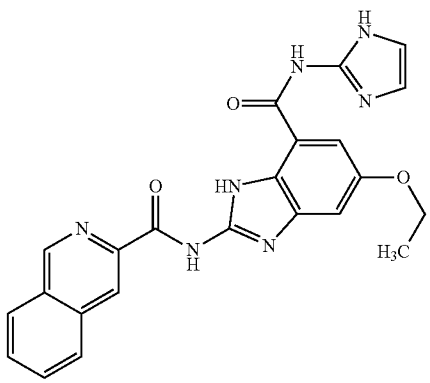 [SMILES: CCOc1cc(C(=O)Nc2ncc[nH]2)c2[nH]c(NC(=O)c3cc4ccccc4cn3)nc2c1] | Isoquinoline-3-carboxylic acid [5-ethoxy-7-(1H-imidazol-2-ylcarbamoyl)-1H-benzoimidazol-2-yl]-amide |
| 473 | 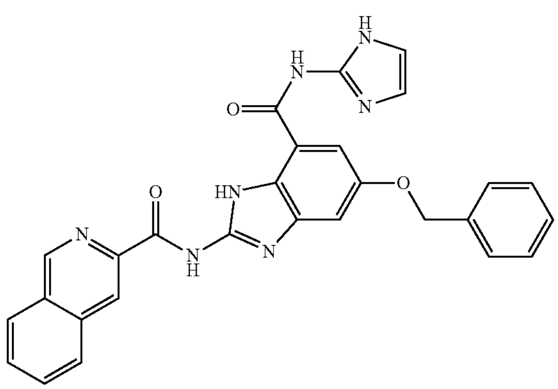 [SMILES: O=C(Nc1nc2cc(OCc3ccccc3)cc(C(=O)Nc3ncc[nH]3)c2[nH]1)c1cc2ccccc2cn1] | Isoquinoline-3-carboxylic acid [5-benzyloxy-7-(1H-imidazol-2-ylcarbamoyl)-1H-benzoimidazol-2-yl]-amide |
| 474 | 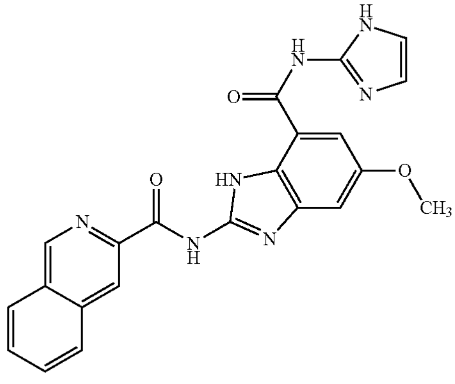 [SMILES: COc1cc(C(=O)Nc2ncc[nH]2)c2[nH]c(NC(=O)c3cc4ccccc4cn3)nc2c1] | Isoquinoline-3-carboxylic acid [7-(1H-imidazol-2-ylcarbamoyl)-5-methoxy-1H-benzoimidazol-2-yl]-amide |

TABLE 1-continued

| Ex. | Structure | Name |
|---|---|---|
| 475 | 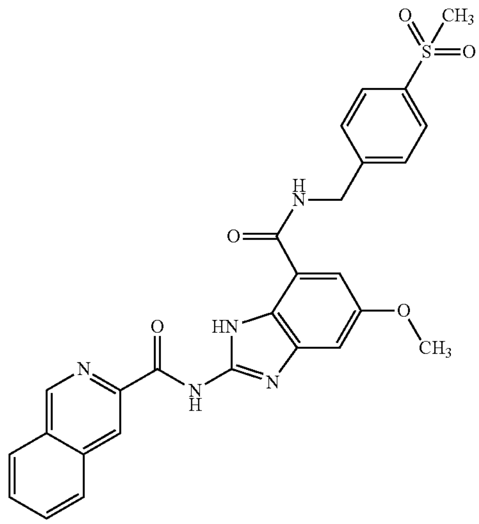 [SMILES: COc1cc(C(=O)NCc2ccc(S(C)(=O)=O)cc2)c2[nH]c(NC(=O)c3cc4ccccc4cn3)nc2c1] | Isoquinoline-3-carboxylic acid [7-(4-methanesulfonyl-benzylcarbamoyl)-5-methoxy-1H-benzoimidazol-2-yl]-amide |
| 476 | 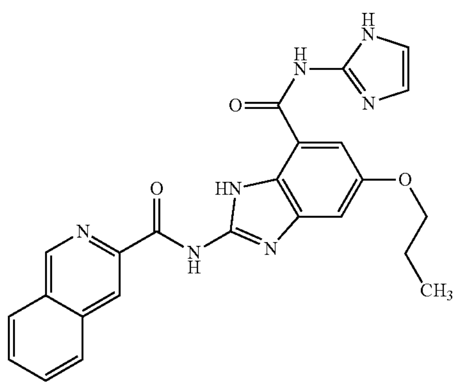 [SMILES: CCCOc1cc(C(=O)Nc2ncc[nH]2)c2[nH]c(NC(=O)c3cc4ccccc4cn3)nc2c1] | Isoquinoline-3-carboxylic acid [7-(1H-imidazol-2-ylcarbamoyl)-5-propoxy-1H-benzoimidazol-2-yl]-amide |
| 477 | 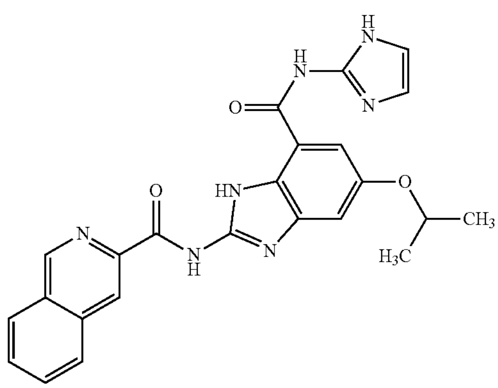 [SMILES: CC(C)Oc1cc(C(=O)Nc2ncc[nH]2)c2[nH]c(NC(=O)c3cc4ccccc4cn3)nc2c1] | Isoquinoline-3-carboxylic acid [7-(1H-imidazol-2-ylcarbamoyl)-5-isopropoxy-1H-benzoimidazol-2-yl]-amide |

TABLE 1-continued

| Ex. | Structure | Name |
|---|---|---|
| 478 | 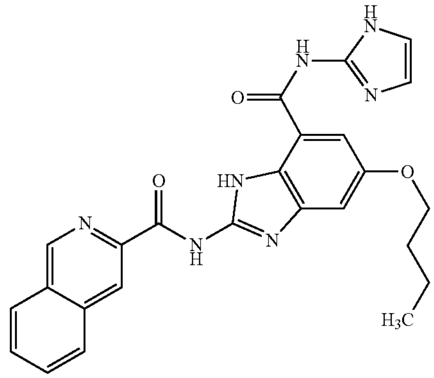 [SMILES: CCCCOc1cc(C(=O)Nc2ncc[nH]2)c2[nH]c(NC(=O)c3cc4ccccc4cn3)nc2c1] | Isoquinoline-3-carboxylic acid [5-butoxy-7-(1H-imidazol-2-ylcarbamoyl)-1H-benzoimidazol-2-yl]-amide |
| 479 | 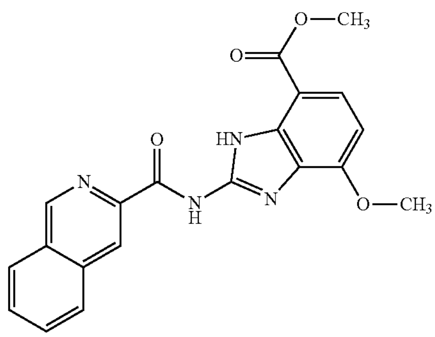 [SMILES: COC(=O)c1ccc(OC)c2nc(NC(=O)c3cc4ccccc4cn3)[nH]c12] | 2-[(Isoquinoline-3-carbonyl)-amino]-7-methoxy-3H-benzoimidazole-4-carboxylic acid methyl ester |
| 480 | 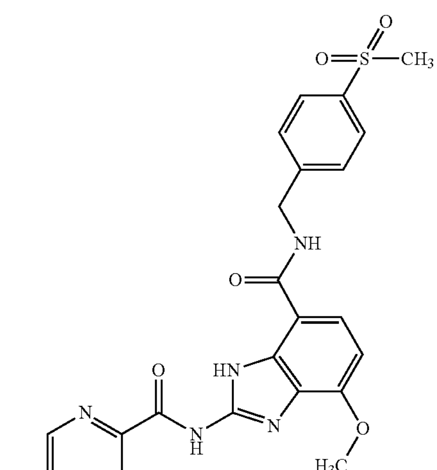 | Isoquinoline-3-carboxylic acid [7-(4-methanesulfonyl-benzylcarbamoyl)-4-methoxy-1H-benzoimidazol-2-yl]-amide |
| 481 | 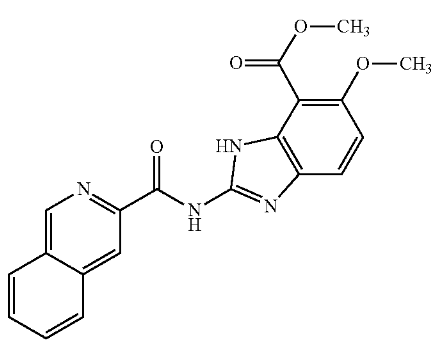 [SMILES: COC(=O)c1c(OC)ccc2nc(NC(=O)c3cc4ccccc4cn3)[nH]c12] | 2-[(Isoquinoline-3-carbonyl)-amino]-5-methoxy-3H-benzoimidazole-4-carboxylic acid methyl ester |

TABLE 1-continued

| Ex. | Structure | Name |
|---|---|---|
| 482 | 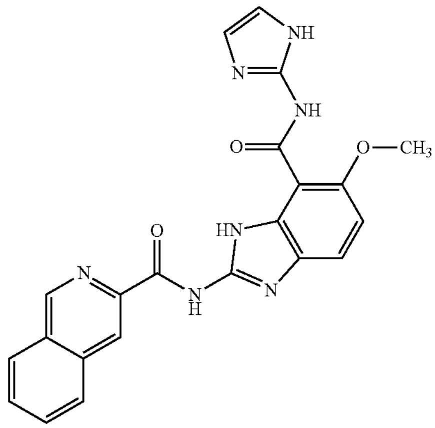 [SMILES: COc1ccc2nc(NC(=O)c3cc4ccccc4cn3)[nH]c2c1C(=O)Nc1ncc[nH]1] | Isoquinoline-3-carboxylic acid [7-(1H-imidazol-2-ylcarbamoyl)-6-methoxy-1H-benzoimidazol-2-yl]-amide |
| 483 | 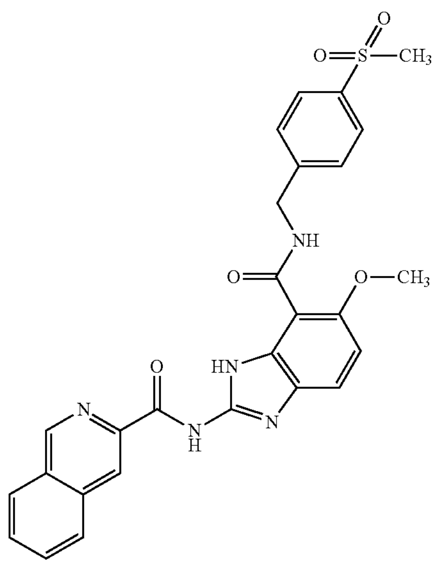 [SMILES: COc1ccc2nc(NC(=O)c3cc4ccccc4cn3)[nH]c2c1C(=O)NCc1ccc(S(C)(=O)=O)cc1] | Isoquinoline-3-carboxylic acid [7-(4-methanesulfonyl-benzylcarbamoyl)-6-methoxy-1H-benzoimidazol-2-yl]-amide |
| 484 | 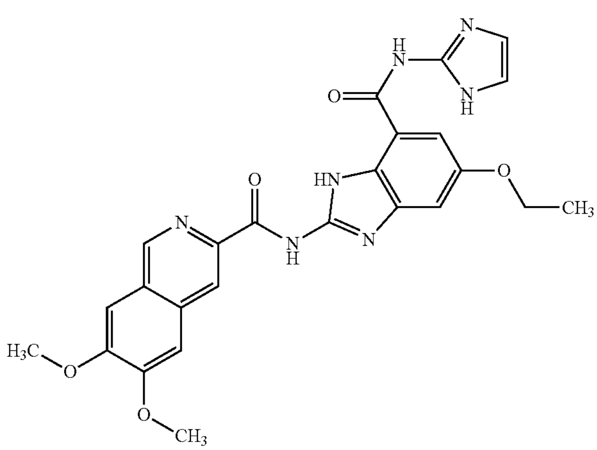 [SMILES: CCOc1cc(C(=O)Nc2ncc[nH]2)c2[nH]c(NC(=O)c3cc4cc(OC)c(OC)cc4cn3)nc2c1] | 6,7-Dimethoxy-isoquinoline-3-carboxylic acid [5-ethoxy-7-(1H-imidazol-2-ylcarbamoyl)-1H-benzoimidazol-2-yl]-amide |

| Ex. | Structure | Name |
|---|---|---|
| 485 | 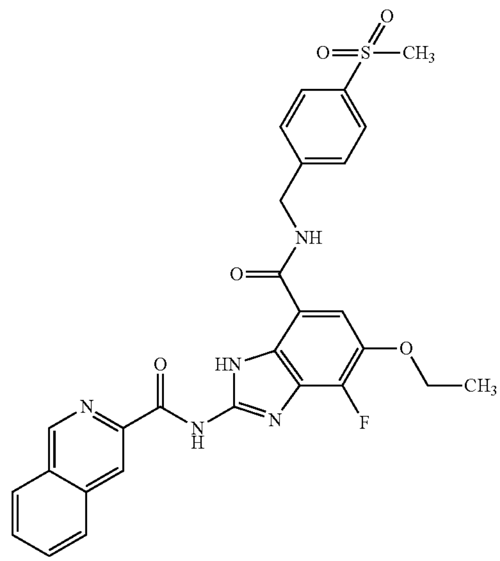 [SMILES: CCOc1cc(C(=O)NCc2ccc(S(C)(=O)=O)cc2)c2[nH]c(NC(=O)c3cc4ccccc4cn3)nc2c1F] | Isoquinoline-3-carboxylic acid [5-ethoxy-4-fluoro-7-(4-methanesulfonyl-benzylcarbamoyl)-1H-benzoimidazol-2-yl]-amide |
| 486 | 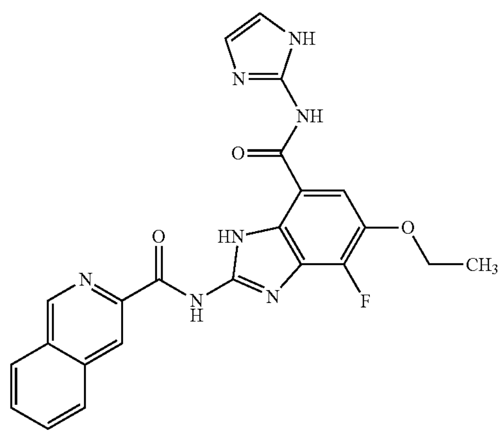 [SMILES: CCOc1cc(C(=O)Nc2ncc[nH]2)c2[nH]c(NC(=O)c3cc4ccccc4cn3)nc2c1F] | Isoquinoline-3-carboxylic acid [5-ethoxy-4-fluoro-7-(1H-imidazol-2-ylcarbamoyl)-1H-benzoimidazol-2-yl]-amide |
| 487 | 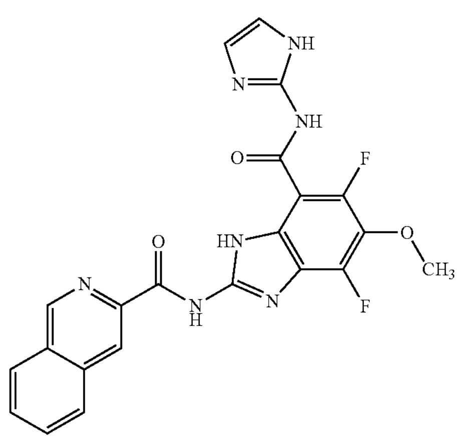 [SMILES: COc1c(F)c(C(=O)Nc2ncc[nH]2)c2[nH]c(NC(=O)c3cc4ccccc4cn3)nc2c1F] | Isoquinoline-3-carboxylic acid [4,6-difluoro-7-(1H-imidazol-2-ylcarbamoyl)-5-methoxy-1H-benzoimidazol-2-yl]-amide |

TABLE 1-continued

| Ex. | Structure | Name |
|---|---|---|
| 488 | 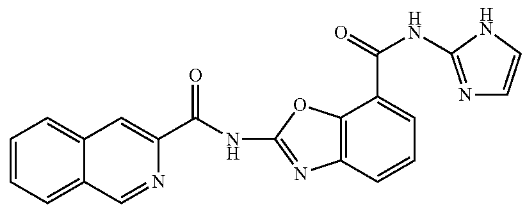 [SMILES: O=C(Nc1nc2cccc(C(=O)Nc3ncc[nH]3)c2o1)c1cc2ccccc2cn1] | Isoquinoline-3-carboxylic acid [7-(1H-imidazol-2-ylcarbamoyl)-benzooxazol-2-yl]-amide |
| 489 | 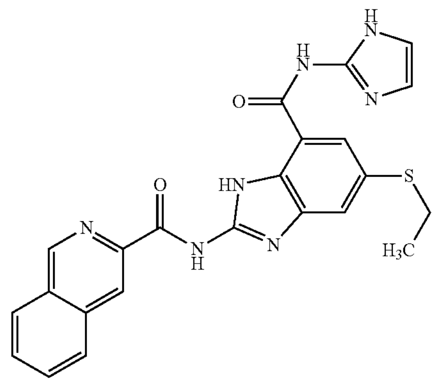 | Isoquinoline-3-carboxylic acid [5-ethylsulfanyl-7-(1H-imidazol-2-ylcarbamoyl)-1H-benzoimidazol-2-yl]-amide |
| 490 | 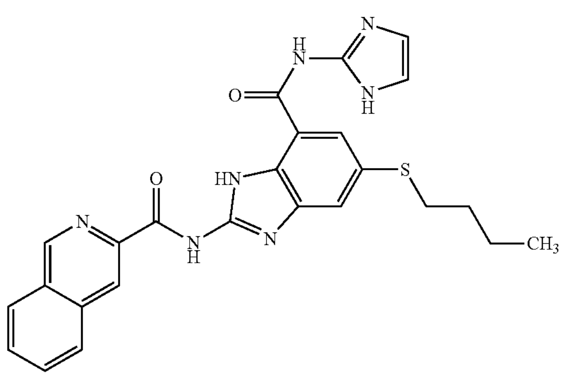 [SMILES: CCCCSc1cc(C(=O)Nc2ncc[nH]2)c2[nH]c(NC(=O)c3cc4ccccc4cn3)nc2c1] | Isoquinoline-3-carboxylic acid [5-butylsulfanyl-7-(1H-imidazol-2-ylcarbamoyl)-1H-benzoimidazol-2-yl]-amide |
| 491 | 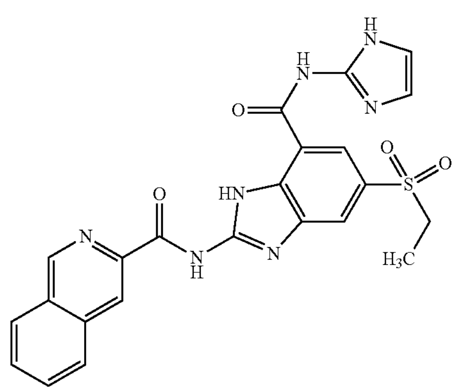 [SMILES: CCS(=O)(=O)c1cc(C(=O)Nc2ncc[nH]2)c2[nH]c(NC(=O)c3cc4ccccc4cn3)nc2c1] | Isoquinoline-3-carboxylic acid [5-ethanesulfonyl-7-(1H-imidazol-2-ylcarbamoyl)-1H-benzoimidazol-2-yl]-amide |

TABLE 1-continued

| Ex. | Structure | Name |
|---|---|---|
| 492 | 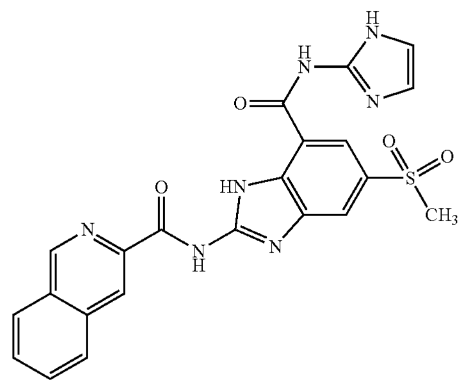 [SMILES: CS(=O)(=O)c1cc(C(=O)Nc2ncc[nH]2)c2[nH]c(NC(=O)c3cc4ccccc4cn3)nc2c1] | Isoquinoline-3-carboxylic acid [7-(1H-imidazol-2-ylcarbamoyl)-5-methanesulfonyl-1H-benzoimidazol-2-yl]-amide |
| 493 | 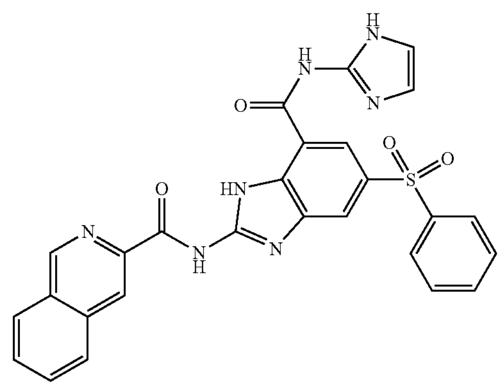 [SMILES: O=C(Nc1nc2cc(S(=O)(=O)c3ccccc3)cc(C(=O)Nc3ncc[nH]3)c2[nH]1)c1cc2ccccc2cn1] | Isoquinoline-3-carboxylic acid [5-benzenesulfonyl-7-(1H-imidazol-2-ylcarbamoyl)-1H-benzoimidazol-2-yl]-amide |
| 494 | 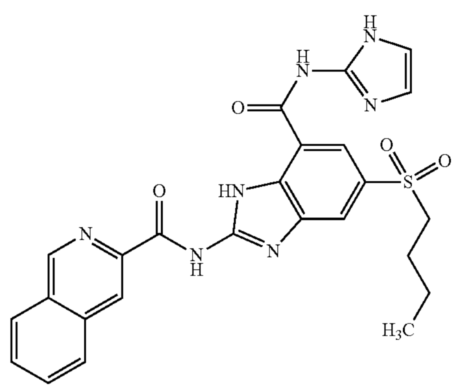 [SMILES: CCCCS(=O)(=O)c1cc(C(=O)Nc2ncc[nH]2)c2[nH]c(NC(=O)c3cc4ccccc4cn3)nc2c1] | Isoquinoline-3-carboxylic acid [5-(butane-1-sulfonyl)-7-(1H-imidazol-2-ylcarbamoyl)-1H-benzoimidazol-2-yl]-amide |
| 495 | 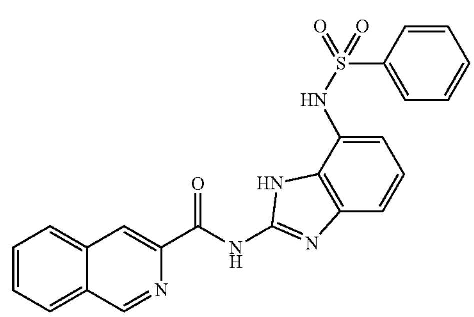 [SMILES: O=C(Nc1nc2cccc(NS(=O)(=O)c3ccccc3)c2[nH]1)c1cc2ccccc2cn1] | Isoquinoline-3-carboxylic acid (7-benzenesulfonylamino-1H-benzoimidazol-2-yl)-amide |

| Ex. | Structure | Name |
|---|---|---|
| 496 | 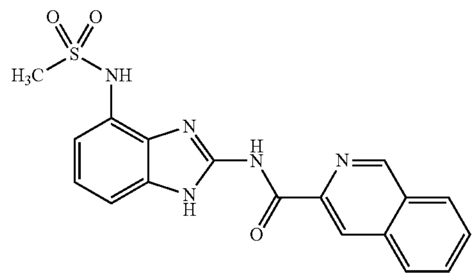 [SMILES: CS(=O)(=O)Nc1cccc2[nH]c(NC(=O)c3cc4ccccc4cn3)nc12] | Isoquinoline-3-carboxylic acid (4-ethanesulfonylamino-1H-benzoimidazol-2-yl)-amide |
| 497 | 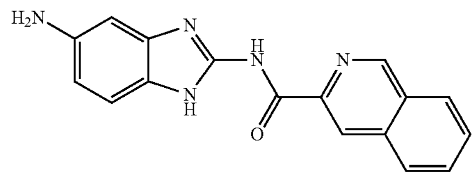 [SMILES: Nc1ccc2[nH]c(NC(=O)c3cc4ccccc4cn3)nc2c1] | Isoquinoline-3-carboxylic acid (5-amino-1H-benzoimidazol-2-yl)-amide |
| 498 | 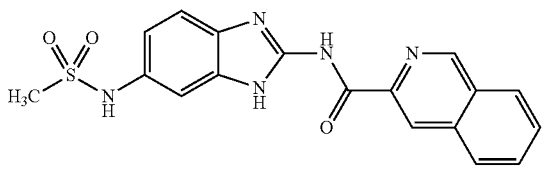 [SMILES: CS(=O)(=O)Nc1ccc2nc(NC(=O)c3cc4ccccc4cn3)[nH]c2c1] | Isoquinoline-3-carboxylic acid (6-ethanesulfonylamino-1H-benzoimidazol-2-yl)-amide |
| 499 | 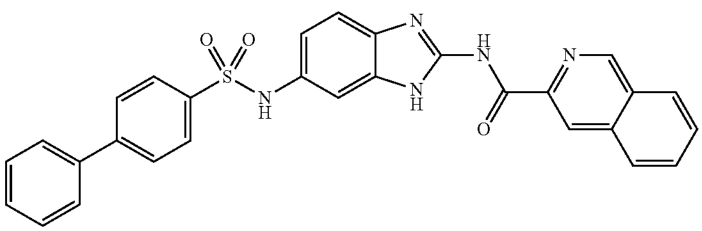 [SMILES: O=C(Nc1nc2ccc(NS(=O)(=O)c3ccc(-c4ccccc4)cc3)cc2[nH]1)c1cc2ccccc2cn1] | Isoquinoline-3-carboxylic acid [6-(biphenyl-4-sulfonylamino)-1H-benzoimidazol-2-yl]-amide |
| 500 | 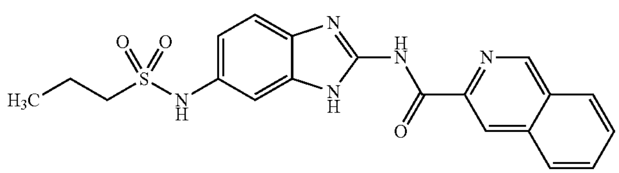 [SMILES: CCCS(=O)(=O)Nc1ccc2nc(NC(=O)c3cc4ccccc4cn3)[nH]c2c1] | Isoquinoline-3-carboxylic acid [6-(propane-1-sulfonylamino)-1H-benzoimidazol-2-yl]-amide |
| 501 | 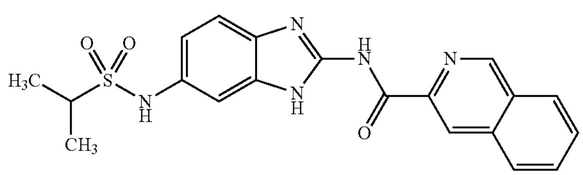 [SMILES: CC(C)S(=O)(=O)Nc1ccc2nc(NC(=O)c3cc4ccccc4cn3)[nH]c2c1] | Isoquinoline-3-carboxylic acid [6-(propane-2-sulfonylamino)-1H-benzoimidazol-2-yl]-amide |

Incomplete valences for heteroatoms such as oxygen and nitrogen in the chemical structures listed in Table 1 are assumed to be completed by hydrogen.

Compounds in Table 1 having a basic group or acidic group are depicted and named as the free base or acid. Depending on the reaction conditions and purification conditions, various compounds in Table 1 having a basic group were isolated in either the free base form, as a salt (such as HCl salt), or in both forms.

In another aspect, the present invention comprises a pharmaceutical composition comprising the compound of Formula (I) and a pharmaceutically acceptable carrier, excipient, diluent, or a mixture thereof.

As used herein, the term "lower" refers to a group having between one and six carbons.

As used herein, the term "alkyl" refers to a straight or branched chain hydrocarbon having from one to ten carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkyl" group may containing one or more O, S, S(O), or S(O)$_2$ atoms. Examples of "alkyl" as used herein include, but are not limited to, methyl, n-butyl, t-butyl, n-pentyl, isobutyl, and isopropyl, and the like.

As used herein, the term "alkylene" refers to a straight or branched chain divalent hydrocarbon radical having from one to ten carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkylene" group may containing one or more O, S, S(O), or S(O)$_2$ atoms. Examples of "allylene" as used herein include, but are not limited to, methylene, ethylene, and the like.

As used herein, the term "alkenyl" refers to a hydrocarbon radical having from two to ten carbons and at least one carbon-carbon double bond, optionally substituted with substituents selected from the group consisting of lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenyl" group may containing one or more O, S, S(O), or S(O)$_2$ atoms.

As used herein, the term "alkenylene" refers to a straight or branched chain divalent hydrocarbon radical having from two to ten carbon atoms and one or more carbon-carbon double bonds, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkenylene" group may containing one or more O, S, S(O), or S(O)$_2$ atoms. Examples of "alkenylene" as used herein include, but are not limited to, ethene-1,2-diyl, propene-1,3-diyl, methylene-1,1-diyl, and the like.

As used herein, the term "alkynyl" refers to a hydrocarbon radical having from two to ten carbons and at least one carbon-carbon triple bond, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynyl" group may containing one or more O, S, S(O), or S(O)$_2$ atoms.

As used herein, the term "alkynylene" refers to a straight or branched chain divalent hydrocarbon radical having from two to ten carbon atoms and one or more carbon-carbon triple bonds, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Such an "alkynylene" group may containing one or more O, S, S(O), or S(O)$_2$ atoms. Examples of "alkynylene" as used herein include, but are not limited to, ethyne-1,2-diyl, propyne-1,3-diyl, and the like.

As used herein, the terms "haloaliphatic", "haloalkyl", "haloalkenyl" and "haloalkoxy" refer to an aliphatic, alkyl, alkenyl or alkoxy group, as the case may be, substituted with one or more halogen atoms.

As used herein, "cycloalkyl" refers to a alicyclic hydrocarbon group optionally possessing one or more degrees of unsaturation, having from three to twelve carbon atoms, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. "Cycloalkyl" includes by way of example cyclopropyl, cyclobutyl, cyclopentyl, cyclohexyl, cycloheptyl, or cyclooctyl, and bicyclic and tricyclic structures such as adamantane.

As used herein, the term "cycloalkylene" refers to an non-aromatic alicyclic divalent hydrocarbon radical having from three to twelve carbon atoms and optionally possessing one or more degrees of unsaturation, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Examples of "cycloalkylene" as used herein include, but are not limited to, cyclopropyl-1,1-diyl, cyclopropyl-1,2-diyl, cyclobutyl-1,2-diyl, cyclopentyl-1,3-diyl, cyclohexyl-1,4-diyl, cycloheptyl-1,4-diyl, or cyclooctyl-1,5-diyl, and bicyclic and tricyclic structures.

As used herein, the term "heterocyclic" or the term "heterocyclyl" refers to a non-aromatic three to twelve-membered heterocyclic ring optionally possessing one or more degrees of unsaturation, containing one or more heteroatomic substitutions selected from S, SO, SO$_2$, O, or N, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one to three benzene rings or to one to three of another "heterocyclic" ring(s) or cycloalkyl ring(s). Examples of "heterocyclic" include, but are not limited to, tetrahydrofuran, 1,4-dioxane, 1,3-dioxane, piperidine, pyrrolidine, morpholine, piperazine, and the like.

As used herein, the term "heterocyclylene" refers to a three to twelve-membered heterocyclic ring diradical optionally having one or more degrees of unsaturation containing one or more heteroatoms selected from S, SO, SO$_2$, O, or N, optionally substituted with substituents selected from the group consisting of halo, lower allyl, lower alkoxy, lower alkylsulfanyl, lower alkylsulfenyl, lower alkylsulfonyl, oxo, hydroxy, mercapto, amino optionally substituted by alkyl, carboxy, carbamoyl optionally substituted by alkyl, aminosulfonyl optionally substituted by alkyl, nitro, cyano, halogen, or lower perfluoroalkyl, multiple degrees of substitution being allowed. Such a ring may be optionally fused to one to three benzene rings or to one to three of another "heterocyclic" rings or cycloalkyl rings. Examples of "heterocyclylene" include, but are not limited to, tetrahydrofuran-2,5-diyl, morpholine-2,3-diyl, pyran-2,4-diyl, 1,4-dioxane-2,3-diyl, 1,3-dioxane-2,4-diyl, piperidine-2,4-diyl, piperidine-1,4-diyl, pyrrolidine-1,3-diyl, morpholine-2,4-diyl, piperazine-1,4-diyl, and the like.

As used herein, the term "aryl" refers to a benzene ring or to an optionally substituted benzene ring system fused to one to three optionally substituted benzene rings, optionally substituted with substituents selected from the group consisting of halo, lower alkyl, lower alkoxy, lower alkylsulfanyl, lower alkylsulfenyl, lower alkylsulfonyl, di(lower alkyl)aminoalkyl, aminoalkyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acylamino, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of aryl include, but are not limited to, phenyl, 2-naphthyl, 1-naphthyl, 1-anthracenyl, and the like.

As used herein, the term "arylene" refers to a benzene ring diradical or to a benzene ring system diradical fused to one to three optionally substituted benzene rings, optionally substituted with substituents selected from the group consisting of halo, lower alkyl, lower alkoxy, lower alkylsulfanyl, lower alkylsulfenyl, lower alkylsulfonyl, di(lower alkyl)aminoalkyl, aminoalkyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acylamino, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. Examples of "arylene" include, but are not limited to, benzene-1,4-diyl, naphthalene-1,8-diyl, and the like.

As used herein, the term "heteroaryl" refers to a five- to seven-membered aromatic ring, or to a polycyclic heterocyclic aromatic ring (up to 3 rings), containing one or more nitrogen, oxygen, or sulfur heteroatoms, where N-oxides and sulfur monoxides and sulfur dioxides are permissible heteroaromatic substitutions, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring systems, one or more of the rings may contain one or more heteroatoms. Examples of "heteroaryl" used herein are furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, quinazoline, benzofuran, benzothiophene, indole, and indazole, and the like.

As used herein, the term "heteroarylene" refers to a five- to seven-membered aromatic ring diradical, or to a polycyclic heterocyclic aromatic ring diradical (up to 3 rings), containing one or more nitrogen, oxygen, or sulfur heteroatoms, where N-oxides and sulfur monoxides and sulfur dioxides are permissible heteroaromatic substitutions, optionally substituted with substituents selected from the group consisting of halo, lower alkyl, lower alkoxy, lower alkylsulfanyl, lower alkylsulfenyl, lower alkylsulfonyl, oxo, hydroxy, mercapto, amino optionally substituted by alkyl, carboxy, tetrazolyl, carbamoyl optionally substituted by alkyl, aminosulfonyl optionally substituted by alkyl, acyl, aroyl, heteroaroyl, acyloxy, aroyloxy, heteroaroyloxy, alkoxycarbonyl, silyloxy optionally substituted by alkoxy, alkyl, or aryl, silyl optionally substituted by alkoxy, alkyl, or aryl, nitro, cyano, halogen, or lower perfluoroalkyl, multiple degrees of substitution being allowed. For polycyclic aromatic ring system diradicals, one or more of the rings may contain one or more heteroatoms. Examples of "heteroarylene" used herein are furan-2,5-diyl, thiophene-2,4-diyl, 1,3,4-oxadiazole-2,5-diyl, 1,3,4-thiadiazole-2,5-diyl, 1,3-thiazole-2,4-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, and the like.

As used herein, the term "fused cycloalkylaryl" refers to a cycloalkyl group fused to an aryl group, the two having two atoms in common, and wherein the aryl group is the point of substitution. Examples of "fused cycloalkylaryl" used herein include 5-indanyl, 5,6,7,8-tetrahydro-2-naphthyl,

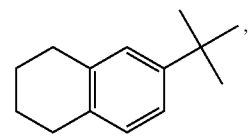

and the like.

As used herein, the term "fused cycloalkylarylene" refers to a fused cycloalkylaryl, wherein the aryl group is divalent. Examples include

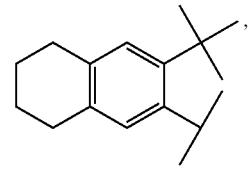 [SMILES: CC(C)c1cc2c(cc1C(C)(C)C)CCCC2]

and the like.

As used herein, the term "fused arylcycloalkyl" refers to an aryl group fused to a cycloalkyl group, the two having two atoms in common, and wherein the cycloalkyl group is the point of substitution. Examples of "fused arylcycloalkyl" used herein include 1-indanyl, 2-indanyl, 1-(1,2,3,4-tetrahydronaphthyl),

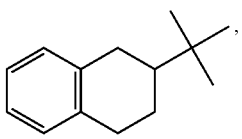

and the like.

As used herein, the term "fused arylcycloalkylene" refers to a fused arylcycloalkyl, wherein the cycloalkyl group is divalent. Examples include

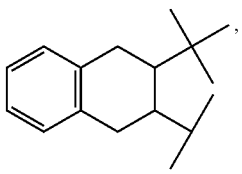 [SMILES: CC(C)C1Cc2ccccc2CC1C(C)(C)C]

and the like.

As used herein, the term "fused heterocyclylaryl" refers to a heterocyclyl group fused to an aryl group, the two having two atoms in common, and wherein the aryl group is the point of substitution. Examples of "fused heterocyclylaryl" used herein include 3,4-methylenedioxy-1-phenyl,

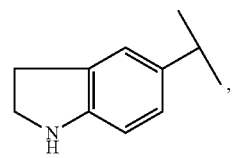

and the like

As used herein, the term "fused heterocyclylarylene" refers to a fused heterocyclylaryl, wherein the aryl group is divalent. Examples include

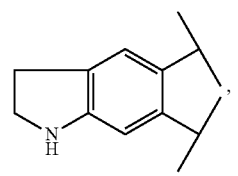

and the like.

As used herein, the term "fused arylheterocyclyl" refers to an aryl group fused to a heterocyclyl group, the two having two atoms in common, and wherein the heterocyclyl group is the point of substitution. Examples of "fused arylheterocyclyl" used herein include 2-(1,3-benzodioxolyl),

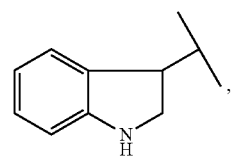

and the like.

As used herein, the term "fused arylheterocyclylene" refers to a fused arylheterocyclyl, wherein the heterocyclyl group is divalent. Examples include

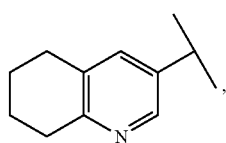

and the like.

As used herein, the term "fused cycloalkylheteroaryl" refers to a cycloalkyl group fused to a heteroaryl group, the two having two atoms in common, and wherein the heteroaryl group is the point of substitution. Examples of "fused cycloalkylheteroaryl" used herein include 5-aza-6-indanyl,

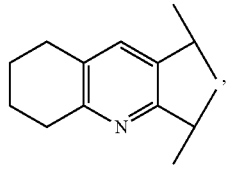 [SMILES: CC(C)c1cc2c(nc1C(C)C)CCCC2]

and the like.

As used herein, the term "fused cycloalkylheteroarylene" refers to a fused cycloalkylheteroaryl, wherein the heteroaryl group is divalent. Examples include

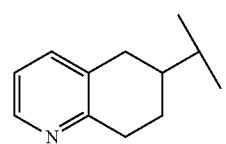

and the like.

As used herein, the term "fused heteroarylcycloalkyl" refers to a heteroaryl group fused to a cycloalkyl group, the two having two atoms in common, and wherein the cycloalkyl group is the point of substitution. Examples of "fused heteroarylcycloalkyl" used herein include 5-aza-1-indanyl,

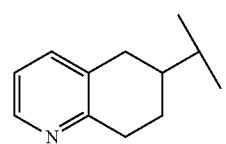

and the like.

As used herein, the term "fused heteroarylcycloalkylene" refers to a fused heteroarylcycloalkyl, wherein the cycloalkyl group is divalent. Examples include

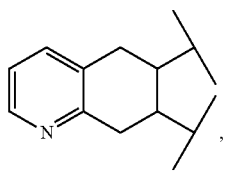 [SMILES: CC(C)C1Cc2cccnc2CC1C(C)C]

and the like.

As used herein, the term "fused heterocyclylheteroaryl" refers to a heterocyclyl group fused to a heteroaryl group, the two having two atoms in common, and wherein the heteroaryl group is the point of substitution. Examples of "fused heterocyclylheteroaryl" used herein include 1,2,3,4-tetrahydro-beta-carbolin-8-yl,

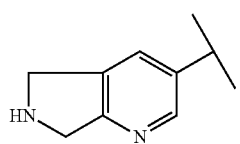

and the like.

As used herein, the term "fused heterocyclylheteroarylene" refers to a fused heterocyclylheteroaryl, wherein the heteroaryl group is divalent. Examples include

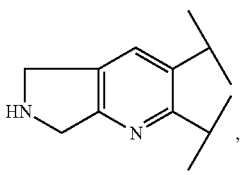

and the like.

As used herein, the term "fused heteroarylheterocyclyl" refers to a heteroaryl group fused to a heterocyclyl group, the two having two atoms in common, and wherein the heterocyclyl group is the point of substitution. Examples of "fused heteroalylheterocyclyl" used herein include-5-aza-2,3-dihydrobenzofuran-2-yl,

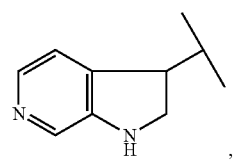

and the like.

As used herein, the term "fused heteroarylheterocyclylene" refers to a fused heteroarylheterocyclyl, wherein the heterocyclyl group is divalent. Examples include

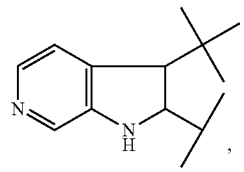 [SMILES: CC(C)C1Nc2cnccc2C1C(C)(C)C]

and the like.

As used herein, the term "direct bond", where part of a structural variable specification, refers to the direct joining of the substituents flanking (preceding and succeeding) the variable taken as a "direct bond". Where two or more consecutive variables are specified each as a "direct bond", those substituents flanking (preceding and succeeding) those two or more consecutive specified "direct bonds" are directly joined.

As used herein, the term "alkoxy" refers to the group $R_aO$—, where $R_a$ is alkyl.

As used herein, the term "alkenyloxy" refers to the group $R_aO$—, where $R_a$ is alkenyl.

As used herein, the term "alkynyloxy" refers to the group $R_aO$—, where $R_a$ is alkynyl.

As used herein, the term "alkylsulfanyl" refers to the group $R_aS$—, where $R_a$ is alkyl.

As used herein, the term "alkenylsulfanyl" refers to the group $R_aS$—, where $R_a$ is alkenyl.

As used herein, the term "alkynylsulfanyl" refers to the group $R_aS$—, where $R_a$ is alkynyl.

As used herein, the term "alkylsulfenyl" refers to the group $R_aS(O)$—, where $R_a$ is alkyl.

As used herein, the term "alkenylsulfenyl" refers to the group $R_aS(O)$—, where $R_a$ is alkenyl.

As used herein, the term "alkynylsulfenyl" refers to the group $R_aS(O)$—, where $R_a$ is alkynyl.

As used herein, the term "alkylsulfonyl" refers to the group $R_aSO_2$—, where $R_a$ is alkyl.

As used herein, the term "alkenylsulfonyl" refers to the group $R_aSO_2$—, where $R_a$ is alkenyl.

As used herein, the term "alkynylsulfonyl" refers to the group $R_aSO_2$—, where $R_a$ is alkynyl.

As used herein, the term "acyl" refers to the group $R_aC(O)$—, where $R_a$ is alkyl, alkenyl, alkynyl, cycloalkyl, cycloalkenyl, or heterocyclyl.

As used herein, the term "aroyl" refers to the group $R_aC(O)$—, where $R_a$ is aryl.

As used herein, the term "heteroaroyl" refers to the group $R_aC(O)$—, where $R_a$ is heteroaryl.

As used herein, the term "alkoxycarbonyl" refers to the group $R_aOC(O)$—, where $R_a$ is alkyl.

As used herein, the term "acyloxy" refers to the group $R_aC(O)O$—, where $R_a$ is alkyl, alkenyl, alkynyl, cycloalkyl, cycloalkenyl, or heterocyclyl.

As used herein, the term "aroyloxy" refers to the group $R_aC(O)O$—, where $R_a$ is aryl.

As used herein, the term "heteroaroyloxy" refers to the group $R_aC(O)O$—, where $R_a$ is heteroaryl.

As used herein, the term "optionally" means that the subsequently described event(s) may or may not occur, and includes both event(s) which occur and events that do not occur.

As used herein, the term "substituted" refers to substitution with the named substituent or substituents, multiple degrees of substitution being allowed unless otherwise stated, provided that the substitution results in a stable or chemically feasible compound. A stable compound or chemically feasible compound is one in which the chemical structure is not substantially altered when kept at a temperature from about −80° C. to about +40° C., in the absence of moisture or other chemically reactive conditions, for at least a week, or a compound which maintains its integrity long enough to be useful for therapeutic or prophylactic administration to a patient. The phrase "one or more substituents", as used herein, refers to a number of substituents that equals from one to the maximum number of substituents possible based on the number of available bonding sites, provided that the above conditions of stability and chemical feasibility are met.

As used herein, the terms "contain" or "containing" can refer to in-line substitutions at any position along the above defined alkyl, alkenyl, alkynyl or cycloalkyl substituents with one or more of any of O, S, SO, $SO_2$, N, or N-alkyl, including, for example, —$CH_2$—O—$CH_2$—, —$CH_2$—$SO_2$—$CH_2$—, —$CH_2$—NH—$CH_3$ and so forth.

As used herein, the term "solvate" is a complex of variable stoichiometry formed by a solute (in this invention, a compound of Formula (I)) and a solvent. Such solvents for the purpose of the invention may not substantially interfere with the biological activity of the solute. Solvents may be, by way of example, water, ethanol, or acetic acid.

As used herein, the term "biohydrolyzable ester" is an ester of a drug substance (in this invention, a compound of Formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable ester is orally absorbed from the gut and is transformed to Formula (I) in plasma. Many examples of such are known in the art and include by way of example lower alkyl esters (e.g., $C_1$-$C_4$), lower acyloxyalkyl esters, lower alkoxyacyloxyalkyl esters, alkoxyacyloxy esters, alkyl acylamino alkyl esters, and choline esters.

As used herein, the term "biohydrolyzable amide" is an amide of a drug substance (in this invention, a compound of general formula (I)) which either a) does not interfere with the biological activity of the parent substance but confers on that substance advantageous properties in vivo such as duration of action, onset of action, and the like, or b) is biologically inactive but is readily converted in vivo by the subject to the biologically active principle. The advantage is that, for example, the biohydrolyzable amide is orally absorbed from the gut and is transformed to Formula (I) in plasma. Many examples of such are known in the art and include by way of example lower alkyl amides, alpha-amino acid amides, alkoxyacyl amides, and alkylaminoalkylcarbonyl amides.

As used herein, the term "prodrug" is a) a biohydrolyzable amide or a biohydrolyzable ester and encompasses compounds in which the biohydrolyzable functionality in such a prodrug is encompassed in the compound of Formula (I) or b) a compound that may be oxidized or reduced biologically at a given functional group to yield drug substance of Formula (I). Examples of these functional groups include, but are not limited to, 1,4-dihydropyridine, N-alkylcarbonyl-1,4-dihydropyridine, 1,4-cyclohexadiene, tert-butyl, and the like.

Whenever the terms "alkyl" or "aryl" or either of their prefix roots appear in a name of a substituent (e.g. arylalkoxyaryloxy) they shall be interpreted as including those limitations given above for "alkyl" and "aryl". Designated numbers of carbon atoms (e.g. $C_{1-10}$) shall refer independently to the number of carbon atoms in an alkyl, alkenyl or alkynyl or cyclic alkyl moiety or to the alkyl portion of a larger substituent in which the term "alkyl" appears as its prefix root.

As used herein, the term "oxo" shall refer to the substituent =O.

As used herein, the term "halogen" or "halo" shall include iodine, bromine, chlorine and fluorine.

As used herein, the term "mercapto" shall refer to the substituent —SH.

As used herein, the term "carboxy" shall refer to the substituent —COOH.

As used herein, the term "cyano" shall refer to the substituent —CN.

As used herein, the term "aminosulfonyl" shall refer to the substituent —$SO_2NH_2$.

As used herein, the term "carbamoyl" shall refer to the substituent —C(O)$NH_2$.

As used herein, the term "sulfanyl" shall refer to the substituent —S—.

As used herein, the term "sulfenyl" shall refer to the substituent —S(O)—.

As used herein, the term "sulfonyl" shall refer to the substituent —$S(O)_2$—.

The compounds can be prepared according to the following reaction Schemes (in which variables are as defined before or are defined) using readily available starting materials, reagents and conventional synthesis procedures. In these reactions, it is also possible to make use of variants which are themselves known to those of ordinary skill in this art, but are not mentioned in greater detail.

The present invention also provides a method for the synthesis of compounds useful as intermediates in the preparation of compounds of Formula (I) along with methods for the preparation of compounds of Formula (I).

The general procedures used in the methods to prepare the compounds of Formula (I) of the present invention are described below where the definitions of the variable groups are the same as those described for the compound of Formula (I).

As shown in Scheme I, diamino methyl benzoate (1) is treated with a carboxylic acid in the presence of a coupling reagent such as, but not limited to, HBTU to form amide (2). Amide (2) is then refluxed in a solvent such as, but not limited to, AcOH to form benzimidazole (3). The methyl ester of benzimidazole (3) is hydrolyzed using a base such as, but not limited to, LiOH to provide the free carboxylic acid, which is then coupled with an amine in the presence of a coupling reagent such as, but not limited to, HBTU to form amide (4).

Scheme I

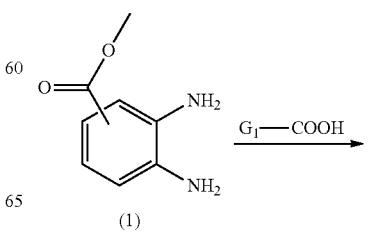

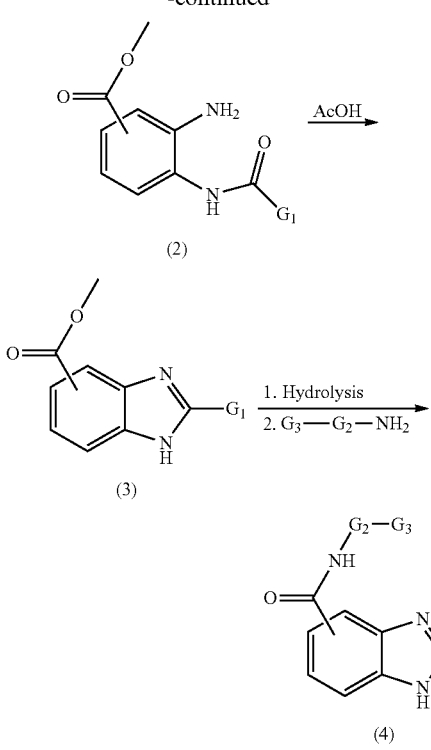

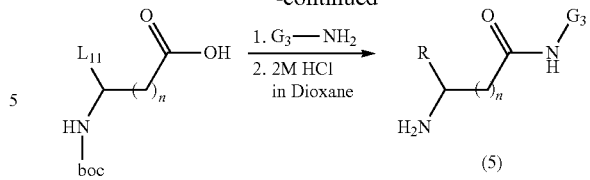

As shown in Scheme III, diamino methyl benzoate (1) is reacted with isothiocyanate (7) by refluxing in a solvent such as, but not limited to, THF to provide intermediate (8). Isothiocyanate (7) is either commercially available or is prepared from a corresponding amine by reacting with 1,1'-thiocarbonyldiimidazole in a solvent such as, but not limited to, THF. The intermediate (8) is treated with coupling reagent such as, but not limited to, DCC to form benzimidazole (9). The methyl ester of benzimidazole (9) is hydrolyzed using a base such as, but not limited to, LiOH to provide the free carboxylic acid, which is then coupled with an amine in the presence of a coupling reagent such as, but not limited to, HBTU to form the amide (10).

As shown in Scheme II, the methyl ester of benzimidazole (3) is hydrolyzed using a base such as, but not limited to, LiOH to provide the free carboxylic acid, which is then coupled with compound (5) in the presence of a coupling reagent such as, but not limited to HBTU, to form the amide (6). Compound (5) is prepared by first coupling an amino protected amino acid, such as a BOC protected amino acid, with an amine and then removing the amino protecting group to provide compound (5).

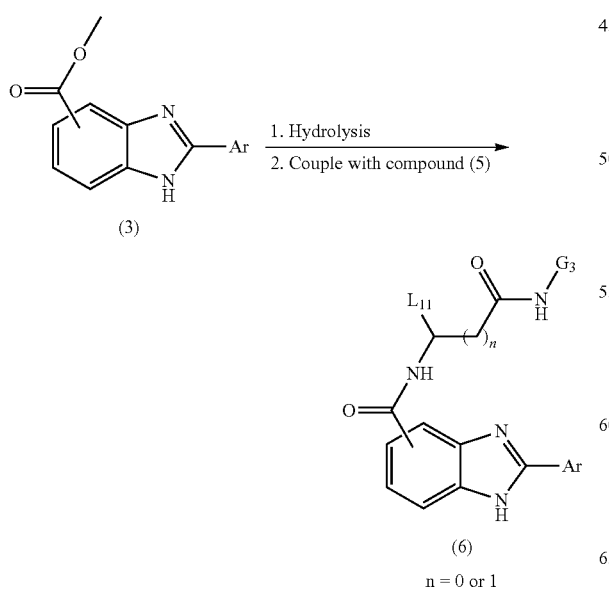

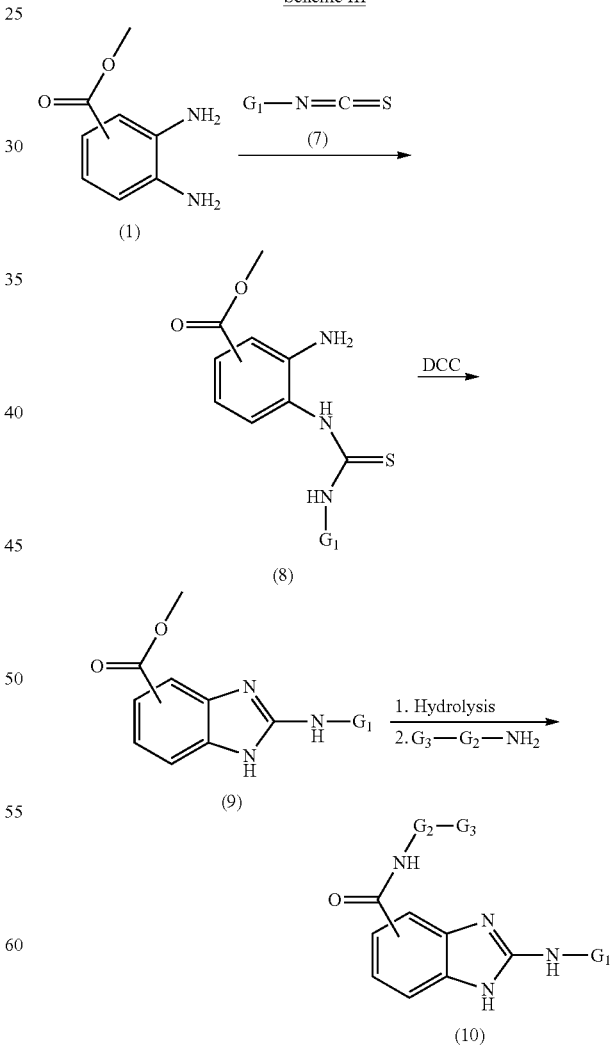

As shown in Scheme IV, diamino methyl benzoate (1) is treated with cyanogen bromide in a mixture of solvents such as, but not limited to, EtOH:H$_2$O to form 2-amino benzimdazole (11). The amine of benzimidazole (11) is coupled with a carboxylic acid in the presence of a coupling reagent such as, but not limited to, HBTU to form the amide (12). The methyl ester of amide (12) is hydrolyzed using a base such as, but not limited to, LiOH to provide the free carboxylic acid, which was then coupled with an amine in the presence of a coupling reagent such as, but not limited to, HBTU to form the amide (13).

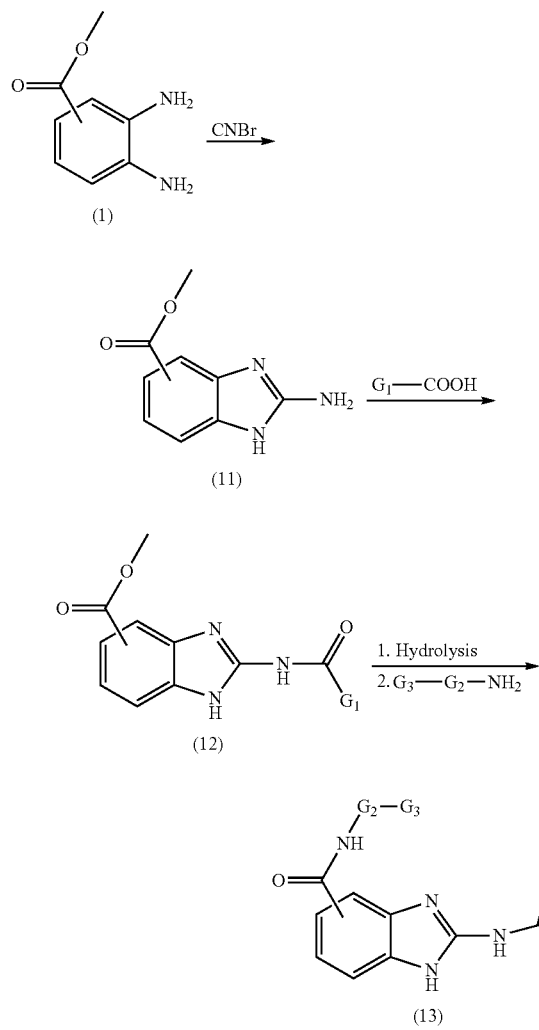

Scheme V shows an alternate general method to prepare amide (13). As shown in Scheme V, nitro-amino benzoic acid (14) is coupled with an amine in the presence of a coupling reagent such as, but not limited to, HBTU to form the amide, which is then reduced under conditions such as, but not limited to, Pd/C under hydrogen atmosphere to provide diamine (15). The resulting diamine (15) is reacted with cyanogen bromide in a mixture of solvents such as, but not limited to, EtOH: H$_2$O to form 2-amino benzimdazole (16). The amino group of benzimidazole (16) is coupled with a carboxylic acid in the presence of a coupling reagent such as, but not limited to, HBTU to provide amide (13).

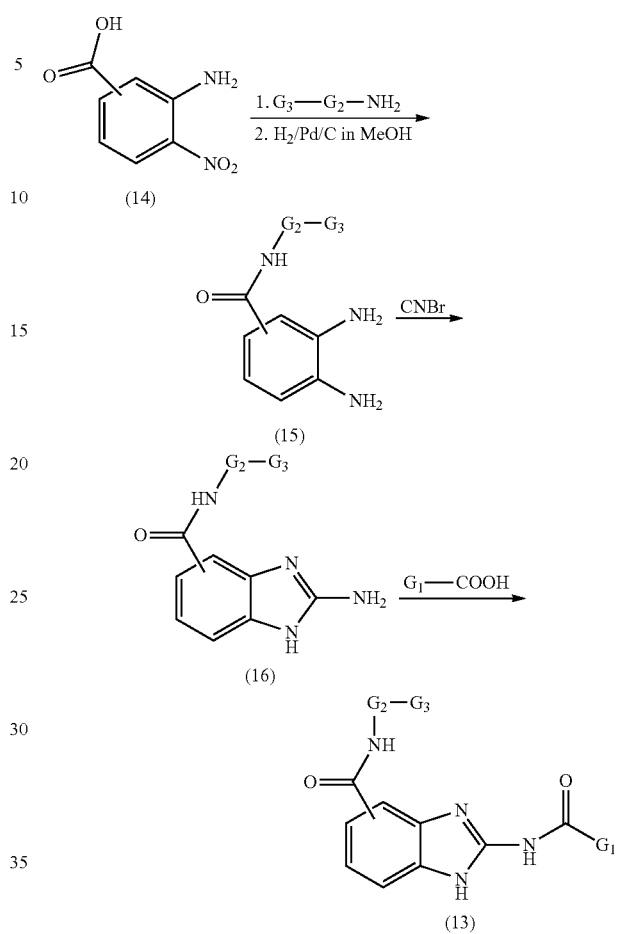

As shown in Scheme VI, compound (11a) is treated with a nitrating reagent such as, but not limited to, KNO$_3$/H$_2$SO$_4$ to provide benzimidazole (17). The amine of benzimidazole (17) is coupled with a carboxylic acid in the presence of a coupling reagent such as, but not limited to, HBTU to form the amide (18). The methyl ester of amide (18) is hydrolyzed using a base such as, but not limited to, LiOH to provide the free carboxylic acid, which is then coupled with an amine in the presence of a coupling reagent such as, but not limited to, HBTU to form the amide (19). The nitro group of amide (19) is reduced under conditions such as, but not limited to, Pd/C under hydrogen atmosphere and the resulting amide is then reacted with an acid chloride in the presence of a base such as, but not limited to, pyridine to provide compound (20).

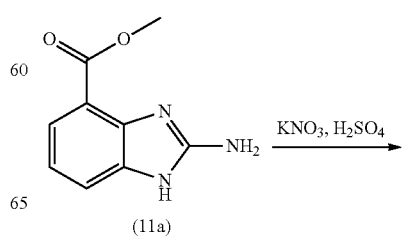

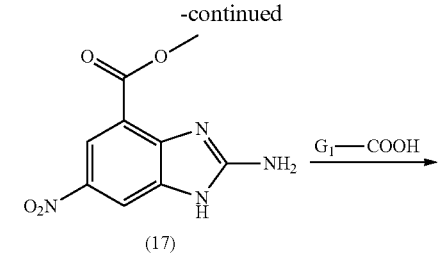

(17)

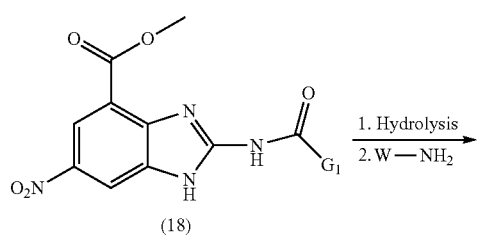

(18)

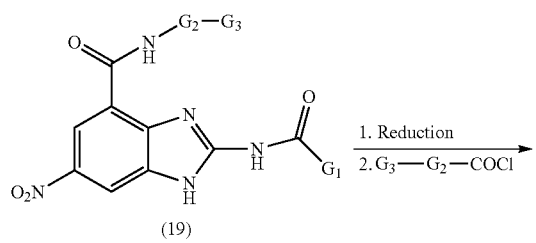

(19)

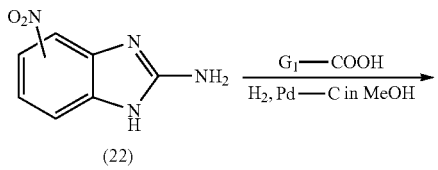

(22)

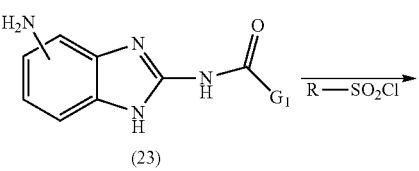

(23)

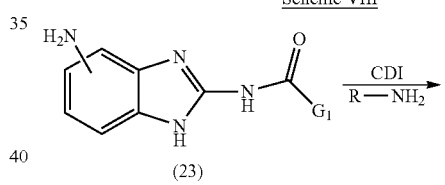

(24)

As shown in Scheme VIII, amine (23) may also be treated with a coupling reagent such as CDI and then reacted with an alkyl or aryl amine to give urea (25). In Scheme VIII, the variable R is a group such as but not limited to aryl, arylalkylene, heteroarylalkylene, or heteroaryl, or their optionally substituted forms.

Scheme VIII (23)

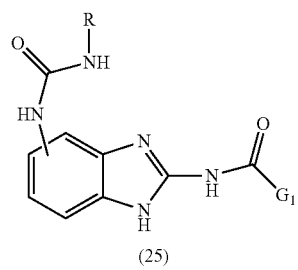

(25)

As shown in Scheme VII, compound (21) is reacted with cyanogen bromide in a mixture of solvents such as, but not limited to, EtOH—H$_2$O to form 2-amino benzimidazole (22). The amino group of benzimidazole (22) is coupled with a carboxylic acid in the presence of a coupling reagent such as, but not limited to, HBTU to form an amide, and the nitro group is then reduced under conditions such as, but not limited to, Pd/C under hydrogen atmosphere to provide amine (23). The amine (23) is then reacted with a sulfonyl chloride in the presence of a base such as, but not limited to, pyridine to provide compound (24). In Scheme VII, the variable R is a group such as but not limited to aryl, arylalkylene, heteroarylalkylene, or heteroaryl, or their optionally substituted forms.

Scheme VII

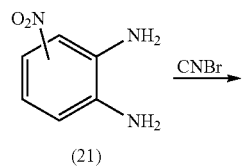

(21)

As shown in Scheme IX, compound (26) is reacted with bromine in solvent such as, but not limited to, AcOH to provide aryl bromide (27). The aryl bromide (27) is then coupled to a boronic acid in the presence of palladium reagent such as, but not limited to, palladium tetrakistriphenylphosphine to form aryl compound (28) that is then subjected to the sequence of reactions as shown in Scheme V to provide benzimidazole (29). The aryl bromide (27) may also be coupled with aryl and alkenyl tin reagents to provide aryl compounds that are then subjected to the sequence of reactions as shown in Scheme V to provide benzimidazole (29). In Scheme IX, the variable R is a group such as but not limited to aryl, heteroaryl, arylalkenylene, alkenyl, heteroarylalkenylene, or their optionally substituted forms.

Scheme IX

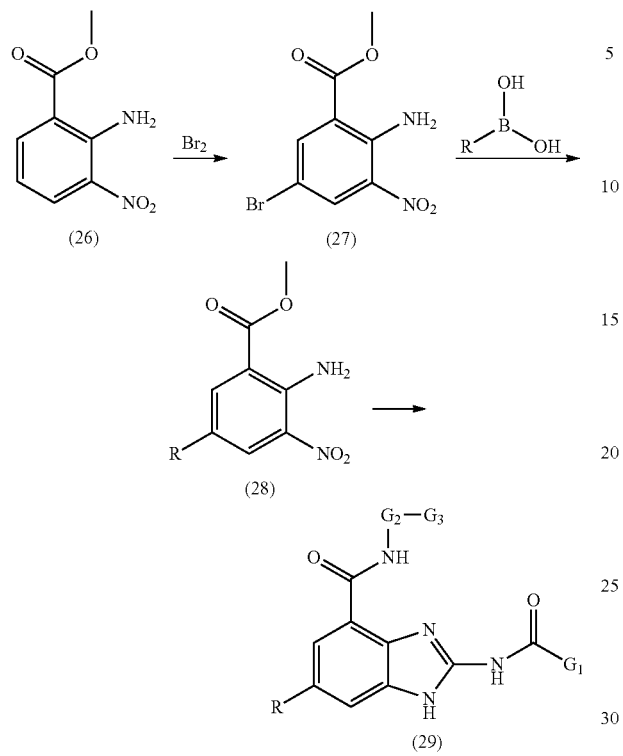

As shown in Scheme X, compound (30) is treated with a nitrating reagent such as, but not limited to, HNO₃/H₂SO₄ to provide nitro compound (31). The nitro compound (31) is treated with ammonium carbonate in a solvent such as DMF to provide an amino nitro compound (32), which is then treated with a sodium alkoxide or sodium aryloxide to provide aryl ether (33). The aryl ether (33) is then subjected to a sequence of reactions as shown in Scheme V to provide benzimidazole (34). In Scheme X, the variable R is a group such as but not limited to aryl, heteroaryl, arylalkylene, alkyl, heteroarylalkylene, or their optionally substituted forms.

As shown in Scheme XI, compound (32) is reacted with a sodium thiolate in the presence or absence of a base such as triethylamine to provide compound (35) which is then subjected to a sequence of reactions as shown in Scheme V to provide the benzimidazole (36). Benzimidazole (36) may then be treated with an oxidizing agent such as a peroxide including, but not limited to, MCPBA to provide sulfone (37). In Scheme XI, the variable R is a group such as but not limited to aryl, heteroaryl, arylalkylene, alkyl, heteroarylalkylene, or their optionally substituted forms.

Scheme X

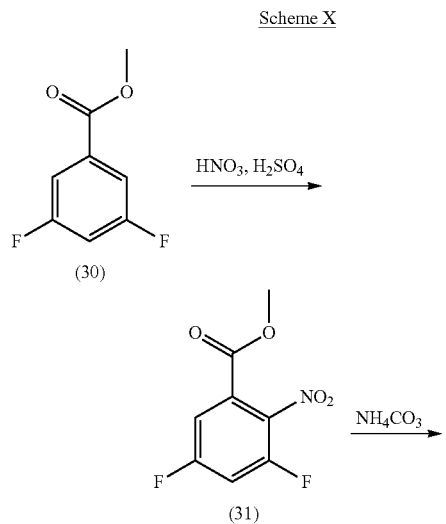

Scheme XI

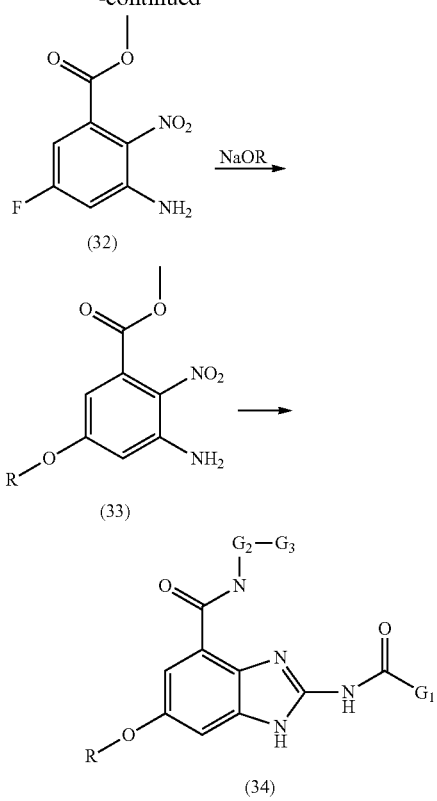

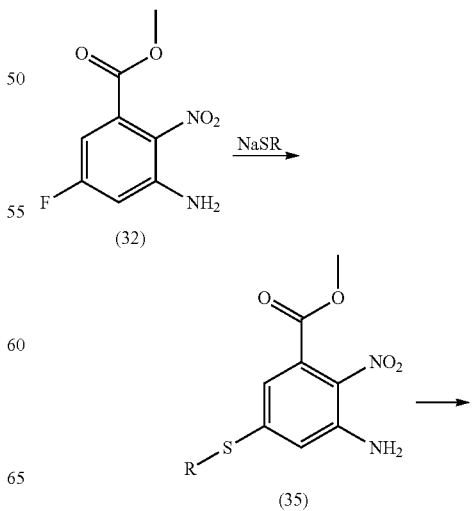

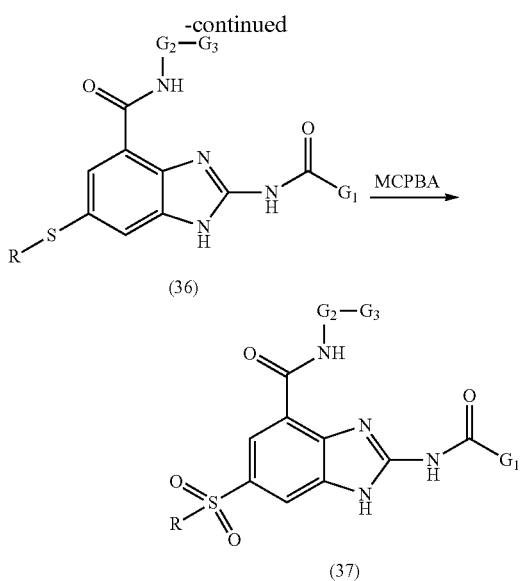

(36)

(37)

As shown in Scheme XII, acid inputs used in above schemes may be prepared from bromo carboxylic acids (38) by reacting with an alkenyl or alkyl boronic acid in the presence of a palladium reagent such as, but not limited to, palladium tetrakistriphenylphosphine to form aryl compound (39). In Scheme XII, the variable R is a group such as but not limited to aryl, heteroaryl, arylalkenylene, alkenyl, heteroarylalkenylene, or their optionally substituted forms. The variable X in Scheme XII may be a group such as but not limited to N or CH, or their optionally substituted forms.

Scheme XII

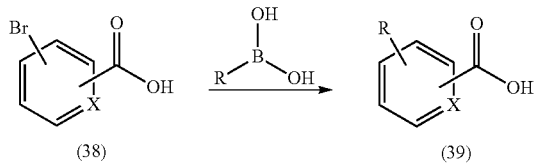

(38)    (39)

As shown in Scheme XIII, acid inputs used in the above schemes may also be prepared from the bromo acid (40), where X is a group such as but not limited to CH or N, by reacting with an acetylene in the presence of a palladium reagent such as, but not limited to, dichlorobis(triphenylphosphine)-palladium (II) to afford acetylene (41). In Scheme XIII, the variable R is a group such as but not limited to aryl, heteroaryl, alkyl, cycloalkyl, or their optionally substituted forms.

Scheme XIII

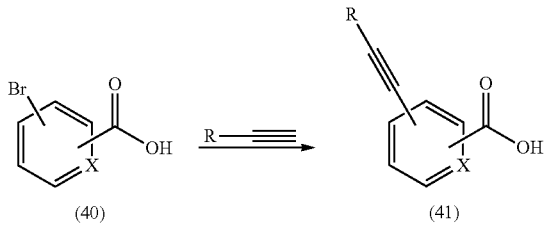

(40)    (41)

The term "amino-protecting group" as used herein refers to substituents of the amino group commonly employed to block or protect the amino functionality while reacting other functional groups on the compound. Examples of such amino-protecting groups include the formyl group, the trityl group, the phthalimido group, the trichloroacetyl group, the chloroacetyl, bromoacetyl and iodoacetyl groups, urethane-type blocking groups such as benzyloxycarbonyl, 4-phenyl-benzyloxycarbonyl, 2-methylbenzyloxycarbollyl, 4-methoxybenzyloxycarbonyl, 4-fluorobenzyloxycarbonyl, 4-chlorobenzyloxycarbonyl, 3-chlorobenzyloxycarbonyl, 2-chlorobenzyloxycarbonyl, 2,4-dichlorobenzyloxycarbonyl, 4-bromobenzyloxycarbonyl, 3-bromobenzyloxycarbonyl, 4-nitrobenzyloxycarbonyl, 4-cyanobenzyloxy-carbonyl, 2-(4-xenyl)iso-propoxycarbonyl, 1,1-diphenyleth-1-yloxy-carbonyl, 1,1-diphenylprop-1-yloxycarbonyl, 2-phenylprop-2-yloxycarbonyl, 2-(p-toluoyl)prop-2-yloxycarbonyl, cyclopentanyloxycarbonyl, 1-methylcyclopentanyloxycarbonyl, cyclohexanyloxycarbonyl, 1-methylcyclohexanyloxycarbonyl, 2-methylcyclohexanyloxycarbonyl, 2-(4-toluoylsulfonyl)ethoxycarbonyl, 2(methylsulfonyl)ethoxycarbonyl, 2-(triphenylphosphino)ethoxycarbonyl, 9-fluorenyl-methoxycarbonyl ("FMOC"), t-butoxycarbonyl ("BOC"), 2-(trimethylsilyl)ethoxycarbonyl, alkyloxycarbonyl, 1-(trimethylsilylmethyl)prop-1-enyloxycarbonyl, 5-benzisoxalyl-methoxycarbonyl, 4-acetoxybenzyloxycarbonyl, 2,2,2-trichloroethoxycarbonyl, 2-ethynyl-2-propoxycarbonyl, cyclopropylmethoxycarbonyl, 4-(decyloxy)benzyloxycarbonyl, isobornyloxycarbonyl, 1-piperidyloxycarbonyl and the like; the benzoylmethylsulfonyl group, the 2-(nitro)phenylsulfenyl group, the diphenylphosphine oxide group and like amino-protecting groups. The species of amino-protecting group employed is not critical so long as the derivatized amino group is stable to the condition of subsequent reaction(s) on other positions of the compound of Formula (I) and can be removed at the desired point without disrupting the remainder of the molecule. Commonly used amino-protecting groups are the alkyloxycarbonyl, the t-butoxycarbonyl, 9-fluorenylmethoxycarbonyl, and the trityl groups. Similar amino-protecting groups used in the cephalosporin, penicillin and peptide art are also embraced by the above terms. The related term "protected amino" or "protected amino group" defines an amino group substituted with an amino-protecting group discussed above.

Further examples of progroups referred to by the above terms are described by J. W. Barton, "Protective Groups In Organic Chemistry", J. G. W. McOmie, Ed., Plenum Press, New York, N.Y., 1973, and T. W. Greene, "Protective Groups in Organic Synthesis", John Wiley and Sons, New York, N.Y., 1981.

The invention further provides pharmaceutical compositions comprising a compound of Formula (I) or a pharmaceutically acceptable salt, ester, or prodrug thereof. The term "pharmaceutical composition" is used herein to denote a composition that may be administered to a mammalian host, e.g., orally, topically, parenterally, by inhalation spray, or rectally, in unit dosage formulations containing conventional non-toxic carriers, diluents, adjuvants, vehicles and the like. The term "parenteral" as used herein, includes subcutaneous injections, intravenous, intramuscular, intracisternal injection, or by infusion techniques.

The term "therapeutically effective amount" is used herein to denote that amount of a drug or pharmaceutical agent that will elicit the therapeutic response of a subject that is being sought. In an embodiment, a therapeutically effective amount is an amount capable of inhibiting the interaction of BACE with its physiological ligands such as, but not limited to, amyloid precursor protein (APP).

As used herein, the phrase "a subject" or "a subject in need thereof" includes mammalian subjects, such as humans, but may also encompass other mammals, such as dogs, cats, mice, rats, cattle, horses, sheep, rabbits, monkeys, chimpanzees or other apes or primates, who either suffer from one or more of the aforesaid diseases or disease states or are at risk for such. In an embodiment, a subject is one for which inhibition of β-secretase enzyme activity or treatment of the above noted disorders is desired. Accordingly, in the context of the therapeutic methods of this invention, this method also is comprised of a method for treating a mammalian subject prophylactically, or prior to the onset of diagnosis such disease(s) or disease state(s). Factors which may influence what constitutes an effective amount will depend upon the size and weight of the subject, the biodegradability of the therapeutic agent, the activity of the therapeutic agent, as well as its bioavailability.

The pharmaceutical compositions containing a compound of the invention may be in a form suitable for oral use, for example, as tablets, troches, lozenges, aqueous, or oily suspensions, dispersible powders or granules, emulsions, hard or soft capsules, or syrups or elixirs. Compositions intended for oral use may be prepared according to any known method, and such compositions may contain one or more agents selected from the group consisting of sweetening agents, flavoring agents, coloring agents, and preserving agents in order to provide pharmaceutically elegant and palatable preparations. Tablets may contain the active ingredient in admixture with non-toxic pharmaceutically-acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques to form osmotic therapeutic tablets for controlled release.

Formulations for oral use may also be presented as hard gelatin capsules where the active ingredient is mixed with an inert solid diluent, for example, calcium carbonate, calcium phosphate or kaolin, or a soft gelatin capsules wherein the active ingredient is mixed with water or an oil medium, for example peanut oil, liquid paraffin, or olive oil.

Aqueous suspensions may contain the active compounds in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents may be a naturally-occurring phosphatide such as lecithin, or condensation products of an alkylene oxide with fatty acids, for example polyoxyethylene stearate, or condensation products of ethylene oxide with long chain aliphatic alcohols, for example, heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as a liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above. Additional excipients, for example, sweetening, flavoring, and coloring agents may also be present.

The pharmaceutical compositions of the invention may also be in the form of oil-in-water emulsions. The oily phase may be a vegetable oil, for example, olive oil or arachis oil, or a mineral oil, for example a liquid paraffin, or a mixture thereof. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleaginous suspension. This suspension may be formulated according to the known methods using suitable dispersing or wetting agents and suspending agents described above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution, and isotonic sodium chloride solution. In addition, sterile, fixed oils are conveniently employed as solvent or suspending medium. For this purpose, any bland fixed oil may be employed using synthetic mono- or diglycerides. In addition, fatty acids such as oleic acid find use in the preparation of injectables.

The compositions may also be in the form of suppositories for rectal administration of the compounds of the invention. These compositions can be prepared by mixing the drug with a suitable non-irritating excipient which is solid at ordinary temperatures but liquid at the rectal temperature and will thus melt in the rectum to release the drug. Such materials include cocoa butter and polyethylene glycols, for example.

For topical use, creams, ointments, jellies, solutions of suspensions, etc., containing the compounds of the invention are contemplated. For the purpose of this application, topical applications shall include mouth washes and gargles.

The compounds of the present invention may also be administered in the form of liposome delivery systems, such as small unilamellar vesicles, large unilamellar vesicles, and multilamellar vesicles. Liposomes may be formed from a variety of phospholipids, such as cholesterol, stearylamine, or phosphatidylcholines.

Also provided by the present invention are prodrugs of the invention.

Pharmaceutically-acceptable salts of the compounds of the present invention, where a basic or acidic group is present in the structure, are also included within the scope of the invention. The term "pharmaceutically acceptable salts" refers to non-toxic salts of the compounds of this invention which are generally prepared by reacting the free base with a suitable organic or inorganic acid or by reacting the acid with a suitable organic or inorganic base. Representative salts include the following salts: Acetate, Benzenesulfonate, Benzoate, Bicarbonate, Bisulfate, Bitartrate, Borate, Bromide, Calcium Edetate, Camsylate, Carbonate, Chloride, Clavulanate, Citrate, Dihydrochloride, Edetate, Edisylate, Estolate, Esylate, Fumarate, Gluceptate, Gluconate, Glutamate, Glycollylarsanilate, Hexylresorcinate, Hydrabamine, Hydrobromide, Hydrochloride, Hydroxynaphthoate, Iodide, Isothionate, Lactate, Lactobionate, Laurate, Malate, Maleate, Mandelate, Methanesulfonate, Methylbromide, Methylnitrate, Methylsulfate, Monopotassium Maleate, Mucate, Napsylate, Nitrate, N-methylglucamine, Oxalate, Pamoate (Embonate), Palmitate, Pantothenate, Phosphate/diphosphate, Polygalacturonate, Potassium, Salicylate, Sodium, Stearate, Subacetate, Succinate, Tannate, Tartrate, Teoclate, Tosylate, Triethiodide, Trimethylammonium and Valerate. When an acidic substituent is present, such as —COOH, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxlate, maleate, pyruvate, malonate, succinate, citrate, tartrate, fumarate, mandelate, benzoate, cinnamate, methanesulfonate, ethanesulfonate, picrate and the like, and include acids related to the pharmaceutically-acceptable salts listed in the Journal of Pharmaceutical Science, 66, 2 (1977) p. 1-19.

In one embodiment, a compound of Formula (I) having one or more basic groups may be used and/or formulated as an HCl salt Other salts which are not pharmaceutically acceptable may be useful in the preparation of compounds of the invention and these form a further aspect of the invention.

In addition, some of the compounds of Formula (I) may form solvates with water or common organic solvents. Such solvates are also encompassed within the scope of the invention.

Thus, in another aspect of the present invention, there is provided a pharmaceutical composition comprising a therapeutically effective amount of a compound of Formula (I), or a pharmaceutically acceptable salt, solvate, or prodrug thereof, and a pharmaceutically acceptable carrier, excipient, diluent, or mixture thereof.

In another aspect of the present invention, there is provided a pharmaceutical composition comprising a therapeutically effective amount of a compound of Formula (I), or a pharmaceutically acceptable salt, solvate, or prodrug thereof, and a pharmaceutically acceptable carrier, excipient, diluents, or mixture thereof wherein said therapeutically effective amount of the compound of Formula (I) preferentially inhibits the interaction of BACE with its physiological ligands relative to the interaction of other secretases, such as α-secretase, with its physiological ligands.

In another aspect, the present invention provides a pharmaceutical composition comprising a therapeutically effective amount of the compound of Formula (I), and a pharmaceutically acceptable carrier, excipient, diluent, or mixture thereof, and further comprising one or more therapeutic agents.

The compounds of Formula (I) may be used in combination with one or more other drugs in the treatment, prevention, control, amelioration, or reduction of risk of diseases or conditions for which the compounds of the present invention have utility. In an embodiment, the combination of the drugs together may be safer or more effective than either drug alone. Additionally, the compounds of Formula (I) may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of Formula (I).

Accordingly, the pharmaceutical compositions of the present invention include those that contain one or more other active ingredients, in addition to the compounds of Formula (I). The combinations may be administered as part of a unit dosage form combination product, or as a kit or treatment protocol wherein one or more additional drugs are administered in separate dosage forms as part of a treatment regimen.

Examples of combinations of the compounds of the present invention with other drugs in either unit dose or kit form include combinations with: anti-Alzheimer's agents, other betasecretase inhibitors, gamma-secretase inhibitors, HMG-CoA reductase inhibitors, non-steroidal anti-inflammatory drugs (NSAID's) including ibuprofen, naproxen, diclofenac, N-methyl-D-aspartate (NMDA) receptor antagonists, such as memantine, cholinesterase inhibitors such as galantamine, rivastigmine, donepezil, and tacrine, vitamin E, CB-1 receptor antagonists or CB-1 receptor inverse agonists, antibiotics such as doxycycline and rifampin, agents that bind Aβ or that induce antibodies that bind Aβ, anti-Aβ antibodies, Aβ vaccines, RAGE/RAGE ligand interaction antagonists, and other drugs that affect receptors or enzymes that either increase the efficacy, safety, convenience, or reduce unwanted side effects or toxicity of the compounds of the present invention.

The foregoing list of combinations is illustrative only and not intended to be limiting in any way.

In another embodiment, the present invention provides a method comprising: administering to a subject a compound of Formula (I), or a pharmaceutically acceptable salt, ester, or prodrug thereof.

In another embodiment, the present invention provides a method for inhibiting the interaction of BACE with its physiological ligands comprising: administering to a subject a compound of Formula (I), or a pharmaceutically acceptable salt, ester, or prodrug thereof. An example of a physiological ligand of BACE includes, but is not limited to, amyloid precursor protein (APP).

In another embodiment, the present invention provides a method for increasing the α-secretory pathway in a subject comprising: administering to a subject a compound of Formula (I), or a pharmaceutically acceptable salt, ester, or prodrug thereof.

In another embodiment, the present invention provides a method of treating or preventing a BACE mediated disease comprising: administering to a subject a therapeutically effective amount of a compound of Formula (I) or a pharmaceutically acceptable salt, ester, or prodrug thereof.

In another embodiment, the present invention provides a method for treating a disorder or condition selected from Alzheimer's disease, mild cognitive impairment, Down's syndrome, Hereditary Cerebral Hemorrhage with Amyloidosis of the Dutch-Type, cerebral amyloid angiopathy, degenerative dementia, diffuse Lewy body type of Alzheimer's disease or central or peripheral amyloid diseases comprising administering to a subject an amount of a compound of Formula (I), or a pharmaceutically acceptable salt, ester, or prodrug thereof, that is effective in treating such disorder or condition.

In another embodiment, the present invention provides a method for treating a disorder or condition method, wherein the disorder or condition being treated is a dementia of the Alzheimer's type and is selected from the group consisting of dementia of the Alzheimer's type with early onset uncomplicated, dementia of the Alzheimer's type with early onset with delusions, dementia of the Alzheimer's type with early onset with depressed mood, dementia of the Alzheimer's type with late onset uncomplicated, dementia of the Alzheimer's type with late onset with delusions and dementia of the Alzheimer's type with late onset with depressed mood, comprising administering to said mammal an amount of a compound of Formula (I), or a pharmaceutically acceptable salt, ester, or prodrug thereof, that is effective in treating such disorder or condition.

In another embodiment, the present invention provides a method for treating one or more conditions associated with plaque accumulation comprising administering to a subject an effective amount of a compound of Formula (I), or a pharmaceutically acceptable salt, ester, or prodrug thereof. In an embodiment, administering the compound of Formula (I) reduces the rate of neurofibrillary tangle formation in a subject. In another embodiment, administering the compound of Formula (I) reduces the rate of plaque accumulation in a subject.

In the methods of the present invention, the compound of Formula (I) may be administered alone or in combination with a therapeutic agent selected from the group consisting of anti-Alzheimer's agents, other betasecretase inhibitors, gamma-secretase inhibitors, HMG-CoA reductase inhibitors, non-steroidal anti-inflammatory drugs (NSAID's) including ibuprofen, naproxen, diclofenac, N-methyl-D-aspartate (NMDA) receptor antagonists, such as memantine, cholinesterase inhibitors such as galantamine, rivastigmine, donepezil, and tacrine, vitamin E, CB-1 receptor antagonists or CB-1 receptor inverse agonists, antibiotics such as doxycycline and rifampin, agents that bind Aβ or that induce antibodies that bind Aβ, anti-Aβ antibodies, Aβ vaccines, RAGE/RAGE ligand interaction antagonists, and other drugs that affect receptors or enzymes that either increase the efficacy, safety, convenience, or reduce unwanted side effects or toxicity of the compounds of the present invention.

The compound of Formula (I) of the present invention, may be administered at a dosage level of from about 0.01 to 1000 mg/kg of the body weight of the subject being treated. In another embodiment, the compound of Formula (I) of the present invention, may be administered at a dosage range between 0.01 and 100 mg/kg. In another embodiment, the compound of Formula (I) of the present invention, may be administered at a dosage range between 0.5 to 10 mg/kg of body weight per day. The amount of active ingredient that may be combined with the carrier materials to produce a single dosage will vary depending upon the host treated and the particular mode of administration. For example, a formulation intended for oral administration to humans may contain 1 mg to 2 grams of a compound of Formula (I) with an appropriate and convenient amount of carrier material which may vary from about 5 to 95 percent of the total composition. Dosage unit forms will generally contain between from about 5 mg to about 500 mg of active ingredient. This dosage may be individualized by the clinician based on the specific clinical condition of the subject being treated. Thus, it will be understood that the specific dosage level for any particular patient may depend upon a variety of factors including the activity of the specific compound employed, the age, body weight, general health, sex, diet, time of administration, route of administration, rate of excretion, drug combination and the severity of the particular disease undergoing therapy.

EXAMPLES

The present invention may be further understood by reference to the following non-limiting examples. Examples of compounds of the present invention and procedures that may be used to prepare and identify useful compounds of the present invention are described below.

Abbreviations used in the Examples are as follows:
AcOH=acetic acid
Boc=tert-butoxycarbonyl
CDI=carbonyl di-imidazole
DCC=N,N-Dicyclohexylcarbodiimide
DCE=1,2-dichloroethane
DCM=dichloromethane
DDQ=2,3-Dichloro-5,6-dicyano-1,4-benzoquinone
DIAD=diisopropyl azodicarboxylate
DIEA=diisopropylethylamine
DME=dimethoxyethane
DMF=N,N-dimethylformamide
DMSO=dimethyl sulfoxide
EDCI=1-ethyl-3-(3-dimethylaminopropyl)-carbodiimide hydrochloride
EDTA=ethylenediaminetetracetic acid
$Et_2O$=diethyl ether
EtOAc=ethyl acetate
h=hour
HBTU=O-benzotriazol-1-yl-N,N,N',N'-tetramethyluronium hexafluorophosphate
m-CPBA=meta-chloroperbenzoic acid
NMP=N-methylpyrrolidine
r.t.=room temperature
TEA=triethyl amine
THF=tetrahydrofuran LC-MS data was obtained using gradient elution on a parallel MUX™ system, running four Waters 1525 binary HPLC pumps, equipped with a Mux-UV 2488 multichannel UV-Vis detector (recording at 215 and 254 nM) and a Leap Technologies HTS PAL Auto sampler using a Waters Xterra MS C18 4.6×50 mm column. A three minute gradient was run from 25% B (97.5% acetonitrile, 2.5% water, 0.05% TFA) and 75% A (97.5% water, 2.5% acetonitrile, 0.05% TFA) to 100% B. The system is interfaced with a Waters Micromass ZQ mass spectrometer using electrospray ionization. All MS data was obtained in the positive mode unless otherwise noted. 1H NMR data was obtained on a Varian 400 MHz spectrometer.

General Procedure A: Amide Formation

To a solution of carboxylic acid (1.0 mmol) in dry DMF (2.5 mL) was added HBTU (1.2 mmol) in one portion, the reaction mixture was stirred at room temperature for 10 min, and then an amine (1.0 mmol) and DIEA (0.8 mL) were added subsequently. The resulting reaction mixture was stirred at room temperature for 12 h or in some cases at 70° C. for 1-3 h. The reaction mixture was diluted with water (50 mL) and the product was precipitated. The product was either isolated after filtration, subsequent washings with water and ethyl acetate or silica gel column chromatography.

General Procedure B: Hydrolysis of Methyl Benzoate

To a suspension of a methyl ester (1.0 mmol) in methanol (5 mL) was added lithium hydroxide monohydrate (5.0 mmol), water (5 mL) and THF (5 mL). The reaction mixture was refluxed for 2 h. After cooling to room temperature, the reaction mixture was neutralized with AcOH (3 mL). After removal of the organic solvent under vacuum, the crude product was suspended in water (50 mL), and collected by filtration. The solid was further washed with water and dried under high vacuum to afford corresponding acid.

General Procedure C: Reduction of Nitro to Amine:

10.0 mmol of the nitro compound was dissolved in a mixture of 20 mL of $CH_3OH$ and 5 mL of acetic acid. To this stirring solution 100 mg of 10% Pd on carbon was added, and the resulting mixture was hydrogenated at 42 psi of $H_2$ at room temperature for 3.0 h. The reaction mixture was filtered, and the solid was washed with portions of methanol. The filtrate and washings were combined and evaporated to give the corresponding amine. This product was directly used in subsequent reactions without further purification.

Example 1

The 2,3-diamino-benzoic acid methyl ester was synthesized from 2-amino-3-nitro-benzoic acid methyl ester (2.0 g, 10.2 mmol) as described in general procedure C. 1.7 g (10.2 mmol) of the above synthesized diamine was reacted with 1.7 g (10.0 mmol) of isoquinoline-3-carboxylic acid and 4.6 g (12.0 mmol) of HBTU as described in general procedure A to provide 2-amino-3-[(isoquinoline-3-carbonyl)-amino]-benzoic acid methyl ester. LCMS: 322 $(M+1)^+$.

To a solution of the above crude product 2-amino-3-[(isoquinoline-3-carbonyl)-amino]-benzoic acid methyl ester in AcOH (25 mL) was added $AcONH_4$ (16 g). The reaction mixture was refluxed for 3 h. After removal of AcOH under vacuum, the reaction mixture was washed with water (150 mL) The crude solid product 2-isoquinolin-3-yl-1H-benzoimidazole-4-carboxylic acid methyl ester was collected after filtration. LCMS: 304 $(M+1)^+$. This product was hydrolyzed according to the general procedure C to provide 2-isoquinolin-3-yl-1H-benzoimidazole-4-carboxylic acid (1.6 g, 55% yield over three steps). LCMS: 290 $(M+1)^+$.

To a solution of 2.0 g (10 mmol) of 2-bromoacetophenone in DMF (30 mL) was added 3.0 g (29 mmol) 1-acetylguanidine in one portion, the reaction mixture was stirred at rt for 2 days. The reaction mixture was diluted with EtOAc (250 mL) and washed with saturated $NH_4Cl$ aq. solution (50 mL). The organic phase was dried over $MgSO_4$ and concentrated under vacuum. The residue was purified by a flash column chromatography eluting with EtOAc to give N-(4-phenyl-1H-imidazol-2-yl)-acetamide. (0.5 g, 24%). LCMS: 203 $(M+1)^+$.

To a solution of the above 0.5 g (2.4 mmol) N-(4-phenyl-1H-imidazol-2-yl)-acetamide in MeOH (20 mL) was added water (20 mL) and conc. $H_2SO_4$ (1 mL). The mixture was refluxed under nitrogen for 2 days. After cooling to rt, the organic solvent was removed under vacuum. The reaction mixture was neutralized with saturated sodium bicarbonate aq. solution (50 mL) and extracted with ethyl acetate (150 mL). The organic layer was dried and condensed. The residue was purified by a flash column chromatography eluting with EtOAc then EtOAc/MeOH=7:1 to give 4-phenyl-1H-imidazol-2-ylamine (160 mg, 41%). LCMS: 160 $(M+1)^+$.

120 mg (0.4 mmol) of 2-isoquinolin-3-yl-1H-benzoimidazole-4-carboxylic acid was reacted with 400 mg (1.1 mmol) of HBTU and 160 mg (1.0 mmol) of 4-phenyl-1H-imidazol-2-ylamine (160 mg, 1 mmol) according to the general procedure A. The residue was purified by flash column chromatography (EtOAc) to provide 2-isoquinolin-3-yl-1H-benzoimidazole-4-carboxylic acid (4-phenyl-1H-imidazol-2-yl)-amide (30 mg, 17.5%). LCMS: 431 $(M+1)^+$.

Analogous procedures to those used to prepare the compound of Example 1 were used to prepare the compounds of Examples 2-7.

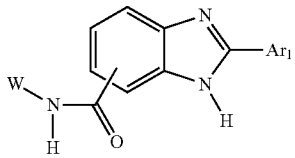

| Ex. | Amide position | W | $Ar_1$ | LCMS $(M+1)^+$ |
|---|---|---|---|---|
| 2 | 5 | isobutyl | 2-isoquinolin-3-yl | 355 |
| 3 | 5 | 1H-benzimidazol-2-yl | pyridin-2yl | 355 |
| 4 | 5 | 1H benzimidazol-2-yl | 2-naphthalen-2yl | 404 |
| 5 | 4 | isobutyl | 2-isoquinolin-3-yl | 345 |
| 6 | 4 | phenyl | 2-isoquinolin-3-yl | 365 |
| 7 | 4 | n-butyl | 2-isoquinolin-3-yl | 345 |

Example 8

1.6 g of 2-isoquinolin-3-yl-1H-benzoimidazole-5-carboxylic acid was made from 1.7 g of (10 mmol) methyl 3,4-diamino benzoate as described in Example 1 for the synthesis of 2-isoquinolin-3-yl-1H-benzoimidazole-4-carboxylic acid.

203 mg (1.0 mmol) of 3-tert-butoxycarbonylamino-3-cyclopropyl-propionic acid (0.23 g, 1 mmol) was reacted with 380 mg (1.0 mmol) of HBTU and 130 mg (1.0 mmol) of 2-aminoimidazole sulfate as described in general procedure A. The desired amide product was isolated by column chromatography (EtOAc/silica) and carried on directly to the next step. The BOC compound in DCM (3 mL) was treated with 4.0 M HCl/dioxane (15 mL) for approximately 1 h. The solid 3-Amino-3-cyclopropyl-N-(1H-imidazol-2-yl)-propionamide (180 mg, 100%) was collected by filtration and used directly in the next step 289 mg (1 mmol) of 2-isoquinolin-3-yl-1H-benzoimidazole-5-carboxylic acid (289 mg, 1 mmol) was reacted with 380 mg (1 mmol) of HBTU and 3-amino-3-cyclopropyl-N-(1H-imidazol-2-yl)-propionamide (230 mg, 1 mmol) as described in general procedure A. A solid precipitated from the solution and was collected by filtration, washed with $1H_2O$ and $Et_2O$, to give 2-isoquinolin-3-yl-1H-benzoimidazole-5-carboxylic acid [1-cyclopropyl-2-(1H-imidazol-2-ylcarbamoyl)-ethyl]-amide (20 mg, 4%). LCMS: 466 $(M+1)^+$. $^1H$ NMR (DMSO-$d_6$, 400 MHz): δ 9.20 (s, 1H), 8.56 (s, 1H), 8.09-7.34 (m, 9H), 6.39 (s, 2H), 3.71 (t, 1H), 2.44 (m, 2H), 0.81 (m, 1H), 0.10 (m, 4H) ppm.

Example 9

229 mg (1.0 mmol) of 1-tert-butoxycarbonylamino-cyclopentanecarboxylic acid (0.23 g, 1 mmol) was reacted with 420 mg (1.2 mmol) of HBTU and 200 mg (1.5 mmol) of 2-aminoimidazole sulfate as described in general procedure A. The BOC compound in DCM (3 mL) was treated with 4.0 M HCl/dioxane (15 mL) for approximately 1 h. The solid 1-Amino-cyclopentanecarboxylic acid (1H-imidazol-2-yl)-amide HCl salt (230 mg, 100%) was collected by filtration and used directly in the next step.

145 mg (0.5 mmol) of 2-isoquinolin-3-yl-1H-benzoimidazole-5-carboxylic acid (Synthesized in Example 1, step 3) was reacted with 280 mg (0.75 mmol) of HBTU and 1-amino-cyclopentanecarboxylic acid (1H-imidazol-2-yl)-amide HCl salt (120 mg, 0.5 mmol) as described in general procedure A. A solid precipitated from the solution and was collected by filtration, washed with $H_2O$ and EtOAc, to give 2-isoquinolin-3-yl-1H-benzoimidazole-5-carboxylic acid [1-(1H-imidazol-2-ylcarbamoyl)-cyclopentyl]-amide (24 mg, 10%). LCMS: 466 (M+1)⁺.

Analogous procedures to those used to prepare the compound of Example 9 were used to prepare the compounds of Examples 10-36.

Example 38

Hydrolysis of 100 mg (0.2 mmol) of (3-(3,5-difluoro-phenyl)-2-[(2-isoquinolin-3-yl-1H-benzoimidazole-4-carbonyl)-amino]-propionic acid methyl ester as described in general procedure B gave 3-(3,5-difluoro-phenyl)-2-[(2-

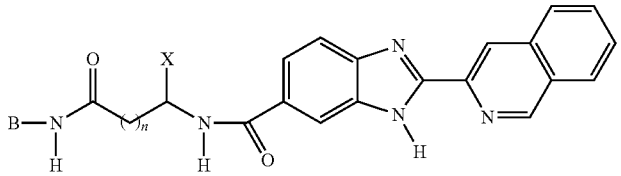

| Ex. | X | Stereo chemistry | B | n | LCMS (M + 1)⁺ |
|---|---|---|---|---|---|
| 10 | 2-fluoro benzyl | S | 1H-imidazol-2-yl | 0 | 520 |
| 11 | Benzyl | S | 1H-imidazol-2-yl | 0 | 502 |
| 12 | 2-chloro-benzyl | S | 1H-imidazol-2-yl | 0 | 536 |
| 13 | 2-fluorophenyl | racemic | 1H-imidazol-2-yl | 1 | 520 |
| 14 | Biphenyl | racemic | 1H-imidazol-2-yl | 1 | 578 |
| 15 | 3,5-difluoro-benzyl | S | 1H-imidazol-2-yl | 0 | 538 |
| 16 | 2-phenyl-ethyl | R | 1H-imidazol-2-yl | 1 | 530 |
| 17 | 4-phenyl-benzyl | racemic | 1H-imidazol-2-yl | 1 | 592 |
| 18 | 3-fluorobenzyl | S | 1H-imidazol-2-yl | 0 | 520 |
| 19 | 4-methoxyphenyl | racemic | 1H-imidazol-2-yl | 1 | 532 |
| 20 | Phenyl | racemic | 1H-imidazol-2-yl | 1 | 502 |
| 21 | 4-chlorobenzyl | S | 1H-imidazol-2-yl | 0 | 536 |
| 22 | 4-methylbenzyl | S | 1H-imidazol-2-yl | 0 | 516 |
| 23 | Benzyl | S | Thiazol-2yl | 0 | 519 |
| 24 | Benzyl | S | Pyridin-2yl | 0 | 513 |
| 25 | 3,4,5-trifluorobenzyl | S | 1H-imidazol-2-yl | 0 | 556 |
| 26 | 3-methoxyphenyl | racemic | 1H-imidazol-2-yl | 1 | 532 |
| 27 | 3-trifluoromethylbenzyl | S | 1H-imidazol-2-yl | 0 | 570 |
| 28 | 2,2 dimethylpropyl | S | 1H-imidazol-2-yl | 0 | 482 |
| 29 | Benzyl | S | 1H-benzimidazol-2-yl | 0 | 552 |
| 30 | 4-fluorobenzyl | S | 1H-imidazol-2-yl | 0 | 520 |
| 31 | 4-phenyl-benzyl | racemic | 1H-imidazol-2-yl | 0 | 578 |
| 32 | Isobutyl | S | 1H-imidazol-2-yl | 0 | 468 |
| 33 | 3-fluorophenyl | racemic | 1H-imidazol-2-yl | 1 | 520 |
| 34 | Butyl-2-yl | S | 1H-imidazol-2-yl | 0 | 468 |
| 35 | Isopropyl | S | 1H-imidazol-2-yl | 0 | 454 |
| 36 | 3-chlorobenzyl | S | 1H-imidazol-2-yl | 0 | 536 |

Example 37

1.05 g (5.0 mmol) of 2-amino-3-(3,5-difluoro-phenyl)-propionic acid (1.05 g, 5 mmol) was dissolved in 30.0 mL of MeOH, then 1.0 mL of thionyl chloride was added dropwise. The mixture was refluxed overnight. Evaporation of the solvent yielded the solid 2-Amino-3-(3,5-difluoro-phenyl)-propionic acid methyl ester HCl salt (1.26 g, 100%), and it was used directly in the next step.

145 mg (0.5 mmol) of 2-isoquinolin-3-yl-1H-benzoimidazole-4-carboxylic acid (synthesized in Example 1, Step 3)) was reacted with 280 mg (0.75 mmol) of HBTU and 2-amino-3-(3,5-difluoro-phenyl)-propionic acid methyl ester HCl salt (126 mg, 0.5 mmol) as described in general procedure A. After cooling to room temperature, the reaction mixture was diluted with ethyl acetate (30 mL). The organic phase was washed with 1% NaOH aq. solution, then dried over Na₂SO₄ and concentrated under vacuum. The residue was purified by flash column chromatography (DCM/EtOAc=1:1 then DCM/EtOAc/MeOH=15:15:1) to give 3-(3,5-difluoro-phenyl)-2-[(2-isoquinolin-3-yl-1H-benzoimidazole-4-carbonyl)-amino]-propionic acid methyl ester (120 mg, 50%). LCMS: 487 (M+1)⁺.

isoquinolin-3-yl-1H-benzoimidazole-4-carbonyl)-amino]-propionic acid (97 mg, 100%). LCMS: 473 (M+1)⁺.

Example 39

602 mg (2.0 mmol) of 2-tert-butoxycarbonylamino-3-(3,5-difluoro-phenyl)-propionic acid (0.60 g, 2 mmol) was reacted with 1140 mg (3.0 mmol) of HBTU and 400 mg (3.0 mmol) of 2-aminoimidazole sulfate as described in general procedure A. The BOC compound in DCM (3 mL) was treated with 4.0 M HCl/dioxane (15 mL) for approximately 1 h. The solid 2-Amino-3-(3,5-difluoro-phenyl)-N-(1H-imidazol-2-yl)-propionamide HCl salt (303 mg, 50%) was collected by filtration and used directly in the next step.

145 mg (0.5 mmol) of 2-isoquinolin-3-yl-1H-benzoimidazole-4-carboxylic acid was reacted with 280 mg (0.75 mmol) of HBTU and 2-Amino-3-(3,5-difluoro-phenyl)-N-(1H-imidazol-2-yl)-propionamide HCl salt (152 mg, 0.5 mmol) as described in general procedure A. A solid precipitated from the solution and was collected by filtration, washed with H₂O and EtOAc, to give 2-isoquinolin-3-yl-1H-benzoimidazole-4-carboxylic acid [2-(3,5-difluoro-phenyl)-1-(1H-imidazol-2-ylcarbamoyl)-ethyl]-amide (60 mg, 22%). LCMS: 538 (M+1)⁺.

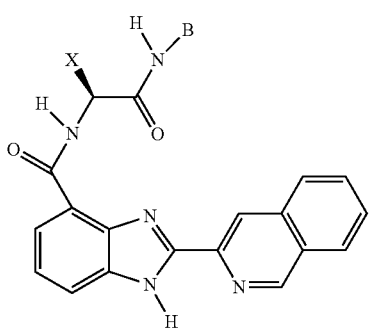

Analogous procedures to those used to prepare the compound of Example 39 were used to prepare the compounds of Examples 40-46.

| Ex. | X | B | LCMS (M + 1)+ |
|---|---|---|---|
| 40 | Benzyl | 1H-benzimidazol-2-yl | 552 |
| 41 | 3,5-difluorobenzyl | methyl | 486 |
| 42 | benzyl | 2-methyl-piperidine-1-carboxylic acid tert-butyl ester | 633 |
| 43 | benzyl | thiazol-2yl | 519 |
| 44 | benzyl | isobutyl | 492 |
| 45 | benzyl | 3-methyl-piperidine-1-carboxylic acid tert-butyl ester | 633 |
| 46 | benzyl | benzthiazol-2yl | 569 |

Example 47

To a stirring solution of 0.86 g (6.0 mmol) of isoquinolin-3-ylamine in dry THF (30 mL) was added 1.25 g (7.0 mmol) of di-imidazol-1-yl-methanethione. The reaction mixture was refluxed for 30 min. After cooling to room temperature, a solution of 1.7 g (10 mmol) of 2,3-diamino-benzoic acid methyl ester (for synthesis see example 1) in THF (40 mL) and DIEA (2 mL) was added subsequently. The reaction mixture was stirred at room temperature for 1 h and diluted with hexanes (40 mL). The resulting precipitate was filtered. The solid was washed with water and ether and dried under vacuum to give 2-amino-3-(3-isoquinolin-3-yl-thioureido)-benzoic acid methyl ester as a solid.

To a solution of above thiourea (6.0 mmol) in DCE (50 ml) was added polymer-supported-DCC (6.0 g, 7.8 mmol) and DMF (25 mL). The reaction mixture was stirred at 85° C. for 1 h. The hot reaction mixture was filtered, and the solid resin on the filter paper was further washed with hot DMF (25 mL). The combined organic solution was concentrated under vacuum to give the 2-(isoquinolin-3-ylamino)-3H-benzoimidazole-4-carboxylic acid methyl ester. This methyl ester was hydrolyzed according to the general procedure C to give 2-(isoquinolin-3-ylamino)-3H-benzoimidazole-4-carboxylic acid (1.3 g, 71% overall yields in 3 steps). LCMS: 305 (M+1)+.

100 mg (0.33 mmol) of the above carboxylic acid was reacted with 200 mg (0.53 mmol) of HBTU and 200 mg (1.2 mmol) of 2-aminoimidazole sulfate according to the general procedure A. The crude product was purified by flash column chromatography (EtOAc then EtOAc/MeOH=10:1) to give 2-(isoquinolin-3-ylamino)-3H-benzoimidazole-4-carboxylic acid (1H-imidazol-2-yl)-amide (20 mg, 15%). LCMS: 370 (M+1)+. 1H NMR (DMSO-d6, 400 MHz): δ 6.82 (s, 1H), 6.89 (s, 1H), 7.20 (dd, 1H), 7.47 (dd, 1H), 7.71 (m, 2H), 7.84 (dd, 1H), 8.04 (s, 1H), 8.08 (d, 1H), 8.18 (d, 1H), 9.21 (s, 1H), 11.14 (s, 1H), 11.84 (s, 1H), 12.11 (s, 1H), 12.60 (s, 1H) ppm.

Analogous procedures to those used to prepare the compound of Example 47 were used to prepare the compounds of Examples 48-57.

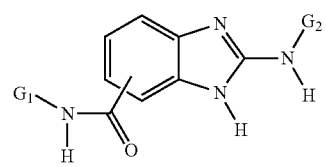

| Ex. | Amide position | $G_1$ | $G_2$ | LCMS (M + 1)+ |
|---|---|---|---|---|
| 48 | 5 | 1H-imidazol-2-yl | 2-isoquinolin-3-yl | 370 |
| 49 | 4 | 4-fluorophenyl | 2-isoquinolin-3-yl | 398 |
| 50 | 4 | phenyl | 2-isoquinolin-3-yl | 380 |
| 51 | 5 | 1H-imidazol-2-yl | pyridin-2-yl | 320 |
| 52 | 4 | 4-chlorophenyl | 2-isoquinolin-3-yl | 414 |
| 53 | 4 | 4-methoxyphenyl | 2-isoquinolin-3-yl | 410 |
| 54 | 4 | benzyl | 2-isoquinolin-3-yl | 394 |
| 55 | 5 | benz1H-imidazol-2-yl | pyridin-2-yl | 370 |
| 56 | 4 | 3-hydroxypropyl | 2-isoquinolin-3-yl | 362 |
| 57 | 4 | methyl | 2-isoquinolin-3-yl | 318 |

Intermediate A—2-Amino-3H-benzoimidazole-4-carboxylic acid methyl ester

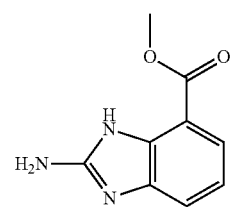

2,3-diamino-benzoic acid methyl ester was synthesized in a quantitative yield (1.7 g) from 2-amino-3-nitro-benzoic acid methyl ester (2.0 g, 8.8 mmol) as described in general procedure C.

1.7 g (10.2 mmol) of the above methyl ester was dissolved in a mixture of 20 mL of ethanol and 10 mL of $H_2O$. To this stirring solution, 1.6 g (15.3 mmol) of BrCN was added in one portion, and the resulting mixture was refluxed for 1.0 h. The reaction mixture was cooled to room temperature, concentrated to 10 mL, and washed with ethyl acetate (20 mL). The EtOAc layer was extracted with water (20 mL). The combined water extracts were neutralized with saturated $NaHCO_3$ solution to ~pH 8, and the resulting suspension was extracted with EtOAc (50 mL). The organic layer was washed with water and brine solution, dried (Na₂SO₄), and evaporated to give 1.7 g (90%) of the title compound. LCMS: 192 (M+1)⁺

Intermediate B—2-Amino-3H-benzoimidazole-4-carboxylic acid (1H-imidazol-2-yl)-amide

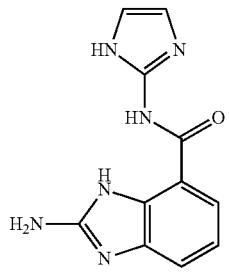 [SMILES: Nc1nc2cccc(C(=O)Nc3ncc[nH]3)c2[nH]1]

5.0 g (27.4 mmol) of 2-amino-3-nitro-benzoic acid, 12.48 g (32.9 mmol) of HBTU were suspended in 20 mL of DMF. To this suspension, 10 mL of DIEA was added, and the resulting mixture was stirred for 10 minutes to form a paste. To this paste, 10 mL of DMF was added followed by 9 g (68.2 mmol) of 2-amino imidazole sulfate. The resulting mixture was heated at 75° C. for 3.0 h. The reaction mixture was cooled to room temperature and 5 mL of 2N NaOH was added followed by 200 mL of brine solution. A solid precipitated from the solution and was collected by filtration, washed with water (300 ml), ethyl acetate (100 ml), and dried under vacuum to provide 5.3 g (75%) of 2-amino-N-(1H-imidazol-2-yl)-3-nitro-benzamide as a yellow solid. The product was hydrogenated according to the general procedure C to give 2,3-diamino-N-(1H-imidazol-2-yl)-benzamide (4.5 g) 4.5 g (21.2 mmol) of the above solid was dissolved in a mixture of 40 mL of ethanol and 8 mL of H₂O. To this stirring solution 3.3 g (31.8 mmol) of BrCN was added and the resulting mixture was refluxed for 1.0 h. The reaction mixture was cooled to room temperature and the solvent was evaporated and adjusted to ~pH 8.0 with aqueous NH₄OH. The resulting solid was filtered. The solid was further washed with water (100 mL), ethyl acetate (50 mL) and dried under vacuum to give 2.5 g (50%) of 2-amino-3H-benzoimidazole-4-carboxylic acid (1H-imidazol-2-yl)-amide. LCMS: 243 (M+1)⁺.

Example 58

2.6 g (75%) of the 2-[(isoquinoline-3-carbonyl)-amino]-1H-benzoimidazole-4-carboxylic acid methyl ester was synthesized from isoquinoline-3-carboxylic acid (1.7 g, 10 mmol), HBTU (4.6 g, 12 mmol), and the above synthesized 2-amino-3H-benzoimidazole-4-carboxylic acid methyl ester (1.9 g, 10 ml) as described in general procedure A. This ester was then hydrolyzed according to general procedure B to give 2.2 g (88%) of acid. LCMS: 333 (M+1)⁺.

332 mg (1.0 mmol) of above 2-[(isoquinoline-3-carbonyl)-amino]-1H-benzoimidazole-4-carboxylic acid (0.33 g, 1.0 mmol) was reacted with 800 mg (2.0 mmol) of HBTU and 2-aminoimidazole sulfate (400 mg, 3.0 mmol) in 3.0 mL of DMF and 1.0 mL of DIEA as described in general procedure A. After cooling to room temperature, the reaction mixture was diluted with 0.6 mL of 5 N NaOH aq. solution and 4.0 mL of brine. The solid was collected by filtration and washed with 2 N NaOH aq. (3.0 mL), followed by H₂O and EtOAc (3× of each), to give 224.0 mg of the crude compound. The crude was heated in 3.0 mL of DMF at 80° C. for 20 minutes. The filter cake was washed by another 1.0 mL of hot DMF. The combined filtrate was reheated to a clear solution, then cooled and addition of 2.0 mL of EtOAc, followed by 4.0 mL of H₂O. The mixture was stirred, and a solid was gradually formed between EtOAc and DMF/H₂O layers. The solid was collected by filtration and washed with H₂O, EtOAc and MeOH (3× of each), then dried, to yield isoquinoline-3-carboxylic acid [4-(1H-imidazol-2-ylcarbamoyl)-1H-benzoimidazol-2-yl]-amide (83.0 mg, 21%). LCMS: 398.0 (M+1)⁺. ¹H NMR (DMSO-d₆, 400 MHz): δ 12.29 (s, 1H), 11.86 (s, 1H), 9.52 (s, 1H), 8.81 (s, 1H), 8.31 (t, 2H), 7.80-7.95 (m, 4H), 7.32 (t, 1H), 6.88 (s, 1H), 6.77 (s, 1H) ppm.

Example 59

70 mg (0.45 mmol) of 4-chloro-benzoic acid 170 mg (0.45 mmol) of HBTU in a mixture of 3 ml of DMF and 1 mL of DIEA was reacted with 100 mg (0.4 mmol) of 2-amino-3H-benzoimidazole-4-carboxylic acid (1H-imidazol-2-yl)-amide synthesized above as described in general procedure A and 2-(4-chloro-benzoylamino)-1H-benzoimidazole-4-carboxylic acid (1H-imidazol-2-yl)-amide (30 mg, 17.24%) was isolated. LCMS: 382 (M+1)⁺. ¹H NMR (DMSO-d₆, 400 MHz): δ 11.99 (d, 1H), 8.16 (d, 2H), 7.94 (d, 1H), 7.70 (dd, 3H), 7.30 (t, 1H), 6.81 (d, 2H) ppm.

Analogous procedures to those used to prepare the compound of Example 59 were used to prepare the compounds of Examples 60-127.

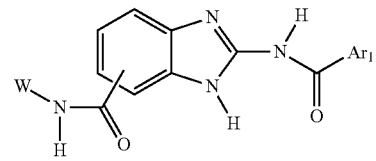

| Ex. | Amide position | W | Ar₁ | LCMS (M+1)⁺ |
|---|---|---|---|---|
| 60 | 4 | 1H-benzimidazol-2-yl | isoquinolin-3-yl | 448 |
| 61 | 4 | benzthiazol-2-yl | isoquinolin-3-yl | 465 |
| 62 | 4 | {1,3,4}-thiadiazol-2yl | isoquinolin-3-yl | 416 |
| 63 | 4 | pyridin-2-yl | isoquinolin-3-yl | 409 |
| 64 | 4 | pyridin-3yl | isoquinolin-3-yl | 409 |
| 65 | 4 | 1H-benzimidazol-2-yl | 1H-indole-2yl | 435 |
| 66 | 5 | 1H-benzimidazol-2-yl | isoquinolin-3-yl | 448 |
| 67 | 4 | 1H-indazole-5-yl | isoquinolin-3-yl | 448 |
| 68 | 4 | quinolin-3-yl | isoquinolin-3-yl | 459 |
| 69 | 5 | benzothiazol-2-yl | isoquinolin-3-yl | 465 |
| 70 | 5 | thiazol-2-yl | isoquinolin-3-yl | 415 |
| 71 | 4 | 1H-imidazol-2-yl | phenyl | 347 |
| 72 | 4 | furan-2-yl methyl | isoquinoline-3yl | 412 |
| 73 | 4 | 2-phenyoxy-phenyl | isoquinolin-3-yl | 500 |
| 74 | 4 | 3-phenoxy-phenyl | isoquinolin-3-yl | 500 |
| 75 | 4 | 4-phenoxy-phenyl | isoquinolin-3-yl | 500 |
| 76 | 4 | (1S)-1-phenyl ethyl | isoquinolin-3-yl | 436 |
| 77 | 4 | (1R)-1-phenyl ethyl | isoquinolin-3-yl | 436 |
| 78 | 4 | 1H-imidazol-2-yl | benzothiophene-2-yl | 403 |
| 79 | 4 | 1H-imidazol-2-yl | naphthalen-2-yl | 397 |
| 80 | 4 | 1H-imidazol-2-yl | 4'-biphenyl | 423 |
| 81 | 4 | 1H-imidazol-2-yl | 1H-indole-2yl | 386 |
| 82 | 4 | 1H-imidazol-2-yl | 3,5-difluorophenyl | 383 |
| 83 | 4 | 1H-imidazol-2-yl | 4-fluorophenyl | 365 |
| 84 | 4 | (thiophene-2-yl)ethyl | isoquinolin-3-yl | 442 |
| 85 | 5 | phenyl | isoquinolin-3-yl | 408 |
| 86 | 4 | (5-methylfuran-2-yl)-methyl | isoquinolin-3-yl | 426 |
| 87 | 4 | benzyl | isoquinolin-3-yl | 422 |
| 88 | 4 | (thiophene-2-yl)methyl | isoquinolin-3-yl | 428 |

-continued

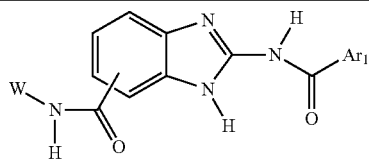

| Ex. | Amide position | W | Ar₁ | LCMS (M+1)+ |
|---|---|---|---|---|
| 89 | 4 | phenethyl | isoquinolin-3-yl | 436 |
| 90 | 4 | ethyl | isoquinolin-3-yl | 360 |
| 91 | 4 | tert-butyl | isoquinolin-3-yl | 388 |
| 92 | 4 | 1H-imidazol-2-yl | benzofuran-2-yl | 387 |
| 93 | 4 | 2,3,4,9-tetrahydro-1H-beta-carboline-2-yl | isoquinolin-3-yl | 487 |
| 94 | 4 | (benzothiophene-2-yl)methyl | isoquinolin-3-yl | 478 |
| 95 | 4 | (benzthiazol-2-yl)methyl | isoquinolin-3-yl | 479 |
| 96 | 4 | (1-methylbenzimidazole-2-yl)methyl | isoquinolin-3-yl | 476 |
| 97 | 4 | 2-(1H-benzimidazole-2-yl)-ethyl | isoquinolin-3-yl | 476 |
| 98 | 4 | 1H-imidazol-2-yl | 4-fluorobenzyl | 379 |
| 99 | 4 | 1H-imidazol-2-yl | 3-methoxy-4-fluoro-phenyl | 395 |
| 100 | 4 | 1H-imidazol-2-yl | 3,4-dimethoxyphenyl | 407 |
| 101 | 4 | thiazole-2-yl-methyl | isoquinolin-3-yl | 429 |
| 102 | 4 | 1H-benzimidazole-2-yl methyl | isoquinolin-3-yl | 462 |
| 103 | 4 | 1H-imidazol-2-yl | 4-trifluoromethyl-phenyl | 415 |
| 104 | 4 | 1H-imidazol-2-yl | 4-phenyoxyphenyl | 439 |
| 105 | 4 | 1H-imidazol-2-yl | quinolin-3-yl | 398 |
| 106 | 4 | 1H-imidazol-2-yl | quinolin-2-yl | 398 |
| 107 | 4 | 1H-imidazol-2-yl | furan-3-yl | 334 |
| 108 | 4 | 1H-imidazol-2-yl | 4-tert-butyl-phenyl | 403 |
| 109 | 4 | 1H-imidazol-2-yl | 4-nitro-phenyl | 392 |
| 110 | 4 | 1H-imidazol-2-yl | 4-methoxy-phenyl | 377 |
| 111 | 4 | 1H-imidazol-2-yl | 1H-imidazol-2-yl | 337 |
| 112 | 4 | 1H-imidazol-2-yl | 4-isopropyl-phenyl | 389 |
| 113 | 4 | 1H-imidazol-2-yl | 3-fluoro-phenyl | 365 |
| 114 | 4 | 1H-imidazol-2-yl | 2-fluoro-phenyl | 365 |
| 115 | 4 | 1H-imidazol-2-yl | 5-chloro-benzofuran-2-yl | 421 |
| 116 | 4 | 1H-imidazol-2-yl | 6,7-dimethoxy-2-isoquinolin-3-yl | 458 |
| 117 | 4 | 1H-imidazol-2-yl | 3-chloro-phenyl | 381 |
| 118 | 4 | 1H-imidazol-2-yl | 2-chloro-phenyl | 381 |
| 119 | 4 | 1H-imidazol-2-yl | 1H-indazole-3-yl | 387 |
| 120 | 4 | 1H-imidazol-2-yl | 1-methyl-indole-2-yl | 400 |
| 121 | 4 | 1H-imidazol-2-yl | 1-methyl-indazole-3-yl | 401 |
| 122 | 4 | 4-phenyl-1H-imidazol-2-yl | isoquinolin-3-yl | 474 |
| 123 | 4 | 1H-imidazol-2-yl | 5-methyl-indole-2-yl | 400 |
| 124 | 4 | 1H-imidazol-2-yl | 5-phenoxy-pyridine-2-yl | 440 |
| 125 | 4 | 1H-imidazol-2-yl | 1-benzyl-indole-2-yl | 476 |
| 126 | 4 | 1H-imidazol-2-yl | 1-n-propyl-indole-2yl | 428 |
| 127 | 4 | 1H-imidazol-2-yl | 1,5-dimethyl-indole-2yl | 414 |

Example 128

1.0 g (5.2 mmol) of 2-amino-3H-benzoimidazole-4-carboxylic acid methyl ester was suspended in 10 mL of conc. $H_2SO_4$ at −15° C. and cooled to −30° C. Potassium nitrate (0.58 g, 5.72 mmol) dissolved in 10 mL of sulfuric acid and cooled to 0° C. was then added dropwise to the reaction mixture. The reaction mixture was stirred −30° C. for 15 min then warmed to −10° C. over 30 min. Then the mixture was poured into a beaker containing ice and neutralized (~pH=8) with concentrated aqueous ammonia solution. The resulting solid was filtered. The solid obtained was washed with cold water and ether, and dried under vacuum to provide 0.85 g (70%) 2-amino-6-nitro-1H-benzoimidazole-4-carboxylic acid methyl ester as a solid. LCMS: 239 (M+1)+.

0.5 g (2.12 mmol) of 2-amino-6-nitro-1H-benzoimidazole-4-carboxylic acid methyl ester was reacted with 0.37 g (2.12 mmol) of isoquinoline 3-carboxylic acid and 0.89 g (2.33 mmol) of HBTU as described in general procedure A to provide 0.67 g (80%) of 2-[(Isoquinoline-3-carbonyl)-amino]-6-nitro-1H-benzoimidazole-4-carboxylic acid methyl ester. LCMS: 392 (M+1)+. The ester was dissolved in dry DMF (5 mL) and 0.22 g (5.1 mmol) of LiCl in one portion was added. The resulting mixture was stirred at 120° C. for 12 h, diluted with water, and the solid was collected by filtration. The solid was washed with water (20 mL), ether (10 mL) and dried under vacuum to provide 0.6 g (93%) of 2-[(isoquinoline-3-carbonyl)-amino]-6-nitro-1H-benzoimidazole-4-carboxylic acid. LCMS: 378 (M+1)+.

0.5 g (1.3 mmol) of the above acid (Example 128) was reacted with 0.6 g (1.6 mmol) of HBTU and 0.35 g (1.3 mmol) 2-amino imidazole as described in general procedure A. After the reaction was complete, the reaction mixture was diluted with water 20 (mL), 3.0 mL of 2 N NaOH, and stirred for 15 min. The resulting solid was filtered, washed with water, diethyl ether and dried under vacuum to provide 0.1 g (17.2%) of isoquinoline-3-carboxylic acid [4-(1H-imidazol-2-ylcarbamoyl)-6-nitro-1H-benzoimidazol-2-yl]-amide. LCMS: 443 (M+1)+.

Example 129

0.1 g (0.2 mmol) of isoquinoline-3-carboxylic acid [4-(1H-imidazol-2-ylcarbamoyl)-6-nitro-1H-benzoimidazol-2-yl]-amide (Example 129) was suspended in a mixture of 2 mL of DMF and 5 mL of acetic acid. To this stirring solution, ~20 mg of 10% Pd on carbon was added, and the resulting mixture was hydrogenated at 42 psi of $H_2$ at room temperature for 3.0 h. The reaction mixture was filtered, and the solid was washed with 5 mL of DMF. The filtrate and washings were combined and evaporated to reduce the volume to 10 mL, then diluted with saturated $NaHCO_3$ (10 mL), and extracted with ethyl acetate. The organic layer was washed with water and brine and evaporated to provide 85 mg (91%) of isoquinoline-3-carboxylic acid [6-amino-4-(1H-imidazol-2-ylcarbamoyl)-1H-benzoimidazol-2-yl]-amide. LCMS: 413 (M+1)+.

Example 130

20 mg (0.04 mmol) of isoquinoline-3-carboxylic acid [6-amino-4-(1H-imidazol-2-ylcarbamoyl)-1H-benzoimidazol-2-yl]-amide (Example 129) was dissolved in pyridine (2 mL). To this stirring solution at 0° C., 5.6 mg (0.053 mmol) of isobutyryl chloride was added in one portion. The reaction mixture was stirred for 10 min at 0° C. and warmed to room temperature. The pyridine was evaporated and water (5 mL) was added to the reaction mixture. The mixture was stirred for 10 min. and the resulting solid was filtered, washed with water (2 mL) and diethyl ether (5 mL), and dried to provide 15.5 mg (66.5%) of isoquinoline-3-carboxylic acid [4-(1H-imidazol-2-ylcarbamoyl)-6-isobutyrylamino-1H-benzoimidazol-2-yl]-amide. LCMS: 483 (M+1)+. $^1$H NMR (CD$_3$OD, 400 MHz): δ 9.43 (s, 1H), 8.77 (s, 1H), 8.06-8.31 (m, 5H), 7.80-7.93 (m, 3H), 7.08 (s, 2H), 2.45 (m, 1H), 1.1 (d, 6H) ppm.

Analogous procedures to those used to prepare the compound of Example 130 were used to prepare the compounds of Examples 131-133.

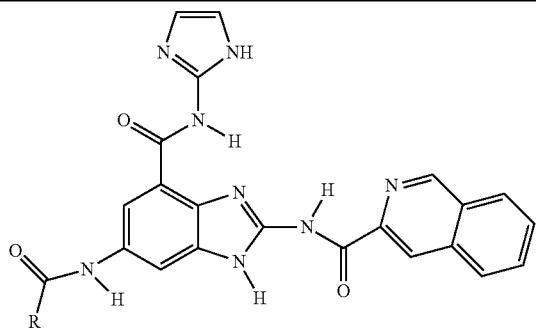

| Ex. | R | LCMS (M + 1)+ |
|---|---|---|
| 131 | phenyl | 517 |
| 132 | isobutyl | 497 |
| 133 | benzyl | 531 |

Example 134

To a solution of 0.1 g (0.52 mmol) of 2-amino-1H-benzoimidazole-4-carboxylic acid methyl ester (intermediate A) in DMSO (1 mL) was added 0.089 g (0.52 mmol) of benzyl bromide, the reaction mixture was stirred at room temperature for 3 h. The conversion was monitored by LCMS. After usual work up, the residue was purified by column chromatography eluting with DCM/methanol (v/v=10:1) to afford 0.08 g (55%) of 2-amino-1-benzyl-1H-benzoimidazole-4-carboxylic acid methyl ester. LCMS: 281 (M+1)+; $^1$H NMR (DMSO-d$_6$, 400 MHz): δ 7.49 (dd, 1H), 7.29 (t, 2H), 7.25 (m, 2H), 7.16(m, 2H), 7.05 (bs, 2H), 6.85 (t, 1H), 5.28 (s, 2H), 3.79 (s, 3H) ppm.

To a solution of 0.031 g (0.18 mmol) of isoquinoline-3-carboxylic acid in DMF (1 mL) was added 0.085 g (0.22 mmol) of HBTU and 0.1 mL of DIEA. The mixture was stirred for 5 min, then added 0.04 g (0.18 mmol) of 2-amino-1-benzyl-1H-benzoimidazole-4-carboxylic acid methyl ester in one portion. The reaction mixture was stirred for 1 h. After usual workup, 45 mg (73%) of 1-benzyl-2-[(isoquinoline-3-carbonyl)-amino]-1H-benzoimidazole-4-carboxylic acid methyl ester was isolated after purification by column chromatography eluting with DCM/methanol (v/v from 15:1 to 10:1). LCMS: 437 (M+1)+; $^1$H NMR (DMSO-d$_6$, 400 MHz): δ 12.8 (s, 1H), 9.41 (s, 1H), 8.92(s, 1H), 8.20 (d, 1H), 8.14 (d, 1H), 7.84 (t, 1H), 7.77 (m, 3H), 7.51 (d, 2H), 7.32 (m, 4H), 5.63 (s, 2H), 3.99 (s, 3H) ppm.

Example 135

To a solution of 45 mg (0.12 mmol) of (1-benzyl-2-[(isoquinoline-3-carbonyl)-amino]-1H-benzoimidazole-4-carboxylic acid methyl ester (Example 134) in THF (1 mL) was added methanol (1 mL) and 1 N LiOH solution (1 mL). The reaction was heated at 65° C. for 45 min., and the conversion was monitored by TLC. After cooling to room temperature, the organic solvents were removed under reduced pressure, the reaction residue was acidified (pH=2) by addition of 1 N HCl solution. The solid product was collected by filtration and further dried to afford 43 mg (100%) 1-benzyl-2-[(isoquinoline-3-carbonyl)-amino]-1H-benzoimidazole-4-carboxylic acid. LCMS: 423 (M+1)+.

To a solution of 43 mg (0.12 mmol) of the above crude acid in DMF (0.7 mL) was added 75 mg (0.2 mmol) of HBTU and DIEA (0.1 mL). The mixture was stirred for 5 min, then 40 mg (0.3 mmol) of 2-aminoimidazole sulfate was added in one portion. The reaction mixture was heated at 80° C. for 1 h. After usual workup as described in General Procedure A, 25 mg (50%) of isoquinoline-3-carboxylic acid [1-benzyl-4-(1H-imidazol-2-ylcarbamoyl)-1H-benzoimidazol-2-yl]-amide was isolated after purification by column chromatography eluting with DCM/methanol (v/v from 15:1 to 7:1). LCMS: 488 (M+1)+.

Example 136

15 mg of isoquinoline-3-carboxylic acid [4-(1H-imidazol-2-ylcarbamoyl)-1-methyl-1H-benzoimidazol-2-yl]-amide was synthesized following the same procedures described for above Example 135, with the exception that methyl iodide was used instead of benzyl bromide. LCMS: 412 (M+1)+.

Example 137

20 mg of isoquinoline-3-carboxylic acid (4-benzylcarbamoyl-1-methyl-1H-benzoimidazol-2-yl)-amide was synthesized following the same procedures described for Example 135, with the exception that methyl iodide was used instead of benzyl bromide and benzyl amine was used instead of 2-aminoimidazole sulfate. LCMS: 436 (M+1)+.

Example 138

To a solution of 48.4 mg (0.2 mmol) of 2-amino-3H-benzoimidazole-4-carboxylic acid (1H-imidazol-2-yl)-amide (Intermediate B) in dry DMF (1.0 mL) was added 49 mg (0.3 mmol) of di-imidazol-1-yl-methanone in one portion. The mixture was heated at 50° C. for 30 min, after cooling to room temperature, 23 mg (0.16 mmol) of isoquinolin-3-ylamine was added to the reaction mixtures. The reaction mixture was stirred at 45° C. for 45 min. After cooling to r.t., the organic solvent was removed under reduced pressure. The residue was purified by column chromatography eluting with DCM/methanol (v/v=10:1 to 8:1) to give 17 mg (20%) of 2-(3-isoquinolin-3-yl-ureido)-1H-benzoimidazole-4-carboxylic acid (1H-imidazol-2-yl)-amide. LCMS: 413 (M+1)+.

Example 139

To a solution of 150 mg (0.95 mmol) of isoquinoline-3-carbaldehyde in dry DCE (1 mL) was added 60 mg (0.25 mmol) of 2-amino-3H-benzoimidazole-4-carboxylic acid (1H-imidazol-2-yl)-amide (intermediate B), and Ti(OiPr)$_4$ (3 mL). The mixture was sonicated for 30 min then stirred at room temperature for 6 h. NaBH$_4$ (0.5 g) was added, and the mixture was stirring for 12 h. The reaction was quenched by addition of methanol (2 mL). After usual workup, the residue was purified by column chromatography eluting with DCM then EtOAc/methanol (v/v=100:5) to give 7 mg (7%) of 2-[(isoquinolin-3-ylmethyl)-amino]-1H-benzoimidazole-4-carboxylic acid (1H-imidazol-2-yl)-amide. LCMS: 384 (M+1)+. $^1$H NMR (DMSO-d$_6$, 400 MHz): δ 12.58 (s, 1H), 11.8 (s, 1H), 11.6 (s, 1H), 9.07 (s, 1H), 8.69 (s, 1H), 8.22 (t, 1H), 7.96 (d, 1H), 7.91 (d, 1H), 7.67 (m, 2H), 7.53 (t, 1H), 7.36 (d, 1H), 7.02 (t, 1H), 6.90 (s, 1H), 6.85 (s, 1H), 4.78 (d, 2H) ppm.

Example 140

3.4 g (20.5 mmol) of methyl 3,4-diaminobenzoate was dissolved in a mixture of 50 mL of ethanol and 10 mL of H$_2$O. To this stirring solution 2.6 g (24.5 mmol) of BrCN was added in one portion, and the resulting mixture was heated under reflux for 1.0 h. The reaction mixture was cooled to room temperature, concentrated to 10 mL, then washed with ethyl acetate (20 mL). The EtOAc layer was extracted with water (20 mL). The combined water extracts were neutralized with saturated NaHCO$_3$ solution to ~pH 8, and the resulting suspension was extracted with EtOAc (50 mL). The organic layer was washed with water and brine solution, dried with Na$_2$SO$_4$, and evaporated to give 2-amino-1H-benzoimidazole-5-carboxylic acid methyl ester, which was used directly in the next step without further purification.

2-[(Isoquinoline-3-carbonyl)-amino]-1H-benzoimidazole-5-carboxylic acid methyl ester was prepared from 1.9 g (10 mmol) of isoquinoline-3-carboxylic acid monohydrate, 4.6 g (12 mmol) of HBTU, and 1.9 g, (10 mmol) of 2-amino-1H-benzoimidazole-5-carboxylic acid methyl ester as described in general procedure A. A 0.35 g (1.0 mmol) portion of 2-[(isoquinoline-3-carbonyl)-amino]-1H-benzoimidazole-5-carboxylic acid methyl ester was subsequently hydrolyzed according to general procedure B to give 2-[(isoquinoline-3-carbonyl)-amino]-1H-benzoimidazole-5-carboxylic acid as a light yellow solid, which was used in the final coupling step without further purification.

0.15 g (0.45 mmol) of 2-[(isoquinoline-3-carbonyl)-amino]-1H-benzoimidazole-5-carboxylic acid was reacted with 0.26 g (0.68 mmol) of HBTU and 0.06 g (0.45 mmol) of 2-aminoimidazole sulfate in 3.0 mL of DMF and 1.0 mL of DIEA as described in general procedure A. After cooling to room temperature, the reaction mixture was diluted with water, the solid was collected by filtration, dissolved with MeOH and evaporated onto silica gel, and isolated by flash column chromatography (500 mL DCM/20 mL NH$_3$/MeOH) to yield ~10 mg of the desired isoquinoline-3-carboxylic acid [5-(1H-imidazol-2-ylcarbamoyl)-1H-benzoimidazol-2-yl]-amide. LCMS: 398.0 (M+1)$^+$ Example 141

To a solution of 1.53 g (10 mmol) of 3-nitro-benzene-1,2-diamine in ethanol (20 mL) was added 1.3 g (12.5 mmol) of BrCN and water (5 mL). The mixture was refluxed for 1.0 h. After cooling to room temperature, the solvent was concentrated, then the residue was dissolved in water, the pH was adjusted to 8.0 with sat. NaHCO$_3$ solution. The resulting solid was filtered, washed with water and dried under vacuum to afford 1.42 g (80%) of the 7-nitro-1H-benzoimidazol-2-ylamine. LCMS: 179 (M+1)$^+$.

1.42 g (8 mmol) of above 7-nitro-1H-benzoimidazol-2-ylamine was reacted with 1.38 g (8 mmol) of isoquinoline-3-carboxylic acid, 3.4 g (9 mmol) of HBTU in 30.0 mL of DMF and 5.0 mL of DIEA as described in general procedure A. After cooling to room temperature, the reaction mixture was diluted with 60 mL of saturated NaHCO$_3$ and 100 mL of water. The solid was collected by filtration and washed with water and dried under reduced pressure, and subsequently subjected to hydrogenation as described in general procedure C to give 1.0 g (41%) of the isoquinoline-3-carboxylic acid (7-amino-1H-benzoimidazol-2-yl)-amide. LCMS: 304 (M+1)$^+$ To a solution of 30 mg (0.1 mmol) of above isoquinoline-3-carboxylic acid (7-amino-1H-benzoimidazol-2-yl)-amide in dry DMF (1 mL) was added 24 mg (0.15 mmol) of di-imidazol-1-yl-methanone in one portion. The mixture was heated at 50° C. for 30 min. After cooling to room temperature, 16 mg (0.15 mmol) of 4-fluoro-phenylamine was added to the reaction. The reaction mixture was stirred at 45° C. for 45 min. After cooling to room temperature, the organic solvent was removed under reduced pressure, and the residue was purified by column chromatography eluting with DCM/methanol (v/v=10:0.5 to 10:1) to provide 17 mg (39%) of isoquinoline-3-carboxylic acid {7-[3-(4-fluoro-phenyl)-ureido]-1H-benzoimidazol-2-yl}-amide. LCMS: 441 (M+1)$^+$.

By analogous methods to those used to prepare Example 141 and those in the relevant above schemes, the following compounds were synthesized.

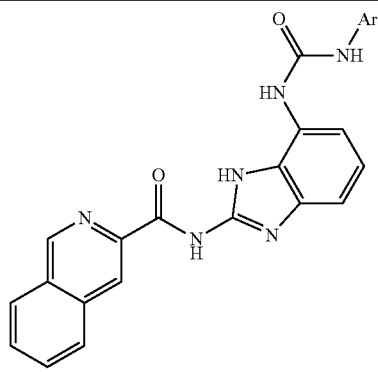

| EX | Ar | LCMS: (M + 1)$^+$ |
|---|---|---|
| 142 | 4-methoxy phenethyl | 481 |
| 143 | 4-methoxy benzyl | 467 |

Example 144

To a stirring solution of 200 mg (0.92 mmol) of 2,3-diamino-N-(1H-imidazol-2-yl)-benzamide (synthesized as described in Intermediate-B) in 2.0 mL of acetic acid was added 200 mg (1.15 mmol) of 2,2,2-trichloroacetamide and stirring continued for 30 min at r.t. Then 0.5 mL of 1% HCl in methanol was added and stirred for another 45 min at r.t. Evaporation of the solvent gave the crude ester, which was dissolved in 4:1 THF and methanol (5 mL) and then 1.0 mL of 2N LiOH was added at r.t. The reaction mixture was stirred at r.t. for 30 min, the pH was adjusted to 3.0 and then extracted with ethyl acetate twice (2×25 mL). The combined organic solvents were dried, evaporated to provide 100 mg (40%) of 4-(1H-imidazol-2-ylcarbamoyl)-1H-benzoimidazole-2-carboxylic acid, which was used, for the next step without further purification. LCMS: 272 (M+1)$^+$.

To a stirring solution of 100 mg (0.36 mmol) of above acid in 2.0 mL of DMF was added 140 mg (0.72 mmol) of EDCI. The reaction mixture was stirred for 10 min then 53 mg (0.36 mmol) of Isoquinolin-3-ylamine was added. The reaction mixture stirred for another 20 h and cooled to room temperature 5.0 mL of water and 5.0 mL of saturated NaHCO$_3$ was added. The resulting solid was filtered washed with water, ether and dried to provide 20 mg (13.6%) of 1H-benzoimidazole-2,4-dicarboxylic acid 4-[(1H-imidazol-2-yl)-amide] 2-isoquinolin-3-ylamide. LCMS: 398 (M+1)⁺.

Example 145

To a solution of 0.33 g (1.0 mmol) of -[(isoquinoline-1-carbonyl)-amino]-3H-benzoimidazole-4-carboxylic acid (from Example 58) in DMF (5 mL) was added 0.47 g (1.25 mmol) of HBTU and DIEA (0.5 mL). The mixture was stirred for 5 min, then 0.22 g (2.0 mmol) of benzene-1,2-diamine was added in one portion. The reaction mixture was heated at 50° C. for 1 h, after cooling to room temperature, the coupling product was precipitated by addition of sat. aq. sodium carbonate solution (15 mL). The solid was filtered, washed with water, and dried to provide 0.35 g (80%) of isoquinoline-1-carboxylic acid [7-(2-amino-phenylcarbamoyl)-1H-benzoimidazol-2-yl]-amide. LCMS: 443 (M+1)⁺.

To a solution of 169 mg (0.4 mmol) of isoquinoline-1-carboxylic acid [7-(2-amino-phenylcarbamoyl)-1H-benzoimidazol-2-yl]-amide in AcOH (15 mL) was added NH₄OAc (0.5 g). The mixture was heated at 130° C. for 30 min. After cooling to room temperature, the AcOH was removed under reduced pressure, extracted with EtOAc (50 mL), washed with sat. aq. sodium bicarbonate solution and brine. The organic phase was dried over sodium sulfate and concentrated. The residue was dissolved in DCM (3 mL), and 5 mL of hexane was added. The resulting solid was filtered and dried to afford 120 mg (75%) of isoquinoline-1-carboxylic acid (1H,3'H-[2,4']bibenzoimidazolyl-2'-yl)-amide. LCMS: 405 (M+1)⁺.

By analogous methods to those used to prepare Example 145 and those in the relevant above schemes, the following compounds were synthesized.

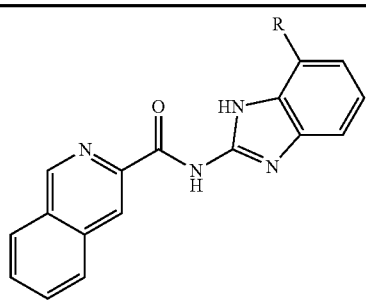

| Ex. | R | LCMS (M + 1)⁺ |
|---|---|---|
| 146 | 3H-Imidazo[4,5-c]pyridine-2-yl | 406 |
| 147 | 4-phenyl-1H-imidazol-2-yl | 431 |
| 148 | 1H-imidazol-2-yl | 355 |
| 149 | 4-(4-chloro-phenyl)-1H-imidazol-2-yl | 465 |

Example 150

To a solution of 61 mg (0.2 mmol) of isoquinoline-3-carboxylic acid (4-amino-1H-benzoimidazol-2-yl)-amide in AcOH (5 mL) was added formaldehyde (0.7 mL, 37% aq. solution), 0.3 mL of ethanedial and NH₄OAc (0.5 g). The mixture was heated at 120° C. for 1 h. After cooling to room temperature and usual workup, the residue was purified by column chromatography eluting with EtOAc/methanol (v/v=110:1) to give 13 mg (18%) of isoquinoline-3-carboxylic acid (4-imidazol-1-yl-1H-benzoimidazol-2-yl)-amide. LCMS: 355 (M+1)⁺.

Example 151

To a solution of 0.17 g (0.5 mmol) of 2-[(isoquinoline-3-carbonyl)-amino]-1H-benzoimidazole-4-carboxylic acid (from Example 58) in DMF (3 mL) was added 0.13 g (1 mmol) of 1-chloro-3,3-dimethyl-butan-2-one and DIEA (1 mL). The mixture was stirred at room temperature for 1 h., extracted with ethyl acetate, washed with water and brine. The organic layer was dried over magnesium sulfate, evaporated under reduced pressure to provide the 0.17 g (85%) of the keto ester which was dissolved in AcOH (5 mL), 0.5 g of NH₄OAc was added, the mixture was stirred at 100° C. for 1 h under microwave (150 W, 250 psi). The solvent was evaporated and the residue was purified by column chromatography eluting with DCM/EtOAc (v/v=1:1) to give 90 mg (73%) of isoquinoline-3-carboxylic acid [4-(4-tert-butyl-oxazol-2-yl)-1H-benzoimidazol-2-yl]-amide. LCMS: 412 (M+1)⁺.

Example 152

To a stirring mixture of 1.0 g (5.2 mmol) of 2-amino-3H-benzoimidazole-4-carboxylic acid methyl ester (Intermediate A) and 0.86 g (5.2 mmol) of CDI in 3.0 mL of DMF was added 0.75 g (5.2 mmol) of Isoquinolin-3-ylamine. The reaction mixture was heated at 60° C. for 30 min, and then cooled to room temperature. 5.0 mL of water was added. The resulting solid was filtered washed with water (10 ml) and ether (10 mL), and dried to provide the 2-(3-isoquinolin-3-yl-ureido)-1H-benzoimidazole-4-carboxylic acid methyl ester as a solid which was hydrolyzed as described in general procedure B to provide 0.75 g (40%) of 2-(3-isoquinolin-3-yl-ureido)-1H-benzoimidazole-4-carboxylic acid. LCMS: 348 (M+1)⁺.

0.2 g (0.57 mmol) of the above acid was reacted with 0.24 g (0.63 mmol) of HBTU and 0.083 g (0.57) of 1H-pyrazole-1-carboxamidine as described in general procedure A. After the reaction was complete the reaction mixture was diluted with water (5.0 mL), and saturated NaHCO₃ was added and stirred for 15 min. The resulting solid was filtered, washed with water, ether, and dried under vacuum to provide 0.15 g (62.5%) of isoquinoline-3-carboxylic acid {4-[(imino-pyrazol-1-yl-methyl)-carbamoyl]-1H-benzoimidazol-2-yl}-amide as a solid. LCMS: 425 (M+1)⁺.

To a stirring solution of 0.05 g (0.12 mmoL) of above amide and 0.088 g (1.12 mmol) of 3-amino-propan-1-ol in DCM (5.0 mL) was added 0.077 g (0.68 mmol) of DIEA. The reaction mixture was stirred at r.t. overnight. 5.0 mL of water was added, and the resulting solid was filtered, washed with water and ether, and dried to provide 0.03 g (57.6%) of 1-{4-[N'-(3-hydroxy-propyl)-guamidinocarbonyl]-1H-benzoimidazol-2-yl}-3-isoquinolin-3-yl-urea. LCMS: 447 (M+1)⁺.

By analogous methods to those used to prepare Example 152 and those in the relevant above schemes, the following compounds were synthesized.

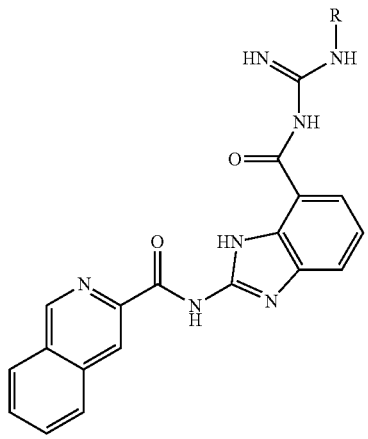

| EX | R | LCMS (M + 1)+ |
|---|---|---|
| 153 | n-propyl | 431 |
| 154 | 4-hydroxy-butyl | 461 |

Example 155

100 mg (0.3 mmol) of 2-[(isoquinoline-3-carbonyl)-amino]-1H-benzoimidazole-4-carboxylic acid (from Example 58) was reacted with 130 mg (0.33 mmol) of HBTU and 55 mg (0.3 mmol) 4-methanesulfonyl-benzylamine in 3.0 mL of DMF and 1.0 mL of DIEA as described in general procedure A. After the usual work up as described in general procedure A, 50 mg (33%) of isoquinoline-3-carboxylic acid [4-(4-methanesulfonyl-benzylcarbamoyl)-1H-benzoimidazol-2-yl]-amide was isolated. LCMS: 500 (M+1)+.

Example 156

To a solution of 5 g (38 mmol) of 2-chloro-cyclohexanone in MeCN (150 mL) was added 7 g (69 mmol) of N-acetyl-guanidine. The mixture was refluxed for 24 h. After removal of all the solvent, the residue was stirred with sat. aq. Na₂CO₃ (50 mL) for 5 min, filtered, and the solid was dried to provide 1 g (14%) of N-(4,5,6,7-tetrahydro-1H-benzoimidazol-2-yl)-acetamide. LCMS: 180 (M+1)+. ¹H NMR (DMSO-d₆, 400 MHz): δ 2.38 (m, 4H), 2.00 (s, 3H), 1.65 (m, 4H) ppm.

To a solution of 150 mg (0.83 mmol) of N-(4,5,6,7-tetrahydro-1H-benzoimidazol-2-yl)-acetamide in methanol (3 mL) was added water (3 mL) and conc. H₂SO₄ (0.3 mL). The mixture was heated at 100° C. under microwave (150 w, 250 psi) for 1 h. After removal of all the solvents, the residue was neutralized with sat. aq. Na₂CO₃ solution then diluted with methanol (50 mL). After removal of the inorganic salts through filtration, the organic phase was concentrated and dried under vacuum to afford 100 mg (86%) of the 4,5,6,7-tetrahydro-1H-benzoimidazol-2-ylamine, which was used for the next step without further purification.

To a solution of 70 mg (0.2 mmol) of 2-[(isoquinoline-3-carbonyl)-amino]-3H-benzoimidazole-4-carboxylic acid in DMF (2 mL) was added 100 mg (0.26 mmol) of HBTU and DIEA (0.3 mL). The mixture was stirred for 5 min, then 100 mg (0.7 mmol) of (4,5,6,7-tetrahydro-1H-benzoimidazol-2-ylamine was added. The resulting reaction mixture was heated at 80° C. for 1.5 h. After usual workup, the residue was purified by column chromatography eluting with DCM/EtOAc (v/v=11:1) to afford 12 mg (13%) of isoquinoline-3-carboxylic acid [4-(4,5,6,7-tetrahydro-1H-benzoimidazol-2-ylcarbamoyl)-1H-benzoimidazol-2-yl]-amide. LCMS: 452 (M+1)+.

Example 157

A mixture of 4.9 g (29.4 mmol) of (1H-imidazol-4-yl)-acetic acid hydrochloride, 4 N HCl in dioxane (22.5 mL) and methanol (70 mL) was refluxed overnight. Evaporation of the solvents gave (1H-imidazol-4-yl)-acetic acid methyl ester hydrochloride. LCMS: 141 (M+1)+.

An aqueous solution (5.1 mL) of sodium nitrite (4.5 mmol, 311 mg) was cooled in an ice bath and added to a mixture of 694 mg (4.5 mmol) of 4-amino-benzoic acid methyl ester in 2.36 N aq. HCl (7.5 mL) at 0° C. The mixture was stirred at 0° C. for 30 min, and the reaction mixture was added to a mixture of 795 mg (4.5 mmol) of (1H-imidazol-4-yl)-acetic acid methyl ester hydrochloride in saturated aqueous sodium tetraborate solution (150 mL). The mixture was stirred at 0° C. for 1.5 h and slowly warmed up to room temperature. The 4-(4-Methoxycarbonylmethyl-1H-imidazol-2-ylazo)-benzoic acid methyl ester was obtained after filtering and washing with water in a quantitative yield. LCMS: 303 (M+1)+.

A mixture of 4-(4-methoxycarbonylmethyl-1H-imidazol-2-ylazo)-benzoic acid methyl ester (2 mmol, 604 mg) synthesized above, platinum (IV) oxide (60 mg) and methanol (50 mL) was hydrogenated (60 psi) for two days (another portion of PtO₂ was added after one day). Trifluoroacetic acid (TFA) (2 mmol, 0.15 mL) was added to the reaction mixture and it was filtered. The filtrate was concentrated and diluted with water, washed with ether (2×50 mL). Evaporation of the water from the aqueous solution gave the (2-Amino-1H-imidazol-4-yl)-acetic acid methyl ester as a TFA salt. (273.8 mg, 51%). LCMS: 156 (M+1)+.

2-({2-[(Isoquinoline-3-carbonyl)-amino]-1H-benzoimidazole-4-carbonyl}-amino)-3H-imidazol-4-yl]-acetic acid methyl ester was synthesized according to the general procedure A using 339 mg (1.02 mmol) of 2-[(isoquinoline-3-carbonyl)-amino]-1H-benzoimidazole-4-carboxylic acid, 1.02 mmol of (2-amino-1H-imidazol-4-yl)-acetic acid methyl ester trifluoro-acetic acid, 387 mg (1.02 mmol) of HBTU, 3 mL of DMF and 0.704 mL (4 mmol) of DIEA heated at 80° C. for 2 h. Purification by column chromatography gave 234 mg (0.50 mmol, yield 49%) of the desired compound. LCMS: 470 (M+1)+.

Example 158

[2-({2-[(Isoquinoline-3-carbonyl)-amino]-1H-benzoimidazole-4-carbonyl}-amino)-3H-imidazol-4-yl]-acetic acid was synthesized according to general Procedure B from 225 mg (0.479 mmol) of 2-({2-[(isoquinoline-3-carbonyl)-amino]-1H-benzoimidazole-4-carbonyl}-amino)-3H-imidazol-4-yl]-acetic acid methyl ester, 0.5 mL of 2 N aq. LiOH, 2 mL of THF and 0.5 mL of methanol stirring at room temperature for 3 h. 116.9 mg (54%) of the product was obtained. LCMS: 456 (M+1)+.

Example 159

Isoquinoline-3-carboxylic acid (4-{5-[(methoxy-methyl-carbamoyl)-methyl]-1H-imidazol-2-ylcarbamoyl}-1H-benzoimidazol-2-yl)-amide was synthesized according to the general procedure A from 109 mg (0.239 mmol) of 2-({2-[(isoquinoline-3-carbonyl)-amino]-1H-benzoimidazole-4-carbonyl}-amino)-3H-imidazol-4-yl]-acetic acid, 50 mg (0.5 mmol) of O,N-dimethyl-hydroxylamine hydrochloride, 91 mg (0.24 mmol) of HBTU, 0.176 mL (1 mmol) of DIEA and 1 mL DMF stirring at room temperature for 1 h. 64.4 mg (54%) of the product was obtained. LCMS: 499 (M+1)$^+$.

By analogous methods to those used to prepare Examples 155 to 159 and those in the relevant above schemes, the following compounds were synthesized.

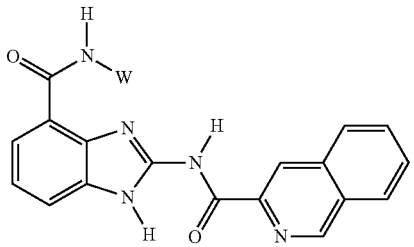

| Ex. | W | LCMS (M + 1)$^+$ |
|---|---|---|
| 160 | 5-Isopropyl-1H-imidazol-2-yl | 440 |
| 161 | 4-fluoro-phenyl | 426 |
| 162 | 1-(4-methanesulfonyl-phenyl)-ethyl | 514 |
| 163 | 3-methanesulfonyl-phenyl | 486 |
| 164 | 4-trifluoromethoxy-benzyl | 506 |
| 165 | 4-methoxy-benzyl | 452 |
| 166 | 4-methyl-benzyl | 436 |
| 167 | 4-fluoro-benzyl | 440 |
| 168 | 4-chloro-benzyl | 456 |
| 169 | 3-trifluoromethyl-benzyl | 490 |
| 170 | 3-fluoro-4-trifluoromethyl-benzyl | 508 |
| 171 | 3,5-difluoro-benzyl | 458 |
| 172 | 4-cyano-benzyl | 447 |
| 173 | N'(4,5-dihydro-1H-imidazol-2-yl)-hydrazino | 415 |
| 174 | 3-methoxy-benzyl | 452 |
| 175 | 4-methoxy-phenyl | 438 |
| 176 | 2-(4-methoxy-phenyl)-ethyl | 466 |
| 177 | 3-fluoro-benzyl | 440 |
| 178 | 4-sulfamoyl-benzyl | 501 |
| 179 | 2-methoxy-benzyl | 452 |
| 180 | 2-ethoxy-benzyl | 466 |
| 181 | 2,2-dioxo-1,3-dihydrobenzo[c]thiophen-5-yl | 498 |
| 182 | 2-(4-phenoxy-phenyl)-ethyl | 528 |
| 183 | butyl | 388 |
| 184 | 3H-imidazo[4,5-c]pyridin-2-yl | 449 |
| 185 | 7H-purin-8-yl | 450 |
| 186 | isoquinolin-6-yl | 459 |
| 187 | 2-methylsulfanyl-ethyl | 406 |
| 188 | 5,5-dimethyl-7-oxo-4,5,6,7-tetrahydro-benzothiazol-2-yl | 511 |
| 189 | 1H-benzoimidazol-5-yl | 448 |
| 190 | 1H-pyrazol-3-yl | 398 |
| 191 | 2-amino-pyrimidin-4-yl | 425 |
| 192 | 4-tert-butyl-1H-imidazol-2-yl | 454 |
| 193 | 4,5-dimethyl-1H-imidazol-2-yl | 426 |
| 194 | 5-ethyl-1H-imidazol-2-yl | 426 |
| 195 | 5-adamantan-1-yl-1H-imidazol-2-yl | 532 |
| 196 | 5-benzyl-1H-imidazol-2-yl | 488 |

Example 197

To a solution of 4 g (20 mmol) of 4-oxo-piperidine-1-carboxylic acid tert-butyl ester in THF (60 mL) was added 10 g (20 mmol) of pyrrolidone hydrotribromide. The reaction mixture was refluxed for 5 min, after cooling to room temperature, the solid (pyrrolidone HBr salt) was filtered off, the organic layer was concentrated and used for the next step without further purification.

The above crude material was dissolved in ethanol (50 mL), and 2.2 g (30 mmol) of thiourea was added. The mixture was refluxed for 3 h, and the solvent was evaporated under reduced pressure. The residue was dissolved in methanol (50 mL), then 4 M HCl solution in 1,4-dioxane (24 mL) was added. The mixtures were refluxed for 5 min. After removal of all solvent, the residue was dissolved in DCM (20 mL), and hexane (20 mL) was added. The resulting solid was filtered and dried to afford 4,5,6,7-tetrahydro-thiazolo[5,4-c]pyridin-2-ylamine HCl salt which was then dissolved in dioxane (25 mL) and sodium carbonate solution (1M, 25 mL). To this stirring solution, 2.2 g (10 mmol) of di-tert-butyl dicarbonate was added. Then the reaction mixture was stirred at room temperature for 2 h., extracted with ethyl acetate, washed with water and brine. The organic layer was dried over magnesium sulfate, concentrated under reduced pressure and purified by column chromatography eluting with hexanes/ethyl acetate (v/v=1:1 then 1:2) to give 1.2 g (24%, 3 steps) of 2-amino-6,7-dihydro-4H-thiazolo[5,4-c]pyridine-5-carboxylic acid tert-butyl ester. $^1$H NMR (DMSO-d$_6$, 400 MHz): δ 6.82 (bs, 2H), 4.29 (s, 2H), 3.58 (t, 2H), 2.41 (t, 2H), 1.41 (s, 9H) ppm.

To a solution of 0.25 g (0.75 mmol) of 2-[(isoquinoline-3-carbonyl)-amino]-3H-benzoimidazole-4-carboxylic acid in DMF (4 mL) was added 0.4 g (1.05 mmol) of HBTU and DIEA (1 mL). The mixture was stirred for 5 min and then 0.18 g (0.7 μmmol) of 2-amino-6,7-dihydro-4H-thiazolo[5,4-c]pyridine-5-carboxylic acid tert-butyl ester was added. The resulting reaction mixture was heated at 80° C. for 2 h. After usual workup, the residue was purified by column chromatography to afford the 0.2 g (55%) of 2-({2-[(isoquinoline-3-carbonyl)-amino]-3H-benzoimidazole-4-carbonyl}-amino)-6,7-dihydro-4H-thiazolo[5,4-c]pyridine-5-carboxylic acid tert-butyl ester. LCMS: 570 (M+1)$^+$. $^1$H NMR (DMSO-d$_6$, 400 MHz): δ 9.56 (s, 1H), 8.84 (s, 1H), 8.35 (m, 2H), 7.96 (m, 4H), 7.84 (d, 1H), 7.35 (t, 1H), 4.58 (bs, 2H), 3.70 (t, 2H), 2.73 (t, 2H), 1.44 (s, 9H) ppm.

Example 198

To a solution of 0.2 g (0.35 mmol) of 2-({2-[(isoquinoline-3-carbonyl)-amino]-3H-benzoimidazole-4-carbonyl}-amino)-6,7-dihydro-4H-thiazolo[5,4-c]pyridine-5-carboxylic acid tert-butyl ester in methanol (1 mL) was added HCl solution (5 mL, 4M HCl in 1,4-dioxane). The mixture was stirred at room temperature for 30 min. The conversion was checked by LCMS. After removal of the organic phase, the residue was diluted with DCM (50 mL) and the organic phase was washed with sat. aq. Na$_2$CO$_3$ solution, water, brine, dried over Na$_2$SO$_4$ and concentrated to afford 160 mg (100%) of isoquinoline-3-carboxylic acid [7-(4,5,6,7-tetrahydro-thiazolo[5,4-c]pyridin-2-ylcarbamoyl)-1H-benzoimidazol-2-yl]-amide. LCMS: 470 (M+1)$^+$.

Example 199

To a solution of 20 mg (0.042 mmol) of isoquinoline-3-carboxylic acid [7-(4,5,6,7-tetrahydro-thiazolo[5,4-c]pyridin-2-ylcarbamoyl)-1H-benzoimidazol-2-yl]-amide (above example) in DCE (3 mL) was added 0.2 g (0.94 mmol) of sodium triacetoxyborohydride and acetaldehyde (0.1 mL). The mixture was stirred at room temperature over night. After LCMS showed that the starting material was completely consumed, the reaction was quenched by addition of methanol (2 mL). After usual workup, the residue was dissolved in DCM (1 mL). The desired product crashed out by addition of hexanes and 12 mg (57%) of isoquinoline-3-carboxylic acid [7-(5-ethyl-4,5,6,7-tetrahydro-thiazolo[5,4-c]pyridin-2-ylcarbamoyl)-1H-benzoimidazol-2-yl]-amide was collected after filtration. LCMS: 498 (M+1)$^+$.

Example 200

To a solution of 25 mg (0.05 mmol) of isoquinoline-3-carboxylic acid [7-(4,5,6,7-tetrahydro-thiazolo[5,4-c]pyridin-2-ylcarbamoyl)-1H-benzoimidazol-2-yl]-amide (Example 198) in pyridine (2 mL) was added 21.3 mg (0.15 mmol) of 1-propanesulfonyl chloride. The mixture was stirred at room temperature for 12 h, extracted with ethyl acetate, washed with 1N HCl, water and brine. The organic layer was dried over magnesium sulfate, evaporated under reduced pressure. The crude product was dissolved in DCM (0.5 mL), hexane was added (4 ml) and the resulting precipitate was filtered and dried to provide 12 mg (57%) of isoquinoline-3-carboxylic acid [7-(5-propanyl-1-sulfonly-4,5,6,7-tetrahydro-thiazolo[5,4-c]pyridin-2-ylcarbamoyl)-1H-benzoimidazol-2-yl]-amide. LCMS: 576(M+1)$^+$.

Example 201

To a solution of 20 mg (0.042 mmol) of isoquinoline-3-carboxylic acid [7-(4,5,6,7-tetrahydro-thiazolo[5,4-c]pyridin-2-ylcarbamoyl)-1H-benzoimidazol-2-yl]-amide (Example 198) in THF (2 mL) was added 0.1 mL of 2-isocyanato-2-methyl-propane and DIEA (0.2 mL). The mixture was stirred at room temperature for 30 min. After LCMS showed that the starting material was completely consumed, the reaction mixture was diluted with ethyl acetate (20 mL). The organic phase was washed with sat. aq. Na$_2$CO$_3$ solution, dried over Na$_2$SO$_4$, and concentrated under reduced pressure. The crude product was dissolved in DCM (0.5 mL), hexane was added (4 ml) and the resulting precipitate was filtered and dried to provide 11 mg (46%) of isoquinoline-3-carboxylic acid [4-(5-tert-butylcarbamoyl-4,5,6,7-tetrahydro-thiazolo[5,4c]pyridin-2-ylcarbamoyl)-1H-benzoimidazol-2-yl]-amide. LCMS: 569 (M+1)$^+$.

Example 202

To a solution of 30 mg (0.063 mmol) of isoquinoline-3-carboxylic acid [7-(4,5,6,7-tetrahydro-thiazolo[5,4-c]pyridin-2-ylcarbamoyl)-1H-benzoimidazol-2-yl]-amide (Example 198) in DCM (2 mL) was added pyridine (0.5 mL) and benzoyl chloride (0.05 mL). The mixture was stirred at room temperature overnight. The reaction mixture was diluted with ethyl acetate (20 mL), the organic phase was washed with sat. aq. Na$_2$CO$_3$ solution, dried over Na$_2$SO$_4$, and concentrated under reduced pressure. The crude product was dissolved in DCM (0.5 mL), hexane was added (4 mL), and the resulting precipitate was filtered and dried to provide 17 mg (47%) of isoquinoline-3-carboxylic acid [4-(5-benzoyl-4,5,6,7-tetrahydro-thiazolo[5,4-c]pyridin-2-ylcarbamoyl)-1H-benzoimidazol-2-yl]-amide. LCMS: 574 (M+1)$^+$.

Example 203

To a solution of 30 mg (0.064 mmol) of isoquinoline-3-carboxylic acid [7-(4,5,6,7-tetrahydro-thiazolo[5,4-c]pyridin-2-ylcarbamoyl)-1H-benzoimidazol-2-yl]-amide (Example 198) in DCE (0.7 mL) was added 3-methylsulfanyl-propionaldehyde (0.1 mL), 0.2 g (0.94 mmol) of sodium triacetoxyborohydride, the mixture was stirred at room temperature for 1 h. The reaction was quenched by addition of methanol (0.5 mL). After usual workup, the reaction was quenched by addition of methanol (2 mL). After usual workup, the residue was dissolved in DCM (1 mL) and the desired product was precipitated by addition of hexanes. 21 mg (58%) of isoquinoline-3-carboxylic acid {4-[5-(3-methylsulfanyl-propyl)-4,5,6,7-tetrahydro-thiazolo[5,4-c]pyridin-2-ylcarbamoyl]-1H-benzoimidazol-2-yl}-amide was collected after filtration. LCMS: 558 (M+1)$^+$.

Example 204

To a solution of 20 mg (0.037 mmol) of thioether (Example 203) in DCM (2.5 mL) was added 25 mg (0.14 mmol) of m-CPBA. The reaction was stirred at room temperature for 2 h. The solvent was evaporated under reduced pressure. The crude product was dissolved in DCM (0.5 mL), hexane was added (4 mL), and the resulting precipitate was filtered and dried to provide 11 mg (47%) of isoquinoline-3-carboxylic acid {4-[5-(3-methanesulfonyl-propyl)-4,5,6,7-tetrahydro-thiazolo[5,4-c]pyridin-2-ylcarbamoyl]-1H-benzoimidazol-2-yl}-amide. LCMS: 590 (M+1)$^+$.

By analogous methods to those used to prepare Examples 197 to 204 and those in the relevant above schemes, the following compounds were synthesized.

| Ex. | W | LCMS (M + 1)$^+$ |
|---|---|---|
| 205 | piperidin-4-yl-1-carboxylic acid tert-butyl ester | 515 |
| 206 | piperidin-4-yl | 488 |
| 207 | piperidin-4-yl-1-carboxylic acid isopropyl ester | 501 |
| 208 | 5-methanesulfonyl-4,5,6,7-tetrahydro-thiazolo[5,4-c]pyridin-2-yl | 548 |
| 209 | 5-benzyl-4,5,6,7-tetrahydro-thiazolo[5,4-c]pyridin-2-yl | 560 |
| 210 | 4,5,6,7-tetrahydro-benzothiazol-2-yl | 469 |
| 211 | 6-methyl-4,5,6,7-tetrahydro-benzothiazol-2-yl | 483 |
| 212 | 5-methyl-4,5,6,7-tetrahydro-thiazolo[5,4-c]pyridin-2-yl | 484 |
| 213 | 5-cyclopentylmethyl-4,5,6,7-tetrahydro-thiazolo[5,4-c]pyridin-2-yl | 662 |
| 214 | 5-pyridin-3-ylmethyl-4,5,6,7-tetrahydro-thiazolo[5,4-c]pyridin-2-yl | 707 |
| 215 | 5-cyclohexylmethyl-4,5,6,7-tetrahydro-thiazolo[5,4-c]pyridin-2-yl | 676 |
| 216 | 5-furan-3-ylmethyl-4,5,6,7-tetrahydro-thiazolo[5,4-c]pyridin-2-yl | 660 |
| 217 | piperidin-3-ylmethyl-1-carboxylic acid tert-butyl ester | 529 |
| 218 | piperidin-4-ylmethyl-1-carboxylic acid tert-butyl ester | 529 |
| 219 | piperidin-3-ylmethyl | 538 |
| 220 | piperidin-4-ylmethyl | 538 |
| 221 | 5-(1-methyl-1H-pyrrol-2-ylmethyl)-4,5,6,7-tetrahydro-thiazolo[5,4-c]pyridin-2-yl | 563 |
| 222 | 5-propyl-4,5,6,7-tetrahydro-thiazolo[5,4-c]pyridin-2-yl | 621 |
| 223 | 5-(2-ethyl-butyl)-4,5,6,7-tetrahydro-thiazolo[5,4-c]pyridin-2-yl | 664 |
| 224 | 5-isobutyl-4,5,6,7-tetrahydro-thiazolo[5,4-c]pyridin-2-yl | 636 |
| 225 | 1-cyclohexylmethyl-piperidin-3-ylmethyl | 635 |
| 226 | 1-cyclohexylmethyl-piperidin-4-ylmethyl | 635 |
| 227 | 2-piperidin-3-yl-ethyl-1-carboxylic acid tert-butyl ester | 543 |
| 228 | 2-piperidin-4-yl-ethyl-1-carboxylic acid tert-butyl ester | 543 |
| 229 | 2-piperidin-3-yl-ethyl | 552 |
| 230 | 2-piperidin-4-yl-ethyl | 552 |
| 231 | 5-(2,4-dimethoxy-benzyl)-4,5,6,7-tetrahydro-thiazolo[5,4-c]pyridin-2-yl | 620 |
| 232 | 5-(4-chloro-benzyl)-4,5,6,7-tetrahydro-thiazolo[5,4-c]pyridin-2-yl | 595 |
| 233 | 5-(4-fluoro-benzyl)-4,5,6,7-tetrahydro-thiazolo[5,4-c]pyridin-2-yl | 578 |

-continued

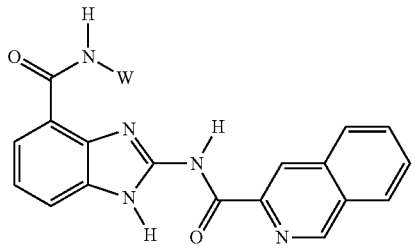

| Ex. | W | LCMS (M + 1)+ |
|---|---|---|
| 234 | 5-(4-isopropoxy-benzyl)-4,5,6,7-tetrahydro-thiazolo[5,4-c]pyridin-2-yl | 618 |
| 235 | 5-(2-methoxy-benzyl)-4,5,6,7-tetrahydro-thiazolo[5,4-c]pyridin-2-yl | 590 |
| 236 | 5-(3-methoxy-benzyl)-4,5,6,7-tetrahydro-thiazolo[5,4-c]pyridin-2-yl | 590 |
| 237 | 5-(4-methoxy-benzyl)-4,5,6,7-tetrahydro-thiazolo[5,4-c]pyridin-2-yl | 590 |
| 238 | 5-phenethyl-4,5,6,7-tetrahydro-thiazolo[5,4-c]pyridin-2-yl | 574 |
| 239 | 5-thiophen-2-ylmethyl-4,5,6,7-tetrahydro-thiazolo[5,4-c]pyridin-2-yl | 566 |
| 240 | 5-thiophen-3-ylmethyl-4,5,6,7-tetrahydro-thiazolo[5,4-c]pyridin-2-yl | 566 |
| 241 | 5-(3-methyl-butyl)-4,5,6,7-tetrahydro-thiazolo[5,4-c]pyridin-2-yl | 540 |
| 242 | piperidin-3S-ylmethyl-1-carboxylic acid tert-butyl ester | 529 |
| 243 | piperidin-3R-ylmethyl-1-carboxylic acid tert-butyl ester | 529 |
| 244 | piperidin-3S-ylmethyl | 429 |
| 245 | piperidin-3R-ylmethyl | 429 |
| 246 | 5-(3H-imidazol-4-ylmethyl)-4,5,6,7-tetrahydro-thiazolo[5,4-c]pyridin-2-yl | 550 |
| 247 | 5-(1-methyl-1H-imidazol-2-ylmethyl)-4,5,6,7-tetrahydro-thiazolo[5,4-c]pyridin-2-yl | 564 |
| 248 | 5-(1H-imidazol-2-ylmethyl)-4,5,6,7-tetrahydro-thiazolo[5,4-c]pyridin-2-yl | 550 |
| 249 | 5-cyclopropylmethyl-4,5,6,7-tetrahydro-thiazolo[5,4-c]pyridin-2-yl | 524 |
| 250 | 5-(3,3-dimethyl-butyl)-4,5,6,7-tetrahydro-thiazolo[5,4-c]pyridin-2-yl | 554 |
| 251 | 1,2,3,4-tetrahydro-isoquinolin-6-yl-2-carboxylic acid tert-butyl ester | 563 |
| 252 | 1,2,3,4-tetrahydro-isoquinolin-6-yl | 572 |
| 253 | 1-cyclohexylmethyl-piperidin-3S-ylmethyl | 635 |
| 254 | 1-cyclohexylmethyl-piperidin-3R-ylmethyl | 635 |
| 255 | 5-thiazol-2-ylmethyl-4,5,6,7-tetrahydro-thiazolo[5,4-c]pyridin-2-yl | 567 |
| 256 | 5-(5-methyl-3H-imidazol-4-ylmethyl)-4,5,6,7-tetrahydro-thiazolo[5,4-c]pyridin-2-yl | 564 |
| 257 | 5-(2-ethyl-5-methyl-3H-imidazol-4-ylmethyl)-4,5,6,7-tetrahydro-thiazolo[5,4-c]pyridin-2-yl | 592 |
| 258 | 2S-[2-amino-6,7-dihydro-4H-thiazolo[5,4-c]pyridin-5-ylmethyl]-pyrrolidine-1-carboxylic acid tert-butyl ester | 653 |
| 259 | 5-quinolin-3-ylmethyl-4,5,6,7-tetrahydro-thiazolo[5,4-c]pyridin-2-yl | 611 |
| 260 | 2S-{3-[amino-methyl]-piperidin-1-ylmethyl}-pyrrolidine-1-carboxylic acid tert-butyl ester | 612 |
| 261 | 2R-{3-[amino-methyl]-pipendin-1-ylmethyl}-pyrrolidine-1-carboxylic acid tert-butyl ester | 612 |
| 262 | 5-pyrrolidin-2S-ylmethyl-4,5,6,7-tetrahydro-thiazolo[5,4-c]pyridin-2-yl | 699 |
| 263 | 1-(1H-imidazol-2-ylmethyl)-piperidin-3-ylmethyl | 509 |
| 264 | 1-(1-methyl-1H-imidazol-2-ylmethyl)-piperidin-3-ylmethyl | 523 |
| 265 | 1-(1H-imidazol-4-ylmethyl)-piperidin-3-ylmethyl | 509 |

Example 266

To a solution of 100 mg (0.3 mmol) of 2-[(isoquinoline-3-carbonyl)-amino]-3H-benzoimidazole-4-carboxylic acid (from Example 58) in DMF (2 mL) was added 200 mg (0.53 mmol) of HBTU and DIEA (0.5 mL). The mixture was stirred for 5 min then 140 mg (1.0 mmol) of N-(4-fluoro-benzyl)-N-methyl-amine was added. The resulted reaction mixture was heated at 70° C. for 1 h. After usual workup as described in general procedure A, the residue was purified by column chromatography eluting with DCM/EtOAc (v/v=1:1) to afford the 90 mg (66%) of isoquinoline-3-carboxylic acid {7-[(4-fluoro-benzyl)-methyl-carbamoyl]-1H-benzoimidazol-2-yl}-amide. LCMS: 454 (M+1)+.

Example 267

Isoquinoline-3-carboxylic acid (4-dibenzylcarbamoyl-1H-benzoimidazol-2-yl)-amide (40 mg) was synthesized according to the general procedure described for the synthesis of Example 266, with the exception that N,N-dibenzylamine was used instead of N-(4-fluorobenzyl)-N-methyl-amine. LCMS: 512 (M+1)+.

Example 268

3.00 g (10 mmol) of tert-Butoxycarbonylamino-(dimethoxy-phosphoryl)-acetic acid methyl ester was added to a solution containing 1.69 g (10 mmol) of 2-formyl-benzoic acid methyl ester and 1.51 mL (10 mmol) of DBU in 50 mL of dichloromethane at 0° C. The reaction was slowly warmed to room temperature overnight, then diluted with dichloromethane (100 mL), washed once with water (150 mL) and dried over sodium sulfate. Purification by column chromatography on silica gel gave 2.12 g (70%) of the product as white solid. LCMS: 304 (M+1)+.

6 mL of 4 N HCl in dioxane (6 mL) was added to a solution of 1-oxo-1H-isoquinoline-2,3-dicarboxylic acid 2-tert-butyl ester 3-methyl ester from the previous step and 10 mL of dichloromethane and stirred overnight. The reaction mixture was concentrated and partitioned between ethyl acetate (100 mL) and saturated NaHCO$_3$ solution (100 mL). The aqueous layer was separated and extracted again with ethyl acetate (100 mL). The combined organic layers were dried over sodium sulfate. Evaporation of solvents in vacuo gave 1.39 g (98%) of the 1-oxo-1,2-dihydro-isoquinoline-3-dicarboxylic acid methyl ester as a white solid. LCMS: 204 (M+1)+.

663 mg (81%) of 1-Oxo-1,2-dihydro-isoquinoline-3-dicarboxylic acid was synthesized according to General Procedure B using above synthesized 877 mg (4.32 mmol) of 1-oxo-1,2-dihydro-isoquinoline-3-dicarboxylic acid methyl ester, 4.3 mL of 2 N aq. LiOH, 16 mL of THF and 4 mL of methanol stirring at r.t. overnight. LCMS: 190 (M+1)+.

76 mg (0.4 mmol) of 1-oxo-1,2-dihydro-isoquinoline-3-dicarboxylic acid was reacted with 73 mg (0.3 mmol) of intermediate B (2-amino-3H-benzoimidazole-4-carboxylic acid (1H-imidazol-2-yl)-amide), 152 mg (0.4 mmol) of HBTU, 0.176 mL (1 mmol) of DIEA and 1.2 mL of DMF stirring at 85° C. for 2 h according to general Procedure A 54.5 mg (0.132 mmol, 44%) of 1-oxo-1,2-dihydro-isoquinoline-3-carboxylic acid [4-(1H-imidazol-2-ylcarbamoyl)-1H-benzoimidazol-2-yl]-amide was obtained. LCMS: 414 (M+1)+.

Example 269

6-(4-Methoxycarbonyl-1H-benzoimidazol-2-ylcarbamoyl)-3,4-dihydro-1H-isoquinoline-2-carboxylic acid tert-butyl ester (114 mg, 90%) was synthesized according to General Procedure A using 798 mg (2.82 mmol) of 3,4-dihydro-1H-isoquinoline-2,6-dicarboxylic acid 2-tert-butyl ester, 540 mg (2.82 mmol) of intermediate A (2-amino-1H-benzoimidazole-4-carboxylic acid methyl ester), 1.28 g (3.38 mmol) of HBTU, 0.992 mL (5.64 mmol) of DIEA and 15 mL of DMF stirring at room temperature overnight. LCMS: 451 (M+1)⁺.

Example 270

109 mg (0.242 mmol) of 6-(4-methoxycarbonyl-1H-benzoimidazol-2-ylcarbamoyl)-3,4-dihydro-1H-isoquinoline-2-carboxylic acid tert-butyl ester was hydrolyzed using 1 mL of 2 N aq. LiOH, 4 mL of THF and 1 mL of methanol stirring at room temperature for one day as described in general procedure B. 76.5 mg (72%) of the 6-(4-Carboxy-1H-benzoimidazol-2-ylcarbamoyl)-3,4-dihydro-1H-isoquinoline-2-carboxylic acid tert-butyl ester product was obtained. LCMS: 437 (M+1)⁺.

72.9 mg (0.167 mmol) of above acid was reacted with 47 mg (0.35 mmol) of 2-aminoimidazole sulfate, 95 mg (0.25 mmol) of HBTU, 0.176 mL (1 mmol) of DIEA and 1 mL DMF. The mixture was stirred at 80° C. for 18 h according to General Procedure A and gave 54.7 mg (65%) 6-[4-(1H-imidazol-2-ylcarbamoyl)-1H-benzoimidazol-2-ylcarbamoyl]-3,4-dihydro-1H-isoquinoline-2-carboxylic acid tert-butyl ester. LCMS: 502 (M+1)⁺.

Example 271

49.8 mg (0.10 mmol) of 6-[4-(1H-imidazol-2-ylcarbamoyl)-1H-benzoimidazol-2-ylcarbamoyl]-3,4-dihydro-1H-isoquinoline-2-carboxylic acid tert-butyl ester in 2 mL of 4 N HCl in dioxane was stirred at r.t. for 2 h. Evaporation of solvents in vacuo gave 1,2,3,4-tetrahydro-isoquinoline-6-carboxylic acid [4-(1H-imidazol-2-ylcarbamoyl)-1H-benzoimidazol-2-yl]-amide in quantitative yield. LCMS: 402 (M+1)⁺.

Example 272

25 mg (0.049 mmol) of 1,2,3,4-tetrahydro-isoquinoline-6-carboxylic acid [4-(1H-imidazol-2-ylcarbamoyl)-1H-benzoimidazol-2-yl]-amide, 0.01 mL of (0.07 mmol) benzenesulfonyl chloride, and 0.07 mL of (0.5 mmol) triethylamine in 0.5 mL DMF was stirred at room temperature for 1 h. The reaction mixture was then treated with 0.024 mL of hydrazine hydrate and diluted with water. The precipitated solid was filtered and washed with water to give 2-benzenesulfonyl-1,2,3,4-tetrahydro-isoquinoline-6-carboxylic acid [4-(1H-imidazol-2-ylcarbamoyl)-1H-benzoimidazol-2-yl]-amide (17.2 mg, 65%). LCMS: 542 (M+1)⁺.

Example 273

A mixture of 25 mg (0.049 mmol) of 1,2,3,4-tetrahydroisoquinoline-6-carboxylic acid [4-(1H-imidazol-2-ylcarbamoyl)-1H-benzoimidazol-2-yl]-amide, 0.0152 mL (0.15 mmol) of benzaldehyde and 0.6 mL of DMF was stirred for 10 min. 67 mg (0.3 mmol) of sodium triacetoxyborohydride was added and the reaction mixture was stirred at room temperature for 24 h. The reaction mixture was partitioned between dichloromethane (10 mL) and water (10 mL). The organic layer was separated and dried over sodium sulfate. Purification by column chromatography on silica gel gave 11.7 mg (49%) of 2-benzyl-1,2,3,4-tetrahydro-isoquinoline-6-carboxylic acid [4-(1H-imidazol-2-ylcarbamoyl)-1H-benzoimidazol-2-yl]-amide. LCMS: 492 (M+1)⁺.

Example 274

41 mg (0.08 mmol) of 1,2,3,4-tetrahydro-isoquinoline-6-carboxylic acid [4-(1H-imidazol-2-ylcarbamoyl)-1H-benzoimidazol-2-yl]-amide in 0.6 mL of DMF and 0.176 mL (1 mmol) of DIEA was treated with 0.024 mL (0.3 mmol) of methyl chloroformate and stirred at room temperature for 14 h. The reaction mixture was then treated with 0.15 mL of 2 N aq. LiOH. Water was added to the reaction mixture. The precipitated solid was collected by filtration and washed with water to yield 11.4 mg (0.0248 mmol, 31%) of 6-[4-(1H-imidazol-2-ylcarbamoyl)-1H-benzoimidazol-2-ylcarbamoyl]-3,4-dihydro-1H-isoquinoline-2-carboxylic acid methyl ester. LCMS: 460 (M+1)⁺.

By analogous methods to those used to prepare Examples 269 to 274 and those in the relevant above schemes, the following compounds were synthesized.

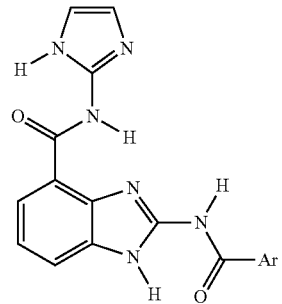

| Ex. | W | LCMS (M + 1)⁺ |
|---|---|---|
| 275 | 2-Methanesulfonyl-1,2,3,4-tetrahydro-isoquinoline-6-yl | 480 |
| 276 | 2-Ethoxycarbonyl-3,4-dihydro-1H-isoquinoline-6-yl | 474 |
| 277 | 2-Propoxycarbonyl-3,4-dihydro-1H-isoquinoline-6-yl | 488 |
| 278 | 2-Isobutoxycarbonyl-3,4-dihydro-1H-isoquinoline-6-yl | 502 |
| 279 | 2-Isopropoxycarbonyl-3,4-dihydro-1H-isoquinoline-6-yl | 488 |
| 280 | 2-Butoxycarbonyl-3,4-dihydro-1H-isoquinoline-6-yl | 502 |
| 281 | (3S)-2-tert-Butoxycarbonyl-3,4-dihydro-1H-isoquinoline-3-yl | 502 |
| 282 | (3S)-1,2,3,4-Tetrahydro-isoquinoline-3-yl | 511 |
| 283 | (3S)-2-Methanesulfonyl-1,2,3,4-tetrahydro-isoquinoline-3-yl | 480 |
| 284 | (3S)-2-Ethyl-1,2,3,4-tetrahydro-isoquinoline-3-yl | 539 |
| 285 | (3S)-2-tert-Butoxycarbonyl-1,3,4,9-tetrahydro-beta-carboline-3-yl | 541 |
| 286 | (3S)-2-tert-Butoxycarbonyl-1-phenyl-1,3,4,9-tetrahydro-beta-carboline-3-yl | 617 |
| 287 | 2,3,4,9-Tetrahydro-1H-beta-carboline-3-yl | 550 |

Example 288

To a stirring solution of 5.0 g (27.5 mmol) of 2-(3,4-dimethoxy-phenyl)-ethylamine was added 3.7 g (27.5 mmol) of ethyl oxalyl chloride at 0° C. The reaction mixture was warmed to r.t. and stirred for 1.0 h and 100 mL of DCM was added. The solvent was washed with 1.0 N HCl, water and brine, dried over the magnesium sulfate, and evaporated under reduced pressure to afford 7.76 g (100%) of the N-[2-(3,4-dimethoxy-phenyl)-ethyl]-oxalamic acid ethyl ester which was used for the next step without further purification. LCMS: 282 (M+1)⁺.

To a refluxing solution 5.0 g (17.7 mmol) of above oxalamide in 100 mL of CH₃CN was added 20 mL of POCl₃. After 12 h at reflux, the reaction mixture was poured onto ice and extracted 3 times with ether (3×50 mL). The ether extracts were washed twice with 1 N HCl. The combined aqueous extracts were brought to pH 8 with solid NaHCO₃. The aqueous extracts were then washed five times with EtOAc (5×50 mL). The combined organic layers were dried over magnesium sulfate and evaporated under reduced pressure to provide 3.2 g (69%) of 6,7-dimethoxy-3,4-dihydro-isoquinoline-1-carboxylic acid ethyl ester. LCMS: 264 (M+1)⁺.

A mixture of 0.26 g (1.0 mmol) of the above imine and 10% Pd—C in 5.0 mL of EtOH was stirred at r.t. under hydrogen (1 atm). After 5 h, the reaction mixture was filtered and evaporated to give a residue that was dissolved in DCM (5.0 mL) containing 0.2 g (2.0 mmol) of triethyl amine. To this stirring solution at r.t., 0.24 g (1.1 mmol) of di-tert-butyl dicarbonate was added and stirring continued for another 2 h. The reaction mixture was extracted with DCM (10 mL), washed with water, brine, dried over magnesium sulfate, and evaporated to provide 0.35 g (97%) of the 6,7-dimethoxy-3,4-dihydro-1H-isoquinoline-1,2-dicarboxylic acid 2-tert-butyl ester 1-ethyl ester. LCMS: 366 (M+1)⁺.

To a stirring solution of 0.35 g (0.95 mmol) of above ester in a mixture of THF (10 mL) and methanol (3.0 mL) was added 3.0 mL of 2N LiOH at r.t. The reaction mixture was stirred at r.t. for 45 min and neutralized (pH=6.0) with 2.0 N HCl and extracted with ethyl acetate. The organic layer was washed with water and brine, dried over magnesium sulfate, and evaporated under reduced pressure to afford 0.3 g (90%) of the 6,7-dimethoxy-3,4-dihydro-1H-isoquinoline-1,2-dicarboxylic acid 2-tert-butyl ester. LCMS: 338 (M+1)⁺.

0.25 g (0.74 mmol) of above acid, 0.30 g (0.81 mmol) of HBTU in a mixture of 4.0 ml of DMF and 0.5 mL of DIEA was reacted with 0.18 g (0.74 mmol) of 2-Amino-3H-benzoimidazole-4-carboxylic acid (1H-imidazol-2-yl)-amide (Intermediate B) as described in general procedure A. The reaction mixture was cooled to r.t. 5.0 mL of water and 5.0 mL of saturated NaHCO₃ was added. The resulting solid was filtered and the solid was washed with water, ether and dried to provide 0.2 g (48%) of 1-[4-(1H-imidazol-2-ylcarbamoyl)-1H-benzoimidazol-2-ylcarbamoyl]-6,7-dimethoxy-3,4-dihydro-1H-isoquinoline-2-carboxylic acid tert-butyl ester. LCMS: 562 (M+1)⁺.

Example 289

To a refluxing solution of 2.0 g (8.0 mmol) of 6,7-dimethoxy-3,4-dihydro-isoquinoline-1-carboxylic acid ethyl ester was added to 2.0 g of 10% Pd—C. After 12 h at reflux, the reaction mixture was cooled, filtered through celite, and evaporated under reduced pressure to provide 2.0 g (98%) of 6,7-dimethoxy-isoquinoline-1-carboxylic acid ethyl ester. LCMS: 262 (M+1)⁺.

To a stirring solution of 0.35 g (1.3 mmol) of above ester in a mixture of THF (10 mL) and methanol (3.0 mL) was added 3.0 mL of 2N LiOH at r.t. The reaction mixture was stirred at r.t. for 45 min and neutralized (pH=6.0) with 2.0 N HCl and extracted with ethyl acetate. The organic layer was washed with water, brine and dried over magnesium sulfate, evaporated the solvent under reduced pressure to afford 0.3 g (96%) of the 6,7-Dimethoxy-isoquinoline-1-carboxylic acid. LCMS: 234 (M+1)⁺.

0.1 g (0.43 mmol) of above acid, 0.17 g (0.47 mmol) of HBTU in a mixture of 2.0 ml of DMF and 0.24 mL of DIEA was reacted with 0.10 g (0.43 mmol) of 2-Amino-3H-benzoimidazole-4-carboxylic acid (1H-imidazol-2-yl)-amide (Intermediate B) as described in general procedure A. The reaction mixture was cooled to r.t. 5.0 mL of water, 5.0 mL of saturated NaHCO₃ was added and the resulting solid was filtered and the solid was washed with water, ether and dried to provide 0.005 g (2.6%) of 6,7-dimethoxy-isoquinoline-1-carboxylic acid [4-(1H-imidazol-2-ylcarbamoyl)-1H-benzoimidazol-2-yl]-amide. LCMS: 458 (M+1)⁺. ¹H NMR (DMSO-d₆, 400 MHz): δ 8.86 (s, 1H), 8.57 (d, 1H), 8.11 (d, 1H), 7.96 (d, 1H), 7.88 (d, 1H), 7.57 (s, 1H), 7.38 (m, 3H), 3.98 (s, 3H), 3.97 (s, 3H) ppm.

Example 290

To a solution of 2.1 g (10 mmol) of 1,2,3,4-Tetrahydro-isoquinoline-3-carboxylic acid HCl salt (2.1 g, 10 mmol) in conc. H₂SO₄ (15 mL) was added HNO₃ (70%, 2 mL) dropwise at −10° C. The mixture was stirred at −10° C. for 1.5 h then poured into ice. The reaction mixture was neutralized with conc. NH₄OH. The white precipitate was collected after filtration, dried under vacuum, dissolved in methanol (50 mL), and 4M HCl in dioxane was added. After refluxing overnight, the solvent was evaporated under reduced pressure to provide 1.5 g (63%) of the 7-nitro-1,2,3,4-tetrahydro-isoquinoline-3-carboxylic acid methyl ester.

To a solution of the above ester in 1,4-dioxane (100 mL) was added 2.8 g (12.7 mmol) of DDQ, and the reaction mixture was refluxed for 6 h. After removal of solvents, the residue was dissolved with ethyl acetate (250 mL) and washed with aq. NaHSO₃ solution (1M solution, 100 mL), water and brine. The ethyl acetate layer was dried over sodium sulfate, evaporated under reduced pressure and purified by column chromatography (eluting with ethyl acetate then EtOAc/methanol v/v=100:5) to provide 1.0 g (71%) of the 7-nitro-isoquinoline-3-carboxylic acid methyl ester. LCMS: 233 (M+1)⁺. The methyl ester was hydrolyzed according to the general procedure B to give 0.9 of 7-nitro-isoquinoline-3-carboxylic acid. LCMS: 219 (M+1)⁺.

To a solution of 44 mg (0.2 mmol) of 7-nitro-isoquinoline-3-carboxylic acid in DMF (1 mL) was added 113 mg (0.3 mmol) of HBTU and DIEA (0.3 mL). The mixture was stirred for 10 min and then 40 mg (0.16 mmol) of 2-amino-3H-benzoimidazole-4-carboxylic acid (1H-imidazol-2-yl)-amide (intermediate B) was added. The reaction was heated at 80° C. for 1 h. After the usual work up, the residue was purified by column chromatography eluting with DCM/methanol (v/v=10:1) to afford 8 mg (9%) of 7-nitro-isoquinoline-3-carboxylic acid [7-(1H-imidazol-2-ylcarbamoyl)-1H-benzoimidazol-2-yl]-amide. LCMS: 443 (M+1)⁺.

Example 291

0.5 g (2.1 mmol) of 7-nitro-isoquinoline-3-carboxylic acid methyl ester in methanol (25 ml) was hydrogenated according to the general procedure C to provide 0.42 g of 7-amino-isoquinoline-3-carboxylic acid methyl ester in quantitative yield. LCMS: 203 (M+1)⁺

To a solution of 0.42 g (2.1 mmol) of above amine in pyridine (2 mL) was added methanesulfonyl chloride (0.2 mL) at 0° C. The reaction mixture was stirred at 0° C. for 30 min, warmed to r.t., and extracted with ethyl acetate (20 mL). The organic phase was washed with 1 N HCl, water, dried over Na₂SO₄, and concentrated. The residue was purified by column chromatography eluting with ethyl acetate to afford the 0.35 g (59%) of 7-methanesulfonylamino-isoquinoline-3-carboxylic acid methyl ester. The methyl ester was hydrolyzed according to the general procedure B to give 0.3 g (90%) of 7-methanesulfonylamino-isoquinoline-3-carboxylic acid. LCMS: 267 (M+1)⁺.

To a solution of 30 mg (0.11 mmol) of 7-methanesulfonylamino-isoquinoline-3-carboxylic acid in DMF (0.8 mL) was added 60 mg (0.15 mmol) of HBTU and DIEA (0.1 mL). The mixture was stirred for 10 min and then 24 mg (0.1 mmol) of 2-amino-3H-benzoimidazole-4-carboxylic acid (1H-imidazol-2-yl)-amide (intermediate B) was added. The reaction was heated at 80° C. for 1 h. After usual work up, the residue was purified by column chromatography eluting with DCM/methanol (v/v=10:1 to 8:1) to afford 5 mg (9%) of 7-methanesulfonylamino-isoquinoline-3-carboxylic acid [7-(1H-imidazol-2-ylcarbamoyl)-1H-benzoimidazol-2-yl]-amide. LCMS: 491 (M+1)+.

Example 292

To a stirring solution of 2.0 g (6.8 mmol) of Boc-7-hydroxy-tetrahydroisoquinoline-3-carboxylic acid in a mixture of DCM (20 mL) and DIEA (2.0 mL) was added 1.93 g (13.7 mmol) of iodomethane at r.t. The reaction mixture was stirred at r.t. for 6.0 h. DCM (20 mL) was added, and the solvent was washed with water, brine, dried over magnesium sulfate, and evaporated under reduced pressure to provide 2.09 g (100%) of 7-hydroxy-3,4-dihydro-1H-isoquinoline-2,3-dicarboxylic acid 2-tert-butyl ester 3-methyl ester which was used for the next step without further purification. LCMS: 308 (M+1)+.

2.09 g (6.8 mmol) of above ester, 1.28 g (0.89 mmol) of benzyl bromide and 1.38 g (10.2 mmol) of $K_2CO_3$ in DMF (30 mL) was stirred at 70° C. for overnight and extracted with ethyl acetate (50 mL). The organic layer was washed with water and brine, dried over magnesium sulfate, and evaporated under reduced pressure to provide 2.2 g (81%) 7-benzyloxy-3,4-dihydro-1H-isoquinoline-2,3-dicarboxylic acid 2-tert-butyl ester 3-methyl ester. LCMS: 398 (M+1)+.

2.2 g (5.5 mmol) of the above ester was dissolved in 4.0 M HCl in dioxane (20 ml) and stirred for 1.0 h at r.t. The solvent was evaporated under vacuum, and the residue was dissolved in toluene (20 mL). To this stirring solution 2.5 g (11.0 mmol) of DDQ was added and heated to reflux for 30 min. The reaction mixture was cooled, and the precipitate was filtered. The filtrate was washed with sat. $NaHSO_3$ (25 mL), water and brine. The organic layer was dried over magnesium sulfate, evaporated under reduced pressure and purified by column chromatography using 20% ethyl acetate in hexane as an eluent to afford 1.0 g (62.5%) of 7-benzyloxy-isoquinoline-3-carboxylic acid methyl ester. LCMS: 294 (M+1)+.

To a stirring solution of 1.0 g (3.4 mmol) of above ester in a mixture of THF (30 mL) and methanol (10 mL) was added 10 mL of 2N LiOH at r.t. The reaction mixture was stirred at r.t. for 45 min., neutralized (pH=6.0-7.0) with 2.0 N HCl, and extracted with ethyl acetate. The organic layer was washed with water and brine, dried over magnesium sulfate, and evaporated under reduced pressure to afford 0.8 g (81%) of the 7-benzyloxy-isoquinoline-3-carboxylic acid. LCMS: 280 (M+1)+.

0.70 g (2.5 mmol) of 7-benzyloxy-isoquinoline-3-carboxylic acid synthesized above, 1.0 g (2.7 mmol) of HBTU in a mixture of 7.5 ml of DMF and 1.7 mL of DIEA was reacted with 0.48 g (2.5 mmol) of 2-Amino-3H-benzoimidazole-4-carboxylic acid methyl ester (Intermediate A) as described in general procedure A. 2-[(7-Benzyloxy-isoquinoline-3-carbonyl)-amino]-1H-benzoimidazole-4-carboxylic acid methyl ester (1.0 g, 88%) was isolated after column chromatography using 1:1 ethyl acetate and hexane as an eluents. LCMS: 453 (M+1)+.

Example 293

0.13 g (0.45 mmol) of 7-benzyloxy-isoquinoline-3-carboxylic acid 0.19 g (0.5 mmol) of HBTU in a mixture of 2.0 ml of DMF and 0.26 mL of DIEA was reacted with 0.1 g (0.41 mmol) of 2-amino-3H-benzoimidazole-4-carboxylic acid (1H-imidazol-2-yl)-amide (Intermediate B) as described in general procedure A. The reaction mixture was cooled to r.t., and 5.0 mL of water and 5.0 mL of saturated $NaHCO_3$ was added. The resulting solid was filtered, and the solid was washed with water and ether, and dried to provide 0.055 g (27%) of 7-benzyloxy-isoquinoline-3-carboxylic acid [4-(1H-imidazol-2-ylcarbamoyl)-1H-benzoimidazol-2-1]-amide. LCMS: 504 (M+1)+.

Example 294

A mixture of 10.12 g (55.9 mmol) of 2-amino-3-(3-hydroxy-phenyl)-propionic acid, 20 mL of 37% formaldehyde solution in water, 10 mL of conc. aq. HCl and 100 mL of methanol was refluxed for 3 h. Evaporation of the solvents gave a mixture of 6-hydroxy-1,2,3,4-tetrahydro-isoquinoline-3-carboxylic acid methyl ester and 8-hydroxy-1,2,3,4-tetrahydro-isoquinoline-3-carboxylic acid methyl ester as light yellow solid in quantitative yield. LCMS: 208 (M+1)+.

A mixture of the previously described 6-hydroxy-1,2,3,4-tetrahydro-isoquinoline-3-carboxylic acid methyl ester and 8-hydroxy-1,2,3,4-tetrahydro-isoquinoline-3-carboxylic acid methyl ester and 15.3 g (70 mmol) of di-tert-butyl dicarbonate in 40 mL of dioxane and 40 mL of 2 N $Na_2CO_3$ solution was stirred at room temperature for 80 min. The reaction mixture was partitioned between ethyl acetate (300 mL) and brine (300 mL). The aqueous layer was separated and extracted again with ethyl acetate (150 mL). The combined organic layers were dried over sodium sulfate and evaporated. Isolation by column chromatography on silica gel gave 6.186 g (36%) of a mixture of 6-hydroxy-3,4-dihydro-1H-isoquinoline-2,3-dicarboxylic acid 2-tert-butyl ester 3-methyl ester and 8-hydroxy-3,4-dihydro-1H-isoquinoline-2,3-dicarboxylic acid 2-tert-butyl ester 3-methyl ester. LCMS: 308 (M+1)+.

The mixture of 6-hydroxy-3,4-dihydro-1H-isoquinoline-2,3-dicarboxylic acid 2-tert-butyl ester 3-methyl ester and 8-hydroxy-3,4-dihydro-1H-isoquinoline-2,3-dicarboxylic acid 2-tert-butyl ester 3-methyl ester from the previous step, 5.04 mL (80 mmol) of methyl iodide, 5.53 g (40 mmol) of potassium carbonate, and 50 mL of DMF was heated at 90° C. overnight. The reaction mixture was partitioned between ethyl acetate (400 mL) and water (400 mL) and separated. The organic layer was dried over sodium sulfate, evaporated and used directly for next step. LCMS: 322 (M+1)+.

A solution of 6-methoxy-3,4-dihydro-1H-isoquinoline-2,3-dicarboxylic acid 2-tert-butyl ester 3-methyl ester and 8-methoxy-3,4-dihydro-1H-isoquinoline-2,3-dicarboxylic acid 2-tert-butyl ester 3-methyl ester from the previous step in 20 mL of dichloromethane was treated with 20 mL of 4 N HCl in dioxane and stirred at room temperature for 3 h. Evaporation of solvents in vacuo gave a mixture of 6-methoxy-1,2,3,4-tetrahydro-isoquinoline-3-carboxylic acid methyl ester hydrochloride and 8-methoxy-1,2,3,4-tetrahydro-isoquinoline-3-carboxylic acid methyl ester hydrochloride, which was washed with hexanes and used directly for next step. LCMS: 222 (M+1)+.

The mixture of 6-methoxy-1,2,3,4-tetrahydro-isoquinoline-3-carboxylic acid methyl ester hydrochloride and 8-methoxy-1,2,3,4-tetrahydro-isoquinoline-3-carboxylic acid methyl ester hydrochloride from the previous step in 100 mL of toluene was treated with 9.50 g (41 mmol) of DDQ and was heated under reflux for 1 h. The reaction mixture was partitioned between 2 M $NaS_2O_3$ (100 mL), 1 M $Na_2CO_3$ (100 mL) and ethyl acetate (150 mL) and separated. The aqueous layer was extracted again with ethyl acetate (200 mL). The combined organic layers were dried over sodium sulfate and evaporated. Purification by column chromatography on silica gel separated the desired products as follows:

6-Methoxy-isoquinoline-3-carboxylic acid methyl ester: 2.35 g (52% in 3 steps). $^1$H-NMR (400 MHz, CDCl$_3$): 9.19 (s, 1H), 8.51 (s, 1H), 7.95 (d, 1H), 7.37 (dd, 1H), 7.21 (d, 1H), 4.07 (s, 3H), 3.98 (s, 3H) ppm; LCMS: 218 (M+1)$^+$.

8-Methoxy-isoquinoline-3-carboxylic acid methyl ester: 90 mg (2% in 3 steps). $^1$H-NMR (400 MHz, CDCl$_3$): 9.69 (s, 1H), 8.53 (s, 1H), 7.69 (dd, 1H), 7.52 (d, 1H), 7.04 (d, 1H), 4.066 (s, 3H), 4.064 (s, 3H) ppm; LCMS: 218 (M+1)$^+$.

2.35 g (10.82 mmol) of 6-methoxy-isoquinoline-3-carboxylic acid methyl ester, was hydrolyzed according to the general procedure B to provide 1.99 g (90%) 6-methoxy-isoquinoline-3-carboxylic acid LCMS: 204 (M+1)$^+$.

224 mg (1.1 mmol) of 6-methoxy-isoquinoline-3-carboxylic acid was reacted with 242 mg (1 mmol) of intermediate B (2-amino-3H-benzoimidazole-4-carboxylic acid (1H-imidazol-2-yl)-amide), 569 mg (1.5 mmol) of HBTU, 0.704 ml (4 mmol) of DIEA and 5 mL of DMF stirring at 80° C. for 2 h as describe in general procedure A to provide 212.4 mg (50%) of the title compound. $^1$H-NMR (400 MHz, DMSO): 9.37(s, 1H), 8.71 (s, 1H), 8.24(d, 1H), 7.94(d, 1H), 7.82(d, 1H), 7.73(d, 1H), 7.49(dd, 1H), 7.34(t, 1H), 6.88(s, 1H), 6.76(s, 1H), 3.98 (s, 3H) ppm; LCMS: 428 (M+1)$^+$.

Example 295

90 mg (0.46 mmol) of 8-methoxy-isoquinoline-3-carboxylic acid methyl ester (synthesized in above examples) was hydrolyzed according to the general procedure B to provide 84 mg (100%) of 8-methoxy-isoquinoline-3-carboxylic acid. LCMS: 204 (M+1)$^+$.

32.3 mg (38%) of the 8-methoxy-isoquinoline-3-carboxylic acid [4-(1H-imidazol-2-ylcarbamoyl)-1H-benzoimidazol-2-yl]-amide was synthesized according to General Procedure A from 41 mg (0.2 mmol) of 8-methoxy-isoquinoline-3-carboxylic acid, 48 mg (0.2 mmol) of intermediate B (2-amino-3H-benzoimidazole-4-carboxylic acid (1H-imidazol-2-yl)-amide), 100 mg (0.264 mmol) of HBTU, 0.167 mL (0.97 mmol) of DIEA and 1 mL of DMF stirring at 80° C. for 2 h. LCMS: 428 (M+1)$^+$.

Example 296

0.25 g (17% in 4 steps) 7-methoxy-isoquinoline-3-carboxylic acid was prepared according to procedure described for the synthesis of 6-methoxy-isoquinoline-3-carboxylic acid (in Example 294) starting from 2.0 g (6.8 mmol) of boc-7-hydroxy-tetrahydroisoquinoline carboxylic acid using 179 mg (0.824 mmol). LCMS: 204 (M+1)$^+$.

71.8 mg (84%) of 7-methoxy-isoquinoline-3-carboxylic acid [4-(1H-imidazol-2-ylcarbamoyl)-1H-benzoimidazol-2-yl]-amide was prepared according to General Procedure A using 41 mg (0.2 mmol) of 7-methoxy-isoquinoline-3-carboxylic acid, 48 mg (0.2 mmol) of intermediate B (2-amino-3H-benzoimidazole-4-carboxylic acid (1H-imidazol-2-yl)-amide), 100 mg (0.246 mmol) of HBTU, 0.07 mL (0.4 mmol) of DIEA and 2 mL of DMF stirring at 80° C. for 2 h. LCMS: 428 (M+1)$^+$.

Example 297

0.2 g (9.1%, 4 steps) of the 6-isopropoxy-1,2,3,4-tetrahydro-isoquinoline-3-carboxylic acid was prepared according to procedure described for the synthesis of 6-methoxy-isoquinoline-3-carboxylic acid (in Example 294) starting from 0.67 g (2.18 mmol) of 6-hydroxy-3,4-dihydro-1H-isoquinoline-2,3-dicarboxylic acid 2-tert-butyl ester 3-methyl ester. LCMS: 232 (M+1)$^+$.

0.05 g (0.23 mmol) of 6-isopropoxy-isoquinoline-3-carboxylic acid and 0.19 g (0.50 mmol) of HBTU were combined in a flask charged with DMF (3 mL) and DIEA (1 mL). This reaction mixture was then treated with 0.1 g (0.4 mmol) 2-amino-3H-benzoimidazole-4-carboxylic acid (1H-imidazol-2-yl)-amide (Intermediate B,) and stirred at 80° C. for 1 h. The reaction mixture was diluted with water, and the resultant solid precipitate was filtered and washed with saturated NaHCO$_3$. The solid was dissolved with MeOH, evaporated onto silica gel and isolated by flash column chromatography (500 mL DCM/20 mL NH$_3$/MeOH) to yield 10 mg (9%) of 6-isopropoxy-isoquinoline-3-carboxylic acid [4-(1H-imidazol-2-ylcarbamoyl)-1H-benzoimidazol-2-yl]-amide. LCMS: 456 (M+1)$^+$.

Example 298

1.556 g (11 mmol) of 3-methylsulfanyl-propionyl chloride was added slowly to a mixture of 2.20 g (10 mmol) of phenylalanine methyl ester hydrochloride, 4.18 mL (30 mmol) of triethyl amine and 50 mL of dichloromethane and stirred at room temperature for 2 h. The reaction mixture was partitioned between DCM (50 mL) and saturated NaHCO$_3$ solution (100 mL). The aqueous layer was separated and extracted again with dichloromethane (100 mL). The combined organic extracts were dried over sodium sulfate and evaporated. Purification by column chromatography on silica gel gave 2.574 g (92%) of 2-(3-methylsulfanyl-propionylamino)-3-phenyl-propionic acid methyl ester. LCMS: 282 (M+1)$^+$.

0.882 mL (10.07 mmol) of oxalyl chloride was added dropwise to a solution of 2-(3-methylsulfanyl-propionylamino)-3-phenyl-propionic acid methyl ester (from previous step) in 30 mL of dichloromethane and stirred at room temperature for 1 h. This reaction mixture was then cooled to −10° C. and treated with 1.82 g (11 mmol) of FeCl$_3$ at this temperature in portions. This reaction mixture was allowed to warm up to room temperature overnight. 30 mL of 2 N aq. HCl was added slowly while stirring for 1 h. 20 mL of dichloromethane was added and separated, washed again with water (50 mL), and dried over sodium sulfate. The organic solvents were evaporated in vacuo. The residual red solid was mixed with 30 mL of methanol and 1.5 mL of conc. H$_2$SO$_4$ and heated under reflux overnight. Water was added to the reaction mixture and the methanol was evaporated under reduced pressure. Ammonium hydroxide was added to adjust pH to basic. The aqueous layer (~50 mL) was extracted with dichloromethane (2×50 mL). The combined organic layers were dried over sodium sulfate and evaporated. Purification by column chromatography on silica gel gave 923 mg (38%) of 1-(2-methylsulfanyl-ethyl)-3,4-dihydro-isoquinoline-3-carboxylic acid methyl ester. LCMS: 264 (M+1)$^+$.

1.297 g (7 mmol) of copper acetate was added to a solution of 923 mg (3.5 mmol) of 1-(2-methylsulfanyl-ethyl)-3,4-dihydro-isoquinoline-3-carboxylic acid methyl ester in 10 mL of dichloromethane, stirring at room temperature overnight. This reaction mixture was concentrated and purified by column chromatography on silica gel to give 266 mg (29%) of 1-(2-methylsulfanyl-ethyl)-isoquinoline-3-carboxylic acid methyl ester. LCMS: 262 (M+1)$^+$.

1-(2-methylsulfanyl-ethyl)-isoquinoline-3-carboxylic acid was prepared according to General Procedure B using 49 mg (0.187 mmol) of 1-(2-methylsulfanyl-ethyl)-isoquinoline-3-carboxylic acid methyl ester, 0.28 mL of 2 N aq. LiOH, 2 mL of THF and 0.5 mL of methanol stirring at room temperature for 1 h. 42.4 mg (91%) of 1-(2-methylsulfanyl-ethyl)-isoquinoline-3-carboxylic acid was obtained. LCMS: 248 (M+1)$^+$.

42.4 mg (0.171 mmol) of 1-(2-methylsulfanyl-ethyl)-isoquinoline-3-carboxylic acid was reacted with 34 mg (0.14 mmol) of intermediate B (2-amino-3H-benzoimidazole-4-carboxylic acid (1H-imidazol-2-yl)-amide), 114 mg (0.3 mmol) of HBTU and 0.106 mL (0.6 mmol) of DIEA in 0.8 mL of DMF stirring at 85° C. for 3 h according to the general procedure A. 44.3 mg (55%) of 1-(2-methylsulfanyl-ethyl)-isoquinoline-3-carboxylic acid [4-(1H-imidazol-2-ylcarbamoyl)-1H-benzoimidazol-2-yl]-amide was obtained. LCMS: 472 (M+1)$^+$.

Example 299

559 mg (0.91 mmol) of oxone monopersulfate was added to a solution of 217 mg (0.83 mmol) of 1-(2-methylsulfanyl-ethyl)-isoquinoline-3-carboxylic acid methyl ester (synthesized in above Example 298) in 4 mL of methanol and stirred at room temperature for 1.5 h. The reaction mixture was partitioned between dichloromethane (40 mL) and water (40 mL). The aqueous layer was separated and extracted again with dichloromethane (40 mL). The combined organic extracts were dried over sodium sulfate and evaporated. Purification by column chromatography on silica gel gave 169 mg (69%) of 1-(2-methylsulfonyl-ethyl)-isoquinoline-3-carboxylic acid methyl ester as off-white solid. LCMS: 294 (M+1)$^+$. The ester was hydrolyzed according to the general procedure B to provide 145 mg (90%) of the 1-(2-methylsulfonyl-ethyl)-isoquinoline-3-carboxylic acid.

51.7 mg (57%) of 1-(2-methanesulfonyl-ethyl)-isoquinoline-3-carboxylic acid [4-(1H-imidazol-2-ylcarbamoyl)-1H-benzoimidazol-2-yl]-amide as prepared according to General Procedure A using 50.3 mg (0.18 mmol) of 1-(2-methylsulfonyl-ethyl)-isoquinoline-3-carboxylic acid, 36.3 mg (0.15 mmol) of intermediate B (2-amino-3H-benzoimidazole-4-carboxylic acid (1H-imidazol-2-yl)-amide), 114 mg (0.3 mmol) of HBTU, 0.106 mL (0.6 mmol) of DIEA and 0.8 mL DMF (0.8 mL) stirring at 85° C. for 3 h. LCMS: 504 (M+1)$^+$.

Example 300

0.25 g (11% overall yield) of 1-methyl-isoquinoline-3-carboxylic acid was synthesized according to the procedure described for the synthesis of 1-(2-methylsulfanyl-ethyl)-isoquinoline-3-carboxylic acid (in Example 298) starting from 2.20 g (10 mmol) of phenylalanine methyl ester hydrochloride. LCMS: 188 (M+1)$^+$.

17.6 mg (15%) of 1-methyl-isoquinoline-3-carboxylic acid [4-(1H-imidazol-2-ylcarbamoyl)-1H-benzoimidazol-2-yl]-amide was synthesized according to General Procedure A using 55 mg (0.29 mmol) of 1-methyl-isoquinoline-3-carboxylic acid, 70 mg (0.29 mmol) of intermediate B (2-amino-3H-benzoimidazole-4-carboxylic acid (1H-imidazol-2-yl)-amide), 144 mg (0.38 mmol) of HBTU, 0.264 mL (1.5 mmol) of DIEA in 0.8 mL of DMF stirring at 85° C. for 2 h. $^1$H-NMR (400 MHz, DMSO): 8.66 (s, 1H), 8.38 (d, 1H), 8.28 (d, 1H), 7.89 (m 4H), 7.34 (m, 1H), 6.85 (b, 2H), 3.07 (s, 3H) ppm. LCMS: 412 (M+1)$^+$.

Example 301

0.083 mL (1 mmol) of sulfuryl chloride was added to a solution of 90 mg (0.41 mmol) of 8-methoxy-isoquinoline-3-carboxylic acid methyl ester (from Example 295) in 1 mL of acetic acid and stirred at room temperature overnight. Ether was added to the reaction mixture, and the precipitated solid was filtered, washed with ether, then partitioned between ethyl acetate (30 mL) and saturated NaHCO$_3$ solution (30 mL) and extracted. The organic layer was dried over sodium sulfate, and evaporation of the solvent in vacuo gave 47.3 mg (46%) of 7-chloro-8-methoxy-isoquinoline-3-carboxylic acid methyl ester. LCMS: 252 (M+1)$^+$. The ester was hydrolyzed according to the general procedure B to provide 40 mg (88%) of the 7-chloro-8-methoxy-isoquinoline-3-carboxylic acid. LCMS: 238 (M+1)$^+$.

10 mg (13%) of 7-chloro-8-methoxy-isoquinoline-3-carboxylic acid [4-(1H-imidazol-2-ylcarbamoyl)-1H-benzoimidazol-2-yl]-amide was synthesized according to the general procedure A using 7-chloro-8-methoxy-isoquinoline-3-carboxylic acid (from previous step), 36.3 mg (0.15 mmol) of intermediate B (2-amino-3H-benzoimidazole-4-carboxylic acid (1H-imidazol-2-yl)-amide), 69 mg (0.18 mmol) of HBTU, 0.106 mL (0.6 mmol) of DIEA in 2 mL of DMF stirring at 80° C. for 2 h. LCMS: 462 (M+1)$^+$.

Example 302

1.0 g (6.8 mmol) of thiophene-2,3-dicarbaldehyde was dissolved in DCM (50 mL) and cooled to 0° C. 2.0 g (7.4 mmol) of (O) Boc-alpha-phosphonoglycine trimethyl ester was dissolved in DCM (25 mL) and 1.14 g (7.5 mmol) of DBU was added at ambient temperature under stirring. This solution was added drop wise to the cold solution of the dialdehyde tinder stirring. The solution was stirred at 0° C. for 1 h and overnight at ambient temperature. The reaction mixture was concentrated, and the residue was dissolved in 4 M HCl in dioxane. The resulting white suspension was stirred at room temperature for 1 h. Solvent was evaporated, extracted with ethyl acetate (100 ml), washed with sat NaHCO$_3$, water and brine. The organic layer was dried over magnesium sulfate, evaporated purified by column chromatography using 20% ethyl acetate in hexane as an eluent to give two regioisomers as follows.

0.34 g (24%) of Thieno[2,3-c]pyridine-5-carboxylic acid methyl ester. $^1$H-NMR (400 MHz, CDCl$_3$): 9.20 (s, 1H), 8.27(s, 1H), 7.82 (d, 1H), 7.50(d, 1H), 4.03 (s, 3H) ppm; LCMS: 180 (M+1)$^+$.

0.17 g (12%) of thieno[3,2-c]pyridine-6-carboxylic acid methyl ester. $^1$H-NMR (400 MHz, CDCl$_3$): 9.191 (s, 1H), 8.7(s, 1H), 7.72 (d, 1H), 7.55 (d, 1H) ppm; LCMS: 180 (M+1)$^+$. The methyl esters were hydrolyzed as shown in general procedure B to give corresponding acids in a quantitative yield.

2.6 mg (3%) of thieno[2,3-c]pyridine-5-carboxylic acid [4-(1H-imidazol-2-ylcarbamoyl)-1H-benzoimidazol-2-yl]-amide was prepared according to general procedure A using 54 mg (0.3 mmol) thieno[2,3-c]pyridine-5-carboxylic acid, 61 mg (0.25 mmol) intermediate B (2-amino-3H-benzoimidazole-4-carboxylic acid (1H-imidazol-2-yl)-amide), 114 mg (0.3 mmol) of HBTU, 0.106 mL (0.6 mmol) of DIEA in 1 mL of DMF stirring at 85° C. for 1 h. LCMS: 404 (M+1)$^+$.

Example 303

5.0 mg (2.9%) of thieno[3,2-c]pyridine-6-carboxylicacid [7-(1H-imidazol-2-ylcarbamoyl)-1H-benzoimidazol-2-yl]-amide was prepared according to general procedure A using 54 mg (0.3 mmol) thieno[3,2-c]pyridine-6-carboxylic acid (synthesized in above example), 61 mg (0.25 mmol) intermediate B (2-amino-3H-benzoimidazole-4-carboxylic acid (1H-imidazol-2-yl)-amide), 114 mg (0.3 mmol) of HBTU, 0.106 mL (0.6 mmol) of DIEA in 1 mL of DMF stirring at 85° C. for 1 h. LCMS: 404 (M+1)$^+$.

Example 304

100 mg (0.56 mmol) of the 2-methyl-1,8a-dihydro-imidazo[1,2-a]pyridine-3-carboxylic acid and 234 mg (0.61 mmol) of HBTU in a mixture of 1.5 mL of DMF and 0.6 mL of DIEA was reacted with 137 mg (0.56 mmol) of the 2-amino-3H-benzoimidazole-4-carboxylic acid (1H-imidazol-2-yl)-amide (Intermediate B) as described in general procedure A. After the reaction was complete, it was diluted with brine (20 mL), and the resulting solid was filtered, washed with water, ethyl acetate and dried under vacuum to give 40 mg (17%) of 2-[(2-methyl-imidazo[1,2-a]pyridine-3-carbonyl)-amino]-1H-benzoimidazole-4-carboxylic acid (1H-imidazol-2-yl)-amide as a solid. LCMS: 401 (M+1)$^+$.

Example 305

1.54 g (10.0 mmol) of 3-methoxy-2-nitropyridine was hydrogenated according to the general procedure C to give 2-amino-3-methoxypyridine. This product was directly treated with 2.5 g (12.0 mmol) of ethyl bromopyruvate in 20.0 mL of THF at r.t. overnight and refluxed for 8 h after addition of 20.0 mL of ethanol. The solvents were evaporated, and the resulting residue was diluted with THF, filtered and washed with THF to give 1.76 g (80%) of 8-methoxy-imidazo[1,2-a]pyridine-2-carboxylic acid ethyl ester.

This ester was hydrolyzed according to general procedure B to give 1.5 g (95%) of the corresponding 8-methoxy-imidazo[1,2-a]pyridine-2-carboxylic acid.

300 mg (3.0 mmol) of the above 8-methoxy-imidazo[1,2-a]pyridine-2-carboxylic acid and 200 mg (0.5 mmol) of HBTU in a mixture of 1.5 mL of DMF and 0.6 mL of DIEA was reacted with 60 mg (0.25 mmol) of the 2-amino-3H-benzoimidazole-4-carboxylic acid (1H-imidazol-2-yl)-amide (Intermediate B) as described in general procedure A. After the reaction was complete, it was diluted with brine (20 mL), and the resulting solid was filtered, washed with water, ethyl acetate and dried under vacuum to give 41 mg (40%) of 2-[(8-methoxy-imidazo[1,2-a]pyridine-3-carbonyl)-amino]-1H-benzoimidazole-4-carboxylic acid (1H-imidazol-2-yl)-amide as a solid. LCMS: 417 (M+1)$^+$.

By analogous methods to those used to prepare Examples 290 to 305, and those in the relevant above schemes, the following compounds were synthesized.

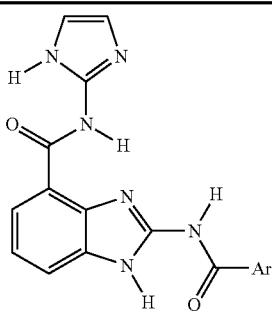

| Ex. | Ar | LCMS (M + 1)$^+$ |
|---|---|---|
| 306 | 6,7-Bis-(2-methoxy-ethoxy)-isoquinoline-3-yl | 546 |
| 307 | Cinnoline-3-yl | 417 |
| 308 | Quinoxaline-2-yl | 399 |
| 309 | 6-Bromo-pyridine-2-yl | 427 |
| 310 | [1,8]Naphthyridine-2-yl | 399 |
| 311 | Isoquinoline-1-yl | 398 |
| 312 | 6,7-Dimethoxy-isoquinoline-3-yl | 458 |
| 313 | 4-Cyano-phenyl | 372 |
| 314 | 6-Cyano-pyridine-3-yl | 373 |
| 315 | Isoquinoline-5-yl | 398 |

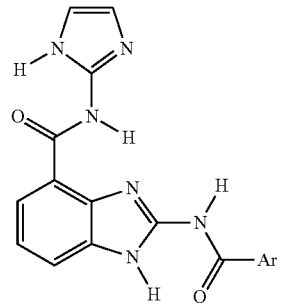

| Ex. | Ar | LCMS (M + 1)$^+$ |
|---|---|---|
| 316 | 2,6-Dimethoxy-pyrimidine-4-yl | 518 |
| 317 | 6-Benzyloxy-isoquinoline-3-yl | 504 |
| 318 | 2,3-Dihydro-[1,4]dioxino[2,3-g]isoquinoline-8-yl | 456 |
| 319 | [1,3]Dioxolo[4,5-g]isoquinoline-7-yl | 442 |
| 320 | 6-Cyclopentyloxy-isoquinoline-3-yl | 482 |
| 321 | 1-Cyclopentylmethyl-7-methoxy-isoquinoline-3-yl | 510 |
| 322 | 1-Isopropyl-isoquinoline-3-yl | 440 |
| 323 | 6-Ethoxy-isoquinoline-3-yl | 442 |
| 324 | 6-Butoxy-isoquinoline-3-yl | 470 |
| 325 | 1-Propyl-isoquinoline-3-yl | 440 |
| 326 | 1-Butyl-isoquinoline-3-yl | 454 |
| 327 | 1-Isobutyl-isoquinoline-3-yl | 454 |
| 328 | 1-Cyclopentyl-isoquinoline-3-yl | 466 |
| 329 | 7-Methoxy-1-methyl-isoquinoline-3-yl | 442 |
| 330 | 1-Methyl-6-trifluoromethoxy-isoquinoline-3-yl | 496 |
| 331 | 7-Methanesulfonyl-1-methyl-isoquinoline-3-yl | 490 |
| 332 | 1-(Tetrahydro-pyran-4-yl)-isoquinoline-3-yl | 482 |
| 333 | 1-Methyl-7-trifluoromethoxy-isoquinoline-3-yl | 496 |
| 334 | 5,8-Dimethoxy-isoquinoline-3-yl | 458 |
| 335 | 4-Methoxy-quinoline-2-yl | 428 |
| 336 | 7-Methoxy-isoquinoline-1-yl | 428 |
| 337 | Imidazo[1,2-a]pyridine-2-yl | 387 |
| 338 | 5-Methyl-imidazo[1,2-a]pyridine-2-yl | 401 |
| 339 | Imidazo[2,1-b]thiazole-6-yl | 393 |
| 340 | 8-Methyl-imidazo[1,2-a]pyridine-2-yl | 401 |
| 341 | [Bis-(4-chloro-phenyl)]-methyl | 505 |

Example 342

To a solution 1.0 g (4.9 mmol) of 6-bromo-pyridine-2-carboxylic acid, 0.9 g (7.4 mmol) of phenylboronic acid, 0.4 g (0.36 mmol) of palladium tetrakistriphenyl phosphine in 25 mL of DME was added 9.9 mL of 2 N Na$_2$CO$_3$ solutions under nitrogen. After 12 h reflux under nitrogen, the reaction mixture was cooled and filtered through a filter paper. The filtrate was acidified using 2 N HCl (pH=5). The resulting white precipitate was filtered, washed with water and dried to afford 0.5 g (51%) of 6-phenyl-pyridine-2-carboxylic acid. LCMS: 200 (M+1)$^+$ 0.1 g (0.5 mmol) of above acid, 0.19 g (0.5 mmol) of HBTU in a mixture of 2.0 ml of DMF and 0.24 mL of DIEA was reacted with 0.12 g (0.5 mmol) of 2-amino-3H-benzoimidazole-4-carboxylic acid (1H-imidazol-2-yl)-amide (Intermediate B) as described in general procedure A. The reaction mixture was cooled to r.t. and 5.0 mL of water and 5.0 mL of saturated NaHCO$_3$ was added. The resulting solid was filtered, washed with water and ether, and dried to provide 0.04 g (20%) of 2-[(6-phenyl-pyridine-2-carbonyl)-amino]-1H-benzoimidazole-4-carboxylic acid (1H-imidazol-2-yl)-amide. LCMS: 424 (M+1)$^+$.

Example 343

0.12 g (0.51 mmol) of 6-(3-cyano-phenyl)-pyridine-2-carboxylic acid, 0.19 g (0.5 mmol) of HBTU in a mixture of 2.0 ml of DMF and 0.26 mL of DIEA was reacted with 0.1 g (0.41 mmol) of 2-amino-3H-benzoimidazole-4-carboxylic acid (1H-imidazol-2-yl)-amide (Intermediate B) as described in general procedure A. The reaction mixture was cooled to r.t. and 5.0 mL of water and 5.0 mL of saturated NaHCO$_3$ was added. The resulting solid was filtered, and the solid was washed with water and ether and dried to provide 0.04 g (17.5%) of 2-{[6-(3-cyano-phenyl)-pyridine-2-carbonyl]-amino}-1H-benzoimidazole-4-carboxylic acid (1H-imidazol-2-yl)-amide. $^1$H-NMR (400 MHz, DMSO): 9.15 (s, 1H), 8.86 (s, 1H), 8.45(m, 1H), 8.24 (m, 2H), 7.99 (d, 1H), 7.92 (d, 1H), 7.87 (d, 1H), 7.72 (t, 1H), 7.41(t, 1H), 7.30 (s, 2H) ppm. LCMS: 449 (M+1)$^+$.

Example 344

0.31 g (2 mmol) of 5-hydroxy-nicotinic acid methyl ester, 0.73 g (4 mmol) of copper acetate, ~1 g of 4 Å molecular sieves and 0.85 g (7 mmol) of phenylboronic acid were combined in a flask charged with 20 mL of DCM and 2.0 mL (14 mmol) of Et$_3$N. This reaction slurry was stirred overnight at r.t. The reaction mixture was then diluted with 200 mL of EtOAc and washed 3 times with 10% K$_2$CO$_3$. The organic layer was then dried with Na$_2$SO$_4$, evaporated and purified by flash column chromatography (EtOAc/hexanes=1:2) to give 5-phenoxy-nicotinic acid methyl ester, which was subsequently hydrolyzed according to general procedure B to give 5-phenoxy-nicotinic acid and used in the next step without further purification.

0.07 g (0.30 mmol) of 5-phenoxy-nicotinic acid and 0.12 g (0.32 mmol) of HBTU were combined in a flask charged with 2 mL of DMF and 0.25 mL of DIEA. The reaction mixture was then treated with 0.05 g (0.20 mmol) of 2-amino-3H-benzoimidazole-4-carboxylic acid (1H-imidazol-2-yl)-amide (Intermediate B) and stirred at 80° C. for 1 h. The reaction mixture was diluted with water, and the resultant solid precipitate was filtered and washed with saturated NaHCO$_3$. The solid was dissolved with MeOH, evaporated onto silica gel and isolated by flash column chromatography (500 mL DCM/20 mL NH$_3$/MeOH) to yield 10 mg (11%) of 2-[(5-phenoxy-pyridine-3-carbonyl)-amino]-1H-benzoimidazole-4-carboxylic acid (1H-imidazol-2-yl)-amide. LCMS: 441 (M+1)$^+$.

Example 345

0.31 g (2 mmol) of 5-hydroxy-nicotinic acid methyl ester and 3.1 g (4 mmol) of polymer-supported triphenylphosphine were combined in a flask charged with 45 mL of THF and 0.31 mL (3 mmol) of benzyl alcohol, and shaken at r.t. until the starting materials dissolved. The reaction mixture was then cooled to 0° C. with a water/brine bath, 0.58 mL (3 mmol) of DIAD was added and the reaction slurry then stirred overnight at r.t. The reaction mixture was filtered and the resin was washed 3 times with DCM/MeOH=1:1. The organic layer was then evaporated and flashed (EtOAc/hexanes=1:2) to give the desired 5-benzyloxy-nicotinic acid methyl ester, which was subsequently hydrolyzed according to general procedure B to give 5-benzyloxy-nicotinic acid which was used in the next step without further purification. LCMS: 230 (M+1)$^+$.

0.07 g (0.30 mmol) of 5-benzyloxy-nicotinic acid and 0.12 g (0.32 mmol) of HBTU were combined in a flask charged with 2 mL DMF and 0.25 mL of DIEA. This reaction mixture was then treated with 0.05 g (0.20 mmol) of 2-Amino-3H-benzoimidazole-4-carboxylic acid (1H-imidazol-2-yl)-amide (Intermediate B) and stirred at 80° C. for 1 h. The reaction mixture was diluted with water, and the resultant solid precipitate was filtered and washed with saturated NaHCO$_3$. The solid was dissolved with MeOH, evaporated onto silica gel and isolated by flash column chromatography (500 mL DCM/20 mL NH$_3$/MeOH) to yield 10 mg (10%) of 2-[(5-benzyloxy-pyridine-3-carbonyl)-amino]-1H-benzoimidazole-4-carboxylic acid (1H-imidazol-2-yl)-amide. LCMS: 455.0 (M+1)$^+$.

By analogous methods to those used to prepare Examples 342 to 345 and those in the relevant above schemes, the following compounds were synthesized.

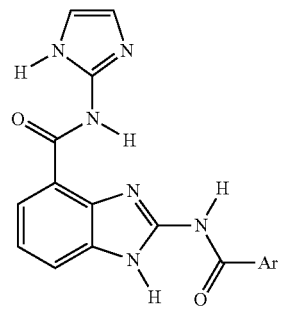

| Ex. | Ar | LCMS (M + 1)$^+$ |
|---|---|---|
| 346 | 6-(2-Carbamoyl-phenyl)-pyridine-2-yl | 467 |
| 347 | 6-(2-Trifluoromethoxy-phenyl)-pyridine-2-yl | 508 |
| 348 | 6-(4-Fluoro-phenyl)-pyridine-3-yl | 442 |
| 349 | 6-(4-Trifluoromethyl-phenyl)-pyridine-3-yl | 492 |
| 350 | 6-(4-Trifluoromethoxy-phenyl)-pyridine-3-yl | 508 |
| 351 | 5-(3-Fluoro-phenyl)-pyridine-3-yl | 442 |
| 352 | 5-(4-Trifluoromethoxy-phenyl)-pyridine-3-yl | 508 |
| 353 | 5-(2,4-Difluoro-phenyl)-pyridine-3-yl | 460 |
| 354 | 5-(3-Trifluoromethoxy-phenyl)-pyridine-3-yl | 508 |
| 355 | 6-(Furan-2-yl)-pyridine-2-yl | 414 |
| 356 | 6-(2-Fluoro-phenyl)-pyridine-2-yl | 442 |
| 357 | 6-(4-Methoxy-phenyl)-pyridine-3-yl | 454 |
| 358 | 5-Phenyl-pyridine-2-yl | 424 |
| 359 | 5-Phenyl-pyridine-3-yl | 424 |
| 360 | 5-(4-Methoxy-phenyl)-pyridine-3-yl | 454 |
| 361 | 4-Phenyl-pyridine-2-yl | 424 |
| 362 | 6-(2-Methoxy-phenyl)-pyridine-2-yl | 454 |
| 363 | 6-(3-Methanesulfonyl-phenyl)-pyridine-2-yl | 502 |
| 364 | 6-(3-Aminomethyl-phenyl)-pyridine-2-yl | 599 |
| 365 | 2-(3-Cyano-phenyl)-pyridine-4-yl | 449 |
| 366 | 6-Phenyl-pyridine-3-yl | 424 |
| 367 | 3-Cyano-phenyl | 372 |
| 368 | 6-(3-Cyanomethyl-phenyl)-pyridine-2-yl | 463 |
| 369 | 6-(4-Methanesulfonyl-phenyl)-pyridine-2-yl | 502 |
| 370 | 3'-Cyano-biphenyl-3-yl | 448 |
| 371 | 4'-Cyano-biphenyl-3-yl | 448 |
| 372 | [2,4']Bipyridinyl-6-yl | 425 |
| 373 | [2,3']Bipyridinyl-6-yl | 425 |
| 374 | 2-Phenoxy-pyridine-3-yl | 440 |
| 375 | 3'-Cyano-biphenyl-4-yl | 448 |
| 376 | 4'-Cyano-biphenyl-4-yl | 448 |
| 377 | 6-(3-Cyano-phenyl)-pyridine-3-yl | 449 |
| 378 | 3-Pyridin-3-phenyl | 424 |
| 379 | 4-Pyridin-3-phenyl | 424 |
| 380 | 2-(4-Fluoro-phenoxy)-pyridine-3-yl | 458 |
| 381 | 4-Pyridin-4-phenyl | 424 |
| 382 | 6-(2-Cyano-phenyl)-pyridine-2-yl | 449 |
| 383 | 3-Benzyloxy-pyridine-2-yl | 454 |
| 384 | 6-Benzyloxy-pyridine-2-yl | 454 |
| 385 | 6-Thiophen-2-yl-pyridine-2-yl | 430 |
| 386 | 5-Cyclopentyloxy-pyridine-3-yl | 432 |
| 387 | 5-Cyclopentylmethoxy-pyridine-3-yl | 446 |
| 388 | 5-(2-Cyclopentyl-ethoxy)-pyridine-3-yl | 460 |
| 389 | (R)-5-(1-Phenyl-ethoxy)-pyridine-3-yl | 468 |
| 390 | (S)-5-(1-Phenyl-ethoxy)-pyridine-3-yl | 468 |
| 391 | 3-(2-Phenethyloxy)-pyridine-2-yl | 468 |
| 392 | 5-Benzyloxy-pyridine-2-yl | 454 |

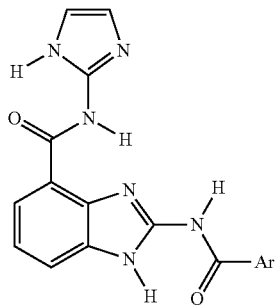

| Ex. | Ar | LCMS (M + 1)+ |
|---|---|---|
| 393 | 5-(2-Phenethyloxy)-pyridine-2-yl | 468 |
| 394 | 5-Cyclopentylmethoxy-pyridine-2-yl | 446 |
| 395 | 5-(2-Cyclopentyl-ethoxy)-pyridine-2-yl | 460 |
| 396 | 5-Isopropoxy-pyridine-3-yl | 406 |
| 397 | 5-(1-Ethyl-propoxy)-pyridine-3-yl | 434 |
| 398 | 5-Cyclopropylmethoxy-pyridine-3-yl | 418 |
| 399 | 5-(1-Cyclopropyl-ethoxy)-pyridine-3-yl | 432 |
| 400 | 5-Propoxy-pyridine-3-yl | 406 |
| 401 | 5-Butoxy-pyridine-3-yl | 420 |
| 402 | 5-Isobutoxy-pyridine-3-yl | 420 |
| 403 | 4-(2-Cyclopentyl-ethoxy)-pyridine-2-yl | 460 |
| 404 | 6-Phenyl-pyrimidine-4-yl | 425 |
| 405 | 6-(4-Fluoro-phenyl)-pyrimidine-4-yl | 443 |
| 406 | 4-(5-Trifluoromethyl-pyridin-2-yl)-phenyl | 492 |
| 407 | 4-(4-Trifluoromethyl-phenoxy)-phenyl | 507 |

Example 408

To a solution of 0.66 g (3.0 mmol) of 6-(3-cyano-phenyl)-pyridine-2-carboxylic acid in DMF (10 mL) was added 1.5 g (3.9 mmol) of HBTU and DIEA (1 mL). The mixture was stirred at room temperature for 10 min then 0.8 g (4.1 mmol) of 2-amino-3H-benzoimidazole-4-carboxylic acid methyl ester (Intermediate A) was added. The reaction was heated at 90° C. for 1 h. Usual work up as described in general procedure A provided 1 g (83%) of 2-{[6-(3-cyano-phenyl)-pyridine-2-carbonyl]-amino}-3H-benzoimidazole-4-carboxylic acid methyl ester. LCMS: 398 (M+1)+. $^1$H NMR (DMSO-d$_6$, 400 MHz): δ 8.85 (s, 1H), 8.60 (d, 1H), 8.23 (m, 2H), 8.11 (m, 1H), 7.95 (m, 2H), 7.76 (dd, 1H), 7.60 (m, 2H), 3.91 (s, 3H) ppm.

0.7 g (1.7 mmol) of above ester was hydrolyzed according to the general procedure B to give 0.53 g (82%) of the 2-{[6-(3-cyano-phenyl)-pyridine-2-carbonyl]-amino}-3H-benzoimidazole-4-carboxylic acid. LCMS: 384 (M+1)+.

To a solution of 76 mg (0.2 mmol) of above acid in DMF (1 mL) was added 113 mg (0.3 mmol) of HBTU and DIEA (0.2 mL), the mixture was stirred at room temperature for 10 min then 0.1 g (1.2 mmol) of butylamine was added. The mixture was heated at 60° C. for 30 min. After cooling to room temperature, usual work up as shown in general procedure A followed by column chromatography purification (eluting with DCM then ethyl acetate) gave 20 mg (22%) of 2-{[6-(3-cyano-phenyl)-pyridine-2-carbonyl]-amino}1-3H-benzoimidazole-4-carboxylic acid butylamide. LCMS: 438 (M+1)+.

By analogous methods to those used to prepare Example 408 and those in the relevant above schemes, the following compounds were synthesized.

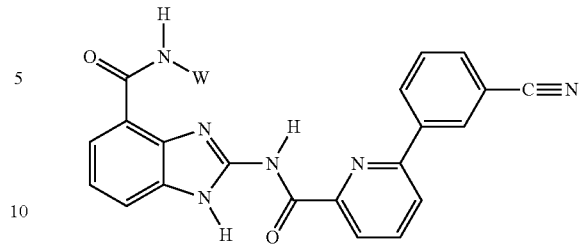

| Ex. | W | LCMS (M + 1)+ |
|---|---|---|
| 409 | phenyl | 459 |
| 410 | isopropyl | 425 |
| 411 | cyclohexyl | 465 |
| 412 | furan-2-ylmethyl | 463 |

Example 413

0.728 mL (6.5 mmol) of phenyl acetylene was added to a mixture of 10.1 g (5 mmol) of 4-bromopicolinic acid, 91 mg (0.13 mmol) of dichlorobis(triphenylphosphine)-palladium (II), 29 mg (0.15 mmol) of copper(I) iodide, 10 mL of triethylamine and 2 mL of DMF and heated at 80° C. overnight. The reaction mixture was filtered. The filtrate was concentrated and partitioned between 5 mL of 2 N Na$_2$CO$_3$ solution, 25 mL of water and 30 mL of ether. The aqueous layer was separated and washed again with ether (30 mL). 10% aq. HCl was added to adjust the pH to 5. The aqueous layer was extracted with dichloromethane (2×50 mL), and the combined organic layers were dried over sodium sulfate. Evaporation of the solvents in vacuo gave 1.028 g (4.61 mmol, 92%) of 4-phenylethynyl-pyridine-2-carboxylic acid. LCMS: 224 (M+1)+.

0.05 (0.23 mmol) of the above synthesized 4-phenylethynyl-pyridine-2-carboxylic acid, 0.095 g (0.25 mmol) of HBTU in a mixture of 2.0 ml of DMF and 0.20 mL of DIEA was reacted with 0.05 g (0.20 mmol) of 2-amino-3H-benzoimidazole-4-carboxylic acid (1H-imidazol-2-yl)-amide (Intermediate B) as described in general procedure A. The reaction mixture was cooled to r.t. 5.0 mL of water and 5.0 mL of saturated NaHCO$_3$ was added, and the resulting solid was filtered. The solid was washed with water and ether, and dried to provide 0.04 g (43%) of 2-[(4-phenylethynyl-pyridine-2-carbon-yl)-amino]-1H-benzoimidazole-4-carboxylic acid (1H-imidazol-2-yl)-amide. LCMS: 448 (M+1)+.

Example 414

0.1 g (0.46 mmol) of 5-Phenylethynyl-nicotinic acid, 0.19 g (0.5 mmol) of HBTU in a mixture of 2.0 ml of DMF and 0.30 mL of DIEA was reacted with 0.1 g (0.40 mmol) of 2-Amino-3H-benzoimidazole-4-carboxylic acid (1H-imidazol-2-yl)-amide (Intermediate B) as described in general procedure A. The reaction mixture was cooled to r.t. 5.0 mL of water and 5.0 mL of saturated NaHCO$_3$ was added, and the resulting solid was filtered. The solid was washed with water, ether and dried to provide 0.08 g (43%) of 2-[(5-phenylethynyl-pyridine-3-carbonyl)-amino]-1H-benzoimidazole-4-carboxylic acid (1H-imidazol-2-yl)-amide. LCMS: 448 (M+1)+.

Example 415

20 mg of (0.44 mmol) of 2-[(5-phenylethynyl-pyridine-3-carbonyl)-amino]-1H-benzoimidazole-4-carboxylic acid (1H-imidazol-2-yl)-amide was dissolved in a mixture of 10 mL of CH₃OH and 0.5 mL of acetic acid. To this stirring solution 10 mg of 10% Pd on carbon was added and the resulting mixture was hydrogenated (1 atm) at room temperature for 3.0 h. The reaction mixture was filtered, and the solid was washed with portions of methanol. The filtrate and washings were combined and evaporated to give 18 mg (88%) of 2-[(5-phenethyl-pyridine-3-carbonyl)-amino]-1H-benzoimidazole-4-carboxylic acid (1H-imidazol-2-yl)-amide. LCMS: 452 (M+1)⁺.

Example 416

To a stirring solution 0.5 g (2.4 mmol) of 6-bromo-pyridine-2-carboxylic acid, 0.05 g (0.07 mmol) of dichlorobis(triphenylphosphine)-palladium(II), and 0.015 g (0.07 mmol) of copper (I) iodide in 10 mL of NEt₃, 9.9 mL of 2 N Na₂CO₃ solution was added 0.38 g (3.7 mmol) of phenyl acetylene under nitrogen. After 12 h reflux under nitrogen, the reaction mixture was cooled and filtered. The filtrate was acidified using 2 N HCl (pH=5), and the resulting white precipitate was filtered, washed with water and dried to afford 0.5 g (51%) of 6-phenylethynyl-pyridine-2-carboxylic acid. LCMS: 224 (M+1)⁺.

0.05 (0.23 mmol) of the above synthesized 6-Phenylethynyl-pyridine-2-carboxylic acid, 0.095 g (0.25 mmol) of HBTU in a mixture of 2.0 ml of DMF and 0.20 mL of DIEA was reacted with 0.05 g (0.20 mmol) of 2-Amino-3H-benzoimidazole-4-carboxylic acid (1H-imidazol-2-yl)-amide (Intermediate B) as described in general procedure A. The reaction mixture was cooled to r.t. 5.0 mL of water and 5.0 mL of saturated NaHCO₃ was added, and the resulting solid was filtered. The solid was washed with water and ether and dried to provide 0.04 g (43%) of 2-[(6-phenylethynyl-pyridine-2-carbonyl)-amino]-1H-benzoimidazole-4-carboxylic acid (1H-imidazol-2-yl)-amide. ¹H-NMR (400 MHz, DMSO): 8.3 (d, 1H), 8.21 (t, 1H), 8.12 (bs, 1H), 8.02 (d, 1H), 7.94 (d, 1H), 7.72 (m, 2H), 7.50 (m, 4H), 7.40 (s, 2H) ppm; LCMS: 448 (M+1)⁺.

Example 417

To a solution of 0.23 g (1 mmol) of 1-bromo-3-methanesulfonyl-benzene in benzene (2 mL) was added 40 mg (0.1 mmol) of PdCl₂(Ph₃P)₂, 30 mg (0.1 mmol) CuI, triethylamine (1 mL) and 0.3 mL of ethynyl-trimethyl-silane. The reaction mixture was heated at 70° C. for 3 h After removal of solvent, the residue was purified by column chromatography elution with hexanes/ethyl acetate (v/v=7:1 then 5:1) to give 0.24 g (95%) of (3-methanesulfonyl-phenylethynyl)-trimethylsilane. ¹H NMR (CDCl₃, 400 MHz): δ 8.4 (s, 1H), 7.88 (d, 1H), 7.70 (d, 1H), 7.52 (dd, 1H), 3.05 (s, 3H), 0.27 (s, 9H) ppm.

To a solution of 0.24 g (0.95 mmol) of the above (3-methanesulfonyl-phenylethynyl)-trimethyl-silane in methanol (2 mL) was added K₂CO₃ aq. solution (1 M, 1 mL), the mixture was stirred at room temperature for 1 h. After usual workup, the residue was purified by column chromatography eluted with hexanes/ethyl acetate (v/v=5:1 then 3:1) to give 140 mg (82%) 1-ethynyl-3-methanesulfonyl-benzene.

136 mg (0.45 mmol) of 6-(3-methanesulfonyl-phenylethyl)-pyridine-2-carboxylic acid was synthesized as described for the synthesis of 6-Phenylethynyl-pyridine-2-carboxylic acid in the above example starting with 100 mg of 6-bromo-pyridine-2-carboxylic acid. LCMS: 302 (M+1)⁺.

To a solution of 136 mg (0.45 mmol) of 6-(3-methanesulfonyl-phenylethynyl)-pyridine-2-carboxylic acid in DMF (2 mL) was added 210 mg (0.55 mmol) of HBTU (210 mg) and DIEA (0.2 mL). The mixture was stirred for 5 min then 96 mg (0.5 mmol) of 2-amino-1H-benzoimidazole-4-carboxylic acid methyl ester (Intermediate A) was added. The reaction mixture was stirred at 30° C. for 30 min. After usual workup as described in general procedure A, 142 mg (60%) of 2-{[6-(3-Methanesulfonyl-phenylethynyl)-pyridine-2-carbonyl]-amino}-1H-benzoimidazole-4-carboxylic acid methyl ester was obtained after column chromatography eluting with DCM/EtOAc (v/v=1:1) then EtOAc. LCMS: 475 (M+1)⁺. This ester was hydrolyzed as described in general procedure B to provide 135 mg (100%) of 2-{[6-(3-methanesulfonyl-phenylethynyl)-pyridine-2-carbonyl]-amino}-1H-benzoimidazole-4-carboxylic acid. LCMS: 461 (M+1)⁺.

To a solution of 46 mg (0.1 mmol) of the above acid in DMF (1 mL) was added 60 mg (0.15 mmol) of HBTU and DIEA (0.1 mL). The mixture was stirred for 5 min then 40 mg (0.3 mmol) of 2-aminoimidazole sulfate was added in one portion. The reaction mixture was heated at 80° C. for 40 min. After usual workup as described in general procedure A, 12 mg (20%) of 2-{[6-(3-methanesulfonyl-phenylethynyl)-pyridine-2-carbonyl]-amino}-1H-benzoimidazole-4-carboxylic acid (1H-imidazol-2-yl)-amide was obtained after purification by column chromatography eluting with DCM/methanol (v/v from 5:1 to 7:1). LCMS: 526 (M+1)⁺.

By analogous methods to those used to prepare Examples 413 to 417 and those in the relevant above schemes, the following compounds were synthesized.

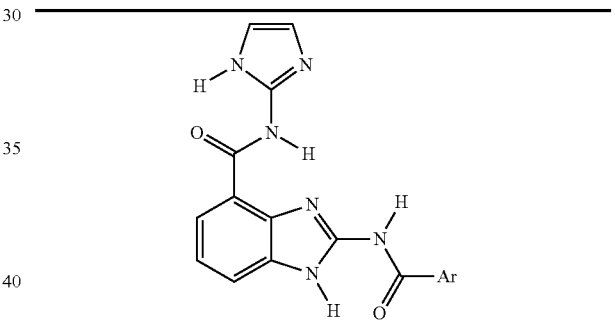

| Ex. | Ar | LCMS (M + 1)⁺ |
|---|---|---|
| 418 | 2-Phenylethynyl-pyridine-4-yl | 448 |
| 419 | 5-Phenylethynyl-pyridine-2-yl | 448 |
| 420 | 6-Cyclohexylethynyl-pyridine-2-yl | 454 |
| 421 | 6-(4-Fluoro-phenylethynyl)-pyridine-2-yl | 466 |
| 422 | 6-(4-Ethyl-phenylethynyl)-pyridine-2-yl | 476 |
| 423 | 6-(4-Methoxy-phenylethynyl)-pyridine-2-yl | 478 |
| 424 | 6-(4-Chloro-phenylethynyl)-pyridine-2-yl | 482 |
| 425 | 3-Phenylethynyl-pyridine-2-yl | 448 |
| 426 | 6-(3-Methyl-but-1-ynyl)-pyridine-2-yl | 414 |
| 427 | 6-(Thiophen-3-ylethynyl)-pyridine-2-yl | 454 |
| 428 | 6-(3,3-Dimethyl-but-1-ynyl)-pyridine-2-yl | 428 |
| 429 | 6-(3-Cyclopentyl-prop-1-ynyl)-pyridine-2-yl | 454 |
| 430 | 6-(3-Hydroxy-3-methyl-but-1-ynyl)-pyridine-2-yl | 430 |
| 431 | 6-(4-Methyl-pent-1-ynyl)-pyridine-2-yl | 428 |
| 432 | 6-(Pent-1-ynyl)-pyridine-2-yl | 414 |
| 433 | 6-(4-Dimethylamino-phenylethynyl)-pyridine-2-yl | 491 |
| 434 | 6-(Pyridin-3-ylethynyl)-pyridine-2-yl | 449 |
| 435 | 6-(3-Methoxy-phenylethynyl)-pyridine-2-yl | 478 |
| 436 | 6-(2-Methoxy-phenylethynyl)-pyridine-2-yl | 478 |
| 437 | 3-(Cyclohexylethynyl)-pyridine-2-yl | 454 |
| 438 | 3-(Thiophen-3-ylethynyl)-pyridine-2-yl | 454 |
| 439 | 6-(Cyclopropylethynyl)-pyridine-2-yl | 521 |
| 440 | 3-(3,3-Dimethyl-but-1-ynyl)-pyridine-2-yl | 428 |
| 441 | 6-(2-Fluoro-phenylethynyl)-pyridine-2-yl | 466 |
| 442 | 6-(m-Tolylethynyl)-pyridine-2-yl | 462 |
| 443 | 6-(3-Fluoro-phenylethynyl)-pyridine-2-yl | 575 |
| 444 | 3-Chloro-6-pent-1-ynyl-pyridine-2-yl | 448 |

-continued

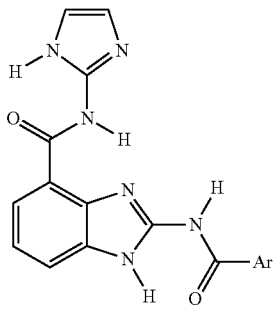

| Ex. | Ar | LCMS (M + 1)+ |
|---|---|---|
| 445 | 6-Ethynyl-pyridine-2-yl | 372 |
| 446 | 6-phenethyl-pyridine-2-yl | 452 |

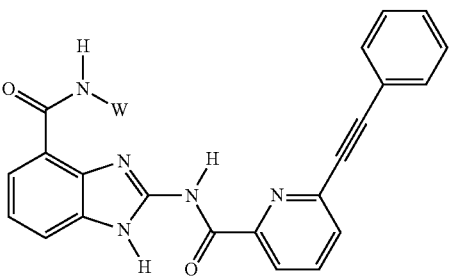

| Ex. | Ar | LCMS (M + 1)+ |
|---|---|---|
| 449 | cyclopentyl | 450 |
| 450 | tert-butyl | 438 |

Example 447

To a solution of 4.4 g (20 mmol) of 6-phenylethynyl-pyridine-2-carboxylic acid in DMF (30 mL) was added 7.6 g (20 mmol) of HBTU and DIEA (4 mL). The resulted mixture was stirred at room temperature for 10 min, then 4 g (21 mmol) of 2-amino-1H-benzoimidazole-4-carboxylic acid methyl ester (Intermediate A) was added, and stirred at room temperature for 1 h. After usual workup as described in general procedure A, 7 g (88%) of 2-[(6-phenylethynyl-pyridine-2-carbonyl)-amino]-1H-benzoimidazole-4-carboxylic acid methyl ester was obtained after column chromatography purification eluting with DCM/EtOAc. LCMS: 397 (M+1)+. $^1$H NMR (DMSO-$d_6$, 400 MHz): δ 8.20 (dd, 1H), 8.13 (dd, 1H), 7.96 (d, 1H), 7.81 (d, 1H), 7.74 (d, 1H), 7.60 (m, 2H), 7.50 (m, 3H), 7.31 (t, 1H), 3.95 (s, 3H) ppm.

Example 448

4.2 g (10.6 mmol) of 2-[(6-phenylethynyl-pyridine-2-carbonyl)-amino]-1H-benzoimidazole-4-carboxylic acid methyl ester was hydrolyzed as described in general procedure B to provide 3.5 g (86%) of 2-[(6-phenylethynyl-pyridine-2-carbonyl)-amino]-1H-benzoimidazole-4-carboxylic acid. LCMS: 383 (M+1)+. $^1$H NMR (DMSO-$d_6$, 400 MHz): δ 8.29 (d, 1H), 8.23 (dd, 1H), 8.06 (d, 1H), 7.95 (m, 2H), 7.68 (m, 2H), 7.52 (m, 4H) ppm.

To a solution of 30 mg (0.07 mmol) of above 2-[(6-Phenylethynyl-pyridine-2-carbonyl)-amino]-1H-benzoimidazole-4-carboxylic acid in DMF (1 mL) was added 40 mg (0.1 mmol) of HBTU and DIEA (0.1 mL), the resulting mixture was stirred at room temperature for 10 min, then 40 mg (0.1 mmol) of 4-methanesulfonyl-benzylamine HCl salt was added. After usual work up as described in general procedure A, 21 mg (48%) of 2-[(6-phenylethynyl-pyridine-2-carbonyl)-amino]-1H-benzoimidazole-4-carboxylic acid 4-methanesulfonyl-benzylamide was obtained after column chromatography purification eluting with DCM/EtOAc (v/v from 5:1 to 1:1). LCMS: 550 (M+1)+.

By analogous methods to those used to prepare Example 448 and those in the relevant above schemes, the following compounds were synthesized.

Example 451

60 mg (0.4 mmol) of 3-phenyl-propionic acid and 170 mg (0.45 mmol) of HBTU in a mixture of 1.0 mL of DMF and 0.5 mL of DIEA was reacted with 120 mg (0.3 mmol) of the isoquinoline-3-carboxylic acid [6-amino-4-(1H-imidazol-2-ylcarbamoyl)-1H-benzoimidazol-2-yl]-amide (See Example 130) as described in general procedure A. After the reaction was complete, it was diluted with brine (20 mL). The resulting solid was filtered, washed with water, ethyl acetate and dried under vacuum to give 101 mg (66%) of isoquinoline-3-carboxylic acid [7-(1H-imidazol-2-ylcarbamoyl)-5-(3-phenyl-propionylamino)-1H-benzoimidazol-2-yl]-amide as a solid. LCMS: 545 (M+1)+.

Example 452

82 mg (0.2 mmol) of the isoquinoline-3-carboxylic acid [6-amino-4-(1H-imidazol-2-ylcarbamoyl)-1H-benzoimidazol-2-yl]-amide (See Example 130) was dissolve in pyridine (0.6 mL). To this stirred solution at 0° C., 0.2 mmol of phenylsulfonyl chloride in 0.2 mL of DCM was added in one portion. The reaction mixture was stirred at r.t. for 2 h. Brine (5 mL) was added and stirred for 10 min. The resulting solid was collected, washed with water (3×2 mL) and ethyl acetate (3×3 mL) and dried to give 55 mg (50%) of isoquinoline-3-carboxylic acid [5-benzenesulfonylamino-7-(1H-imidazol-2-ylcarbamoyl)-1H-benzoimidazol-2-yl]-amide as a solid. LCMS: 553 (M+1)+.

Example 453

Isoquinoline-3-carboxylic acid [4-(1H-imidazol-2-ylcarbamoyl)-6-methanesulfonylamino-1H-benzoimidazol-2-yl]-amide (20 mg) was synthesized according to the same procedure described above, with the exception that methane sulfonylchloride was used instead of phenyl sulfonylchloride. LCMS: 491 (M+1)+.

Example 454

15.1 g (100 mmol) of 2-amino-5-methyl-benzoic acid was refluxed with 60 mL of ethyl chloroformate for 6 h, and then was refluxed for another 3 h after addition of 60 mL of acetyl chloride. The solid was collected, washed with hexane to give 14.2 g (80%) of the 5-methylisatoic anhydride.

6.9 g (40 mmol) of the above 5-Methylisatoic anhydride was suspended in 40 mL of conc. $H_2SO_4$ at −10° C. and cooled to −20° C. Next, 1.05 eq of potassium nitrate dissolved in 12 mL of sulfuric acid and cooled to 0° C., was then added dropwise. The reaction mixture was stirred 20° C. for 15 min then kept between −5° C. and 0° C. for 3 h. The mixture was poured into a beaker containing ice. The resulting solid was collected, washed with cold water and dried to give 3.9 g (44%) of 5-methyl-3-nitroisatoic anhydride as a solid.

3.9 g (17.6 mmol) of the above 5-methyl-3-nitroisatoic anhydride in ethyl acetate (50 mL) was treated with NaOH at r.t. for 2 h. The mixture was neutralized with dilute HCl solution and the resulting solid was filtered and washed with water and dried to give 2.5 g (72%) of 2-amino-5-methyl-3-nitrobenzoic acid.

0.25 g of 2-amino-6-methyl-1H-benzoimidazole-4-carboxylic acid (1H-imidazol-2-yl)-amide was synthesized according to procedures described for the synthesis of 2-amino-3H-benzoimidazole-4-carboxylic acid (1H-imidazol-2-yl)-amide (intermediate B) starting from 2.5 g (12.7 mmol) of above synthesized 2-amino-5-methyl-3-nitrobenzoic acid. LCMS: 257 (M+1)$^+$.

96 mg (0.5 mmol) of isoquinoline-3-carboxylic acid and 200 mg (0.52 mmol) of HBTU in a mixture of 3.0 mL of DMF and 0.3 mL of DIEA was reacted with 40 mg (0.16 mmol) of the above synthesized 2-amino-6-methyl-1H-benzoimidazole-4-carboxylic acid (1H-imidazol-2-yl)-amide as described in general procedure A. After the reaction was complete, it was diluted with brine (20 mL). The resulting solid was filtered, washed with water, ethyl acetate and dried under vacuum to give 32 mg (50%) of isoquinoline-3-carboxylic acid [7-1H-imidazol-2-ylcarbamoyl)-5-methyl-1H-benzoimidazol-2-yl]-amide. LCMS: 412 (M+1)$^+$.

Example 455

To a solution of 2.23 g (10.4 mmol) of 2-amino-3-nitrobenzoic acid methyl ester in 12 mL of acetic acid was added dropwise a solution of 0.53 mL (10.4 mmol) of Br$_2$ in 2.0 mL of acetic acid. The mixture was stirred at r.t. for 30 min and poured into 100 g of ice. The solid was collected by filtration and dried to afford 2.5 g (82%) of 2-Amino-5-bromo-3-nitrobenzoic acid methyl ester. $^1$H NMR (CDCl$_3$, 400 MHz): δ 8.6 (d, 1H), 8.53 (s, 1H), 3.95 (s, 3H) ppm.

A solution of 0.5 g (1.8 mmol) of the above ester 0.9 g (2.7 mmol) of tributyl-propenyl-stannane, 0.18 g (0.18 mmol) of (tetrakistriphenyl phosphine) palladium (0) in 25 mL of dioxane was degassed with nitrogen for 20 min then refluxed under nitrogen for 12 h. The reaction mixture was cooled, 20 mL of 2 M KF solution was added. The mixture was stirred for 20 min, extracted with ethyl acetate washed with water and brine. The residue was purified by column chromatography using 8:2 hexane and ethyl acetate to afford 0.35 g (77%) of the 2-amino-3-nitro-5-propenyl-benzoic acid methyl ester as a solid LCMS: 239 (M+1)$^+$.

0.3 g (85% overall yield) 2-amino-6-propyl-1H-benzoimidazole-4-carboxylic acid methyl ester was synthesized according to procedures described for the synthesis of 2-Amino-1H-benzoimidazole-4-carboxylic acid methyl ester (intermediate A) starting from 0.35 g (1.5 mmol) of above synthesized 2-amino-5-methyl-3-nitrobenzoic acid methyl ester. LCMS: 234 (M+1)$^+$.

0.4 g (75%) of 2-[(isoquinoline-3-carbonyl)-amino]-6-propyl-1H-benzoimidazole-4-carboxylic acid methyl ester was synthesized from 0.25 g (1.4 mmol) of isoquinoline-3-carboxylic acid, 0.6 g (1.6 mmol) of HBTU, and 0.3 g (1.3 mmol) of the above synthesized 2-Amino-6-propyl-1H-benzoimidazole-4-carboxylic acid methyl ester as described in general procedure A. LCMS: 389 (M+1)$^+$.

Example 456

0.2 g (0.5 mmol) of 2-[(isoquinoline-3-carbonyl)-amino]-6-propyl-1H-benzoimidazole-4-carboxylic acid methyl ester was hydrolyzed according to the general procedure B to provide 0.17 g (89%) of the 2-[(Isoquinoline-3-carbonyl)-amino]-6-propyl-1H-benzoimidazole-4-carboxylic acid as a solid. LCMS: 375 (M+1)$^+$.

0.1 (0.27 mmol) of the above synthesized acid, 0.11 g (0.29 mmol) of HBTU in a mixture of 2.0 ml of DMF and 0.20 mL of DIEA was reacted with 0.05 g (0.27 mmol) of 4-Methanesulfonyl-benzylamine as described in general procedure A. The reaction mixture was cooled to r.t. 5.0 mL of water and 5.0 mL of saturated NaHCO$_3$ was added, and the resulting solid was filtered. The solid was washed with water, ether and dried to provide 0.05 g (33%) of isoquinoline-3-carboxylic acid [4-(4-methanesulfonyl-benzylcarbamoyl)-6-propyl-1H-benzoimidazol-2-yl]-amide. LCMS: 542 (M+1)$^+$.

Example 457

A solution of 1.0 g (3.6 mmol) of 2-amino-5-bromo-3-nitro-benzoic acid methyl ester, 0.9 g (7.2 mmol) of pyridine-4-boronic acid, 0.42 g (0.36 mmol) of (tetrakistriphenyl phosphine) palladium (0) in 50 mL of DME and 8.4 mL of 2 N Na$_2$CO$_3$ was degassed with nitrogen for 20 min and then heated at 90° C. for 12 h. The reaction mixture was cooled to r.t., extracted with ethyl acetate (100 mL), washed with water, brine, dried over magnesium sulfate, and filtered. The filtrate was concentrated under reduced pressure. The residue was purified by column chromatography using 8:2 hexane and ethyl acetate to afford 0.5 g (50%) of the 2-Amino-3-nitro-5-pyridin-4-yl-benzoic acid methyl ester as a solid. LCMS: 273 (M+1)$^+$.

0.25 g (50% overall yield) of 2-amino-6-pyridin-4-yl-1H-benzoimidazole-4-carboxylic acid methyl ester was synthesized according to procedures described for the synthesis of 2-Amino-1H-benzoimidazole-4-carboxylic acid methyl ester (intermediate A) starting from 0.5 g (1.8 mmol) of above synthesized 2-Amino-3-nitro-5-pyridin-4-yl-benzoic acid methyl ester. LCMS: 269 (M+1)$^+$.

0.3 g (75%) of 2-[(isoquinoline-3-carbonyl)-amino]-6-pyridin-4-yl-3H-benzoimidazole-4-carboxylic acid methyl ester was synthesized from 0.16 g (0.09 mmol) of isoquinoline-3-carboxylic acid, 0.4 g (1 mmol) of HBTU, and 0.25 g (0.09 mmol) of the above synthesized 2-amino-6-pyridin-4-yl-1H-benzoimidazole-4-carboxylic acid methyl ester as described in general procedure A. LCMS: 424 (M+1)$^+$.

Example 458

0.2 g (0.5 mmol) of above ester was hydrolyzed according to the general procedure B to provide 0.17 g (89%) of 2-[(isoquinoline-3-carbonyl)-amino]-6-pyridin-4-yl-1H-benzoimidazole-4-carboxylic acid as a solid. LCMS: 414 (M+1)$^+$.

0.1 (0.25 mmol) of the above synthesized acid, 0.11 g (0.29 mmol) of HBTU in a mixture of 2.0 ml of DMF and 0.20 mL of DIEA was reacted with 0.05 g (0.27 mmol) of 4-Methanesulfonyl-benzylamine as described in general procedure A. The reaction mixture was cooled to r.t. 5.0 mL of water and 5.0 mL of saturated NaHCO$_3$ was added and the resulting solid was filtered. The solid was washed with water, ether and dried to provide 0.05 g (33%) of isoquinoline-3-carboxylic acid [4-(4-methanesulfonyl-benzylcarbamoyl)-6-pyridin-4-yl-1H-benzoimidazol-2-yl]-amide. LCMS: 577 (M+1)⁺.

Example 459

To a stirring solution of 4.48 g (20 mmol) of 2-chloro-5-trifluoromethyl-benzoic acid suspended in 40 mL of conc. H$_2$SO$_4$ at −20° C. was added dropwise a cold solution of 1.05 eq of potassium nitrate dissolved in 12 mL of sulfuric acid. The reaction mixture was stirred −20° C. for 15 min then warmed up to r.t. overnight. The mixture was poured into a beaker containing ice. The resulting solid was collected, washed with cold water and dried to give 4.8 g (90%) of 2-chloro-3-nitro-5-trifluoromethyl-benzoic acid as a solid. LCMS: 270 (M+1)⁺.

To a stirring solution of 0.81 g (3.0 mmol) of the above 2-chloro-3-nitro-5-trifluoromethyl-benzoic acid in 6.0 mL of DMF was added 6.0 mL of TEA, followed by 3.0 mmol of Benzylamine. The mixture was heated at 80° C. for 6 h. After cooling to r.t., 3.0 mL of 6N HCl solution was added. The solid was collected, washed with fresh water to give 2-benzylamino-3-nitro-5-trifluoromethyl-benzoic acid. LCMS: 341 (M+1)⁺. This product was hydrogenated according to the general procedure C to give 0.25 g of 2,3-diamino-5-trifluoromethyl-benzoic acid. LCMS: 221 (M+1)⁺.

0.25 g of 2-amino-6-trifluoromethyl-1H-benzoimidazole-4-carboxylic acid was synthesized according to procedures described for the synthesis of 2-Amino-3H-benzoimidazole-4-carboxylic acid methyl ester starting from 0.25 g of above 2,3-diamino-5-trifluoromethyl-benzoic acid. This acid was refluxed in methanol and HCl/ether to give 0.26 g of 2-amino-6-trifluoromethyl-1H-benzoimidazole-4-carboxylic acid methyl ester. LCMS: 260 (M+1)⁺.

166 mg (0.9 mmol) of Isoquinoline-3-carboxylic acid and 364 mg (0.9 mmol) of HBTU in a mixture of DMF (5 ml) and DIEA (1.0 mL) was reacted with 0.25 g (0.9 mmol) of the above amino methyl ester as described in general procedure A to give 2-[(isoquinoline-3-carbonyl)-amino]-6-trifluoromethyl-1H-benzoimidazole-4-carboxylic acid methyl ester. LCMS: 416 (M+1)⁺. This ester was hydrolyzed according to general procedure B to give 0.2 g of 2-[(isoquinoline-3-carbonyl)-amino]-6-trifluoromethyl-1H-benzoimidazole-4-carboxylic acid. LCMS: 401 (M+1)⁺.

50 mg (0.25 mmol) of the above acid and 190 mg (0.5 mmol) of HBTU in a mixture of 1.0 mL of DMF and 0.5 mL of DIEA was reacted with 100 mg (0.75 mmol) of 2-aminoimidazole sulfate as described in general procedure A. After the reaction was complete, diluted with brine (20 mL). The resulting solid was filtered, washed with water, ethyl acetate and dried under vacuum to give 29 mg (25%) of isoquinoline-3-carboxylic acid [7-(1H-imidazol-2-ylcarbamoyl)-5-trifluoromethyl-1H-benzoimidazol-2-yl]-amide as a solid. LCMS: 467 (M+1)⁺.

Example 460

5.0 g (18.2 mmol) of 2-Amino-5-bromo-3-nitro-benzoic acid methyl ester was dissolved in 50 mL of NMP and treated with 2.5 g (27.3 mmol) of CuCN, then heated under reflux until the disappearance of starting material was observed by TLC (EtOAc/hexanes 1:3). Upon completion, the contents of the reaction were poured into EtOAc followed by water. The organic layer was extracted, dried, evaporated and isolated by flash column chromatography (EtOAc/hexanes=1:9 to 3:7 gradient) to yield 1.0 g (22%) of 2-amino-5-cyano-3-nitro-benzoic acid methyl ester.

0.28 g (50% overall yield) of 2-Amino-6-cyano-3H-benzoimidazole-4-carboxylic acid methyl ester was synthesized according to procedures described for the synthesis of 2-Amino-3H-benzoimidazole-4-carboxylic acid methyl ester starting from 1.0 g of 2-amino-5-cyano-3-nitro-benzoic acid methyl ester. LCMS: 269 (M+1)⁺.

0.28 g (1.3 mmol) of 2-amino-6-cyano-1H-benzoimidazole-4-carboxylic acid methyl ester was added to a mixture of 0.22 g (1.3 mmol) of isoquinoline-3-carboxylic acid monohydrate, 0.49 g (1.3 mmol) of HBTU, 3 mL of DMF and 1 mL of DIEA to produce 6-cyano-2-[(isoquinoline-3-carbonyl)-amino]-1H-benzoimidazole-4-carboxylic acid methyl ester, according to General Procedure A. LCMS: 373.0 (M+1)⁺.

Example 461

0.2 g (0.56 mmol) of 6-cyano-2-[(isoquinoline-3-carbonyl)-amino]-1H-benzoimidazole-4-carboxylic acid methyl ester was hydrolyzed according to general procedure B to produce 2-amino-6-cyano-1H-benzoimidazole-4-carboxylic acid, which was used in the next step without further purification.

0.20 g (0.56 mmol) of 6-cyano-2-[(isoquinoline-3-carbonyl)-amino]-1H-benzoimidazole-4-carboxylic acid and 0.21 g (0.56 mmol) of HBTU were combined in a flask charged with 3 mL of DMF and 1 mL of DIEA. This reaction mixture was then treated with 0.07 g (0.56 mmol) of 2-amino-imidazole sulfate and stirred at 80° C. for 1 h. The reaction mixture was diluted with water, and the resultant solid precipitate was filtered and washed with saturated NaHCO$_3$. The solid was dissolved with MeOH, evaporated onto silica gel and isolated by flash column chromatography (500 mL DCM/20 mL NH$_3$/MeOH) to yield 10 mg of isoquinoline-3-carboxylic acid [6-cyano-4-(1H-imidazol-2-ylcarbamoyl)-1H-benzoimidazol-2-yl]-amide. LCMS: 424.0 (M+1)⁺.

By analogous methods to those used to prepare Examples and 454-461 and those in the relevant above schemes, the following compounds were synthesized.

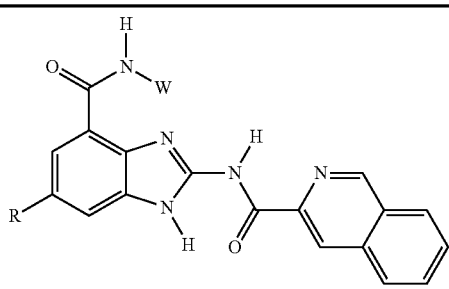

| Ex. | W | R | LCMS (M + 1)⁺ |
|---|---|---|---|
| 462 | 4-methanesulfonyl-benzyl | phenyl | 577 |
| 463 | 4-methanesulfonyl-benzyl | isopropyl | 543 |
| 464 | 1H-imidazol-2-yl | phenyl | 475 |
| 465 | 4-methanesulfonyl-benzyl | furan-3-yl | 567 |
| 466 | 4-methanesulfonyl-benzyl | trifluoromethyl | 569 |
| 467 | 1H-imidazol-2-yl | pyridin-4-yl | 476 |
| 468 | 4-methanesulfonyl-benzyl | thiophen-3-yl | 583 |
| 469 | ethyl | pyridin-4-yl | 438 |
| 470 | cyclopentyl | pyridin-4-yl | 478 |

Example 471

10.0 mL of conc. HNO$_3$ at 0° C. was treated with 20.0 mL of conc. H$_2$SO$_4$, then 6.4 g (40 mmol) of 3,5-difluorobenzoic acid. The reaction mixture was warmed to room temperature and stirred overnight, then poured into a beaker containing ice. The resulting solid was collected, washed with cold water and dried to produce 8.0 g (80%) of 3,5-difluoro-2-nitro-benzoic acid. LCMS: 204 (M+1)$^+$.

6.0 g (30.0 mmol) of 3,5-difluoro-2-nitro-benzoic acid was dissolved in DMF, treated with 8.5 g (60.0 mmol) of MeI and 9.5 g (90.0 mmol) of Na$_2$CO$_3$, and heated at 80° C. for 2 h. Water was added to the reaction mixture, and extraction with EtOAc produced 3,5-difluoro-2-nitro-benzoic acid methyl ester. LCMS: 218 (M+1)$^+$.

6.0 g (27.5 mmol) of 3,5-difluoro-2-nitro-benzoic acid methyl ester was dissolved in DMF and treated with 2.9 g (30.25 mmol) of ammonium carbonate. The reaction was heated at 60° C. for 6 h. Water was added to the reaction mixture. The solid produced was collected by filtration and washed with water to produce 3-amino-5-fluoro-2-nitro-benzoic acid methyl ester. LCMS: 215 (M+1)$^+$.

5.0 g (23.3 mmol) of 3-amino-5-fluoro-2-nitro-benzoic acid methyl ester was dissolved in ethanol and treated with 2.6 g (25.6 mmol) of triethylamine and 1.8 g (25.6 mmol) of NaOEt. The reaction was heated at 60° C. for 0.5 h to produce 3-amino-5-ethoxy-2-nitro-benzoic acid ethyl ester. LCMS: 255 (M+1)$^+$.

5.0 g (19.7 mmol) of 3-amino-5-ethoxy-2-nitro-benzoic acid ethyl ester was hydrogenated according to general procedure C to produce 2,3-diamino-5-ethoxy-benzoic acid ethyl ester. LCMS: 225 (M+1)$^+$.

4.0 g (17.9 mmol) of 2,3-diamino-5-ethoxy-benzoic acid ethyl ester was subjected to a similar cyclization condition as illustrated in intermediate A by using 5.7 g (53.7 mmol) of BrCN in methanol to produce 2-amino-6-ethoxy-1H-benzoimidazole-4-carboxylic acid ethyl ester. LCMS: 250 (M+1)$^+$.

600 mg (3.0 mmol) of isoquinoline-3-carboxylic acid and 1200 mg (3.1 mmol) of HBTU were dissolved in 3.0 mL of DMF and 0.6 mL of DIEA and reacted with 500 mg (2.0 mmol) of 2-amino-6-ethoxy-1H-benzoimidazole-4-carboxylic acid ethyl ester as described in general procedure A. Upon completion, the reaction was diluted with brine. The resulting solid was filtered, washed with water and EtOAc, and dried under vacuum to produce 500 mg (62%) of 6-ethoxy-2-[(isoquinoline-3-carbonyl)-amino]-3H-benzoimidazole-4-carboxylic acid ethyl ester. LCMS: 406 (M+1)$^+$.

Example 472

0.3 g (0.74 mmol) of 6-ethoxy-2-[(isoquinoline-3-carbonyl)-amino]-3H-benzoimidazole-4-carboxylic acid ethyl ester was hydrolyzed according to general procedure B to produce 2-[(isoquinoline-3-carbonyl)-amino]-6-ethoxy-1H-benzoimidazole-4-carboxylic acid. LCMS: 378 (M+1)$^+$.

100 mg (0.3 mmol) of 2-[(isoquinoline-3-carbonyl)-amino]-6-ethoxy-1H-benzoimidazole-4-carboxylic acid and 200 mg (0.53 mmol) of HBTU were dissolved in 1.0 mL of DMF and 0.5 mL of DIEA and reacted with 132 mg (1.0 mmol) of 2-aminoimidazole sulfate as described in general procedure A. Upon completion, the reaction was diluted with brine. The resulting solid was filtered, washed with water and EtOAc, and dried under vacuum to produce 30 mg (23%) of isoquinoline-3-carboxylic acid [5-ethoxy-7-(1H-imidazol-2-ylcarbamoyl)-1H-benzoimidazol-2-yl]-amide. LCMS: 443 (M+1)$^+$.

Example 473

3.0 g (14.0 mmol) of 3-amino-5-fluoro-2-nitro-benzoic acid methyl ester in 1.6 g (15.4 mmol) of triethylamine and 2.1 g (15.4 mmol) of NaOBn/BnOH was heated at 60° C. for 0.5 h to produce 3-amino-5-benzyloxy-2-nitro-benzoic acid benzyl ester. LCMS: 380 (M+1)$^+$.

3.0 g (7.9 mmol) of 3-amino-5-benzyloxy-2-nitro-benzoic acid benzyl ester was reduced by 5.4 g (23.7 mmol) of SnCl$_2$2H$_2$O in 30 mL of ethanol at 80° C. for 3 h to produce 2,3-diamino-5-benzyloxy-benzoic acid benzyl ester. LCMS: 350 (M+1)$^+$.

2.5 g (7.2 mmol) of 2,3-diamino-5-benzyloxy-benzoic acid benzyl ester was subjected to a similar cyclization condition as illustrated in intermediate A by using 2.3 g (21.6 mmol) of BrCN in methanol to produce 2-amino-6-benzyloxy-1H-benzoimidazole-4-carboxylic acid benzyl ester. LCMS: 375 (M+1)$^+$.

600 mg (3.0 mmol) of isoquinoline-3-carboxylic acid and 1200 mg (3.1 mmol) of HBTU were dissolved in 3.0 mL of DMF and 0.6 mL of DIEA and reacted with 1.1 g (3.0 mmol) of 2-amino-6-benzyloxy-1H-benzoimidazole-4-carboxylic acid benzyl ester as described in general procedure A to produce 6-benzyloxy-2-[(isoquinoline-3-carbonyl)-amino]-3H-benzoimidazole-4-carboxylic acid benzyl ester. LCMS: 530 (M+1)$^+$.

0.7 g (1.3 mmol) of 6-benzyloxy-2-[(isoquinoline-3-carbonyl)-amino]-3H-benzoimidazole-4-carboxylic acid benzyl ester was hydrolyzed according to general procedure B to produce 6-benzyloxy-2-[(isoquinoline-3-carbonyl)-amino]-3H-benzoimidazole-4-carboxylic acid. LCMS: 440 (M+1)$^+$.

300 mg (0.75 mmol) of 6-benzyloxy-2-[(isoquinoline-3-carbonyl)-amino]-3H-benzoimidazole-4-carboxylic acid and 600 mg (1.58 mmol) of HBTU were dissolved in 2.0 mL of DMF and 1.0 mL of DIEA and reacted with 390 mg (3.0 mmol) of 2-aminoimidazole sulfate as described in general procedure A. Upon completion, the reaction was diluted with brine. The resulting solid was filtered, washed with water and EtOAc, and dried under vacuum to produce 300 mg (80%) of isoquinoline-3-carboxylic acid [5-benzyloxy-7-(1H-imidazol-2-ylcarbamoyl)-1H-benzoimidazol-2-yl]-amide. LCMS: 505 (M+1)$^+$.

By analogous methods to those used to prepare Examples 471-473 and those in the relevant above schemes, the following compounds were synthesized.

| Ex. | W | R | LCMS (M + 1)$^+$ |
|---|---|---|---|
| 474 | 1H-imidazol-2-yl | methyl | 429 |
| 475 | 4-methanesulfonyl-benzyl | methyl | 531 |
| 476 | 1H-imidazol-2-yl | propyl | 457 |
| 477 | 1H-imidazol-2-yl | isopropyl | 457 |
| 478 | 1H-imidazol-2-yl | butyl | 471 |

Example 479

A solution of 2.65 mL (52.0 mmol) of bromine in 10 mL of acetic acid was added dropwise over 15 minutes to a solution of 8.89 g (52.0 mmol) of 2-amino-4-chloro-benzoic acid in 60 mL of acetic acid. The mixture was stirred at room temperature for 1 h and poured into 500 grams of ice. The solid was collected by filtration, washed with cold water and dried to produce 11.2 g (86%) of 2-amino-5-bromo-4-chloro-benzoic acid. LCMS: 251 (M+1)$^+$.

7.5 g (30 mmol) of 2-amino-5-bromo-4-chloro-benzoic acid was heated under reflux with 18 mL of ethyl chloroformate for 6 h, and was further heated under reflux for another 3 h after addition of 18 mL of acetyl chloride. The solid was collected and washed with hexanes to produce 5.8 g (70%) of 5-bromo-4-chloroisatoic anhydride. LCMS: 277 (M+1)$^+$.

5.4 g (20 mmol) of 5-bromo-4-chloroisatoic anhydride was suspended in 20 ml of conc. H$_2$SO$_4$ at −10° C. and cooled to −20° C. 2.1 g (21 mmol) of potassium nitrate was dissolved in 6 mL of sulfuric acid and cooled to 0° C., was then added dropwise to the reaction mixture. The reaction mixture was then stirred −10° C. for 15 min and warmed to room temperature overnight. The mixture was poured in to a beaker containing ice. The resulting solid was collected by filtration, washed with cold water and dried to produce 3.2 g (50%) of 5-bromo-4-chloro-3-nitroisatoic anhydride. LCMS: 323 (M+1)$^+$.

2.0 g (6.2 mmol) of 5-bromo-4-chloro-3-nitrolisatoic anhydride was dissolved in methanol and treated with 2.02 g (37.4 mmol) of NaOMe. The reaction mixture was heated at 100° C. for 12 h to produce 2-amino-5-bromo-4-methoxy-2-nitro-benzoic acid. LCMS: 292 (M+1)$^+$.

1.5 g (5.15 mmol) of 2-amino-5-bromo-4-methoxy-2-nitro-benzoic acid was hydrogenated according to general procedure C to produce 2,3-diamino-4-methoxy-benzoic acid. LCMS: 183 (M+1)$^+$.

0.9 g (4.9 mmol) of 2,3-diamino-4-methoxy-benzoic acid was subjected to a similar cyclization condition as illustrated in intermediate A by using 2.6 g (24.5 mmol) of BrCN in methanol to produce 2-amino-7-methoxy-1H-benzoimidazole-4-carboxylic acid. LCMS: 208 (M+1)$^+$.

1.0 g (4.8 mmol) of 2-amino-7-methoxy-1H-benzoimidazole-4-carboxylic acid was heated under reflux in methanol and HCl/ether to produce 2-amino-7-methoxy-1H-benzoimidazole-4-carboxylic acid methyl ester. LCMS: 222 (M+1)$^+$.

300 mg (1.5 mmol) of isoquinoline-3-carboxylic acid and 570 mg (1.50 mmol) of HBTU were dissolved in 1.0 mL of DMF and 0.8 mL of DIEA and reacted with 110 mg (0.5 mmol) of 2-amino-7-methoxy-1H-benzoimidazole-4-carboxylic acid methyl ester as described in general procedure A. Upon completion, the reaction was diluted with brine. The resulting solid was filtered, washed with water and EtOAc, and dried under vacuum to produce 70 mg (37%) of 2-[(isoquinoline-3-carbonyl)-amino]-7-methoxy-3H-benzoimidazole-4-carboxylic acid methyl ester. LCMS: 378 (M+1)$^+$.

Example 480

0.06 g (0.16 mmol) of 2-[(Isoquinoline-3-carbonyl)-amino]-7-methoxy-3H-benzoimidazole-4-carboxylic acid methyl ester was hydrolyzed according to general procedure B to produce 0.05 g (0.14 mmol, 87%) of 2-[(isoquinoline-3-carbonyl)-amino]-7-methoxy-1H-benzoimidazole-4-carboxylic acid. LCMS: 363 (M+1)$^+$.

33 mg (0.1 mmol) of 2-[(isoquinoline-3-carbonyl)-amino]-7-methoxy-1H-benzoimidazole-4-carboxylic acid and 100 mg (0.25 mmol) of HBTU were dissolved in 1.0 mL of DMF and 0.4 mL of DIEA and reacted with 32 mg (0.15 mmol) of 4-methanesulfonyl-benzylamine hydrochloride as described in general procedure A. Upon completion, the reaction was diluted with brine. The resulting solid was filtered, washed with water and EtOAc, and dried under vacuum to produce 14 mg (26%) of isoquinoline-3-carboxylic acid [7-(4-methanesulfonyl-benzylcarbamoyl)-4-methoxy-1H-benzoimidazol-2-yl]-amide. LCMS: 530 (M+1)$^+$.

Example 481

5.0 mL of conc. HNO$_3$ at 0° C. was slowly treated with 10.0 mL of colic. H$_2$SO$_4$, then 3.2 g (20 mmol) of 2,6-difluoro-benzoic acid. The reaction mixture was warmed to room temperature and stirred overnight. The mixture was poured into a beaker containing ice. The resulting solid was collected by filtration, washed with cold water and dried to produce 4.0 g (80%) of 2,6-difluoro-3-nitro-benzoic acid as a white solid. LCMS: 204 (M+1)$^+$.

2.0 g (9.9 mmol) of 2,6-difluoro-3-nitro-benzoic acid in methanol and 3.0 g (30.0 mmol) of ammonium acetate was stirred at room temperature for 12 h. The solvent was evaporated and dilute HCl solution was added. The precipitated solid was collected by filtration and washed with water to produce 2-amino-6-fluoro-3-nitro-benzoic acid. LCMS: 201 (M+1)$^+$.

1.8 g (9.0 mmol) of 2-amino-6-fluoro-3-nitro-benzoic acid in methanol and 2.9 g (54 mmol) of NaOMe was heated at 90° C. overnight to produce 1.6 g (7.5 mmol 83%) of 2-amino-6-methoxy-3-nitro-benzoic acid. LCMS: 213 (M+1)$^+$.

1.0 g (4.7 mmol) of 2-amino-6-methoxy-3-nitro-benzoic acid was hydrogenated according to general procedure C to produce 2,3-diamino-6-methoxy-benzoic acid. LCMS: 183 (M+1)$^+$.

0.8 g (4.4 mmol) of 2,3-diamino-6-methoxy-benzoic acid was subjected to a similar cyclization condition as illustrated in intermediate A by using 0.7 g (6.6 mmol) of BrCN in methanol to produce 2-amino-5-methoxy-1H-benzoimidazole-4-carboxylic acid. LCMS: 208 (M+1)$^+$.

0.9 g (4.3 mmol) of 2-amino-5-methoxy-1H-benzoimidazole-4-carboxylic acid was heated under reflux in methanol and HCl/ether to produce 2-amino-5-methoxy-1H-benzoimidazole-4-carboxylic acid methyl ester. LCMS: 222 (M+1)$^+$.

400 mg (2.0 mmol) of isoquinoline-3-carboxylic acid and 800 mg (2.1 mmol) of HBTU were dissolved in 2.0 mL of DMF and 1.3 mL of DIEA and treated with 300 mg (1.5 mmol) of 2-amino-5-methoxy-1H-benzoimidazole-4-carboxylic acid methyl ester as described in general procedure A. Upon completion, the reaction was diluted with brine. The resulting solid was filtered, washed with water and EtOAc, and dried under vacuum to produce 160 mg (28%) of 2-[(isoquinoline-3-carbonyl)-amino]-5-methoxy-3H-benzoimidazole-4-carboxylic acid methyl ester. LCMS: 377 (M+1)$^+$.

Example 482

0.14 g (0.38 mmol) of 2-[(Isoquinoline-3-carbonyl)-amino]-5-methoxy-3H-benzoimidazole-4-carboxylic acid methyl ester was hydrolyzed according to general procedure B to produce 0.12 g (0.33 mmol, 87%) of 2-[(isoquinoline-3-carbonyl)-amino]-5-methoxy-1H-benzoimidazole-4-carboxylic acid. LCMS: 363 (M+1)$^+$.

66 mg (0.18 mmol) of 2-[(isoquinoline-3-carbonyl)-amino]-5-methoxy-1H-benzoimidazole-4-carboxylic acid and 200 mg (0.53 mmol) of HBTU were dissolved in 1.0 mL of DMF and 0.5 mL of DIEA was treated with 132 mg (1.0 mmol) of 2-aminoimidazole sulfate as described in general procedure A. Upon completion, the reaction was diluted with brine. The resulting solid was filtered, washed with water and EtOAc, and dried under vacuum to produce 26 mg (34%) of isoquinoline-3-carboxylic acid [7-(1H-imidazol-2-ylcarbamoyl)-6-methoxy-1H-benzoimidazol-2-yl]-amide. LCMS: 428 (M+1)$^+$.

Example 483

33 mg (0.1 mmol) of 2-[(isoquinoline-3-carbonyl)-amino]-5-methoxy-1H-benzoimidazole-4-carboxylic acid and 100 mg (0.25 mmol) of HBTU were dissolved in 1.0 mL of DMF and 0.4 mL of DIEA was treated with 32 mg (0.15 mmol) of 4-methanesulfonyl-benzylamine hydrochloride as described in general procedure A. Upon completion, the reaction was diluted with brine. The resulting solid was filtered, washed with water and EtOAc, and dried under vacuum to produce 25 mg (47%) of isoquinoline-3-carboxylic acid [7-(4-methanesulfonyl-benzylcarbamoyl)-6-methoxy-1H-benzoimidazol-2-yl]-amide. LCMS: 530 (M+1)$^+$.

Example 484

2.0 g (8.44 mmol) of 6,7-dimethoxy-1,2,3,4-tetrahydro-isoquinoline-3-carboxylic acid was heated under reflux in methanol and HCl/ether to produce 2.1 g (8.40 mmol, 99%) of 6,7-dimethoxy-1,2,3,4-tetrahydro-isoquinoline-3-carboxylic acid methyl ester. LCMS: 252 (M+1)$^+$.

1.8 g (6.26 mmol) of 6,7-dimethoxy-1,2,3,4-tetrahydro-isoquinoline-3-carboxylic acid methyl ester and 3.3 g (37.6 mmol) of MnO$_2$ in toluene/dioxane/THF was heated under reflux overnight. After gravity filtration, the hot filtrate was evaporated to produce 0.4 g (1.62 mmol, 26%) of 6,7-dimethoxy-isoquinoline-3-carboxylic acid methyl ester. LCMS: 248 (M+1)$^+$.

0.4 g (1.62 mmol) of 6,7-dimethoxy-isoquinoline-3-carboxylic acid methyl ester was hydrolyzed according to general procedure B to produce 0.38 g (1.60 mmol, 98%) of 6,7-dimethoxy-isoquinoline-3-carboxylic acid. LCMS: 234 (M+1)$^+$.

235 mg (1.0 mmol) of 6,7-dimethoxy-isoquinoline-3-carboxylic acid and 400 mg (1.0 mmol) of HBTU were dissolved in 1.5 mL of DMF and 0.5 mL of DIEA and treated with 249 mg (1.0 mmol) of 2-amino-6-ethoxy-1H-benzoimidazole-4-carboxylic acid ethyl ester (prepared in Example 471) as described in general procedure A. Upon completion, the reaction was diluted with brine. The resulting solid was filtered, washed with water and EtOAc, and dried under vacuum to produce 290 mg (0.63 mmol, 63%) of 2-[(6,7-dimethoxy-isoquinoline-3-carbonyl)-amino]-6-ethoxy-1H-benzoimidazole-4-carboxylic acid ethyl ester. LCMS: 465 (M+1)$^+$.

This 2-[(6,7-dimethoxy-isoquinoline-3-carbonyl)-amino]-6-ethoxy-1H-benzoimidazole-4-carboxylic acid ethyl ester was hydrolyzed according to general procedure B to produce 2-[(6,7-dimethoxy-isoquinoline-3-carbonyl)-amino]-6-ethoxy-1H-benzoimidazole-4-carboxylic acid. LCMS: 437 (M+1)$^+$.

100 mg (0.25 mmol) of 2-[(6,7-dimethoxy-isoquinoline-3-carbonyl)-amino]-6-ethoxy-1H-benzoimidazole-4-carboxylic acid and 200 mg (0.53 mmol) of HBTU were dissolved in 1.0 mL of DMF and 0.5 mL of DIEA and treated with 200 mg (1.5 mmol) of 2-aminoimidazole sulfate as described in general procedure A. Upon completion, the reaction was diluted with brine. The resulting solid was filtered, washed with water and EtOAc, and dried under vacuum to produce 60 mg (47%) of 6,7-dimethoxy-isoquinoline-3-carboxylic acid [5-ethoxy-7-(1H-imidazol-2-ylcarbamoyl)-1H-benzoimidazol-2-yl]-amide. LCMS: 502 (M+1)$^+$.

Example 485

5.0 mL of conc. HNO$_3$ at 0° C. was slowly treated with 10.0 mL of conc. H$_2$SO$_4$, then 3.52 g (20.0 mmol) of 3,4,5-trifluoro-benzoic acid. The reaction mixture was warmed up to room temperature and stirred overnight. The mixture was poured into a beaker containing ice. The resulting solid was collected by filtration, washed with cold water and dried to produce 3.4 g (16.0 mmol, 80%) of 2-nitro-3,4,5-trifluoro-benzoic acid. LCMS: 222 (M+1)$^+$.

1.4 g (6.3 mmol) of 2-nitro-3,4,5-trifluoro-benzoic acid was treated with ammonium hydroxide to produce 3-amino-4,5-difluoro-2-nitro-benzoic acid. LCMS: 219 (M+1)$^+$.

1.2 g (5.5 mmol) of 3-amino-4,5-difluoro-2-nitro-benzoic acid was heated with excess 21% NaOEt in ethanol at 90° C. for 6 h to yield 3-amino-5-ethoxy-4-fluoro-2-nitro-benzoic acid. LCMS: 245 (M+1)$^+$.

1.0 g (4.1 mmol) of 3-amino-5-ethoxy-4-fluoro-2-nitro-benzoic acid was hydrogenated according to general procedure C to produce 2,3-diamino-5-ethoxy-4-fluoro-benzoic acid. LCMS: 215 (M+1)$^+$.

0.8 g (3.7 mmol) of 2,3-diamino-5-ethoxy-4-fluoro-benzoic acid was subjected to a similar cyclization condition as illustrated in intermediate A by using 1.2 g (11.2 mmol) of BrCN in methanol to produce 2-amino-6-ethoxy-7-fluoro-1H-benzoimidazole-4-carboxylic acid. LCMS: 240 (M+1)$^+$.

0.8 g (3.3 mmol) of 2-amino-6-ethoxy-7-fluoro-1H-benzoimidazole-4-carboxylic acid was heated under reflux in methanol and HCl/ether to produce 2-amino-6-ethoxy-7-fluoro-1H-benzoimidazole-4-carboxylic acid methyl ester. LCMS: 254 (M+1)$^+$.

0.3 g (1.5 mmol) of isoquinoline-3-carboxylic acid and 0.6 g (1.6 mmol) of HBTU were dissolved in 3.0 mL of DMF and 0.6 mL of DIEA and treated with 0.25 g (1.0 mmol) of 2-amino-6-ethoxy-7-fluoro-1H benzoimidazole-4-carboxylic acid methyl ester as described in general procedure A to produce 0.18 g (0.44 mmol, 44%) of 6-ethoxy-7-fluoro-2-[(isoquinoline-3-carbonyl)-amino]-3H-benzoimidazole-4-carboxylic acid methyl ester. LCMS: 409 (M+1)$^+$.

0.17 g (0.42 mmol) of 6-ethoxy-7-fluoro-2-[(isoquinoline-3-carbonyl)-amino]-3H-benzoimidazole-4-carboxylic acid methyl ester was hydrolyzed according to general procedure B to produce 0.16 g (0.41 mmol, 98%) of 6-ethoxy-7-fluoro-2-[(isoquinoline-3-carbonyl)-amino]-3H-benzoimidazole-4-carboxylic acid. LCMS: 395 (M+1)$^+$.

30 mg (0.08 mmol) of 6-ethoxy-7-fluoro-2-[(isoquinoline-3-carbonyl)-amino]-3H-benzoimidazole-4-carboxylic acid and 100 mg (0.25 mmol) of HBTU were dissolved in 1.0 mL of DMF and 0.3 mL of DIEA and treated with 30 mg (0.14 mmol) of 4-methanesulfonyl-benzylamine hydrochloride as described in general procedure A. Upon completion, the reaction was diluted with brine. The resulting solid was filtered, washed with water and EtOAc, and dried under vacuum to produce 19 mg (45%) of isoquinoline-3-carboxylic acid [5-ethoxy-4-fluoro-7-(4-methanesulfonyl-benzylcarbamoyl)-1H-benzoimidazol-2-yl]-amide. LCMS: 562 (M+1)$^+$.

Example 486

60 mg (0.15 mmol) of 6-ethoxy-7-fluoro-2-[(isoquinoline-3-carbonyl)-amino]-3H-benzoimidazole-4-carboxylic acid (from Example 485) and 100 mg (0.25 mmol) of HBTU were dissolved in 1.0 mL of DMF and 0.2 mL of DIEA and treated with 50 mg (0.5 mmol) of 2-aminoimidazole sulfate as described in general procedure A. Upon completion, the reaction was diluted with brine. The resulting solid was filtered, washed with water and EtOAc, and dried under vacuum to produce 32 mg (46%) of Isoquinoline-3-carboxylic acid

[5-ethoxy-4-fluoro-7-(1H-imidazol-2-ylcarbamoyl)-1H-benzoimidazol-2-yl]-amide. LCMS: 460 (M+1)$^+$.

Example 487

5.0 mL of conc. HNO$_3$ at 0° C. was slowly treated with 10.0 mL of conc. H$_2$SO$_4$, then 4.12 g (20 mmol) of 3-methoxy-2,4,5-trifluoro-benzoic acid. The reaction mixture was warmed to room temperature and stirred overnight. The mixture was poured in to a beaker containing ice. The resulting solid was collected by filtration, washed with cold water and dried to produce 4.0 g (16 mmol, 80%) of 3-methoxy-6-nitro-2,4,5-trifluoro-benzoic acid. LCMS: 252 (M+1)$^+$.

2.0 g (8 mmol) of 3-methoxy-6-nitro-2,4,5-trifluoro-benzoic acid was treated with ammonium hydroxide to produce 1.6 g (6.45 mmol, 80%) of 3-amino-4,6-difluoro-5-methoxy-2-nitro-benzoic acid. LCMS: 249 (M+1)$^+$.

1.6 g (6.45 mmol) of 3-amino-4,6-difluoro-5-methoxy-2-nitro-benzoic acid was hydrogenated according to general procedure C to produce 2,3-diamino-4,6-difluoro-5-methoxy-benzoic acid. LCMS: 219 (M+1)$^+$.

1.2 g (5.5 mmol) of 2,3-diamino-4,6-difluoro-5-methoxy-benzoic acid was subjected to a similar cyclization condition as illustrated in intermediate A by using 1.7 g (16.5 mmol) of BrCN in methanol to produce 2-amino-5,7-difluoro-6-methoxy-1H-benzoimidazole-4-carboxylic acid. LCMS: 244 (M+1)$^+$.

1.0 g (4.1 mmol) of 2-amino-5,7-difluoro-6-methoxy-1H-benzoimidazole-4-carboxylic acid was heated under reflux in methanol and HCl/ether to produce 0.9 g (3.6 mmol, 88%) of 2-amino-5,7-difluoro-6-methoxy-1H-benzoimidazole-4-carboxylic acid methyl ester. LCMS: 258 (M+1)$^+$.

0.4 g (2.0 mmol) of isoquinoline-3-carboxylic acid and 800 mg (2.1 mmol) HBTU were dissolved in 3.0 mL of DMF and 0.6 mL of DIEA and treated with 0.35 g (1.5 mmol) of 2-amino-5,7-difluoro-6-methoxy-1H-benzoimidazole-4-carboxylic acid methyl ester as described in general procedure A to produce 0.3 g (0.73 mmol, 49%) of 5,7-difluoro-2-[(isoquinoline-3-carbonyl)-amino]-6-methoxy-3H-benzoimidazole-4-carboxylic acid methyl ester. LCMS: 413 (M+1)$^+$.

0.21 g (0.5 mmol) of 5,7-difluoro-2-[(isoquinoline-3-carbonyl)-amino]-6-methoxy-3H-benzoimidazole-4-carboxylic acid methyl ester was hydrolyzed according to general procedure B to produce 0.20 g (0.5 mmol, 100%) of 5,7-difluoro-2-[(isoquinoline-3-carbonyl)-amino]-6-methoxy-3H-benzoimidazole-4-carboxylic acid. LCMS: 399 (M+1)$^+$.

60 mg (0.15 mmol) of the above 5,7-difluoro-2-[(isoquinoline-3-carbonyl)-amino]-6-methoxy-3H-benzoimidazole-4-carboxylic acid and 100 mg (0.25 mmol) of HBTU were dissolved in 1.0 mL of DMF and 0.5 mL of DIEA and treated with 68 mg (0.5 mmol) of 2-aminoimidazole sulfate as described in general procedure A. Upon completion, the reaction was diluted with brine. The resulting solid was filtered, washed with water and EtOAc, and dried under vacuum to produce 24 mg (35%) of isoquinoline-3-carboxylic acid [4,6-difluoro-7-(1H-imidazol-2-ylcarbamoyl)-5-methoxy-1H-benzoimidazol-2-yl]-amide. LCMS: 464 (M+1)$^+$.

Example 488

A mixture of 2.01 g (10 mmol) 2-hydroxy-3-nitro-benzoic acid methyl ester, 0.8 g of palladium (10 wt. % on carbon powder) and 30 mL of methanol was hydrogenated at 40 psi overnight. The reaction mixture was filtered over celite. Evaporation of the solvents in vacuo gave 3-Amino-2-hydroxy-benzoic acid methyl ester. LCMS: 168 (M+1)$^+$.

A mixture of 913 mg (5.46 mmol) 3-amino-2-hydroxy-benzoic acid methyl ester, 894 mg (8.19 mmol) of cyanogen bromide, 14.4 mL of ethanol and 1.6 mL of water was heated under reflux for 1 h. Ethanol was evaporated under reduced pressure and 20 mL of 2 N aq. Na$_2$CO$_3$ was added to the residue. The precipitated solid was filtered and washed with water. The remaining product was treated with methanol and the soluble filtrate containing the product was evaporated in vacuo to provide 797 mg (4.15 mmol, 76%) of 2-amino-benzooxazole-7-carboxylic acid methyl ester. LCMS: 193 (M+1)$^+$.

2-[(Isoquinoline-3-carbonyl)-amino]-benzooxazole-7-carboxylic acid methyl ester was prepared according to general procedure A using 1.052 g (5.5 mmol) of isoquinoline 3-carboxylic acid hydrate, 797 mg (4.15 mmol) of 2-amino-benzooxazole-7-carboxylic acid methyl ester, 2.09 g (5.5 mmol) of HBTU, 1.58 mL (9 mmol) of DIEA and 14 mL of DMF stirring at 90° C. for 3 h. 684 mg (1.97 mmol, 48%) of the product was obtained. LCMS: 348 (M+1)$^+$.

2-[(Isoquinoline-3-carbonyl)-amino]-benzooxazole-7-carboxylic acid was synthesized according to General Procedure B using 417 mg (1.2 mmol) 2-[(isoquinoline-3-carbonyl)-amino]-benzooxazole-7-carboxylic acid methyl ester, 2.4 mL of 2 N aq. LiOH, 12 mL of THF and 3 mL of methanol at 40° C. for 4 h. 141 mg (0.423 mmol, 35%) of the product was obtained. LCMS: 334 (M+1)$^+$.

Isoquinoline-3-carboxylic acid [7-(1H-imidazol-2-ylcarbamoyl)-benzooxazol-2-yl]-amide was synthesized according to General Procedure A using 137 mg (0.411 mmol) of 2-[(isoquinoline-3-carbonyl)-amino]-benzooxazole-7-carboxylic acid, 111 mg (0.822 mmol) 2-aminoimidazole sulfate, 171 mg (0.45 mmol) HBTU, 0.29 mL (1.65 mmol,) of DIEA and 2 mL of DMF stirring at 90° C. for 2 h. 98.9 mg (0.248 mmol, 60%) of the product was obtained. LCMS: 399 (M+1)$^+$.

Example 489

10.0 mL of conc. HNO$_3$ at 0° C. was slowly treated with 20.0 mL of conc. H$_2$SO$_4$, then 7.6 g (40 mmol) of 3,5-difluoro-benzoic acid ethyl ester. The reaction mixture was warmed up to room temperature and stirred overnight. This mixture was poured into a beaker containing ice. The resulting mixture was extracted with ethyl acetate, washed with cold water and evaporated to produce 7.4 g (32 mmol, 80%) of 3,5-difluoro-2-nitro-benzoic acid ethyl ester. LCMS: 232 (M+1)$^+$.

4.64 g (20 mmol) of 3,5-difluoro-2-nitro-benzoic acid ethyl ester in DMF and 2.1 g (22 mmol) of ammonium carbonate was heated at 60° C. for 6 h. The reaction mixture was treated with water. The resulting solid was collected by filtration and washed with water to produce 3.4 g (15.0 mmol, 75%) of 3-amino-5-fluoro-2-nitro-benzoic acid ethyl ester. LCMS: 229 (M+1)$^+$.

2.31 g (10 mmol) of 3-amino-5-fluoro-2-nitro-benzoic acid ethyl ester in DMF, 1.1 g (11 mmol) of triethylamine and 1.4 g (16 mmol) of NaSEt were heated at 80° C. for 6 h. After cooling to room temperature, EtOAc extraction provided 3-amino-5-ethylsulfanyl-2-nitro-benzoic acid ethyl ester. LCMS: 271 (M+1)$^+$.

1.5 g (5.5 mmol) of 3-amino-5-ethylsulfanyl-2-nitro-benzoic acid ethyl ester was reduced by 2.9 g (16.6 mmol) of Na$_2$S$_2$O$_4$ in 28 mL of ethanol/ethyl acetate/water (3:3:1) at 80° C. for 3 h to produce 2,3-diamino-5-ethylsulfanyl-benzoic acid ethyl ester. LCMS: 241 (M+1)$^+$.

0.9 g (3.75 mmol) of 2,3-diamino-5-ethylsulfanyl-benzoic acid ethyl ester was subjected to a similar cyclization condition as illustrated in intermediate A by using 1.2 g (11.3 mmol) of BrCN in methanol to produce 0.9 g (3.4 mmol, 90%) of 2-amino-6-ethylsulfanyl-1H-benzoimidazole-4-carboxylic acid ethyl ester. LCMS: 266 (M+1)$^+$.

0.4 g (2.0 mmol) of isoquinoline-3-carboxylic acid and 800 mg (2.1 mmol) HBTU were dissolved in 3.0 mL of DMF and 0.6 mL of DIEA and treated with 0.26 g (1.0 mmol) of 2-amino-6-ethylsulfanyl-1H-benzoimidazole-4-carboxylic acid ethyl ester as described in general procedure A to produce 0.35 g (0.83 mmol, 83%) of 6-ethylsulfanyl-2-[(isoquinoline-3-carbonyl)-amino]-3H-benzoimidazole-4-carboxylic acid ethyl ester. LCMS: 421 (M+1)$^+$.

0.34 g (0.81 mmol) of 6-ethylsulfanyl-2-[(isoquinoline-3-carbonyl)-amino]-3H-benzoimidazole-4-carboxylic acid ethyl ester was hydrolyzed according to general procedure B to produce 0.30 g (0.77 mmol, 95%) of 6-ethylsulfanyl-2-[(isoquinoline-3-carbonyl)-amino]-3H-benzoimidazole-4-carboxylic acid. LCMS: 393 (M+1)$^+$.

80 mg (0.2 mmol) of 6-ethylsulfanyl-2-[(isoquinoline-3-carbonyl)-amino]-3H-benzoimidazole-4-carboxylic acid and 300 mg (0.76 mmol) of HBTU were dissolved in 1.0 mL of DMF and 0.5 mL of DIEA and treated with 132 mg (1.0 mmol) of 2-aminoimidazole sulfate as described in general procedure A. Upon completion, the reaction was diluted with brine. The resulting solid was filtered, washed with water and EtOAc, and dried under vacuum to produce 66 mg (71%) of isoquinoline-3-carboxylic acid [5-ethylsulfanyl-7-(1H-imidazol-2-ylcarbamoyl)-1H-benzoimidazol-2-yl]-amide. LCMS: 458 (M+1)$^+$.

Example 490

Isoquinoline-3-carboxylic acid [5-butylsulfanyl-7-(1H-imidazol-2-ylcarbamoyl)-1H-benzoimidazol-2-yl]-amide (15 mg) was synthesized by analogous procedures to those used to prepare the Example 489, with the exception that NaS(CH$_2$)$_3$CH$_3$ was used instead of NaSEt.

Example 491

0.26 g (1.0 mmol) of 2-amino-6-ethylsulfanyl-1H-benzoimidazole-4-carboxylic acid ethyl ester (See Example 489) in DCM was stirred with 0.35 g (2.0 mmol) of MCPBA and 0.34 g (4.0 mmol) of NaHCO$_3$ at room temperature for 3 h. The reaction mixture was treated with Na$_2$S$_2$O$_3$ solution and stirred for 0.5 h at room temperature. EtOAc extraction, followed by washing with dilute NaOH solution and brine, and evaporation of the solvent produced 0.28 g (0.94 mmol, 94%) of 2-amino-6-ethylsulfonyl-1H-benzoimidazole-4-carboxylic acid ethyl ester. LCMS: 298 (M+1)$^+$.

0.30 g (1.5 mmol) of isoquinoline-3-carboxylic acid and 800 mg (2.1 mmol) HBTU were dissolved in 3.0 mL of DMF and 0.6 mL of DIEA and treated with 0.28 g (0.94 mmol) of 2-amino-6-ethylsulfonyl-1H-benzoimidazole-4-carboxylic acid ethyl ester as described in general procedure A to produce 6-ethylsulfonyl-2-[(isoquinoline-3-carbonyl)-amino]-3H-benzoimidazole-4-carboxylic acid ethyl ester. LCMS: 453 (M+1)$^+$.

0.36 g (0.79 mmol) of 6-ethylsulfonyl-2-[(isoquinoline-3-carbonyl)-amino]-3H-benzoimidazole-4-carboxylic acid ethyl ester was hydrolyzed according to general procedure B to produce 0.30 g (0.71 mmol, 90%) of 6-ethylsulfonyl-2-[(isoquinoline-3-carbonyl)-amino]-3H-benzoimidazole-4-carboxylic acid. LCMS: 425 (M+1)$^+$.

62 mg (0.15 mmol) of 6-ethylsulfonyl-2-[(isoquinoline-3-carbonyl)-amino]-3H-benzoimidazole-4-carboxylic acid and 200 mg (0.53 mmol) of HBTU were dissolved in 1.0 mL of DMF and 0.5 mL of DIEA and treated with 132 mg (1.0 mmol) of 2-aminoimidazole sulfate as described in general procedure A. After the reaction was complete, diluted with brine 10 (mL). The resulting solid was filtered, washed with water, EtOAc and dried under vacuum to produce 36 mg (57%) of isoquinoline-3-carboxylic acid [5-ethanesulfonyl-7-(1H-imidazol-2-ylcarbamoyl)-1H-benzoimidazol-2-yl]-amide. LCMS: 490 (M+1)$^+$.

By analogous methods to those used to prepare Example 491 and those in the relevant above schemes, the following compounds were synthesized.

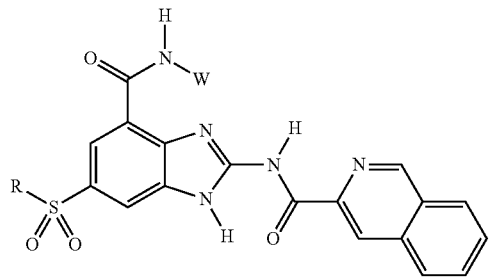

| Ex. | W | R | LCMS: (M + 1)$^+$ |
|---|---|---|---|
| 492 | 1H-imidazol-2-yl | methyl | 477 |
| 493 | 1H-imidazol-2-yl | phenyl | 539 |
| 494 | 1H-imidazol-2-yl | butyl | 519 |

Example 495

A solution of 1.53 g (10 mmol) of 3-nitro-benzene-1,2-diamine in 20 mL of methanol was treated with 1.3 g (12.5 mmol) of BrCN, and the mixture was heated under reflux for 1.0 h. After cooling to r.t., the reaction was concentrated and the residue were washed with sat. NaHCO$_3$ solution. The solid was collected, washed with water and dried to produce 1H-benzoimidazole-4-nitro-2-amine. LCMS: 179 (M+1)$^+$.

1.6 g (8 mmol) of isoquinoline-3-carboxylic acid and HBTU were dissolved in DMF and DIEA was treated with 1.4 g (8 mmol) of 1H-benzoimidazole-4-nitro-2-amine as described in general procedure A to produce 1.9 g (6 mmol, 75%) of isoquinoline-3-carboxylic acid (1H-benzoimidazol-4-nitro-2-yl)-amide. LCMS: 335 (M+1)$^+$.

1.6 g (6 mmol) of isoquinoline-3-carboxylic acid (1H-benzoimidazol-4-nitro-2-yl)-amide was hydrogenated according to general procedure C to produce 0.9 g (3 mmol, 50%) of isoquinoline-3-carboxylic acid (4-amino-1H-benzoimidazol-2-yl)-amide. LCMS: 305 (M+1)$^+$.

66 mg (0.2 mmol) of isoquinoline-3-carboxylic acid (4-amino-1H-benzoimidazol-2-yl)-amide was dissolved in pyridine (0.6 mL). To this stirred solution at 0° C., 0.2 mmol of phenylsulfonyl chloride in 0.2 mL of DCM was added in one portion. The reaction mixture was stirred at room temperature for 2 h. Brine (5 mL) was added and stirred for 10 min. The resulting solid was collected by filtration, washed with water (3×2 ml) and EtOAc (3×3 mL) and dried to yield 46 mg (52%) of isoquinoline-3-carboxylic acid (7-benzenesulfonylamino-1H-benzoimidazol-2-yl)-amide. LCMS: 444 (M+1)$^+$.

Example 496

0.10 g (0.30 mmol) of isoquinoline-3-carboxylic acid (4-amino-1H-benzoimidazol-2-yl)-amide in 2 mL of pyridine was treated with 0.06 mL (0.75 mmol) of methanesulfonyl chloride and shaken at room temperature for 4 hours. After such time, this crude reaction mixture was treated with 0.10 mL hydrazine monohydrate and heated at 60° C. for 1 hour. The reaction mixture was diluted with water and the resulting solid isoquinoline-3-carboxylic acid (4-methanesulfonylamino-1H-benzoimidazol-2-yl)-amide was collected by filtration and required no further purification. LCMS: 382.9 (M+1)$^+$.

Example 497

7.6 g (50 mmol) of 4-nitro-ortho-phenylenediamine was dissolved were dissolved in 100 mL of ethanol and 20 mL of $H_2O$. 7.9 g (75 mmol) of BrCN was added in one portion to this stirring solution, and the resulting mixture was heated under reflux for 1.0 h. The reaction mixture was cooled to room temperature, concentrated to 20 mL then neutralized with saturated $NaHCO_3$ solution to pH 8, and resulting solid 5-nitro-1H-benzoimidazol-2-ylamine collected via filtration was used directly in the next step without further purification.

Isoquinoline-3-carboxylic acid (5-nitro-1H-benzoimidazol-2-yl)-amide was synthesized from 3.5 g (20 mmol) of isoquinoline-3-carboxylic acid monohydrate, 7.6 g (20 mmol) of HBTU, and 3.56 g (20 mmol) of the above described 5-nitro-1H-benzoimidazol-2-ylamine as described in general procedure A. A 0.50 g (1.5 mmol) portion of this isoquinoline-3-carboxylic acid (5-nitro-1H-benzoimidazol-2-yl)-amide was subsequently hydrogenated according to general procedure C to produce isoquinoline-3-carboxylic acid (5-amino-1H-benzoimidazol-2-yl)-amide. LCMS: 304 (M+1)$^+$.

Example 498

0.10 g (0.30 mmol) of isoquinoline-3-carboxylic acid (5-amino-1H-benzoimidazol-2-yl)-amide in 2 mL of pyridine was treated with 0.06 mL (0.75 mmol) of methanesulfonyl chloride and shaken at room temperature for ~4 hours. After such time, this crude reaction mixture was treated with 0.10 mL hydrazine monohydrate and heated at 60° C. for ~1 hour. The reaction mixture was diluted with water, and the resulting solid isoquinoline-3-carboxylic acid (5-methanesulfonylamino-1H-benzoimidazol-2-yl)-amide was collected by filtration and required no further purification. LCMS: 382 (M+1)$^+$. $^1$H NMR (DMSO-$d_6$, 400 MHz): δ 9.49 (s, 1H), 9.45 (s, 1M), 8.78 (s, 1H), 8.30 (t, 2H), 7.94-7.87 (m, 2H), 7.46-7.44 (m, 2H), 7.03 (d, 1H), 2.89 (s, 3H) ppm.

By analogous methods to those used to prepare Example 498 and those in the relevant above schemes, the following compounds were synthesized.

| Ex. | R | LCMS (M + 1)$^+$ |
|---|---|---|
| 499 | 4-biphenyl | 521 |
| 500 | propyl | 411 |
| 501 | isopropyl | 411 |

Biological Assay

The following assay methods were used to identify and evaluate compounds of Formula (I) that are effective in reducing the proteolytic activity of BACE. BACE Fluorescence Resonance Energy Transfer (FRET) Assay In the following assay, the proteolytic activity of BACE is measured by observing cleavage of a fluorescent group from a peptide substrate containing a rhodamine fluorescent donor and a quenching acceptor.

The inhibitory activity of compounds of Formula (I) is compared to a statine derived control inhibitor STA200 (KTEEISEVN(Statine)VAEF-OH, MP Biomedical Cat. # STA-200). The cleavage reaction occurs when a BACE-1 substrate (Rhodamine-EVNLDAEFK-Quencher, Invitrogen, Cat.# P2947) was added to a reaction mixture containing BACE-1 and allowed to proceed for one hour. Fluorescence, used as a marker of BACE activity, is monitored using 540 nm excitation and 585 nm emission wavelengths (Envision, Perkin Elmer).

A typical assay reaction contains BACE—in assay buffer (50 mM sodium acetate, pH 4-4.5, 0.0125% CHAPS (3-[(3-Cholamidopropyl)dimethylammino]-1-propanesulfonate), 0.0125% TritonX-100, 0.006% EDTA) which is pre-incubated for 30 minutes with test compound in 7.5% DMSO. The reaction is initiated with the addition of BACE-1 substrate in assay buffer and allowed to proceed for one hour at room temperature. Assays are conducted in black 384-well microtiter plates and scanned at room temperature using 540 nm excitation and 585 nm emission wavelengths.

A test compound's activity is reported as the $IC_{50}$. Compounds in Examples 1-501 inhibited the proteolytic activity of BACE in the FRET assay with an $IC_{50}$ of less than 30 μM.

Aβ Cell Based Assay Procedure

In the following assay, the proteolytic activity of BACE in cells exposed to varying concentrations of a compound of interest is measured by observing the amount of $Aβ_{1-40}$ secreted from HEK293 cells (Human Embryonic Kidney epithelial cell line) stably expressing either wildtype human APP695 protein (HEK-APPwt cells).

HEK-APPwt cells were grown in high glucose DMEM (Dulbecco's Modified Eagles Medium) with 4500 mg glucose/L,L-glutamine, $NaHCO_3$, pyrdoxin HCl, 10 mM HEPES (4-(2-hydroxyethyl)-1-piperazineethanesulfonic acid) (pH 7.4), 0.1 mM NEAA (Non-essential Amino Acids) (GIBCO Cat#11140-050), 10% fetal bovine serum and 250 μg/ml hygromycin in T-225 flasks at 37° C. with $CO_2$ and humidity control.

Test compounds were initially prepared in DMSO and diluted with DMEM media containing 2% FBS (Fetal bovine serum) and 0.05% Tween20. Ten standard compound solutions were prepared having a range of concentrations. The standard compound solutions were used to determine the $EC_{50}$ of the test compound. The range of concentrations chosen may depend on the compound's predicted potency.

To prepare the cells for the assay, a flask containing HEK-APPwt cells were trypsinized briefly (1 mL trypsin), and once the cells detached, 4 mL of 10% FBS-DMEM was added to the flask. The detached cells were centrifuged at 900 rpm for 5 min to form a pellet.

The HEK-APPwt cell pellet was re-suspended with 10 mL DMEM media containing 2% FBS. 80 μL of the cell suspension was added to each well of a 96-well cell culture plate to give 100,000 cells/well. 10 μL of a standard compound solution was added to each well of the 96-well cell culture plate followed by 10 μL of Alamar blue solution. The cells were incubated at room temperature for 1 hr, followed by a five-hour incubation in the $CO_2$ incubator at 37° C.

At the end of the incubation, the plates were removed from incubator, and the supernatant was collected. $A\beta_{1-40}$ concentration in the medium was measured by using a commercial $A\beta_{1-40}$ ELISA kit (IBL, Japan). Briefly, the ELISA plates were coated with anti-human $A\beta_{35-40}$ mouse IgG monoclonal antibody. A horseradish peroxidase enzyme conjugated anti-human Aβ11-28 mouse IgG monoclone antibody was used for detection. The cell culture supernatant was diluted 1:4 fold with (EIA buffer+Protease inhibitor (buffer containing Protease Inhibitor (1 mL PI/30 mL buffer). A 100 µL aliquot of the diluted supernatant was added to each well of the ELISA plate and incubated for 6 hrs at 4° C. The ELISA plate was washed 8 times with phosphate buffered saline (PBS) containing 0.05% Tween 20.

A 100 µL of detection antibody was then added and incubated for 1 hour at 4° C. The plate was washed 8 times with PBS buffer containing 0.05% Tween 20 followed by addition of 100 µL of the substrate with the chromogen tetramethyl benzidine (TMB). The plate was incubated in the dark at room temperature for about 30 min and a stop solution (1N $H_2SO_4$) was added.

The intensity of the color developed was measured at 450 nm. The optical density at 450 nm (OD450) is proportional to the concentration of human $A\beta_{1-40}$ secreted by the cell. As a reference, N—[N-(3,5-difluorophenacetyl-L-alanyl)]-S-phenylglycine t-butyl ester (DAPT, a γ-secretase inhibitor) was used to indicate 100% inhibition of BACE activity. Thus, the assay measures the ability of a compound of interest to reduce $A\beta_{1-40}$ secretion. Compound potency was reported as the $EC_{50}$ by calculating the percent inhibition at all concentration levels and the data were fit with non-linear curve fitting algorithm using in GraphPad Prism.

Various compounds of the present invention including the compounds of Examples 58, 140, 155, 165, 176, 193, 198, 212, 247, 289, 294, 295, 296, 300, 311, 312, 318, 343, 351, 355, 414, 416, 417, 428, 434, 439, 458, 472, and 491 exhibited an $EC_{50}$ value of less than or equal to 2.0 µM in the cell based assay described above.

While the invention has been described and illustrated with reference to certain embodiments thereof, those skilled in the art will appreciate that various changes, modifications and substitutions can be made therein without departing from the spirit and scope of the invention. For example, effective dosages other than the dosages as set forth herein may be applicable as a consequence of variations in the responsiveness of the subject being treated. Likewise, the specific pharmacological responses observed may vary according to and depending on the particular active compound selected or whether there are present pharmaceutical carriers, as well as the type of formulation and mode of administration employed, and such expected variations or differences in the results are contemplated in accordance with the objects and practices of the present invention. Moreover, all compounds that are recited in the written description are contemplated as possibilities for any of the recited methods, processes, compositions, and/or compounds as appear in the written description and the appended claims.

We claim:

1. A compound selected from the group consisting of:
2-(4-Chloro-benzoylamino)-3H-benzoimidazole-4-carboxylic acid (1H-imidazol-2-yl)-amide,
Isoquinoline-3-carboxylic acid [7-(1H-benzoimidazol-2-ylcarbamoyl)-1H-benzoimidazol-2-yl]-amide,
Isoquinoline-3-carboxylic acid [7-(benzothiazol-2-ylcarbamoyl)-1H-benzoimidazol-2-yl]-amide,
Isoquinoline-3-carboxylic acid [7-([1,3,4]thiadiazol-2-ylcarbamoyl)-1H-benzoimidazol-2-yl]-amide,
Isoquinoline-3-carboxylic acid [4-(pyridin-2-ylcarbamoyl)-1H-benzoimidazol-2-yl]-amide,
Isoquinoline-3-carboxylic acid [4-(pyridin-3-ylcarbamoyl)-1H-benzoimidazol-2-yl]-amide,
2-[(1H-Indole-2-carbonyl)-amino]-1H-benzoimidazole-4-carboxylic acid (1H-benzoimidazol-2-yl)-amide,
Isoquinoline-3-carboxylic acid [5-(1H-benzoimidazol-2-ylcarbamoyl)-1H-benzoimidazol-2-yl]-amide,
Isoquinoline-3-carboxylic acid [4-(1H-indazol-5-ylcarbamoyl)-1H-benzoimidazol-2-yl]-amide,
Isoquinoline-3-carboxylic acid [4-(quinolin-3-ylcarbamoyl)-1H-benzoimidazol-2-yl]-amide,
Isoquinoline-3-carboxylic acid [5-(benzothiazol-2-ylcarbamoyl)-1H-benzoimidazol-2-yl]-amide,
Isoquinoline-3-carboxylic acid [5-(thiazol-2-ylcarbamoyl)-1H-benzoimidazol-2-yl]-amide,
2-Benzoylamino-3H-benzoimidazole-4-carboxylic acid (1H-imidazol-2-yl)-amide,
Isoquinoline-3-carboxylic acid {4-[(furan-2-ylmethyl)-carbamoyl]-1H-benzoimidazol-2-yl}-amide,
Isoquinoline-3-carboxylic acid [4-(2-phenoxy-phenylcarbamoyl)-1H-benzoimidazol-2-yl]-amide,
Isoquinoline-3-carboxylic acid [4-(3-phenoxy-phenylcarbamoyl)-1H-benzoimidazol-2-yl]-amide,
Isoquinoline-3-carboxylic acid [4-(4-phenoxy-phenylcarbamoyl)-1H-benzoimidazol-2-yl]-amide,
Isoquinoline-3-carboxylic acid [4-(1S-phenyl-ethylcarbamoyl)-1H-benzoimidazol-2-yl]-amide,
2-[(Benzo[b]thiophene-2-carbonyl)-amino]-3H-benzoimidazole-4-carboxylic acid (1H-imidazol-2-yl)-amide,
2-[(Naphthalene-2-carbonyl)-amino]-1H-benzoimidazole-4-carboxylic acid (1H-imidazol-2-yl)-amide,
2-[(1H-Indole-2-carbonyl)-amino]-1H-benzoimidazole-4-carboxylic acid (1H-imidazol-2-yl)-amide,
2-(3,5-Difluoro-benzoylamino)-3H-benzoimidazole-4-carboxylic acid (1H-imidazol-2-yl)-amide,
2-(4-Fluoro-benzoylamino)-3H-benzoimidazole-4-carboxylic acid (1H-imidazol-2-yl)-amide,
Isoquinoline-3-carboxylic acid [4-(2-thiophen-2-yl-ethylcarbamoyl)-1H-benzoimidazol-2-yl]-amide,
Isoquinoline-3-carboxylic acid (7-phenylcarbamoyl-1H-benzoimidazol-2-yl)-amide,
Isoquinoline-3-carboxylic acid {4-[(5-methyl-furan-2-ylmethyl)-carbamoyl]-1H-benzoimidazol-2-yl}-amide,
Isoquinoline-3-carboxylic acid (7-benzylcarbamoyl-1H-benzoimidazol-2-yl)-amide,
Isoquinoline-3-carboxylic acid {4-[(thiophen-2-ylmethyl)-carbamoyl]-1H-benzoimidazol-2-yl}-amide,
Isoquinoline-3-carboxylic acid (7-phenethylcarbamoyl-1H-benzoimidazol-2-yl)-amide,
Isoquinoline-3-carboxylic acid (7-ethylcarbamoyl-1H-benzoimidazol-2-yl)-amide,
Isoquinoline-3-carboxylic acid (7-tert-butylcarbamoyl-1H-benzoimidazol-2-yl)-amide,
2-[(Benzofuran-2-carbonyl)-amino]-1H-benzoimidazole-4-carboxylic acid (1H-imidazol-2-yl)-amide,
Isoquinoline-3-carboxylic acid {4-[(benzo[b]thiophen-2-ylmethyl)-carbamoyl]-1H-benzoimidazol-2-yl}-amide,
Isoquinoline-3-carboxylic acid {4-[(benzothiazol-2-ylmethyl)-carbamoyl]-1H-benzoimidazol-2-yl}-amide,
Isoquinoline-3-carboxylic acid {4-[(1-methyl-1H-benzoimidazol-2-ylmethyl)-carbamoyl]-1H-benzoimidazol-2-yl}-amide,
Isoquinoline-3-carboxylic acid {4-[2-(1H-benzoimidazol-2-yl)-ethylcarbamoyl]-1H-benzoimidazol-2-yl}-amide, 2-[2-(4-Fluoro-phenyl)-acetylamino]-3H-benzoimidazole-4-carboxylic acid (1H-imidazol-2-yl)-amide,
2-(4-Fluoro-3-methoxy-benzoylamino)-3H-benzoimidazole-4-carboxylic acid (1H-imidazol-2-yl)-amide,
2-(3,4-Dimethoxy-benzoylamino)-3H-benzoimidazole-4-carboxylic acid (1H-imidazol-2-yl)-amide,
Isoquinoline-3-carboxylic acid {4-[(thiazol-2-ylmethyl)-carbamoyl]-1H-benzoimidazol-2-yl}-amide,
Isoquinoline-3-carboxylic acid {4-[(1H-benzoimidazol-2-ylmethyl)-carbamoyl]-1H-benzoimidazol-2-yl}-amide,
2-(4-Trifluoromethyl-benzoylamino)-1H-benzoimidazole-4-carboxylic acid (1H-imidazol-2-yl)-amide,
2-(4-Phenoxy-benzoylamino)-1H-benzoimidazole-4-carboxylic acid (1H-imidazol-2-yl)-amide,
Quinoline-3-carboxylic acid [7-(1H-imidazol-2-ylcarbamoyl)-1H-benzoimidazol-2-yl]-amide,
Quinoline-2-carboxylic acid [7-(1H-imidazol-2-ylcarbamoyl)-1H-benzoimidazol-2-yl]-amide,
2-[(Furan-3-carbonyl)-amino]-3H-benzoimidazole-4-carboxylic acid (1H-imidazol-2-yl)-amide,
2-(4-tert-Butyl-benzoylamino)-3H-benzoimidazole-4-carboxylic acid (1H-imidazol-2-yl)-amide,
2-(4-Nitro-benzoylamino)-3H-benzoimidazole-4-carboxylic acid (1H-imidazol-2-yl)-amide,
2-(4-Methoxy-benzoylamino)-3H-benzoimidazole-4-carboxylic acid (1H-imidazol-2-yl)-amide,
2-[(1H-Imidazole-2-carbonyl)-amino]-3H-benzoimidazole-4-carboxylic acid (1H-imidazol-2-yl)-amide,
2-(4-Isopropyl-benzoylamino)-3H-benzoimidazole-4-carboxylic acid (1H-imidazol-2-yl)-amide,
2-(3-Fluoro-benzoylamino)-3H-benzoimidazole-4-carboxylic acid (1H-imidazol-2-yl)-amide,
2-(2-Fluoro-benzoylamino)-3H-benzoimidazole-4-carboxylic acid (1H-imidazol-2-yl)-amide,
2-[(5-Chloro-benzofuran-2-carbonyl)-amino]-1H-benzoimidazole-4-carboxylic acid (1H-imidazol-2-yl)-amide,
6,7-Dimethoxy-isoquinoline-3-carboxylic acid [7-(1H-imidazol-2-ylcarbamoyl)-1H-benzoimidazol-2-yl]-amide,
6,7-Dimethoxy-isoquinoline-3-carboxylic acid [7-(1H-imidazol-2-ylcarbamoyl)-1H-benzoimidazol-2-yl]-amide,
2-(2-Chloro-benzoylamino)-3H-benzoimidazole-4-carboxylic acid (1H-imidazol-2-yl)-amide,
1H-Indazole-3-carboxylic acid [7-(1H-imidazol-2-ylcarbamoyl)-1H-benzoimidazol-2-yl]-amide,
2-[(1-Methyl-1H-indole-2-carbonyl)-amino]-3H-benzoimidazole-4-carboxylic acid (1H-imidazol-2-yl)-amide,
1-Methyl-1H-indazole-3-carboxylic acid [7-(1H-imidazol-2-ylcarbamoyl)-1H-benzoimidazol-2-yl]-amide,
Isoquinoline-3-carboxylic acid [4-(5-phenyl-1H-imidazol-2-ylcarbamoyl)-1H-benzoimidazol-2-yl]-amide,
2-[(5-Methyl-1H-indole-2-carbonyl)-amino]-3H-benzoimidazole-4-carboxylic acid (1H-imidazol-2-yl)-amide,
2-[(6-Phenoxy-pyridine-2-carbonyl)-amino]-3H-benzoimidazole-4-carboxylic acid (1H-imidazol-2-yl)-amide,
2-[(1-Benzyl-1H-indole-2-carbonyl)-amino]-3H-benzoimidazole-4-carboxylic acid (1H-imidazol-2-yl)-amide,
2-[(1-Propyl-1H-indole-2-carbonyl)-amino]-3H-benzoimidazole-4-carboxylic acid (1H-imidazol-2-yl)-amide,
2-[(1,5-Dimethyl-1H-indole-2-carbonyl)-amino]-3H-benzoimidazole-4-carboxylic acid (1H-imidazol-2-yl)-amide,
Isoquinoline-3-carboxylic acid [4-(1H-imidazol-2-ylcarbamoyl)-6-nitro-1H-benzoimidazol-2-yl]-amide,
Isoquinoline-3-carboxylic acid [6-amino-4-(1H-imidazol-2-ylcarbamoyl)-1H-benzoimidazol-2-yl]-amide,
Isoquinoline-3-carboxylic acid [4-(1H-imidazol-2-ylcarbamoyl)-6-isobutyrylamino-1H-benzoimidazol-2-yl]-amide,
Isoquinoline-3-carboxylic acid [6-benzoylamino-4-(1H-imidazol-2-ylcarbamoyl)-1H-benzoimidazo-1-2-yl]-amide,
Isoquinoline-3-carboxylic acid [4-(1H-imidazol-2-ylcarbamoyl)-6-(3-methyl-butyrylamino)-1H-benzoimidazol-2-yl]-amide,
Isoquinoline-3-carboxylic acid [7-(1H-imidazol-2-ylcarbamoyl)-5-phenylacetylamino-1H-benzoimidazo-1-2-yl]-amide,
2-[(5-Phenylethynyl-pyridine-3-carbonyl)-amino]-1H-benzoimidazole-4-carboxylic acid (1H-imidazol-2-yl)-amide, and
2-[(6-Phenylethynyl-pyridine-2-carbonyl)-amino]-1H-benzoimidazole-4-carboxylic acid (1H-imidazol-2-yl)-amide,
or a pharmaceutically acceptable salt thereof.

2. A pharmaceutical composition comprising a compound of claim 1 and a pharmaceutically acceptable carrier, excipient, or diluent.

3. 1-Methyl-1H-indazole-3-carboxylic acid [7-(1H-imidazol-2-ylcarbamoyl)-1H-benzoimidazol-2-yl]-amide or a pharmaceutically acceptable salt thereof.

4. A pharmaceutical composition comprising the compound of claim 3.

5. Isoquinoline-3-carboxylic acid [5-(1H-imidazol-2-ylcarbamoyl)-1H-benzoimidazol-2-yl]-amide or a pharmaceutically acceptable salt thereof.

6. A pharmaceutical composition comprising the compound of claim 5.

7. Isoquinoline-3-carboxylic acid [4-(4,5,6,7-tetrahydro-1H-benzoimidazol-2-ylcarbamoyl)-1H-benzoimidazol-2-yl]-amide or a pharmaceutically acceptable salt thereof.

8. A pharmaceutical composition comprising the compound of claim 7.

9. 1-Methyl-isoquinoline-3-carboxylic acid [4-(1H-imidazol-2-ylcarbamoyl)-1H-benzoimidazol-2-yl]-amide or a pharmaceutically acceptable salt thereof.

10. A pharmaceutical composition comprising the compound of claim 9.

11. Isoquinoline-1-carboxylic acid [4-(1H-imidazol-2-ylcarbamoyl)-1H-benzoimidazol-2-yl]-amide or a pharmaceutically acceptable salt thereof.

12. A pharmaceutical composition comprising the compound of claim 11.

13. 2-[(6-Cyclopropylethynyl-pyridine-2-carbonyl)-amino]-1H-benzoimidazole-4-carboxylic acid (1H-imidazol-2-yl)-amide or a pharmaceutically acceptable salt thereof.

14. A pharmaceutical composition comprising the compound of claim 13.

* * * * *